US012790328B2

(12) United States Patent
Kitamura Fujiwara et al.

(10) Patent No.: US 12,790,328 B2
(45) Date of Patent: Nov. 10, 2026

(54) PHARMACEUTICAL COMPOSITION CONTAINING GLP-1 RECEPTOR AGONIST HAVING FUSED RING

(71) Applicant: Shionogi & Co., Ltd., Osaka (JP)

(72) Inventors: Misato Kitamura Fujiwara, Osaka (JP); Shomitsu Maeno, Osaka (JP); Yuji Nishiura, Osaka (JP)

(73) Assignee: SHIONOGI & CO., LTD., Osaka (JP)

( * ) Notice: Subject to any disclaimer, the term of this patent is extended or adjusted under 35 U.S.C. 154(b) by 445 days.

(21) Appl. No.: 18/281,848

(22) PCT Filed: Mar. 23, 2022

(86) PCT No.: PCT/JP2022/013362
§ 371 (c)(1),
(2) Date: Sep. 13, 2023

(87) PCT Pub. No.: WO2022/202864
PCT Pub. Date: Sep. 29, 2022

(65) Prior Publication Data

US 2024/0217966 A1 Jul. 4, 2024

(30) Foreign Application Priority Data

Mar. 24, 2021 (JP) ................................ 2021-050798
Oct. 8, 2021 (JP) ................................ 2021-165955

(51) Int. Cl.

| | |
|---|---|
| ***C07D 471/04*** | (2006.01) |
| ***A61K 31/4375*** | (2006.01) |
| ***A61K 31/444*** | (2006.01) |
| ***A61K 31/4709*** | (2006.01) |
| ***C07D 405/14*** | (2006.01) |

(52) U.S. Cl.
CPC ........ *C07D 471/04* (2013.01); *A61K 31/4375* (2013.01); *A61K 31/444* (2013.01); *A61K 31/4709* (2013.01); *C07D 405/14* (2013.01)

(58) Field of Classification Search
CPC .. C07D 471/04; C07D 405/14; C07D 401/14; C07D 417/14; C07D 413/14;
(Continued)

(56) References Cited

U.S. PATENT DOCUMENTS

2022/0193063 A1 6/2022 Bessire et al.
2022/0396569 A1 12/2022 Du et al.

FOREIGN PATENT DOCUMENTS

CN 113480534 10/2021
CN 113493447 10/2021

(Continued)

OTHER PUBLICATIONS

International Search Report and Written Opinion mailed Jun. 7, 2022 in International Application No. PCT/JP2022/013362 (with English translation).

(Continued)

*Primary Examiner* — Sahar Javanmard
(74) *Attorney, Agent, or Firm* — Wenderoth, Lind & Ponack, L.L.P.

(57) ABSTRACT

The present invention relates to a compound that has GLP-1 receptor agonist activity and is useful as a therapeutic or prophylactic agent for diseases associated with the GLP-1 receptor, or a pharmaceutically acceptable salt thereof, and relates to a pharmaceutical composition containing the compound or its pharmaceutically acceptable salt.
Provided is a compound represented by formula (I):

(I)

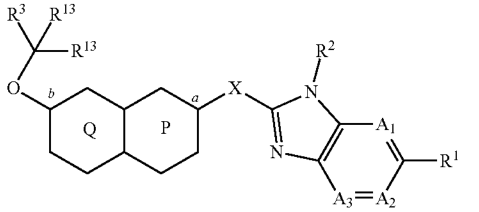

wherein $A_1$ is $C(R^5)$ or the like, $A_2$ is $C(R^6)$ or the like, $A_3$ is $C(R^7)$ or the like, $R^5$, $R^6$, and $R^7$ are each independently a hydrogen atom or the like, $R^1$ is carboxy or the like, $R^2$ is substituted or unsubstituted alkyl or the like, —X— is —O— or the like, the ring represented by:

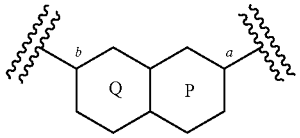

is a ring represented by:

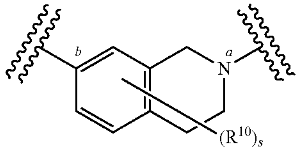

and the like
wherein
$R^{10}$ is each independently halogen or the like,
s is 0 or the like,
$R^{13}$ is each independently a hydrogen atom or the like, and $R^3$ is substituted or unsubstituted aromatic carbocyclyl or the like, or
a pharmaceutically acceptable salt thereof.

19 Claims, No Drawings

(58) Field of Classification Search
CPC ................ C07D 519/00; C07D 401/06; A61K 31/4375; A61K 31/444; A61K 31/4709
See application file for complete search history.

(56) References Cited

FOREIGN PATENT DOCUMENTS

| | | |
|---|---|---|
| CN | 113773310 | 12/2021 |
| CN | 113801136 | 12/2021 |
| CN | 113816948 | 12/2021 |
| CN | 114478497 | 5/2022 |
| CN | 114716423 | 7/2022 |
| CN | 115594669 | 1/2023 |
| CN | 118084936 | 5/2024 |
| EP | 4119555 | 1/2023 |
| EP | 4130003 | 2/2023 |
| EP | 4155313 | 3/2023 |
| EP | 4166142 | 4/2023 |
| WO | 2018/056453 | 3/2018 |
| WO | 2018/109607 | 6/2018 |
| WO | 2019/239319 | 12/2019 |
| WO | 2019/239371 | 12/2019 |
| WO | 2020/103815 | 5/2020 |
| WO | 2020/207474 | 10/2020 |
| WO | 2020/263695 | 12/2020 |
| WO | 2021/018023 | 2/2021 |
| WO | 2021/081207 | 4/2021 |
| WO | 2021/096284 | 5/2021 |
| WO | 2021/096304 | 5/2021 |
| WO | 2021/112538 | 6/2021 |
| WO | 2021/160127 | 8/2021 |
| WO | 2021/219019 | 11/2021 |
| WO | 2021/242817 | 12/2021 |
| WO | 2021/254470 | 12/2021 |
| WO | 2021/259309 | 12/2021 |
| WO | 2022/028572 | 2/2022 |
| WO | 2022/031994 | 2/2022 |
| WO | 2022/040600 | 2/2022 |
| WO | 2022/042691 | 3/2022 |
| WO | 2022/068772 | 4/2022 |
| WO | 2022/078152 | 4/2022 |
| WO | 2022/078352 | 4/2022 |
| WO | 2022/078380 | 4/2022 |
| WO | 2022/078407 | 4/2022 |
| WO | 2022/109182 | 5/2022 |
| WO | 2022/111624 | 6/2022 |
| WO | 2022/116693 | 6/2022 |
| WO | 2022/184849 | 9/2022 |
| WO | 2022/192428 | 9/2022 |
| WO | 2022/192430 | 9/2022 |
| WO | 2022/199458 | 9/2022 |
| WO | 2022/199661 | 9/2022 |
| WO | 2022/219495 | 10/2022 |
| WO | 2022/225914 | 10/2022 |
| WO | 2022/225941 | 10/2022 |
| WO | 2022/228490 | 11/2022 |
| WO | 2022/246019 | 11/2022 |
| WO | 2022/268152 | 12/2022 |
| WO | 2023/138684 | 7/2023 |
| WO | 2023/179542 | 9/2023 |

OTHER PUBLICATIONS

Zhang et al., "Differential GLP-1R Binding and Activation by Peptide and Non-peptide Agonists," Molecular Cell, Nov. 5, 2020, 80(3), pp. 485-500.

Bode, "Design, findings and implications of the liraglutide Phase III clinical trial program," Clinical Investigation, 2012, 2(1), pp. 59-72.

Astrup et al., "Effects of liraglutide in the treatment of obesity: a randomised, double-blind, placebo-controlled study," The Lancet, Nov. 7, 2009, 374, pp. 1606-1616.

Kawai et al., "Structural basis for GLP-1 receptor activation by LY3502970, an orally active nonpeptide agonist," Proceedings of the National Academy of Sciences, Nov. 24, 2020, 117(47), pp. 29959-29967.

Griffith et al., "A Small-Molecule Oral Agonist of the Human Glucagon-like Peptide-1 Receptor," Journal of Medicinal Chemistry, Jun. 1, 2022, 65(12), pp. 8208-8226.

English translation of International Preliminary Report on Patentability mailed Oct. 5, 2023 in corresponding International (PCT) Application No. PCT/JP2022/013362, pp. 1-5.

Extended European Search Report issued Feb. 10, 2025 in corresponding European Patent Application No. 22775646.7.

PHARMACEUTICAL COMPOSITION CONTAINING GLP-1 RECEPTOR AGONIST HAVING FUSED RING

TECHNICAL FIELD

The present invention relates to a compound that has GLP-1 receptor agonist activity and is useful as a therapeutic or prophylactic agent for diseases associated with the GLP-1 receptor, or its pharmaceutically acceptable salt, and a pharmaceutical composition containing thereof, particularly a prophylactic and/or therapeutic agent for non-insulin-dependent diabetes mellitus (type 2 diabetes mellitus) or obesity.

BACKGROUND ART

Glucagon-like peptide-1 (GLP-1) is an incretin hormone that is secreted by L cells in the intestine in response to ingestion of food. GLP-1 is known to exhibit effects via the GLP-1 receptor such as promotion of glucose-dependent insulin secretion, reduction of glucagon secretion, delayed gastric emptying, and reduction of appetite. So far, it has been studied that an agonist of the GLP-1 receptor is used for treating diabetes and obesity (Non Patent Documents 1 and 2). Liraglutide, an analog formulation of human GLP-1, is known as a representative agonist, but it has been found that it exhibits a potent HbA1c lowering action and body weight reduction. Due to such attractive effects, a plurality of GLP-1 analog formulation have been put into practical use as therapeutic agents for diabetes and obesity. However, most of these GLP-1 analog formulations are sold as injectable formulations because of their poor oral absorbability. Therefore, development of an orally administrable GLP-1 receptor agonist is expected. Specifically, a method of causing semaglutide, which is an analog of GLP-1, to be orally absorbed by using an absorption promoting agent (Patent Document 1) has been put into practical use, but improvement of pharmaceutical properties such as bioavailability is required. In addition, attempts have been made to create a plurality of small molecule pharmaceutical products as non-peptidic GLP-1 receptor agonists (Patent Documents 2 to 33), but the substantially disclosed compounds have structures different from that of the compound of the present invention.

PRIOR ART REFERENCES

Patent Documents

[Patent Document 1] International Publication WO 2012/080471A

[Patent Document 2] International Publication WO 2009/111700A

[Patent Document 3] International Publication WO 2010/114824A

[Patent Document 4] International Publication WO 2018/056453A

[Patent Document 5] International Publication WO 2018/109607A

[Patent Document 6] International Publication WO 2019/239319A

[Patent Document 7] International Publication WO 2019/239371A

[Patent Document 8] International Publication WO 2020/103815A

[Patent Document 9] International Publication WO 2020/207474A

[Patent Document 10] International Publication WO 2020/263695A

[Patent Document 11] International Publication WO 2021/018023A

[Patent Document 12] International Publication WO 2021/081207A

[Patent Document 13] International Publication WO 2021/096284A

[Patent Document 14] International Publication WO 2021/096304A

[Patent Document 15] International Publication WO 2021/112538A

[Patent Document 16] International Publication WO 2021/155841A

[Patent Document 17] International Publication WO 2021/160127A

[Patent Document 18] International Publication WO 2021/187886A

[Patent Document 19] Chinese Patent Application Publication CN 113493447A

[Patent Document 20] International Publication WO 2021/197464A

[Patent Document 21] International Publication WO 2021/219019A

[Patent Document 22] Chinese Patent Application Publication CN 113480534A

[Patent Document 23] International Publication WO 2021/244645A

[Patent Document 24] International Publication WO 2021/249492A

[Patent Document 25] International Publication WO 2021/242817A

[Patent Document 26] Chinese Patent Application Publication CN 113773310A

[Patent Document 27] Chine se Patent Application Publication CN 113816948A

[Patent Document 28] Chinese Patent Application Publication CN 113801136A

[Patent Document 29] International Publication WO 2021/254470A

[Patent Document 30] International Publication WO 2021/259309A

[Patent Document 31] International Publication WO 2022/028572A

[Patent Document 32] International Publication WO 2022/031994A

[Patent Document 33] International Publication WO 2022/040600A

Non-Patent Documents

[Non-patent Document 1] Lancet, 2009, 374, 1606-1616

[Non-patent Document 2] Clin. Invest., 2012, 2, 59-72

SUMMARY OF THE INVENTION

Problems to be Solved by the Invention

An object of the present invention is to provide a compound that has GLP-1 receptor agonist activity and is useful as a therapeutic or prophylactic agent for diseases relating to the GLP-1 receptor, or its pharmaceutically acceptable salt, and a pharmaceutical composition containing thereof, particularly a prophylactic and/or therapeutic agent for non-insulin-dependent diabetes mellitus (type 2 diabetes mellitus) or obesity.

Means for Solving the Problem

The present invention relates to the following.

(1) A compound represented by formula (I):

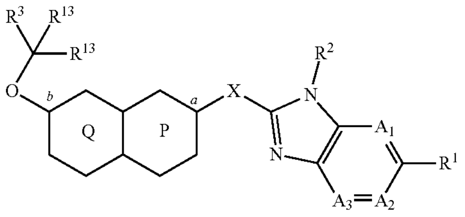

(I)

wherein $A_1$ is $C(R^5)$ or N, $A_2$ is $C(R^6)$ or N, $A_3$ is $C(R^7)$ or N, $R^5$, $R^6$, and $R^7$ are each independently a hydrogen atom, halogen, cyano, substituted or unsubstituted alkyl, or substituted or unsubstituted alkyloxy, $R^1$ is carboxy or an equivalent thereof, $R^2$ is substituted or unsubstituted alkyl, —X— is $—C(R^8)(R^9)—$, —O—, or $—N(R^{11})—$, $R^8$ and $R^9$ are each independently a hydrogen atom, halogen, or substituted or unsubstituted alkyl, $R^{11}$ is a hydrogen atom, or substituted or unsubstituted alkyl, the ring represented by:

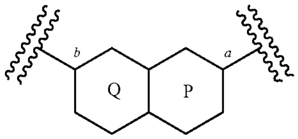

is a ring represented by:

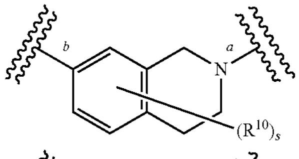

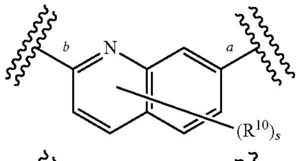

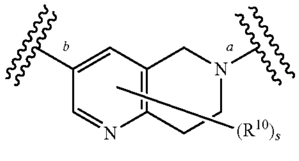

-continued

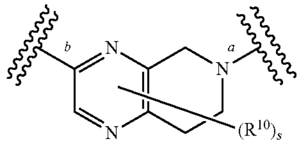

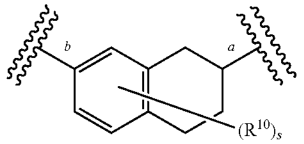

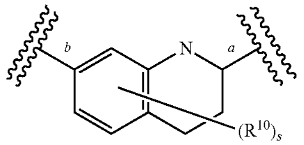

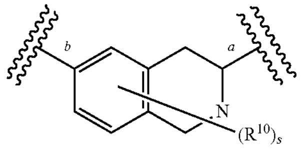

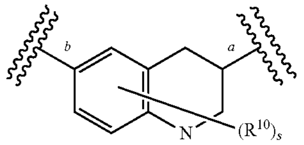

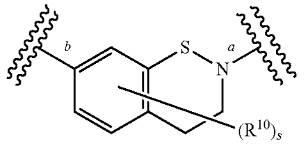

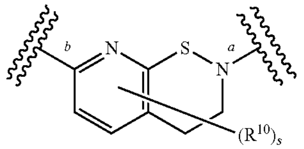

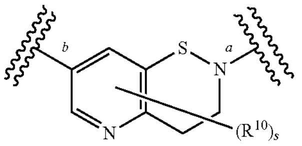

or

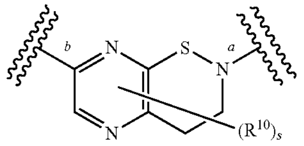

wherein $R^{10}$ is each independently halogen, cyano, hydroxy, substituted or unsubstituted alkyl, oxo, substituted or unsubstituted non-aromatic carbocyclyl, or substituted or unsubstituted alkyloxy, and s is an integer of 0 to 9, $R^{13}$ is each independently a hydrogen atom, halogen, or substituted or unsubstituted alkyl, and $R^3$ is substituted or unsubstituted aromatic carbocyclyl, or substituted or unsubstituted aromatic heterocyclyl, or a pharmaceutically acceptable salt thereof.

(2) The compound according to the above (1) or a pharmaceutically acceptable salt thereof, wherein s is an integer of 1 to 9.

(3) The compound according to the above (1) or a pharmaceutically acceptable salt thereof, wherein the ring represented by:

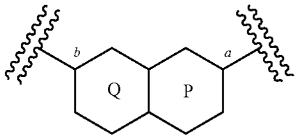

is a ring represented by:

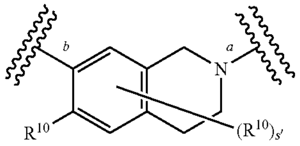

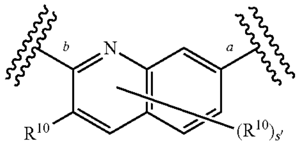

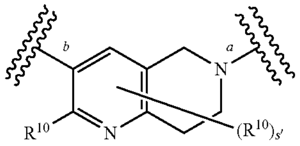

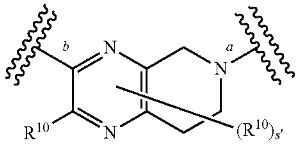

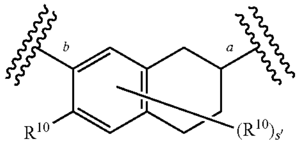

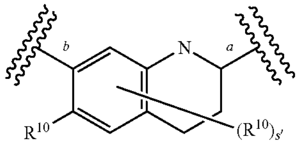

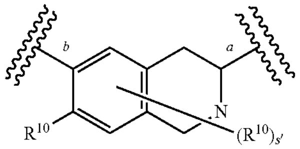

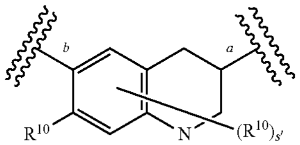

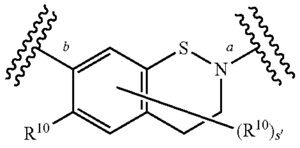

-continued

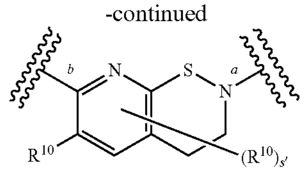

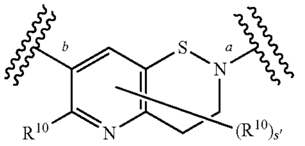

or

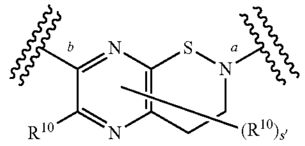

wherein s' is an integer of 0 to 8, and the other symbols are the same as those in the above (1).

(4) The compound according to the above (1) or (3) or a pharmaceutically acceptable salt thereof, wherein the ring represented by:

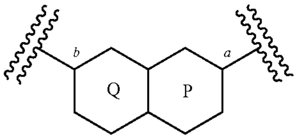

is a ring represented by:

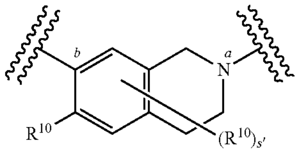

or

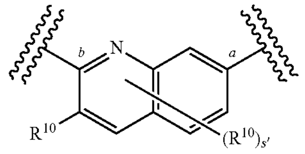

wherein s' is an integer of 0 to 8, and the other symbols are the same as those in the above (1) or (3).

(5) The compound according to any of the above (1) to (4) or a pharmaceutically acceptable salt thereof, wherein each $R^{10}$ is independently halogen, cyano, or substituted or unsubstituted alkyl.

(6) The compound according to any one of the above (1) to (5) or a pharmaceutically acceptable salt thereof, wherein $R^3$ is a group represented by:

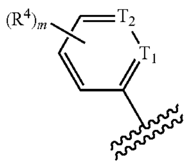

wherein $T_1$ is a carbon atom or a nitrogen atom, $T_2$ is a carbon atom or a nitrogen atom, $R^4$ is each independently halogen, cyano, substituted or unsubstituted alkyl, or substituted or unsubstituted alkyloxy, and m is an integer of 0 to 5.

(7) The compound according to any one of the above (1) to (6) or a pharmaceutically acceptable salt thereof, wherein $R^3$ is a group represented by:

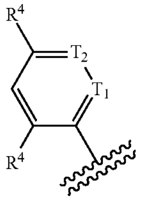

wherein the other symbols are the same as the above (6).

(8) The compound according to the above (6) or (7) or a pharmaceutically acceptable salt thereof, wherein $R^4$ is each independently halogen.

(9) The compound according to any one of the above (1) to (8) or a pharmaceutically acceptable salt thereof, wherein each $R^{13}$ is independently a hydrogen atom or substituted or unsubstituted alkyl.

(10) The compound according to any one of the above (1) to (9) or a pharmaceutically acceptable salt thereof, wherein (i) $A_1$ is $C(R^5)$, $A_2$ is $C(R^6)$, and $A_3$ is $C(R^7)$, (ii) $A_1$ is N, $A_2$ is $C(R^6)$, and $A_3$ is $C(R^7)$, (iii) $A_1$ is $C(R^5)$, $A_2$ is $C(R^6)$, and $A_3$ is N, or (iv) $A_1$ is N, $A_2$ is $C(R^6)$, and $A_3$ is N.

(11) The compound according to any one of the above (1) to (10) or a pharmaceutically acceptable salt thereof, wherein (i) $A_1$ is $C(R^5)$, $A_2$ is $C(R^6)$, and $A_3$ is $C(R^7)$, or (ii) $A_1$ is N, $A_2$ is $C(R^6)$, and $A_3$ is $C(R^7)$.

(12) The compound according to any one of the above (1) to (11) or a pharmaceutically acceptable salt thereof, wherein $R^5$, $R^6$, and $R^7$ are hydrogen atoms.

(13) The compound according to any one of the above (1) to (12) or a pharmaceutically acceptable salt thereof, wherein $R^1$ is carboxy.

(14) The compound according to any one of the above (1) to (13) or a pharmaceutically acceptable salt thereof, wherein $R^2$ is alkyl, alkyl substituted with substituted or unsubstituted non-aromatic heterocycle, or alkyl substituted with substituted or unsubstituted aromatic heterocycle.

(15) The compound according to any one of the above (1) to (14) or a pharmaceutically acceptable salt thereof, wherein $R^2$ is alkyl substituted with substituted or unsubstituted non-aromatic heterocycle, or alkyl substituted with substituted or unsubstituted aromatic heterocycle.

(16) The compound according to any one of the above (1) to (15) or a pharmaceutically acceptable salt thereof, wherein —X— is —$C(R^8)(R^9)$—.

(17) The compound according to any one of the above (1) to (16) or a pharmaceutically acceptable salt thereof, wherein $R^8$ and $R^9$ are hydrogen atoms.

(1') A compound represented by formula (I):

(I)

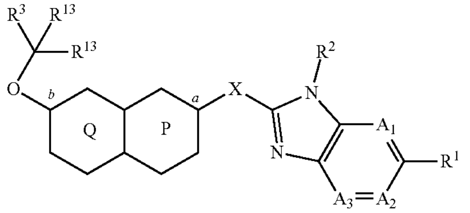

wherein $A_1$ is $C(R^5)$ or N, $A_2$ is $C(R^6)$ or N, $A_3$ is $C(R^7)$ or N, $R^5$, $R^6$, and $R^7$ are each independently a hydrogen atom, halogen, cyano, substituted or unsubstituted alkyl, or substituted or unsubstituted alkyloxy, $R^1$ is carboxy, an equivalent thereof, or $CH_2COOH$, $R^2$ is substituted or unsubstituted alkyl, or substituted or unsubstituted non-aromatic heterocyclyl, —X— is —$C(R^8)(R^9)$—, —O—, or —$N(R^{11})$—, $R^8$ and $R^9$ are each independently a hydrogen atom, halogen, or substituted or unsubstituted alkyl, $R^{11}$ is a hydrogen atom, or substituted or unsubstituted alkyl, the ring represented by:

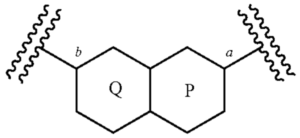

is a ring represented by:

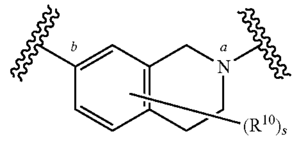

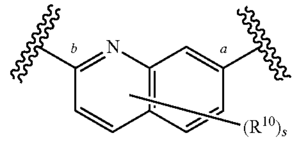

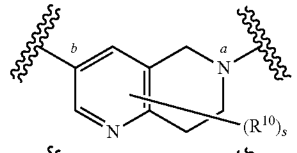

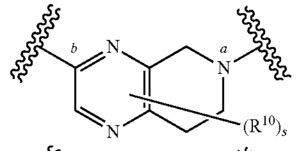

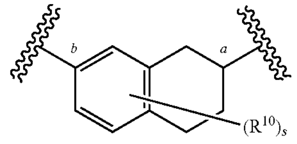

-continued
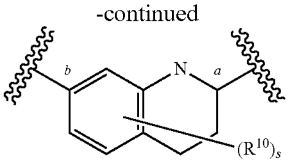
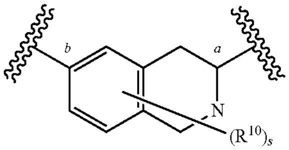
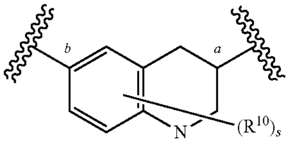
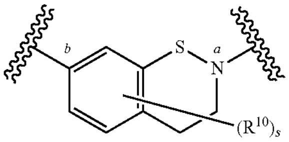
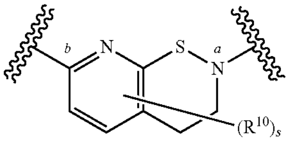
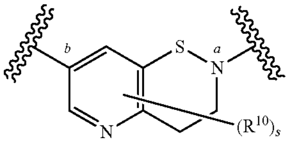
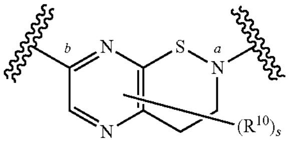
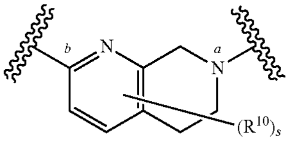
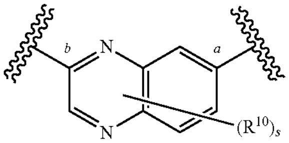
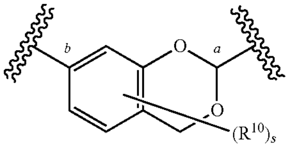
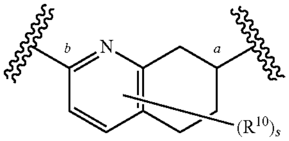
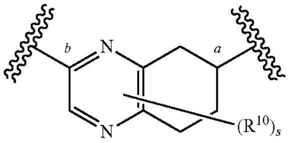
-continued
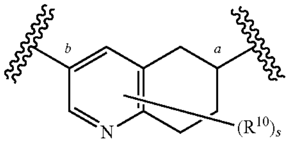
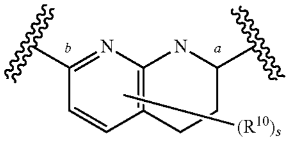
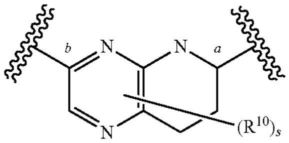
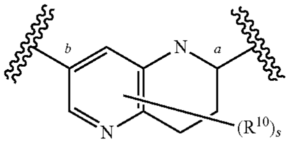
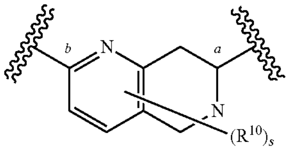
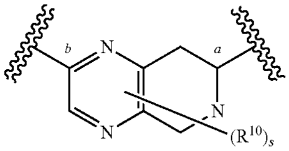
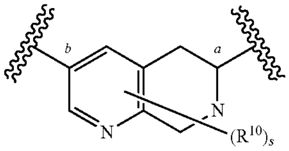
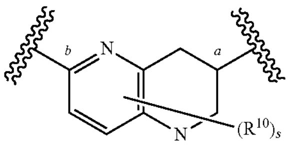
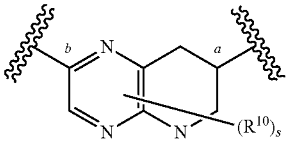
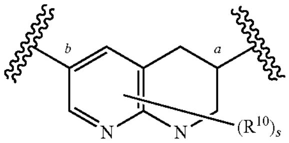
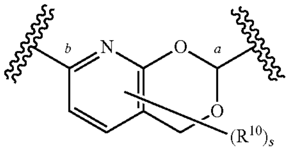

-continued
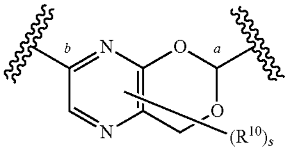
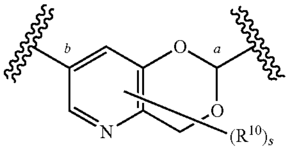
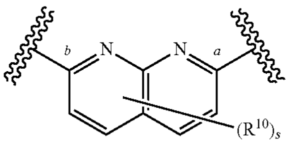
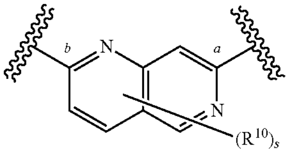
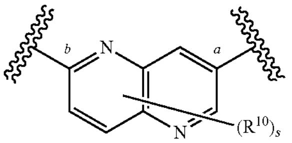
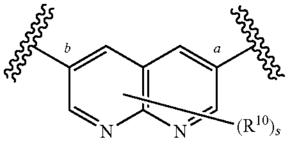
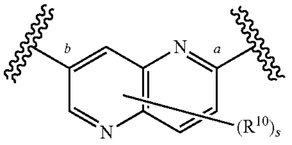
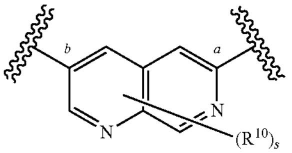
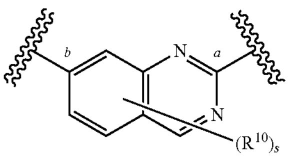
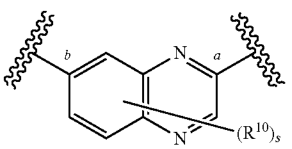
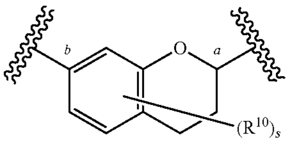
-continued
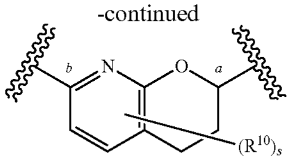
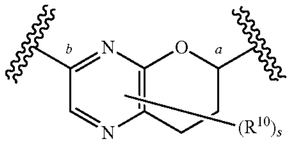
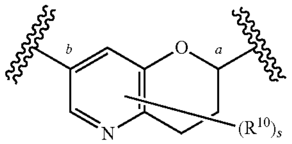
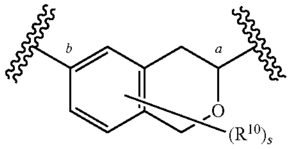
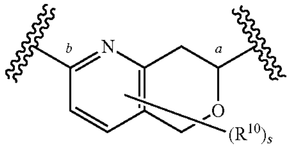
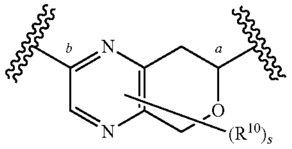
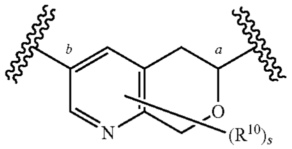
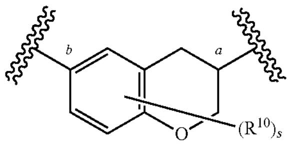
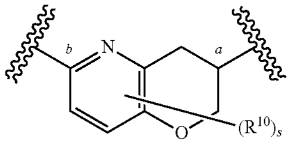
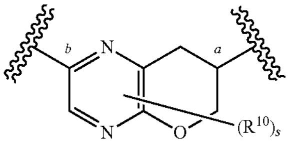
or
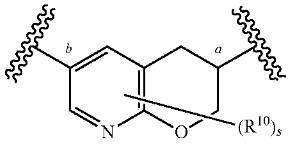
wherein
$R^{10}$ is each independently halogen, cyano, hydroxy, substituted or unsubstituted alkyl, oxo, substituted or unsubstituted non-aromatic carbocyclyl, or substituted or unsubstituted alkyloxy, and s is an integer of 0 to 9), $R^{13}$ is each independently a hydrogen atom, halogen, or substituted or unsubstituted alkyl, and $R^3$ is substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or a pharmaceutically acceptable salt thereof.

(1'-2) A compound represented by formula (II):

(II)

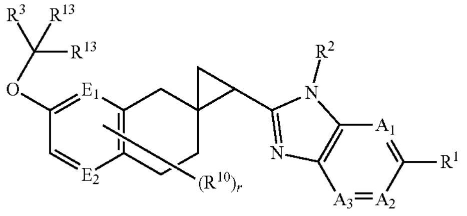

wherein $A_1$ is $C(R^5)$ or N, $A_2$ is $C(R^6)$ or N, $A_3$ is $C(R^7)$ or N, $R^5$, $R^6$, and $R^7$ are each independently a hydrogen atom, halogen, cyano, substituted or unsubstituted alkyl, or substituted or unsubstituted alkyloxy, $R^1$ is carboxy, an equivalent thereof, or $CH_2COOH$, $R^2$ is substituted or unsubstituted alkyl, or substituted or unsubstituted non-aromatic heterocyclyl, $R^{13}$ is each independently a hydrogen atom, halogen, or substituted or unsubstituted alkyl, $R^3$ is substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, $E_1$ is a carbon atom or a nitrogen atom, $E_2$ is a carbon atom or a nitrogen atom, $R^{10}$ is each independently halogen, cyano, hydroxy, substituted or unsubstituted alkyl, oxo, substituted or unsubstituted non-aromatic carbocyclyl, or substituted or unsubstituted alkyloxy, and r is an integer of 0 to 9, or a pharmaceutically acceptable salt thereof.

(2') The compound according to the above (1') or a pharmaceutically acceptable salt thereof, wherein s is an integer of 1 to 9.

(3') The compound according to the above (1') or a pharmaceutically acceptable salt thereof, wherein the ring represented by:

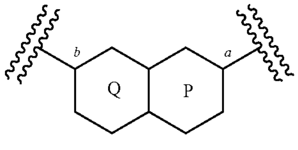

is a ring represented by:

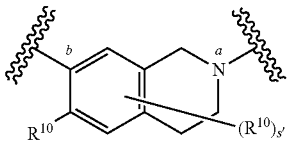

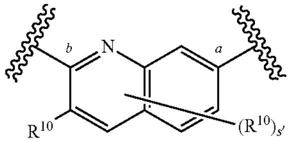

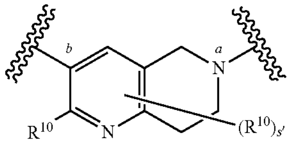

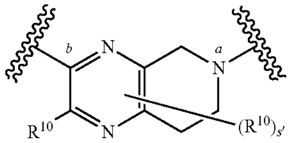

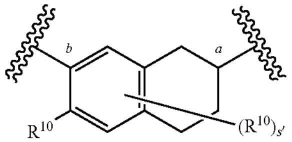

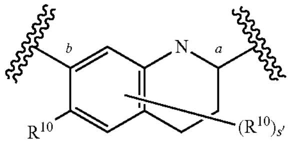

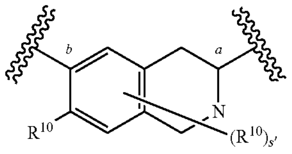

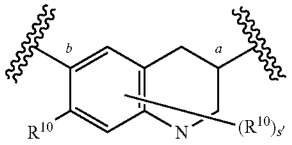

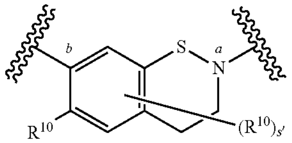

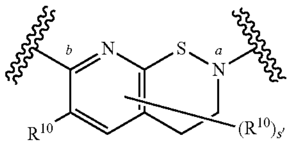

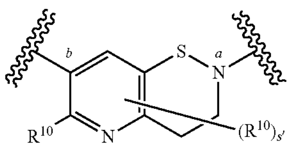

-continued
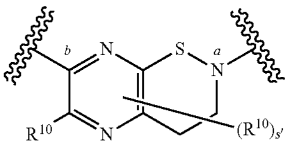
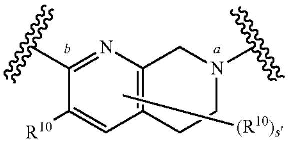
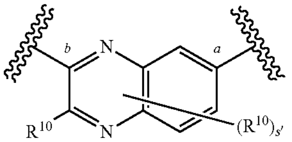
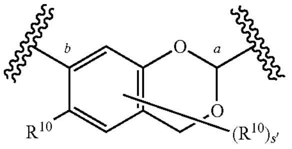
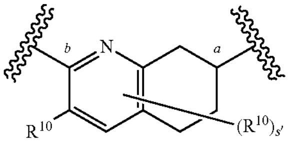
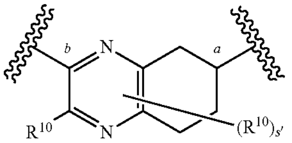
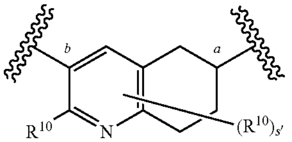
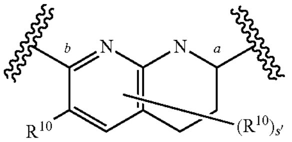
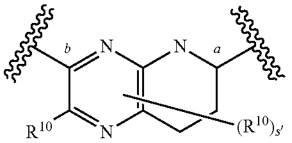
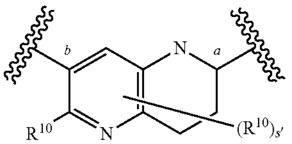
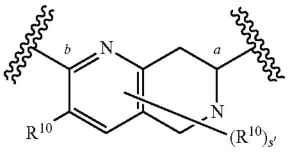
-continued
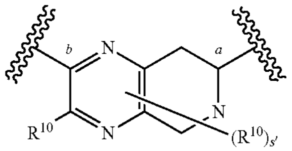
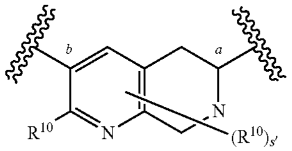
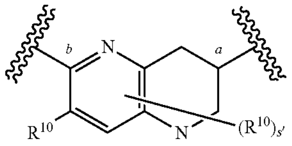
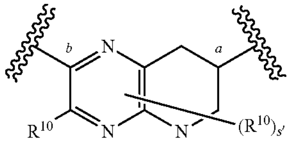
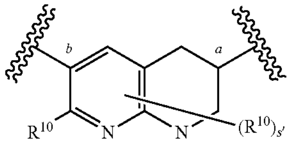
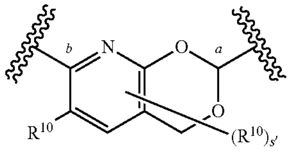
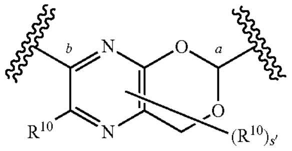
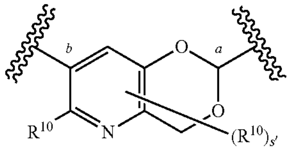
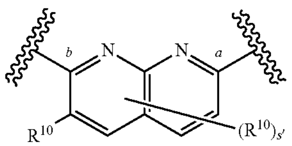
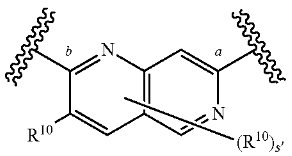
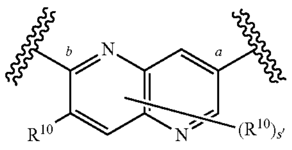

-continued
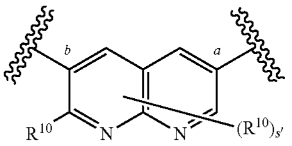
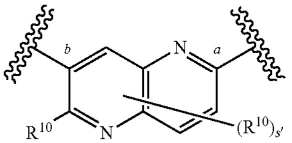
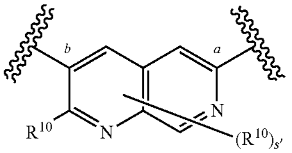
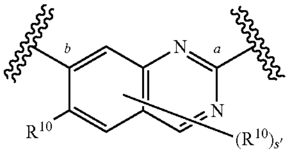
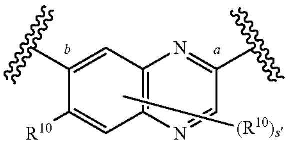
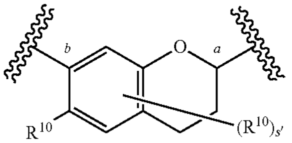
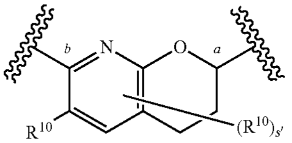
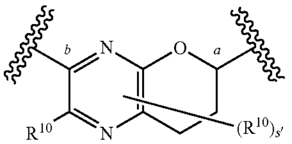
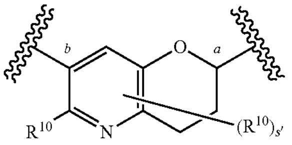
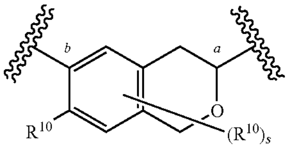
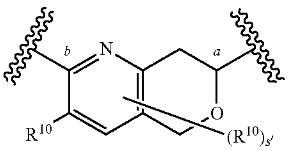
-continued
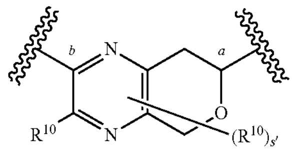
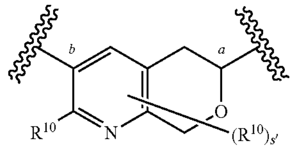
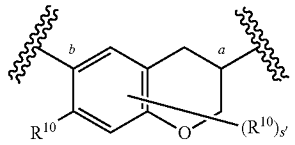
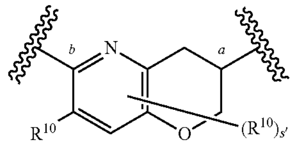
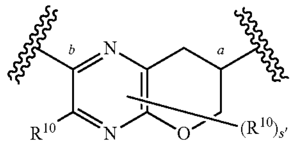
or
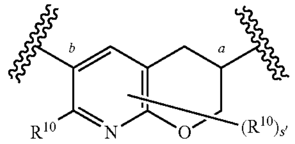
wherein s' is an integer of 0 to 8, and the other symbols are the same as those in the above (1').
(4') The compound according to the above (1') or a pharmaceutically acceptable salt thereof, wherein the ring represented by:
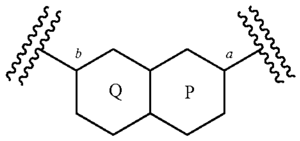
is a ring represented by:
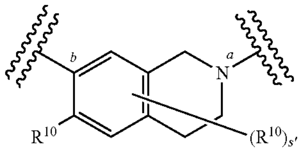
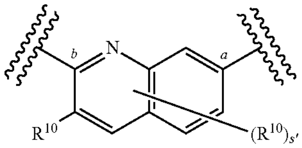

-continued

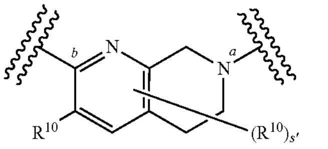

or

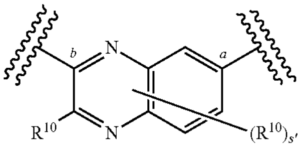

wherein s' is an integer of 0 to 8, and the other symbols are the same as those in the above item (1').

(5') The compound according to any of the above (1') to (4') and (1'-2) or a pharmaceutically acceptable salt thereof, wherein $R^{10}$ is each independently halogen, cyano, or substituted or unsubstituted alkyl.

(6') The compound according to any one of the above (1') to (5') and (1'-2) or a pharmaceutically acceptable salt thereof, wherein $R^3$ is a group represented by:

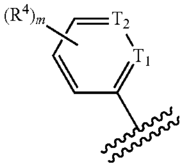

or

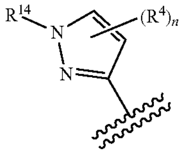

wherein $T_1$ is a carbon atom or a nitrogen atom, $T_2$ is a carbon atom or a nitrogen atom, $R^4$ is each independently halogen, cyano, substituted or unsubstituted alkyl, substituted or unsubstituted alkyloxy, substituted or unsubstituted aromatic carbocyclyl, substituted or unsubstituted non-aromatic carbocyclyl, or substituted or unsubstituted alkylsulfonyl, $R^{14}$ is a hydrogen atom, or substituted or unsubstituted alkyl, m is an integer of 0 to 5, and n is an integer of 0 to 2.

(7') The compound according to the above (6') or a pharmaceutically acceptable salt thereof, wherein $R^3$ is a group represented by:

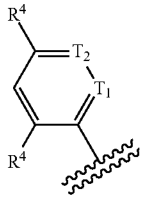

wherein $T_1$ is $C(R^{12})$ or N, $T_2$ is $C(R^{12})$ or N, $R^{12}$ is each independently a hydrogen atom, halogen, cyano, substituted or unsubstituted alkyl, substituted or unsubstituted alkyloxy, substituted or unsubstituted aromatic carbocyclyl, substituted or unsubstituted non-aromatic carbocyclyl, or substituted or unsubstituted alkylsulfonyl, and $R^4$ is the same as that in the above (6').

(8') The compound according to the above (6') or (7') or a pharmaceutically acceptable salt thereof, wherein $R^4$ is each independently halogen, and $R^{12}$ is each independently a hydrogen atom or halogen.

(9') The compound according to any one of the above (1') to (8') and (1'-2) or a pharmaceutically acceptable salt thereof, wherein $R^{13}$ is each independently a hydrogen atom or substituted or unsubstituted alkyl.

(10') The compound according to any one of the above (1') to (9') and (1'-2) or a pharmaceutically acceptable salt thereof, wherein (i) $A_1$ is $C(R^5)$, $A_2$ is $C(R^6)$, and $A_3$ is $C(R^7)$, (ii) $A_1$ is N, $A_2$ is $C(R^6)$, and $A_3$ is $C(R^7)$, (iii) $A_1$ is $C(R^5)$, $A_2$ is $C(R^6)$, and $A_3$ is N, or (iv) $A_1$ is N, $A_2$ is $C(R^6)$, and $A_3$ is N.

(11') The compound according to the above (10') or a pharmaceutically acceptable salt thereof, wherein (i) $A_1$ is $C(R^5)$, $A_2$ is $C(R^6)$, and $A_3$ is $C(R^7)$, or (ii) $A_1$ is N, $A_2$ is $C(R^6)$, and $A_3$ is $C(R^7)$.

(12') The compound according to the above (10') or (11') or a pharmaceutically acceptable salt thereof, wherein $R^6$ is halogen, and $R^5$ and $R^7$ are each independently a hydrogen atom or halogen.

(13') The compound according to any one of the above (1') to (12') and (1'-2) or a pharmaceutically acceptable salt thereof, wherein R' is carboxy.

(14') The compound according to any one of the above (1') to (13') and (1'-2) or a pharmaceutically acceptable salt thereof, wherein $R^2$ is alkyl, alkyl substituted with substituted or unsubstituted non-aromatic heterocycle, or alkyl substituted with substituted or unsubstituted aromatic heterocycle.

(15') The compound according to the above (14') or a pharmaceutically acceptable salt thereof, wherein $R^2$ is alkyl substituted with substituted or unsubstituted non-aromatic heterocycle, or alkyl substituted with substituted or unsubstituted aromatic heterocycle.

(16') The compound according to any one of the above (1') to (15') or a pharmaceutically acceptable salt thereof, wherein —X— is —$C(R^8)(R^9)$—.

(17') The compound according to the above (16') or a pharmaceutically acceptable salt thereof, wherein $R^8$ and $R^9$ are hydrogen atoms.

(1") A compound represented by formula (I):

(I)

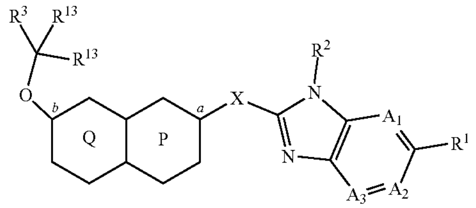

wherein $A_1$ is $C(R^5)$ or N, $A_2$ is $C(R^6)$ or N, $A_3$ is $C(R^7)$ or N, $R^5$, $R^6$, and $R^7$ are each independently a hydrogen atom, halogen, cyano, substituted or unsubstituted alkyl, substituted or unsubstituted alkyloxy, or substituted or unsubstituted non-aromatic carbocyclyl, $R^1$ is carboxy, an equivalent thereof, or $CH_2COOH$, $R^2$ is substituted or unsubstituted alkyl, or substituted or unsubstituted non-aromatic heterocyclyl, —X— is —C($R^8$)($R^9$)—, —O—, or —N($R^{11}$)—, $R^8$ and $R^9$ are each independently a hydrogen atom, halogen, or substituted or unsubstituted alkyl, $R^{11}$ is a hydrogen atom, or substituted or unsubstituted alkyl, the ring represented by:

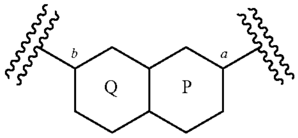

is a ring represented by:

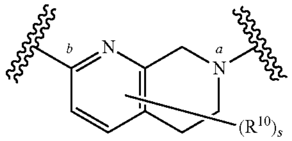

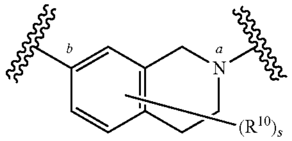

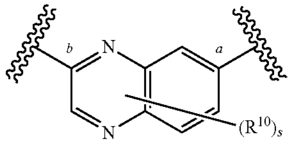

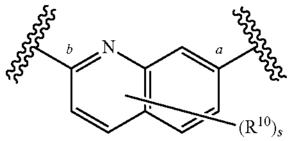

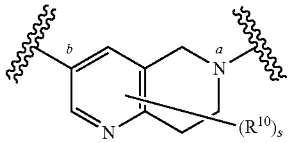

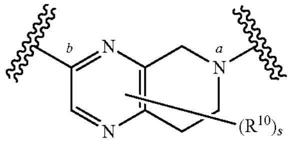

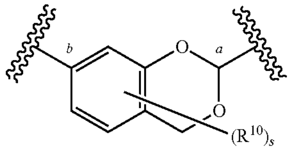

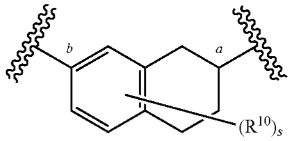

-continued

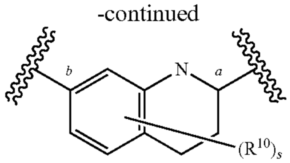

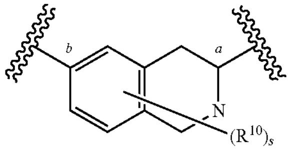

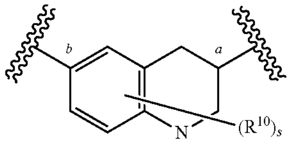

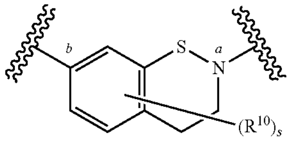

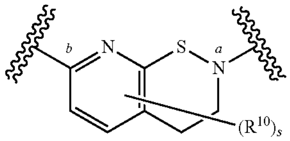

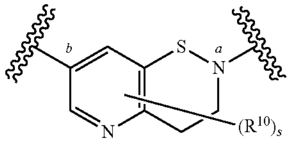

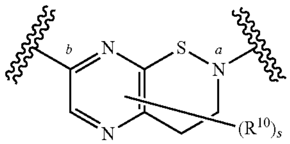

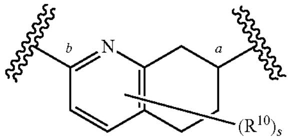

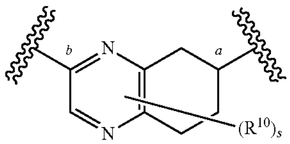

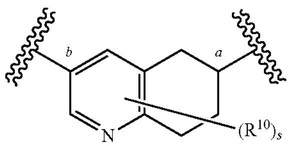

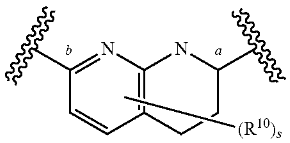

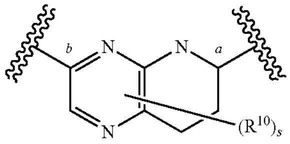

-continued
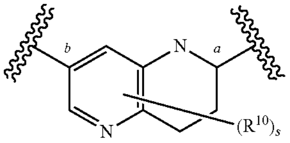
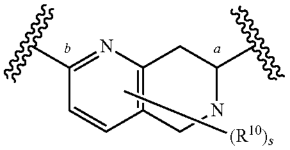
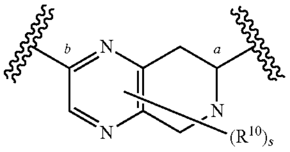
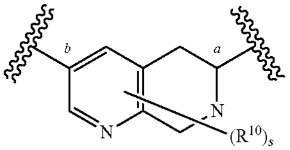
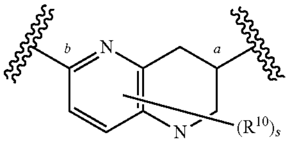
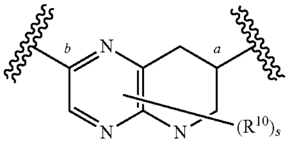
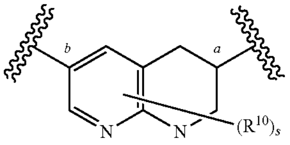
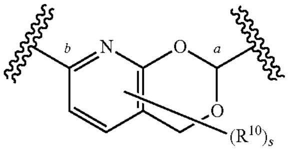
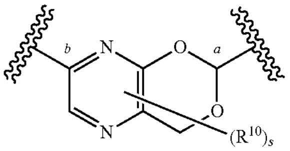
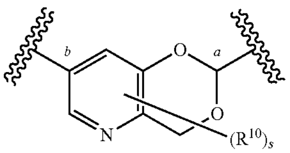
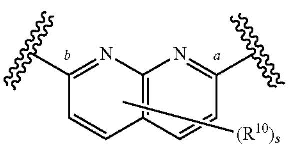
-continued
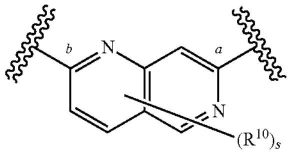
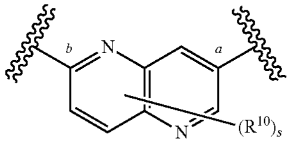
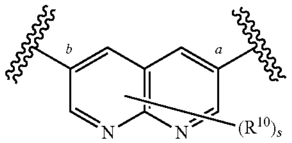
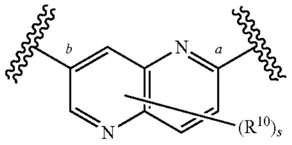
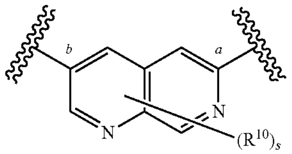
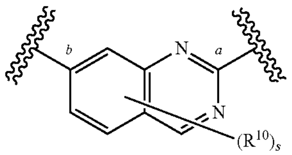
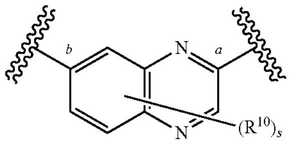
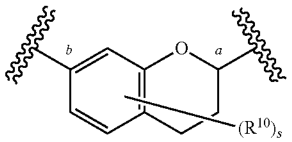
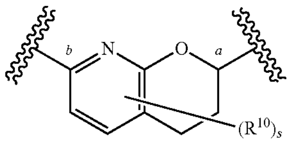
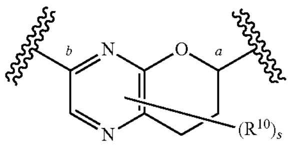
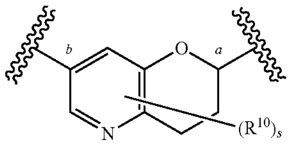

-continued

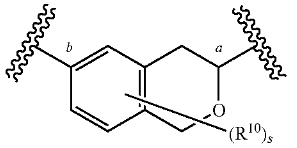

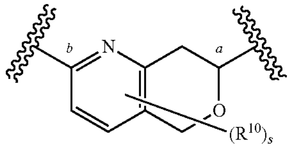

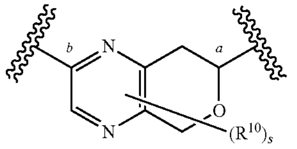

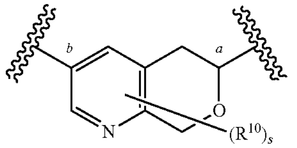

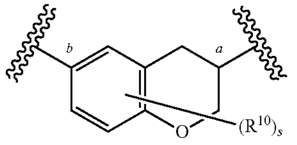

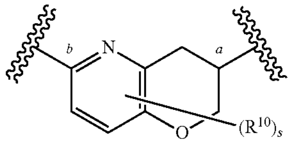

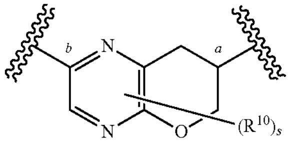

or

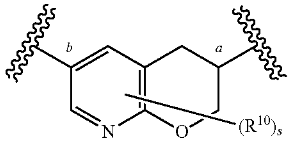

wherein $R^{10}$ is each independently halogen, cyano, hydroxy, substituted or unsubstituted alkyl, oxo, substituted or unsubstituted non-aromatic carbocyclyl, or substituted or unsubstituted alkyloxy, and s is an integer of 0 to 9, $R^{13}$ is each independently a hydrogen atom, halogen, or substituted or unsubstituted alkyl, $R^3$ is substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or a pharmaceutically acceptable salt thereof.

(2") A compound represented by formula (II):

(II)

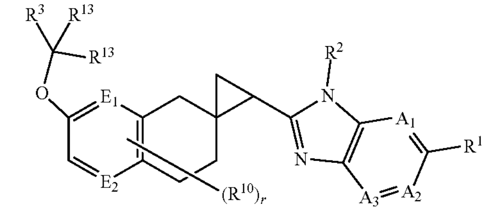

wherein $A_1$ is $C(R^5)$ or N, $A_2$ is $C(R^6)$ or N, $A_3$ is $C(R^7)$ or N, $R^5$, $R^6$, and $R^7$ are each independently a hydrogen atom, halogen, cyano, substituted or unsubstituted alkyl, substituted or unsubstituted alkyloxy, or substituted or unsubstituted non-aromatic carbocyclyl, $R^1$ is carboxy, an equivalent thereof, or $CH_2COOH$, $R^2$ is substituted or unsubstituted alkyl, or substituted or unsubstituted non-aromatic heterocyclyl, $R^{13}$ is each independently a hydrogen atom, halogen, or substituted or unsubstituted alkyl, $R^3$ is substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, $E_1$ is a carbon atom or a nitrogen atom, $E_2$ is a carbon atom or a nitrogen atom, $R^{10}$ is each independently halogen, cyano, hydroxy, substituted or unsubstituted alkyl, oxo, substituted or unsubstituted non-aromatic carbocyclyl, or substituted or unsubstituted alkyloxy, and r is an integer of 0 to 9, or a pharmaceutically acceptable salt thereof.

(3") The compound according to the above (1") or a pharmaceutically acceptable salt thereof, wherein s is an integer of 1 to 9.

(4") The compound according to the above (1") or a pharmaceutically acceptable salt thereof, wherein the ring represented by:

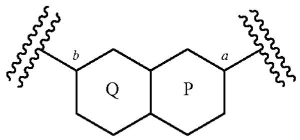

is a ring represented by:

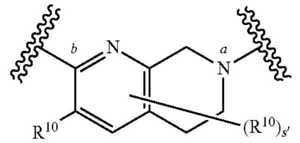

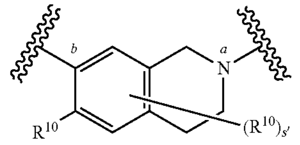

-continued
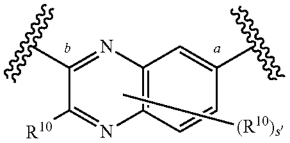
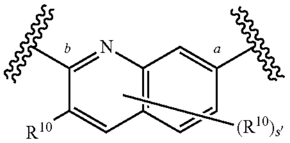
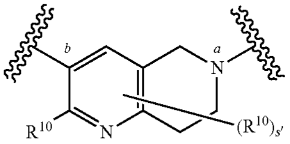
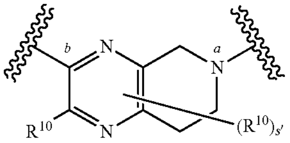
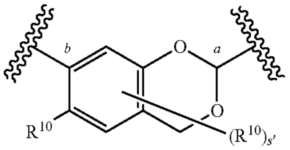
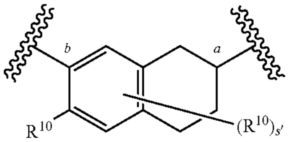
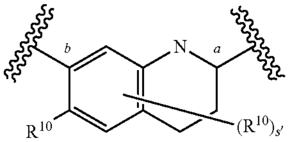
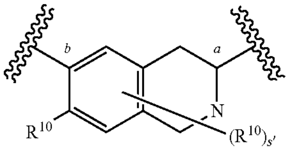
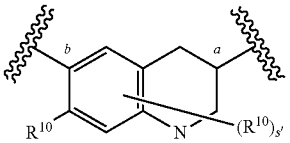
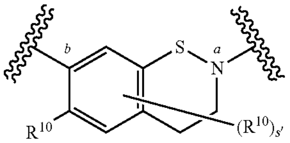
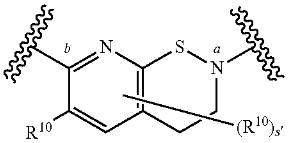
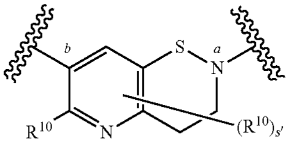
-continued
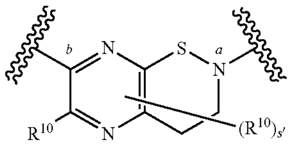
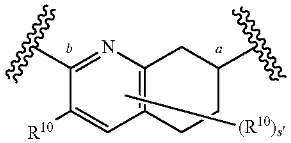
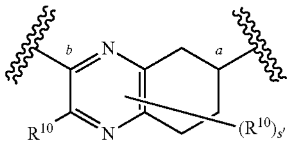
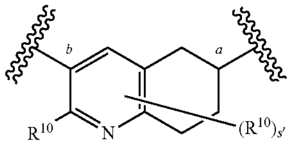
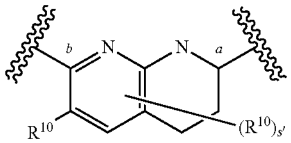
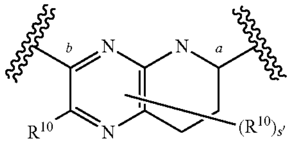
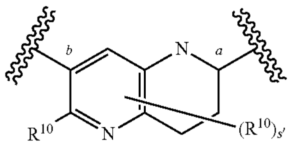
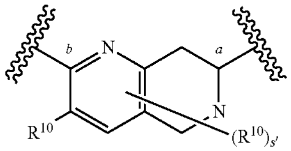
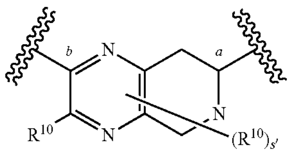
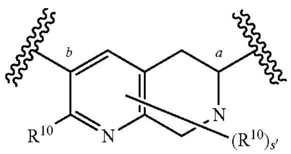
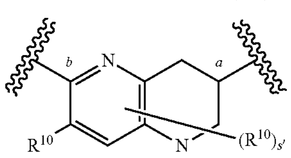

-continued
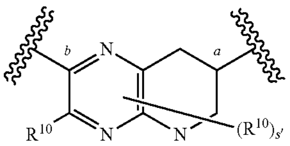
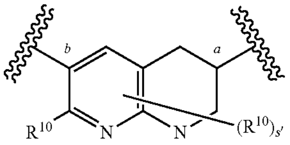
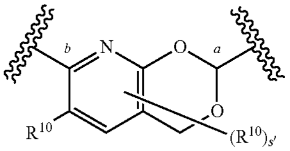
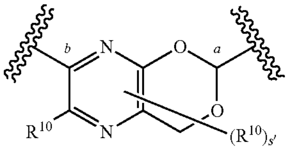
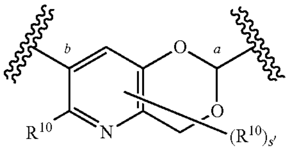
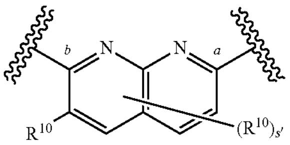
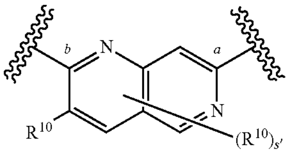
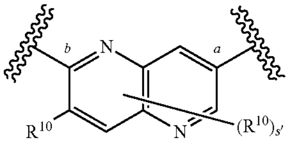
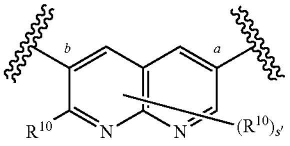
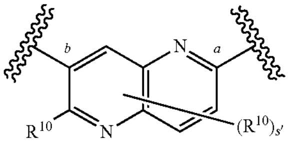
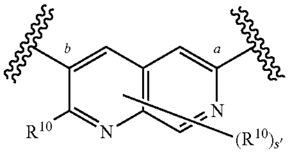
-continued
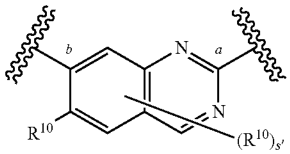
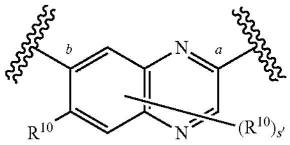
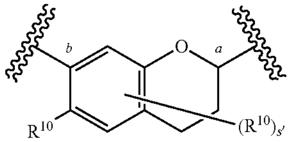
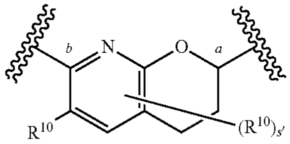
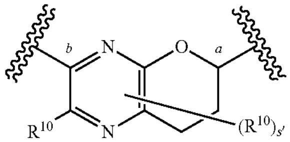
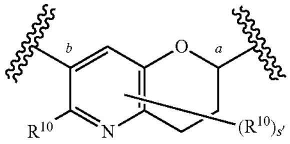
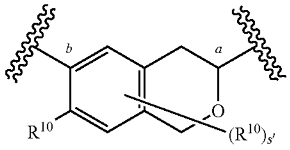
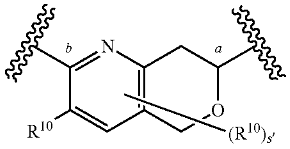
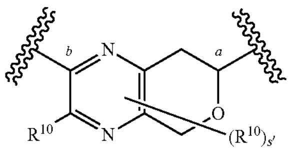
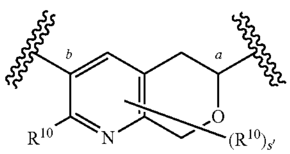
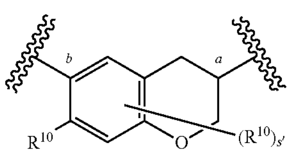

-continued

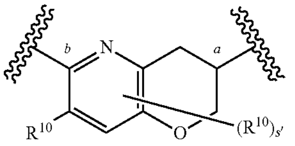

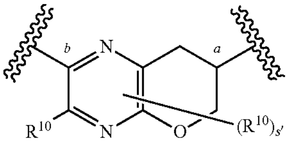

or

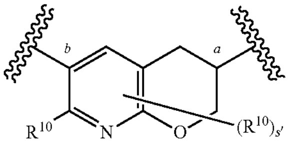

wherein s' is an integer of 0 to 8, and the other symbols are the same as those in the above (1").

(5") The compound according to the above (1") or a pharmaceutically acceptable salt thereof, wherein the ring represented by:

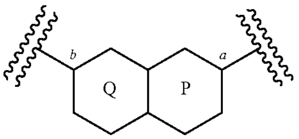

is a ring represented by:

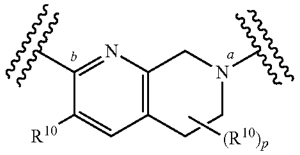

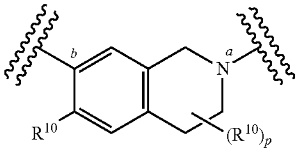

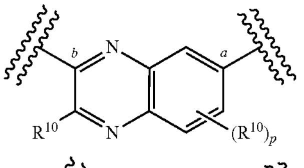

or

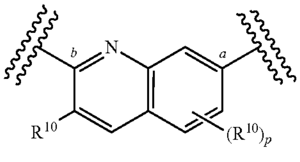

wherein p is an integer of 0 to 6, and the other symbols are the same as those in the above (1").

(5"-2) The compound according to the above (1") or a pharmaceutically acceptable salt thereof, wherein the ring represented by:

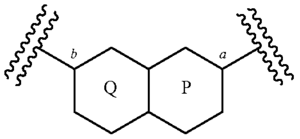

is a ring represented by:

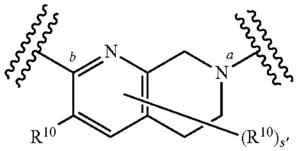

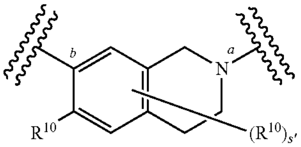

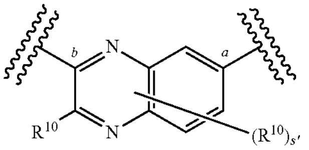

or

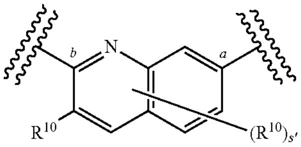

wherein s' is an integer of 0 to 8, and the other symbols are the same as those in the above (1").

(5"-3) The compound according to the above (1") or a pharmaceutically acceptable salt thereof, wherein the ring represented by:

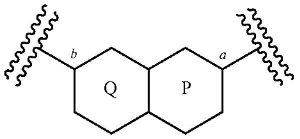

is a ring represented by:

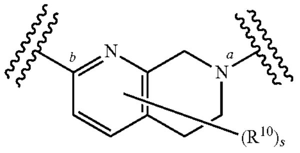

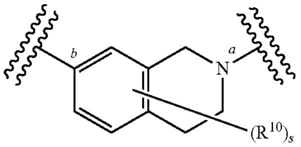

-continued

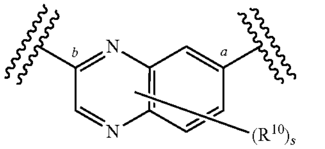

or

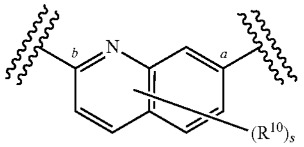

wherein s' is an integer of 1 to 9, and the other symbols are the same as those in the above (1").

(6") The compound according to any one of the above (1") to (5"), (5"-2), and (5"-3) or a pharmaceutically acceptable salt thereof, wherein $R^{10}$ is each independently halogen, cyano, or substituted or unsubstituted alkyl.

(7") The compound according to any one of the above (1") to (6"), (5"-2), and (5"-3) or a pharmaceutically acceptable salt thereof, wherein $R^3$ is a group represented by:

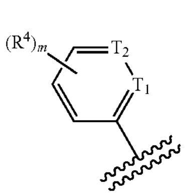

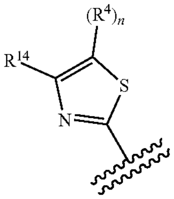

or

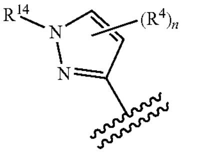

wherein $T_1$ is a carbon atom or a nitrogen atom, $T_2$ is a carbon atom or a nitrogen atom, $R^4$ is each independently halogen, cyano, substituted or unsubstituted alkyl, substituted or unsubstituted alkyloxy, substituted or unsubstituted aromatic carbocyclyl, substituted or unsubstituted non-aromatic carbocyclyl, or substituted or unsubstituted alkylsulfonyl, $R^{14}$ is a hydrogen atom, or substituted or unsubstituted alkyl, m is an integer of 0 to 5, and n is an integer of 0 to 2.

(8") The compound according to the above (7") or a pharmaceutically acceptable salt thereof, wherein $R^3$ is a group represented by:

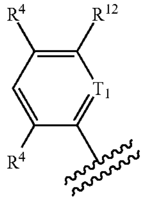

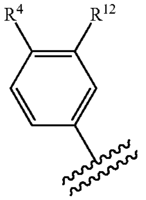

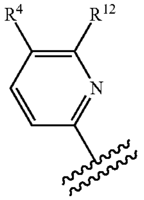

or

-continued

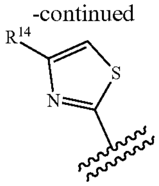

wherein $T_1$ is $C(R^{12})$ or N, $R^{12}$ is each independently a hydrogen atom, halogen, cyano, substituted or unsubstituted alkyl, substituted or unsubstituted alkyloxy, substituted or unsubstituted aromatic carbocyclyl, substituted or unsubstituted non-aromatic carbocyclyl, or substituted or unsubstituted alkylsulfonyl, and $R^4$ and $R^{14}$ are the same as those in the above (7").

(9") The compound according to the above (8") or a pharmaceutically acceptable salt thereof, wherein $R^3$ is a group represented by:

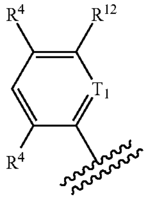

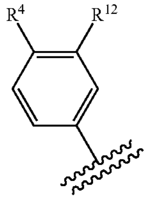

or

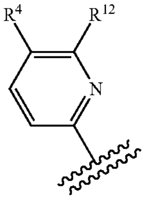

wherein $T_1$ is $C(R^{12})$ or N, $R^{12}$ is each independently a hydrogen atom or halogen, $R^4$ is each independently halogen, cyano, substituted or unsubstituted alkyl, substituted or unsubstituted alkyloxy, or substituted or unsubstituted non-aromatic carbocyclyl.

(10") The compound according to any one of the above (7") to (9") or a pharmaceutically acceptable salt thereof, wherein $R^4$ is each independently halogen, and $R^{12}$ is each independently a hydrogen atom or halogen.

(11") The compound according to any one of the above (1") to (10"), (5"-2) and (5"-3) or a pharmaceutically acceptable salt thereof, wherein $R^{13}$ is each independently a hydrogen atom or substituted or unsubstituted alkyl.

(12") The compound according to any one of the above (1") to (11"), (5"-2) and (5"-3) or a pharmaceutically acceptable salt thereof, wherein (i) $A_1$ is $C(R^5)$, $A_2$ is $C(R^6)$, and $A_3$ is $C(R^7)$, (ii) $A_1$ is N, $A_2$ is $C(R^6)$, and $A_3$ is $C(R^7)$, (iii) $A_1$ is $C(R^5)$, $A_2$ is $C(R^6)$, and $A_3$ is N, or (iv) $A_1$ is N, $A_2$ is $C(R^6)$, and $A_3$ is N.

(13") The compound according to the above (12") or a pharmaceutically acceptable salt thereof, wherein (i) $A_1$ is $C(R^5)$, $A_2$ is $C(R^6)$, and $A_3$ is $C(R^7)$, or (ii) $A_1$ is N, $A_2$ is $C(R^6)$, and $A_3$ is $C(R^7)$.

(14") The compound according to the above (12") or (13") or a pharmaceutically acceptable salt thereof, wherein $R^5$ is a hydrogen atom or halogen, $R^6$ is a hydrogen atom, and $R^7$ is a hydrogen atom, halogen, or substituted or unsubstituted alkyloxy.

(15") The compound according to any one of the above (1") to (14"), (5"-2) and (5"-3) or a pharmaceutically acceptable salt thereof, wherein $R^1$ is carboxy.

(16") The compound according to any one of the above (1") to (15"), (5"-2) and (5"-3) or a pharmaceutically acceptable salt thereof, wherein $R^2$ is alkyl, alkyl substituted with substituted or unsubstituted non-aromatic heterocycle, or alkyl substituted with substituted or unsubstituted aromatic heterocycle.

(17") The compound according to the above (16") or a pharmaceutically acceptable salt thereof, wherein $R^2$ is alkyl substituted with substituted or unsubstituted non-aromatic heterocycle, or alkyl substituted with substituted or unsubstituted aromatic heterocycle.

(18") The compound according to any one of the above (1"), (3") to (17"), (5"-2) and (5"-3) or a pharmaceutically acceptable salt thereof, wherein —X— is —$C(R^8)(R^9)$—.

(19") The compound according to the above (18") or a pharmaceutically acceptable salt thereof, wherein $R^8$ and $R^9$ are hydrogen atoms.

(20") The compound according to the above (1") or a pharmaceutically acceptable salt thereof, wherein the compound is selected from the group consisting of I-035, I-145, I-160, I-218, I-223, I-239, I-242, I-243, I-244, I-245, I-246, I-247, I-249, I-250, I-254, I-255, I-257, I-258, I-259, I-273 and I-274.

(18) A pharmaceutical composition comprising the compound according to any one of the above (1) to (17), (1') to (17'), (1'2), (1") to (20"), (5"-2) and (5"-3) or a pharmaceutically acceptable salt thereof.

(19) The pharmaceutical composition according to (18), which is a GLP-1 receptor agonist.

(20) A method for treating and/or preventing a disease associated with GLP-1 receptor, comprising administering the compound according to any one of the above (1) to (17), (1') to (17'), (1'2), (1") to (20"), (5"-2) and (5"-3) or a pharmaceutically acceptable salt thereof.

(21) Use of the compound according to any one of the above (1) to (17), (1') to (17'), (1'-2), (1") to (20"), (5"-2) and (5"-3), or a pharmaceutically acceptable salt thereof, for the manufacture of a medicament for treating and/or preventing a disease associated with GLP-1 receptor.

(22) The compound according to any one of the above (1) to (17), (1') to (17'), (1'-2), (1") to (20"), (5"-2) and (5"-3), or a pharmaceutically acceptable salt thereof, for use in treating and/or preventing a disease associated with GLP-1 receptor.

Effect of the Invention

The compound of the present invention has GLP-1 receptor agonist effect, and is useful as a prophylactic and/or therapeutic agent for diseases associated with GLP-1 receptor, particularly non-insulin-dependent diabetes mellitus, such as type 2 diabetes mellitus or obesity.

MODE FOR CARRYING OUT THE INVENTION

Terms used in this description are explained below. Each term, unless otherwise indicated, has the same meaning when it is used alone or together with other terms.

The term of "consisting of" means having only components.

The term of "comprising" means not restricting with components and not excluding undescribed factors.

Hereinafter, the present invention will be described while showing exemplary embodiments. Throughout the present specification, it should be understood that, unless particularly stated otherwise, an expression of a singular form also includes the concept of a plural form thereof. Therefore, it should be understood that, unless particularly stated otherwise, an article for a singular form (for example, in the case of English, "a", "an", "the", or the like) also includes the concept of a plural form thereof. Furthermore, it should be understood that, unless particularly stated otherwise, the terms used in the present specification are used in the meanings normally used in the above-described art. Accordingly, unless otherwise defined, all terminologies and scientific and technical terms used in the present specification have the same meanings as commonly understood by those having ordinary skill in the art to which the present invention belongs. In a case of contradiction, priority is given to the present specification including definitions.

"Halogen" includes a fluorine atom, a chlorine atom, a bromine atom and an iodine atom. Particularly, a fluorine atom and a chlorine atom are preferred.

"Alkyl" includes a C1 to C15, preferably C1 to C10, more preferably C1 to C6 and further preferably C1 to C4 linear or branched hydrocarbon group. Examples include methyl, ethyl, n-propyl, isopropyl, n-butyl, isobutyl, sec-butyl, tert-butyl, n-pentyl, isopentyl, neopentyl, n-hexyl, isohexyl, n-heptyl, isoheptyl, n-octyl, isooctyl, n-nonyl and n-decyl.

Preferred embodiments of "alkyl" include methyl, ethyl, n-propyl, isopropyl, n-butyl, isobutyl, sec-butyl, tert-butyl and n-pentyl. More preferred embodiments include methyl, ethyl, n-propyl, isopropyl and tert-butyl.

"Alkenyl" includes a C2 to C15, preferably a C2 to C10, more preferably a C2 to C6 and further preferably a C2 to C4 linear or branched hydrocarbon group having one or more double bond(s) at any position(s). Examples include vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl and pentadecenyl.

Preferred embodiments of "alkenyl" include vinyl, allyl, propenyl, isopropenyl and butenyl.

"Alkynyl" includes a C2 to C10, preferably a C2 to C8, more preferably a C2 to C6 and further preferably a C2 to C4 linear or branched hydrocarbon group having one or more triple bond(s) at any position(s). Alkynyl may further have double bond(s) at any position(s). Examples include ethynyl, propynyl, butynyl, pentynyl, hexynyl, heptynyl, octynyl, nonynyl and decynyl.

Preferred embodiments of "alkynyl" include ethynyl, propynyl, butynyl and pentynyl.

"Aromatic carbocyclyl" means a cyclic aromatic hydrocarbon group having a single ring or two or more rings. Examples include phenyl, naphthyl, anthryl and phenanthryl.

Preferred embodiments of the "aromatic carbocyclyl" include phenyl.

"Aromatic carbocycle" means a ring derived from the above "aromatic carbocyclyl".

Preferred embodiment of "aromatic carbocycle" include a benzene ring.

"Non-aromatic carbocyclyl" means a cyclic saturated hydrocarbon group or a cyclic non-aromatic unsaturated hydrocarbon group, both having a single ring or two or more rings. A "non-aromatic carbocyclyl" having two or more rings also includes a fused ring group wherein a non-aromatic carbocyclyl having two or more rings is fused with a ring of the above "aromatic carbocyclyl", and the linking bond may be carried by any of the rings.

Examples include rings as follows.

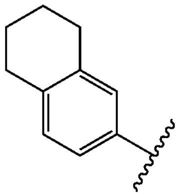

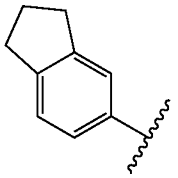

Furthermore, the "non-aromatic carbocyclyl" also includes a group having a bridged group or a group forming a spiro ring, such as follows.

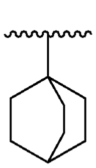

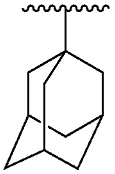

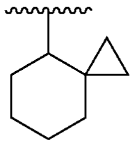

A non-aromatic carbocyclyl having a single ring is preferably C3 to C16, more preferably C3 to C12 and further preferably C4 to C8 non-aromatic carbocyclyl. Examples include cyclopropyl, cyclobutyl, cyclopentyl, cyclohexyl, cycloheptyl, cyclooctyl, cyclononyl, cyclodecyl, cyclopropenyl, cyclobutenyl, cyclopentenyl, cyclohexenyl, cycloheptenyl and cyclohexadienyl.

The non-aromatic carbocyclyl which is polycyclic having two or more rings preferably includes C8 to C20, more preferably C8 to C16 non-aromatic carbocyclyl. Examples include indanyl, indenyl, acenaphthyl, tetrahydronaphthyl and fluorenyl.

"Non-aromatic carbocycle" means a ring derived from the above "non-aromatic carbocyclyl".

"Aromatic heterocyclyl" means an aromatic cyclyl having a single ring or two or more rings, which has one or more identical or different heteroatoms optionally selected from O, S, and N in the ring(s).

An aromatic heterocyclyl having two or more rings also includes a fused ring group wherein an aromatic heterocyclyl having a single ring or two or more rings is fused with a ring of the above "aromatic carbocyclyl", and the linking bond may be carried by any of the rings.

The aromatic heterocyclyl having a single ring is preferably a 5- to 8-membered ring, and more preferably a 5-membered or 6-membered ring. Examples of 5-membered aromatic heterocyclyl include pyrrolyl, imidazolyl, pyrazolyl, triazolyl, tetrazolyl, furyl, thienyl, isoxazolyl, oxazolyl, oxadiazolyl, isothiazolyl, thiazolyl and thiadiazolyl. Examples of 6-membered aromatic heterocyclyl include pyridyl, pyridazinyl, pyrimidinyl, pyrazinyl and triazinyl. The aromatic heterocyclyl having two rings is preferably an 8- to 10-membered ring, and more preferably a 9-membered or 10-membered ring. Examples thereof include indolyl, isoindolyl, indazolyl, indolizinyl, quinolinyl, isoquinolinyl, cinnolinyl, phthalazinyl, quinazolinyl, naphthyridinyl, quinoxalinyl, purinyl, pteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, oxazolopyridyl and thiazolopyridyl.

The aromatic heterocyclyl having three or more rings is preferably a 13- to 15-membered group. Examples include carbazolyl, acridinyl, xanthenyl, phenothiazinyl, phenoxathiinyl, phenoxazinyl and dibenzofuryl.

"Aromatic heterocycle" means a ring derived from the above "aromatic heterocyclyl".

The aromatic heterocycle having a single ring is preferably a 5- to 8-membered ring and more preferably a 5-membered or 6-membered ring. Examples of the 5-membered aromatic heterocycle include a pyrroline ring, an imidazoline ring, a pyrazoline ring, a triazole ring, a tetrazole ring, a furan ring, a thiophen ring, an isoxazole ring, an oxazole ring, an oxadiazole ring, an isothiazole ring, a thiazole ring and a thiadiazole ring. Examples of 6-membered aromatic heterocycle include a pyridine ring, a pyridazine ring, a pyrimidine ring, a pyrazine ring and a triazine ring.

The aromatic heterocyclyl having two rings is preferably an 8- to 10-membered ring, and more preferably a 9-membered or 10-membered ring. Examples include an indole ring, an isoindole ring, an indazole ring, an indolizine ring, a quinoline ring, an isoquinoline ring, a cinnoline ring, a phthalazine ring, a quinazoline ring, a naphthyridine ring, a quinoxaline ring, a purine ring, a pteridine ring, a benzimidazole ring, a benzisoxazole ring, a benzoxazole ring, a benzoxadiazole ring, a benzisothiazole ring, a benzothiazole ring, a benzothiadiazole ring, a benzofuran ring, an isobenzofuran ring, a benzothiophene ring, a benzotriazole ring, an imidazopyridine ring, a triazolopyridine ring, an imidazothiazole ring, a pyrazinopyridazine ring, an oxazolopyridine ring and a thiazolopyridine ring.

An aromatic heterocycle having three or more rings is preferably a 13- to 15-membered group. Examples include a carbazole ring, an acridine ring, a xanthene ring, a phenothiazine ring, a phenoxathiin ring, a phenoxazine ring and a dibenzofuran ring.

"Non-aromatic heterocyclyl" means a non-aromatic cyclyl having a single ring or two or more rings, which has one or more identical or different heteroatoms optionally selected from O, S, and N in the ring(s). A non-aromatic heterocyclyl having two or more rings also includes a fused ring group wherein a non-aromatic heterocyclyl having a single ring or two or more rings is fused with a ring in each of the above "aromatic carbocyclyl", "non-aromatic carbocyclyl" and/or "aromatic heterocyclyl", as well as a non-aromatic carbocyclyl having a single ring or two or more rings is fused with a ring in the above "aromatic heterocyclyl", and the linking bond may be carried by any of the rings.

Furthermore, the "non-aromatic heterocyclyl" also includes a group having a bridged group or a group forming a spiro ring, such as follows.

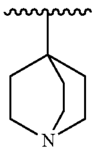

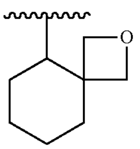

The non-aromatic heterocyclyl having a single ring is preferably a 3- to 8-membered and more preferably a 4- to 6-membered ring.

Examples of the 3-membered non-aromatic heterocyclyl include thiiranyl, oxiranyl and aziridinyl. Examples of 4-membered non-aromatic heterocyclyl include oxetanyl and azetidinyl. Examples of 5-membered non-aromatic heterocyclyl include oxathiolanyl, thiazolidinyl, pyrrolidinyl, pyrrolinyl, imidazolidinyl, imidazolinyl, pyrazolidinyl, pyrazolinyl, tetrahydrofuryl, dihydrothiazolyl, tetrahydroisothiazolyl, dioxolanyl, dioxolyl and thiolanyl. Examples of 6-membered non-aromatic heterocyclyl include dioxanyl, thianyl, piperidyl, piperazinyl, morpholinyl, morpholino, thiomorpholinyl, thiomorpholino, dihydropyridyl, tetrahydropyridyl, tetrahydropyranyl, dihydroxazinyl, tetrahydropyridazinyl, hexahydropyrimidinyl, dioxazinyl, thiinyl and thiazinyl. Examples of the 7-membered non-aromatic heterocyclyl include hexahydroazepinyl, tetrahydrodiazepinyl and oxepanyl.

The non-aromatic heterocyclyl having two or more rings is preferably a 8- to 20-membered group, and more preferably a 8- to 10-membered group. Examples include indolinyl, isoindolinyl, chromanyl and isochromanyl.

"Non-aromatic heterocycle" means a ring derived from the above "non-aromatic heterocyclyl".

The alkyl moiety of "alkyloxy", "haloalkyloxy", "alkylcarbonyloxy", "alkylcarbonyl", "alkyloxycarbonyl", "alkylsulfanyl", "alkylsulfinyl", "alkylsulfonyl", "alkyloxyalkyloxy", and "alkyloxyalkyl" have the same meanings as the aforementioned "alkyl".

The alkenyl moiety of "alkenyloxy", "alkenylcarbonyloxy", "alkenylcarbonyl", "alkenyloxycarbonyl", "alkenylsulfanyl", "alkenylsulfinyl", and "alkenylsulfonyl" have the same meanings as the aforementioned"alkenyl".

The alkynyl moiety of "alkynyloxy", "alkynylcarbonyloxy", "alkynylcarbonyl", "alkynyloxycarbonyl", "alkynylsulfanyl", "alkynylsulfinyl", and "alkynylsulfonyl" is synonymous with the aforementioned"alkynyl".

Examples of "an equivalent thereof" in "carboxy or an equivalent thereof" include:

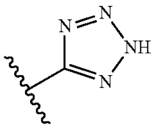
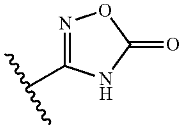
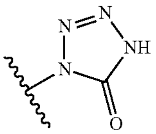
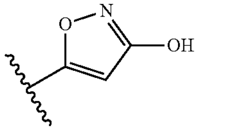
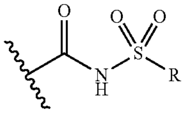

or

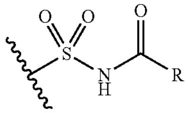

wherein R is substituted or unsubstituted alkyl, substituted or unsubstituted amine, substituted or unsubstituted non-aromatic carbocyclyl, substituted or unsubstituted aromatic carbocyclyl, substituted or unsubstituted non-aromatic heterocyclyl, or substituted or unsubstituted aromatic heterocyclyl.

In the present specification, the phrase "optionally substituted with substituent group A" means that "optionally substituted with one or more group(s) selected from substituent group A". The same applies to substituent groups B, C, α, ß, γ, γ', and the like.

Substituents for "substituted alkyl", "substituted alkenyl", "substituted alkynyl", "substituted alkyloxy", "substituted alkenyloxy", "substituted alkynyloxy", "substituted alkylcarbonyloxy", "substituted alkenylcarbonyloxy", "substituted alkynylcarbonyloxy", "substituted alkylcarbonyl", "substituted alkenylcarbonyl", "substituted alkynylcarbonyl", "substituted alkyloxycarbonyl", "substituted alkenyloxycarbonyl", "substituted alkynyloxycarbonyl", "substituted alkylsulfanyl", "substituted alkenylsulfanyl", "substituted alkynylsulfanyl", "substituted alkylsulfinyl", "substituted alkenylsulfinyl", "substituted alkynylsulfinyl", "substituted alkylsulfonyl", "substituted alkenylsulfonyl", "substituted alkynylsulfonyl" and the like include the following substituent group A. A carbon atom at any position may be bonded to one or more group(s) selected from the following substituent group A.

Substituent group A: halogen, hydroxy, carboxy, formyl, formyloxy, sulfanyl, sulfino, sulfo, thioformyl, thiocarboxy, dithiocarboxy, thiocarbamoyl, cyano, nitro, nitroso, azide, hydrazino, ureido, amidino, guanidino, pentafluorothio, trialkylsilyl, alkyloxy optionally substituted with substituent group α, alkenyloxy optionally substituted with substituent group α, alkynyloxy optionally substituted with substituent group α, alkylcarbonyloxy optionally substituted with substituent group α, alkenylcarbonyloxy optionally substituted with substituent group α, alkynylcarbonyloxy optionally substituted with substituent group α, alkylcarbonyl optionally substituted with substituent group α, alkenylcarbonyl optionally substituted with substituent group α, alkynylcarbonyl optionally substituted with substituent group α, alkyloxycarbonyl optionally substituted with substituent group α, alkenyloxycarbonyl optionally substituted with substituent group α, alkynyloxycarbonyl optionally substituted with substituent group α, alkylsulfanyl optionally substituted with substituent group α, alkenylsulfanyl optionally substituted with substituent group α, alkynylsulfanyl optionally substituted with substituent group α, alkylsulfinyl optionally substituted with substituent group α, alkenylsulfinyl optionally substituted with substituent group α, alkynylsulfinyl optionally substituted with substituent group α, alkylsulfonyl optionally substituted with substituent group α, alkenylsulfonyl optionally substituted with substituent group α, alkynylsulfonyl optionally substituted with substituent group α, amino optionally substituted with substituent group ß, imino optionally substituted with substituent group ß, carbamoyl optionally substituted with substituent group ß, sulfamoyl optionally substituted with substituent group ß, aromatic carbocyclyl optionally substituted with substituent group γ, non-aromatic carbocyclyl optionally substituted with substituent group γ', aromatic heterocyclyl optionally substituted with substituent group γ, non-aromatic heterocyclyl optionally substituted with substituent group γ', aromatic carbocyclyloxy optionally substituted with substituent group γ, non-aromatic carbocyclyloxy optionally substituted with substituent group γ', aromatic heterocyclyloxy optionally substituted with substituent group γ, non-aromatic heterocyclyloxy optionally substituted with substituent group γ', aromatic carbocyclylcarbonyloxy optionally substituted with substituent group γ, non-aromatic carbocyclylcarbonyloxy optionally substituted with substituent group γ', aromatic heterocyclylcarbonyloxy optionally substituted with substituent group γ, non-aromatic heterocyclylcarbonyloxy optionally substituted with substituent group γ', aromatic carbocyclylcarbonyl optionally substituted with substituent group γ, non-aromatic carbocyclylcarbonyl optionally substituted with substituent group γ', aromatic heterocyclylcarbonyl optionally substituted with substituent group γ, non-aromatic heterocyclylcarbonyl optionally substituted with substituent group γ', aromatic carbocyclyloxycarbonyl optionally substituted with substituent group γ, non-aromatic carbocyclyloxycarbonyl optionally substituted with substituent group γ', aromatic heterocyclyloxycarbonyl optionally substituted with substituent group γ, non-aromatic heterocyclyloxycarbonyl optionally substituted with substituent group γ', aromatic carbocyclylalkyloxy optionally substituted with substituent group γ, non-aromatic carbocyclylalkyloxy optionally substituted with substituent group γ', aromatic heterocyclylalkyloxy optionally substituted with substituent group γ, non-aromatic heterocyclylalkyloxy optionally substituted with substituent group γ', aromatic carbocyclylalkyloxycarbonyl optionally substituted with substituent group γ, non-aromatic carbocyclylalkyloxycarbonyl optionally substituted with substituent group γ', aromatic heterocyclylalkyloxycarbonyl optionally substituted with substituent group γ, non-aromatic heterocyclylalkyloxycarbonyl optionally substituted with substituent group γ', aromatic carbocyclylsulfanyl optionally substituted with substituent group γ, non-aromatic carbocyclylsulfanyl optionally substituted with substituent group γ', aromatic heterocyclylsulfanyl optionally substituted with substituent group γ, non-aromatic heterocyclylsulfanyl optionally substituted with substituent group γ', aromatic carbocyclylsulfinyl optionally substituted with substituent group γ, non-aromatic carbocyclylsulfinyl optionally substituted with substituent group γ', aromatic heterocyclylsulfinyl optionally substituted with substituent group γ, non-aromatic heterocyclylsulfinyl optionally substituted with substituent group γ', aromatic carbocyclylsulfonyl optionally substituted with substituent group γ, non-aromatic carbocyclylsulfonyl optionally substituted with substituent group γ', aromatic heterocyclylsulfonyl optionally substituted with substituent group γ, and non-aromatic heterocyclylsulfonyl optionally substituted with substituent group γ'.

Substituent group α: halogen, hydroxy, carboxy, alkyloxy, haloalkyloxy, alkenyloxy, alkynyloxy, sulfanyl and cyano.

Substituent group ß: halogen, hydroxy, carboxy, cyano, alkyl optionally substituted with substituent group α, alkenyl optionally substituted with substituent group α, alkynyl optionally substituted with substituent group α, alkylcarbonyl optionally substituted with substituent group α, alkenylcarbonyl optionally substituted with substituent group α, alkynylcarbonyl optionally substituted with substituent group α, alkylsulfanyl optionally substituted with substituent group α, alkenylsulfanyl optionally substituted with substituent group α, alkynylsulfanyl optionally substituted with substituent group α, alkylsulfinyl optionally substituted with substituent group α, alkenylsulfinyl optionally substituted with substituent group α, alkynylsulfinyl optionally substituted with substituent group α, alkylsulfonyl optionally substituted with substituent group α, alkenylsulfonyl optionally substituted with substituent group α, alkynylsulfonyl optionally substituted with substituent group α, aromatic carbocyclyl optionally substituted with substituent group γ, non-aromatic carbocyclyl optionally substituted with substituent group γ', aromatic heterocyclyl optionally substituted with substituent group γ, non-aromatic heterocyclyl optionally substituted with substituent group γ', aromatic carbocyclylalkyl optionally substituted with substituent group γ, non-aromatic carbocyclylalkyl optionally substituted with substituent group γ', aromatic heterocyclylalkyl optionally substituted with substituent group γ, non-aromatic heterocyclylalkyl optionally substituted with substituent group γ', aromatic carbocyclylcarbonyl optionally substituted with substituent group γ, non-aromatic carbocyclylcarbonyl optionally substituted with substituent group γ', aromatic heterocyclylcarbonyl optionally substituted with substituent group γ, non-aromatic heterocyclylcarbonyl optionally substituted with substituent group γ', aromatic carbocyclyloxycarbonyl optionally substituted with substituent group γ, non-aromatic carbocyclyloxycarbonyl optionally substituted with substituent group γ', aromatic heterocyclyloxycarbonyl optionally substituted with substituent group γ, non-aromatic heterocyclyloxycarbonyl optionally substituted with substituent group γ', aromatic carbocyclylsulfanyl optionally substituted with substituent group γ, non-aromatic carbocyclylsulfanyl optionally substituted with substituent group γ', aromatic heterocyclylsulfanyl optionally substituted with substituent group γ, non-aromatic heterocyclylsulfanyl optionally substituted with substituent group γ', aromatic carbocyclylsulfinyl optionally substituted with substituent group γ, non-aromatic carbocyclylsulfinyl optionally substituted with substituent group γ', aromatic heterocyclylsulfinyl optionally substituted with substituent group γ, non-aromatic heterocyclylsulfinyl optionally substituted with substituent group γ', aromatic carbocyclylsulfonyl optionally substituted with substituent group γ, non-aromatic carbocyclylsulfonyl optionally substituted with substituent group γ', aromatic heterocyclylsulfonyl optionally substituted with substituent group γ, and non-aromatic heterocyclylsulfonyl optionally substituted with substituent group γ'.

Substituent group γ: substituent group α, alkyl, haloalkyl, cyanoalkyl, hydroxyalkyl, alkenyl, alkynyl, alkylcarbonyl, haloalkylcarbonyl, alkenylcarbonyl, and alkynylcarbonyl.

Substituent group γ': substituent group γ and oxo.

The substituents on the rings of "aromatic carbocycle" and "aromatic heterocycle", such as "substituted aromatic carbocyclyl", "substituted aromatic heterocyclyl", "substituted aromatic carbocyclyloxy", "substituted aromatic heterocyclyloxy", "substituted aromatic carbocyclylcarbonyloxy", "substituted aromatic heterocyclylcarbonyloxy", "substituted aromatic carbocyclylcarbonyl", "substituted aromatic heterocyclylcarbonyl", "substituted aromatic carbocyclyloxycarbonyl", "substituted aromatic heterocyclyloxycarbonyl", "substituted aromatic carbocyclylsulfanyl", "substituted aromatic heterocyclylsulfanyl", "substituted aromatic carbocyclylsulfinyl", "substituted aromatic heterocyclylsulfinyl", "substituted aromatic carbocyclylsulfonyl", and "substituted aromatic heterocyclylsulfonyl" include the following substituent group B. An atom at any position on the ring may be bonded to one or more group(s) selected from the following substituent group B.

Substituent group B: halogen, hydroxy, carboxy, formyl, formyloxy, sulfanyl, sulfino, sulfo, thioformyl, thiocarboxy, dithiocarboxy, thiocarbamoyl, cyano, nitro, nitroso, azide, hydrazino, ureido, amidino, guanidino, pentafluorothio, trialkylsilyl, alkyl optionally substituted with substituent group α, alkenyl optionally substituted with substituent group α, alkynyl optionally substituted with substituent group α, alkyloxy optionally substituted with substituent group α, alkenyloxy optionally substituted with substituent group α, alkynyloxy optionally substituted with substituent group α, alkylcarbonyloxy optionally substituted with substituent group α, alkenylcarbonyloxy optionally substituted with substituent group α, alkynylcarbonyloxy optionally substituted with substituent group α, alkylcarbonyl optionally substituted with substituent group α, alkenylcarbonyl optionally substituted with substituent group α, alkynylcarbonyl optionally substituted with substituent group α, alkyloxycarbonyl optionally substituted with substituent group α, alkenyloxycarbonyl optionally substituted with substituent group α, alkynyloxycarbonyl optionally substituted with substituent group α, alkylsulfanyl optionally substituted with substituent group α, alkenylsulfanyl optionally substituted with substituent group α, alkynylsulfanyl optionally substituted with substituent group α, alkylsulfinyl optionally substituted with substituent group α, alkenylsulfinyl optionally substituted with substituent group α, alkynylsulfinyl optionally substituted with substituent group α, alkylsulfonyl optionally substituted with substituent group α, alkenylsulfonyl optionally substituted with substituent group α, alkynylsulfonyl optionally substituted with substituent group α, amino optionally substituted with substituent group ß, imino optionally substituted with substituent group ß, carbamoyl optionally substituted with substituent group ß, sulfamoyl optionally substituted with substituent group ß, aromatic carbocyclyl optionally substituted with substituent group γ, non-aromatic carbocyclyl optionally substituted with substituent group γ', aromatic heterocyclyl optionally substituted with substituent group γ, non-aromatic heterocyclyl optionally substituted with substituent group γ', aromatic carbocyclyloxy optionally substituted with substituent group γ, non-aromatic carbocyclyloxy optionally substituted with substituent group γ', aromatic heterocyclyloxy optionally substituted with substituent group γ, non-aromatic heterocyclyloxy optionally substituted with substituent group γ', aromatic carbocyclylcarbonyloxy optionally substituted with substituent group γ, non-aromatic carbocyclylcarbonyloxy optionally substituted with substituent group γ', aromatic heterocyclylcarbonyloxy optionally substituted with substituent group γ, and non-aromatic heterocyclylcarbonyloxy optionally substituted with substituent group γ', aromatic carbocyclylcarbonyl optionally substituted with substituent group γ, non-aromatic carbocyclylcarbonyl optionally substituted with substituent group γ', aromatic heterocyclylcarbonyl optionally substituted with substituent group γ, non-aromatic heterocyclylcarbonyl optionally substituted with substituent group γ', aromatic carbocyclyloxycarbonyl optionally substituted with substituent group γ, non-aromatic carbocyclyloxycarbonyl optionally substituted with substituent group γ', aromatic heterocyclyloxycarbonyl optionally substituted with substituent group γ, non-aromatic heterocyclyloxycarbonyl optionally substituted with substituent group γ', aromatic carbocyclylalkyl optionally substituted with substituent group γ, non-aromatic carbocyclylalkyl optionally substituted with substituent group γ', aromatic heterocyclylalkyl optionally substituted with substituent group γ, non-aromatic heterocyclylalkyl optionally substituted with substituent group γ', aromatic carbocyclylalkyloxy optionally substituted with substituent group γ, non-aromatic carbocyclylalkyloxy optionally substituted with substituent group γ', aromatic heterocyclylalkyloxy optionally substituted with substituent group γ, non-aromatic heterocyclylalkyloxy optionally substituted with substituent group γ', aromatic carbocyclylalkyloxycarbonyl optionally substituted with substituent group γ, non-aromatic carbocyclylalkyloxycarbonyl optionally substituted with substituent group γ', aromatic heterocyclylalkyloxycarbonyl optionally substituted with substituent group γ, non-aromatic heterocyclylalkyloxycarbonyl optionally substituted with substituent group γ', aromatic carbocyclylalkyloxyalkyl optionally substituted with substituent group γ, non-aromatic carbocyclylalkyloxyalkyl optionally substituted with substituent group γ', aromatic heterocyclylalkyloxyalkyl optionally substituted with substituent group γ, non-aromatic heterocyclylalkyloxyalkyl optionally substituted with substituent group γ', aromatic carbocyclylsulfanyl optionally substituted with substituent group γ, non-aromatic carbocyclylsulfanyl optionally substituted with substituent group γ', aromatic heterocyclylsulfanyl optionally substituted with substituent group γ, non-aromatic heterocyclylsulfanyl optionally substituted with substituent group γ', aromatic carbocyclylsulfinyl optionally substituted with substituent group γ, non-aromatic carbocyclylsulfinyl optionally substituted with substituent group γ', aromatic heterocyclylsulfinyl optionally substituted with substituent group γ, non-aromatic heterocyclylsulfinyl optionally substituted with substituent group γ', aromatic carbocyclylsulfonyl optionally substituted with substituent group γ, non-aromatic carbocyclylsulfonyl optionally substituted with substituent group γ', aromatic heterocyclylsulfonyl optionally substituted with substituent group γ, and non-aromatic heterocyclylsulfonyl optionally substituted with substituent group γ'.

Cyclic substituents for "non-aromatic carbocycle" and "aromatic heterocycle" of "substituted non-aromatic carbocyclyl", "substituted non-aromatic heterocyclyl", "substituted non-aromatic carbocyclyloxy", "substituted non-aromatic heterocyclyloxy", "substituted non-aromatic carbocyclylcarbonyloxy", "substituted non-aromatic heterocyclylcarbonyloxy", "substituted non-aromatic carbocyclylcarbonyl", "substituted non-aromatic heterocyclylcarbonyl", "substituted non-aromatic carbocyclyloxycarbonyl", "substituted non-aromatic heterocyclyloxycarbonyl", "substituted non-aromatic carbocyclylsulfanyl", "substituted non-aromatic heterocyclylsulfanyl", "substituted non-aromatic carbocyclylsulfinyl", "substituted non-aromatic heterocyclylsulfinyl", "substituted non-aromatic carbocyclylsulfonyl" and "substituted non-aromatic heterocyclylsulfonyl" include the following substituent group C. An atom at an arbitrary position on the ring may be bonded to one or more groups selected from the following substituent group C.

Substituent group C: substituent group B and oxo.

When the "non-aromatic carbocycle", the "non-aromatic heterocycle", the "non-aromatic carbocyclyl" and the "non-aromatic heterocyclyl" are substituted with "oxo", this means a ring in which two hydrogen atoms on a carbon atom are substituted as follows.

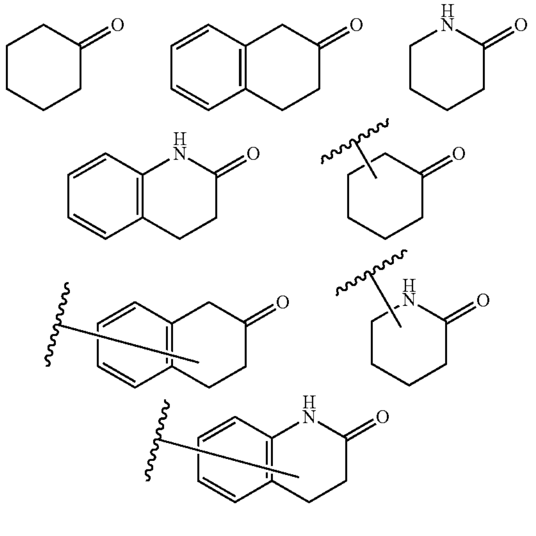

Examples of the substituents for "substituted amino", "substituted imino", "substituted carbamoyl" and "substituted sulfamoyl" include the following substituent group D. These moieties may be substituted with one or two group(s) selected from substituent group D.

Substituent group D: halogen, hydroxy, carboxy, cyano, alkyl optionally substituted with substituent group α, alkenyl optionally substituted with substituent group α, alkynyl optionally substituted with substituent group α, alkylcarbonyl optionally substituted with substituent group α, alkenylcarbonyl optionally substituted with substituent group α, alkynylcarbonyl optionally substituted with substituent group α, alkylsulfanyl optionally substituted with substituent group α, alkenylsulfanyl optionally substituted with substituent group α, alkynylsulfanyl optionally substituted with substituent group α, alkylsulfinyl optionally substituted with substituent group α, alkenylsulfinyl optionally substituted with substituent group α, alkynylsulfinyl optionally substituted with substituent group α, alkylsulfonyl optionally substituted with substituent group α, alkenylsulfonyl optionally substituted with substituent group α, alkynylsulfonyl optionally substituted with substituent group α, amino optionally substituted with substituent group ß, imino optionally substituted with substituent group ß, carbamoyl optionally substituted with substituent group ß, sulfamoyl optionally substituted with substituent group ß, aromatic carbocyclyl optionally substituted with substituent group γ, non-aromatic carbocyclyl optionally substituted with substituent group γ', aromatic heterocyclyl optionally substituted with substituent group γ, non-aromatic heterocyclyl optionally substituted with substituent group γ', aromatic carbocyclylalkyl optionally substituted with substituent group γ, non-aromatic carbocyclylalkyl optionally substituted with substituent group γ', aromatic heterocyclylalkyl optionally substituted with substituent group γ, non-aromatic heterocyclylalkyl optionally substituted with substituent group γ', aromatic carbocyclylcarbonyl optionally substituted with substituent group γ, non-aromatic carbocyclylcarbonyl optionally substituted with substituent group γ', aromatic heterocyclylcarbonyl optionally substituted with substituent group γ, non-aromatic heterocyclylcarbonyl optionally substituted with substituent group γ', aromatic carbocyclyloxycarbonyl optionally substituted with substituent group γ, non-aromatic carbocyclyloxycarbonyl optionally substituted with substituent group γ', aromatic heterocyclyloxycarbonyl optionally substituted with substituent group γ, non-aromatic heterocyclyloxycarbonyl optionally substituted with substituent group γ', aromatic carbocyclylsulfanyl optionally substituted with substituent group γ, non-aromatic carbocyclylsulfanyl optionally substituted with substituent group γ', aromatic heterocyclylsulfanyl optionally substituted with substituent group γ, non-aromatic heterocyclylsulfanyl optionally substituted with substituent group γ', aromatic carbocyclylsulfinyl optionally substituted with substituent group γ, non-aromatic carbocyclylsulfinyl optionally substituted with substituent group γ', aromatic heterocyclylsulfinyl optionally substituted with substituent group γ, non-aromatic heterocyclylsulfinyl optionally substituted with substituent group γ', aromatic carbocyclylsulfonyl optionally substituted with substituent group γ, non-aromatic carbocyclylsulfonyl optionally substituted with substituent group γ', aromatic heterocyclylsulfonyl optionally substituted with substituent group γ, and non-aromatic heterocyclylsulfonyl optionally substituted with substituent group γ'.

In formula (I), the atom to which a of ring P is attached is bonded to a group represented by —X—, and the atom to which b of ring Q is attached is bonded to a group represented by —O—.

In formula (III), the atom to which a of ring P is attached is bonded to a group represented by —$CH_2$—, and the atom to which b of ring Q is attached is bonded to a group represented by —O—. In ring represented by the following formula:

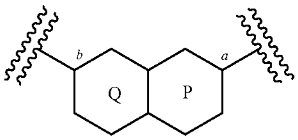

, ring P and/or ring Q may be substituted by $R^{10}$, and examples include the following rings:

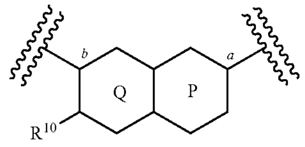

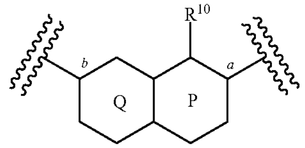

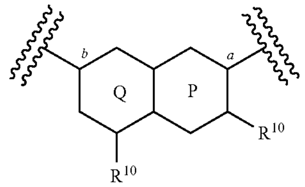

When the ring represented by:

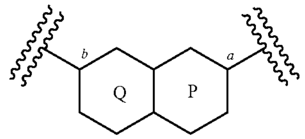

is represented by:

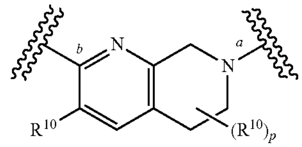

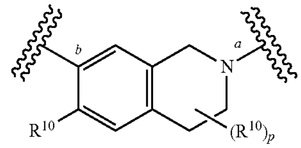

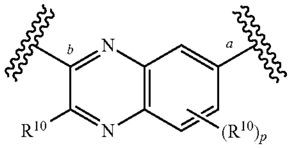

or

-continued

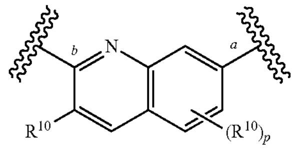

this shows that $(R^{10})_p$ may be bonded on ring P, and when the above ring is represented by:

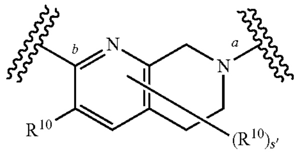

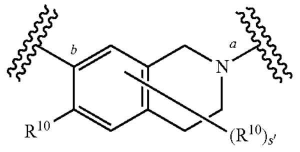

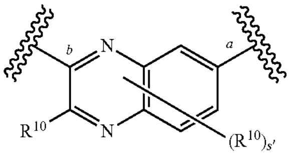

or

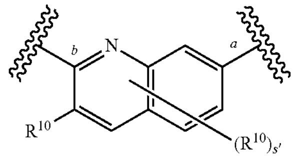

this shows that $(R^{10})_{s'}$ may be bonded on ring P and/or ring Q.

Preferred embodiments of $A_1$, $A_2$, $A_3$, $R^1$, $R^2$, —X—, $R^3$, $R^{13}$, $E_1$, $E_2$, r, $R^{10}$ in the compound represented by formula (I) or formula (II) and ring represented by:

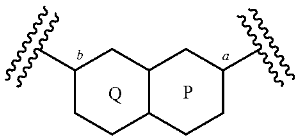

are shown below. Regarding the compound represented by formula (I) or formula (II), embodiments of all the combinations of specific examples shown below are mentioned as examples.

$A_1$ includes $C(R^5)$ or N (referred to as A-1).

$A_1$ includes $C(R^5)$ (referred to as A-2).

$A_1$ includes C(H) (referred to as A-3).

$A_1$ includes C(F) (referred to as A-4).

$A_1$ includes N (referred to as A-5).

$A_2$ includes $C(R^6)$ or N (referred to as B-1).

$A_2$ includes $C(R^6)$ (referred to as B-2).

$A_2$ includes C(H) (referred to as B-3).

$A_2$ includes N (referred to as B-4).

$A_3$ includes $C(R^7)$ or N (referred to as C-1).

$A_3$ includes $C(R^7)$ (referred to as C-2).

$A_3$ includes C(F) (referred to as C-3).

$A_3$ includes C(Cl) (referred to as C-4).

$A_3$ includes C(H) (referred to as C-5).

$A_3$ includes N (referred to as C-6).

$R^5$, $R^6$, and $R^7$ includes each independently a hydrogen atom, halogen, cyano, substituted or unsubstituted alkyl, substituted or unsubstituted alkyloxy, or substituted or unsubstituted non-aromatic carbocyclyl (referred to as D-1).

$R^5$, $R^6$, and $R^7$ includes each independently a hydrogen atom, halogen, cyano, substituted or unsubstituted alkyl, or substituted or unsubstituted alkyloxy (referred to as D-2).

$R^5$, $R^6$, and $R^7$ includes each independently a hydrogen atom, halogen or cyano (referred to as D-3).

$R^5$, $R^6$, and $R^7$ includes each independently a hydrogen atom, halogen, or substituted or unsubstituted alkyloxy (referred to as D-4).

$R^5$, $R^6$, and $R^7$ includes each independently a hydrogen atom or halogen (referred to as D-5).

$R^5$, $R^6$, and $R^7$ includes a hydrogen atom (referred to as D-6).

$R^5$ includes a hydrogen atom or halogen, $R^6$ includes a hydrogen atom and $R^7$ includes a hydrogen atom, halogen, or substituted or unsubstituted alkyloxy (referred to as D-7).

$R^6$ includes a hydrogen atom, and $R^5$ and $R^7$ includes each independently a hydrogen atom or halogen (referred to as D-8).

$R^1$ includes carboxy, an equivalent thereof or $CH_2COOH$ (referred to as E-1).

$R^1$ includes carboxy or an equivalent thereof (referred to as E-2).

$R^1$ includes carboxy or any of the groups shown below:

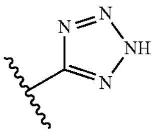

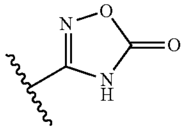

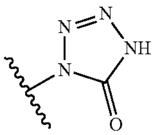

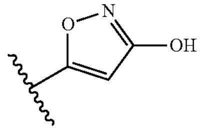

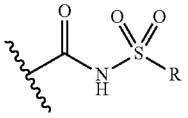

or

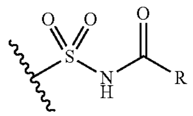

wherein R is substituted or unsubstituted alkyl, substituted or unsubstituted amine, substituted or unsubstituted non-aromatic carbocyclyl, substituted or unsubstituted aromatic carbocyclyl, substituted or unsubstituted non-aromatic heterocyclyl, or substituted or unsubstituted aromatic heterocyclyl (referred to as E-3).

$R^1$ includes carboxy (referred to as E-4).

$R^2$ includes substituted or unsubstituted alkyl or substituted or unsubstituted non-aromatic heterocyclyl (referred to as F-1).

$R^2$ includes substituted or unsubstituted alkyl (referred to as F-2).

$R^2$ includes substituted or unsubstituted methyl (referred to as F-3).

$R^2$ includes alkyl substituted with substituted or unsubstituted non-aromatic heterocycle, alkyl substituted with substituted or unsubstituted aromatic heterocyclyl, or unsubstituted alkyl (referred to as F-4).

$R^2$ includes oxetanylalkyl or alkylimidazolylalkyl (referred to as F-5).

$R^2$ includes oxetanylmethyl or ethylimidazolylmethyl (referred to as F-6).

$R^2$ includes oxetanylmethyl (referred to as F-7).

$R^2$ includes alkylimidazolylmethyl (referred to as F-8)

$R^2$ includes ethylimidazolylmethyl (referred to as F-9).

—X— includes —C($R^8$)($R^9$)—, —O—, or —N($R^{11}$)— (referred to as G-1).

—X— includes —C($R^8$)($R^9$)— or —O— (referred to as G-2).

—X— includes —O— (referred to as G-3).

—X— includes —C($R^8$)($R^9$)— (referred to as G-4).

—X— includes —C(H)(H)— (referred to as G-5).

—X— includes —N($R^{11}$)— (referred to as G-6).

$R^8$ and $R^9$ includes each independently a hydrogen atom, halogen, or substituted or unsubstituted alkyl (referred to as H-1).

$R^8$ and $R^9$ includes each independently a hydrogen atom or halogen (referred to as H-2).

$R^8$ and $R^9$ includes a hydrogen atom (referred to as H-3).

$R^{11}$ includes a hydrogen atom or substituted or unsubstituted alkyl (referred to as I-1).

$R^{11}$ includes a hydrogen atom (referred to as I-2).

$R^{11}$ includes substituted or unsubstituted alkyl (referred to as I-3).

Ring represented by:

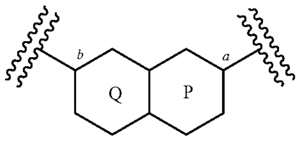

include rings shown below (referred to as J-1):

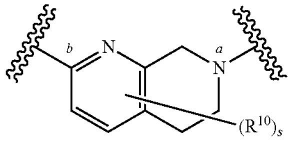

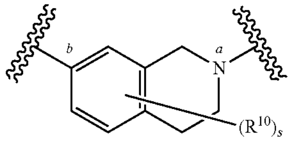

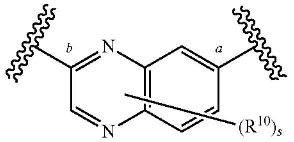

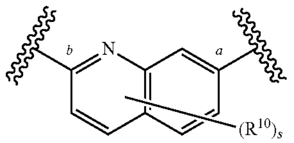

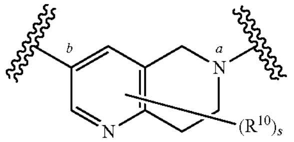

-continued

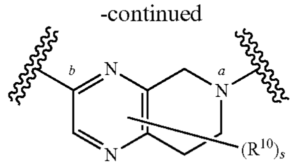

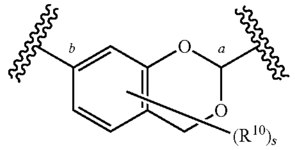

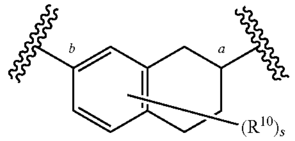

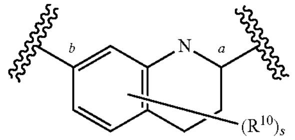

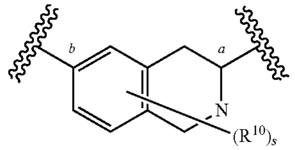

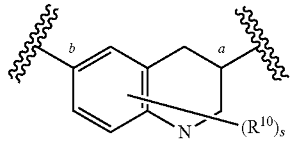

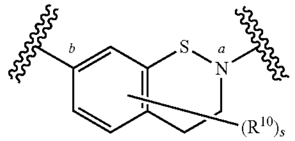

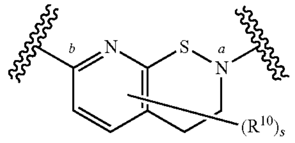

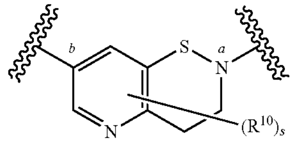

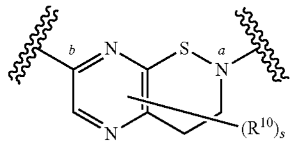

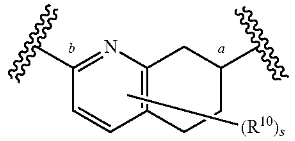

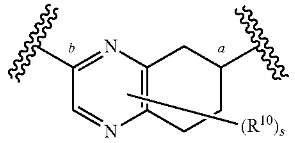

-continued
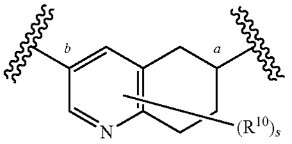
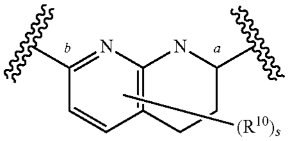
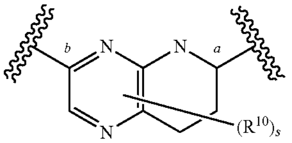
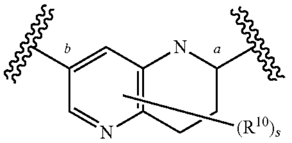
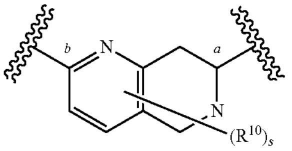
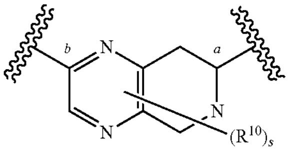
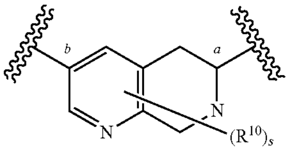
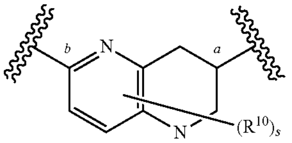
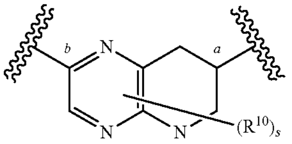
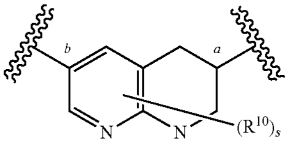
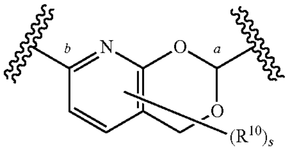
-continued
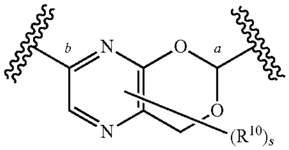
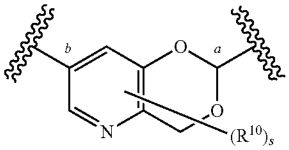
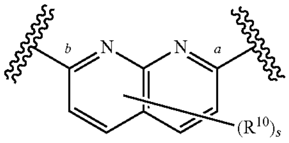
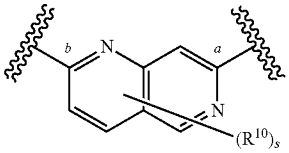
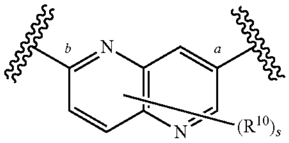
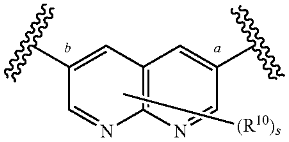
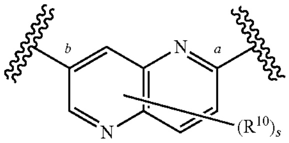
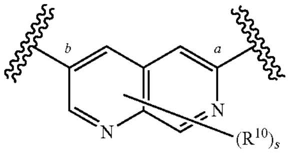
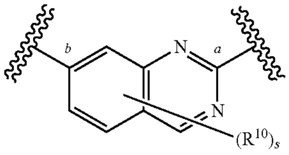
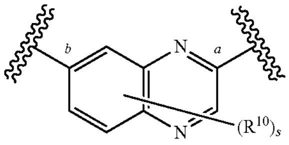
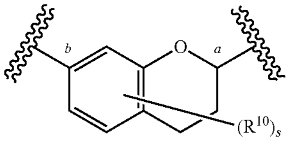

-continued
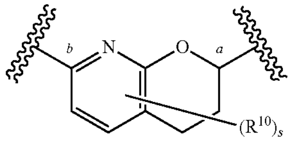
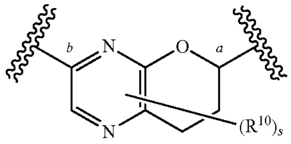
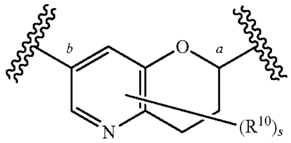
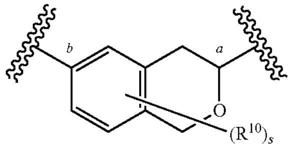
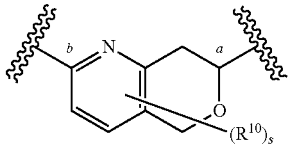
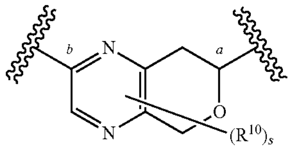
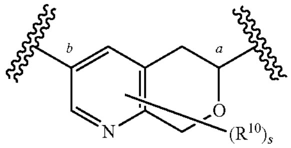
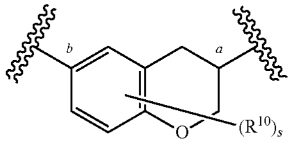
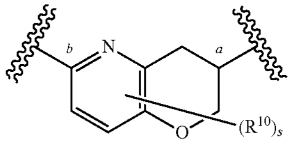
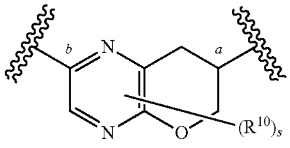
or
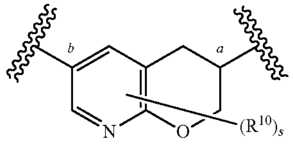
.
Ring represented by:
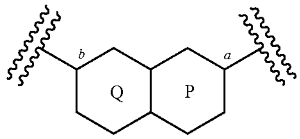
include rings shown below (referred to as J-2):
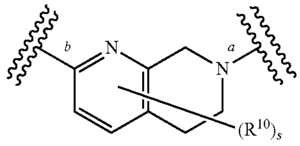
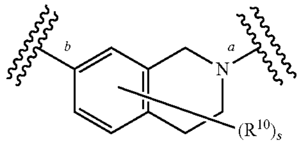
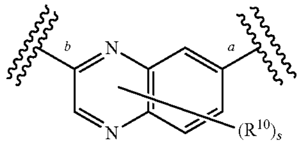
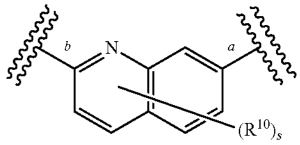
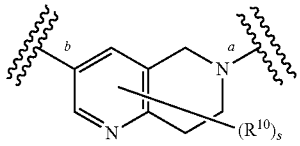
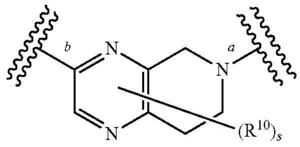
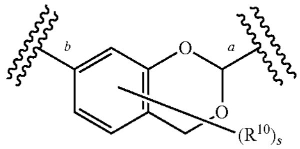
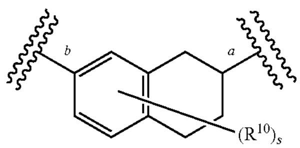
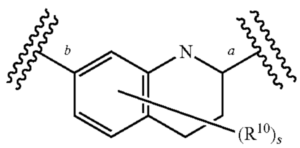

-continued
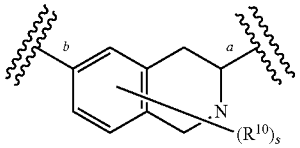
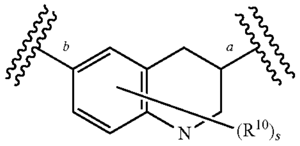
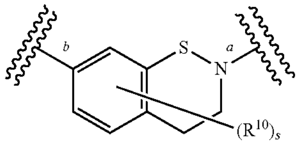
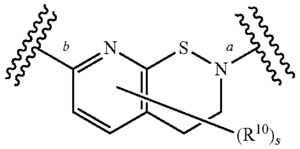
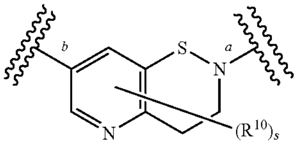
or
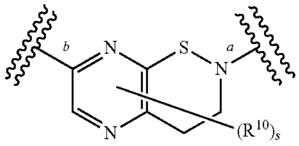
.
Ring represented by:
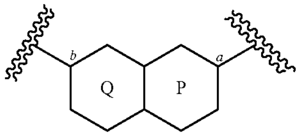
include rings shown below (referred to as J-3):
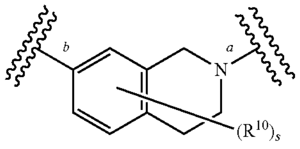
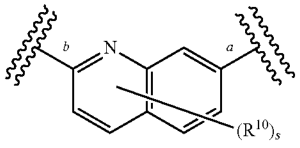
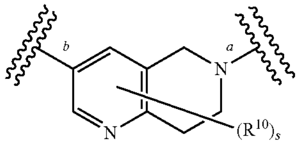
-continued
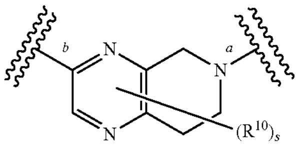
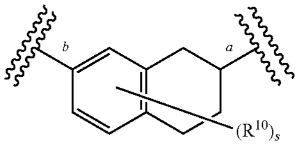
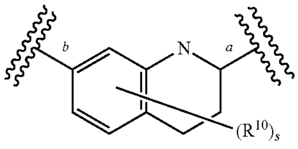
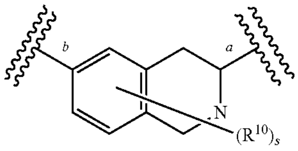
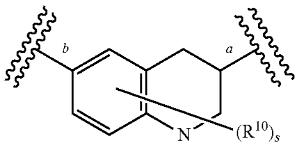
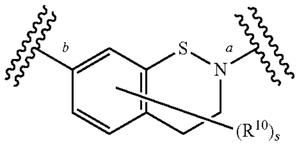
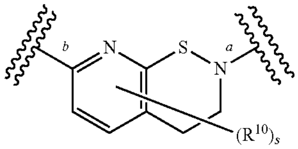
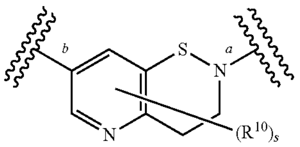
or
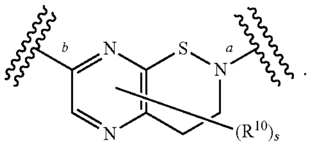
.
Ring represented by:
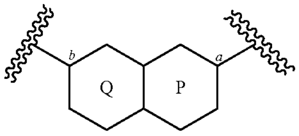
include rings shown below (referred to as J-4):

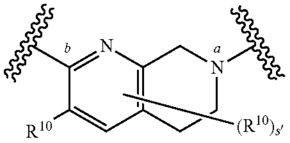
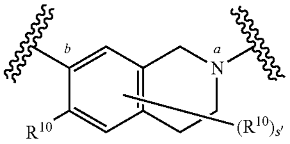
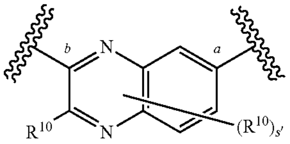
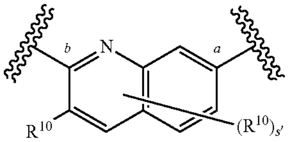
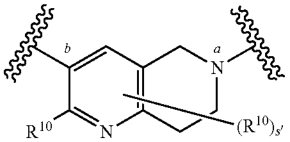
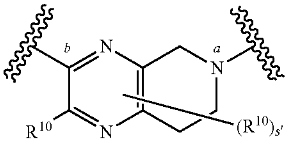
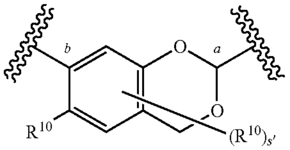
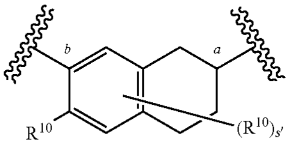
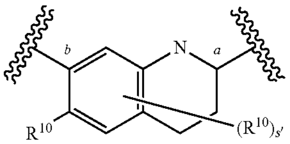
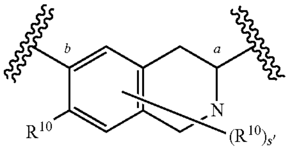
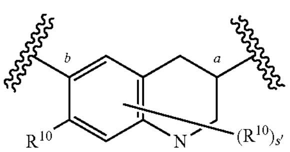
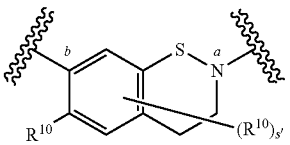
-continued
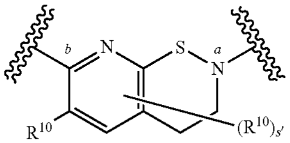
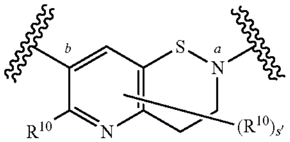
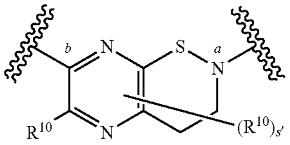
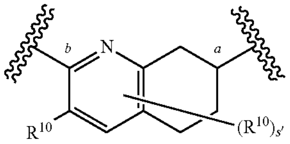
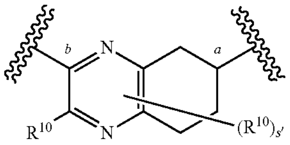
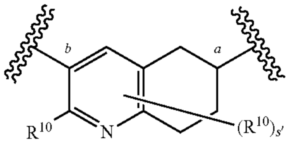
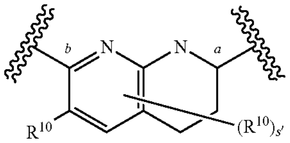
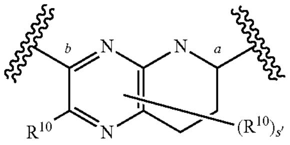
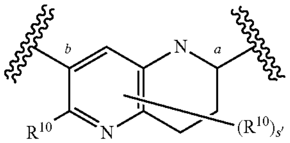
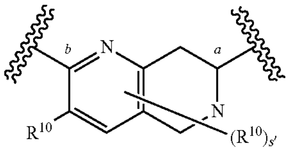
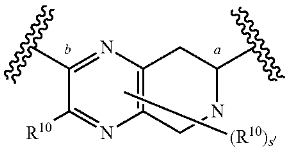

-continued
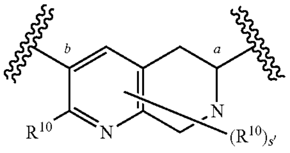
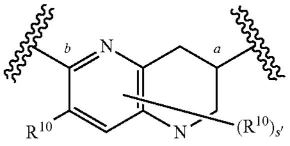
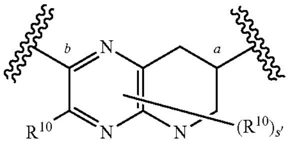
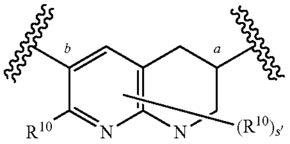
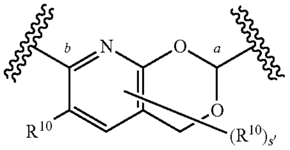
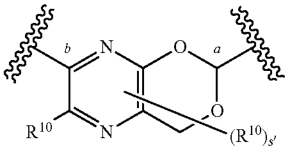
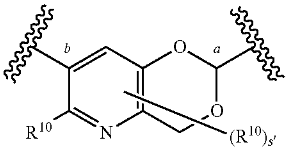
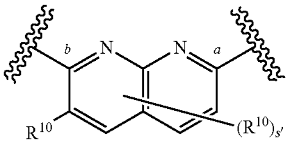
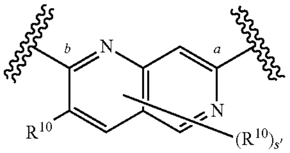
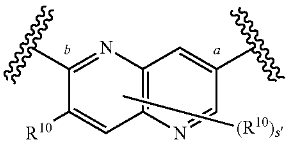
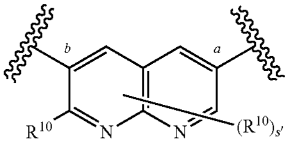
-continued
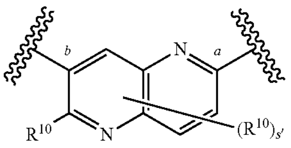
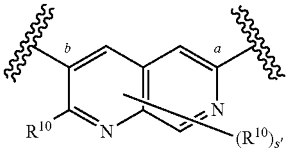
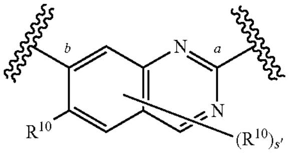
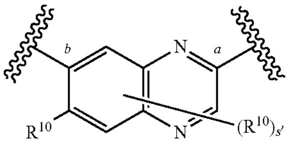
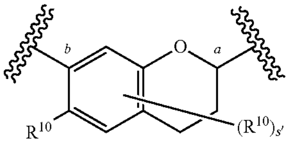
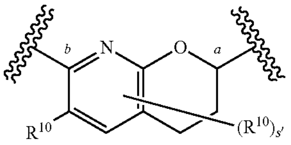
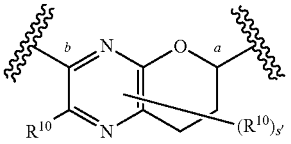
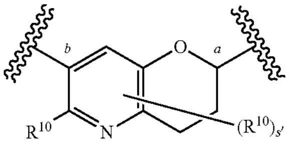
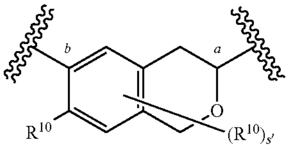
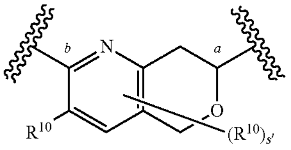
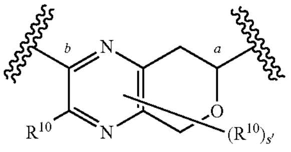

-continued
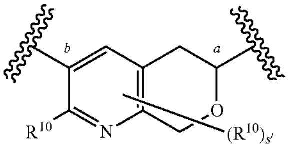
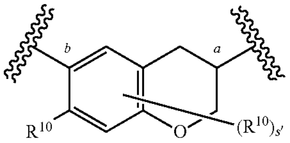
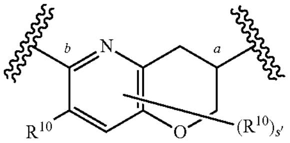
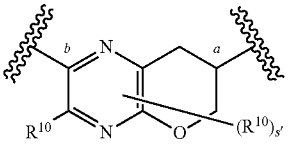
or
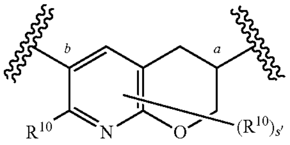
Ring represented by:
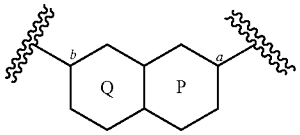
include rings shown below (referred to as J-5):
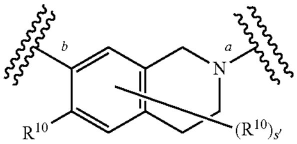
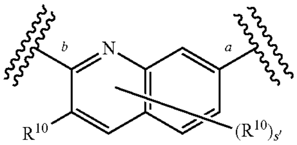
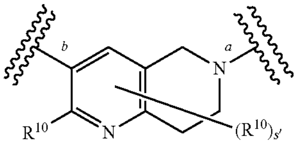
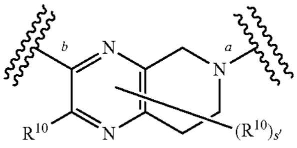
-continued
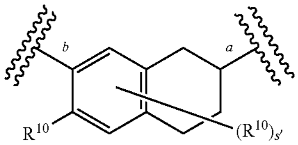
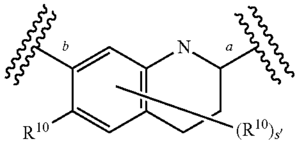
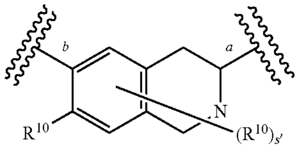
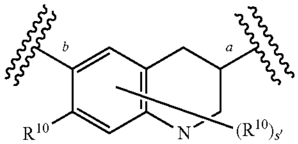
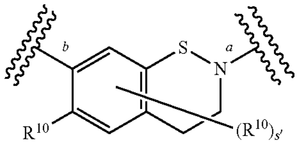
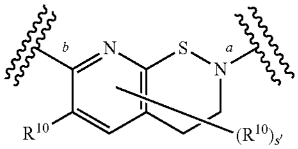
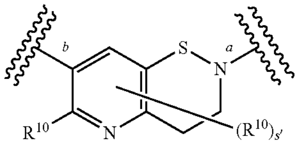
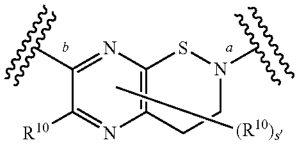
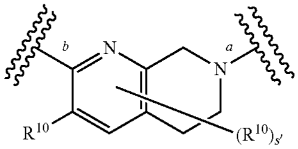
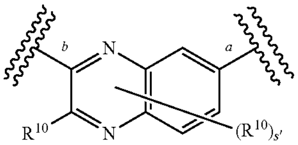
or
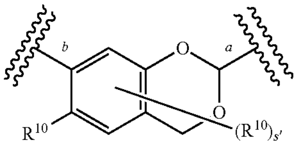
.

Ring represented by:
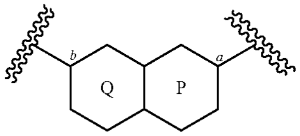
include rings shown below (referred to as J-6):
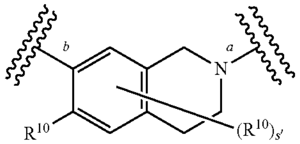
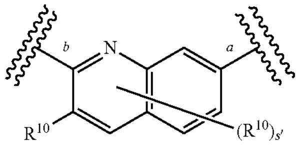
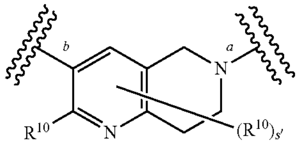
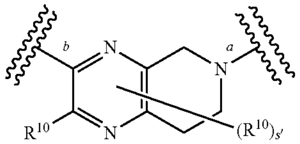
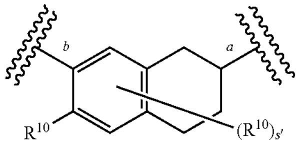
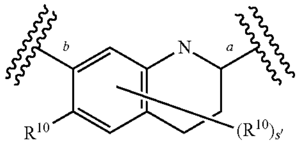
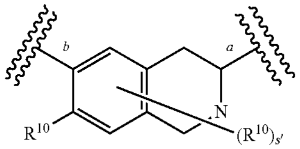
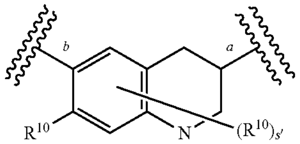
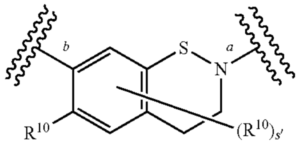
-continued
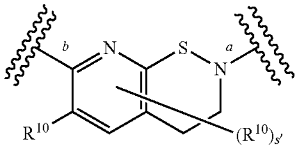
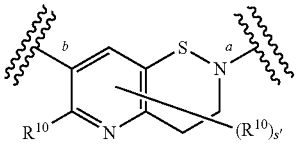
or
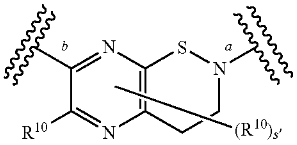
.
Ring represented by:
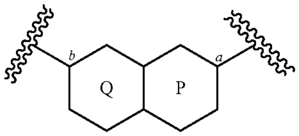
include rings shown below (referred to as J-7):
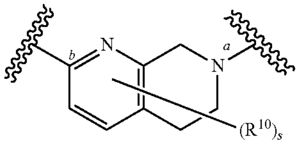
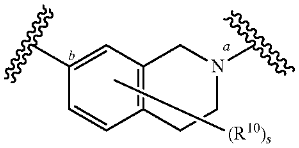
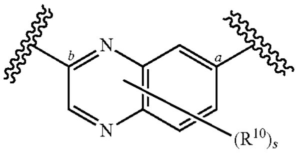
or
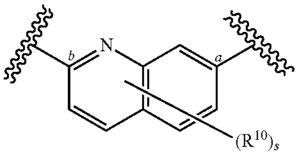
.

Ring represented by:
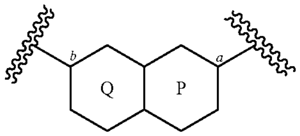
include rings shown below (referred to as J-8):
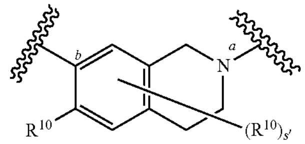
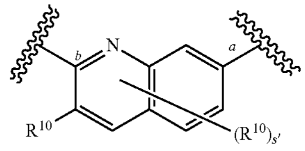
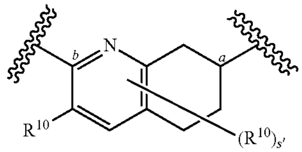
or
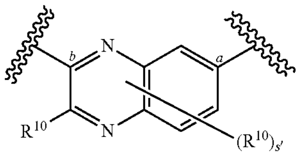
.
Ring represented by:
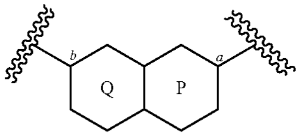
include rings shown below (referred to as J-9):
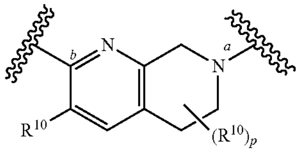
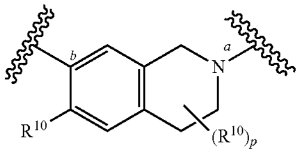
-continued
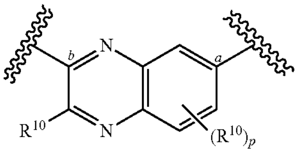
or
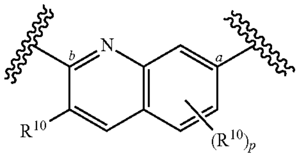
Ring represented by:
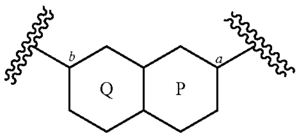
include rings shown below (referred to as J-10):
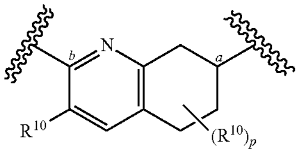
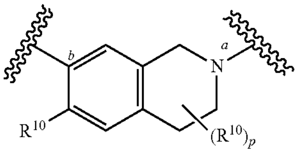
or
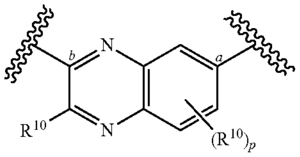
Ring represented by:
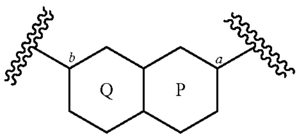
include rings shown below (referred to as J-11):
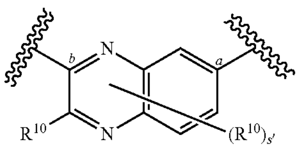

Ring represented by:

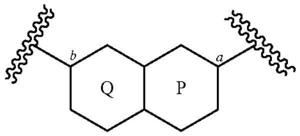

include rings shown below (referred to as J-12):

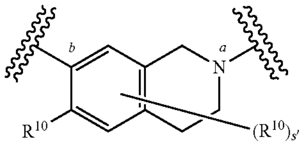

Ring represented by:

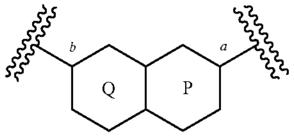

include rings shown below (referred to as J-13):

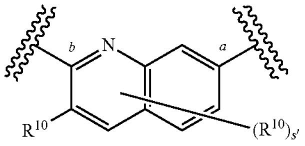

Ring represented by:

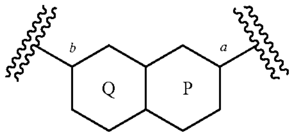

include rings shown below (referred to as J-14):

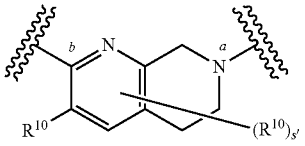

Ring represented by:

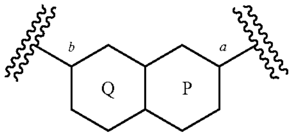

include rings shown below (referred to as J-15):

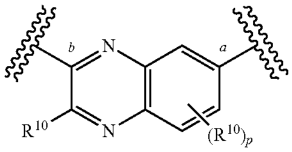

Ring represented by:

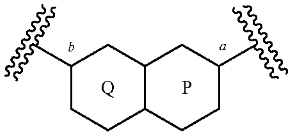

include rings shown below (referred to as J-16):

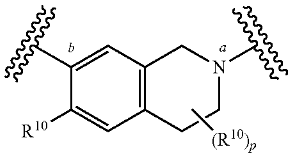

Ring represented by

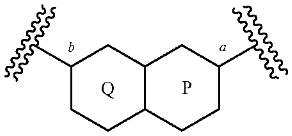

include rings shown below (referred to as J-17):

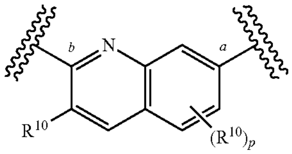

Ring represented by

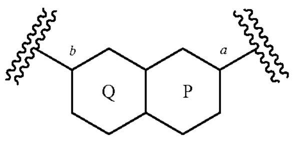

include rings shown below (referred to as J-18):

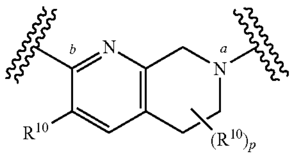

$R^{10}$ includes each independently halogen, cyano, hydroxy, substituted or unsubstituted alkyl, oxo, substituted or unsubstituted non-aromatic carbocyclyl, or substituted or unsubstituted alkyloxy (referred to as K-1).

$R^{10}$ includes each independently halogen, cyano, substituted or unsubstituted alkyl, oxo, or substituted or unsubstituted alkyloxy (referred to as K-2).

$R^{10}$ includes each independently halogen or cyano (referred to as K-3).

$R^{10}$ includes each independently halogen (referred to as K-4).

$R^{10}$ includes each independently cyano (referred to as K-5).

$R^{10}$ includes each independently substituted or unsubstituted alkyl (referred to as K-6).

$R^{10}$ includes each independently substituted or unsubstituted alkyloxy (referred to as K-7).

When $R^{10}$ is bonded to ring P, $R^{10}$ includes each independently halogen, or substituted or unsubstituted alkyl (referred to as K-8).

When $R^{10}$ is bonded to ring P, $R^{10}$ includes each independently halogen or alkyl (referred to as K-9).

When $R^{10}$ is bonded to ring P, $R^{10}$ includes each independently alkyl (referred to as K-10).

When $R^{10}$ is bonded to ring P, $R^{10}$ includes each independently halogen (referred to as K-11).

When $R^{10}$ is bonded to ring Q, $R^{10}$ includes each independently halogen, or substituted or unsubstituted alkyl (referred to as K-12).

When $R^{10}$ is bonded to ring Q, $R^{10}$ includes each independently halogen, or alkyl substituted with halogen (referred to as K-13).

When $R^{10}$ is bonded to ring Q, $R^{10}$ includes each independently halogen, or alkyl substituted with fluorine (referred to as K-14).

When $R^{10}$ is bonded to ring Q, $R^{10}$ includes each independently alkyl substituted with halogen (referred to as K-15).

When $R^{10}$ is bonded to ring Q, $R^{10}$ includes each independently alkyl substituted with fluorine (referred to as K-16).

When $R^{10}$ is bonded to ring Q, $R^{10}$ includes each independently halogen (referred to as K-17).

s includes an integer of 0 to 9 (referred to as L-1).

s includes an integer of 0 to 3 (referred to as L-2).

s includes an integer of 0 to 2 (referred to as L-3).

s includes an integer of 0 or 1 (referred to as L-4).

s includes an integer of 1 or 2 (referred to as L-5).

s includes an integer of 0 (referred to as L-6).

s includes an integer of 1 (referred to as L-7).

s includes an integer of 2 (referred to as L-8).

s' includes an integer of 0 to 8 (referred to as M-1).

s' includes an integer of 0 to 3 (referred to as M-2).

s' includes an integer of 0 to 2 (referred to as M-3).

s' includes an integer of 0 or 1 (referred to as M-4).

s' includes an integer of 0 (referred to as M-5).

s' includes an integer of 1 (referred to as M-6).

$R^3$ includes substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl (referred to as N-1).

$R^3$ includes substituted or unsubstituted aromatic carbocyclyl, or substituted or unsubstituted aromatic heterocyclyl (referred to as N-2).

$R^3$ includes aromatic carbocyclyl optionally substituted with substituent group $A_1$ (halogen, substituted or unsubstituted alkyl, substituted or unsubstituted alkyloxy or cyano), or aromatic heterocyclyl optionally substituted with substituent group $A_1$ (referred to as N-3).

$R^3$ includes phenyl optionally substituted by substituent group $A_2$ (halogen, alkyl, haloalkyl, haloalkyloxy, and cyano), pyridyl optionally substituted by substituent group A2, pyrimidyl optionally substituted by substituent group A2, pyrazyl optionally substituted by substituent group A2, pyrazolyl optionally substituted by substituent group A2, imidazolyl optionally substituted by substituent group A2, isoxazolyl optionally substituted by substituent group A2, or thiazolyl optionally substituted by substituent group $A_2$ (referred to as N-4).

$R^3$ includes phenyl optionally substituted with substituent group $A_2$ (halogen, alkyl, haloalkyl, haloalkyloxy, and cyano) (referred to as N-5).

$R^3$ includes a group represented by:

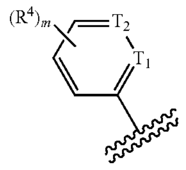
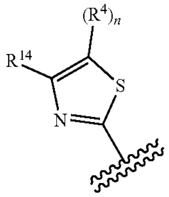
or
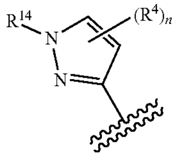

(referred to as N-6).

$R^3$ includes a group represented by:

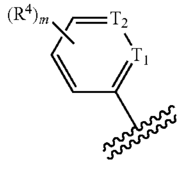
or
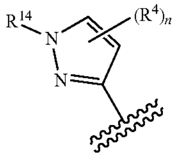

(referred to as N-7).

$R^3$ includes a group represented by:

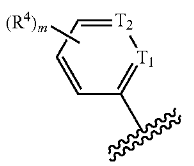

(referred to as N-8).

$R^3$ includes a group represented by:

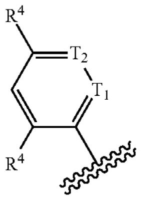

(referred to as N-9).

$R^3$ includes a group represented by:

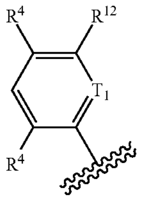
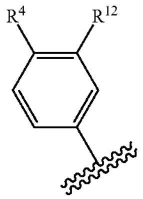
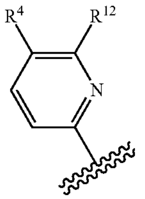
or
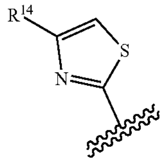

(referred to as N-10).

$R^3$ includes a group represented by:

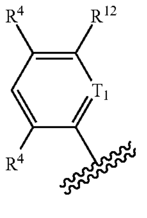
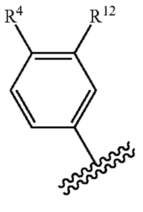
or
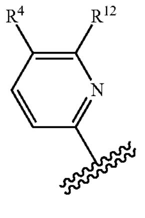

(referred to as N-11).

$R^3$ includes a group represented by:

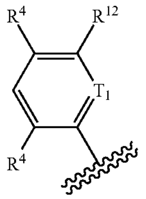

(referred to as N-12).

$R^3$ may be a group represented by:

[Chemical Formula 102]

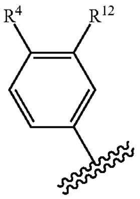

(referred to as N-13).

$R^3$ includes a group represented by:

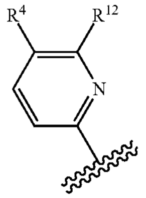

(referred to as N-14).

$T_1$ includes a carbon atom or a nitrogen atom (referred to as O-1).

$T_1$ includes $C(R^{12})$ or N (referred to as O-2).

$T_1$ includes a carbon atom (referred to as O-3).

$T_1$ includes $C(R^{12})$ (referred to as O-4).

$T_1$ includes a nitrogen atom (referred to as O-5).

$T_2$ includes a carbon atom or a nitrogen atom (referred to as P-1).

$T_2$ includes $C(R^{12})$ or N (referred to as P-2).

$T_2$ includes a carbon atom (referred to as P-3).

$T_2$ includes $C(R^{12})$ (referred to as P-4).

$T_2$ includes a nitrogen atom (referred to as P-5).

$R^4$ includes each independently halogen, cyano, substituted or unsubstituted alkyl, substituted or unsubstituted alkyloxy, substituted or unsubstituted aromatic carbocyclyl, substituted or unsubstituted non-aromatic carbocyclyl, or substituted or unsubstituted alkylsulfonyl (referred to as Q-1).

$R^4$ includes each independently halogen, cyano, substituted or unsubstituted alkyl, substituted or unsubstituted alkyloxy, or substituted or unsubstituted non-aromatic carbocyclyloxy (referred to as Q-2).

$R^4$ includes each independently halogen, cyano, substituted or unsubstituted alkyl, or substituted or unsubstituted alkyloxy (referred to as Q-3).

$R^4$ includes each independently a hydrogen atom, halogen, or substituted or unsubstituted alkyl (referred to as Q-4).

$R^4$ includes each independently halogen, or alkyl substituted or unsubstituted with halogen (referred to as Q-5).

$R^4$ includes each independently halogen, or substituted or unsubstituted alkyloxy (referred to as Q-6).

$R^4$ includes each independently halogen, or alkyloxy substituted or unsubstituted with halogen (referred to as Q-7).

$R^4$ includes each independently halogen, alkyloxy substituted with fluorine, or unsubstituted alkyloxy (referred to as Q-8).

$R^4$ includes each independently halogen, cyano, unsubstituted alkyl, unsubstituted alkyloxy, or unsubstituted non-aromatic carbocyclyl (referred to as Q-9).

$R^4$ includes each independently halogen (referred to as Q-10).

$R^{14}$ includes a hydrogen atom or substituted or unsubstituted alkyl (referred to as R-1).

$R^{14}$ includes substituted or unsubstituted alkyl (referred to as R-2).

$R^{14}$ includes alkyl (referred to as R-3).

$R^{12}$ includes each independently a hydrogen atom, halogen, cyano, substituted or unsubstituted alkyl, substituted or unsubstituted alkyloxy, substituted or unsubstituted aromatic carbocyclyl, substituted or unsubstituted non-aromatic carbocyclyl, or substituted or unsubstituted alkylsulfonyl (referred to as S-1).

$R^{12}$ includes each independently a hydrogen atom or halogen (referred to as S-2).

$R^{12}$ includes a hydrogen atom (referred to as S-3).

$R^{12}$ includes each independently halogen (referred to as S-4).

m includes an integer of 0 to 5 (referred to as T-1).

m includes an integer of 0 to 3 (referred to as T-2).

m includes 1 or 2 (referred to as T-3).

m includes 1 (referred to as T-4).

m includes 2 (referred to as T-5).

n includes an integer of 0 to 2 (referred to as U-1).

n includes 0 or 1 (referred to as U-2).

n includes 0 (referred to as U-3).

n includes 1 (referred to as U-4).

n includes 2 (referred to as U-5).

$R^{13}$ includes each independently a hydrogen atom, halogen, or substituted or unsubstituted alkyl (referred to as V-1).

$R^{13}$ includes each independently a hydrogen atom or substituted or unsubstituted alkyl (referred to as V-2).

$R^{13}$ includes each independently substituted or unsubstituted alkyl (referred to as V-3).

One $R^{13}$ includes a hydrogen atom, and the other $R^{13}$ includes substituted or unsubstituted alkyl (referred to as V-4).

$R^{13}$ includes a hydrogen atom (referred to as V-5).

$E_1$ includes a carbon atom or a nitrogen atom (referred to as W-1).

$E_1$ includes a carbon atom (referred to as W-2).

$E_1$ includes a nitrogen atom (referred to as W-3).

E2 includes a carbon atom or a nitrogen atom (referred to as X-1).

E2 includes a carbon atom (referred to as X-2).

E2 includes a nitrogen atom (referred to as X-3).

r includes an integer of 0 to 9 (referred to as Y-1).

r includes an integer of 1 to 9 (referred to as Y-2).

r includes an integer of 1 to 3 (referred to as Y-3).

r includes an integer of 1 to 2 (referred to as Y-4).

r includes 3 (referred to as Y-5).

r includes 2 (referred to as Y-6).

r includes 1 (referred to as Y-7).

p includes an integer of 0 to 6 (referred to as Z-1).

p includes an integer of 0 to 3 (referred to as Z-2).

p includes an integer of 0 to 2 (referred to as Z-3).

p includes an integer of 0 or 1 (referred to as Z-4).

p includes 0 (referred to as Z-5).

p includes 1 (referred to as Z-6).

Preferred embodiments of $A_1$, $R^2$, $R^3$, $R^7$, and ring represented by

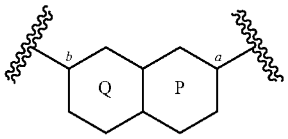

in a compound represented by formula (III):

(III)

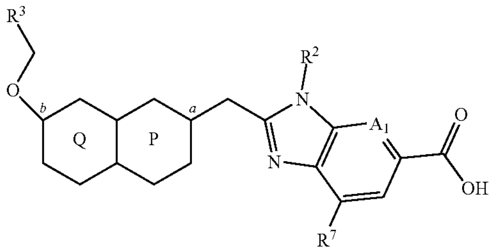

are shown below. Regarding the compound represented by formula (III), embodiments of all the combinations of specific examples shown below are mentioned as examples.

$A_1$ includes $C(R^5)$ or N (referred to as A'-1).

$A_1$ includes $C(R^5)$ (referred to as A'-2).

$A_1$ includes C(H) (referred to as A'-3).

$A_1$ includes C(F) (referred to as A'-4).

$A_1$ includes N (referred to as A'-5).

$R^5$ includes a hydrogen atom or halogen (referred to as B'-1).

$R^5$ includes a hydrogen atom (referred to as B'-2).

$R^5$ includes halogen (referred to as B'-3).

$R^7$ includes a hydrogen atom, halogen, or substituted or unsubstituted alkyloxy (referred to as C'-1).

$R^7$ includes a hydrogen atom or halogen (referred to as C'-2).

$R^7$ includes a hydrogen atom (referred to as C'-3).

$R^7$ includes halogen (referred to as C'-4).

$R^2$ includes alkyl substituted with substituted or unsubstituted non-aromatic heterocycle, or alkyl substituted with substituted or unsubstituted aromatic heterocycle (referred to as D'-1).

$R^2$ includes oxetanylalkyl or alkylimidazolylalkyl (referred to as D'-2).

$R^2$ includes oxetanylmethyl or ethylimidazolylmethyl (referred to as D'-3).

$R^2$ includes oxetanylmethyl (referred to as D'-4).

$R^2$ includes alkylimidazolylmethyl (referred to as D'-5).

$R^2$ includes ethylimidazolylmethyl (referred to as D'-6).

Ring represented by

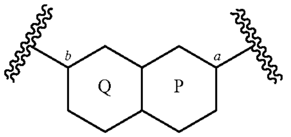

include rings shown below (referred to as E'-1):

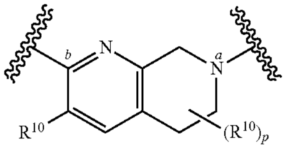

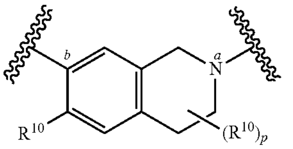

or

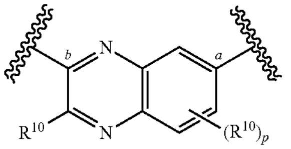

Ring represented by

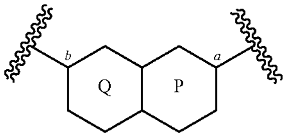

include rings shown below (referred to as E'-2):

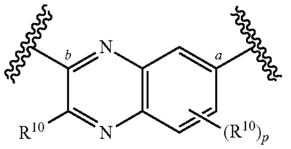

Ring represented by

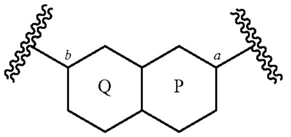

include rings shown below (referred to as E'-3):

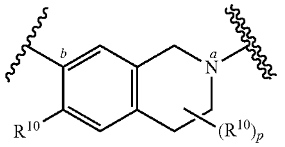

Ring represented by

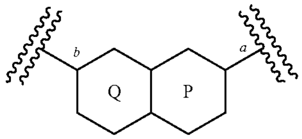

include rings shown below (referred to as E'-4):

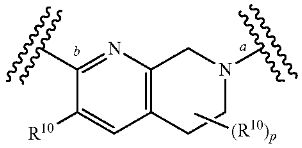

$R^{10}$ includes each independently halogen, cyano, or substituted or unsubstituted alkyl (referred to as F'-1).

$R^{10}$ includes each independently halogen, or substituted or unsubstituted alkyl (referred to as F'-2).

$R^{10}$ includes each independently halogen (referred to as F'-3).

$R^{10}$ includes each independently cyano (referred to as F'-4).

$R^{10}$ includes each independently substituted or unsubstituted alkyl (referred to as F'-5).

When $R^{10}$ is bonded to ring P, $R^{10}$ includes each independently halogen, or substituted or unsubstituted alkyl (referred to as F'-6).

When $R^{10}$ is bonded to ring P, $R^{10}$ includes each independently halogen or alkyl (referred to as F'-7).

When $R^{10}$ is bonded to ring P, $R^{10}$ includes each independently alkyl (referred to as F'-8).

When $R^{10}$ is bonded to ring P, $R^{10}$ includes each independently halogen (referred to as F'-9).

When $R^{10}$ is bonded to ring Q, $R^{10}$ includes halogen, or substituted or unsubstituted alkyl (referred to as F'-10).

When $R^{10}$ is bonded to ring Q, $R^{10}$ includes halogen, or alkyl substituted with halogen (referred to as F'-11).

When $R^{10}$ is bonded to ring Q, $R^{10}$ includes halogen, or alkyl substituted with fluorine (referred to as F'-12).

When $R^{10}$ is bonded to ring Q, $R^{10}$ includes alkyl substituted with halogen (referred to as F'-13).

When $R^{10}$ is bonded to ring Q, $R^{10}$ includes alkyl substituted with fluorine (referred to as F'-14).

When $R^{10}$ is bonded to ring Q, $R^{10}$ includes halogen (referred to as F'-15).

p includes an integer of 0 or 1 (referred to as G'-1).

p includes 0 (referred to as G'-2).

p includes 1 (referred to as G'-3).

$R^3$ includes a group represented by:

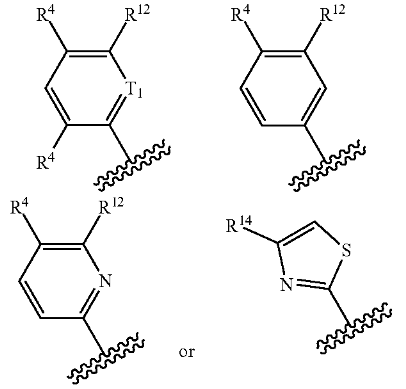

or (referred to as H'-1).

$R^3$ includes a group represented by:

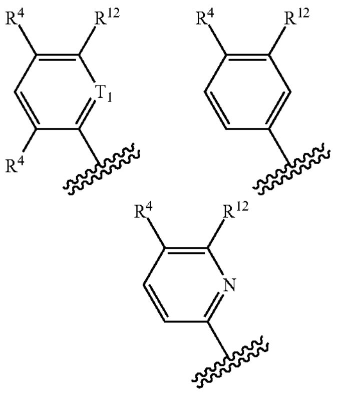

or (referred to as H'-2).

$R^3$ includes a group represented by:

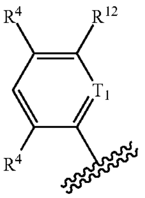

(referred to as H'-3).

$R^3$ includes a group represented by:

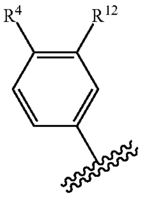

(referred to as H'-4).

$R^3$ includes a group represented by:

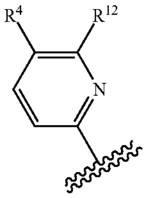

(referred to as H'-5).

$T_1$ includes $C(R^{12})$ or N (referred to as I'-1).

$T_1$ includes $C(R^{12})$ (referred to as I'-2).

$T_1$ includes N (referred to as I'-3).

$R^4$ includes each independently halogen, cyano, substituted or unsubstituted alkyl, substituted or unsubstituted alkyloxy, or substituted or unsubstituted non-aromatic carbocyclyloxy (referred to as J'-1).

$R^4$ includes each independently halogen, cyano, substituted or unsubstituted alkyl, or substituted or unsubstituted alkyloxy (referred to as J'-2).

$R^4$ includes each independently a hydrogen atom, halogen, or substituted or unsubstituted alkyl (referred to as J'-3).

$R^4$ includes each independently halogen, alkyl substituted with halogen, or unsubstituted alkyl (referred to as J'-4).

$R^4$ includes each independently halogen, or substituted or unsubstituted alkyloxy (referred to as J'-5).

$R^4$ includes each independently halogen, alkyloxy substituted with halogen, or unsubstituted alkyloxy (referred to as J'-6).

$R^4$ includes each independently halogen, alkyloxy substituted with fluorine, or unsubstituted alkyloxy (referred to as J'-7).

$R^4$ includes each independently halogen, cyano, unsubstituted alkyl, unsubstituted alkyloxy, or unsubstituted non-aromatic carbocyclyl (referred to as J'-8).

$R^4$ includes each independently halogen (referred to as J'-9).

$R^{14}$ includes unsubstituted alkyl (referred to as K'-1).

$R^{14}$ includes methyl, ethyl, n-propyl, or isopropyl (referred to as K'-2).

$R^{14}$ includes methyl or ethyl (K'-3).

$R^{14}$ includes methyl (K'-4).

$R^{12}$ includes each independently a hydrogen atom or halogen (referred to as L'-1).

$R^{12}$ includes a hydrogen atom (referred to as L'-2).

$R^{12}$ includes each independently halogen (referred to as L'-3).

In particular, the following embodiments are preferable.

(i) A compound represented by formula (I):

(I)

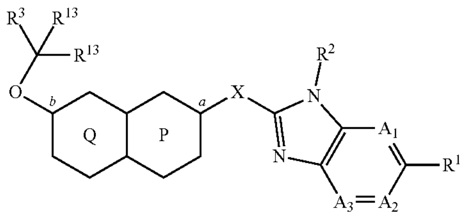

wherein $A_1$ is $C(R^5)$ or N, $A_2$ is $C(R^6)$ or N, $A_3$ is $C(R^7)$ or N, $R^5$, $R^6$, and $R^7$ are each independently a hydrogen atom, halogen, cyano, substituted or unsubstituted alkyl, or substituted or unsubstituted alkyloxy, $R^1$ is carboxy, $R^2$ is alkyl substituted with substituted or unsubstituted non-aromatic heterocycle, or alkyl substituted with substituted or unsubstituted aromatic heterocycle, —X— is —$C(R^8)(R^9)$—, $R^8$ and $R^9$ is each independently a hydrogen atom, halogen, or substituted or unsubstituted alkyl, a ring represented by:

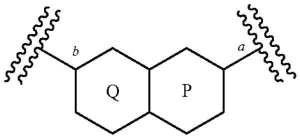

is a ring represented by:

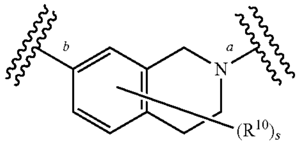

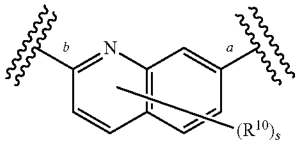

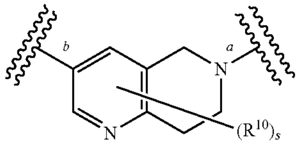

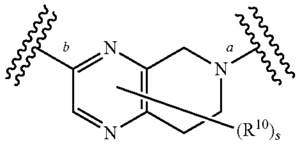

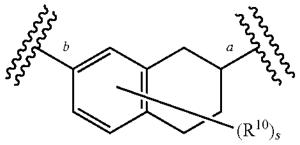

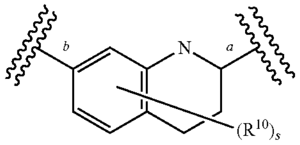

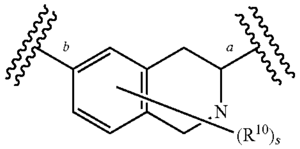

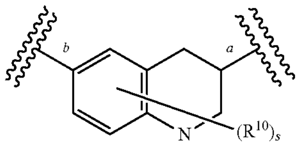

-continued

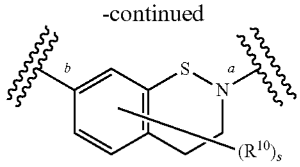

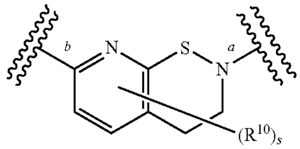

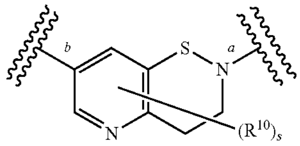

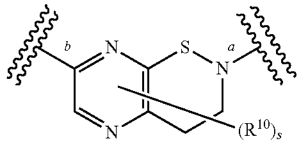

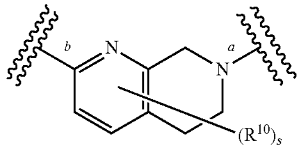

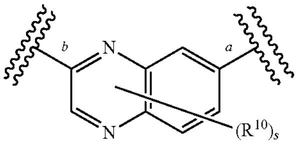

or

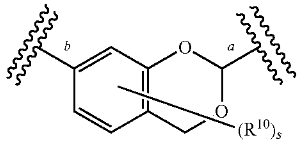

wherein $R^{10}$ is each independently halogen, cyano, hydroxy, substituted or unsubstituted alkyl, oxo, substituted or unsubstituted non-aromatic carbocyclyl, or substituted or unsubstituted alkyloxy, and s is an integer of 0 to 9, $R^{13}$ is each independently a hydrogen atom, halogen, or substituted or unsubstituted alkyl, $R^3$ is substituted or unsubstituted aromatic carbocyclyl, or substituted or unsubstituted aromatic heterocyclyl, or a pharmaceutically acceptable salt of the compound.

(ii) A compound represented by formula (I):

(I)

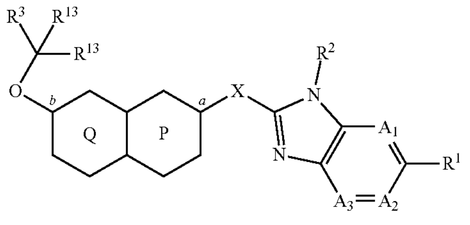

wherein $A_1$ is $C(R^5)$ or N, $A_2$ is $C(R^6)$ or N, $A_3$ is $C(R^7)$ or N, $R^5$, $R^6$, and $R^7$ are each independently a hydrogen atom, halogen, cyano, substituted or unsubstituted alkyl, or substituted or unsubstituted alkyloxy, $R^1$ is carboxy, $R^2$ is alkyl substituted with substituted or unsubstituted non-aromatic heterocycle, or alkyl substituted with substituted or unsubstituted aromatic heterocycle, —X— is —$C(R^8)(R^9)$—, $R^8$ and $R^9$ is each independently a hydrogen atom, halogen, or substituted or unsubstituted alkyl, a ring represented by:

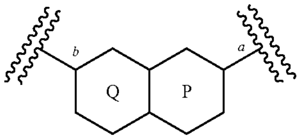

is a ring represented by:

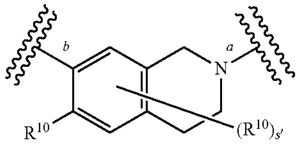

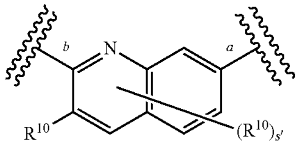

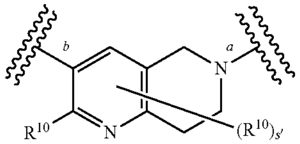

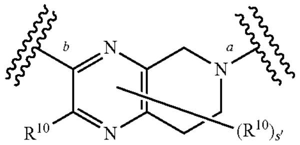

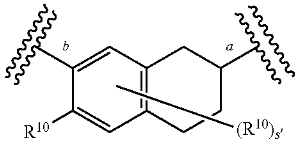

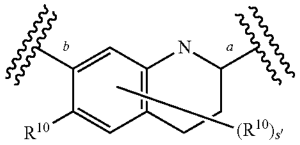

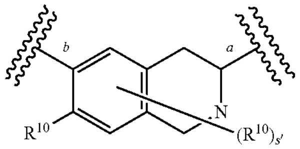

-continued

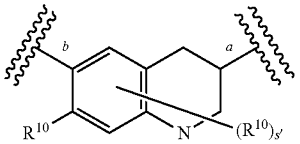

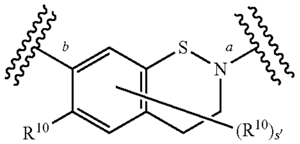

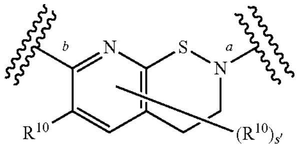

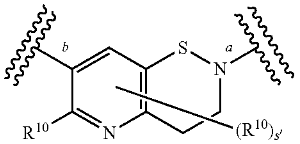

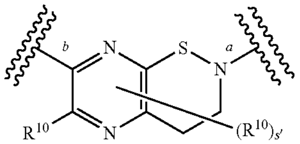

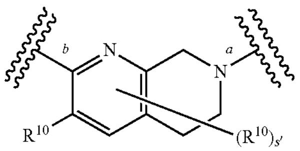

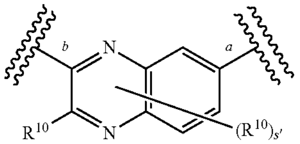

or

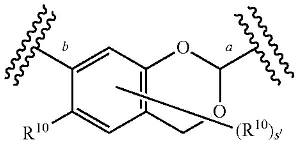

wherein $R^{10}$ is each independently halogen, cyano, hydroxy, substituted or unsubstituted alkyl, oxo, substituted or unsubstituted non-aromatic carbocyclyl, or substituted or unsubstituted alkyloxy, and s' is an integer of 0 to 8, $R^{13}$ is each independently a hydrogen atom, halogen, or substituted or unsubstituted alkyl, $R^3$ is substituted or unsubstituted aromatic carbocyclyl, or substituted or unsubstituted aromatic heterocyclyl, or a pharmaceutically acceptable salt of the compound.

(iii) A compound represented by formula (I):

(I)

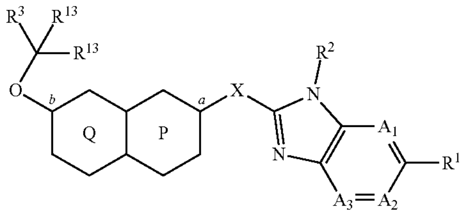

wherein (i) $A_1$ is $C(R^5)$, $A_2$ is $C(R^6)$, and $A_3$ is $C(R^7)$, or (ii) $A_1$ is N, $A_2$ is $C(R^6)$, and $A_3$ is $C(R^7)$, $R^5$, $R^6$, and $R^7$ are each independently a hydrogen atom, halogen, cyano, substituted or unsubstituted alkyl, or substituted or unsubstituted alkyloxy, $R^1$ is carboxy, $R^2$ is alkyl substituted with substituted or unsubstituted non-aromatic heterocycle, or alkyl substituted with substituted or unsubstituted aromatic heterocycle, —X— is —$C(R^8)(R^9)$—, $R^8$ and $R^9$ is each independently a hydrogen atom, halogen, or substituted or unsubstituted alkyl, a ring represented by:

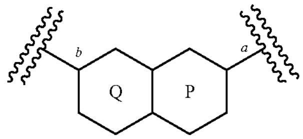

is a ring represented by:

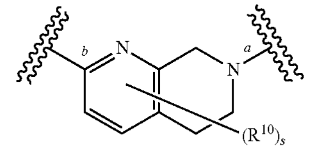

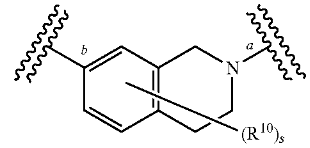

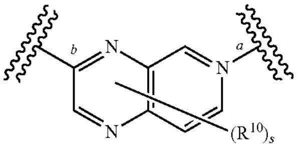

or

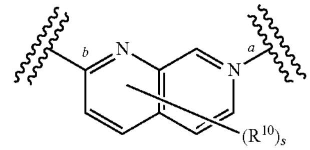

wherein $R^{10}$ is each independently halogen, cyano, hydroxy, substituted or unsubstituted alkyl, oxo, substituted or unsubstituted non-aromatic carbocyclyl, or substituted or unsubstituted alkyloxy, and s is an integer of 1 to 9, $R^{13}$ is each independently a hydrogen atom, halogen, or substituted or unsubstituted alkyl, $R^3$ is substituted or unsubstituted aromatic carbocyclyl, or substituted or unsubstituted aromatic heterocyclyl, or a pharmaceutically acceptable salt of the compound.

(iv) A compound represented by formula (I):

(I)

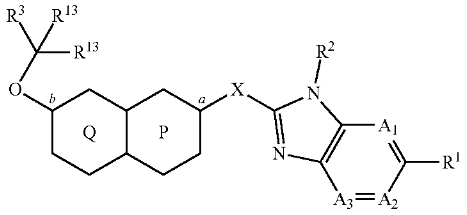

wherein (i) $A_1$ is $C(R^5)$, $A_2$ is $C(R^6)$, and $A_3$ is $C(R^7)$, or (ii) $A_1$ is N, $A_2$ is $C(R^6)$, and $A_3$ is $C(R^7)$, $R^5$, $R^6$, and $R^7$ are each independently a hydrogen atom, halogen, cyano, substituted or unsubstituted alkyl, or substituted or unsubstituted alkyloxy, $R^1$ is carboxy, $R^2$ is alkyl substituted with substituted or unsubstituted non-aromatic heterocycle, or alkyl substituted with substituted or unsubstituted aromatic heterocycle, —X— is —$C(R^8)(R^9)$—, $R^8$ and $R^9$ are each independently a hydrogen atom, halogen, or substituted or unsubstituted alkyl, a ring represented by:

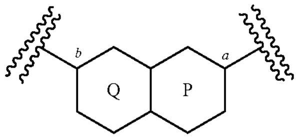

is a ring represented by:

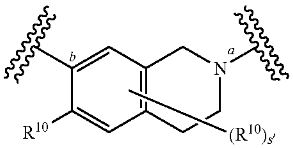

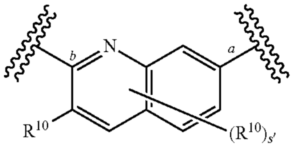

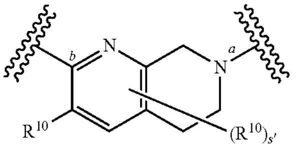

or

-continued

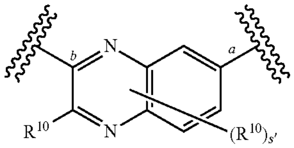

wherein $R^{10}$ is each independently halogen, cyano, hydroxy, substituted or unsubstituted alkyl, oxo, substituted or unsubstituted non-aromatic carbocyclyl, or substituted or unsubstituted alkyloxy, and s' is an integer of 0 to 8, $R^{13}$ is each independently a hydrogen atom, halogen, or substituted or unsubstituted alkyl, $R^3$ is substituted or unsubstituted aromatic carbocyclyl, or substituted or unsubstituted aromatic heterocyclyl, or a pharmaceutically acceptable salt of the compound.

(v) A compound represented by formula (I):

(I)

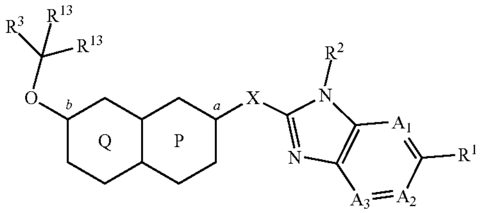

wherein (i) $A_1$ is $C(R^5)$, $A_2$ is $C(R^6)$, and $A_3$ is $C(R^7)$, or (ii) $A_1$ is N, $A_2$ is $C(R^6)$, and $A_3$ is $C(R^7)$, $R^5$, $R^6$, and $R^7$ are each independently a hydrogen atom, halogen, cyano, substituted or unsubstituted alkyl, or substituted or unsubstituted alkyloxy, $R^1$ is carboxy, $R^2$ is alkyl substituted with substituted or unsubstituted non-aromatic heterocycle, or alkyl substituted with substituted or unsubstituted aromatic heterocycle, —X— is —$C(R^8)(R^9)$—, $R^8$ and $R^9$ are each independently a hydrogen atom, halogen, or substituted or unsubstituted alkyl, a ring represented by:

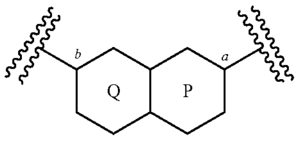

is a ring represented by:

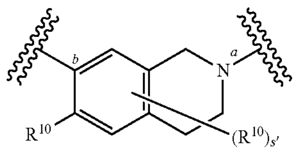

-continued

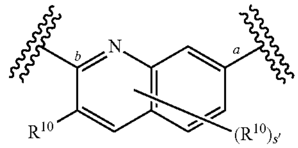

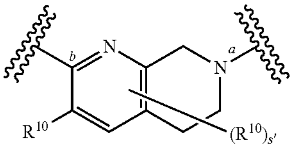

or

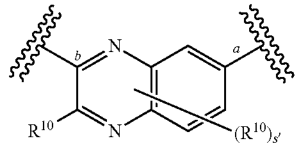

wherein each $R^{10}$ is independently halogen, cyano, hydroxy, substituted or unsubstituted alkyl, oxo, substituted or unsubstituted non-aromatic carbocyclyl, or substituted or unsubstituted alkyloxy, and s' is an integer of 0 to 8, $R^{13}$ is each independently a hydrogen atom, halogen, or substituted or unsubstituted alkyl, $R^3$ is a group represented by:

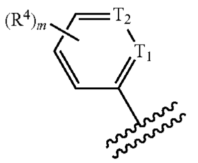

or

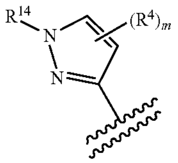

wherein $T_1$ is a carbon atom or a nitrogen atom, $T_2$ is a carbon atom or a nitrogen atom, $R^4$ is each independently halogen, cyano, substituted or unsubstituted alkyl, or substituted or unsubstituted alkyloxy, and $R^{14}$ is a hydrogen atom, or substituted or unsubstituted alkyl, m is an integer of 0 to 5, and n is an integer of 0 to 2), or a pharmaceutically acceptable salt of the compound.

(vi) A compound represented by formula (I):

(I)

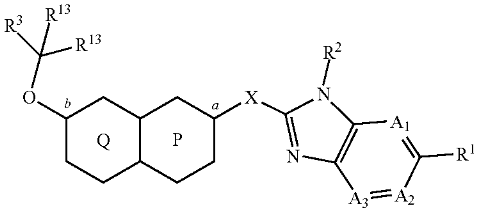

wherein (i) $A_1$ is $C(R^5)$, $A_2$ is $C(R^6)$, and $A_3$ is $C(R^7)$, or (ii) $A_1$ is N, $A_2$ is $C(R^6)$, and $A_3$ is $C(R^7)$, $R^5$, $R^6$, and $R^7$ are each independently a hydrogen atom, halogen, cyano, substituted or unsubstituted alkyl, or substituted or unsubstituted alkyloxy, $R^1$ is carboxy, $R^2$ is alkyl substituted with substituted or unsubstituted non-aromatic heterocycle, or alkyl substituted with substituted or unsubstituted aromatic heterocycle, —X— is —$C(R^8)(R^9)$—, $R^8$ and $R^9$ are each independently a hydrogen atom, halogen, or substituted or unsubstituted alkyl, a ring represented by:

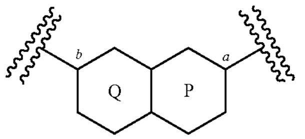

is a ring represented by:

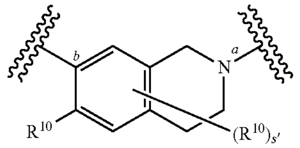

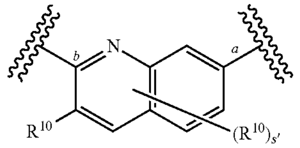

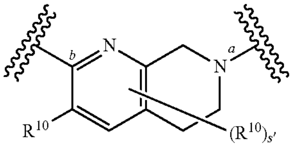

or

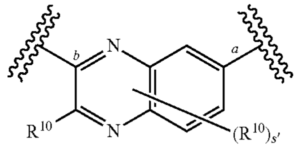

wherein $R^{10}$ is each independently halogen, cyano, hydroxy, substituted or unsubstituted alkyl, oxo, substituted or unsubstituted non-aromatic carbocyclyl, or substituted or unsubstituted alkyloxy, and s' is an integer of 0 to 8, $R^{13}$ is each independently a hydrogen atom, halogen, or substituted or unsubstituted alkyl, $R^3$ is a group represented by:

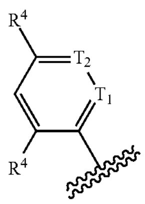

wherein $T_1$ is $C(R^{12})$ or N, $T_2$ is $C(R^{12})$ or N, $R^{12}$ is each independently a hydrogen atom, halogen, cyano, substituted or unsubstituted alkyl, substituted or unsubstituted alkyloxy, substituted or unsubstituted aromatic carbocyclyl, substituted or unsubstituted non-aromatic carbocyclyl, or substituted or unsubstituted alkylsulfonyl, and $R^4$ is each independently halogen, cyano, substituted or unsubstituted alkyl, or substituted or unsubstituted alkyloxy), or a pharmaceutically acceptable salt of the compound.

(vii) A compound represented by formula (I):

(I)

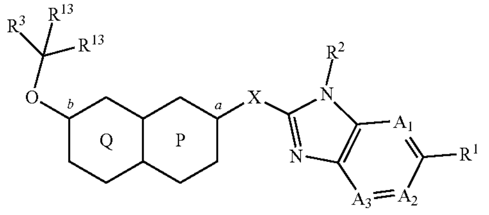

wherein (i) $A_1$ is $C(R^5)$, $A_2$ is $C(R^6)$, and $A_3$ is $C(R^7)$, or (ii) $A_1$ is N, $A_2$ is $C(R^6)$, and $A_3$ is $C(R^7)$, $R^5$, $R^6$, and $R^7$ are each independently a hydrogen atom, halogen, cyano, substituted or unsubstituted alkyl, or substituted or unsubstituted alkyloxy, $R^1$ is carboxy, $R^2$ is oxetanylmethyl or alkylimidazolylmethyl, —X— is —$C(R^8)(R^9)$—, $R^8$ and $R^9$ are each independently a hydrogen atom, halogen, or substituted or unsubstituted alkyl, a ring represented by:

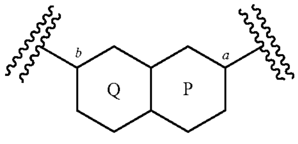

is a ring represented by:

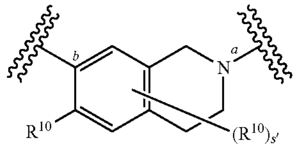

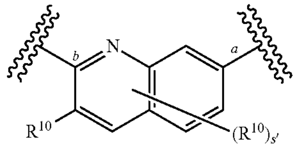

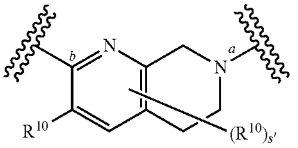

or

-continued

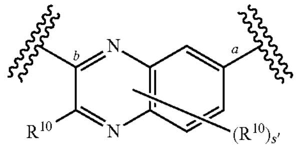

wherein $R^{10}$ is each independently halogen, cyano, hydroxy, substituted or unsubstituted alkyl, oxo, substituted or unsubstituted non-aromatic carbocyclyl, or substituted or unsubstituted alkyloxy, and s' is an integer of 0 to 8, $R^{13}$ is each independently a hydrogen atom, halogen, or substituted or unsubstituted alkyl, $R^3$ is a group represented by:

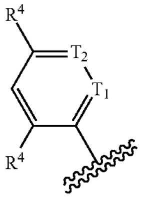

wherein $T_1$ is $C(R^{12})$ or N, $T_2$ is $C(R^{12})$ or N, $R^{12}$ is each independently a hydrogen atom or halogen, and $R^4$ is each independently halogen, cyano, substituted or unsubstituted alkyl, or substituted or unsubstituted alkyloxy, or a pharmaceutically acceptable salt of the compound.

(viii) A compound represented by formula (I):

(I)

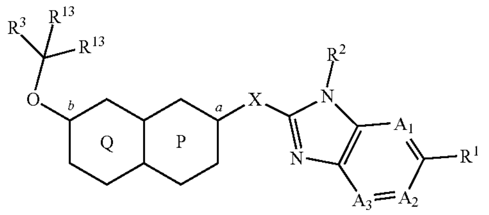

wherein (i) $A_1$ is $C(R^5)$, $A_2$ is $C(R^6)$, and $A_3$ is $C(R^7)$, or (ii) $A_1$ is N, $A_2$ is $C(R^6)$, and $A_3$ is $C(R^7)$, $R^5$, $R^6$, and $R^7$ are each independently a hydrogen atom, halogen, cyano, substituted or unsubstituted alkyl, or substituted or unsubstituted alkyloxy, $R^1$ is carboxy, $R^2$ is oxetanylmethyl or alkylimidazolylmethyl, —X— is $—C(R^8)(R^9)—$, $R^8$ and $R^9$ are hydrogen atoms, a ring represented by:

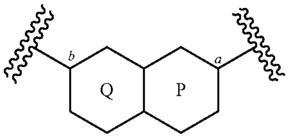

is a ring represented by:

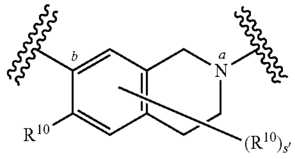

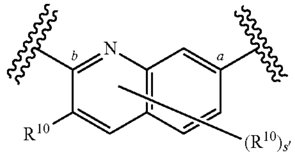

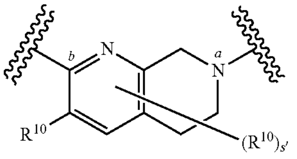

or

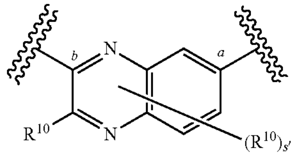

wherein $R^{10}$ is each independently halogen, cyano, hydroxy, substituted or unsubstituted alkyl, oxo, substituted or unsubstituted non-aromatic carbocyclyl, or substituted or unsubstituted alkyloxy, and s' is an integer of 0 to 8, $R^{13}$ is a hydrogen atom, and $R^3$ is a group represented by:

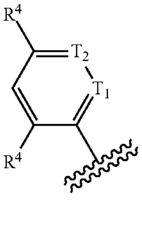

wherein $T_1$ is $C(R^{12})$ or N, $T_2$ is $C(R^{12})$, $R^{12}$ is each independently a hydrogen atom or halogen, and $R^4$ is each independently halogen, cyano, substituted or unsubstituted alkyl, or substituted or unsubstituted alkyloxy, or a pharmaceutically acceptable salt of the compound.

(ix) A compound represented by formula (I):

(I)

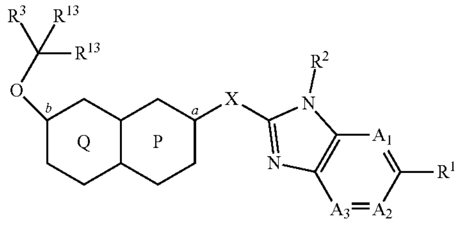

wherein (i) $A_1$ is $C(R^5)$, $A_2$ is $C(R^6)$, and $A_3$ is $C(R^7)$, or (ii) $A_1$ is N, $A_2$ is $C(R^6)$, and $A_3$ is $C(R^7)$, $R^5$, $R^6$, and $R^7$ are each independently a hydrogen atom, halogen, cyano, substituted or unsubstituted alkyl, or substituted or unsubstituted alkyloxy, $R^1$ is carboxy, $R^2$ is oxetanylmethyl or alkylimidazolylmethyl, —X— is —$C(R^8)(R^9)$—, $R^8$ and $R^9$ are hydrogen atoms, a ring represented by:

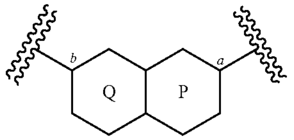

is a ring represented by:

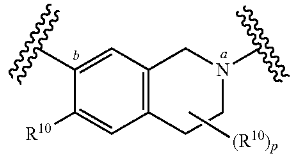

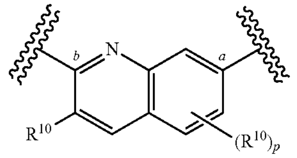

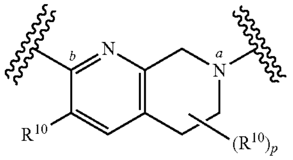

or

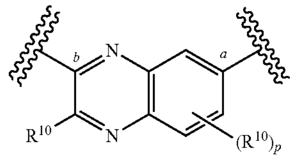

wherein $R^{10}$ is each independently halogen, cyano, hydroxy, substituted or unsubstituted alkyl, oxo, substituted or unsubstituted non-aromatic carbocyclyl, or substituted or unsubstituted alkyloxy, and p is an integer of 0 to 6, $R^{13}$ is a hydrogen atom, and $R^3$ is a group represented by:

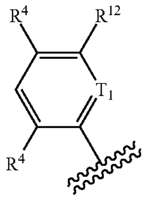

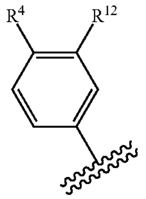

or

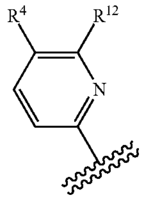

wherein $T_1$ is $C(R^{12})$ or N, $R^{12}$ is each independently a hydrogen atom or halogen, and $R^4$ is each independently halogen, cyano, substituted or unsubstituted alkyl, substituted or unsubstituted alkyloxy, or substituted or unsubstituted non-aromatic carbocyclyl, or a pharmaceutically acceptable salt of the compound.

(x) A compound represented by formula (III):

(III)

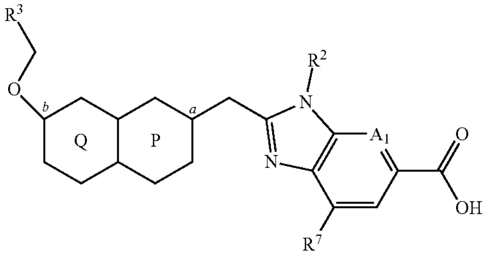

wherein $A_1$ is $C(R^5)$ or N, $R^5$ is a hydrogen atom or halogen, $R^7$ is a hydrogen atom, halogen or substituted or unsubstituted alkyloxy, $R^2$ is alkyl substituted with substituted or unsubstituted non-aromatic heterocycle, or alkyl substituted with substituted or unsubstituted aromatic heterocycle, a ring represented by:

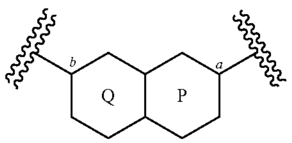

is a ring represented by:

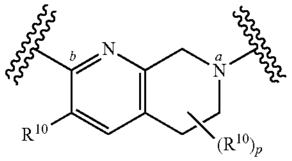

-continued

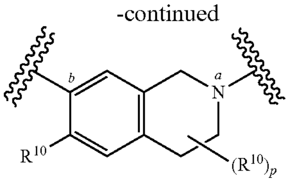

or

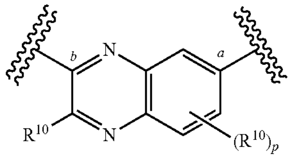

wherein $R^{10}$ is each independently halogen, cyano, or substituted or unsubstituted alkyl, and p is 0 or 1, $R^3$ is a group represented by:

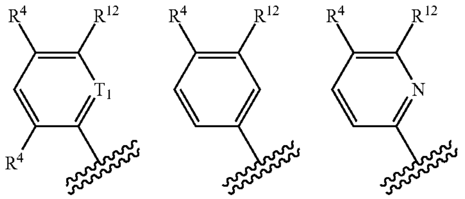

or

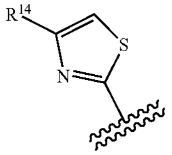

wherein $T_1$ is $C(R^{12})$ or N, $R^{12}$ is each independently a hydrogen atom or halogen, and $R^4$ is each independently a hydrogen atom, halogen, cyano, substituted or unsubstituted alkyl, substituted or unsubstituted alkyloxy, or substituted or unsubstituted non-aromatic carbocyclyl, and $R^{14}$ is unsubstituted alkyl, or a pharmaceutically acceptable salt of the compound.

(xi) A compound represented by formula (III):

(III)

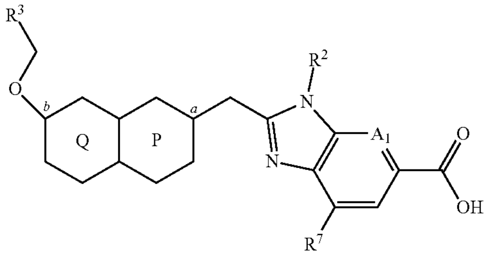

$A_1$ is $C(R^5)$ or N, $R^5$ is a hydrogen atom or halogen, $R^7$ is a hydrogen atom, halogen or substituted or unsubstituted alkyloxy, $R^2$ is alkyl substituted with substituted or unsubstituted non-aromatic heterocycle, or alkyl substituted with substituted or unsubstituted aromatic heterocycle, a ring represented by:

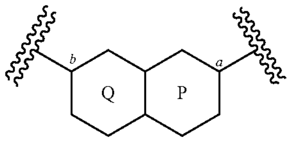

is a ring represented by:

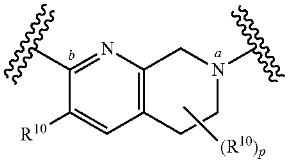

or

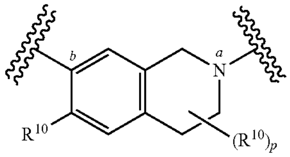

wherein $R^{10}$ is each independently halogen, cyano, or substituted or unsubstituted alkyl, and p is 0 or 1, $R^3$ is a group represented by:

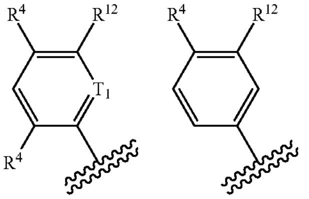

or

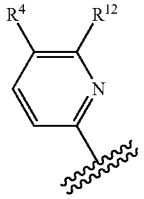

wherein $T_1$ is $C(R^{12})$ or N, $R^{12}$ is each independently a hydrogen atom or halogen, and $R^4$ is each independently halogen, cyano, substituted or unsubstituted alkyl, substituted or unsubstituted alkyloxy, or substituted or unsubstituted non-aromatic carbocyclyl, or a pharmaceutically acceptable salt of the compound.

The compounds represented by formula (I), formula (II), or formula (III) are not limited to specific isomers, but include all possible isomers (e.g., keto-enol isomers, imine-enamine isomers, diastereoisomers, optical isomers, rotational isomers, tautomers as shown below, etc.), racemates, or mixtures thereof.

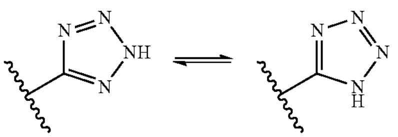

-continued

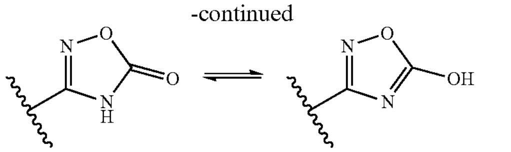

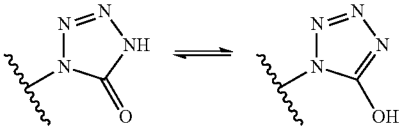

or

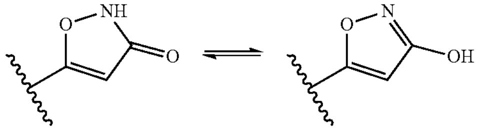

One or more hydrogen, carbon, and/or other atom(s) of the compounds represented by formula (I), formula (II), or formula (III) may be substituted with isotope(s) of hydrogen, carbon, and/or other atom(s), respectively. Examples of such isotopes include hydrogen, carbon, nitrogen, oxygen, phosphorus, sulfur, fluorine, iodine, and chlorine, as in the cases of $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{123}I$, and $^{36}Cl$, respectively. The compounds represented by formula (I), formula (II), or formula (III) also include compounds substituted with such isotopes. The compounds substituted with the isotopes are also useful as pharmaceutical products and include all radiolabeled forms of the compounds represented by formula (I), formula (II), or formula (III). Furthermore, a "radiolabeling method" for producing the "radiolabeled forms" is also included in the present invention, and the "radiolabeled forms" are useful as tools for metabolic pharmacokinetics studies, studies on binding assay, and/or diagnostics.

Radiolabeled forms of the compounds represented by formula (I), formula (II), or formula (III) can be prepared by methods well known in the pertinent art. For example, a tritium-labeled compound represented by formula (I), formula (II), or formula (III) can be prepared by introducing tritium into a specific compound represented by formula (I), formula (II), or formula (III), by a catalytic dehalogenation reaction using tritium. This method comprises reacting an appropriately-halogenated precursor of the compound represented by formula (I), formula (II), or formula (III) with tritium gas in the presence of an appropriate catalyst, such as Pd/C, and in the presence or absence of a base. Regarding other appropriate methods for preparing tritium-labeled compounds, "Isotopes in the Physical and Biomedical Sciences, Vol. 1, Labeled Compounds (Part A), Chapter 6 (1987)" can be referred to. A $^{14}C$-labeled compound can be prepared by using a raw material having $^{14}C$ carbon.

The pharmaceutically acceptable salts of the compounds represented by formula (I), formula (II), or formula (III) include, for example, salts of compounds represented by formula (I), formula (II), or formula (III) with alkaline metal (e.g., lithium, sodium, or potassium), alkaline earth metal (e.g., calcium or barium), magnesium, transition metal (e.g., zinc or iron), ammonia, organic bases (e.g., trimethylamine, triethylamine, dicyclohexylamine, ethanolamine, diethanolamine, triethanolamine, meglumine, ethylenediamine, pyridine, picoline, or quinoline), or amino acids, or salts with inorganic acids (e.g., hydrochloric acid, sulfuric acid, nitric acid, carbonic acid, hydrobromic acid, phosphoric acid, or hydroiodic acid) or organic acids (e.g., formic acid, acetic acid, propionic acid, trifluoroacetic acid, citric acid, lactic acid, tartaric acid, oxalic acid, maleic acid, fumaric acid, succinic acid, mandelic acid, glutaric acid, malic acid, benzoic acid, phthalic acid, ascorbic acid, benzenesulfonic acid, p-toluenesulfonic acid, methanesulfonic acid, ethanesulfonic acid, or trifluoroacetic acid). Particularly, examples of salts include hydrochloric acid, phosphoric acid, tartaric acid, or methanesulfonic acid. These salts can be formed according to methods that are conventionally carried out.

The compounds represented by formula (I), formula (II), or formula (III) of the present invention or pharmaceutically acceptable salts thereof may form solvates (e.g., hydrates), co-crystals, and/or crystal polymorphs. The present invention encompasses those various solvates, co-crystals, and crystal polymorphs. The "solvates" may have the compounds represented by formula (I), formula (II), or formula (III) coordinated with any number of solvent molecules (e.g., water molecules). When the compounds represented by formula (I), formula (II), or formula (III), or pharmaceutically acceptable salts thereof are allowed to stand in the atmosphere, the compounds may absorb water, resulting in attachment of adsorbed water or formation of hydrates. Recrystallization of the compounds represented by formula (I), formula (II), or formula (III), or pharmaceutically acceptable salts thereof may produce crystal polymorphs. The "co-crystal" means that a compound represented by formula (I), formula (II), or formula (III), or a salt thereof and a counter molecule exist in the same crystal lattice, and it can include any number of counter molecules.

The compounds represented by formula (I), formula (II), or formula (III) or pharmaceutically acceptable salts thereof may form prodrugs. The present invention also encompasses such various prodrugs. A prodrug is a derivative of a compound of the present invention having a group that can be chemically or metabolically degraded, and is a compound which becomes a pharmaceutically active compound of the present invention in vivo as a result of solvolysis or under physiological conditions. Prodrugs include compounds that are converted to the compounds represented by formula (I), formula (II), or formula (III) through enzymatic oxidation, reduction, hydrolysis, or the like under physiological conditions in vivo, compounds that are converted to the compounds represented by formula (I), formula (II), or formula (III) through hydrolysis by gastric acid etc., and the like. Methods for selecting and preparing suitable prodrug derivatives are described in, for example, "Design of Prodrugs, Elsevier, Amsterdam, 1985". A prodrug may have activity per se.

When the compounds represented by formula (I), formula (II), or formula (III) or pharmaceutically acceptable salts thereof have hydroxyl group(s), prodrugs include acyloxy derivatives and sulfonyloxy derivatives that are prepared by, for example, reacting compounds having hydroxyl group(s) with suitable acyl halide, suitable acid anhydride, suitable sulfonyl chloride, suitable sulfonyl anhydride, and mixed anhydride, or with a condensing agent. Examples include $CH_3COO$—, $C_2H_5COO$—, tert-BuCOO—, $C_{15}H_{31}COO$—, PhCOO—, (m-NaOOCPh)COO—, $NaOOCCH_2CH_2COO$—, $CH_3CH(NH_2)COO$—, $CH_2N(CH_3)_2COO$—, $CH_3SO_3$—, $CH_3CH_2SO_3$—, $CF_3SO_3$—, $CH_2FSO_3$—, $CF_3CH_2SO_3$—, p-$CH_3O$-$PhSO_3$—, $PhSO_3$—, and p-$CH_3PhSO_3$—.

(Method for Producing Compound of Present Invention)

The compounds represented by formula (I), formula (II), or formula (III) can be produced by, for example, the general synthesis method described below. Starting materials and reaction reagents used in such synthesis are commercially available or can be synthesized according to methods well known in the art using compounds commercially available. Regarding extraction, purification, and the like, the treatments carried out in ordinary experiments of organic chemistry may be carried out.

The compounds of the present invention can be synthesized with reference to methods known in the art.

In the following steps, when a substituent which interferes with the reaction, e.g. hydroxy, mercapto, amino, formyl, carbonyl, carboxy, is possessed, the substituent is protected by the method such as those described in Protective Groups in Organic Synthesis, Theodora W Greene (John Wiley & Sons) in advance, and the protective group may be removed at a desirable step.

In addition, in the all steps, an order of steps to be implemented may be appropriately changed, and each intermediate may be isolated, and used in a next step. All of reaction time, reaction temperature, solvents, reagents, protecting groups, etc. are mere exemplification and not limited as long as they do not cause an adverse effect on a reaction.

General procedures for the synthesis of the compounds of the present invention are described below. Starting materials and reaction reagents used in such synthesis are commercially available or can be synthesized according to methods well known in the art using compounds commercially available.

For example, the compounds represented by formula (I), formula (II), or formula (III) of the present invention can be prepared by the general synthetic methods described below.

General Synthetic Method 1

[Method A]

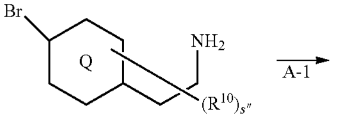

a1

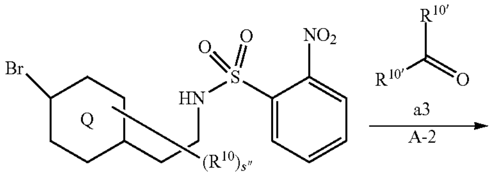

a2

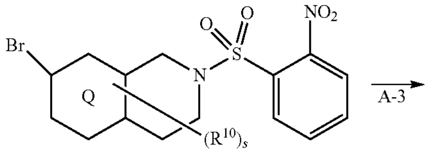

a4

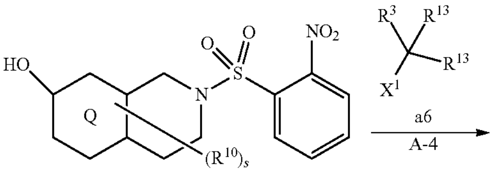

a5

-continued

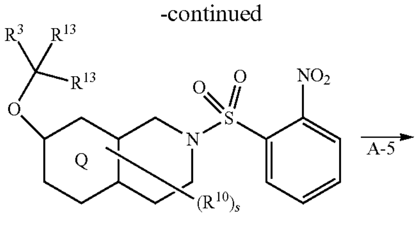

a7

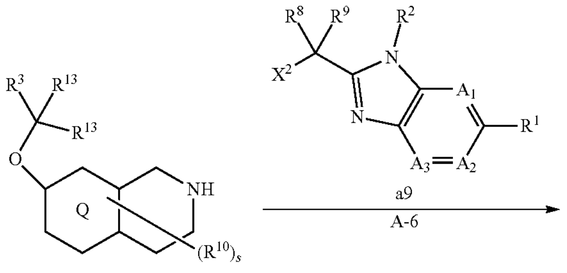

a8

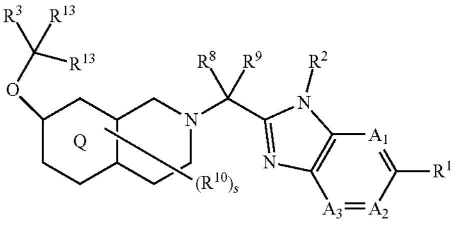

a10 wherein $R^{10}$ is each independently cyano, substituted or unsubstituted alkyl, or a substituted or unsubstituted non-aromatic carbocyclyl, s" is an integer of 0 to 7, $X^1$ is a leaving group such as halogen, $X^2$ is a leaving group such as halogen, and other symbols are the same as those in the above (1).

[Step A-1]

Compound a2 can be obtained by reacting Compound a1 with 2-nitrobenzenesulfonyl chloride in the presence of a base.

Examples of the base include sodium hydroxide, sodium carbonate, sodium hydrogen carbonate, potassium carbonate, calcium carbonate, cesium carbonate, pyridine, and triethylamine, and the base can be used at 1 to 5 molar equivalents relative to Compound a1.

The reaction temperature is −10° C. to 80° C., preferably 10° C. to 60° C.

The reaction time is 0.5 hours to 24 hours, and preferably 1 hour to 12 hours.

Examples of the reaction solvent, dichloromethane, tetrahydrofuran, dioxane, and acetonitrile, and one of or a mixture of these can be used.

[Step A-2]

Compound a4 can be obtained by reacting Compound a2 and Compound a3 in an acid solvent.

The reaction temperature is 20° C. to 80° C., preferably 30° C. to 60° C.

The reaction time is 0.5 hours to 24 hours, and preferably 1 hour to 12 hours.

Examples of the reaction solvent include acetic acid and concentrated sulfuric acid, and one of or a mixture of these can be used.

[Step A-3]

Compound a5 can be obtained by reacting Compound a4 with a metal catalyst and potassium acetate, as well as bis(pinacolato)diborane, and then adding hydrogen peroxide water and water thereto.

Examples of the metal catalyst include [1,1'-bis(diphenylphosphino)ferrocene]palladium(II) dichloride dichloromethane adduct, palladium acetate, bis(dibenzylideneacetone)palladium, tetrakis(triphenylphosphine)palladium, bis(triphenylphosphine)palladium (II) dichloride, and bis(tri-tert-butylphosphine)palladium, and the metal catalyst can be used at 0.001 to 0.5 molar equivalents relative to Compound a4.

The reaction temperature may be 0° C. to reflux temperature of solvent, and if necessary, by a microwave irradiation.

The reaction time is 0.1 hours to 48 hours, and preferably 0.5 hours to 12 hours.

Examples of the reaction solvent include tetrahydrofuran, toluene, DMF, and dioxane, and one of or a mixture of these can be used.

[Step A-4]

Compound a7 can be obtained by reacting Compound a5 with Compound a6 in the presence of a base.

The reaction temperature is 0° C. to the reflux temperature of the solvent.

The reaction time is 0.5 hours to 12 hours, and preferably 1 hour to 6 hours.

As the base, potassium tert-butoxide, sodium tert-butoxide, sodium carbonate, potassium carbonate, cesium carbonate, or the like can be used.

Examples of the reaction solvent include methanol, ethanol, acetonitrile, tetrahydrofuran, and dimethylformamide, and one of or a mixture of these can be used.

[Step A-5]

Compound a8 can be obtained by reacting Compound a7 with thiol in the presence of a base.

The reaction temperature is 0° C. to 80° C., preferably 30° C. to 60° C.

The reaction time is 0.5 hours to 24 hours, and preferably 1 hour to 12 hours.

As the base, potassium tert-butoxide, sodium tert-butoxide, sodium carbonate, potassium carbonate, cesium carbonate, or the like can be used.

As the thiol, ethanethiol, dodecane-1-thiol, or the like can be used.

Examples of the reaction solvent acetonitrile, tetrahydrofuran and DMF, and one of or a mixture of these can be used.

[Step A-6]

Compound a10 can be obtained by reacting Compound a8 with Compound a9 in the presence of a base.

The reaction temperature is 0° C. to the reflux temperature of the solvent.

The reaction time is 0.5 hours to 12 hours, and preferably 1 hour to 6 hours.

As the base, potassium tert-butoxide, sodium tert-butoxide, sodium carbonate, potassium carbonate, cesium carbonate, or the like can be used.

Examples of the reaction solvent include methanol, ethanol, acetonitrile, tetrahydrofuran, and DMF, and one of or a mixture of these can be used.

General Synthetic Method 2

[Method B]

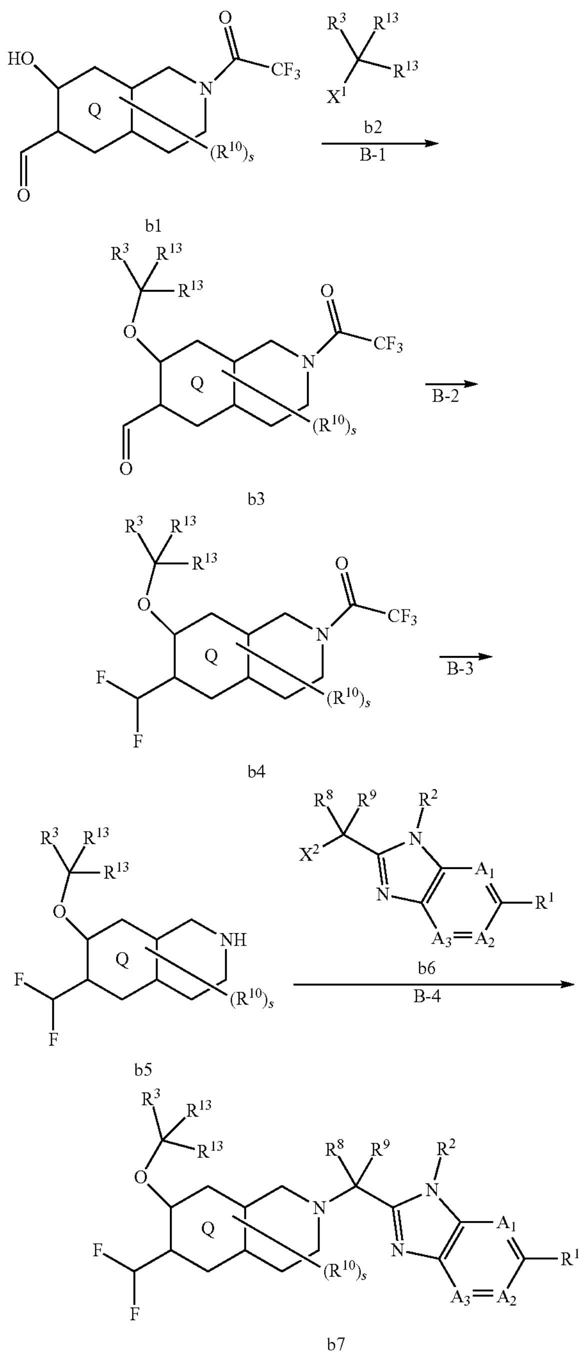

wherein $X^1$ and $X^2$ are the same as those in the above-described method A, and the other symbols are the same as those in the above (1).

[Step B-1]

Compound b3 can be obtained by reacting Compound b1 with Compound b2 in the presence of a base.

The reaction temperature is 0° C. to the reflux temperature of the solvent.

The reaction time is 0.5 hours to 12 hours, and preferably 1 hour to 6 hours.

As the base, potassium tert-butoxide, sodium tert-butoxide, sodium carbonate, potassium carbonate, cesium carbonate, or the like can be used.

Examples of the reaction solvent include methanol, ethanol, acetonitrile, tetrahydrofuran, and dimethylformamide, and one of or a mixture of these can be used.

[Step B-2]

Compound b4 can be obtained by reacting Compound b3 with a fluorinating agent.

The reaction temperature is 0° C. to 80° C., preferably 30° C. to 60° C.

The reaction time is 0.5 hours to 24 hours, and preferably 1 hour to 12 hours.

As the fluorinating agent, N,N-diethylaminosulfur trifluoride or the like can be used.

Examples of the reaction solvent include dichloromethane and tetrahydrofuran, and one of or a mixture of these can be used.

[Step B-3]

Compound b5 can be obtained by reacting Compound b4 with a basic aqueous solution.

The reaction temperature is 0° C. to 50° C., preferably 0° C. to 30° C.

The reaction time is 0.5 hours to 12 hours, and preferably 1 hour to 6 hours.

As the base, sodium carbonate, potassium carbonate, cesium carbonate, lithium hydroxide, sodium hydroxide, potassium hydroxide, or the like can be used.

Examples of the reaction solvent include methanol, ethanol, water, acetone, acetonitrile, and tetrahydrofuran, and one of or a mixture of these can be used.

[Step B-4]

Compound b7 can be obtained by reacting Compound b5 with Compound b6 in the presence of a base.

The reaction temperature is 0° C. to the reflux temperature of the solvent.

The reaction time is 0.5 hours to 12 hours, and preferably 1 hour to 6 hours.

As the base, potassium tert-butoxide, sodium tert-butoxide, sodium carbonate, potassium carbonate, cesium carbonate, or the like can be used.

Examples of the reaction solvent include methanol, ethanol, acetonitrile, tetrahydrofuran, and dimethylformamide, and one of or a mixture of these can be used.

General Synthetic Method 3

-continued

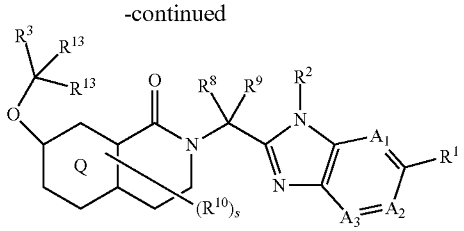

c5 wherein $X^1$ and $X^2$ are the same as those in the above-described method A, and the other symbols are the same as those in the above (1).

[Step C-1]

Compound c3 can be obtained by reacting Compound c1 with Compound c2 in the presence of a base.

The reaction temperature is 0° C. to the reflux temperature of the solvent.

The reaction time is 0.5 hours to 12 hours, and preferably 1 hour to 6 hours.

As the base, potassium tert-butoxide, sodium tert-butoxide, sodium carbonate, potassium carbonate, cesium carbonate, or the like can be used.

Examples of the reaction solvent include methanol, ethanol, acetonitrile, tetrahydrofuran, and DMF, and one of or a mixture of these can be used.

[Step C-2]

Compound c5 can be obtained by reacting Compound c3 with Compound c4 in the presence of a base.

The reaction temperature is 0° C. to the reflux temperature of the solvent.

The reaction time is 0.5 hours to 12 hours, and preferably 1 hour to 6 hours.

As the base, sodium hydride, potassium tert-butoxide, sodium tert-butoxide, or the like can be used.

Examples of the reaction solvent include methanol, ethanol, acetonitrile, tetrahydrofuran, and DMF, and one of or a mixture of these can be used.

General Synthetic Method 4

[Method C]

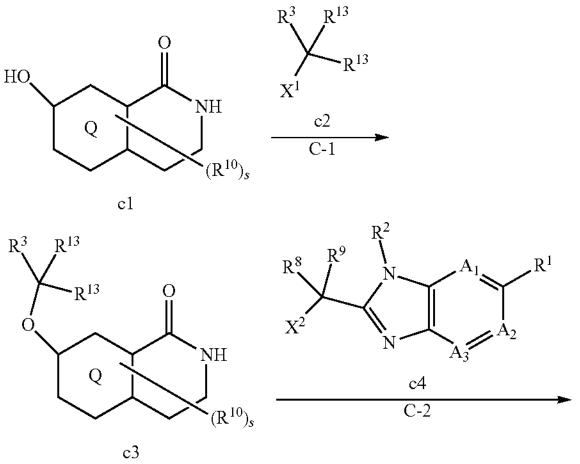

[Method D]

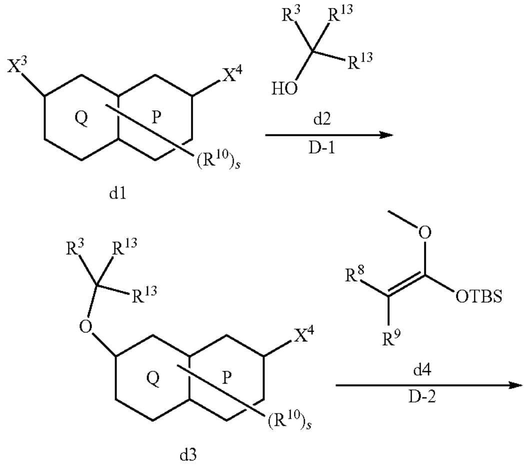

-continued

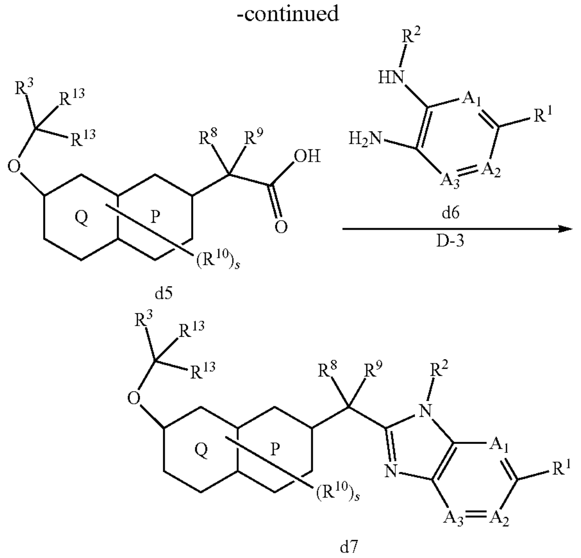

d5
d7 wherein $X^3$ is a leaving group such as halogen, $X^4$ is a leaving group such as halogen, and other symbols are the same as those in the above (1).

[Step D-1]

Compound d3 can be obtained by reacting Compound d1 with Compound d2 in the presence of a base.

The reaction temperature is 0° C. to 50° C., preferably 0° C. to 30° C.

The reaction time is 0.5 hours to 12 hours, and preferably 1 hour to 6 hours.

As the base, potassium tert-butoxide, sodium tert-butoxide, sodium carbonate, potassium carbonate, cesium carbonate, sodium hydride, or the like can be used.

Examples of the reaction solvent include methanol, ethanol, acetonitrile, tetrahydrofuran, and dimethylformamide, and one of or a mixture of these can be used.

[Step D-2]

Compound d5 can be obtained by reacting Compound d3 and Compound d4 in the presence of a metal catalyst and zinc fluoride.

Examples of the metal catalyst include bis-tert-tributylphosphine palladium, and the metal catalyst can be used at 0.001 to 0.5 molar equivalents relative to compound d3.

The reaction temperature may be 20° C. to reflux temperature of solvent, and if necessary, by a microwave irradiation.

The reaction time is 0.1 hours to 48 hours, and preferably 0.5 hours to 12 hours.

Examples of the reaction solvent include tetrahydrofuran, toluene, DMF, dioxane, and water, and one of or a mixture of these can be used.

[Step D-3]

Compound d7 can be obtained by reacting Compound d6 on Compound d5 in the presence of a condensing agent, with a base being also acted thereon as required, followed by a reaction in an acid solution.

Examples of the condensing agent include dicyclohexylcarbodiimide, carbonyldiimidazole, dicyclohexylcarbodiimide-N-hydroxybenzotriazole, EDC, 4-(4,6-dimethoxy-1,3,5-triazin-2-yl)-4-methylmorpholinium chloride, and HATU. The condensing agent can be used at 1 to 5 molar equivalents relative to Compound d6.

Examples of the base include triethylamine, diisopropylethylamine, and paradimethylaminopyridine.

Examples of the acid include hydrochloric acid and acetic acid.

The reaction temperature is −20° C. to 60° C., preferably 0° C. to 30° C. for the condensation reaction, and 10° C. to 80° C. for the subsequent reaction in the acid solution.

The reaction time is 0.1 hours to 24 hours, preferably 1 hour to 12 hours for the condensation reaction, and 0.5 hours to 10 hours for the subsequent reaction in the acid solution.

General Synthetic Method 5

[Method E]

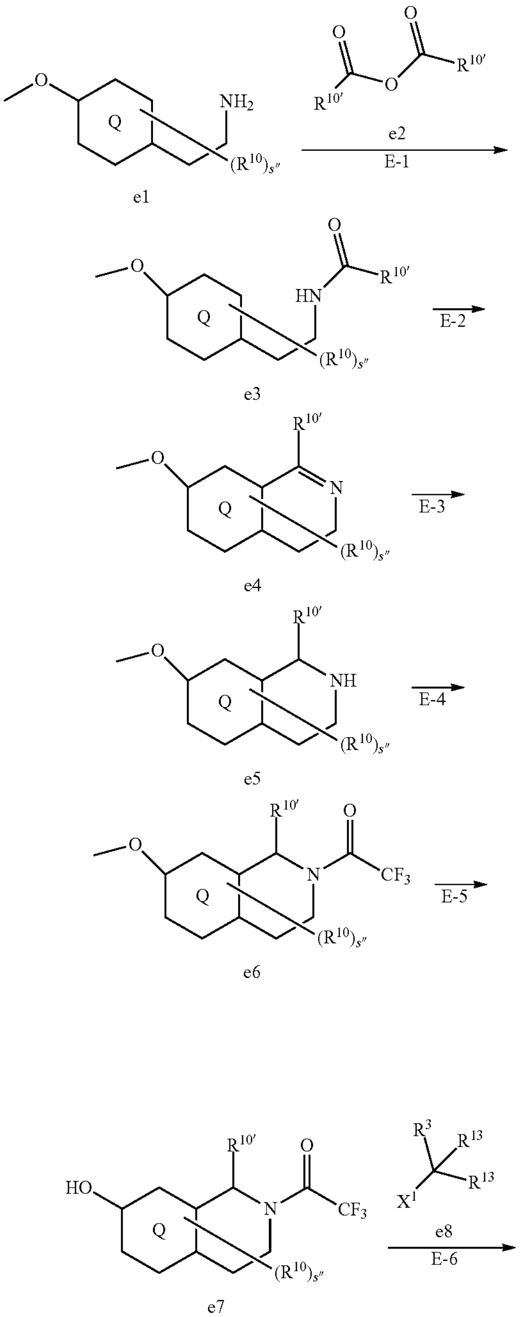

e1
e3
e4
e5
e6
e7

-continued

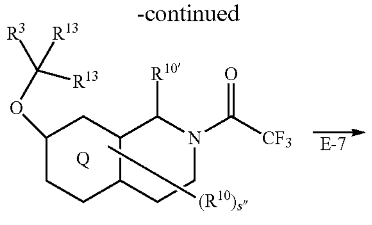

e9

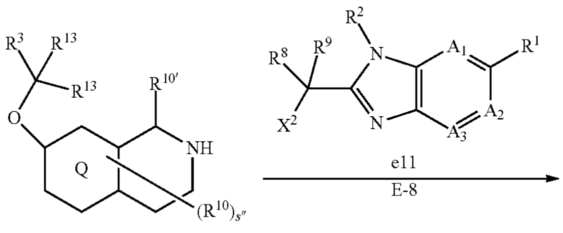

e10

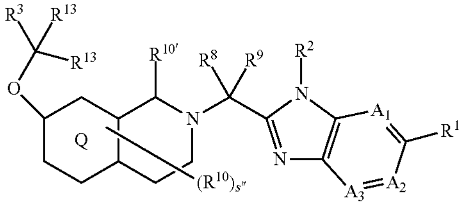

e12 wherein $R^{10'}$, s", $X^1$, and $X^2$ are the same as those in the above-described method A, and the other symbols are the same as those in the above (1).

[Step E-1]

Compound e3 can be obtained by reacting Compound e1 with Compound e2 in the presence of a base.

Examples of the base include sodium hydroxide, sodium carbonate, sodium hydrogen carbonate, potassium carbonate, calcium carbonate, cesium carbonate, pyridine, and triethylamine, and it can be used at 1 to 5 molar equivalents relative to Compound e 1.

The reaction temperature is −10° C. to 80° C., preferably 10° C. to 60° C.

The reaction time is 0.5 hours to 24 hours, and preferably 1 hour to 12 hours.

Examples of the reaction solvent, dichloromethane, tetrahydrofuran, dioxane, and acetonitrile, toluene, and one of or a mixture of these can be used.

[Step E-2]

Compound e4 can be obtained by reacting Compound e3 with diphosphorus pentaoxide, phosphoryl chloride, and the like.

The reaction temperature is −10° C. to 80° C., preferably 10° C. to 60° C.

The reaction time is 0.5 hours to 24 hours, and preferably 1 hour to 12 hours.

As the reaction solvent, toluene or the like can be also used.

[Step E-3]

Compound e5 can be obtained by reacting Compound e4 with formic acid and amine in the presence of a ruthenium catalyst.

Examples of the ruthenium catalyst include [(R,R)—N-(2-amino-1,2-diphenylethyl)-p-toluenesulfonamide]chloro (p-cymene)ruthenium and [(S,S)—N-(2-amino-1,2-diphenylethyl)-p-toluenesulfonamide]chloro(p-cymene)

ruthenium, and the ruthenium catalyst can be used at 0.05 to 1 molar equivalents relative to Compound e4.

Examples of the base include triethylamine, and the base can be used at 1 to 3 molar equivalents relative to Compound e4.

The reaction temperature is −10° C. to 80° C., preferably 10° C. to 60° C.

The reaction time is 0.5 hours to 24 hours, and preferably 1 hour to 12 hours.

As the reaction solvent, acetonitrile or the like can be used.

Step E-3' can be employed as an alternative method to Step E-3.

[Step E-3']

Compound e5 can be obtained by reacting Compound e4 with a reducing agent.

Examples of the reducing agent include sodium borohydride, and the reducing agent can be used at 1 to 5 molar equivalents relative to Compound e4.

The reaction temperature is −10° C. to 80° C., preferably 0° C. to 30° C.

The reaction time is 0.5 hours to 24 hours, and preferably 1 hour to 12 hours.

As the reaction solvent, methanol or the like can be used.

[Step E-4]

Compound e6 can be obtained by reacting Compound e5 with trifluoroacetic anhydride.

The reaction temperature is −10° C. to 80° C., preferably 10° C. to 40° C.

The reaction time is 0.5 hours to 24 hours, and preferably 1 hour to 12 hours.

Examples of the reaction solvent, dichloromethane, tetrahydrofuran, dioxane, and acetonitrile, and one of or a mixture of these can be used.

[Step E-5]

Compound e7 can be obtained by reacting Compound e6 with boron tribromide, aluminum chloride, or the like.

The reaction temperature is −10° C. to 80° C., preferably 0° C. to 40° C.

The reaction time is 0.5 hours to 24 hours, and preferably 1 hour to 12 hours.

As the reaction solvent, dichloromethane, toluene, or the like can be also used.

[Step E-6]

Compound e9 can be obtained by reacting Compound e7 with Compound e8 in the presence of a base.

The reaction temperature is 0° C. to the reflux temperature of the solvent.

The reaction time is 0.5 hours to 12 hours, and preferably 1 hour to 6 hours.

As the base, potassium tert-butoxide, sodium tert-butoxide, sodium carbonate, potassium carbonate, cesium carbonate, or the like can be used.

Examples of the reaction solvent include methanol, ethanol, acetonitrile, tetrahydrofuran, and dimethylformamide, and one of or a mixture of these can be used.

[Step E-7]

Compound e10 can be obtained by reacting Compound e9 with a base.

The reaction temperature is 0° C. to 80° C., preferably 10° C. to 60° C.

The reaction time is 0.5 hours to 12 hours, and preferably 1 hour to 10 hours.

As the base, sodium carbonate, potassium carbonate, cesium carbonate, lithium hydroxide, sodium hydroxide, potassium hydroxide, or the like can be used.

Examples of the reaction solvent include methanol, ethanol, water, acetone, acetonitrile, and tetrahydrofuran, and one of or a mixture of these can be used.

[Step E-8]

Compound e12 can be obtained by reacting Compound e10 with Compound e11 in the presence of a base.

The reaction temperature is 0° C. to the reflux temperature of the solvent.

The reaction time is 0.5 hours to 12 hours, and preferably 1 hour to 6 hours.

As the base, potassium tert-butoxide, sodium tert-butoxide, sodium carbonate, potassium carbonate, cesium carbonate, or the like can be used.

Examples of the reaction solvent include methanol, ethanol, acetonitrile, tetrahydrofuran, and dimethylformamide, and one of or a mixture of these can be used.

General Synthetic Method 6

[Method F]

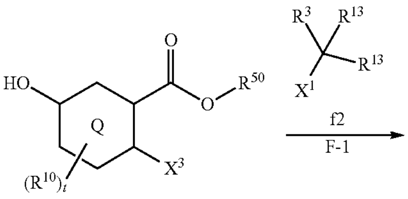

f1

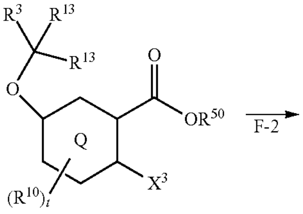

f3

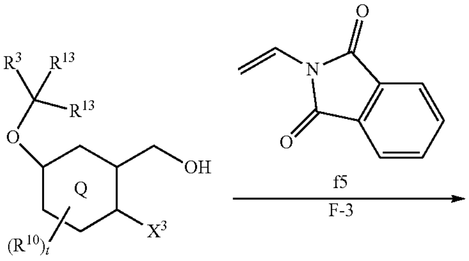

f4

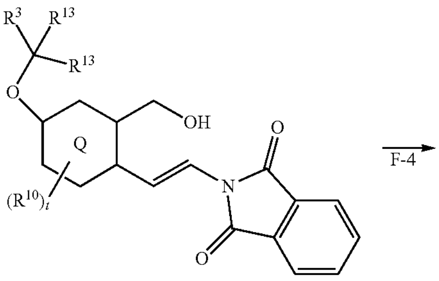

f6

-continued

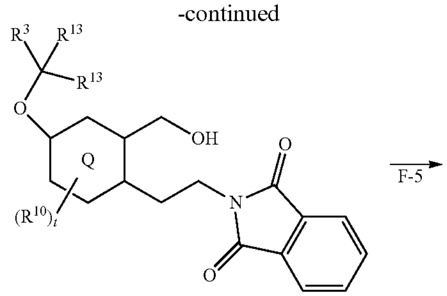

f7

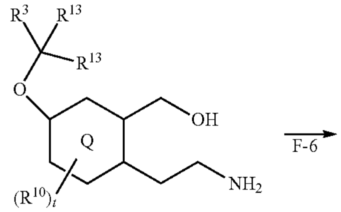

f8

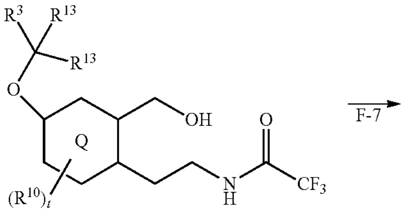

f9

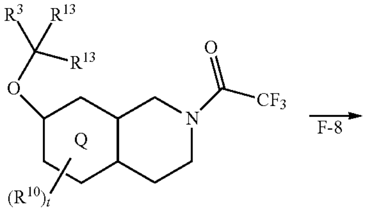

f10

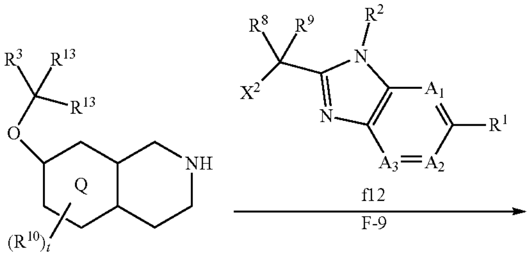

f11

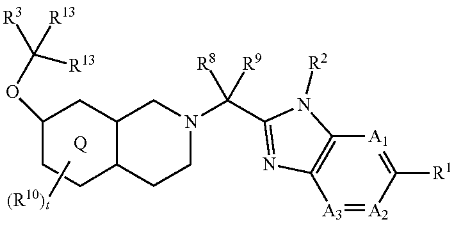

f13 wherein $R^{50}$ is alkyl, t is an integer of 0 to 3, $X^3$ is a leaving group such as halogen, $X^1$ and $X^2$ are the same as those in the above-described Method A, and other symbols are the same as those in the above (1).

[Step F-1]

Compound f3 can be obtained by reacting Compound f1 with Compound f2 in the presence of a base.

The reaction temperature is 0° C. to the reflux temperature of the solvent.

The reaction time is 0.5 hours to 12 hours, and preferably 1 hour to 6 hours.

As the base, potassium tert-butoxide, sodium tert-butoxide, sodium carbonate, potassium carbonate, cesium carbonate, silver carbonate, or the like can be used.

Examples of the reaction solvent include methanol, ethanol, acetonitrile, tetrahydrofuran, dimethylformamide, and dioxane, and one of or a mixture of these can be used.

[Step F-2]

Compound f4 can be obtained by reacting Compound f3 with a reducing agent.

Examples of the reducing agent include sodium borohydride, lithium borohydride, lithium aluminum hydride, and diisobutylaluminum hydride, and the reducing agent can be used at 1 to 10 molar equivalents relative to Compound f3.

The reaction temperature is 0° C. to the reflux temperature, preferably 20° C. to the reflux temperature.

The reaction time is 0.2 hours to 48 hours, and preferably 1 hour to 24 hours.

Examples of the reaction solvent include methanol, ethanol, propanol, isopropanol, butanol, tetrahydrofuran, diethyl ether, dichloromethane, and water, and one of or a mixture of these can be used.

[Step F-3]

In the presence of a metal catalyst and a base, tetrabutylammonium bromide or the like is added as necessary, and Compounds f4 and f5 are reacted with each other, whereby Compound f6 can be obtained.

Examples of the metal catalyst include palladium acetate, bis(dibenzylideneacetone)palladium, tetrakis(triphenylphosphine)palladium, bis(triphenylphosphine)palladium (II) dichloride, and bis(tri-tert-butylphosphine)palladium, and the metal catalyst can be used at 0.001 to 0.5 molar equivalents relative to Compound f4.

Examples of the base include dicyclohexylamine, potassium tert-butoxide, sodium carbonate, and potassium carbonate, and the base can be used at 1 to 10 molar equivalents relative to Compound f4.

The reaction temperature may be 20° C. to reflux temperature of solvent, and if necessary, by a microwave irradiation.

The reaction time is 0.1 hours to 48 hours, and preferably 0.5 hours to 12 hours.

Examples of the reaction solvent include tetrahydrofuran, toluene, DMF, dioxane, and water, and one of or a mixture of these can be used.

[Step F-4]

Compound f7 can be obtained by reacting compound f6 with hydrogen gas in the presence of a metal catalyst.

Examples of the metal catalyst include palladium-carbon, platinum oxide, rhodium-aluminum oxide, and chlorotris(triphenylphosphine)rhodium(I), and the metal catalyst can be used at 0.01 to 100 weight percent relative to Compound f6.

The hydrogen pressure can be 1 to 50 atm. As the hydrogen source, cyclohexene, 1,4-cyclohexadiene, formic acid, ammonium formate, or the like can also be used.

The reaction temperature is 0° C. to the reflux temperature, preferably 20° C. to 40° C.

The reaction time is 0.5 to 72 hours, preferably 1 to 12 hours.

Examples of the reaction solvent include methanol, ethanol, propanol, isopropanol, butanol, tetrahydrofuran, diethyl ether, toluene, ethyl acetate, acetic acid, and water, and one of or a mixture of these can be used.

[Step F-5]

Compound f8 can be obtained by reacting Compound f7 with hydrazine monohydrate or the like.

The reaction temperature is 0° C. to 100° C., preferably 20° C. to 80° C.

The reaction time is 0.5 hours to 24 hours, and preferably 1 hour to 12 hours.

As the reaction solvent, ethanol or the like can be used.

[Step F-6]

Compound f9 can be obtained by reacting Compound f8 with trifluoroacetic anhydride.

The reaction temperature is −10° C. to 80° C., preferably 0° C. to 40° C.

The reaction time is 0.5 hours to 24 hours, and preferably 1 hour to 12 hours.

Examples of the reaction solvent, dichloromethane, tetrahydrofuran, dioxane, and acetonitrile, and one of or a mixture of these can be used.

[Step F-7]

Compound f10 can be obtained by reacting Compound f9 with triphenylphosphine and a Mitsunobu reagent.

Examples of the Mitsunobu reagent include DEAD and DIAD, and the Mitsunobu reagent can be used at 1 to 5 molar equivalents relative to Compound f9.

The reaction temperature is 0° C. to 60° C., preferably 10° C. to 40° C.

The reaction time is 0.1 hours to 12 hours, and preferably 0.2 hour to 6 hours.

As the reaction solvent, tetrahydrofuran, dioxane, ethyl acetate, toluene, and acetonitrile are exemplified, and one of or a mixture of these can be used.

[Step F-8]

Compound f11 can be obtained by reacting Compound f10 with a base.

The reaction temperature is 0° C. to 80° C., preferably 10° C. to 60° C.

The reaction time is 0.5 hours to 12 hours, and preferably 1 hour to 10 hours.

As the base, sodium carbonate, potassium carbonate, cesium carbonate, lithium hydroxide, sodium hydroxide, potassium hydroxide, or the like can be used.

Examples of the reaction solvent include methanol, ethanol, water, acetone, acetonitrile, and tetrahydrofuran, and one of or a mixture of these can be used.

[Step F-9]

Compound f13 can be obtained by reacting Compound f11 with Compound f12 in the presence of a base.

The reaction temperature is 0° C. to the reflux temperature of the solvent.

The reaction time is 0.5 hours to 12 hours, and preferably 1 hour to 6 hours.

As the base, potassium tert-butoxide, sodium tert-butoxide, sodium carbonate, potassium carbonate, cesium carbonate, or the like can be used.

Examples of the reaction solvent include methanol, ethanol, acetonitrile, tetrahydrofuran, and dimethylformamide, and one of or a mixture of these can be used.

General Synthetic Method 7

[Method G]

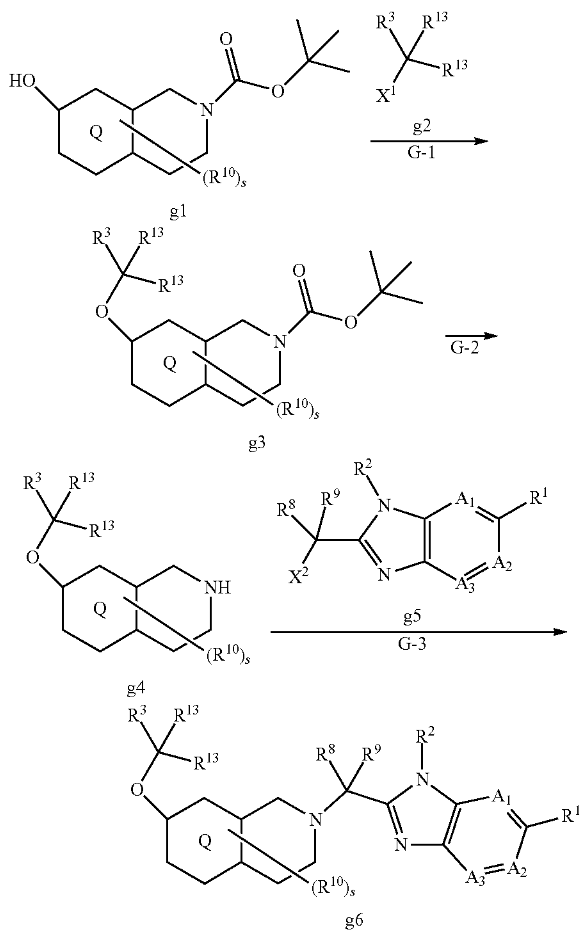

wherein $X^1$ and $X^2$ are the same as those in the above-described method A, and the other symbols are the same as those in the above (1).

[Step G-1]

Compound g3 can be obtained by reacting Compound g1 with Compound g2 in the presence of a base.

The reaction temperature is 0° C. to the reflux temperature of the solvent.

The reaction time is 0.5 hours to 12 hours, and preferably 1 hour to 6 hours.

As the base, potassium tert-butoxide, sodium tert-butoxide, sodium carbonate, potassium carbonate, cesium carbonate, or the like can be used.

Examples of the reaction solvent include methanol, ethanol, acetonitrile, tetrahydrofuran, dimethylformamide, and dioxane, and one of or a mixture of these can be used.

[Step G-2]

Compound g4 can be obtained by reacting Compound g3 with an acid or Lewis acid.

Examples of the acid include hydrochloric acid-ethyl acetate, hydrochloric acid-methanol, hydrochloric acid-dioxane, sulfuric acid, formic acid, and trifluoroacetic acid. Examples of the Lewis acid include trimethylsilyl iodide, $BBr_3$, $AlCl_3$, and $BF_3 \cdot (Et_2O)$, and the Lewis acid can be used at 1 to 10 molar equivalents relative to Compound g3.

The reaction temperature is 0° C. to 60° C., preferably 0° C. to 20° C.

The reaction time is 0.5 hours to 12 hours, and preferably 1 hour to 6 hours.

Examples of the reaction solvent, methanol, ethanol, water, acetone, acetonitrile, DMF, and dichloromethane, and one of or a mixture of these can be used.

[Step G-3]

Compound g6 can be obtained by reacting Compound g4 with Compound g5 in the presence of a base.

The reaction temperature is 0° C. to the reflux temperature of the solvent.

The reaction time is 0.5 hours to 12 hours, and preferably 1 hour to 6 hours.

As the base, potassium tert-butoxide, sodium tert-butoxide, sodium carbonate, potassium carbonate, cesium carbonate, or the like can be used.

Examples of the reaction solvent include methanol, ethanol, acetonitrile, tetrahydrofuran, and dimethylformamide, and one of or a mixture of these can be used.

General Synthetic Method 8

[Method H]

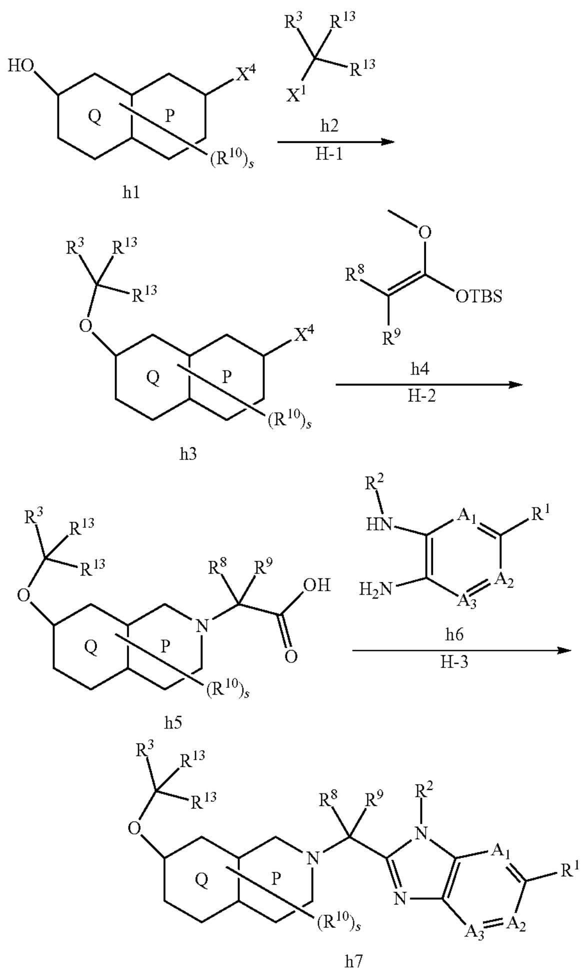

wherein $X^4$ is a leaving group such as halogen, $X^1$ is the same as that in the above-described Method A, and other symbols are the same as those the above (1).

[Step H-1]

Compound h3 can be obtained by reacting Compound h1 with Compound h2 in the presence of a base.

The reaction temperature is 0° C. to the reflux temperature of the solvent.

The reaction time is 0.5 hours to 12 hours, and preferably 1 hour to 6 hours.

As the base, potassium tert-butoxide, sodium tert-butoxide, sodium carbonate, potassium carbonate, cesium carbonate, silver carbonate, or the like can be used.

Examples of the reaction solvent include methanol, ethanol, acetonitrile, tetrahydrofuran, dimethylformamide, and dioxane, and one of or a mixture of these can be used.

[Step H-2]

Compound h5 can be obtained by reacting Compound h3 and Compound h4 in the presence of a metal catalyst and zinc fluoride.

Examples of the metal catalyst include bis-tert-tributylphosphine palladium, and the metal catalyst can be used at 0.001 to 0.5 molar equivalents relative to compound h3.

The reaction temperature may be 20° C. to reflux temperature of solvent, and if necessary, by a microwave irradiation.

The reaction time is 0.1 hours to 48 hours, and preferably 0.5 hours to 12 hours.

Examples of the reaction solvent include tetrahydrofuran, toluene, DMF, dioxane, and water, and one of or a mixture of these can be used.

[Step H-3]

Compound h7 can be obtained by reacting Compound h5 with Compound h6 in the presence of a condensing agent, with a base being also acted thereon as required, followed by a reaction in an acid solution.

Examples of the condensing agent include dicyclohexylcarbodiimide, carbonyldiimidazole, dicyclohexylcarbodiimide-N-hydroxybenzotriazole, EDC, 4-(4,6-dimethoxy-1,3,5-triazin-2-yl)-4-methylmorpholinium chloride, and HATU. The condensing agent can be used at 1 to 5 molar equivalents relative to Compound h5.

Examples of the base include triethylamine, diisopropylethylamine, and paradimethylaminopyridine.

Examples of the acid include hydrochloric acid and acetic acid.

The reaction temperature is −20° C. to 60° C., preferably 0° C. to 30° C. for the condensation reaction, and 10° C. to 80° C. for the subsequent reaction in the acid solution.

The reaction time is 0.1 hours to 24 hours, preferably 1 hour to 12 hours for the condensation reaction, and 0.5 hours to 10 hours for the subsequent reaction in the acid solution.

General Synthetic Method 9

[Method I]

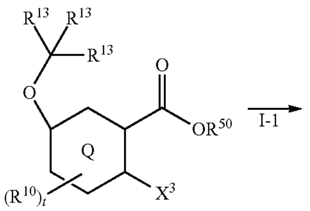

f3

-continued

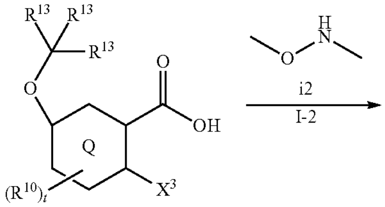

i1

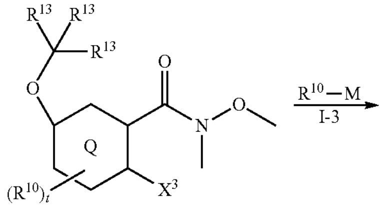

i3

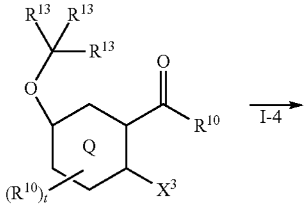

i4

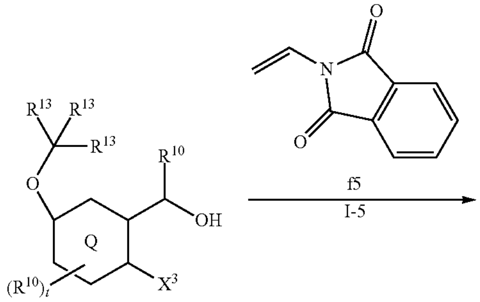

i5

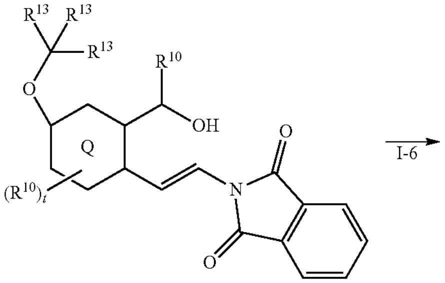

i6

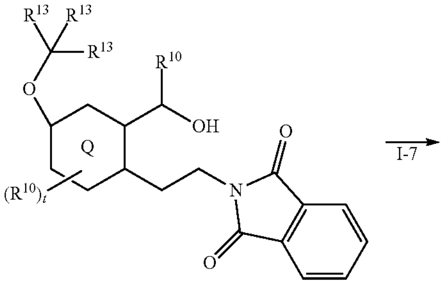

i7

-continued

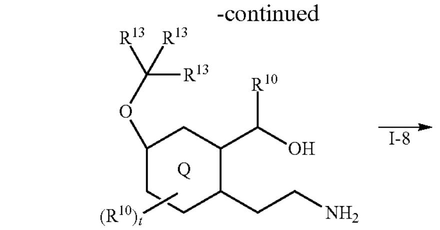

i8

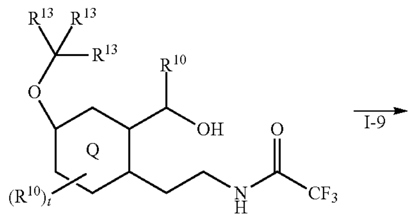

i9

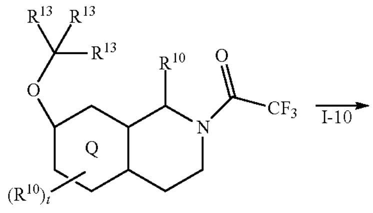

i10

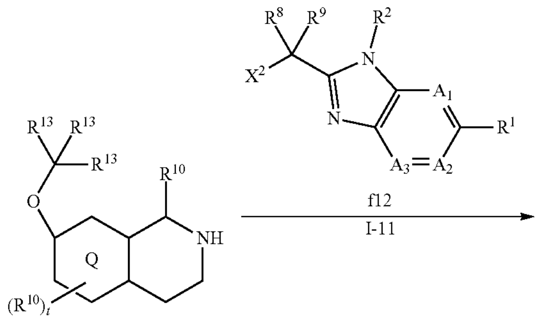

i11

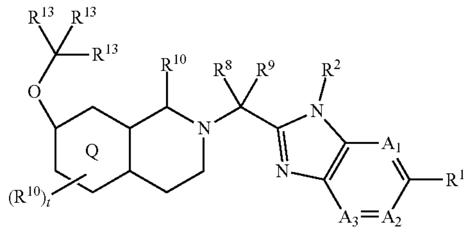

i12 wherein $R^{50}$ is alkyl, t is an integer of 0 to 3, $X^3$ is a leaving group such as halogen, M is Li, MgCl, MgBr, or the like, $X^1$ and $X^2$ are the same as those in the above-described Method A, and other symbols are the same as those in the above (1).

[Step I-1]

Compound it can be obtained by reacting Compound f3 with a basic aqueous solution.

The reaction temperature is 0° C. to 70° C., preferably 0° C. to 50° C.

The reaction time is 0.5 hours to 12 hours, and preferably 1 hour to 6 hours.

As the base, sodium carbonate, potassium carbonate, cesium carbonate, lithium hydroxide, sodium hydroxide, potassium hydroxide, or the like can be used.

Examples of the reaction solvent include methanol, ethanol, water, acetone, acetonitrile, and tetrahydrofuran, and one of or a mixture of these can be used.

[Step I-2]

Compound i3 can be obtained by reacting Compound i1 with Compound i2 in the presence of a condensing agent.

Examples of the condensing agent include dicyclohexylcarbodiimide, carbonyldiimidazole, dicyclohexylcarbodiimide-N-hydroxybenzotriazole, EDC, and HATU. These can be used at 1 to 5 molar equivalents relative to Compound i2.

Examples of the base include triethylamine, diisopropylethylamine, and paradimethylaminopyridine.

The reaction temperature is −20° C. to 80° C., preferably 10° C. to 70° C.

The reaction time is 0.1 hours to 24 hours, and preferably 1 hour to 12 hours.

Examples of the reaction solvent include tetrahydrofuran, dichloromethane, and DMF, and one of or a mixture of these can be used.

[Step I-3]

Compound i4 can be obtained by reacting Compound i3 with an organometallic reagent.

Examples of the organometallic reagent include Grignard reagent, and organolithium reagent, and the organometallic reagent can be used at 1 to 10 molar equivalents relative to compound i3.

The reaction temperature is −40° C. to 60° C., preferably −20° C. to 40° C.

The reaction time is 0.5 hours to 24 hours, and preferably 1 hour to 12 hours.

Examples of the reaction solvent include tetrahydrofuran, diethyl ether, and dioxane, and one of or a mixture of these can be used alone or in combination.

[Step I-4]

Compound i5 can be obtained by reacting Compound i4 with formic acid and amine in the presence of a ruthenium catalyst.

Examples of the ruthenium catalyst include [(R,R)—N-(2-amino-1,2-diphenylethyl)-p-toluenesulfonamide]chloro (p-cymene)ruthenium and [(S,S)—N-(2-amino-1,2-diphenylethyl)-p-toluenesulfonamide]chloro(p-cymene) ruthenium, and the ruthenium catalyst can be used at 0.05 to 1 molar equivalents relative to Compound i4.

Examples of the base include triethylamine, and 1 to 5 molar equivalents of the same can be used with respect to Compound i4.

The reaction temperature is −10° C. to 80° C., preferably 10° C. to 60° C.

The reaction time is 0.5 hours to 24 hours, and preferably 1 hour to 12 hours.

As the reaction solvent, acetonitrile or the like can be used.

[Step I-5]

In the presence of a metal catalyst and a base, tetrabutylammonium bromide or the like is added as necessary, and Compounds i5 and f5 are reacted with each other, whereby Compound i6 can be obtained.

Examples of the metal catalyst include palladium acetate, bis(dibenzylideneacetone)palladium, tetrakis(triphenylphosphine)palladium, bis(triphenylphosphine)palladium (II) dichloride, and bis(tri-tert-butylphosphine)palladium, and the metal catalyst can be used at 0.001 to 0.5 molar equivalents relative to Compound i5.

Examples of the base include dicyclohexylamine, potassium tert-butoxide, sodium carbonate, and potassium carbonate, and the base can be used at 1 to 10 molar equivalents relative to Compound i5.

The reaction temperature may be 20° C. to reflux temperature of solvent, and if necessary, by a microwave irradiation.

The reaction time is 0.1 hours to 48 hours, and preferably 0.5 hours to 12 hours.

Examples of the reaction solvent include tetrahydrofuran, toluene, DMF, dioxane, and water, and one of or a mixture of these can be used.

[Step I-6]

Compound i7 can be obtained by reacting compound i6 with hydrogen gas in the presence of a metal catalyst.

Examples of the metal catalyst include palladium-carbon, platinum oxide, rhodium-aluminum oxide, and chlorotris (triphenylphosphine)rhodium(I), and the metal catalyst can be used at 0.01 to 100 weight percent relative to Compound i6.

The hydrogen pressure can be 1 to 50 atm. As the hydrogen source, cyclohexene, 1,4-cyclohexadiene, formic acid, ammonium formate, or the like can also be used.

The reaction temperature is 0° C. to the reflux temperature, preferably 20° C. to 40° C.

The reaction time is 0.5 to 72 hours, preferably 1 to 12 hours.

Examples of the reaction solvent include methanol, ethanol, propanol, isopropanol, butanol, tetrahydrofuran, diethyl ether, toluene, ethyl acetate, acetic acid, and water, and one of or a mixture of these can be used.

[Step I-7]

Compound i8 can be obtained by reacting Compound i7 with hydrazine monohydrate or the like.

The reaction temperature is 0° C. to 100° C., preferably 20° C. to 80° C.

The reaction time is 0.5 hours to 24 hours, and preferably 1 hour to 12 hours.

As the reaction solvent, ethanol or the like can be used.

[Step I-8]

Compound i9 can be obtained by reacting Compound i8 with trifluoroacetic anhydride.

The reaction temperature is −10° C. to 80° C., preferably 0° C. to 40° C.

The reaction time is 0.5 hours to 24 hours, and preferably 1 hour to 12 hours.

Examples of the reaction solvent, dichloromethane, tetrahydrofuran, dioxane, and acetonitrile, and one of or a mixture of these can be used.

[Step I-9]

Compound i10 can be obtained by reacting Compound i9 with triphenylphosphine and a Mitsunobu reagent.

Examples of the Mitsunobu reagent include DEAD and DIAD, and the Mitsunobu reagent can be used at 1 to 5 molar equivalents relative to Compound i9.

The reaction temperature is 0° C. to 60° C., preferably 10° C. to 40° C.

The reaction time is 0.1 hours to 12 hours, and preferably 0.2 hour to 6 hours.

As the reaction solvent, tetrahydrofuran, dioxane, ethyl acetate, toluene, and acetonitrile are exemplified, and one of or a mixture of these can be used.

[Step I-10]

Compound i11 can be obtained by reacting Compound i10 with a base.

The reaction temperature is 0° C. to 80° C., preferably 10° C. to 60° C.

The reaction time is 0.5 hours to 12 hours, and preferably 1 hour to 10 hours.

As the base, sodium carbonate, potassium carbonate, cesium carbonate, lithium hydroxide, sodium hydroxide, potassium hydroxide, or the like can be used.

Examples of the reaction solvent include methanol, ethanol, water, acetone, acetonitrile, and tetrahydrofuran, and one of or a mixture of these can be used.

[Step I-11]

Compound i12 can be obtained by reacting Compound i11 with Compound f12 in the presence of a base.

The reaction temperature is 0° C. to the reflux temperature of the solvent.

The reaction time is 0.5 hours to 12 hours, and preferably 1 hour to 6 hours.

As the base, potassium tert-butoxide, sodium tert-butoxide, sodium carbonate, potassium carbonate, cesium carbonate, or the like can be used.

Examples of the reaction solvent include methanol, ethanol, acetonitrile, tetrahydrofuran, and dimethylformamide, and one of or a mixture of these can be used.

As the compounds according to the present invention have GLP-1 receptor agonist activity, they are useful as a therapeutic and/or preventive agent for diseases associated with the GLP-1 receptor.

When the term "therapeutic agent and/or prophylactic agent" is used in the present invention, this also encompasses a symptom ameliorating agent.

Examples of the disease associated with the GLP-1 receptor include non-insulin-dependent diabetes mellitus (type 2 diabetes mellitus), hyperglycemia, impaired glucose tolerance, insulin-dependent diabetes mellitus (type 1 diabetes mellitus), diabetic complications, obesity, hypertension, dyslipidemia, arteriosclerosis, myocardial infarction, coronary heart disease, cerebral infarction, non-alcoholic steatohepatitis, Parkinson's disease, and dementia.

In the present invention, "diabetes" means a disease or condition in which the metabolism in the production and utilization of glucose is abnormal due to the inability to maintain an appropriate blood glucose level in the body, and encompasses insulin-dependent diabetes (type 1 diabetes mellitus) and non-insulin-dependent diabetes mellitus (type 2 diabetes mellitus).

"Hyperglycemia" refers to a state in which the plasma glucose level is higher than a normal value (for example, in humans, 80 to 110 mg/dL on an empty stomach) at fasting and after glucose load, and is also one of representative symptoms of diabetes.

"Impaired glucose tolerance" includes insulin resistant impaired glucose tolerance and insulin hyposecretion.

"Diabetic complication" means a complication caused by diabetes or hyperglycemia, and may be either an acute complication or a chronic complication. Examples of the "acute complications" include ketoacidosis and infections (for example, skin infections, soft tissue infections, biliary tract infections, respiratory infections, urinary tract infections), and examples of the "chronic complications" include microangiopathies (for example, nephropathy, retinopathy), neurological disorders (for example, a sensory nerve disorder, a motor nerve disorder, or an autonomic nerve disorder), and leg/foot gangrene. Examples of the diabetic complication include diabetic retinopathy, diabetic nephropathy, and diabetic neuropathy. The "coronary heart disease" encompasses myocardial infarction, angina pectoris, and the like.

Examples of the "dementia" include Alzheimer's disease, vascular dementia, and diabetic dementia.

The compound of the present invention has not only GLP-1 receptor agonist activity but also is useful as a medicine, and has any or all of the following excellent characteristics:

a) Inhibitory activity against CYP enzymes (for example, CYP1A2, CYP2C9, CYP2C19, CYP2D6, and CYP3A4) is weak.
b) Satisfactory pharmacokinetics such as high bioavailability and adequate clearance are exhibited.
c) Metabolic stability is high.
d) Irreversible inhibitory activity is not exhibited against CYP enzymes (for example, CYP3A4) within the concentration range of the measurement conditions described in the present specification.
e) Mutagenicity is not exhibited.
f) The cardiovascular risk is low.
g) There is a low risk of hematotoxicity.
h) High solubility is exhibited.

The pharmaceutical composition of the present invention can be administered by either an oral method or a parenteral method. Examples of a parenteral administration method include percutaneous, subcutaneous, intravenous, intra-arterial, intramuscular, intraperitoneal, transmucosal, inhalation, transnasal, ocular instillation, ear instillation, and intravaginal administration.

In the case of oral administration, the pharmaceutical composition may be prepared into any dosage form that is commonly used, such as a solid preparation for internal use (for example, a tablet, a powder preparation, a granular preparation, a capsule, a pill, or a film preparation), or a liquid preparation for internal use (for example, a suspension, an emulsion, an elixir, a syrup, a limonade, a spirit preparation, an aromatic water preparation, an extraction, a decoction, or a tincture) and administered. The tablet may be a dragee, a film-coated tablet, an enteric-coated tablet, a sustained release tablet, a troche, a sublingual tablet, a buccal tablet, a chewable tablet, or an orally disintegrating tablet; the powder preparation and granular preparation may be dry syrups; and the capsule may be a soft capsule, a microcapsule, or a sustained release capsule.

In the case of parenteral administration, the pharmaceutical composition can be suitably administered in any dosage form that is commonly used, such as an injectable preparation, an infusion, or a preparation for external use (for example, an eye drop, a nasal drop, an ear drop, an aerosol, an inhalant, a lotion, an impregnating agent, a liniment, a gargling agent, an enema, an ointment, a plaster, a jelly, a cream, a patch, a poultice, a powder preparation for external use, or a suppository). The injectable preparation may be an emulsion of O/W type, W/O type, O/W/O type, W/O/W type, or the like.

A pharmaceutical composition can be obtained by mixing an effective amount of the compound of the present invention with various pharmaceutical additives appropriate for the dosage form, such as an excipient, a binder, a disintegrating agent, and a lubricating agent, as necessary. Furthermore, the pharmaceutical composition can be prepared into a pharmaceutical composition for use for a child, an elderly, a patient with a serious case, or a surgical operation, by appropriately changing the effective amount of the compound of the present invention, the dosage form, and/or various pharmaceutical additives. The pharmaceutical composition for children is preferably administered to patients under the age of 12 or 15. Also, the pharmaceutical composition for children may be administered to patients under 27 days after birth, of 28 days to 23 months after birth, or 2 years to 11 years, of 12 years to 17 years, or of 18 years of age. The pharmaceutical composition for the elderly is preferably administered to patients of 65 years of age or older.

It is desirable to set the amount of administration of the pharmaceutical composition of the present invention, after considering the age and body weight of the patient, the type and degree of the disease, the route of administration, and the like; however, in the case of oral administration, the amount of administration is usually 0.05 to 100 mg/kg/day and is preferably in the range of 0.1 to 10 mg/kg/day. Although varying depending on the administration route, the dose in the case of parenteral administration is within a range of usually 0.005 to 10 mg/kg/day, preferably 0.01 to 1 mg/kg/day. This may be administered once a day or several times a day.

The compound of the present invention can be used in combination of a combined drug, to increase the activity of the compound or reduce the dose of the compound, or the like. At this time, the timing of administration for the compound of the present invention and the concomitant drug is not limited, and these may be administered simultaneously to the target of administration or may be administered with a time difference.

The amount of administration of the concomitant drug can be appropriately selected based on the clinically used dosage. Furthermore, the blending ratio of the compound of the present invention and the concomitant drug can be appropriately selected according to the target of administration, the route of administration, the target disease, symptoms, combination, and the like. For example, when the target of administration is a human, 0.01 to 100 parts by weight of the concomitant drug may be used with respect to 1 part by weight of the compound of the present invention.

The pharmaceutical composition of the present invention can be used in combination with other anti-obesity agent(s) (the pharmaceutical composition comprising compounds having anti-obesity effect, or the medicinal agent for obesity or for the weight management for obesity). For example, a combination treatment with a pharmaceutical composition comprising a compound having an anti-obesity effect and the compound of the present invention can be used for the prevention and/or treatment of obesity or the weight management for obesity. A combination treatment with the pharmaceutical composition comprising the compound of the present invention and a pharmaceutical composition(s) comprising a compound having an anti-obesity effect can be used for the prevention and/or treatment of obesity or the weight management for obesity. Furthermore, a method of treatment by administering the pharmaceutical composition of the invention can be used in combination of the diet therapy, drug therapy, exercise and the like.

EXAMPLES

Hereinafter, the present invention will be described in more detail by way of Examples, Reference Examples, and Test Examples; however, the present invention is not intended to be limited by these.

Furthermore, abbreviations used in the present specification denote the following meanings.

$CHCl_3$: chloroform
$CDCl_3$: deuterated chloroform
MeOH: methanol
DMSO-$d_6$: deuterated dimethyl sulfoxide
DMSO: dimethyl sulfoxide
DMA: dimethylacetamide
DMF: dimethylformamide THF: tetrahydrofuran
NMP: N-methylpyrrolidone
Ns: 2-nitrobenzenesulfonyl
HOAt: 1-hydroxy-7-azabenzotriazole
HOBt: 1-hydroxybenzotriazole
EDC: 1-ethyl-3-(3-dimethylaminopropyl)carbodiimide
HATU: 2-(7-azabenzotriazol-1-yl)-1,1,3,3-tetramethyluronium hexafluorophosphate
DIBAL: diisobutylaluminum hydride
DIAD: diisopropyl azodicarboxylate
DEAD: diethyl azodicarboxylate
$BBr_3$: boron tribromide
$AlCl_3$: ammonium chloride
$BF_3(Et_2O)$: boron trifluoride diethyl ether complex
TLC: thin layer chromatography
SFC: supercritical fluid chromatography
ODS: octadecylsilyl (Method for Identifying Compound)

The NMR analysis obtained in each Example was performed at 400 MHz, and measurement was made using DMSO-$d_6$, or $CDCl_3$. Furthermore, when NMR data are shown, there are occasions in which all the measured peaks are not described.

The term RT in the specification indicates retention time in an LC/MS: liquid chromatography/mass analysis, and the retention time was measured under the following conditions.

Incidentally, in the specification, the descriptions of [M+H] and [M−H] indicate values observed by mass analysis.

(Measurement Conditions 1)

Column: ACQUITY UPLC BEH C18 (1.7 μm i.d. 2.1×50 mm) (Waters)
Flow rate: 0.8 mL/min
UV detection wavelength: 254 nm
Mobile phase: [A] was 0.1% formic acid-containing aqueous solution, and [B] was 0.1% formic acid-containing acetonitrile solution.
Gradient: A linear gradient of 5% to 100% solvent [B] was carried out for 3.5 minutes, and then 100% solvent [B] was maintained for 0.5 minutes.

(Measurement Conditions 2)

Column: Shim-pack XR-ODS (2.2 μm, i.d. 3.0×50 mm) (Shimadzu)
Flow rate: 1.6 mL/min; UV detection wavelength: 254 nm;
Mobile phase: [A] was 0.1% formic acid-containing aqueous solution, and [B] was 0.1% formic acid-containing acetonitrile solution.
Gradient: linear gradient of 10% to 100% solvent [B] was performed in 3 minutes, and 100% solvent [B] was kept for 0.5 minutes.

(Measurement Conditions 3)

Column: ACQUITY UPLC BEH C18 (1.7 μm i.d. 2.1×50 mm) (Waters)
Flow rate: 0.8 mL/min; UV detection wavelength: 254 nm;
Mobile phase: [A] was 0.1% formic acid-containing aqueous solution, and [B] was 0.1% formic acid-containing acetonitrile solution.
Gradient: linear gradient of 5% to 100% solvent [B] for 3.5 minutes was performed, and then 100% solvent FBI was maintained for 0.5 minute.

(Measurement Conditions 4)

Column: ACQUITY UPLC BEH C18 (1.7 μm i.d. 2.1×50 mm) (Waters)
Flow rate: 0.8 mL/min
UV detection wavelength: 254 nm
Mobile phase: [A] is 10 mM ammonium carbonate in aqueous solution, and [B] is acetonitrile.
Gradient: A linear gradient of 5% to 100% solvent [B] was carried out for 3.5 minutes, and then 100% solvent [B] was maintained for 0.5 minutes.

(Measurement Conditions 5)

Column: L-column 2 ODS (3 μm i.d. 3×50 mm) (manufactured by Chemicals Evaluation and Research Institute)
Flow rate: 1.5 mL/min
UV detection wavelength: 220 nm
Mobile phase: [A] was 0.05% trifluoroacetic acid-containing aqueous solution, and [B] was 0.05% trifluoroacetic acid-containing acetonitrile solution.
Gradient: linear gradient of 5% to 95% solvent FBI was performed in 3.5 minutes, and 95% solvent [B] was kept for 2 minutes.

Example 1 Synthesis of Compound I-023

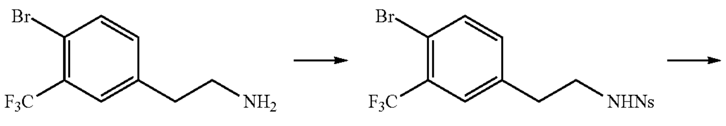

1 2

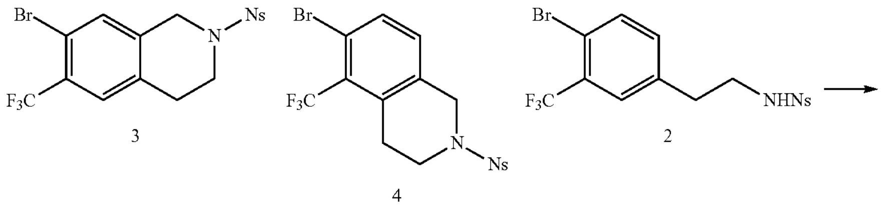

3 4 2

(3:4:2 = 1:0.05:0.2)

-continued
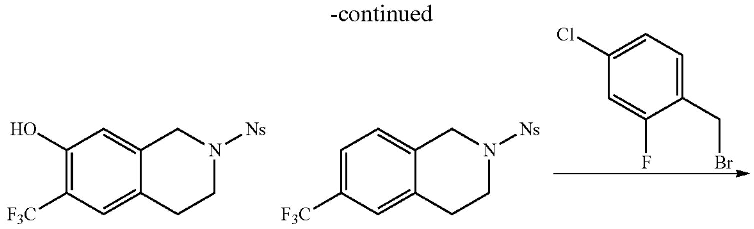
5 6
(5:6 = 1:0.5)
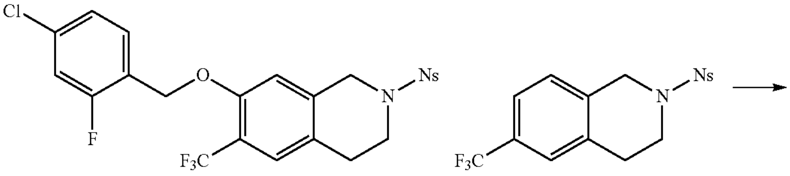
7 6
(7:6 = 1:0.5)
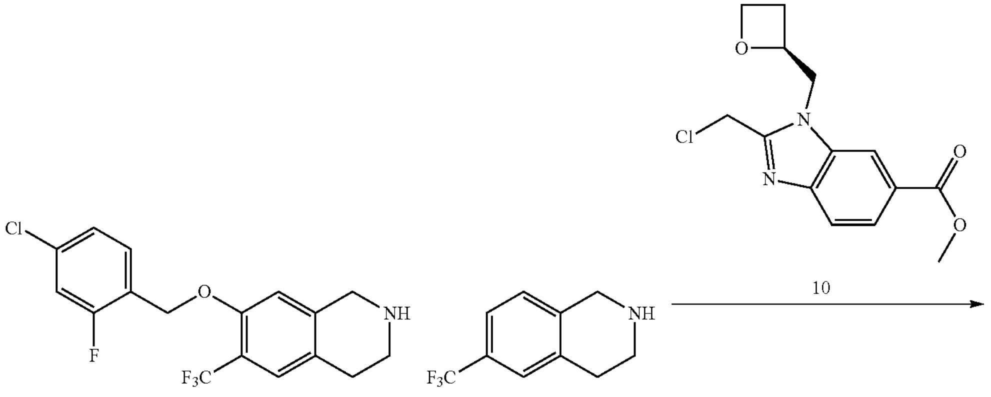
8 9
(8:9 = 1:0.5)
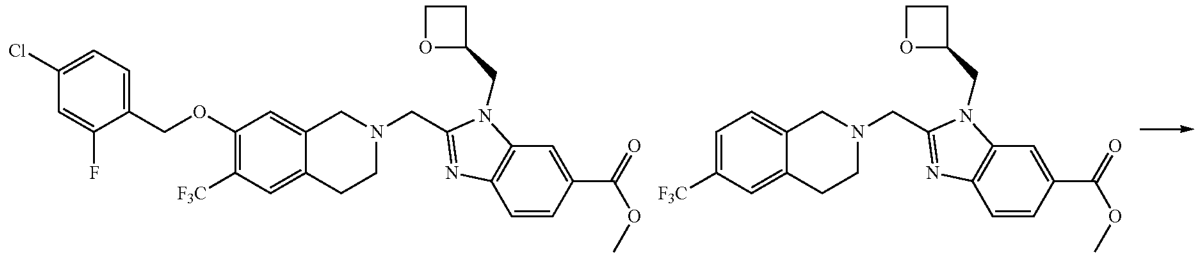
11 12
(11:12 = 1:0.5)
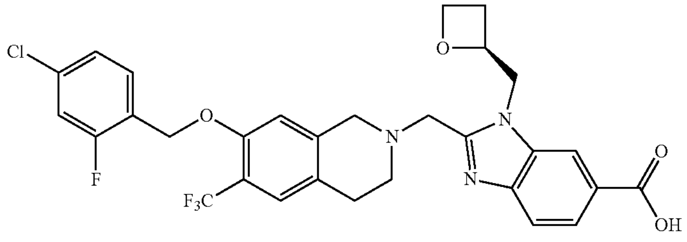
I-023

Step 1 Synthesis of Compound 2

Compound 1 (500 mg, 1.87 mmol) and triethylamine (0.776 mL, 5.60 mmol) were dissolved in dichloromethane (5 mL), and 2-nitrobenzenesulfonyl chloride (434 mg, 1.96 mmol) was added thereto, then the mixture was stirred at room temperature for 75 minutes. Water and dichloromethane were added to the reaction solution, and the solution was extracted with dichloromethane. The organic layer was washed with a 2 mol/L aqueous hydrochloric acid solution, a saturated aqueous sodium hydrogen carbonate solution, and water, and then dried over anhydrous magnesium sulfate. The solvent was evaporated under reduced pressure to give Compound 2 (623 mg, yield 74%). Furthermore, a residue generated in the aqueous layer after liquid separation was collected by filtration and dried to give Compound 2 (178 mg, 21% yield).

$^1$H-NMR ($CDCl_3$) δ: 2.87 (2H, t, J=6.8 Hz), 3.44 (2H, q, J=6.6 Hz), 5.32-5.37 (1H, m), 7.17 (1H, d, J=7.3 Hz), 7.38 (1H, s), 7.54 (1H, d, J=8.3 Hz), 7.69-7.76 (2H, m), 7.83 (1H, d, J=7.4 Hz), 8.03 (1H, dd, J=7.4 Hz, 1.5 Hz). [M+H] =450.98, measurement condition 1: retention time 2.34 min Step 2 Synthesis of Compound 3

Compound 2 (427 mg, 0.942 mmol) was dissolved in acetic acid (4 mL), and paraformaldehyde (141 mg, 4.71 mmol) and concentrated sulfuric acid (2 mL) were added thereto at room temperature. The reaction solution was ice-cooled, concentrated sulfuric acid (2 mL) was added thereto, and the mixture was stirred at 60° C. for 5 hours. The reaction solution was slowly added dropwise to an ice-cooled 2 mol/L aqueous sodium hydroxide solution, and the solution was extracted with ethyl acetate. The organic layer was washed with a 2 mol/L aqueous sodium hydroxide solution and water, and then dried over anhydrous magnesium sulfate. The solvent was evaporated under reduced pressure, and the resulting residue was purified by column chromatography (hexane-ethyl acetate) to give Compound 3 as a mixture with Compound 4 and Compound 2 (431 mg, 80 wt %, 79% yield, Compound 3:Compound 4:Compound 2=1:0.05:0.2).

[M+H]=465.10, measurement condition 1: retention time 2.53 min

Step 3 Synthesis of Compound 5

Compound 3 (430 mg, 0.924 mmol) and 4,4,4',4',5,5,5',5'-octamethyl-2,2'-bis(1,3,2-dioxaborolane) (352 mg, 1.39 mmol) were dissolved in 1,4-dioxane (8 mL), potassium acetate (454 mg, 4.62 mmol) and (1,1-bis(diphenylphosphino)ferrocene) palladium (II) dichloromethane adduct (75 mg, 0.092 mmol) were added thereto, and the mixture was stirred at 100° C. for 9 hours under a nitrogen stream. The reaction solution was ice-cooled, water (4 mL) and 30% hydrogen peroxide water (0.944 mL, 9.24 mmol) were added thereto, and the mixture was allowed to stand at room temperature for a whole day and night. The reaction solution was added to water and ethyl acetate, and the solution was extracted with ethyl acetate. The organic layer was washed with a 10% aqueous sodium thiosulfate solution and water, and then dried over anhydrous magnesium sulfate. The solvent was evaporated under reduced pressure, and the resulting residue was purified by column chromatography (hexane-ethyl acetate) to give Compound 5 as a mixture with Compound 6 (312 mg, 68 wt %, 57% yield, Compound 5:Compound 6=1:0.5).

[M+H]=403.19, measurement condition 1: retention time 2.10 min

Step 4 Synthesis of Compound 7

Compound 5 (160 mg, 0.398 mmol), cesium carbonate (259 mg, 0.795 mmol) and 1-(bromomethyl)-4-chloro-2-fluorobenzene (0.065 mL, 0.477 mmol) were dissolved in DMF (1.6 mL), and the mixture was stirred at room temperature for 90 minutes. The reaction solution was ice-cooled, and water was added thereto, and the solution was extracted with ethyl acetate. The organic layer was washed with water, and then dried over anhydrous magnesium sulfate. The solvent was evaporated under reduced pressure, and the resulting residue was purified by column chromatography (hexane-ethyl acetate) to give Compound 7 as a mixture with Compound 6 (138 mg, 74 wt %, 47% yield).

$^1$H-NMR ($CDCl_3$) δ: 2.89-2.93 (2H, m), 3.64 (2H, t, J=5.8 Hz), 4.55 (2H, s), 5.15 (2H, s), 6.78 (1H, s), 7.13 (1H, dd, J=9.7 Hz, 1.5 Hz), 7.19 (1H, d, J=8.3 Hz), 7.35 (1H, s), 7.49 (1H, t, J=8.0 Hz), 7.64-7.66 (1H, m), 7.70-7.74 (2H, m), 8.07-8.09 (1H, m).

[M+H]=545.07, measurement condition 1: retention time 2.88 min

Step 5 Synthesis of Compound 8

Compound 7 (135 mg, 0.248 mmol) was dissolved in DMF (1 mL), cesium carbonate (242 mg, 0.743 mmol) and dodecane-1-thiol (0.177 mL, 0.743 mmol) were added thereto, and the mixture was stirred at room temperature for 1.5 hours. Dodecane-1-thiol (0.087 mL) was added thereto, and the mixture was allowed to stand for a whole day and night. The reaction solution was added to water and ethyl acetate, and the solution was extracted with ethyl acetate. The organic layer was washed with a 2 mol/L aqueous sodium carbonate solution and water, and then dried over anhydrous magnesium sulfate. The solvent was evaporated under reduced pressure, and the obtained residue was purified by amino silica gel column chromatography (hexane-ethyl acetate, ethyl acetate-methanol) to give Compound 8 as a mixture with Compound 9 (35 mg, 78 wt %, 31% yield, Compound 8:Compound 9=1:0.5).

$^1$H-NMR ($CDCl_3$) δ: 2.75 (2H, t, J=5.8 Hz), 3.13 (2H, t, J=5.8 Hz), 4.01 (2H, s), 5.14 (2H, s), 6.69 (1H, s), 7.12 (1H, d, J=9.8 Hz), 7.18 (1H, d, J=8.3 Hz), 7.32 (1H, s), 7.51 (1H, t, J=8.3 Hz).

[M+H]=360.19, measurement condition 1: retention time 1.91 min

Step 6 Synthesis of Compound 11

Compound 8 (35 mg, 0.097 mmol) and Compound 10 (29 mg, 0.097 mmol) were dissolved in acetonitrile (1.0 mL), and potassium carbonate (27 mg, 0.195 mmol) was added thereto, then the mixture was stirred at 60° C. for 2 hours. The reaction solution was added to water and ethyl acetate, and the solution was extracted with ethyl acetate. The organic layer was washed with water, and then dried over anhydrous magnesium sulfate. The solvent was evaporated under reduced pressure, and the obtained residue was purified by amino silica gel column chromatography (hexane-ethyl acetate) to give Compound 11 as a mixture with Compound 12 (50 mg, 73 wt %, 61% yield, Compound 11:Compound 12=1:0.5).

[M+H]=618.27, measurement condition 1: retention time 2.43 min

Step 7 Synthesis of Compound I-023

Compound 11 (49 mg, 0.079 mmol) was dissolved in tetrahydrofuran (0.5 mL) and methanol (0.5 mL), and a 2 mol/L aqueous sodium hydroxide solution (0.159 mL, 0.317 mmol) was added thereto, then the mixture was stirred at 50° C. for 90 minutes. An ice-cooled 2 mol/L aqueous hydrochloric acid solution (0.159 mL, 0.317 mmol) and water were added to the reaction solution. The reaction solution was filtered and washed with water. The obtained residue was purified by reverse-phase chromatography (water-acetonitrile) using an ODS column to give Compound I-023 (11.6 mg, yield 24%).

$^1$H-NMR ($CDCl_3$) δ: 2.36-2.45 (1H, m), 2.65-2.71 (1H, m), 2.87 (4H, br-s), 3.70 (2H, s), 4.14-4.22 (2H, m), 4.33-4.38 (1H, m), 4.58-4.75 (3H, m), 5.09 (2H, s), 5.16-5.21 (1H, m), 6.66 (1H, s), 7.10 (1H, d, J=9.8 Hz), 7.17 (1H, d, J=8.3 Hz), 7.34 (1H, s), 7.48 (1H, t, J=8.3 Hz), 7.82 (1H, d, J=8.5 Hz), 8.06 (1H, d, J=8.5), 8.21 (1H, s).

[M+H]=604, measurement condition 1: retention time 2.18 min

Example 2 Synthesis of Compound I-027

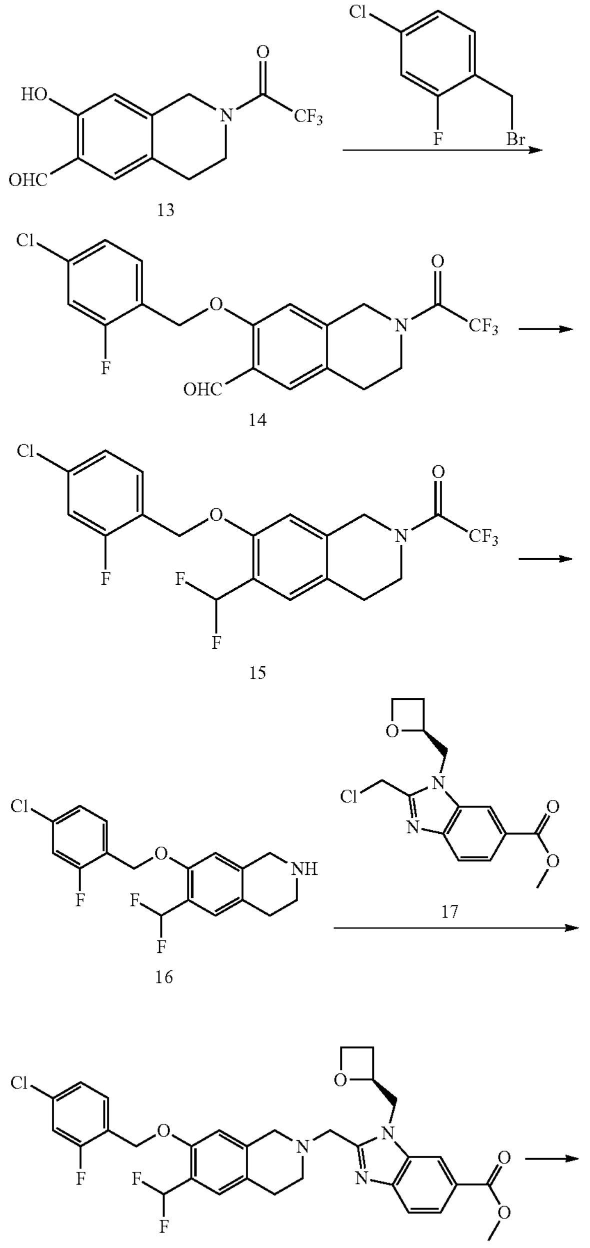

13

14

15

16

17

18

-continued

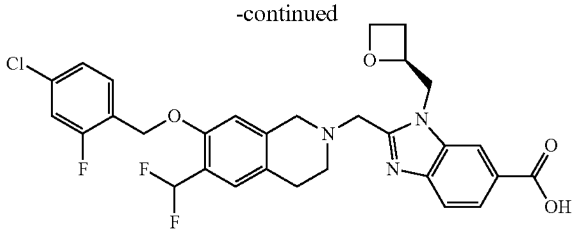

I-027

Step 1 Synthesis of Compound 14

Compound 13 (WO2012033195A) (275 mg, 1.01 mmol) was dissolved in DMF (2.5 mL), cesium carbonate (984 mg, 3.02 mmol) and 1-(bromomethyl)-4-chloro-2-fluorobenzene (0.204 mL, 1.51 mmol) were added thereto, and the mixture was stirred at room temperature for 2 hours. The reaction solution was ice-cooled, water was added thereto, and solids were collected by filtration. The residue was washed with water and diisopropyl ether and then dried to give Compound 14 (176 mg, yield 42%).

$^1$H-NMR ($CDCl_3$) δ: 2.95 (2H, t, J=5.4 Hz), 3.83-3.92 (2H, m), 4.77 (0.6H, s), 4.82 (1.4H, s), 5.19 (2H, s), 6.81-6.84 (1H, m), 7.16-7.23 (2H, m), 7.41-7.47 (1H, m), 7.65-7.69 (1H, m), 10.44 (1H, s).

[M+H]=416.19, measurement condition 2: retention time 2.55 min

Step 2 Synthesis of Compound 16

Compound 14 (66 mg, 0.159 mmol) was dissolved in dichloromethane (1 mL), and N,N-diethylaminosulfur trifluoride (0.117 mL, 0.794 mmol) were added thereto under ice cooling, then the temperature was raised to room temperature, and the reaction solution was stirred for 1 hour. Thereafter, N,N-diethylaminosulfur trifluoride (0.117 mL, 0.794 mmol) was added to the reaction solution, and the mixture was stirred at room temperature for 1 hour. Again, N,N-diethylaminosulfur trifluoride (0.117 mL, 0.794 mmol) was added to the reaction solution, and the mixture was allowed to stand for a whole day and night. The resultant reaction solution was added to a saturated aqueous sodium hydrogen carbonate solution and ethyl acetate, and the solution was extracted with ethyl acetate. The organic layer was dried over anhydrous magnesium sulfate, and evaporated under reduced pressure. The obtained residue (Compound 15) was dissolved in tetrahydrofuran (0.5 mL) and methanol (0.5 mL), a 2 mol/L aqueous sodium hydroxide solution (0.318 mL, 0.636 mmol) was added thereto, and then, the mixture was stirred at 50° C. for 50 minutes. The reaction solution was added to water and ethyl acetate, and the solution was extracted with ethyl acetate. The organic layer was dried over anhydrous magnesium sulfate, and evaporated under reduced pressure. The obtained residue was purified by amino column chromatography (hexane-ethyl acetate, and subsequently, ethyl acetate-methanol) to give Compound 16 (19.7 mg, two-step yield 36%).

$^1$H-NMR ($CDCl_3$) δ: 2.76 (2H, t, J=5.6 Hz), 3.13 (2H, t, J=5.6 Hz), 4.00 (2H, s), 5.10 (2H, s), 6.63 (1H, s), 6.92 (1H, t, J=55.7 Hz), 7.10-7.20 (2H, m), 7.30 (1H, s), 7.42 (1H, t, J=8.0 Hz).

Step 3 Synthesis of Compound 18

Compound 16 (19 mg, 0.056 mmol) and Compound 17 (16 mg, 0.056 mmol) were dissolved in acetonitrile (0.7 mL), potassium carbonate (15 mg, 0.111 mmol) was added thereto, and then the mixture was stirred at 70° C. for 2 hours. The reaction solution was ice-cooled, and solids were collected by filtration. The obtained residue was purified by amino silica gel column chromatography (hexane-ethyl acetate) to obtain Compound 18 (23.1 mg, yield 69%).

$^1$H-NMR ($CDCl_3$) δ: 2.36-2.45 (1H, m), 2.64-2.73 (1H, m), 2.86 (4H, br-s), 3.67 (2H, s), 3.95 (3H, s), 4.11-4.19 (2H, m), 4.33-4.38 (1H, m), 4.57-4.65 (1H, m), 4.68-4.71 (2H, m), 5.05 (2H, s), 5.15-5.23 (1H, m), 6.59 (1H, s), 6.90 (1H, t, J=55.7 Hz), 7.09-7.19 (2H, m), 7.32 (1H, s), 7.38 (1H, t, J=8.0 Hz), 7.78 (1H, d, J=8.4 Hz), 7.99 (1H, d, J=8.4 Hz), 8.14 (1H, s).

[M+H]=600.30, measurement condition 1: retention time 2.25 min

Step 4 Synthesis of Compound I-027

Compound 18 (22 mg, 0.037 mmol) was dissolved in tetrahydrofuran (0.3 mL) and methanol (0.3 mL), a 2 mol/L aqueous sodium hydroxide solution (0.073 mL, 0.147 mmol) was added thereto, and then the reaction solution was stirred at 50° C. for 90 minutes. An ice-cooled 2 mol/L aqueous hydrochloric acid solution (0.073 mL, 0.147 mmol) and water were added to the reaction solution. The reaction solution was filtered, and the residue was washed with water. The obtained residue was dried to give Compound I-027 (15.9 mg, yield 74%).

$^1$H-NMR ($CDCl_3$) δ: 2.37-2.46 (1H, m), 2.65-2.74 (1H, m), 2.88 (4H, br-s), 3.69 (2H, s), 4.17 (2H, s), 4.34-4.40 (1H, m), 4.58-4.77 (3H, m), 5.05 (2H, s), 5.16-5.23 (1H, m), 6.60 (1H, s), 6.90 (1H, t, J=55.7 Hz), 7.10-7.18 (2H, m), 7.33 (1H, s), 7.38 (1H, t, J=8.0 Hz), 7.83 (1H, d, J=8.5 Hz), 8.05 (1H, d, J=8.5 Hz), 8.21 (1H, s).

[M+H]=586, measurement condition 1: retention time 2.03 min

Example 3 Synthesis of Compound I-031

Step 1 Synthesis of Compound 20

Cesium carbonate (789 mg, 2.42 mmol) and 4-chloro-2-fluorobenzyl bromide (164 μL, 1.21 mmol) were added to a DMF (10 mL) solution of Compound 19 (350 mg, 1.21 mmol), and then the reaction solution was stirred at room temperature for 2 hours. Further, 4-chloro-2-fluorobenzyl bromide (23 μL, 0.138 mmol) was added to the reaction solution, and the mixture was again stirred at room temperature for 1 hour. Water was added to the reaction solution, and the resulting solids were collected by filtration to give Compound 20 (0.53 g, yield 100%). [M+H]=432, measurement condition 1: retention time 2.33 min Step 2 Synthesis of Compound 21

Copper iodide (48.5 mg, 0.255 mmol) and methyl difluoro(fluorosulfonyl)acetate (146 μL, 1.16 mmol) were sequentially added to a DMF (1 mL) solution of Compound 20 (100 mg, 0.232 mmol), then degassed under reduced pressure, and purged with nitrogen. The reaction solution was stirred at 100° C. for 5 hours under a nitrogen atmosphere. Water was added to the reaction solution, and the solution was extracted with ethyl acetate twice.

The organic layer was dried over anhydrous sodium sulfate, and the solvent was evaporated under reduced pressure. The obtained residue was purified by silica gel column chromatography (hexane-ethyl acetate) to give Compound 21 (27 mg, yield 31%).

[M+H]=374, measurement condition 1: retention time 2.30 min

Step 3 Synthesis of Compound I-031

Sodium hydride (4.1 mg, 0.101 mmol) was added to a tetrahydrofuran (0.5 mL) solution of Compound 21 (27 mg,

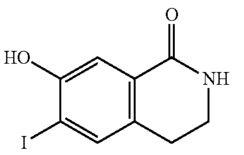

19

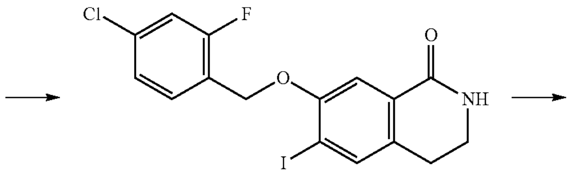

20

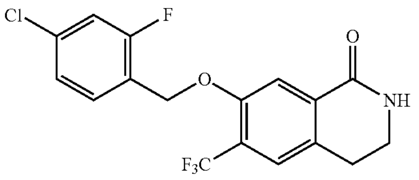

21

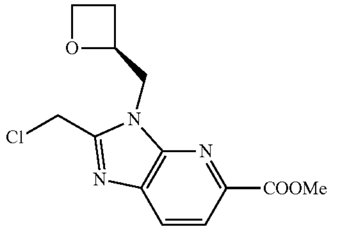

22

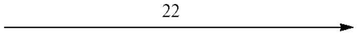

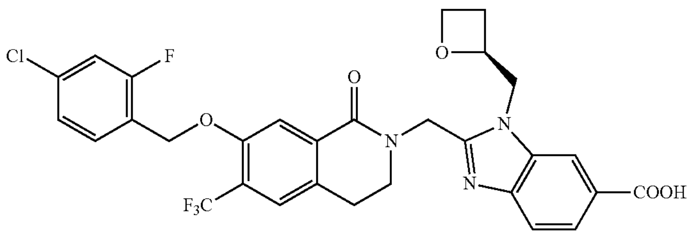

I-031

0.072 mmol) under ice cooling, and the mixture was stirred under ice cooling for 10 minutes. Compound 22 (30 mg, 0.101 mmol) was added to the reaction solution, and the mixture was stirred at room temperature for 2.5 hours. Sodium hydride (2.0 mg, 0.050 mmol) was added thereto, and the mixture was stirred again at room temperature for 1 hour. Methanol (0.5 mL) and a 1 mol/L aqueous sodium hydroxide solution (72 μL) were added to the reaction solution, and then the mixture was stirred at room temperature for 2 hours. Water was added to the reaction solution, and then 2 mol/L hydrochloric acid was added until the pH reached about 4. The resulting solids were collected by filtration to give a crude product. The obtained crude product was purified by silica gel column chromatography (chloroform-methanol) to give Compound I-031 (20 mg, yield 45%).

$^1$H-NMR (DMSO-D$_6$) δ: 2.34-2.43 (1H, m), 2.68-2.76 (1H, m), 3.05 (2H, t, J=6.5 Hz), 3.78 (2H, t, J=7.8 Hz), 4.31 (1H, dt, J=11.2, 4.4 Hz), 4.47 (1H, q, J=7.1 Hz), 4.63 (1H, dd, J=15.0, 3.1 Hz), 4.78 (1H, dd, J=15.0, 6.5 Hz), 5.13-5.17 (2H, m), 5.28 (1H, d, J=16.4 Hz), 5.36 (2H, s), 7.37 (1H, d, J=8.3 Hz), 7.51-7.58 (2H, m), 7.67 (1H, s), 7.79 (1H, s), 7.99 (1H, d, J=8.3 Hz), 8.12 (1H, d, J=8.3 Hz).

[M+H]=619, measurement condition 1: retention time 2.35 min

Example 4 Synthesis of Compound I-006

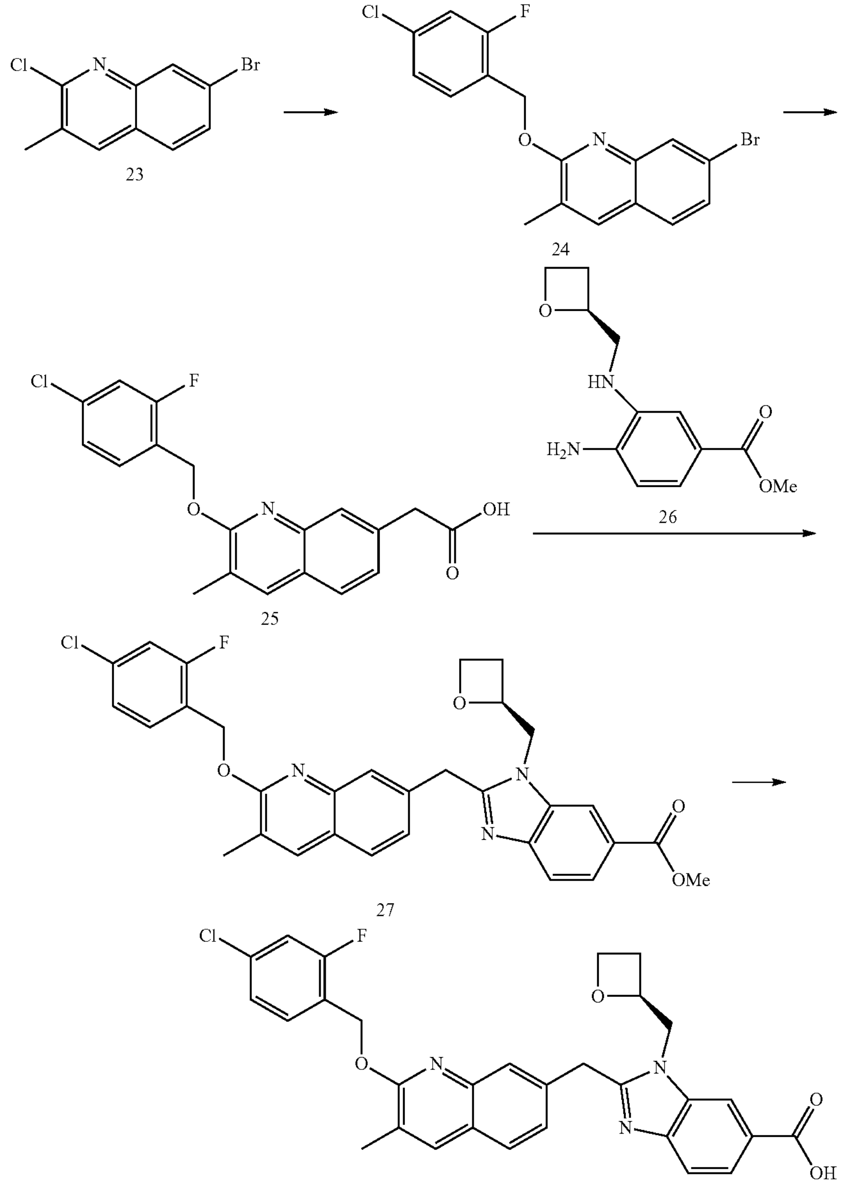

23

24

26

25

27

I-006

Step 1 Synthesis of Compound 24

Compound 23 (100 mg, 0.390 mmol) and (4-chloro-2-fluorophenyl)methanol (94.0 mg, 0.585 mmol) were dissolved in tetrahydrofuran (1.5 mL), and tert-butoxy potassium (87 mg, 0.780 mmol) was added thereto under ice cooling, then the mixture was stirred at room temperature for 30 minutes. Water was added to the reaction solution. The reaction solution was filtered, the residue was washed with water, and then dried. The obtained residue was purified by column chromatography (hexane-ethyl acetate) to give Compound 24 (121 mg, yield 81.5%).

$^1$H-NMR ($CDCl_3$) δ: 2.33 (3H, s), 5.57 (2H, s), 7.13-7.16 (2H, m), 7.43-7.46 (1H, m), 7.49-7.53 (2H, m), 7.75 (1H, s), 8.01 (1H, d, J=1.5 Hz).

[M+H]=380.15, measurement condition 3: retention time 3.10 min

Step 2 Synthesis of Compound 25

Compound 24 (113 mg, 0.297 mmol), 1-(tert-butyldimethylsilyloxy)-1-methoxyethene (168 mg, 0.891 mmol), zinc fluoride (92 mg, 0.891 mmol), and bis-tert-tributylphosphine palladium (15.2 mg, 0.030 mmol) were dissolved in DMF (3.4 mL), and the mixture was stirred in a sealed tube state under microwave irradiation at 130° C. for 3 hours. After cooled to room temperature, water and ethyl acetate were added to the reaction solution, and the solution was extracted with ethyl acetate. The organic layer was washed with water, and then dried over anhydrous magnesium sulfate. The solvent was evaporated under reduced pressure, and the obtained residue was purified by column chromatography (hexane-ethyl acetate) to give residue (32.3 mg). The obtained residue was dissolved in a mixed solvent of tetrahydrofuran (0.31 mL) and methanol (0.31 mL), and a 1 mol/L aqueous sodium hydroxide solution (0.250 ml, 0.250 mmol) was added thereto, then the mixture was stirred at room temperature for 1 hour. A 10% aqueous citric acid solution was added to the reaction solution. The reaction solution was filtered, the residue was washed with water, and then, dried, to give residue (27.3 mg). The obtained residue was purified by column chromatography (hexane-ethyl acetate) to obtain Compound 25 (23.8 mg, two-step yield 23.0%).

$^1$H-NMR ($CDCl_3$) δ: 2.34 (3H, s), 3.83 (2H, s), 5.58 (2H, s), 5.58 (2H, s), 7.12-7.15 (2H, m), 7.29-7.32 (1H, dd, J=8.0, 1.5 Hz), 7.52 (1H, t, J=8.0 Hz), 7.64 (1H, d, J=8.0 Hz), 7.76 (1H, d, J=10.3 Hz).

[M+H]=360.20, measurement condition 3: retention time 2.48 min

Step 3 Synthesis of Compound 27

Compound 25 (23.5 mg, 0.065 mmol) and compound 26 (15.4 mg, 0.065 mmol) were dissolved in DMF (0.35 mL), and triethylamine (0.091 ml, 0.065 mmol) and 1-(bis(dimethylamino)methylene)-1H-1,2,3-triazolo(4,5-b)pyridinium 3-oxide hexafluorophosphate (24.8 mg, 0.065 mmol) were added thereto. Then, the mixture was stirred at room temperature for 1 hour. Water was added to the reaction solution. The reaction solution was filtered, the residue was washed with water, and then, dried, to give residue (30 mg). The obtained residue (30 mg) was dissolved in acetic acid (0.30 ml) and stirred at 60° C. for 1 hour. The reaction solution was concentrated, the obtained residue was purified by column chromatography (hexane-ethyl acetate), to give Compound 27 (21 mg, two-step yield 56.9%).

$^1$H-NMR ($CDCl_3$) δ: 2.28-2.35 (1H, m), 2.34 (3H, s), 2.56-2.63 (1H, m), 3.94 (3H, s), 4.24-4.40 (3H, m), 4.57-4.70 (3H, m), 5.05-5.08 (1H, m), 5.55 (2H, s), 7.10-7.15 (2H, m), 7.26-7.29 (1H, m), 7.49 (1H, t, J=8.0 Hz), 7.60 (1H, d, J=8.3 Hz), 7.68 (1H, s), 7.76 (1H, s), 7.80 (1H, d, J=8.6 Hz), 7.99 (1H, dd, J=8.6, 1.3 Hz), 8.08 (1H, s). [M+H]=560.10, measurement condition 3: retention time 2.56 min Step 4 Synthesis of Compound I-006

Compound 27 (20.8 mg, 0.037 mmol) was dissolved in tetrahydrofuran (0.16 mL) and methanol (0.16 mL), and a 1 mol/L aqueous sodium hydroxide solution (0.11 mL, 0.11 mmol) was added thereto, then the mixture was stirred at 60° C. for 2 hours. After cooled to room temperature, a 10% aqueous citric acid solution was added to the reaction solution. The reaction solution was filtered, the residue was washed with water, and then, dried, to give Compound I-006 (18.0 mg, yield 88.8%).

$^1$H-NMR (DMSO-d6) δ: 2.23 (3H, s), 2.23-2.36 (1H, m), 2.50-2.63 (1H, m), 4.31-4.36 (1H, m), 4.41-4.47 (1H, m), 4.51-4.60 (3H, m), 4.64-4.70 (1H, m), 4.87-4.93 (1H, m), 5.52 (2H, s), 7.32 (1H, dd, J=8.3, 1.5 Hz), 7.39 (1H, dd, J=8.3, 1.5 Hz), 7.49 (1H, dd, J=10.0, 1.5 Hz), 7.64 (2H, t, 8.3 Hz), 7.66 (1H, s), 7.75-7.81 (2H, m), 8.05 (1H, s), 8.23 (1H, s)

[M+H]=546, measurement condition 3: retention time 2.27 min

Example 5 Synthesis of Compound I-035

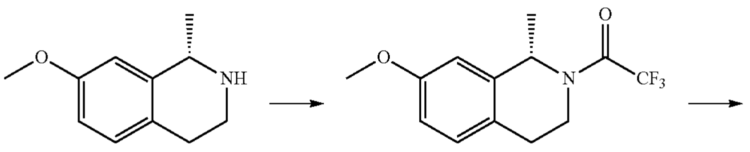

28 29

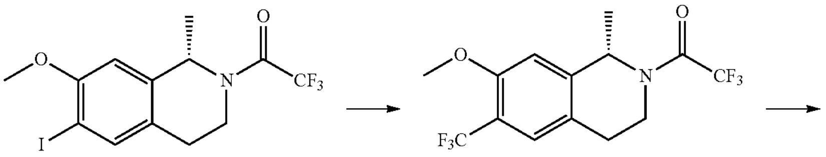

30 31

-continued

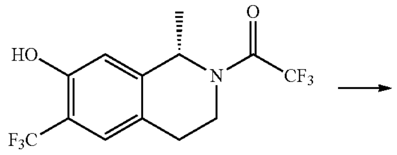

32

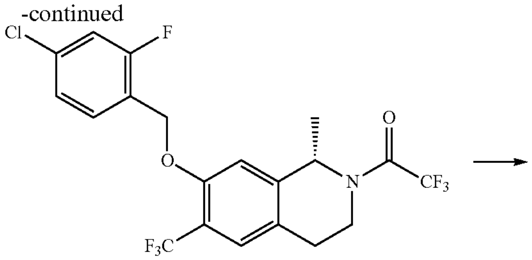

33

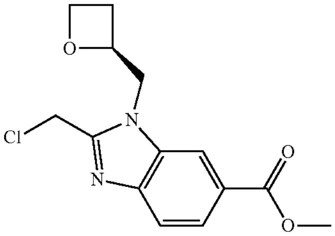

35

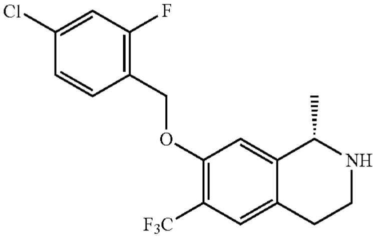

34

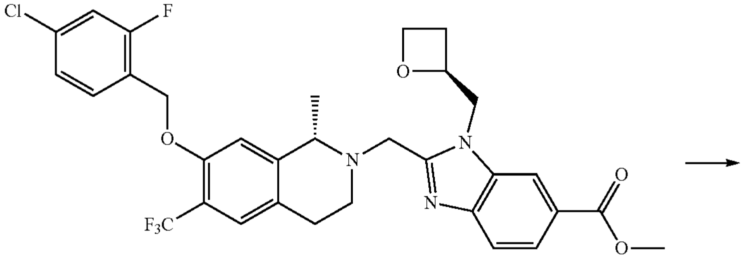

36

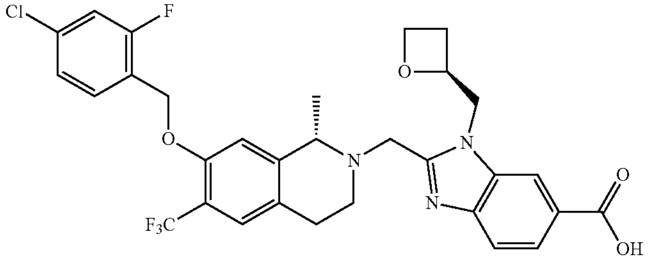

I-035

Step 1 Synthesis of Compound 29

Compound 28 (WO2019200120A) (1.90 g, 10.72 mmol) was dissolved in dichloromethane (19 mL), and trifluoroacetic anhydride (2.27 mL, 16.08 mmol) was added thereto, then the mixture was stirred at room temperature for 3 hours and 15 minutes. Trifluoroacetic anhydride (0.23 mL, 1.61 mmol) was added thereto, and the mixture was stirred at room temperature for 75 minutes. Water was added to the reaction solution, and the solution was extracted with dichloromethane. The solvent was evaporated under reduced pressure, and the obtained residue was purified by silica gel column chromatography (hexane-ethyl acetate) to give Compound 29 (2.25 g, yield 74%).

[M+H]=274.2, measurement condition 1: retention time 2.28 min $^1$H-NMR ($CDCl_3$) δ: 1.53 (2.4H, d, J=6.8 Hz), 1.61 (0.6H, d, J=6.7 Hz), 2.74-2.82 (1H, m), 2.91-3.00 (1H, m), 3.26 (0.2H, td, J=12.5, 4.4 Hz), 3.56 (0.8H, td, J=12.5, 4.3 Hz), 3.79 (2.4H, s), 3.80 (0.6H, s), 4.04 (0.8H, d, J=12.8 Hz), 4.59 (0.2H, dd, J=12.8, 5.6 Hz), 5.10 (0.2H, q, J=6.8 Hz), 5.53 (0.8H, q, J=6.8 Hz), 6.62 (0.2H, d, J=2.5 Hz), 6.66 (0.8H, d, J=2.5 Hz), 6.75-6.80 (1H, m), 7.03-7.07 (1H, m).

Step 2 Synthesis of Compound 30

Compound 29 (1.95 g, 7.13 mmol) was dissolved in dichloromethane (19 mL), and silver trifluoroacetate (1.74 g, 7.87 mmol) and iodine (1.99 g, 7.84 mmol) were added thereto, then the mixture was stirred at room temperature for 1 hour. Insolubles were removed by filtration, an aqueous sodium thiosulfate solution was added to the filtrate, and the solution was extracted with dichloromethane. The organic layer was washed with water, and then dried over anhydrous sodium sulfate. The solvent was evaporated under reduced pressure, and the obtained residue was purified by silica gel column chromatography (hexane-ethyl acetate) to give Compound 30 (2.00 g, yield 70%).

[M+H]=400.2, measurement condition 1: retention time 2.55 min $^1$H-NMR ($CDCl_3$) δ: 1.53 (2.4H, d, J=6.8 Hz), 1.61 (0.6H, d, J=6.8 Hz), 2.71-2.79 (1H, m), 2.89-2.97 (1H, m), 3.23 (0.2H, td, J=12.7, 4.5 Hz), 3.50-3.57 (0.8H, m), 3.86 (2.4H, s), 3.88 (0.6H, s), 4.01-4.05 (0.8H, m), 4.59 (0.2H, dd, J=13.3, 5.3 Hz), 5.08 (0.2H, q, J=6.5 Hz), 5.52 (0.8H, q, J=6.8 Hz), 6.51 (0.2H, s), 6.55 (0.8H, s), 7.55 (0.8H, s), 7.57 (0.2H, s).

Step 3 Synthesis of Compound 31

Compound 30 (1.99 g, 4.99 mmol) was dissolved in N,N-dimethylformamide (20 mL), and methyl difluoro(fluorosulfonyl)acetate (3.15 mL, 24.93 mmol) and copper iodide (1.14 g, 5.98 mmol) were added thereto, then the mixture was degassed under reduced pressure, and purged with nitrogen. The mixture was stirred at 100° C. for 3 hours under a nitrogen atmosphere, and then water was added thereto. The solution was extracted with ethyl acetate. After the organic layer was washed with water and dried over anhydrous sodium sulfate, the solvent was evaporated under reduced pressure, and the obtained residue was purified by silica gel column chromatography (hexane-ethyl acetate) to give Compound 31 (1.56 g, yield 94%).

[M+H]=342.2, measurement condition 1, retention time 2.51 min $^1$H-NMR ($CDCl_3$) δ: 1.56 (2.4H, d, J=6.9 Hz), 1.64 (0.6H, d, J=6.8 Hz), 2.77-2.86 (1H, m), 2.92-3.02 (1H, m), 3.26 (0.2H, td, J=12.3, 5.2 Hz), 3.52-3.60 (0.8H, m), 3.89 (2.4H, s), 3.90 (0.6H, s), 4.02-4.13 (0.8H, m), 4.65 (0.2H, dd, J=13.0, 5.6 Hz), 5.14 (0.2H, q, J=6.8 Hz), 5.59 (0.8H, q, J=6.9 Hz), 6.69 (0.2H, s), 6.74 (0.8H, s), 7.33 (0.8H, s), 7.35 (0.2H, s).

Step 4 Synthesis of Compound 32

Compound 31 (1.55 g, 4.41 mmol) was dissolved in dichloromethane (7.8 mL), and 1 mol/L boron tribromide in a dichloromethane solution (13.2 mL, 13.2 mmol) was added thereto under ice cooling, then the mixture was stirred at room temperature for 2.5 hours. Methanol (7.8 mL) was added to the solution under ice cooling, then water was added thereto, and the solution was extracted with dichloromethane. The solvent was evaporated under reduced pressure, and the obtained residue was purified by silica gel column chromatography (hexane-ethyl acetate) to give Compound 32 (1.20 g, 78%).

[M+H]=326.2, measurement condition 1: retention time 2.18 min

Step 5 Synthesis of Compound 33

N,N-dimethylformamide (1.1 mL) was added to Compound 32 (114 mg, 0.33 mmol), cesium carbonate (212 mg, 0.651 mmol), and 1-(bromomethyl)-4-chloro-2-fluorobenzene (0.051 mL, 0.377 mmol), and the mixture was stirred at room temperature for 90 minutes. Water was added to the reaction solution, the solution was extracted with ethyl acetate, and the organic layer was washed with water. The solvent was evaporated under reduced pressure, and the obtained residue was purified by column chromatography (hexane-ethyl acetate) to give Compound 33 (142 mg, 92%).

$^1$H-NMR ($CDCl_3$) δ: 1.53 (2.4H, d, J=6.9 Hz), 1.62 (0.6H, d, J=6.8 Hz), 2.78-2.86 (1H, m), 2.94-3.02 (1H, m), 3.25 (0.2H, td, J=12.6, 5.2 Hz), 3.51-3.58 (0.8H, m), 4.09 (0.8H, d, J=15.8 Hz), 4.65 (0.2H, dd, J=13.7, 5.6 Hz), 5.12-5.21 (2.2H, m), 5.57 (0.8H, q, J=6.7 Hz), 6.78 (0.2H, s), 6.80 (0.8H, s), 7.14 (1H, dd, J=9.8, 1.9 Hz), 7.18-7.21 (1H, m), 7.36 (0.8H, s), 7.39 (0.2H, s), 7.47-7.53 (1.0H, m).

Step 6 Synthesis of Compound 34

Compound 33 (140 mg, 0.298 mmol) was dissolved in tetrahydrofuran (1.4 mL) and methanol (1.4 mL), potassium carbonate (82 mg, 0.596 mmol) was added thereto, and then the mixture was stirred at 50° C. for 8 hours and 45 minutes. Water was added to the reaction solution, and the solution was extracted with chloroform, and the organic layer was washed with water. The solvent was evaporated under reduced pressure to give Compound 34 (104 mg, 94% yield) as a crude product.

[M+H]=374.3, measurement condition 1: retention time 2.03 min $^1$H-NMR ($CDCl_3$) δ: 1.45 (3H, d, J=6.8 Hz), 2.69 (1H, dt, J=16.1, 4.6 Hz), 2.77-2.84 (1H, m), 2.96-3.02 (1H, m), 3.26 (1H, dt, J=12.6, 5.1 Hz), 4.09 (1H, q, J=6.7 Hz), 5.16 (2H, dd, J=17.4, 12.7 Hz), 6.80 (1H, s), 7.12 (1H, dd, J=9.9, 1.9 Hz), 7.18 (1H, dd, J=8.2, 1.7 Hz), 7.30 (1H, s), 7.52 (1H, t, J=8.0 Hz).

Step 7 Synthesis of Compound 36

Compound 34 (51 mg, 0.136 mmol) was dissolved in acetonitrile (0.5 mL), Compound 35 (42 mg, 0.143 mmol) and potassium carbonate (38 mg, 0.273 mmol) were added thereto, and then the mixture was stirred at 60° C. for 6 hours. Water was added to the reaction solution, and the solution was extracted with ethyl acetate. The organic layer was washed with water, then the solvent was evaporated under reduced pressure, and the obtained residue was purified by silica gel column chromatography (hexane-ethyl acetate) to give Compound 36 (80 mg, 90% yield).

[M+H]=632.5, measurement condition 1: retention time 2.50 min $^1$H-NMR ($CDCl_3$) δ: 1.40 (3H, d, J=6.8 Hz), 2.35-2.44 (1H, m), 2.61-2.72 (2H, m), 2.76-2.81 (1H, m), 2.85-2.93 (1H, m), 3.07-3.13 (1H, m), 3.90 (1H, q, J=6.7 Hz), 3.95 (3H, s), 4.11-4.35 (3H, m), 4.55-4.77 (3H, m), 5.10-5.22 (3H, m), 6.72 (1H, s), 7.11 (1H, dd, J=9.8, 2.0 Hz), 7.18 (1H, dd, J=8.2, 1.6 Hz), 7.32 (1H, s), 7.51 (1H, t, J=8.1 Hz), 7.76 (1H, d, J=8.5 Hz), 7.98 (1H, dd, J=8.5, 1.5 Hz), 8.13 (1H, d, J=0.9 Hz).

Step 8 Synthesis of Compound I-035

Compound 36 (79 mg, 0.121 mmol) was dissolved in tetrahydrofuran (0.8 mL) and methanol (0.8 mL), a 1 mol/L aqueous sodium hydroxide solution (0.61 mL, 0.61 mmol) was added thereto, and then the mixture was stirred at 40° C. for 80 minutes. At room temperature, a 2 mol/L aqueous hydrochloric acid solution was added thereto to adjust the pH to 4. Water was added to the reaction solution after pH adjustment, and the solution was extracted with ethyl acetate. The organic layer was washed with water, then the solvent was evaporated under reduced pressure, and the obtained residue was purified by silica gel column chromatography (chloroform-methanol). A fraction containing a target product was concentrated to give a solid residue, then the residue was suspended in methyl tert-butyl ether and collected by filtration to give Compound I-035 (54 mg, 72% yield).

[M+H]=618.0, measurement condition 2: retention time 2.01 min $^1$H-NMR ($CDCl_3$) δ: 1.40 (3H, d, J=6.7 Hz), 2.36-2.45 (1H, m), 2.63-2.74 (2H, m), 2.78-2.95 (2H, m), 3.09-3.16 (1H, m), 3.92 (1H, q, J=6.7 Hz), 4.17-4.37 (3H, m), 4.59-4.79 (3H, m), 5.08-5.24 (3H, m), 6.72 (1H, s), 7.10 (1H, dd, J=9.7, 1.8 Hz), 7.18 (1H, dd, J=8.2, 1.3 Hz), 7.32 (1H, s), 7.50 (1H, t, J=8.1 Hz), 7.83 (1H, d, J=8.5 Hz), 8.05 (1H, d, J=8.4 Hz), 8.20 (1H, s).

Example 6 Synthesis of Compound I-110

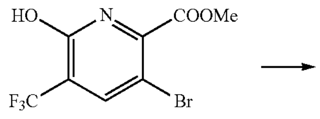

37

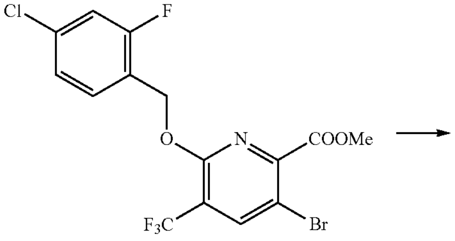

38

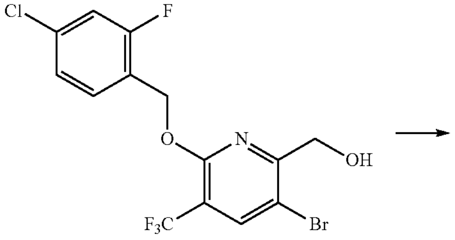

39

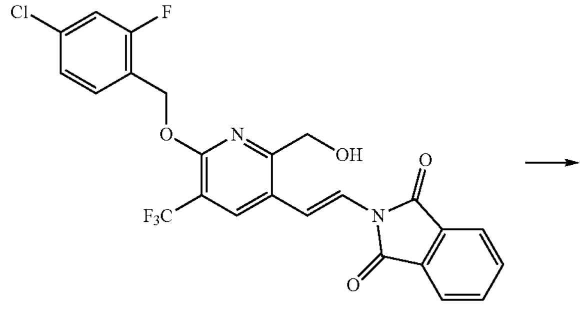

40

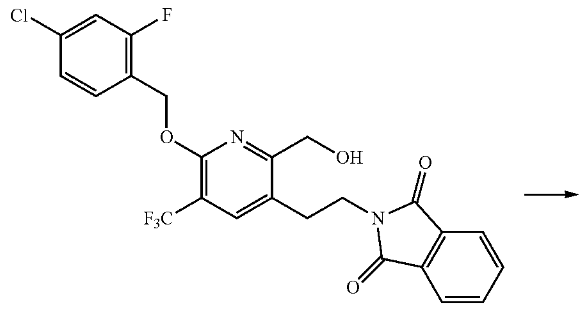

41

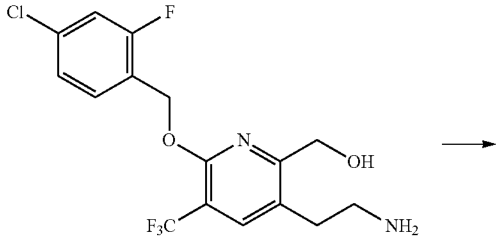

42

-continued

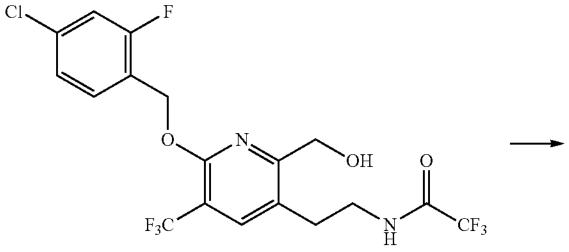

43

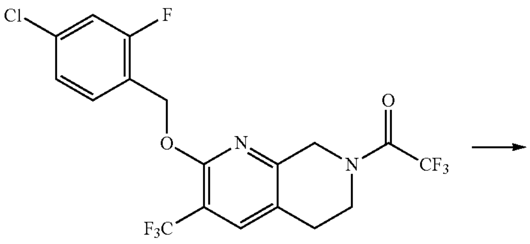

44

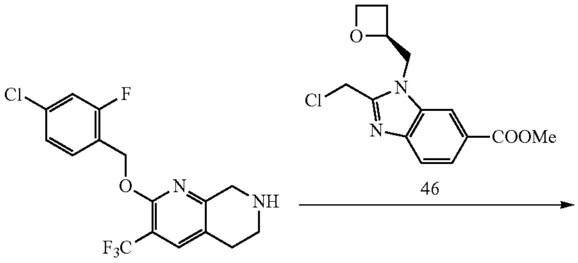

46

45

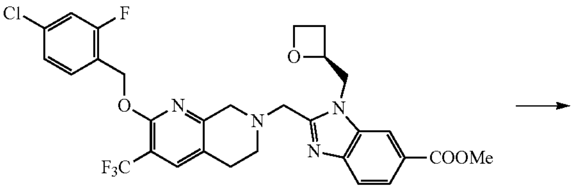

47

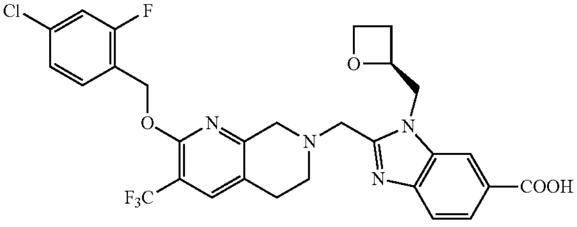

I-110

Step 1 Synthesis of Compound 38

To a suspension of Compound 37 (WO2020146682) (2.07 g, 6.89 mmol) in 1,4-dioxane (10 mL), silver carbonate (2.85 g, 10.3 mmol) and 4-chloro-2-fluorobenzyl bromide (1.85 g, 8.26 mmol) were added, then the mixture was stirred at 65° C. for 3.5 hours. After insolubles were removed by filtration, the solvent was evaporated under reduced pressure, and the obtained residue was purified by silica gel column chromatography (hexane-ethyl acetate) to give Compound 38 (3.11 g, 100%).

[M+H]=442, measurement condition 1: retention time 2.83 min $^{1}$H-NMR ($CDCl_3$) δ: 4.01 (3H, s), 5.51 (2H, s), 7.12 (1H, dd, J=9.6, 1.8 Hz), 7.15 (1H, dd, J=8.2, 1.8 Hz), 7.46 (1H, t, J=8.0 Hz), 8.10 (1H, s).

Step 2 Synthesis of Compound 39

A 1 mol/L DIBAL hexane solution (4.97 mL, 4.97 mmol) was added to a tetrahydrofuran (10 mL) solution of Compound 38 (1.0 g, 2.26 mmol) under ice cooling, and then the mixture was stirred under ice cooling for 3 hours. Sodium sulfate 10-hydrate was added thereto little by little until foaming ceased, and then the mixture was stirred at room temperature for 30 minutes. After insolubles were removed by filtration, the solvent was evaporated under reduced pressure, and the thus obtained residue was purified by silica gel column chromatography (hexane-ethyl acetate) to give Compound 39 (780 mg, 83%).

[M+H]=414, measurement condition 1: retention time 2.60 min $^1$H-NMR ($CDCl_3$) δ: 3.59 (1H, td, J=5.1, 1.4 Hz), 4.73 (2H, dd, J=5.0, 0.9 Hz), 5.55 (2H, s), 7.13-7.18 (2H, m), 7.43 (1H, t, J=7.9 Hz), 8.01 (1H, s).

Step 3 Synthesis of Compound 40

To an N,N-dimethylformamide (4.5 mL) solution of Compound 39 (300 mg, 0.724 mmol), N-vinylphthalimide (125 mg, 0.724 mmol), tetrabutylammonium bromide (233 mg, 0.724 mmol), palladium acetate (16.3 mg, 0.074 mmol), and dicyclohexylmethylamine (230 μL, 1.09 mmol) were added. After degassing under reduced pressure, the mixture was purged with nitrogen, and stirred at 110° C. for 1.5 hours. Water was added to the reaction solution, and the resulting solids were collected by filtration, then the solids were washed with isopropyl acetate to give Compound 40 (234 mg, 64% yield).

[M+H]=507, measurement condition 1: retention time 2.78 min $^1$H-NMR ($CDCl_3$) δ: 3.87 (1H, t, J=4.6 Hz), 4.83 (2H, d, J=4.6 Hz), 5.59 (2H, s), 7.13-7.23 (3H, m), 7.47 (1H, t, J=8.0 Hz), 7.58 (1H, d, J=14.8 Hz), 7.80 (2H, dd, J=5.5, 3.0 Hz), 7.93 (2H, dd, J=5.3, 3.0 Hz), 8.04 (1H, s).

Step 4 Synthesis of Compound 41

After 10% palladium-carbon (containing 50% of water) (94 mg, 0.044 mmol) was added to a methanol (2.2 mL) and tetrahydrofuran (6.7 mL) solution of Compound 40 (224 mg, 0.442 mmol), then the mixture was stirred at room temperature for 5 hours under a hydrogen atmosphere (1 atm). Insolubles were removed by filtration, and then the solvent was evaporated under reduced pressure to give Compound 41 (163 mg, 73% yield). The obtained Compound 41 was used in the next step without purification or any other processing.

[M+H]=509, measurement condition 1: retention time 2.76 min $^1$H-NMR ($CDCl_3$) δ: 2.90 (2H, t, J=7.7 Hz), 3.80 (1H, t, J=4.8 Hz), 3.86 (2H, t, J=7.7 Hz), 4.83 (2H, d, J=4.8 Hz), 5.54 (2H, s), 7.11-7.17 (2H, m), 7.44 (1H, t, J=8.0 Hz), 7.73-7.76 (3H, m), 7.82-7.86 (2H, m).

Step 5 Synthesis of Compound 42

Hydrazine monohydrate (77.8 μL, 1.6 mmol) was added to an ethanol (3.2 mL) solution of Compound 41 (163 mg, 0.32 mmol), and then the mixture was stirred at 80° C. for 2.5 hours. After insolubles were removed by filtration, the solvent was evaporated under reduced pressure, and dichloromethane was added to the obtained residue. Precipitated insolubles were again removed by filtration, and then the solvent was evaporated under reduced pressure to give a crude product (122 mg) containing Compound 42. The obtained Compound 42 was used in the next step without purification or any other processing.

[M+H]=379, measurement condition 1: retention time 1.84 min

Step 6 Synthesis of Compound 43

After trifluoroacetic anhydride (136 μL, 0.96 mmol) was added under ice cooling to a dichloromethane (1.2 mL) solution of the entire amount (0.32 mmol) of the crude product of Compound 42 obtained in Step 5, then the mixture was stirred at room temperature for 2 hours. The solvent was evaporated under reduced pressure, and the obtained residue was dissolved in ethyl acetate and then slowly poured into an aqueous sodium hydrogen carbonate solution. The mixture was stirred at room temperature for 1 hour, and then extracted with ethyl acetate twice. The resultant was dried over anhydrous sodium sulfate, the solvent was evaporated under reduced pressure, and the obtained residue was purified by the silica gel column chromatography (hexane-ethyl acetate) to give Compound 43 (47 mg, yield 31%).

[M+H]=475, measurement condition 1: retention time 2.42 min $^1$H-NMR ($CDCl_3$) δ: 2.87 (2H, t, J=7.2 Hz), 3.52 (1H, t, J=5.0 Hz), 3.57 (2H, q, J=6.7 Hz), 4.77 (2H, d, J=5.0 Hz), 5.55 (2H, s), 6.77 (1H, s), 7.13 (1H, dd, J=9.8, 1.9 Hz), 7.16 (1H, dd, J=8.2, 1.9 Hz), 7.45 (1H, t, J=8.0 Hz), 7.71 (1H, s).

Step 7 Synthesis of Compound 44

After triphenylphosphine (39 mg, 0.15 mmol) and DIAD (29 μL, 0.15 mmol) were added to a tetrahydrofuran (2.5 mL) solution of Compound 43 (47 mg, 0.099 mmol), then the mixture was stirred at room temperature for 1 hour. The solvent was evaporated under reduced pressure, and the obtained residue was purified by the silica gel column chromatography (hexane-ethyl acetate) to give Compound 44 (40 mg, yield 89%)

[M+H]=457, measurement condition 1: retention time 2.88 min $^1$H-NMR ($CDCl_3$) δ: 2.88-2.93 (2H, m), 3.87 (1.2H, t, J=5.6 Hz), 3.95 (0.8H, t, J=5.9 Hz), 4.74 (0.8H, s), 4.78 (1.2H, s), 5.49 (2H, s), 7.11-7.16 (2H, m), 7.45 (1H, t, J=7.9 Hz), 7.67 (0.6H, s), 7.70 (0.4H, s).

Step 8 Synthesis of Compound 45

After potassium carbonate (24.2 mg, 0.175 mmol) was added to a methanol (0.5 mL) and tetrahydrofuran (0.5 mL) solution of Compound 44 (40 mg, 0.088 mmol), then the mixture was stirred at 50° C. for 4 hours under a nitrogen atmosphere. After brine was added to the reaction solution, the solution was extracted with ethyl acetate twice. The organic layer was dried over anhydrous sodium sulfate, and then the solvent was evaporated under reduced pressure to give a crude product (36 mg) containing Compound 45. The obtained Compound 45 was used in the next step without purification or any other processing.

[M+H]=361, measurement condition 1: retention time 1.72 min $^1$H-NMR ($CDCl_3$) δ: 2.75 (2H, t, J=5.8 Hz), 3.13 (2H, t, J=5.8 Hz), 3.99 (2H, s), 5.47 (2H, s), 7.10 (1H, dd, J=9.7, 1.9 Hz), 7.13 (1H, d, J=8.3 Hz), 7.46 (1H, t, J=8.0 Hz), 7.58 (1H, s).

Step 9 Synthesis of Compound 47

To an acetonitrile (0.6 mL) solution of the whole amount (36 mg) of the crude product of Compound 45 obtained in Step 8, Compound 46 (27 mg, 0.092 mmol) and potassium carbonate (24.2 mg, 0.175 mmol) were added, then the mixture was stirred at 60° C. for 2 hours under a nitrogen atmosphere. After brine was added to the reaction solution, the solution was extracted with ethyl acetate twice. The resultant was dried over anhydrous sodium sulfate, the solvent was evaporated under reduced pressure, and the obtained residue was purified by the silica gel column chromatography (chloroform-ethyl acetate) to give Compound 47 (51 mg, yield 94%).

[M+H]=619, measurement condition 1: retention time 2.49 min $^1$H-NMR ($CDCl_3$) δ: 2.36-2.45 (1H, m), 2.66-2.74 (1H, m), 2.82-2.87 (4H, m), 3.73 (2H, s), 3.95 (3H, s), 4.19 (2H, dd, J=14.7, 13.8 Hz), 4.36 (1H, dt, J=11.0, 4.6 Hz), 4.59-4.67 (2H, m), 4.72 (1H, dd, J=15.4, 6.0 Hz), 5.19 (1H, ddd, J=13.4, 7.2, 3.0 Hz), 5.43 (2H, s), 7.08 (1H, dd, J=9.7, 2.0 Hz), 7.12 (1H, dd, J=8.3, 1.7 Hz), 7.43 (1H, t, J=8.0 Hz), 7.61 (1H, s), 7.79 (1H, d, J=8.5 Hz), 8.00 (1H, dd, J=8.4, 1.5 Hz), 8.14 (1H, d, J=1.0 Hz).

Step 10 Synthesis of Compound I-110

After a 2 mol/L aqueous sodium hydroxide solution (206 μL, 0.412 mmol) was added to a methanol (0.5 mL) and tetrahydrofuran (0.5 mL) solution of Compound 47 (51 mg, 0.082 mmol), then the mixture was stirred at 45° C. for 4.5 hours under a nitrogen atmosphere. Water was added to the reaction solution, then dilute sulfuric acid was added thereto until the pH reached about 4, and the solution was extracted with ethyl acetate twice. The resultant was dried over anhydrous sodium sulfate, the solvent was evaporated under reduced pressure, and the obtained residue was purified by the silica gel column chromatography (chloroform-methanol) to give Compound I-110 (38 mg, yield 76%).

[M+H]=605.5, measurement condition 1: retention time: 2.18 min $^1$H-NMR (DMSO-$D_6$) δ: 2.32-2.41 (1H, m), 2.59-2.67 (1H, m), 2.81-2.85 (4H, m), 3.69 (2H, dd, J=23.5, 17.0 Hz), 4.03 (1H, d, J=13.6 Hz), 4.16 (1H, d, J=13.7 Hz), 4.34 (1H, dt, J=10.9, 4.5 Hz), 4.45 (1H, dd, J=13.7, 7.7 Hz), 4.64 (1H, dd, J=15.2, 2.5 Hz), 4.78 (1H, dd, J=15.2, 7.2 Hz), 5.04 (1H, ddd, J=14.1, 7.2, 2.5 Hz), 5.42 (2H, s), 7.30 (1H, dd, J=8.3, 1.9 Hz), 7.46 (1H, dd, J=10.0, 1.9 Hz), 7.51 (1H, t, J=8.3 Hz), 7.69 (1H, d, J=8.5 Hz), 7.82 (1H, dd, J=8.5, 1.4 Hz), 7.92 (1H, s), 8.27 (1H, s).

Example 7 Synthesis of Compound I-062

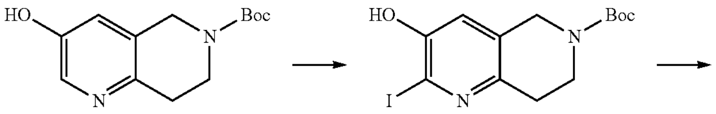

48 49

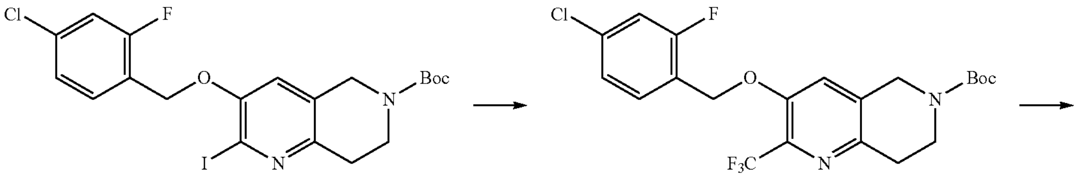

50 51

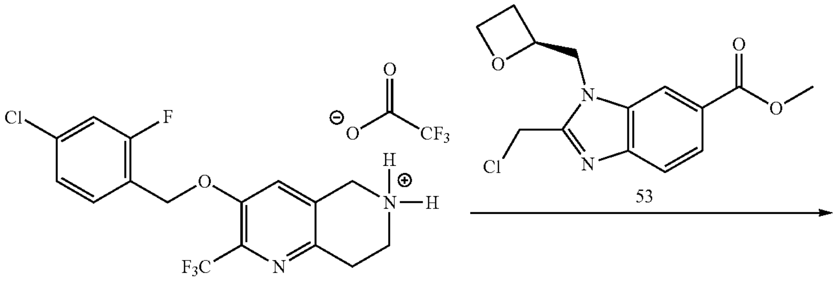

52 53

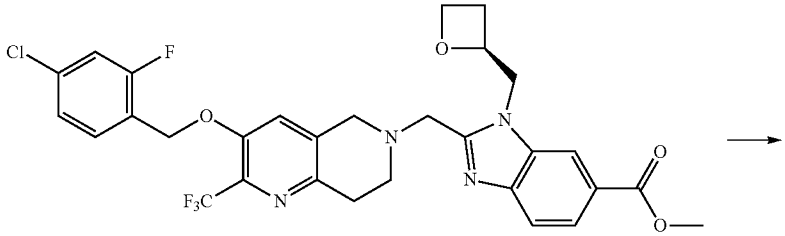

54

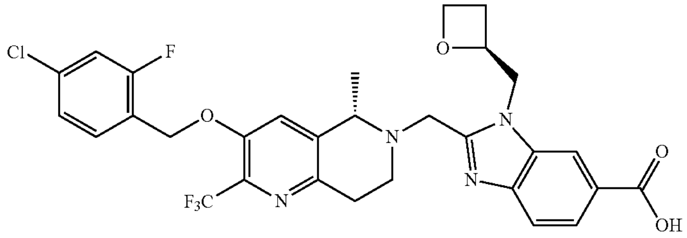

I-062

Step 1 Synthesis of Compound 49

Compound 48 (107 mg, 0.43 mmol) and sodium carbonate (91 mg, 0.86 mmol) were dissolved in tetrahydrofuran (2 mL)/water (2 mL), and iodine (114 mg, 0.45 mmol) was added thereto, then the mixture was stirred at room temperature for 4.5 hours. The reaction solution was added to a sodium thiosulfate solution, and the solution was extracted with ethyl acetate. The organic layer was washed with a 10% aqueous citric acid solution and brine, and then dried over anhydrous sodium sulfate. The solvent was evaporated under reduced pressure, and the obtained residue was purified by column chromatography (hexane-ethyl acetate) to give Compound 49 (58 mg, yield 36%).

[M+H]=377.00, measurement condition 1: retention time: 1.63 min $^1$H-NMR ($CDCl_3$) δ: 1.49 (9H, s), 2.92 (2H, t, J=5.8 Hz), 3.70 (2H, t, J=5.9 Hz), 4.52 (2H, s), 6.96 (1H, s)

Step 2 Synthesis of Compound 50

Compound 49 (58 mg, 0.154 mmol), cesium carbonate (100 mg, 0.308 mmol), and 1-(bromomethyl)-4-chloro-2-fluorobenzene (0.021 mL, 0.154 mmol) were dissolved in N,N-dimethylformamide (1.0 mL), and the mixture was stirred at room temperature for 2.5 hours. The reaction solution was added to water. The solution was extraction with ethyl acetate. The organic layer was washed with water, and dried over anhydrous sodium sulfate. The solvent was evaporated under reduced pressure, and the obtained residue was purified by column chromatography (hexane-ethyl acetate) to give Compound 50 (53 mg, yield 66%).

[M+H]=519.00, measurement condition 1: retention time: 1.78 min $^1$H-NMR ($CDCl_3$) δ: 1.50 (9H, s), 2.94 (2H, t, J=5.3 Hz), 3.70 (2H, t, J=5.8 Hz), 4.53 (2H, s), 5.14 (2H, s), 6.79 (1H, s), 7.15 (1H, dd, J=9.8 Hz, 1.9 Hz), 7.22 (1H, d, J=8.3 Hz), 7.61 (1H, t, J=7.9 Hz).

Step 3 Synthesis of Compound 51

Compound 50 (20 mg, 0.039 mmol) was dissolved in N,N-dimethylformamide (0.1 mL) and N-methylpyrrolidone (0.1 mL), and copper iodide (59 mg, 0.308 mmol) and fluorosulfonyl difluoroacetic acid methyl ester (0.039 mL, 0.308 mmol) were added thereto at room temperature, then the mixture was stirred at 100° C. for 1 hour. The reaction solution was added to ice-water. The solution was extracted with ethyl acetate. The organic layer was washed with a 5% aqueous sodium hydrogen carbonate solution and brine, and dried over anhydrous sodium sulfate. The solvent was evaporated under reduced pressure to give Compound 51 (21 mg, yield 100%).

[M+H]=461.10, measurement condition 1: retention time: 2.84 min $^1$H-NMR ($CDCl_3$) δ: 1.50 (9H, s), 2.98 (2H, t, J=5.8 Hz), 3.75 (2H, t, J=5.8 Hz), 4.63 (2H, s), 5.18 (2H, s), 6.79 (1H, s), 7.15 (2H, m), 7.21 (1H, m), 7.48 (1H, t, J=8.2 Hz).

Step 4 Synthesis of Compound 54

Compound 51 (21 mg, 0.046 mmol) was dissolved in dichloromethane (0.2 mL), trifluoroacetic acid (0.029 mL, 2.730 mmol) was added thereto at room temperature, and the mixture was stirred at room temperature for 40 minutes. The reaction solution was allowed to stand overnight and the solvent was evaporated under reduced pressure to give Compound 52. The obtained residue was dissolved in acetonitrile (1 mL), and potassium carbonate (80 mg, 0.579 mmol) and Compound 53 (13 mg, 0.046 mmol) were added thereto, then the mixture was stirred at 50° C. for 2 hours. Furthermore, the reaction solution was stirred at 60° C. for 3 hours, and then allowed to stand for a whole day and night. The reaction solution was added to ice-water. The solution was extracted with ethyl acetate. The organic layer was washed with water, and dried over anhydrous sodium sulfate. The solvent was evaporated under reduced pressure. The obtained residue was purified by silica gel column chromatography (hexane-ethyl acetate, subsequently chloroform-methanol) to give Compound 54 (12 mg, yield 43%).

[M+H]=619.15, measurement condition 1: retention time: 2.22 min $^1$H-NMR ($CDCl_3$) δ: 2.41 (1H, m), 2.69 (1H, m), 2.90-3.10 (4H, m), 3.73 (2H, s), 3.95 (3H, s), 4.20 (2H, q, J=8.8 Hz), 4.34 (1H, m), 4.55-4.75 (3H, m), 5.11 (2H, s), 5.19 (1H, m), 7.03 (1H, s), 7.12 (1H, dd, J=10.4 Hz, 2.0 Hz), 7.18 (1H, m), 7.45 (1H, t, J=2.0 Hz), 7.79 (1H, d, J=8.4 Hz), 8.00 (1H, dd, J=8.4 Hz, 1.2 Hz), 8.14 (1H, d, J=0.8 Hz).

Step 5 Synthesis of Compound I-062

Compound 54 (12 mg, 0.019 mmol) was dissolved in tetrahydrofuran (0.2 mL), and a 1 mol/L aqueous sodium hydroxide solution (0.1 mL, 0.100 mmol) was added thereto, then the mixture was stirred at room temperature for 1 hour, and then stirred at 60° C. for 1.5 hours. Further, a 1 mol/L aqueous sodium hydroxide solution (0.1 mL, 0.100 mmol) was added thereto, and the mixture was stirred at 60° C. for 1 hour. The reaction solution was added to water, the mixture was rendered acidic with a 10% aqueous citric acid solution. The solution was extracted with ethyl acetate. The organic layer was washed with water, and dried over anhydrous sodium sulfate. The solvent was evaporated under reduced pressure. The obtained residue was solidified with n-hexane to give Compound I-062 (6.7 mg, yield 57%).

[M+H]=605.2, measurement condition 1: retention time: 2.02 min $^1$H-NMR ($CDCl_3$) δ: 2.42 (1H, m), 2.70 (1H, m), 2.95-3.10 (4H, m), 3.74 (2H, s), 4.22 (2H, dd, J=19.6 Hz, 13.2 Hz), 4.36 (1H, m), 4.55-4.75 (3H, m), 5.11 (2H, s), 5.15 (1H, m), 7.04 (1H, s), 7.11 (1H, dd, J=9.6 Hz, 2.0 Hz), 7.18 (1H, m), 7.45 (1H, t, J=8.0 Hz), 7.83 (1H, d, J=8.8 Hz), 8.06 (1H, m), 8.21 (1H, m).

Example 8 Synthesis of Compound I-076

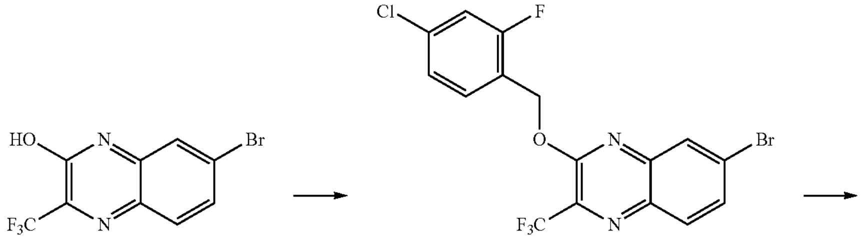

55

56

-continued

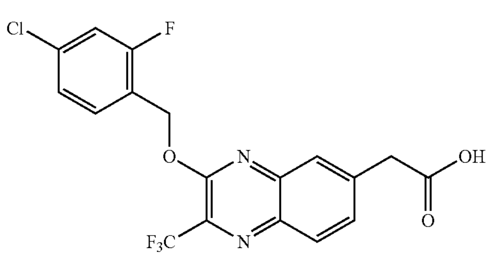

57

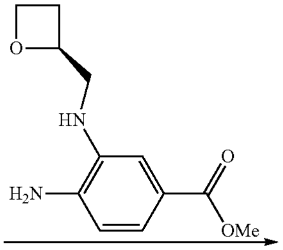

58

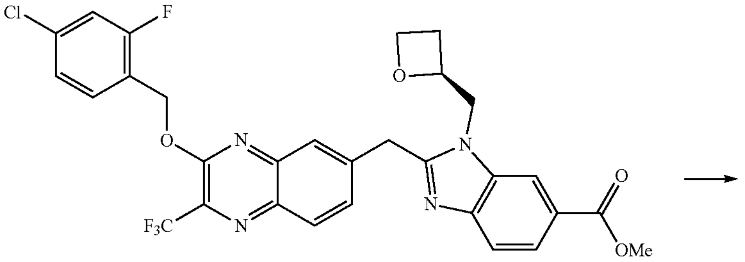

59

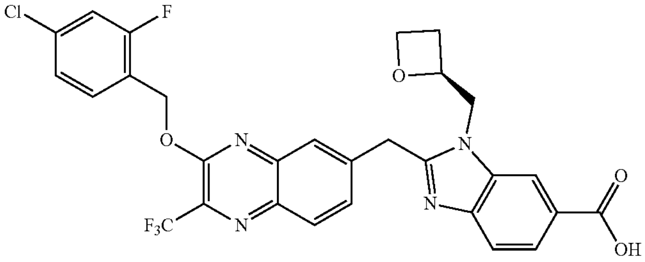

I-076

Step 1 Synthesis of Compound 56

Compound 55 (WO2021013735A) (1.02 g, 3.48 mmol) and 4-chloro-2-fluorobenzyl bromide (0.856 g, 3.83 mmol) were dissolved in acetonitrile (20.4 mL), and silver carbonate (1.92 g, 6.96 mmol) was added thereto, then the mixture was stirred at 60° C. for 6 hours. After cooled to room temperature, the reaction solution was filtered through Celite®, and Celite® was washed with ethyl acetate to give a filtrate. The filtrate was concentrated, and the obtained residue was purified by column chromatography (hexane-ethyl acetate) to give Compound 56 (0.897 g, yield 59%).

[M+H]=434.90, measurement condition 1: retention time 3.05 min $^1$H-NMR ($CDCl_3$) δ: 5.66 (2H, s), 7.14-7.19 (2H, m), 7.50 (1H, t, J=8.0 Hz), 7.76 (2H, dd, J=8.8, 2.0 Hz), 7.98 (1H, d, J=8.8 Hz), 8.11 (1H, d, J=2.0 Hz).

Step 2 Synthesis of Compound 57

Compound 56 (100 mg, 0.230 mmol), 1-(tert-butyldimethylsilyloxy)-1-methoxyethene (130 mg, 0.689 mmol), zinc fluoride (71.2 mg, 0.689 mmol), and bis-tert-tributylphosphine palladium (11.3 mg, 0.023 mmol) were dissolved in N,N-dimethylformamide (2.0 mL), and the mixture was stirred at 130° C. for 3 hours under microwave irradiation. After cooled to room temperature, water and ethyl acetate were added to the reaction solution. The solution was extracted with ethyl acetate. The organic layer was washed with water, and dried over anhydrous magnesium sulfate. The solvent was evaporated under reduced pressure, and the obtained residue was purified by column chromatography (hexane-ethyl acetate) to give residue (40.0 mg). The obtained residue was dissolved in a solution of tetrahydrofuran (0.39 mL) and methanol (0.39 mL), and a 1 mol/L aqueous sodium hydroxide solution (0.270 ml, 0.270 mmol) was added thereto, then the mixture was stirred at room temperature for 1 hour. A 10% aqueous citric acid solution was added to the reaction solution, then the reaction solution was separated by filtration, and the residue was washed with water and dried to give Compound 57 (32.8 mg, two-step yield 36%).

[M+H]=414.85, measurement condition 1: retention time 2.43 min $^1$H-NMR ($CDCl_3$) δ: 3.92 (2H, s), 5.69 (2H, s), 7.54 (1H, dd, J=10.0, 2.0 Hz), 7.66 (1H, t, J=10.0 Hz), 7.71 (1H, dd, J=8.5, 1.6 Hz), 7.89 (1H, s), 8.11 (1H, d, J=8.5 Hz).

Step 3 Synthesis of Compound 59

Compound 57 (32.0 mg, 0.077 mmol) and Compound 58 (20.1 mg, 0.085 mmol) were dissolved in N,N-dimethylformamide (0.64 mL), and triethylamine (0.021 ml, 0.154 mmol) and 1-(bis(dimethylaminomethylene)-1H-1,2,3-triazolo(4,5-b)pyridinium 3-oxide hexafluorophosphate (44.0 mg, 0.116 mmol) were added thereto. The mixture was stirred at room temperature for 30 minutes. Saturated sodium bicarbonate water was added to the reaction solution. The solution was separated by filtration, the residue was washed with water, and dried, to give residue (44.4 mg). The obtained residue (44.0 mg) was dissolved in acetic acid (0.44 ml) and stirred at 60° C. for 2 hours. The reaction solution was concentrated, the obtained residue was purified by column chromatography (hexane-ethyl acetate), to give Compound 59 (26.0 mg, two-step yield 55%).

[M+H]=615.15, measurement condition 1: retention time 2.63 min $^1$H-NMR ($CDCl_3$) δ: 2.32-2.41 (1H, m), 2.65-2.73 (1H, m), 3.95 (3H, s), 4.27-4.40 (3H, m), 4.65 (1H, dd, J=14.0, 7.6 Hz), 4.68-4.77 (2H, m), 5.12-5.18 (1H, m), 5.63 (2H, s), 7.12-7.18 (2H, m), 7.49 (1H, t, J=8.0 Hz), 7.62 (1H, dd, J=8.5, 2.0 Hz), 7.77-7.82 (2H, m), 8.01 (1H, dd, J=8.4, 1.5 Hz), 8.08 (1H, s), 8.08 (1H, d, J=8.4 Hz).

Step 4 Synthesis of Compound I-076

Compound 59 (24.5 mg, 0.040 mmol) was dissolved in tetrahydrofuran (0.25 mL) and methanol (0.25 mL), and a 1 mol/L aqueous sodium hydroxide solution (0.12 mL, 0.12 mmol) was added thereto, then the mixture was stirred at 60° C. for 1 hour. After cooled to room temperature, a 10% aqueous citric acid solution was added to the reaction solution. The reaction solution was separated by filtration, the residue was washed with water, and dried, to give residue. The obtained residue was purified by preparative TLC (0.5 mm, CHCl3-MeOH—H2O), and then subjected to SFC fractionation to give Compound I-076 (14.4 mg, 18% yield).

[M+H]=601.1, measurement condition 1: retention time 2.39 min $^1$H-NMR (DMSO-d6) δ: 2.32-2.40 (1H, m), 2.49-2.69 (1H, m), 4.32-4.37 (1H, m), 4.43-4.48 (1H, m), 4.55-4.74 (4H, m), 4.95-5.02 (1H, m), 5.66 (2H, s), 7.36 (1H, dd, J=8.2, 1.6 Hz), 7.52-7.57 (2H, m), 7.62-7.73 (1H, m), 7.78 (2H, dd, J=8.5, 1.2 Hz), 7.90 (1H, s), 8.13 (1H, d, J=8.6 Hz), 8.19 (1H, s).

Example 9 Synthesis of Compound I-145

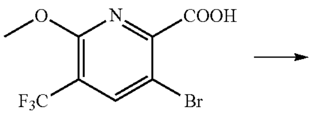

60

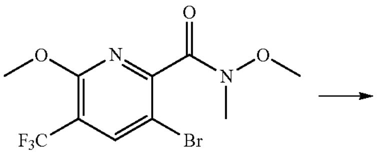

61

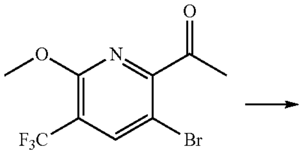

62

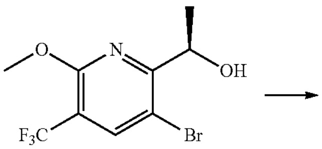

63

-continued

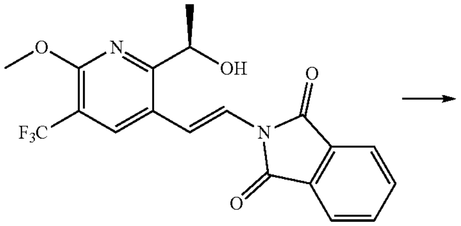

64

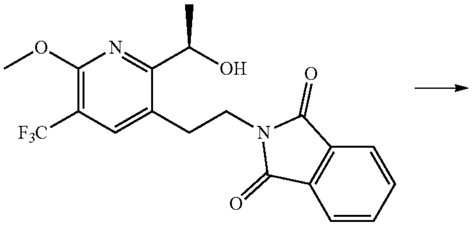

65

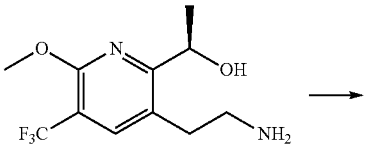

66

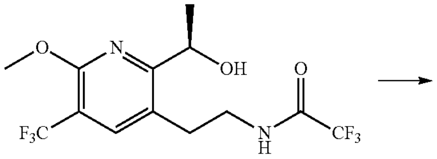

67

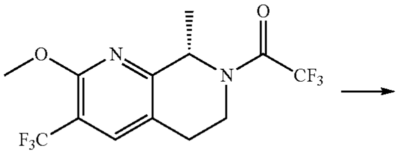

68

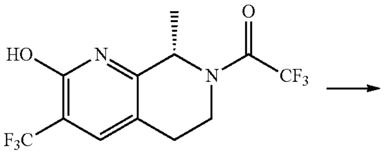

69

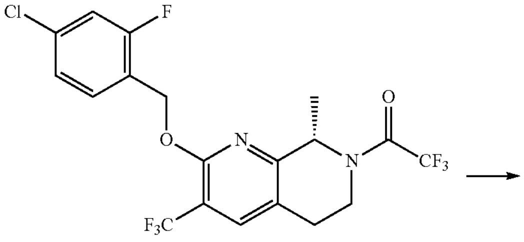

70

-continued

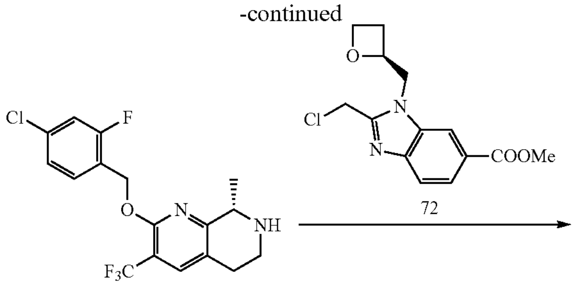

72

71

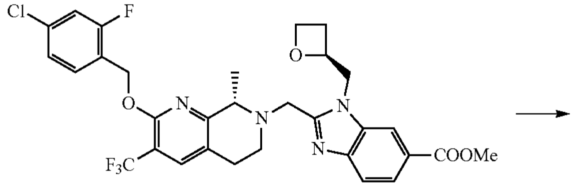

73

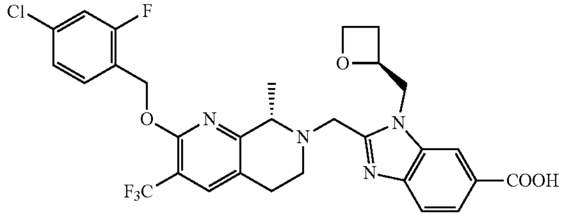

I-145

Step 1 Synthesis of Compound 61

N,O-dimethylhydroxylamine hydrochloride (20 g, 205 mmol), HOBt (4.6 g, 34 mmol), EDC hydrochloride (49 g, 257 mmol) and triethylamine (28 mL, 205 mmol) were added to a suspension of Compound 60 (51.3 g, 171 mmol) in dichloromethane (400 mL) synthesized by the synthesis method described in the patent WO2020146682, and then the mixture was stirred at room temperature for 1 hour. Water was added to the reaction solution, the organic layer was separated. The aqueous layer was extracted with ethyl acetate. The organic layer was combined therewith, dried over anhydrous magnesium sulfate. The solvent was evaporated under reduced pressure. Isopropyl ether was added to the obtained residue, and the resulting solids were collected by filtration to give Compound 61 (45.2 g, yield 77%).

$^1$H-NMR ($CDCl_3$) δ: 3.41 (3H, s), 3.63 (3H, s), 4.04 (3H, s), 8.02 (1H, s).

[M+H]=343, measurement condition 1: retention time 2.48 min

Step 2 Synthesis of Compound 62

A 3 mol/L methylmagnesium bromide diethyl ether solution (159 mL, 478 mmol) was added dropwise to a tetrahydrofuran (550 mL) solution of Compound 61 (54.7 g, 159 mmol) over 30 minutes under ice cooling. The mixture was stirred for 3 hours under ice cooling, and the reaction solution was added to an ice-cooled aqueous ammonium chloride solution. After a 2 mol/L hydrochloric acid was added thereto until the pH reached about 6, the solution was extracted with ethyl acetate twice. The resultant was dried over anhydrous magnesium sulfate. The solvent was evaporated under reduced pressure, and the obtained residue was purified by the silica gel column chromatography (hexane-ethyl acetate), thereby to give Compound 62 (29.1 g, yield 61%).

$^1$H-NMR ($CDCl_3$) δ: 2.67 (3H, s), 4.07 (3H, s), 8.10 (1H, s).

[M+H]=298, measurement condition 1: retention time 2.93 min

Step 3 Synthesis of Compound 63

Formic acid (16.1 mL, 420 mmol), triethylamine (33.8 mL, 244 mmol) and [(R,R)—N-(2-amino-1,2-diphenylethyl)-p-toluene sulfonamide]chloro (p-cymene)ruthenium (II) (1.24 g, 1.95 mmol) were added to an acetonitrile (400 mL) solution of Compound 62 (29.1 g, 98 mmol), and the mixture was stirred at room temperature for 2.5 hours. Water was added to the reaction solution. The solution was extracted with ethyl acetate. The resultant was washed with an aqueous sodium hydrogen carbonate solution. After the resultant was dried over anhydrous sodium sulfate, the solvent was evaporated under reduced pressure, and the obtained residue was purified by silica gel column chromatography (hexane-ethyl acetate) to give Compound 63 (28.5 g, yield 97%).

$^1$H-NMR ($CDCl_3$) δ: 1.47 (3H, d, J=6.5 Hz), 3.69 (1H, d, J=8.7 Hz), 4.08 (3H, s), 5.10 (1H, dt, J=15.1, 6.5 Hz), 7.98 (1H, s).

[M+H]=300, measurement condition 1: retention time 2.10 min

Step 4 Synthesis of Compound 64

To a solution of Compound 63 (32 g, 107 mmol) in N,N-dimethylformamide (250 mL), N-vinylphthalimide (18.9 g, 107 mmol), tetrabutylammonium bromide (34.4 g, 107 mmol), palladium acetate (2.4 g, 10.7 mmol), and N,N-dicyclohexyl-N-methylamine (34 mL, 160 mmol) were added. After degassing under reduced pressure, the mixture was purged with nitrogen, and stirred at 110° C. for 4 hours. Water was added to the reaction solution, and the resulting solids were collected by filtration, then the solids were washed with diisopropyl ether to give Compound 64 (37 g, 88% yield).

$^1$H-NMR ($CDCl_3$) δ: 1.47 (3H, d, J=6.5 Hz), 4.10-4.15 (4H, m), 5.12-5.18 (1H, m), 7.21 (1H, d, J=14.9 Hz), 7.74 (1H, d, J=14.9 Hz), 7.79-7.82 (2H, m), 7.91-7.95 (2H, m), 8.02 (1H, s).

[M+H]=393, measurement condition 1: retention time 2.35 min

Step 5 Synthesis of Compound 65

After 10% palladium-carbon (containing 50% of water) (20 g, 9.4 mmol) was added to a methanol (250 mL) and tetrahydrofuran (500 mL) solution of Compound 64 (37 g, 94 mmol), the mixture was stirred at room temperature for 8.5 hours under a hydrogen atmosphere (1 atm). Insolubles were removed by filtration, and the solvent was evaporated under reduced pressure to give a crude product (53 g) containing a compound 65. The obtained Compound 65 was used in the next step without purification or any other processing.

$^1$H-NMR ($CDCl_3$) δ: 1.50 (3H, d, J=6.4 Hz), 2.90-3.04 (2H, m), 3.87-3.91 (2H, m), 4.06 (3H, s), 5.13 (1H, d, J=5.9 Hz), 7.72-7.76 (3H, m), 7.84-7.88 (2H, m).

[M+H]=395, measurement condition 1: retention time 2.16 min

Step 6 Synthesis of Compound 66

Hydrazine monohydrate (22.8 mL, 470 mmol) was added to an ethanol (500 mL) solution of the whole amount (94 mmol) of the crude product of Compound 65 obtained in Step 5, and the mixture was stirred at 80° C. for 1 hour. After insolubles were removed by filtration, the solvent was evaporated under reduced pressure, and dichloromethane was added to the obtained residue. Precipitated insolubles were again removed by filtration, and the solvent was evaporated under reduced pressure to give a crude product (24.6 g) containing Compound 66. The obtained Compound 66 was used in the next step without purification or any other processing.

$^1$H-NMR ($CDCl_3$) δ: 1.49 (3H, d, J=6.4 Hz), 2.69-2.92 (3H, m), 3.03-3.09 (1H, m), 4.06 (3H, s), 5.06 (1H, q, J=6.4 Hz), 7.68 (1H, s). [M+H]=265, measurement condition 1: retention time 1.15 min Step 7 Synthesis of Compound 67

Trifluoroacetic anhydride (40 mL, 282 mmol) was added dropwise to a dichloromethane (200 mL) solution of the whole amount (94 mmol) of the crude product of Compound 66 obtained in Step 6 under ice cooling, and the mixture was stirred at room temperature for 1 hour. After the solvent was evaporated under reduced pressure, the obtained residue was dissolved in toluene, and the solvent was evaporated under reduced pressure again. The resulting residue was dissolved in ethyl acetate and slowly poured into an aqueous sodium hydrogen carbonate solution. The mixture was stirred at 30° C. for 6 hours. The solution was extracted with ethyl acetate twice. The resultant was dried over anhydrous magnesium sulfate, the solvent was evaporated under reduced pressure, and the obtained residue was purified by the silica gel column chromatography (hexane-ethyl acetate) to give Compound 67 (22.9 g, yield 68%).

$^1$H-NMR ($CDCl_3$) δ: 1.51 (3H, d, J=6.4 Hz), 2.87-2.99 (2H, m), 3.43 (1H, d, J=8.4 Hz), 3.51-3.66 (2H, m), 4.06 (3H, s), 5.05 (1H, dt, J=14.6, 6.5 Hz), 6.81 (1H, s), 7.68 (1H, s).

[M+H]=361, measurement condition 1: retention time 1.93 min

Step 8 Synthesis of Compound 68

Triphenylphosphine (23.5 g, 89 mmol) was added to a solution of Compound 67 (21.5 g, 60 mmol) in tetrahydrofuran (500 mL), and DIAD (17.4 mL, 89 mmol) was added dropwise thereto over 20 minutes under water cooling. The resultant was stirred at room temperature for 1.5 hour, the solvent was evaporated under reduced pressure, and the obtained residue was purified by silica gel column chromatography (hexane-ethyl acetate) to give Compound 68 (16.4 g, Yield 81%).

$^1$H-NMR ($CDCl_3$) δ: 1.60 (2.1H, d, J=6.9 Hz), 1.67 (0.9H, d, J=6.8 Hz), 2.71-2.80 (1H, m), 2.91-3.02 (1H, m), 3.18 (0.3H, dt, J=18.6, 6.4 Hz), 3.44-3.52 (0.7H, m), 4.00-4.01 (3H, m), 4.13-4.19 (0.7H, m), 4.74 (0.3H, dd, J=13.3, 5.6 Hz), 5.05 (0.3H, q, J=6.7 Hz), 5.48 (0.7H, q, J=6.9 Hz), 7.62-7.64 (1H, m).

[M+H]=343, measurement condition 1: retention time 2.56 min

Step 9 Synthesis of Compound 69

Sodium iodide (21.6 g, 144 mmol) and trimethylsilyl chloride (18.4 mL, 144 mmol) were added to an acetonitrile (200 mL) solution of Compound 68 (16.4 g, 48 mmol), and the mixture was stirred at 45° C. for 1 hour. An aqueous sodium hydrogen carbonate solution and an aqueous sodium thiosulfate solution were added to the reaction solution. The solution was extracted with ethyl acetate twice. The resultant was dried over anhydrous sodium sulfate, and the solvent was evaporated under reduced pressure to give a crude product (15.8 g) of Compound 69. The obtained Compound 69 was used in the next step without purification or any other processing.

$^1$H-NMR ($CDCl_3$) δ: 1.66 (2.25H, d, J=6.9 Hz), 1.75 (0.75H, d, J=6.7 Hz), 2.57-2.65 (1H, m), 2.77-2.89 (1H, m), 3.15-3.22 (0.25H, m), 3.45-3.52 (0.75H, m), 4.16 (0.75H, dd, J=14.3, 4.6 Hz), 4.73 (0.25H, dd, J=13.7, 5.8 Hz), 5.01 (0.25H, dd, J=13.7, 6.8 Hz), 5.50 (0.75H, q, J=6.7 Hz), 7.63-7.65 (1H, m).

[M+H]=329, measurement condition 1: retention time 1.57 min

Step 10 Synthesis of Compound 70

Silver carbonate (8.95 g, 32 mmol) and 4-chloro-2-fluorobenzyl bromide (5.8 g, 26 mmol) were added to a 1,4 dioxane (70 mL) solution of Compound 69 (7.1 g, 21.6 mmol), and the mixture was stirred at 65° C. for 1 hour. After insolubles were removed by filtration, the solvent was evaporated under reduced pressure, and the obtained residue was purified by silica gel column chromatography (hexane-ethyl acetate) to give Compound 70 (9.89 g, 97%).

$^1$H-NMR ($CDCl_3$) δ: 1.56 (2.1H, d, J=4.8 Hz), 1.63 (0.9H, d, J=6.9 Hz), 2.72-2.80 (1H, m), 2.91-3.02 (1H, m), 3.17 (0.3H, td, J=12.9, 3.8 Hz), 3.43-3.51 (0.7H, m), 4.16 (0.7H, dd, J=14.2, 3.8 Hz), 4.73 (0.3H, dd, J=13.2, 5.6 Hz), 5.04 (0.3H, dd, J=13.2, 6.8 Hz), 5.45-5.55 (2.7H, m), 7.11-7.16 (2H, m), 7.41-7.46 (1H, m), 7.65-7.67 (1H, m).

[M+H]=471, measurement condition 1: retention time 3.11 min

Step 11 Synthesis of Compound 71

After potassium carbonate (5.8 g, 42 mmol) was added to a methanol (80 mL) and tetrahydrofuran (80 mL) solution of Compound 70 (9.89 g, 21 mmol), the mixture was stirred at 50° C. for 8 hours. The solvent was evaporated under reduced pressure. Water was added to the residue. The solution was extraction with ethyl acetate twice. The resultant was dried over anhydrous sodium sulfate, and the solvent was evaporated under reduced pressure to give a crude product (9.31 g) of Compound 71. The obtained Compound 71 was used in the next step without purification or any other processing.

$^1$H-NMR ($CDCl_3$) δ: 1.47 (3H, d, J=6.8 Hz), 2.68 (1H, dt, J=16.0, 4.0 Hz), 2.80-2.88 (1H, m), 2.97-3.04 (1H, m), 3.27 (1H, dt, J=12.2, 4.7 Hz), 4.00 (1H, q, J=6.5 Hz), 5.47 (1H, d, J=13.4 Hz), 5.52 (1H, d, J=13.4 Hz), 7.08-7.14 (2H, m), 7.44 (1H, t, J=8.0 Hz), 7.57 (1H, s).

[M+H]=375, measurement condition 1: retention time 2.13 min

Step 12 Synthesis of Compound 73

Compound 72 (4.0 g, 13.6 mmol) and potassium carbonate (4.0 g, 29 mmol) were added to an acetonitrile (64 mL) solution of ⅔ (14 mmol) of the whole amount of the crude product of Compound 71 obtained in step 11, and the mixture was stirred at 65° C. for 6 hours. After brine was added to the reaction solution, the solution was extracted with ethyl acetate twice. The solvent was evaporated under reduced pressure. The residue was dissolved in chloroform, then dried over anhydrous magnesium sulfate, and the solvent was evaporated under reduced pressure to give a crude product (9.67 g) of Compound 73. The obtained Compound 73 was used in the next step without purification or any other processing.

$^1$H-NMR ($CDCl_3$) δ: 1.47 (3H, d, J=6.7 Hz), 2.35-2.44 (1H, m), 2.61-2.83 (4H, m), 3.00-3.06 (1H, m), 3.84 (1H, q, J=6.6 Hz), 3.95 (3H, s), 4.10 (1H, d, J=13.6 Hz), 4.32 (1H, dt, J=11.0, 4.6 Hz), 4.39 (1H, d, J=13.6 Hz), 4.60 (1H, dd, J=13.8, 8.0 Hz), 4.67 (1H, dd, J=15.4, 5.7 Hz), 4.73 (1H, dd, J=15.4, 3.1 Hz), 5.17-5.23 (1H, m), 5.44 (1H, d, J=13.3 Hz), 5.52 (1H, d, J=13.3 Hz), 7.07-7.14 (2H, m), 7.44 (1H, t, J=8.0 Hz), 7.59 (1H, s), 7.77 (1H, d, J=8.5 Hz), 7.99 (1H, dd, J=8.5, 1.5 Hz), 8.14 (1H, d, J=1.0 Hz).

[M+H]=633, measurement condition 1: retention time 2.49 min

Step 13 Synthesis of Compound I-145

After a 2 mol/L aqueous sodium hydroxide solution (21.5 mL, 43 mmol) was added to a methanol (55 mL) and tetrahydrofuran (55 mL) solution of the entire amount (14 mmol) of the crude product of Compound 73 obtained in Step 12, the mixture was stirred at 45° C. for 2 hours. After an aqueous citric acid solution was added to the reaction solution, the solution was extracted with ethyl acetate twice. The resultant was dried over anhydrous sodium sulfate, and the solvent was evaporated under reduced pressure. Ethanol was added to the obtained residue, and the solvent was evaporated again under reduced pressure. Ethanol (20 mL) and water (10 mL) were added to the residue, and the resulting suspension was stirred at 40° C. for 15 minutes and then stirred at room temperature for 30 minutes. Solids were collected from the obtained suspension by filtration to give Compound I-145 (6.55 g, yield 74%).

$^1$H-NMR (DMSO-$D_6$) δ: 1.37 (3H, d, J=6.8 Hz), 2.30-2.38 (1H, m), 2.57-2.85 (4H, m), 2.96-3.01 (1H, m), 3.86 (1H, dd, J=13.3, 6.4 Hz), 4.09 (1H, d, J=13.9 Hz), 4.20 (1H, d, J=13.9 Hz), 4.29 (1H, dt, J=10.8, 4.5 Hz), 4.45 (1H, dd, J=13.7, 7.8 Hz), 4.68 (1H, dd, J=15.4, 2.8 Hz), 4.77 (1H, dd, J=15.4, 6.7 Hz), 5.06-5.12 (1H, m), 5.43 (1H, d, J=12.9 Hz), 5.52 (1H, d, J=12.9 Hz), 7.31 (1H, dd, J=8.3, 1.8 Hz), 7.46-7.53 (2H, m), 7.68 (1H, d, J=8.5 Hz), 7.82 (1H, dd, J=8.5, 1.3 Hz), 7.89 (1H, s), 8.27 (1H, s).

The following compounds were also synthesized in the same manner by using the general synthesis method described above or the synthesis method described in Examples. I-032, I-044, I-066, and I-133 in the tables are diastereomeric mixtures, and I-144 in the table is a racemate.

TABLE 1

| Ex. No. | Structural formula | RT | [M + H] | Measurement condition |
|---|---|---|---|---|
| I-001 | 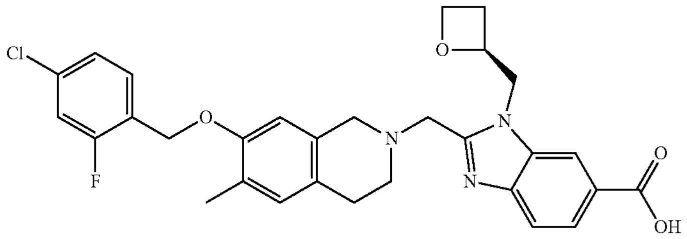 [SMILES: Cc1cc2c(cc1OCc1ccc(Cl)cc1F)CN(Cc1nc3ccc(C(=O)O)cc3n1C[C@@H]1CCO1)CC2] | 1.63 | 550 | 2 |
| I-002 | 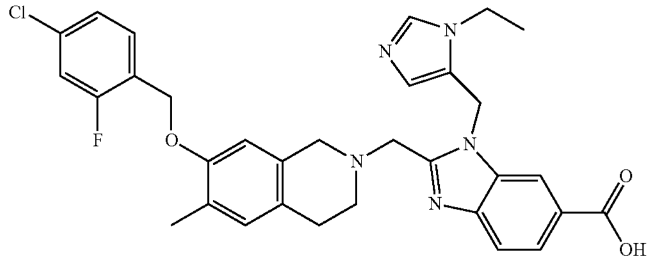 [SMILES: CCn1cncc1Cn1c(CN2CCc3cc(C)c(OCc4ccc(Cl)cc4F)cc3C2)nc2ccc(C(=O)O)cc21] | 1.95 | 588 | 4 |
| I-003 | 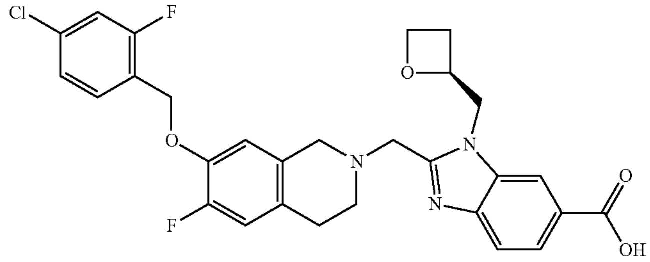 [SMILES: O=C(O)c1ccc2nc(CN3CCc4cc(F)c(OCc5ccc(Cl)cc5F)cc4C3)n(C[C@@H]3CCO3)c2c1] | 1.55 | 554 | 2 |
| I-004 | 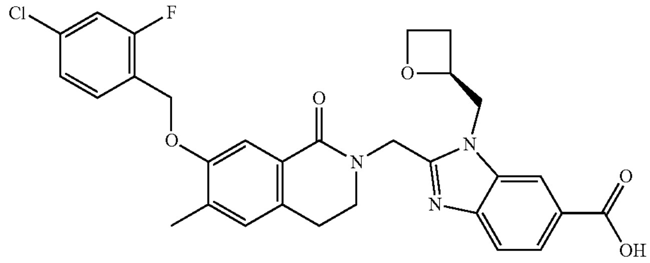 [SMILES: Cc1cc2c(cc1OCc1ccc(Cl)cc1F)C(=O)N(Cc1nc3ccc(C(=O)O)cc3n1C[C@@H]1CCO1)CC2] | 2.14 | 564 | 2 |

TABLE 1-continued
| Ex. No. | Structural formula | RT | [M + H] | Measurement condition |
|---|---|---|---|---|
| I-005 | 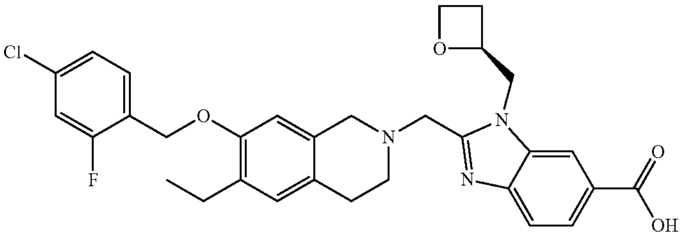 [SMILES: CCc1cc2c(cc1OCc1ccc(Cl)cc1F)CN(Cc1nc3ccc(C(=O)O)cc3n1C[C@@H]1CCO1)CC2] | 2.27 | 564 | 1 |
| I-006 | 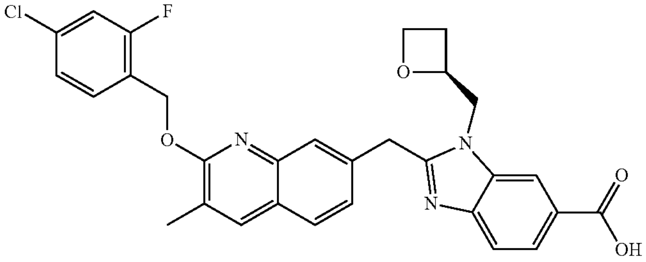 [SMILES: Cc1cc2ccc(Cc3nc4ccc(C(=O)O)cc4n3C[C@@H]3CCO3)cc2nc1OCc1ccc(Cl)cc1F] | 2.27 | 546 | 3 |
TABLE 2
| | | | | |
|---|---|---|---|---|
| I-007 | 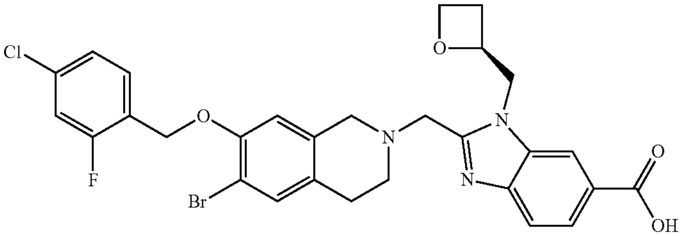 | 2.08 | 614 | 1 |
| I-008 | 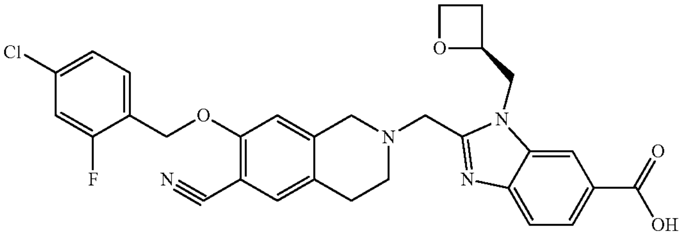 [SMILES: N#Cc1cc2c(cc1OCc1ccc(Cl)cc1F)CN(Cc1nc3ccc(C(=O)O)cc3n1C[C@@H]1CCO1)CC2] | 1.8 | 561 | 1 |
| I-009 | 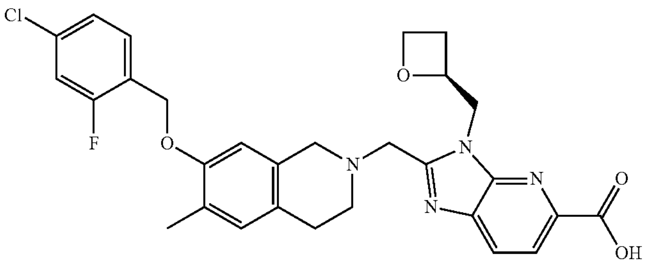 [SMILES: Cc1cc2c(cc1OCc1ccc(Cl)cc1F)CN(Cc1nc3ccc(C(=O)O)nc3n1C[C@@H]1CCO1)CC2] | 2.11 | 551 | 2 |

TABLE 2-continued
| | | | | |
|---|---|---|---|---|
| I-010 | 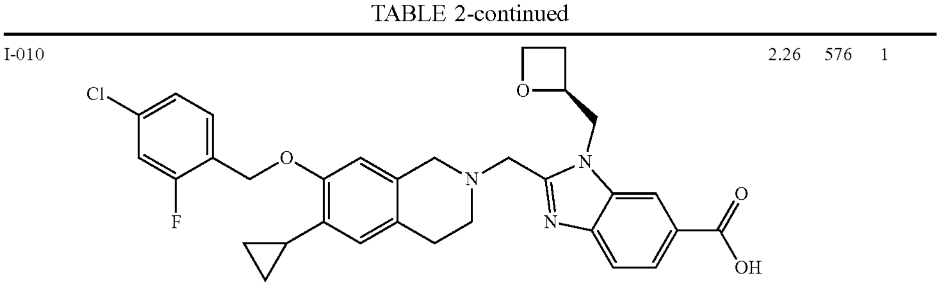 | 2.26 | 576 | 1 |
| I-011 | 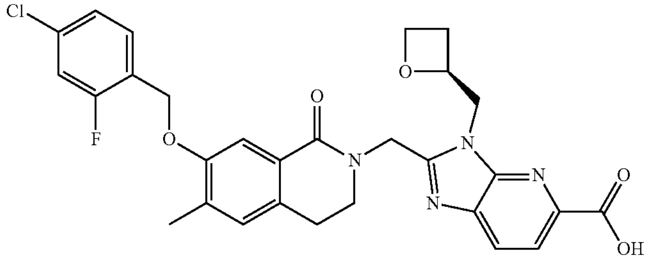 [SMILES: Cc1cc2c(cc1OCc1ccc(Cl)cc1F)C(=O)N(Cc1nc3ccc(C(=O)O)nc3n1C[C@@H]1CCO1)CC2] | 2.26 | 565 | 3 |
| I-012 | 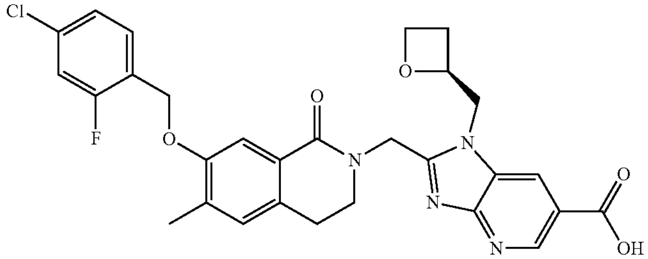 [SMILES: Cc1cc2c(cc1OCc1ccc(Cl)cc1F)C(=O)N(Cc1nc3ncc(C(=O)O)cc3n1C[C@@H]1CCO1)CC2] | 2.17 | 565 | 3 |
TABLE 3
| | | | | |
|---|---|---|---|---|
| I-013 | 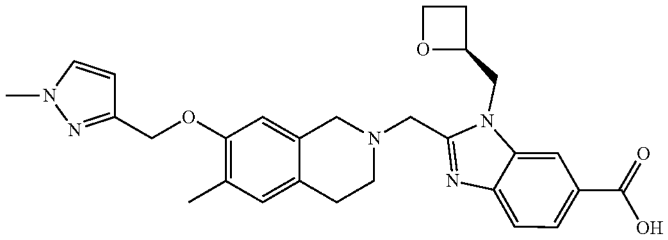 [SMILES: Cc1cc2c(cc1OCc1ccn(C)n1)CN(Cc1nc3ccc(C(=O)O)cc3n1C[C@@H]1CCO1)CC2] | 1.12 | 502 | 2 |
| I-014 | 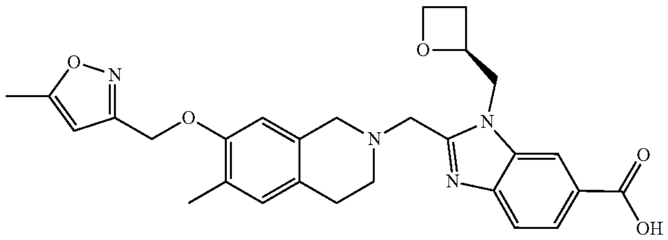 [SMILES: Cc1cc(COc2cc3c(cc2C)CCN(Cc2nc4ccc(C(=O)O)cc4n2C[C@@H]2CCO2)C3)no1] | 1.23 | 503 | 2 |

TABLE 3-continued
| | | | | |
|---|---|---|---|---|
| I-015 | 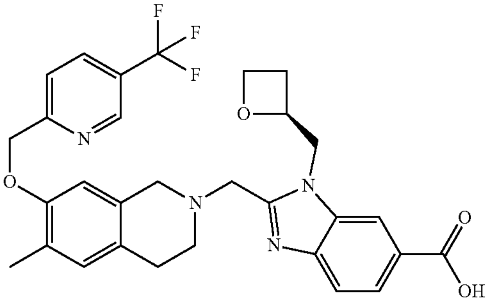 [SMILES: Cc1cc2c(cc1OCc1ccc(C(F)(F)F)cn1)CN(Cc1nc3ccc(C(=O)O)cc3n1C[C@@H]1CCO1)CC2] | 1.42 | 567 | 2 |
| I-016 | 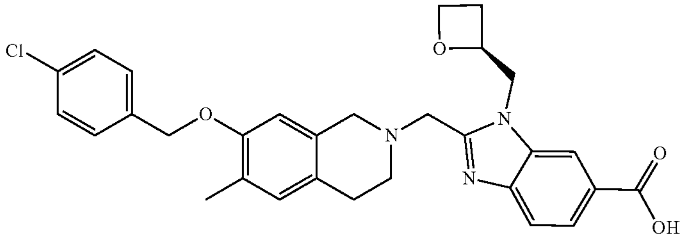 [SMILES: Cc1cc2c(cc1OCc1ccc(Cl)cc1)CN(Cc1nc3ccc(C(=O)O)cc3n1C[C@@H]1CCO1)CC2] | 1.57 | 532 | 2 |
| I-017 | 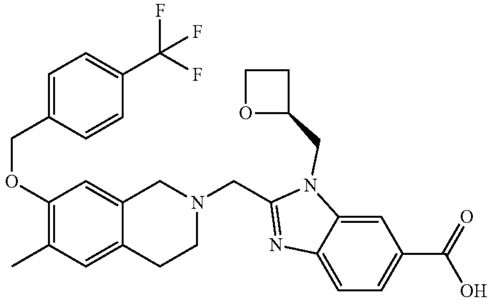 [SMILES: Cc1cc2c(cc1OCc1ccc(C(F)(F)F)cc1)CN(Cc1nc3ccc(C(=O)O)cc3n1C[C@@H]1CCO1)CC2] | 2 | 566 | 2 |
| I-018 | 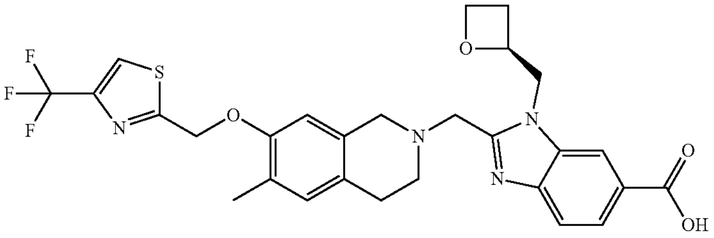 [SMILES: Cc1cc2c(cc1OCc1nc(C(F)(F)F)cs1)CN(Cc1nc3ccc(C(=O)O)cc3n1C[C@@H]1CCO1)CC2] | 1.78 | 573 | 2 |
TABLE 4
| | | | | |
|---|---|---|---|---|
| I-019 | 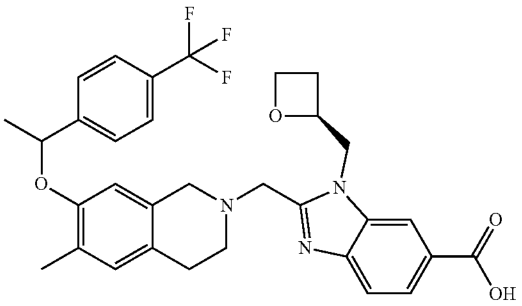 [SMILES: Cc1cc2c(cc1OC(C)c1ccc(C(F)(F)F)cc1)CN(Cc1nc3ccc(C(=O)O)cc3n1C[C@@H]1CCO1)CC2] | 1.69 | 580 | 2 |

TABLE 4-continued
| | | | | |
|---|---|---|---|---|
| I-020 | 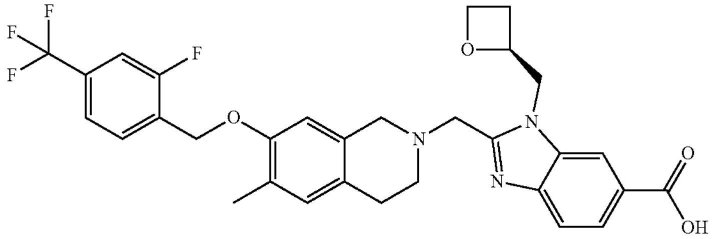 [SMILES: Cc1cc2c(cc1OCc1ccc(C(F)(F)F)cc1F)CN(Cc1nc3ccc(C(=O)O)cc3n1C[C@@H]1CCO1)CC2] | 2.02 | 584 | 2 |
| I-021 | 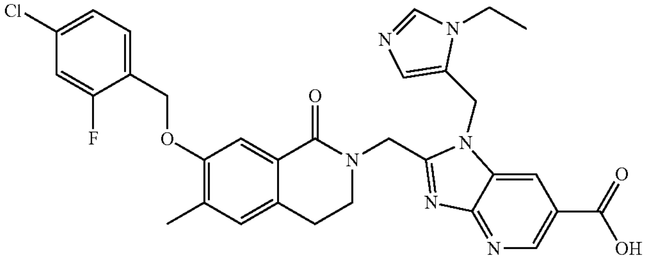 [SMILES: CCn1cncc1Cn1c(CN2CCc3cc(C)c(OCc4ccc(Cl)cc4F)cc3C2=O)nc2ncc(C(=O)O)cc21] | 1.69 | 603 | 3 |
| I-022 | 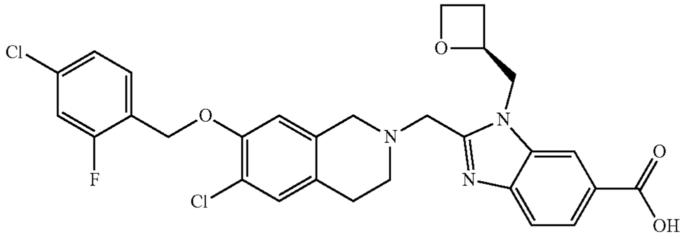 [SMILES: O=C(O)c1ccc2nc(CN3CCc4cc(Cl)c(OCc5ccc(Cl)cc5F)cc4C3)n(C[C@@H]3CCO3)c2c1] | 2.05 | 570 | 1 |
| I-023 | 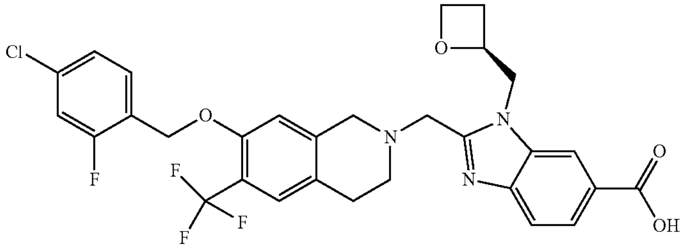 [SMILES: O=C(O)c1ccc2nc(CN3CCc4cc(C(F)(F)F)c(OCc5ccc(Cl)cc5F)cc4C3)n(C[C@@H]3CCO3)c2c1] | 2.18 | 604 | 1 |
| I-024 | 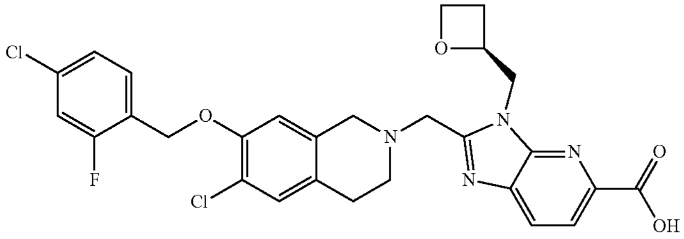 [SMILES: O=C(O)c1ccc2nc(CN3CCc4cc(Cl)c(OCc5ccc(Cl)cc5F)cc4C3)n(C[C@@H]3CCO3)c2n1] | 2.01 | 571 | 1 |
TABLE 5
| | | | | |
|---|---|---|---|---|
| I-025 | 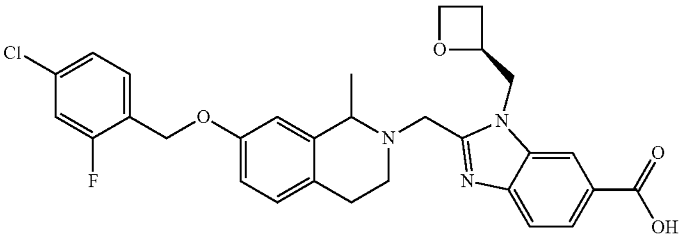 [SMILES: CC1c2cc(OCc3ccc(Cl)cc3F)ccc2CCN1Cc1nc2ccc(C(=O)O)cc2n1C[C@@H]1CCO1] | 2.09 | 550 | 2 |

TABLE 5-continued
| | | | | |
|---|---|---|---|---|
| I-026 | 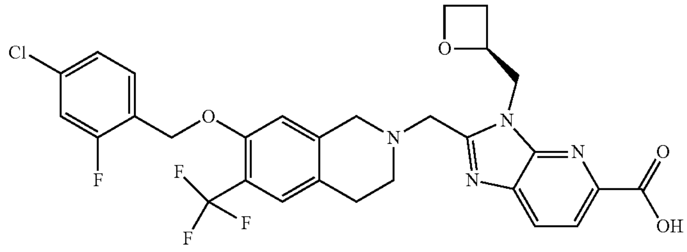 [SMILES: O=C(O)c1ccc2nc(CN3CCc4cc(C(F)(F)F)c(OCc5ccc(Cl)cc5F)cc4C3)n(C[C@@H]3CCO3)c2n1] | 2.09 | 605 | 1 |
| I-027 | 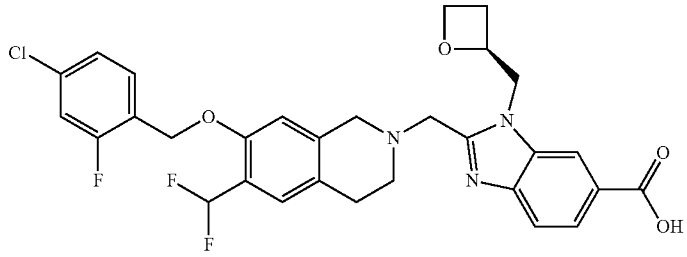 [SMILES: O=C(O)c1ccc2nc(CN3CCc4cc(C(F)F)c(OCc5ccc(Cl)cc5F)cc4C3)n(C[C@@H]3CCO3)c2c1] | 2.03 | 586 | 1 |
| I-028 | 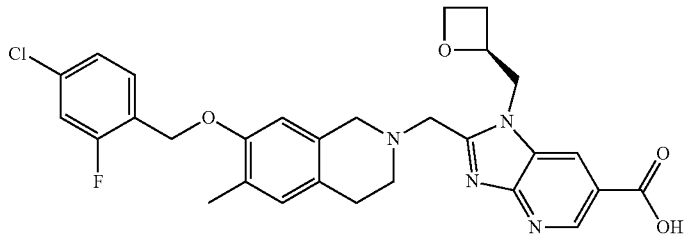 [SMILES: Cc1cc2c(cc1OCc1ccc(Cl)cc1F)CN(Cc1nc3ncc(C(=O)O)cc3n1C[C@@H]1CCO1)CC2] | 2 | 551 | 2 |
| I-029 | 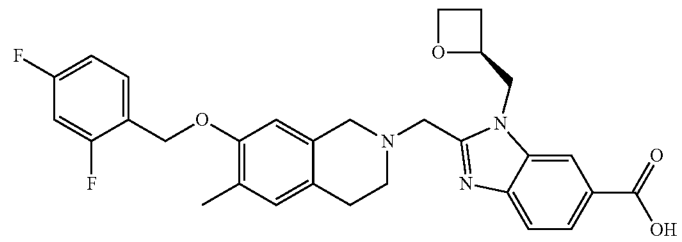 [SMILES: Cc1cc2c(cc1OCc1ccc(F)cc1F)CN(Cc1nc3ccc(C(=O)O)cc3n1C[C@@H]1CCO1)CC2] | 1.95 | 534 | 1 |
| I-030 | 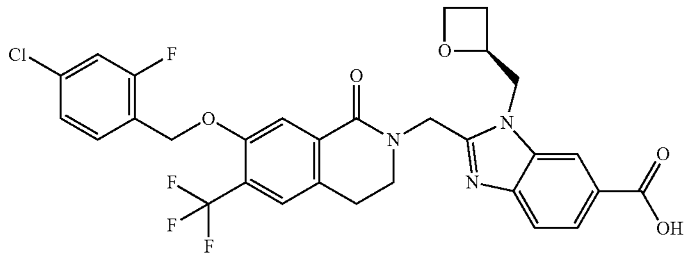 [SMILES: O=C(O)c1ccc2nc(CN3CCc4cc(C(F)(F)F)c(OCc5ccc(Cl)cc5F)cc4C3=O)n(C[C@@H]3CCO3)c2c1] | 2.31 | 618 | 3 |
TABLE 6
| | | | | |
|---|---|---|---|---|
| I-031 | 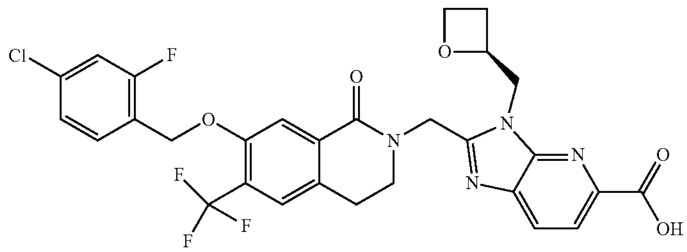 [SMILES: O=C(O)c1ccc2nc(CN3CCc4cc(C(F)(F)F)c(OCc5ccc(Cl)cc5F)cc4C3=O)n(C[C@@H]3CCO3)c2n1] | 2.35 | 619 | 1 |

TABLE 7
| | | | | |
|---|---|---|---|---|
| I-032 | 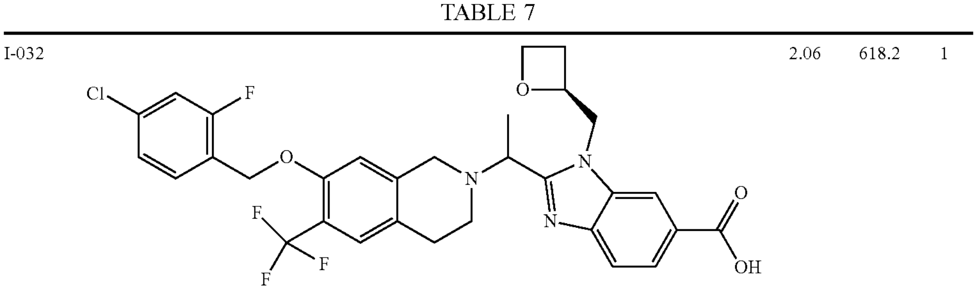 | 2.06 | 618.2 | 1 |
| I-033 | 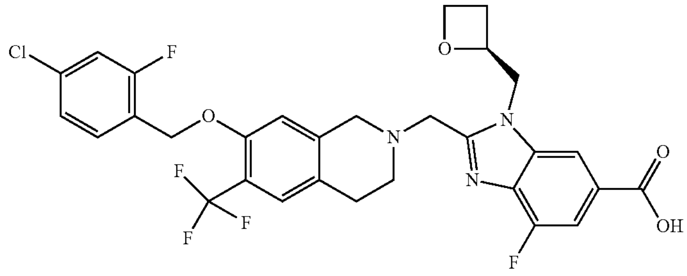 [SMILES: O=C(O)c1cc(F)c2nc(CN3CCc4cc(C(F)(F)F)c(OCc5ccc(Cl)cc5F)cc4C3)n(C[C@@H]3CCO3)c2c1] | 2.07 | 622.0 | 2 |
| I-034 | 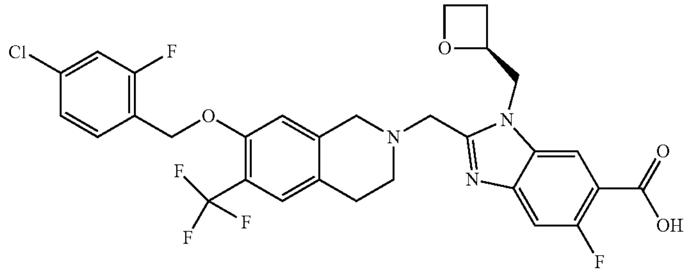 [SMILES: O=C(O)c1cc2c(cc1F)nc(CN1CCc3cc(C(F)(F)F)c(OCc4ccc(Cl)cc4F)cc3C1)n2C[C@@H]1CCO1] | 1.99 | 622.0 | 2 |
| I-035 | 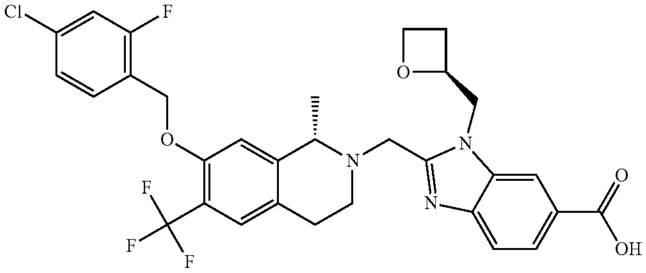 [SMILES: C[C@H]1c2cc(OCc3ccc(Cl)cc3F)c(C(F)(F)F)cc2CCN1Cc1nc2ccc(C(=O)O)cc2n1C[C@@H]1CCO1] | 2.01 | 618.0 | 2 |
TABLE 8
| | | | | |
|---|---|---|---|---|
| I-036 | 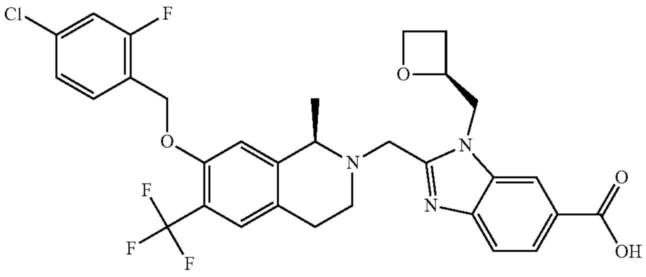 [SMILES: C[C@@H]1c2cc(OCc3ccc(Cl)cc3F)c(C(F)(F)F)cc2CCN1Cc1nc2ccc(C(=O)O)cc2n1C[C@@H]1CCO1] | 2 | 618.0 | 2 |

TABLE 8-continued
| | | | | |
|---|---|---|---|---|
| I-037 | 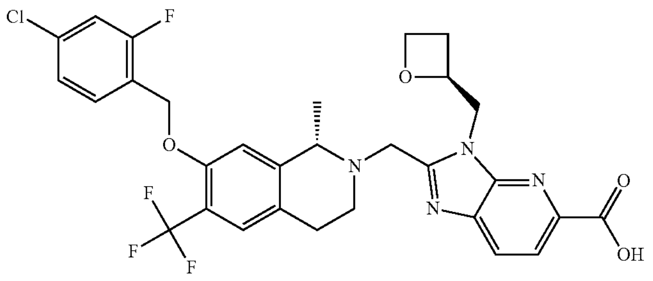 [SMILES: C[C@H]1c2cc(OCc3ccc(Cl)cc3F)c(C(F)(F)F)cc2CCN1Cc1nc2ccc(C(=O)O)nc2n1C[C@@H]1CCO1] | 2 | 619.2 | 2 |
| I-038 | 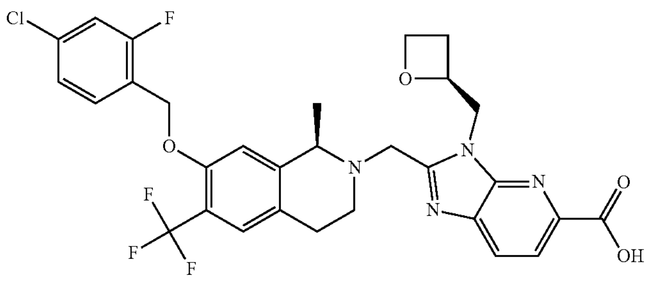 [SMILES: C[C@@H]1c2cc(OCc3ccc(Cl)cc3F)c(C(F)(F)F)cc2CCN1Cc1nc2ccc(C(=O)O)nc2n1C[C@@H]1CCO1] | 1.99 | 619.0 | 2 |
| I-039 | 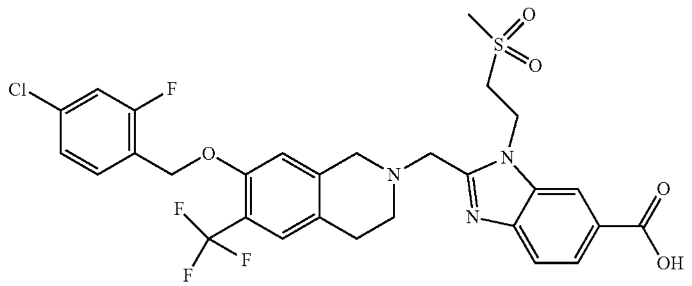 [SMILES: CS(=O)(=O)CCn1c(CN2CCc3cc(C(F)(F)F)c(OCc4ccc(Cl)cc4F)cc3C2)nc2ccc(C(=O)O)cc21] | 2.17 | 640.1 | 1 |
| I-040 | 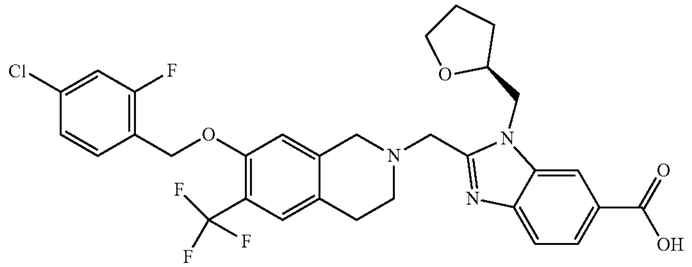 [SMILES: O=C(O)c1ccc2nc(CN3CCc4cc(C(F)(F)F)c(OCc5ccc(Cl)cc5F)cc4C3)n(C[C@@H]3CCCO3)c2c1] | 2.15 | 618.2 | 1 |
| I-041 | 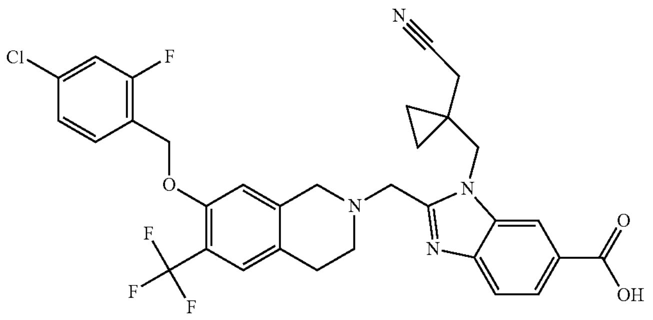 [SMILES: N#CCC1(Cn2c(CN3CCc4cc(C(F)(F)F)c(OCc5ccc(Cl)cc5F)cc4C3)nc3ccc(C(=O)O)cc32)CC1] | 2.26 | 627.2 | 1 |

TABLE 9
| | | | | |
|---|---|---|---|---|
| I-042 | 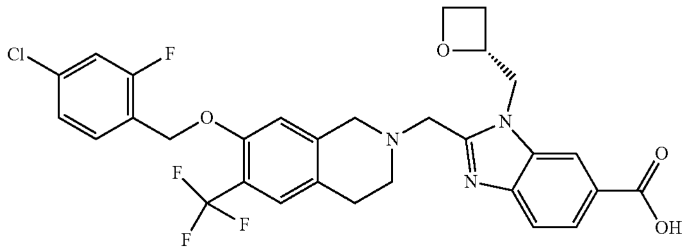 [SMILES: O=C(O)c1ccc2nc(CN3CCc4cc(C(F)(F)F)c(OCc5ccc(Cl)cc5F)cc4C3)n(C[C@H]3CCO3)c2c1] | 2.1 | 604.2 | 1 |
| I-043 | 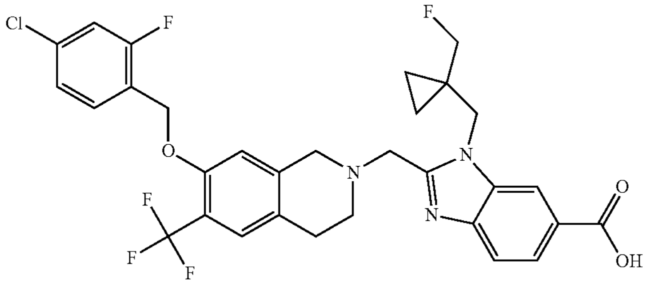 [SMILES: O=C(O)c1ccc2nc(CN3CCc4cc(C(F)(F)F)c(OCc5ccc(Cl)cc5F)cc4C3)n(CC3(CF)CC3)c2c1] | 2.2 | 620.0 | 2 |
| I-044 | 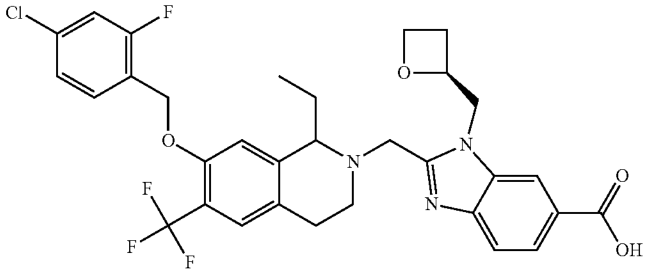 [SMILES: CCC1c2cc(OCc3ccc(Cl)cc3F)c(C(F)(F)F)cc2CCN1Cc1nc2ccc(C(=O)O)cc2n1C[C@@H]1CCO1] | 2.21 | 632.2 | 1 |
| I-045 | 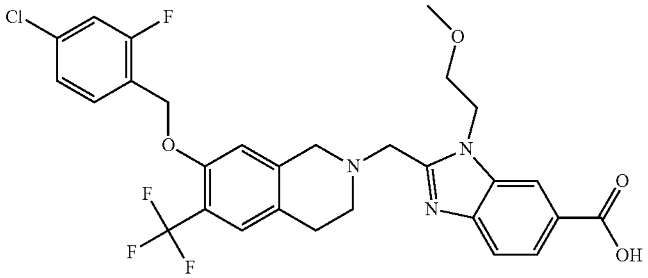 [SMILES: COCCn1c(CN2CCc3cc(C(F)(F)F)c(OCc4ccc(Cl)cc4F)cc3C2)nc2ccc(C(=O)O)cc21] | 2.19 | 592.5 | 1 |
| I-046 | 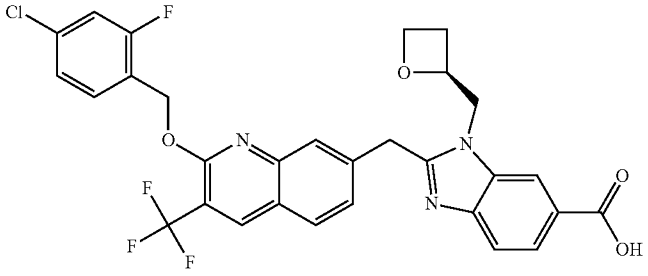 [SMILES: O=C(O)c1ccc2nc(Cc3ccc4cc(C(F)(F)F)c(OCc5ccc(Cl)cc5F)nc4c3)n(C[C@@H]3CCO3)c2c1] | 2.4 | 600.1 | 1 |

TABLE 9-continued
| | | | | |
|---|---|---|---|---|
| I-047 | 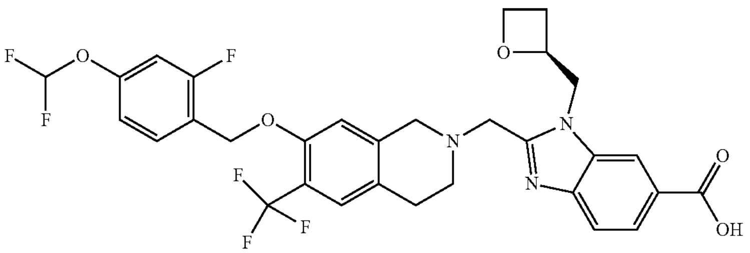 [SMILES: O=C(O)c1ccc2nc(CN3CCc4cc(C(F)(F)F)c(OCc5ccc(OC(F)F)cc5F)cc4C3)n(C[C@@H]3CCO3)c2c1] | 2.03 | 636.2 | 1 |
TABLE 10
| | | | | |
|---|---|---|---|---|
| I-048 | 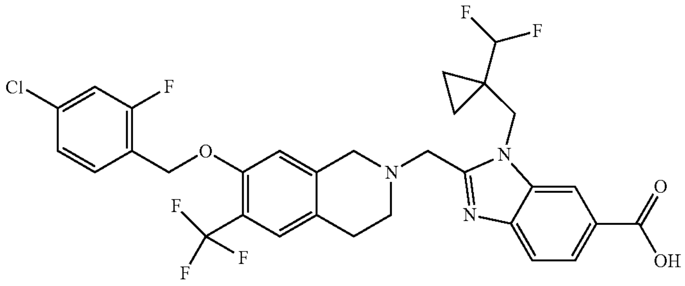 [SMILES: O=C(O)c1ccc2nc(CN3CCc4cc(C(F)(F)F)c(OCc5ccc(Cl)cc5F)cc4C3)n(CC3(C(F)F)CC3)c2c1] | 2.43 | 638.0 | 2 |
| I-049 | 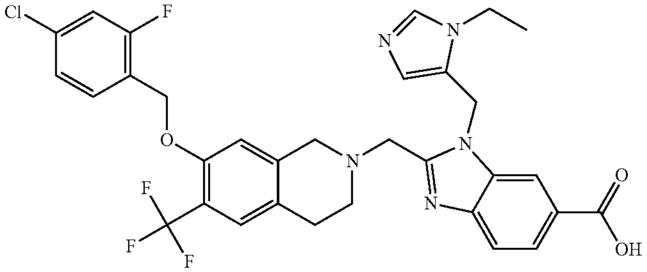 [SMILES: CCn1cncc1Cn1c(CN2CCc3cc(C(F)(F)F)c(OCc4ccc(Cl)cc4F)cc3C2)nc2ccc(C(=O)O)cc21] | 2.09 | 643.5 | 1 |
| I-050 | 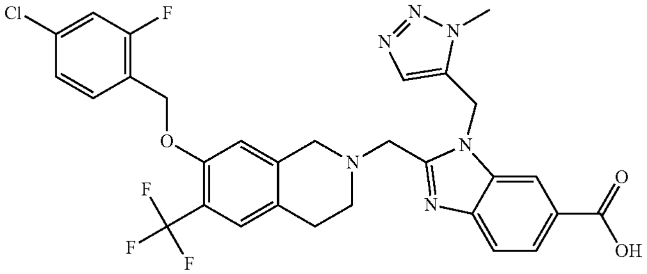 [SMILES: Cn1nncc1Cn1c(CN2CCc3cc(C(F)(F)F)c(OCc4ccc(Cl)cc4F)cc3C2)nc2ccc(C(=O)O)cc21] | 2.22 | 629.5 | 1 |
| I-051 | 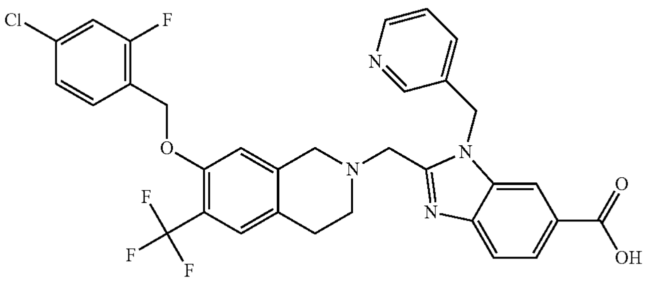 [SMILES: O=C(O)c1ccc2nc(CN3CCc4cc(C(F)(F)F)c(OCc5ccc(Cl)cc5F)cc4C3)n(Cc3cccnc3)c2c1] | 2.17 | 625.5 | 1 |

TABLE 10-continued
| | | | | |
|---|---|---|---|---|
| I-052 | 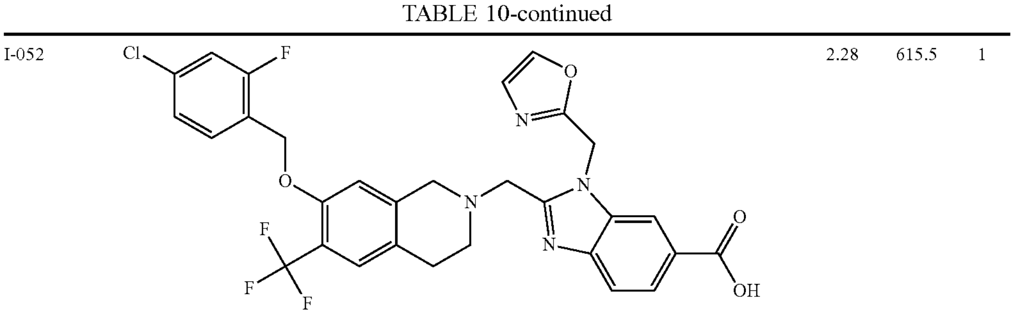 | 2.28 | 615.5 | 1 |
| I-053 | 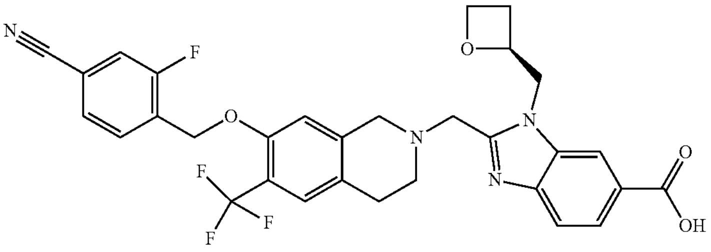 [SMILES: N#Cc1ccc(COc2cc3c(cc2C(F)(F)F)CCN(Cc2nc4ccc(C(=O)O)cc4n2C[C@@H]2CCO2)C3)c(F)c1] | 1.87 | 595.2 | 1 |
TABLE 11
| | | | | |
|---|---|---|---|---|
| I-054 | 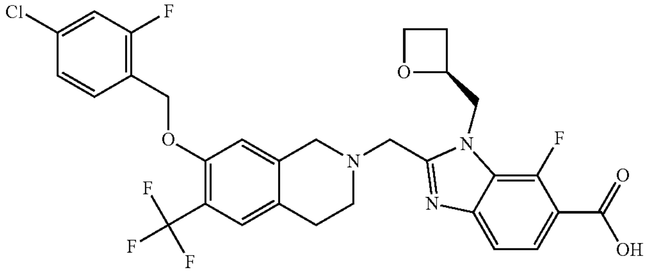 | 2.14 | 622.5 | 1 |
| I-055 | 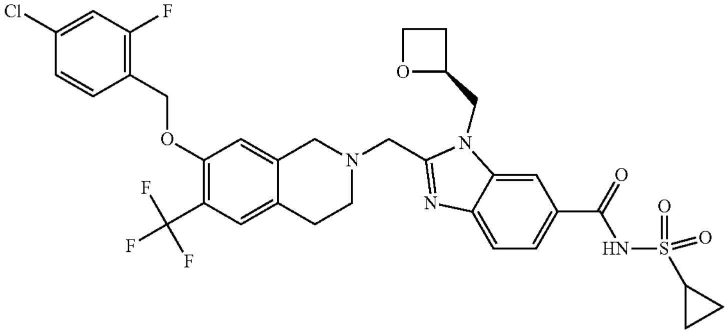 [SMILES: O=C(NS(=O)(=O)C1CC1)c1ccc2nc(CN3CCc4cc(C(F)(F)F)c(OCc5ccc(Cl)cc5F)cc4C3)n(C[C@@H]3CCO3)c2c1] | 2.16 | 707.2 | 1 |
| I-056 | 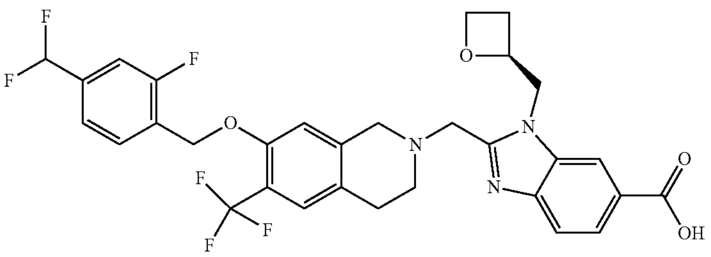 [SMILES: O=C(O)c1ccc2nc(CN3CCc4cc(C(F)(F)F)c(OCc5ccc(C(F)F)cc5F)cc4C3)n(C[C@@H]3CCO3)c2c1] | 1.99 | 620.2 | 1 |

TABLE 11-continued
| | | | | |
|---|---|---|---|---|
| I-057 | 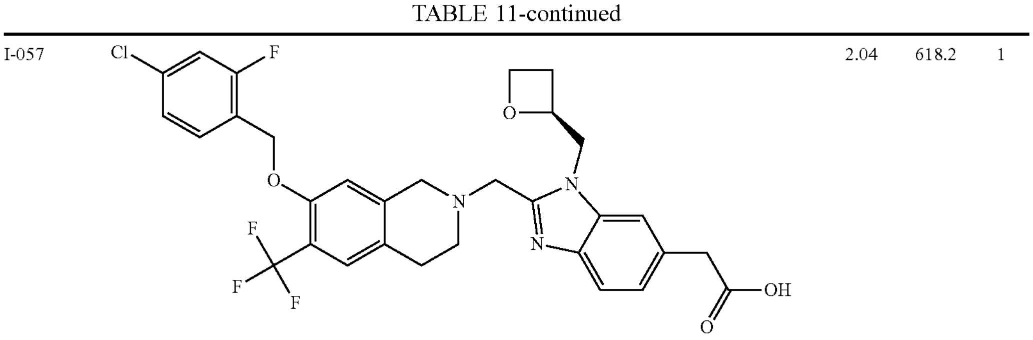 | 2.04 | 618.2 | 1 |
| I-058 | 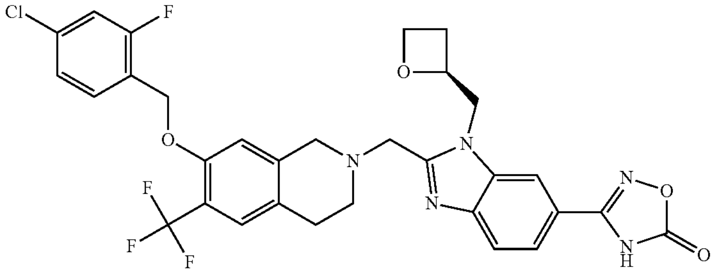 [SMILES: O=c1[nH]c(-c2ccc3nc(CN4CCc5cc(C(F)(F)F)c(OCc6ccc(Cl)cc6F)cc5C4)n(C[C@@H]4CCO4)c3c2)no1] | 2.13 | 644.2 | 1 |
| I-059 | 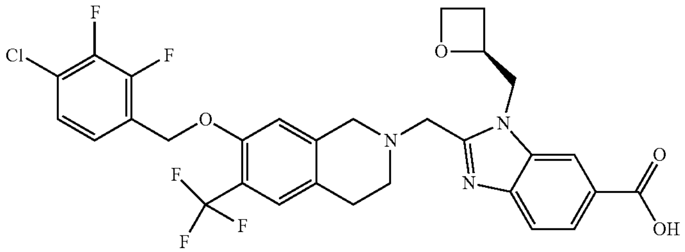 [SMILES: O=C(O)c1ccc2nc(CN3CCc4cc(C(F)(F)F)c(OCc5ccc(Cl)c(F)c5F)cc4C3)n(C[C@@H]3CCO3)c2c1] | 2.09 | 622.2 | 1 |
TABLE 12
| | | | | |
|---|---|---|---|---|
| I-060 | 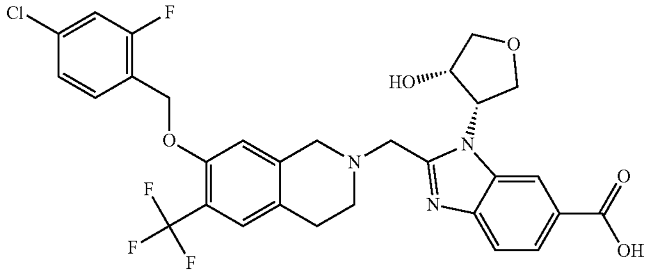 [SMILES: O=C(O)c1ccc2nc(CN3CCc4cc(C(F)(F)F)c(OCc5ccc(Cl)cc5F)cc4C3)n([C@H]3COC[C@H]3O)c2c1] | 2.06 | 620.2 | 1 |
| I-061 | 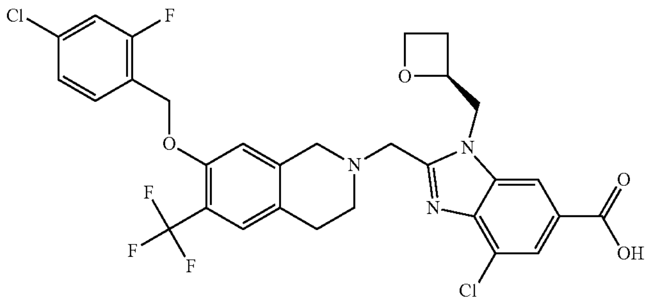 [SMILES: O=C(O)c1cc(Cl)c2nc(CN3CCc4cc(C(F)(F)F)c(OCc5ccc(Cl)cc5F)cc4C3)n(C[C@@H]3CCO3)c2c1] | 2.29 | 638.4 | 1 |

TABLE 12-continued
| | | | | |
|---|---|---|---|---|
| I-062 | 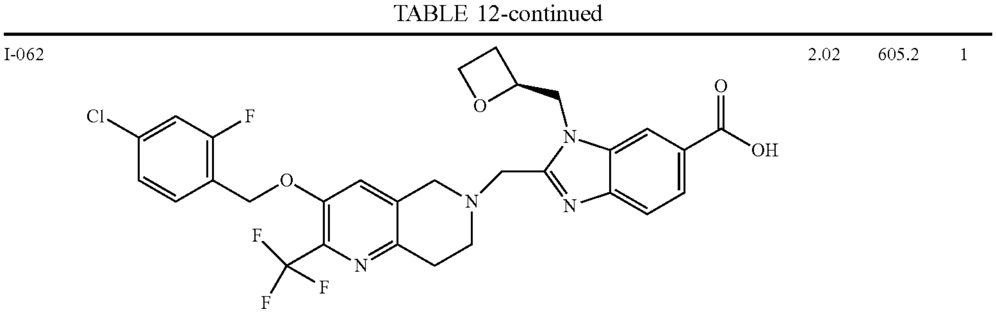 | 2.02 | 605.2 | 1 |
| I-063 | 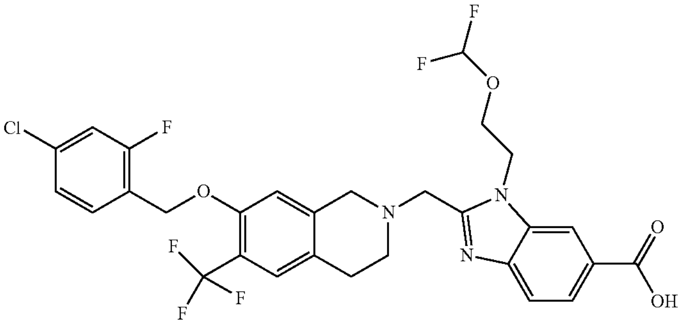 [SMILES: O=C(O)c1ccc2nc(CN3CCc4cc(C(F)(F)F)c(OCc5ccc(Cl)cc5F)cc4C3)n(CCOC(F)F)c2c1] | 2.28 | 628.1 | 1 |
| I-064 | 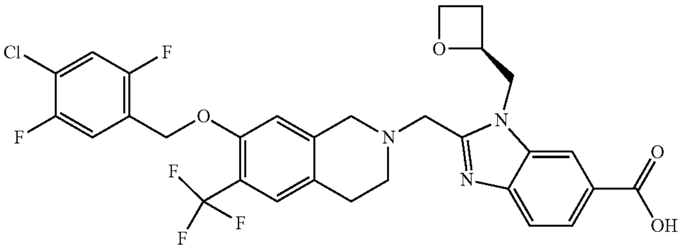 [SMILES: O=C(O)c1ccc2nc(CN3CCc4cc(C(F)(F)F)c(OCc5cc(F)c(Cl)cc5F)cc4C3)n(C[C@@H]3CCO3)c2c1] | 2.11 | 622.2 | 1 |
| I-065 | 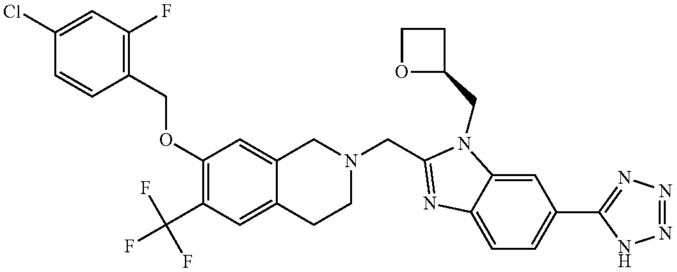 [SMILES: Fc1cc(Cl)ccc1COc1cc2c(cc1C(F)(F)F)CCN(Cc1nc3ccc(-c4nnn[nH]4)cc3n1C[C@@H]1CCO1)C2] | 2.1 | 628.2 | 1 |
TABLE 13
| | | | | |
|---|---|---|---|---|
| I-066 | 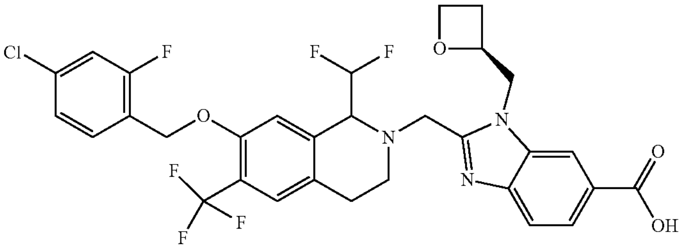 [SMILES: O=C(O)c1ccc2nc(CN3CCc4cc(C(F)(F)F)c(OCc5ccc(Cl)cc5F)cc4C3C(F)F)n(C[C@@H]3CCO3)c2c1] | 2.55 | 654.5 | 1 |

TABLE 13-continued
| | | | | |
|---|---|---|---|---|
| I-067 | 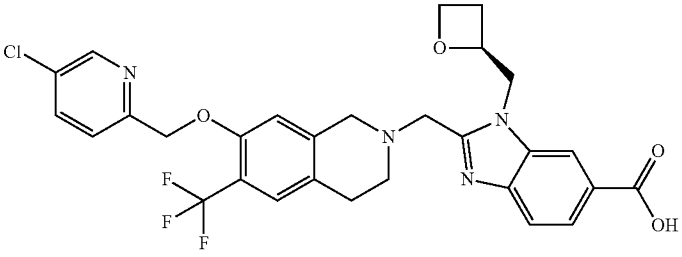 [SMILES: O=C(O)c1ccc2nc(CN3CCc4cc(C(F)(F)F)c(OCc5ccc(Cl)cn5)cc4C3)n(C[C@@H]3CCO3)c2c1] | 1.89 | 587.0 | 1 |
| I-068 | 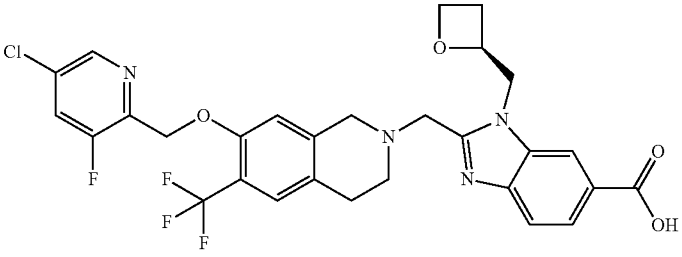 [SMILES: O=C(O)c1ccc2nc(CN3CCc4cc(C(F)(F)F)c(OCc5ncc(Cl)cc5F)cc4C3)n(C[C@@H]3CCO3)c2c1] | 1.858 | 605.1 | 1 |
| I-069 | 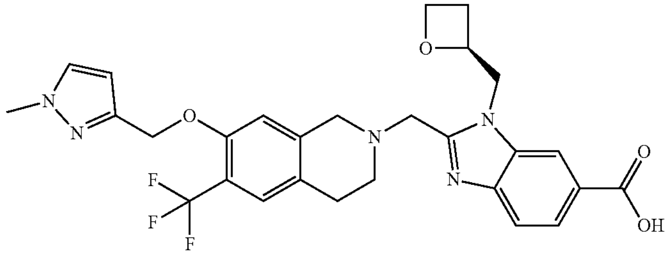 | 1.596 | 556.1 | 1 |
| I-070 | 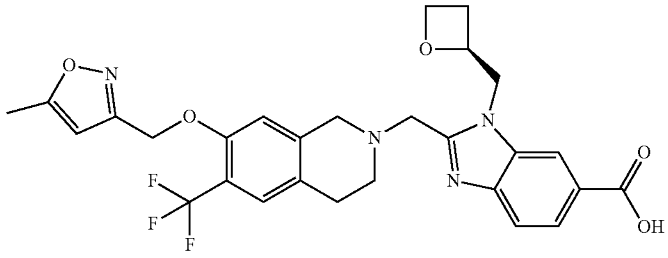 [SMILES: Cc1cc(COc2cc3c(cc2C(F)(F)F)CCN(Cc2nc4ccc(C(=O)O)cc4n2C[C@@H]2CCO2)C3)no1] | 1.724 | 557.1 | 1 |
| I-071 | 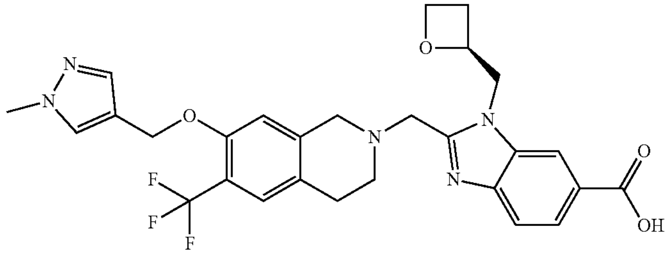 [SMILES: Cn1cc(COc2cc3c(cc2C(F)(F)F)CCN(Cc2nc4ccc(C(=O)O)cc4n2C[C@@H]2CCO2)C3)cn1] | 1.529 | 556.1 | 1 |

TABLE 14
| | | | | |
|---|---|---|---|---|
| I-072 | 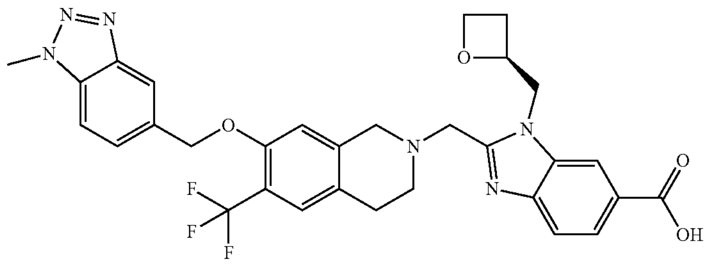 [SMILES: Cn1nnc2cc(COc3cc4c(cc3C(F)(F)F)CCN(Cc3nc5ccc(C(=O)O)cc5n3C[C@@H]3CCO3)C4)ccc21] | 1.67 | 607.1 | 1 |
| I-073 | 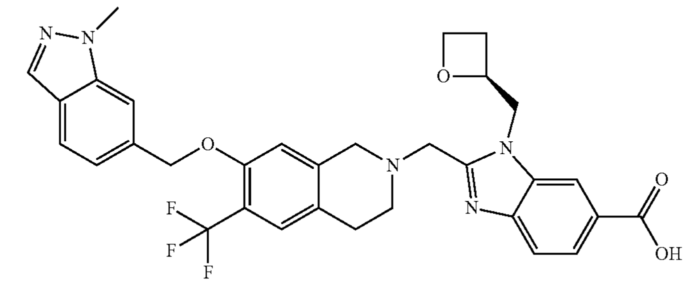 [SMILES: Cn1ncc2ccc(COc3cc4c(cc3C(F)(F)F)CCN(Cc3nc5ccc(C(=O)O)cc5n3C[C@@H]3CCO3)C4)cc21] | 1.795 | 606.1 | 1 |
| I-074 | 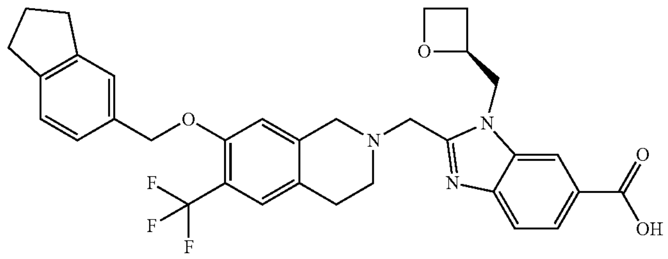 [SMILES: O=C(O)c1ccc2nc(CN3CCc4cc(C(F)(F)F)c(OCc5ccc6c(c5)CCC6)cc4C3)n(C[C@@H]3CCO3)c2c1] | 2.181 | 592.1 | 1 |
| I-075 | 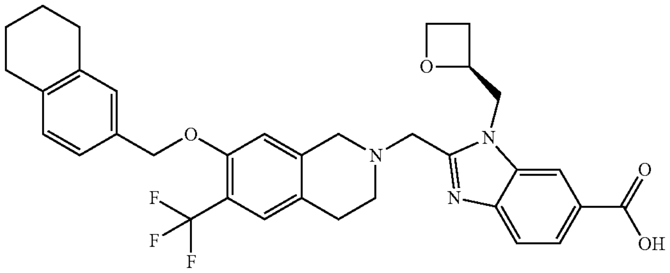 [SMILES: O=C(O)c1ccc2nc(CN3CCc4cc(C(F)(F)F)c(OCc5ccc6c(c5)CCCC6)cc4C3)n(C[C@@H]3CCO3)c2c1] | 2.262 | 606.2 | 1 |
| I-076 | 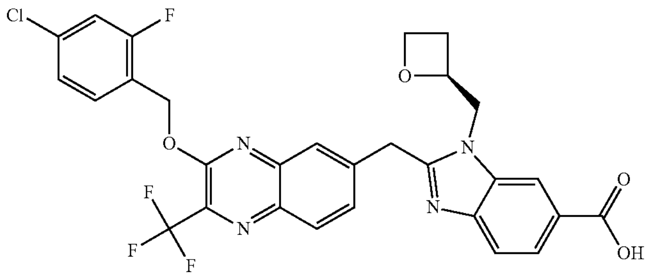 [SMILES: O=C(O)c1ccc2nc(Cc3ccc4nc(C(F)(F)F)c(OCc5ccc(Cl)cc5F)nc4c3)n(C[C@@H]3CCO3)c2c1] | 2.39 | 601.1 | 1 |

TABLE 14-continued
| | | | | |
|---|---|---|---|---|
| I-077 | 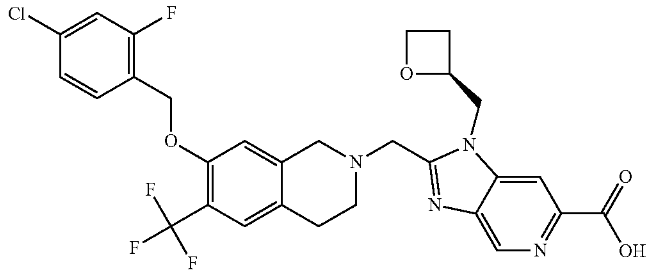 [SMILES: O=C(O)c1cc2c(cn1)nc(CN1CCc3cc(C(F)(F)F)c(OCc4ccc(Cl)cc4F)cc3C1)n2C[C@@H]1CCO1] | 1.92 | 605.5 | 1 |
TABLE 15
| | | | | |
|---|---|---|---|---|
| I-078 | 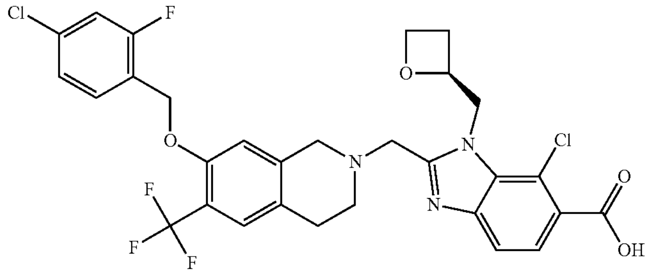 [SMILES: O=C(O)c1ccc2nc(CN3CCc4cc(C(F)(F)F)c(OCc5ccc(Cl)cc5F)cc4C3)n(C[C@@H]3CCO3)c2c1Cl] | 2.13 | 638.5 | 1 |
| I-079 | 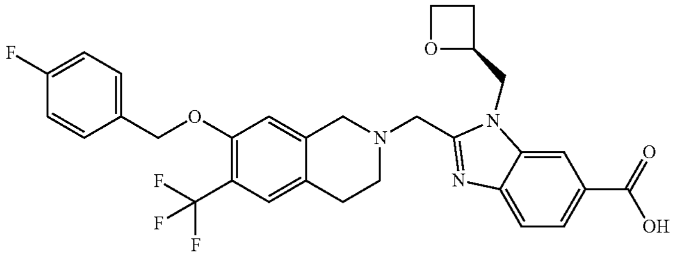 | 1.97 | 570.2 | 1 |
| I-080 | 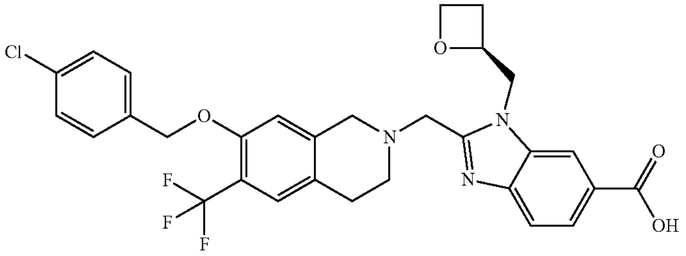 [SMILES: O=C(O)c1ccc2nc(CN3CCc4cc(C(F)(F)F)c(OCc5ccc(Cl)cc5)cc4C3)n(C[C@@H]3CCO3)c2c1] | 2.08 | 586.2 | 1 |
| I-081 | 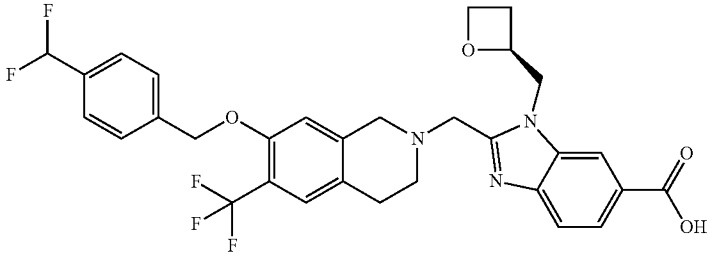 [SMILES: O=C(O)c1ccc2nc(CN3CCc4cc(C(F)(F)F)c(OCc5ccc(C(F)F)cc5)cc4C3)n(C[C@@H]3CCO3)c2c1] | 1.98 | 602.2 | 1 |

TABLE 15-continued
| | | | | |
|---|---|---|---|---|
| I-082 | 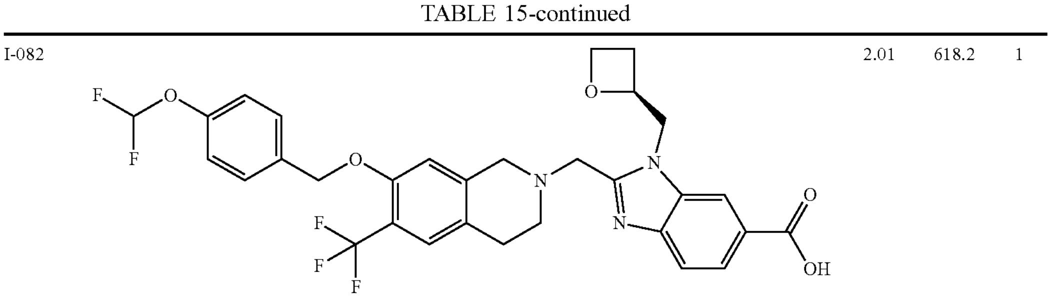 | 2.01 | 618.2 | 1 |
| I-083 | 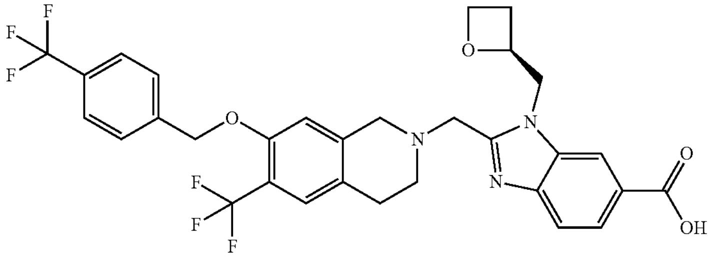 [SMILES: O=C(O)c1ccc2nc(CN3CCc4cc(C(F)(F)F)c(OCc5ccc(C(F)(F)F)cc5)cc4C3)n(C[C@@H]3CCO3)c2c1] | 2.15 | 620.2 | 1 |
TABLE 16
| | | | | |
|---|---|---|---|---|
| I-084 | 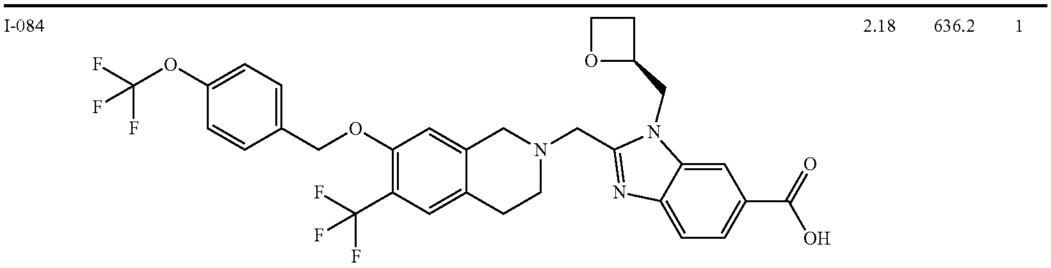 | 2.18 | 636.2 | 1 |
| I-085 | 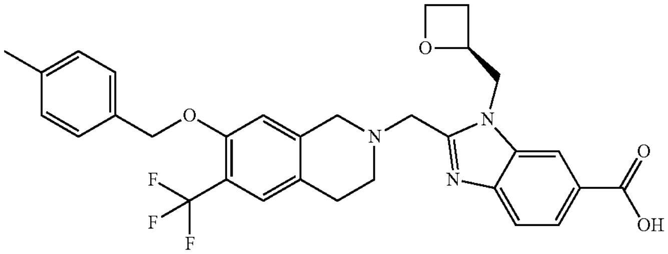 [SMILES: Cc1ccc(COc2cc3c(cc2C(F)(F)F)CCN(Cc2nc4ccc(C(=O)O)cc4n2C[C@@H]2CCO2)C3)cc1] | 2.03 | 566.2 | 1 |
| I-086 | 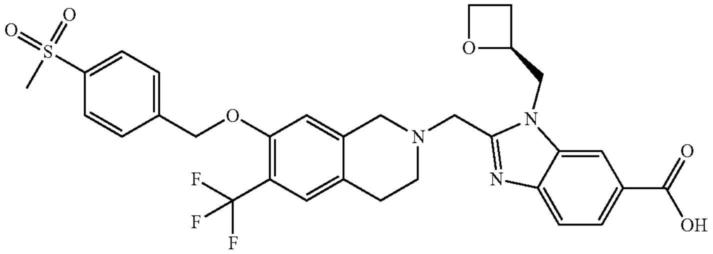 [SMILES: CS(=O)(=O)c1ccc(COc2cc3c(cc2C(F)(F)F)CCN(Cc2nc4ccc(C(=O)O)cc4n2C[C@@H]2CCO2)C3)cc1] | 1.68 | 630.2 | 1 |

TABLE 16-continued
| | | | | |
|---|---|---|---|---|
| I-087 | 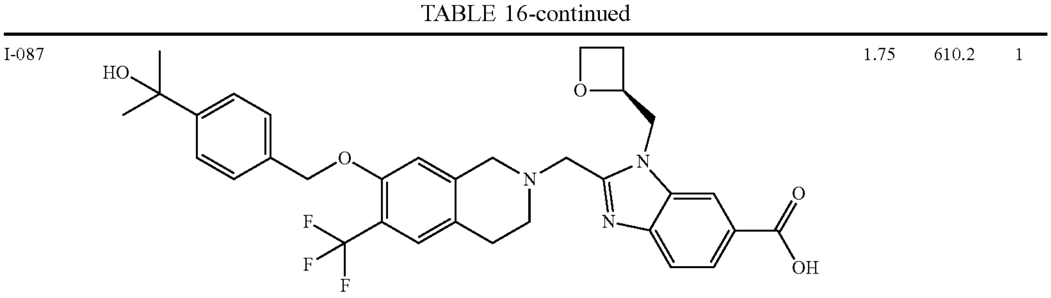 | 1.75 | 610.2 | 1 |
| I-088 | 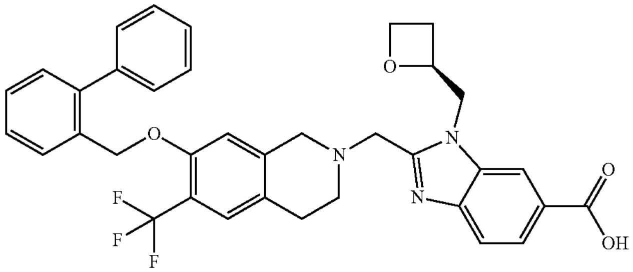 [SMILES: O=C(O)c1ccc2nc(CN3CCc4cc(C(F)(F)F)c(OCc5ccccc5-c5ccccc5)cc4C3)n(C[C@@H]3CCO3)c2c1] | 2.18 | 628.2 | 1 |
| I-089 | 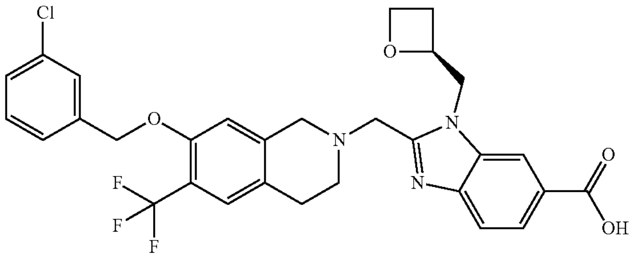 [SMILES: O=C(O)c1ccc2nc(CN3CCc4cc(C(F)(F)F)c(OCc5cccc(Cl)c5)cc4C3)n(C[C@@H]3CCO3)c2c1] | 2.07 | 586.2 | 1 |
TABLE 17
| | | | | |
|---|---|---|---|---|
| I-090 | 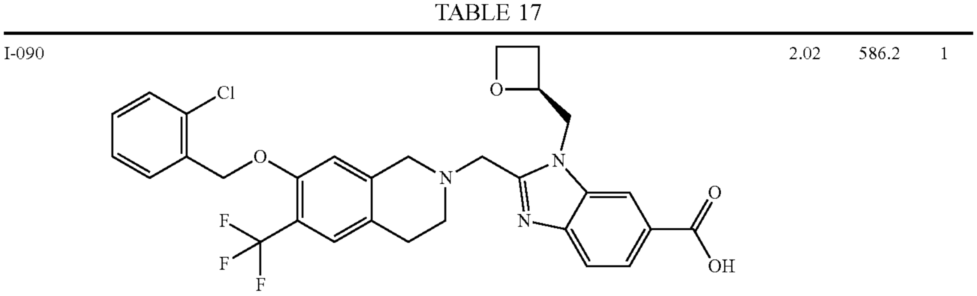 | 2.02 | 586.2 | 1 |
| I-091 | 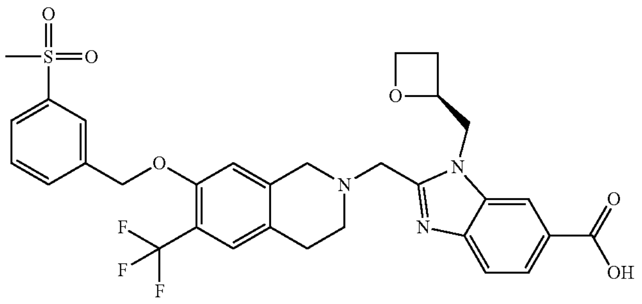 [SMILES: CS(=O)(=O)c1cccc(COc2cc3c(cc2C(F)(F)F)CCN(Cc2nc4ccc(C(=O)O)cc4n2C[C@@H]2CCO2)C3)c1] | 1.68 | 630.2 | 1 |

TABLE 17-continued
| | | | | |
|---|---|---|---|---|
| I-092 | 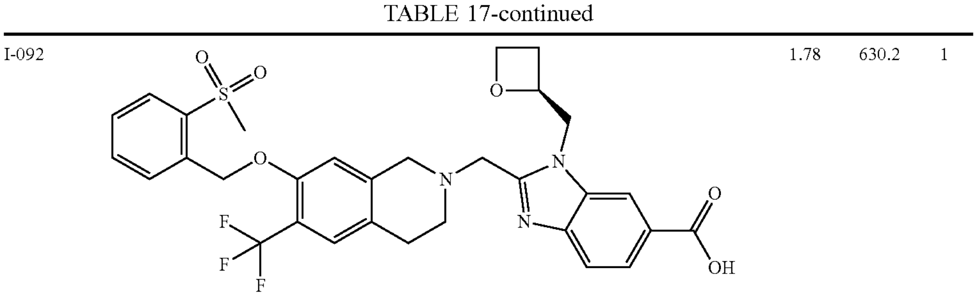 | 1.78 | 630.2 | 1 |
| I-093 | 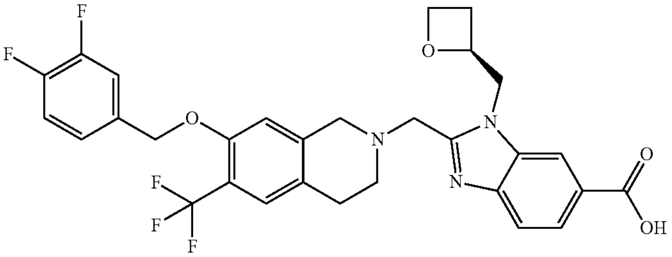 [SMILES: O=C(O)c1ccc2nc(CN3CCc4cc(C(F)(F)F)c(OCc5ccc(F)c(F)c5)cc4C3)n(C[C@@H]3CCO3)c2c1] | 2.02 | 588.2 | 1 |
| I-094 | 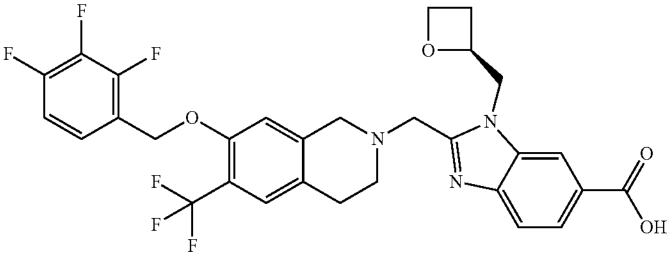 [SMILES: O=C(O)c1ccc2nc(CN3CCc4cc(C(F)(F)F)c(OCc5ccc(F)c(F)c5F)cc4C3)n(C[C@@H]3CCO3)c2c1] | 2.03 | 606.2 | 1 |
| I-095 | 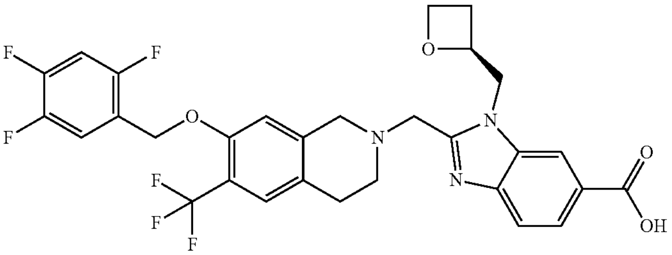 [SMILES: O=C(O)c1ccc2nc(CN3CCc4cc(C(F)(F)F)c(OCc5cc(F)c(F)cc5F)cc4C3)n(C[C@@H]3CCO3)c2c1] | 2.02 | 606.2 | 1 |
TABLE 18
| | | | | |
|---|---|---|---|---|
| I-096 | 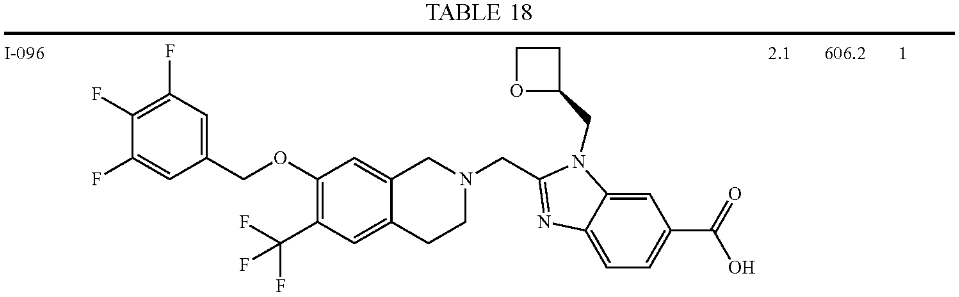 | 2.1 | 606.2 | 1 |

TABLE 18-continued
| | | | | |
|---|---|---|---|---|
| I-097 | 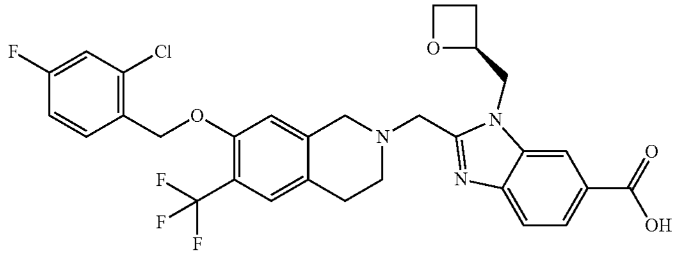 | 2.07 | 604.2 | 1 |
| I-098 | 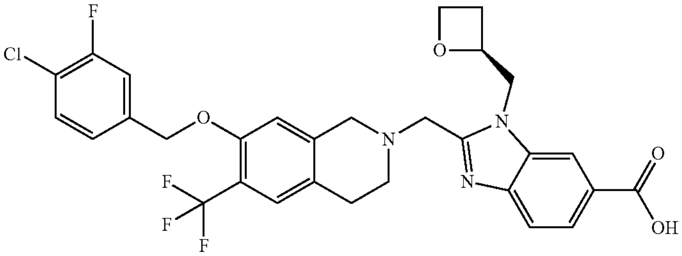 [SMILES: O=C(O)c1ccc2nc(CN3CCc4cc(C(F)(F)F)c(OCc5ccc(Cl)c(F)c5)cc4C3)n(C[C@@H]3CCO3)c2c1] | 2.13 | 604.2 | 1 |
| I-099 | 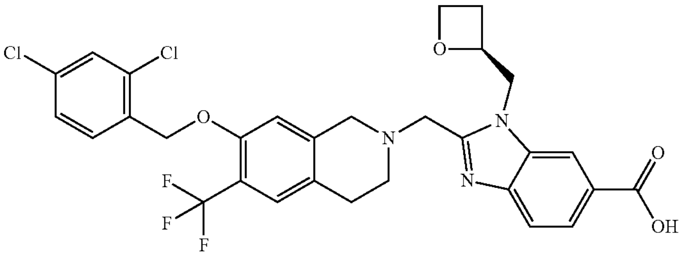 [SMILES: O=C(O)c1ccc2nc(CN3CCc4cc(C(F)(F)F)c(OCc5ccc(Cl)cc5Cl)cc4C3)n(C[C@@H]3CCO3)c2c1] | 2.22 | 620.1 | 1 |
| I-100 | 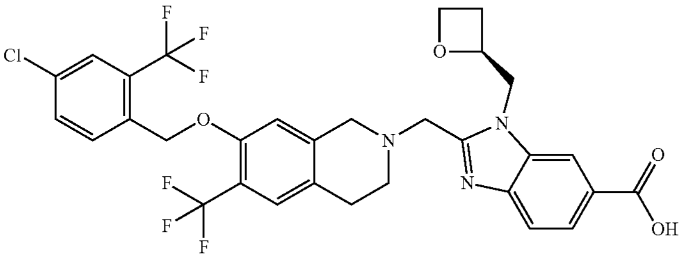 [SMILES: O=C(O)c1ccc2nc(CN3CCc4cc(C(F)(F)F)c(OCc5ccc(Cl)cc5C(F)(F)F)cc4C3)n(C[C@@H]3CCO3)c2c1] | 2.27 | 654.2 | 1 |
| I-101 | 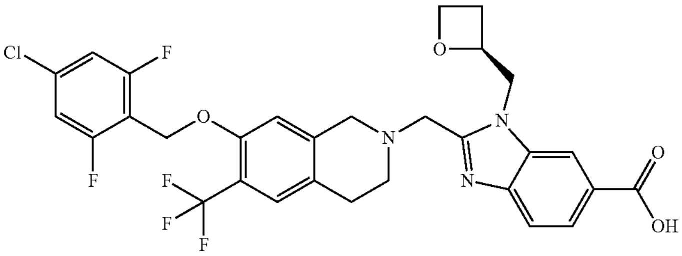 [SMILES: O=C(O)c1ccc2nc(CN3CCc4cc(C(F)(F)F)c(OCc5c(F)cc(Cl)cc5F)cc4C3)n(C[C@@H]3CCO3)c2c1] | 2.06 | 622.1 | 1 |

TABLE 19
| | | | | |
|---|---|---|---|---|
| I-102 | 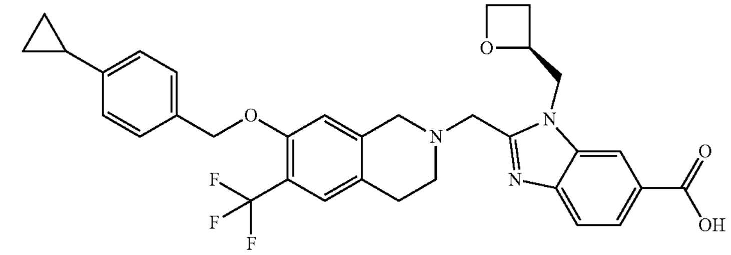 [SMILES: O=C(O)c1ccc2nc(CN3CCc4cc(C(F)(F)F)c(OCc5ccc(C6CC6)cc5)cc4C3)n(C[C@@H]3CCO3)c2c1] | 2.12 | 591.2 | 1 |
| I-103 | 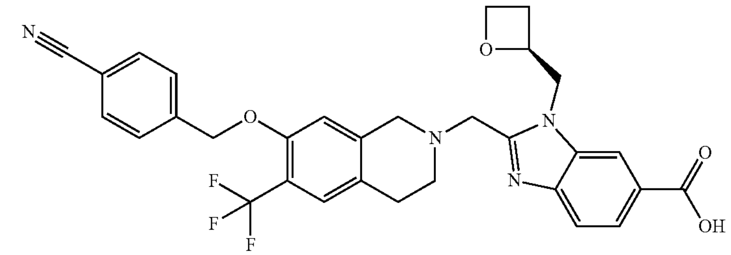 [SMILES: N#Cc1ccc(COc2cc3c(cc2C(F)(F)F)CCN(Cc2nc4ccc(C(=O)O)cc4n2C[C@@H]2CCO2)C3)cc1] | 1.861 | 577.1 | 1 |
| I-104 | 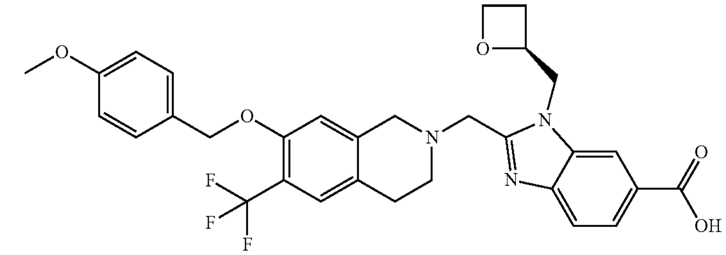 [SMILES: COc1ccc(COc2cc3c(cc2C(F)(F)F)CCN(Cc2nc4ccc(C(=O)O)cc4n2C[C@@H]2CCO2)C3)cc1] | 1.914 | 582.1 | 1 |
| I-105 | 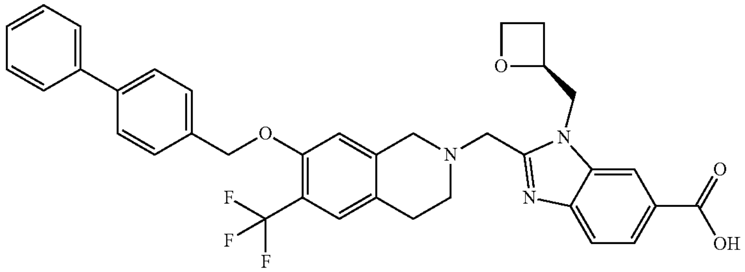 [SMILES: O=C(O)c1ccc2nc(CN3CCc4cc(C(F)(F)F)c(OCc5ccc(-c6ccccc6)cc5)cc4C3)n(C[C@@H]3CCO3)c2c1] | 2.258 | 628.1 | 1 |
| I-106 | 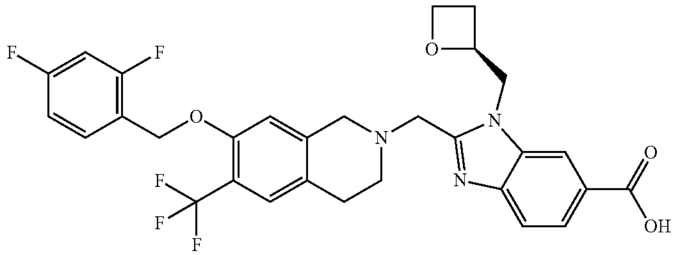 [SMILES: O=C(O)c1ccc2nc(CN3CCc4cc(C(F)(F)F)c(OCc5ccc(F)cc5F)cc4C3)n(C[C@@H]3CCO3)c2c1] | 1.979 | 588.1 | 1 |
| I-107 | 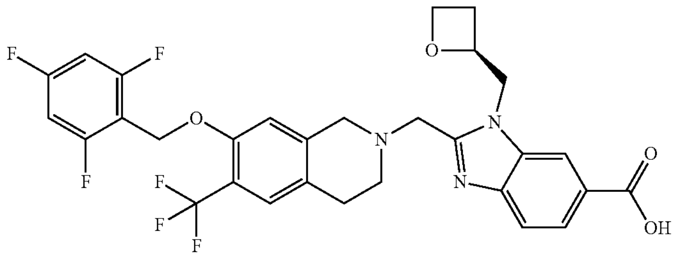 [SMILES: O=C(O)c1ccc2nc(CN3CCc4cc(C(F)(F)F)c(OCc5c(F)cc(F)cc5F)cc4C3)n(C[C@@H]3CCO3)c2c1] | 1.955 | 606.1 | 1 |

TABLE 20
| | | | | |
|---|---|---|---|---|
| I-108 | 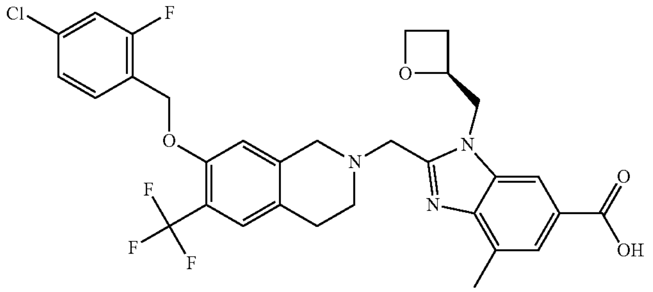 [SMILES: Cc1cc(C(=O)O)cc2c1nc(CN1CCc3cc(C(F)(F)F)c(OCc4ccc(Cl)cc4F)cc3C1)n2C[C@@H]1CCO1] | 2.16 | 618.5 | 1 |
| I-109 | 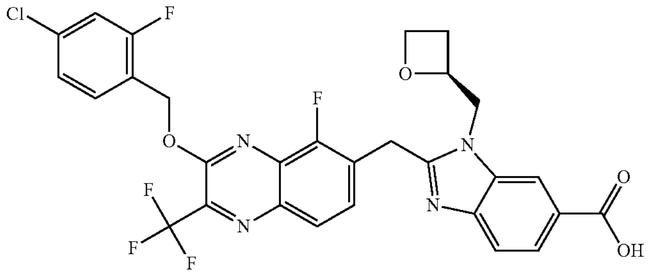 [SMILES: O=C(O)c1ccc2nc(Cc3ccc4nc(C(F)(F)F)c(OCc5ccc(Cl)cc5F)nc4c3F)n(C[C@@H]3CCO3)c2c1] | 2.46 | 619.2 | 1 |
| I-110 | 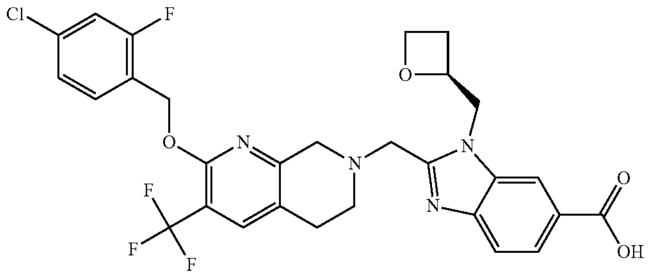 [SMILES: O=C(O)c1ccc2nc(CN3CCc4cc(C(F)(F)F)c(OCc5ccc(Cl)cc5F)nc4C3)n(C[C@@H]3CCO3)c2c1] | 2.18 | 605.5 | 1 |
| I-111 | 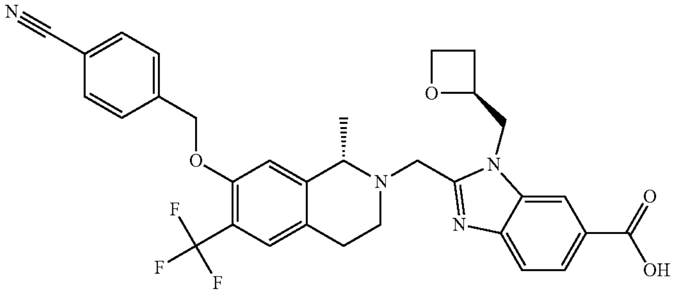 [SMILES: C[C@H]1c2cc(OCc3ccc(C#N)cc3)c(C(F)(F)F)cc2CCN1Cc1nc2ccc(C(=O)O)cc2n1C[C@@H]1CCO1] | 1.91 | 591.2 | 1 |
| I-112 | 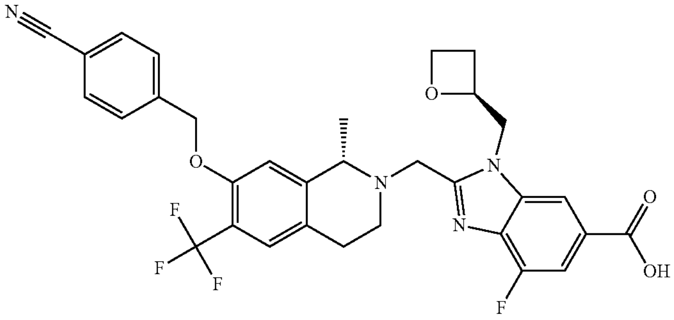 [SMILES: C[C@H]1c2cc(OCc3ccc(C#N)cc3)c(C(F)(F)F)cc2CCN1Cc1nc2c(F)cc(C(=O)O)cc2n1C[C@@H]1CCO1] | 1.98 | 609.3 | 1 |

TABLE 20-continued
| | | | | |
|---|---|---|---|---|
| I-113 | 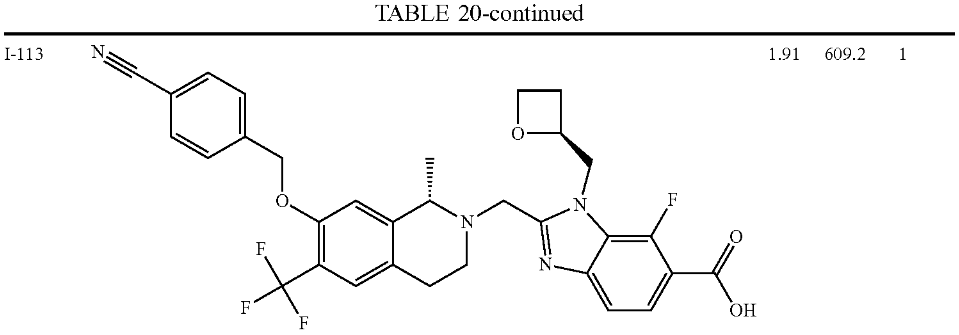 | 1.91 | 609.2 | 1 |
TABLE 21
| | | | | |
|---|---|---|---|---|
| I-114 | 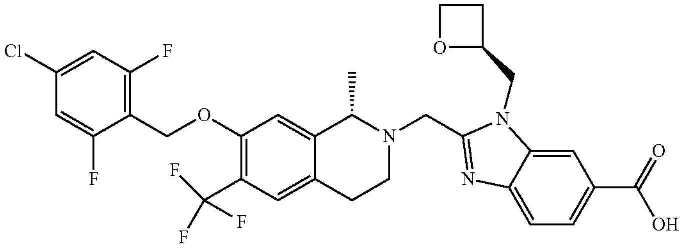 [SMILES: C[C@H]1c2cc(OCc3c(F)cc(Cl)cc3F)c(C(F)(F)F)cc2CCN1Cc1nc2ccc(C(=O)O)cc2n1C[C@@H]1CCO1] | 2.11 | 636.2 | 1 |
| I-115 | 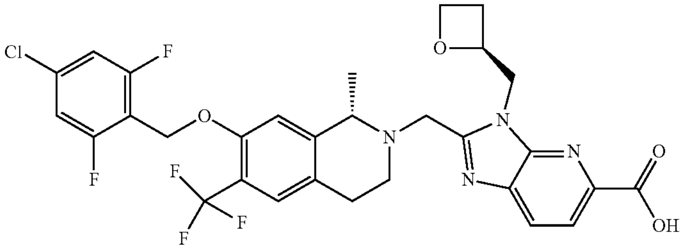 [SMILES: C[C@H]1c2cc(OCc3c(F)cc(Cl)cc3F)c(C(F)(F)F)cc2CCN1Cc1nc2ccc(C(=O)O)nc2n1C[C@@H]1CCO1] | 1.9 | 637.1 | 2 |
| I-116 | 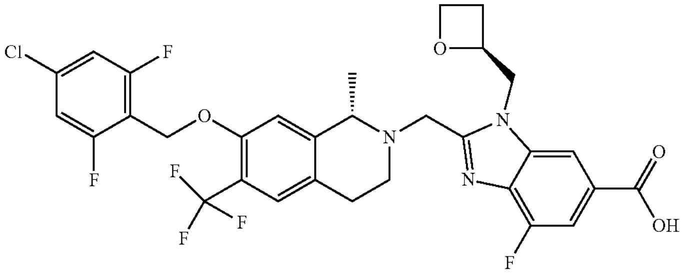 [SMILES: C[C@H]1c2cc(OCc3c(F)cc(Cl)cc3F)c(C(F)(F)F)cc2CCN1Cc1nc2c(F)cc(C(=O)O)cc2n1C[C@@H]1CCO1] | 2.22 | 636.5 | 1 |
| I-117 | 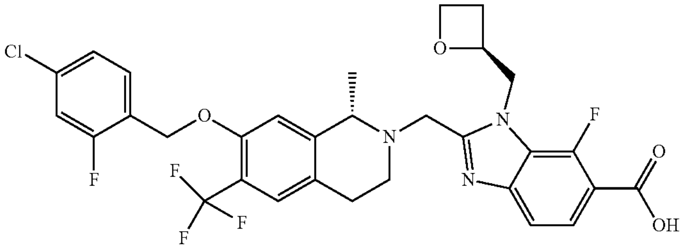 [SMILES: C[C@H]1c2cc(OCc3ccc(Cl)cc3F)c(C(F)(F)F)cc2CCN1Cc1nc2ccc(C(=O)O)c(F)c2n1C[C@@H]1CCO1] | 2.14 | 636.5 | 1 |

TABLE 21-continued
| | | | | |
|---|---|---|---|---|
| I-118 | 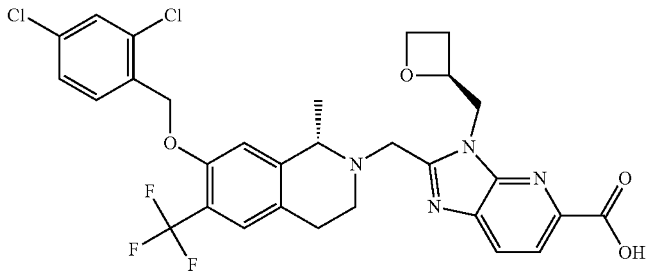 [SMILES: C[C@H]1c2cc(OCc3ccc(Cl)cc3Cl)c(C(F)(F)F)cc2CCN1Cc1nc2ccc(C(=O)O)nc2n1C[C@@H]1CCO1] | 2.2 | 635.5 | 1 |
| I-119 | 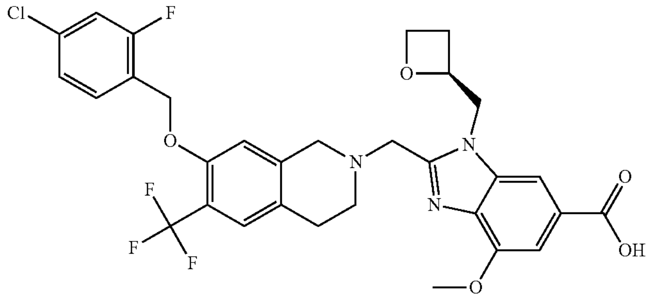 [SMILES: COc1cc(C(=O)O)cc2c1nc(CN1CCc3cc(C(F)(F)F)c(OCc4ccc(Cl)cc4F)cc3C1)n2C[C@@H]1CCO1] | 2.09 | 634.5 | 1 |
TABLE 22
| | | | | |
|---|---|---|---|---|
| I-120 | 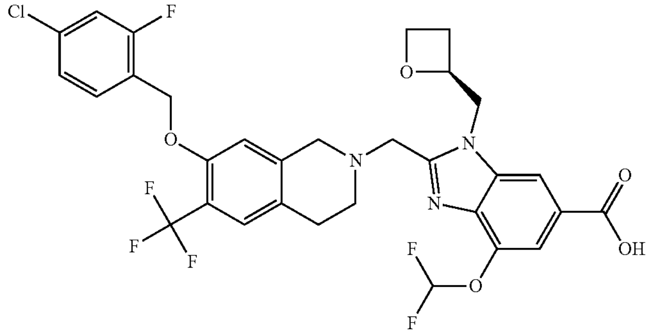 [SMILES: O=C(O)c1cc(OC(F)F)c2nc(CN3CCc4cc(C(F)(F)F)c(OCc5ccc(Cl)cc5F)cc4C3)n(C[C@@H]3CCO3)c2c1] | 2.3 | 670.5 | 1 |
| I-121 | 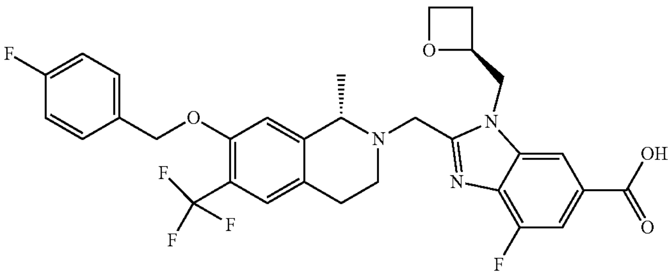 [SMILES: C[C@H]1c2cc(OCc3ccc(F)cc3)c(C(F)(F)F)cc2CCN1Cc1nc2c(F)cc(C(=O)O)cc2n1C[C@@H]1CCO1] | 2.07 | 602.2 | 1 |
| I-122 | 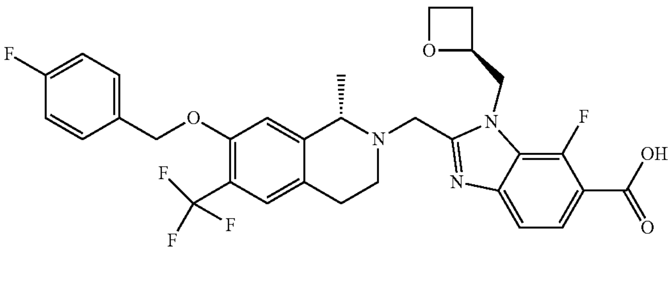 [SMILES: C[C@H]1c2cc(OCc3ccc(F)cc3)c(C(F)(F)F)cc2CCN1Cc1nc2ccc(C(=O)O)c(F)c2n1C[C@@H]1CCO1] | 1.84 | 602.1 | 2 |

TABLE 22-continued
| | | | | |
|---|---|---|---|---|
| I-123 | 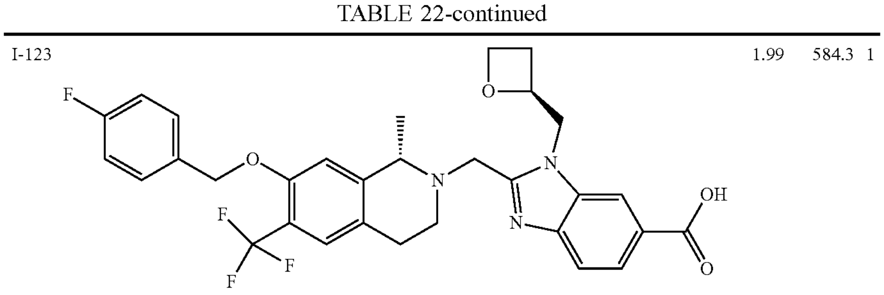 | 1.99 | 584.3 | 1 |
| I-124 | 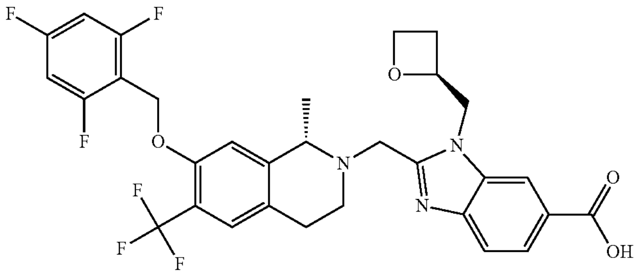 [SMILES: C[C@H]1c2cc(OCc3c(F)cc(F)cc3F)c(C(F)(F)F)cc2CCN1Cc1nc2ccc(C(=O)O)cc2n1C[C@@H]1CCO1] | 1.77 | 620.1 | 2 |
| I-125 | 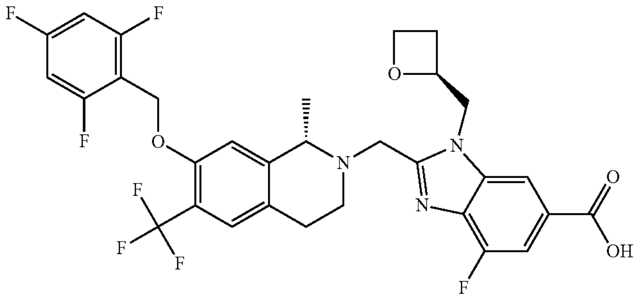 [SMILES: C[C@H]1c2cc(OCc3c(F)cc(F)cc3F)c(C(F)(F)F)cc2CCN1Cc1nc2c(F)cc(C(=O)O)cc2n1C[C@@H]1CCO1] | 2.06 | 638.2 | 1 |
TABLE 23
| | | | | |
|---|---|---|---|---|
| I-126 | 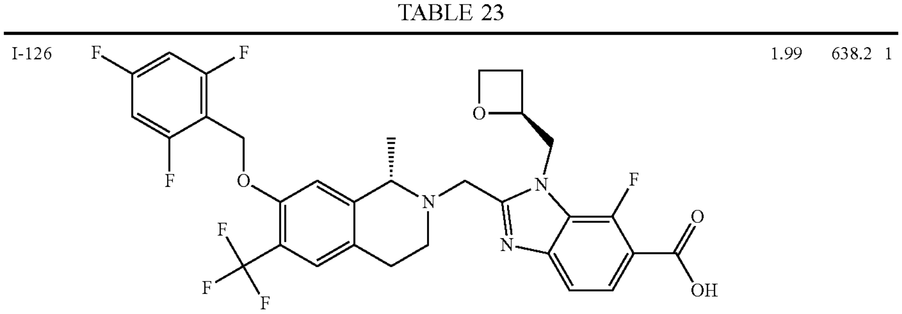 | 1.99 | 638.2 | 1 |
| I-127 | 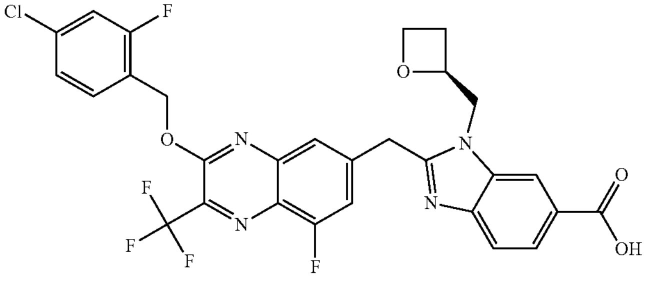 [SMILES: O=C(O)c1ccc2nc(Cc3cc(F)c4nc(C(F)(F)F)c(OCc5ccc(Cl)cc5F)nc4c3)n(C[C@@H]3CCO3)c2c1] | 2.45 | 619.1 | 1 |

TABLE 23-continued
| | | | | |
|---|---|---|---|---|
| I-128 | 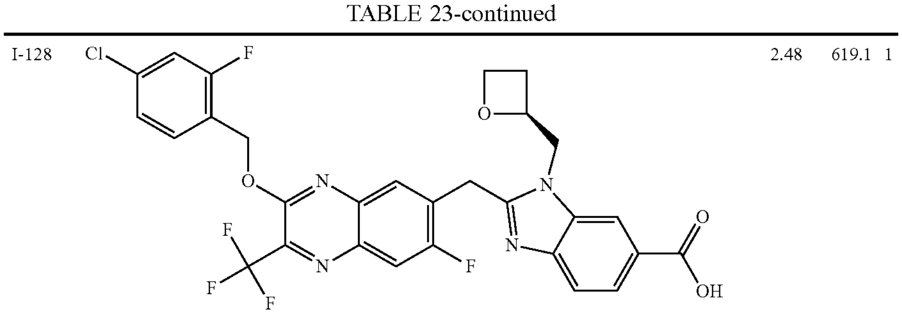 | 2.48 | 619.1 | 1 |
| I-129 | 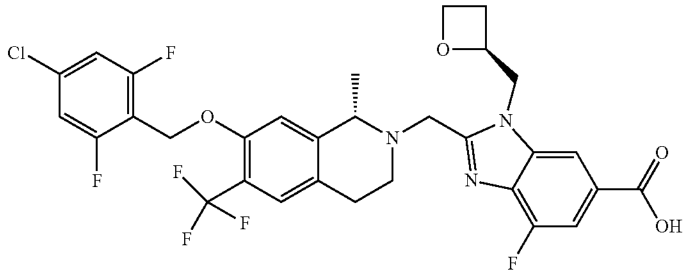 [SMILES: C[C@H]1c2cc(OCc3c(F)cc(Cl)cc3F)c(C(F)(F)F)cc2CCN1Cc1nc2c(F)cc(C(=O)O)cc2n1C[C@@H]1CCO1] | 2.17 | 654.2 | 1 |
| I-130 | 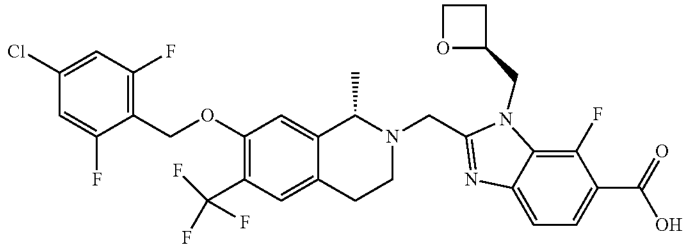 [SMILES: C[C@H]1c2cc(OCc3c(F)cc(Cl)cc3F)c(C(F)(F)F)cc2CCN1Cc1nc2ccc(C(=O)O)c(F)c2n1C[C@@H]1CCO1] | 2.1 | 654.2 | 1 |
TABLE 24
| | | | | |
|---|---|---|---|---|
| I-131 | 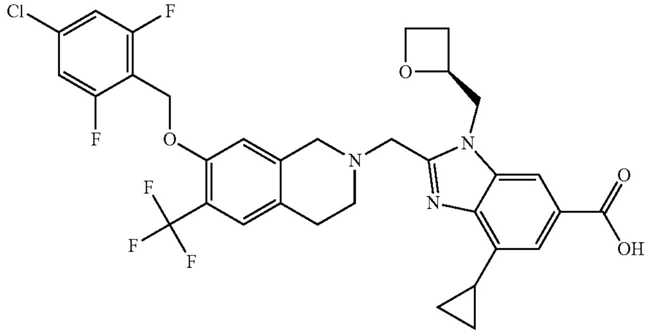 [SMILES: O=C(O)c1cc(C2CC2)c2nc(CN3CCc4cc(C(F)(F)F)c(OCc5c(F)cc(Cl)cc5F)cc4C3)n(C[C@@H]3CCO3)c2c1] | 2.28 | 644.5 | 1 |
| I-132 | 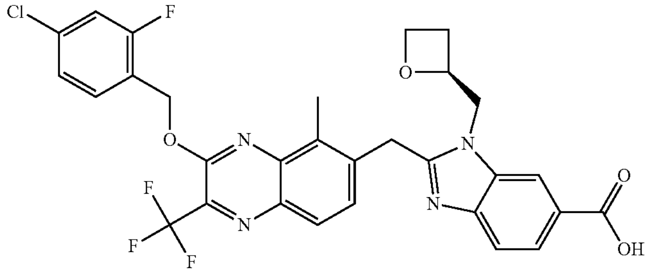 | 2.46 | 615.2 | 3 |

TABLE 24-continued
| | | | | |
|---|---|---|---|---|
| I-133 | 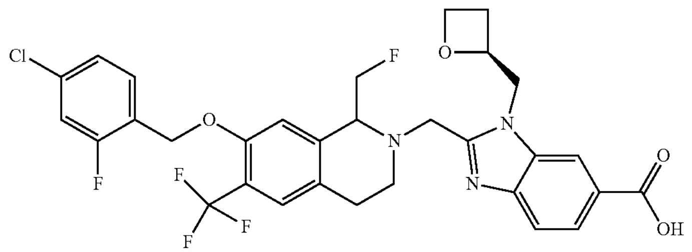 [SMILES: O=C(O)c1ccc2nc(CN3CCc4cc(C(F)(F)F)c(OCc5ccc(Cl)cc5F)cc4C3CF)n(C[C@@H]3CCO3)c2c1] | 2.4 | 636.5 | 1 |
| I-134 | 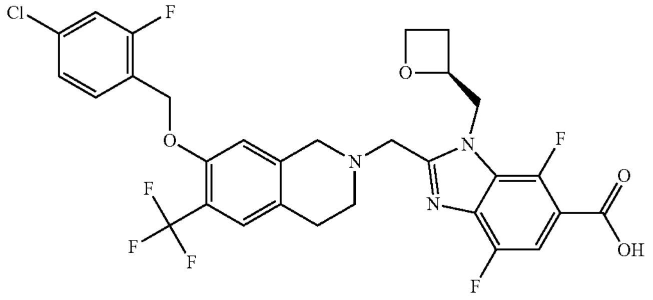 [SMILES: O=C(O)c1cc(F)c2nc(CN3CCc4cc(C(F)(F)F)c(OCc5ccc(Cl)cc5F)cc4C3)n(C[C@@H]3CCO3)c2c1F] | 2.25 | 640.5 | 1 |
| I-135 | 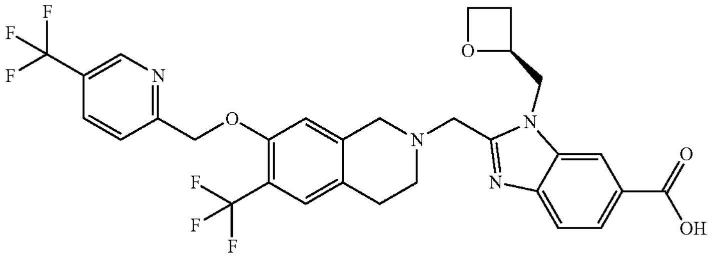 [SMILES: O=C(O)c1ccc2nc(CN3CCc4cc(C(F)(F)F)c(OCc5ccc(C(F)(F)F)cn5)cc4C3)n(C[C@@H]3CCO3)c2c1] | 1.962 | 621.1 | 3 |
| I-136 | 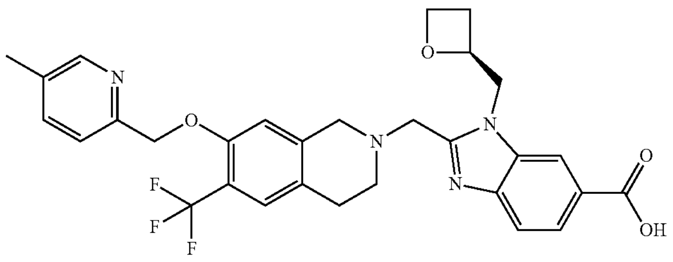 | 1.65 | 567.2 | 3 |
| I-137 | 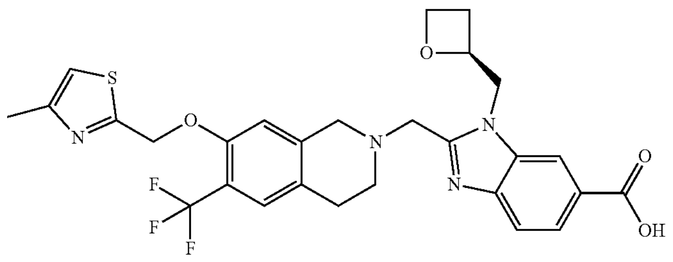 [SMILES: Cc1csc(COc2cc3c(cc2C(F)(F)F)CCN(Cc2nc4ccc(C(=O)O)cc4n2C[C@@H]2CCO2)C3)n1] | 1.74 | 573.1 | 3 |

TABLE 25
| | | | | |
|---|---|---|---|---|
| I-138 | 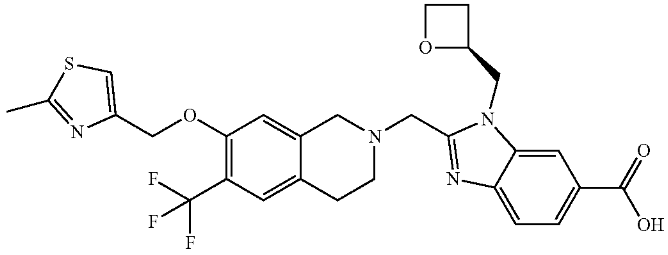 [SMILES: Cc1nc(COc2cc3c(cc2C(F)(F)F)CCN(Cc2nc4ccc(C(=O)O)cc4n2C[C@@H]2CCO2)C3)cs1] | 1.71 | 573.1 | 3 |
| I-139 | 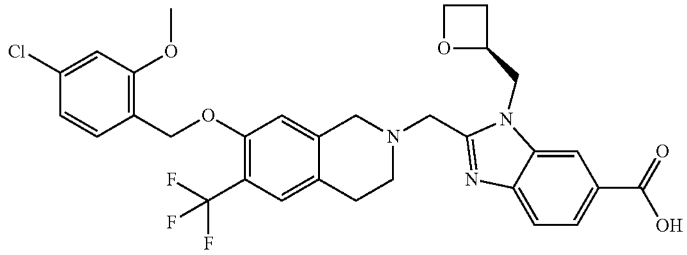 [SMILES: COc1cc(Cl)ccc1COc1cc2c(cc1C(F)(F)F)CCN(Cc1nc3ccc(C(=O)O)cc3n1C[C@@H]1CCO1)C2] | 2.12 | 616.1 | 3 |
| I-140 | 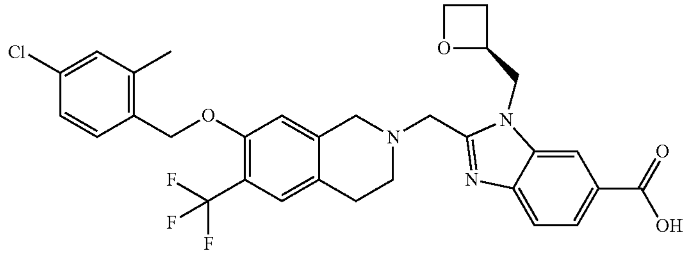 | 2.17 | 600.1 | 3 |
| I-141 | 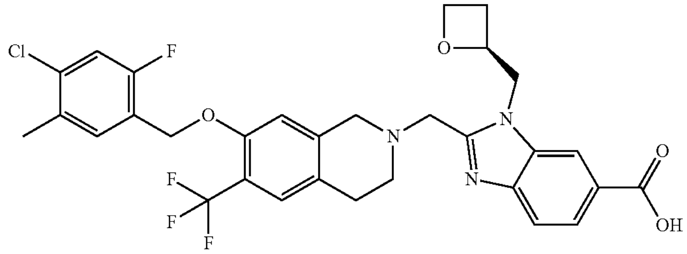 [SMILES: Cc1cc(COc2cc3c(cc2C(F)(F)F)CCN(Cc2nc4ccc(C(=O)O)cc4n2C[C@@H]2CCO2)C3)c(F)cc1Cl] | 2.21 | 618.1 | 3 |
| I-142 | 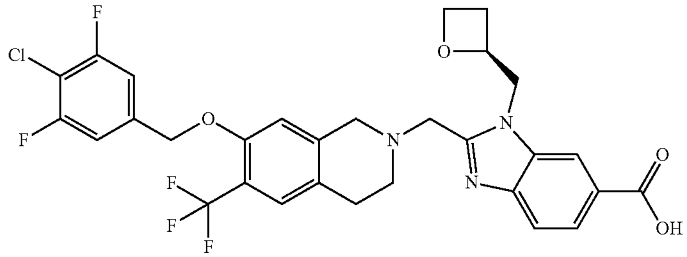 [SMILES: O=C(O)c1ccc2nc(CN3CCc4cc(C(F)(F)F)c(OCc5cc(F)c(Cl)c(F)c5)cc4C3)n(C[C@@H]3CCO3)c2c1] | 2.19 | 622.1 | 3 |
| I-143 | 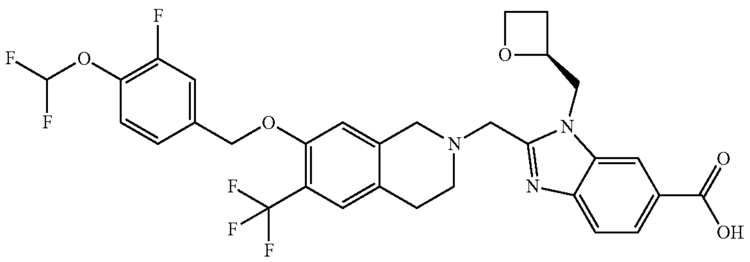 [SMILES: O=C(O)c1ccc2nc(CN3CCc4cc(C(F)(F)F)c(OCc5ccc(OC(F)F)c(F)c5)cc4C3)n(C[C@@H]3CCO3)c2c1] | 2.03 | 636.0 | 3 |

TABLE 25-continued
| | | | | |
|---|---|---|---|---|
| I-144 | 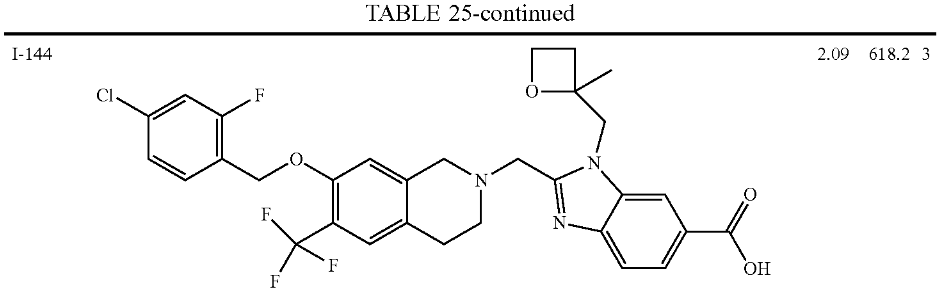 | 2.09 | 618.2 | 3 |
TABLE 26
| | | | | |
|---|---|---|---|---|
| I-145 | 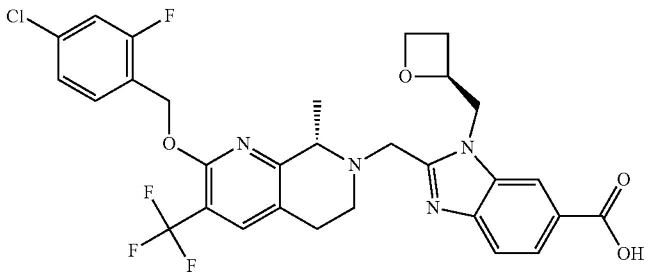 [SMILES: C[C@H]1c2nc(OCc3ccc(Cl)cc3F)c(C(F)(F)F)cc2CCN1Cc1nc2ccc(C(=O)O)cc2n1C[C@@H]1CCO1] | 2.25 | 619.4 | 1 |
| I-146 | 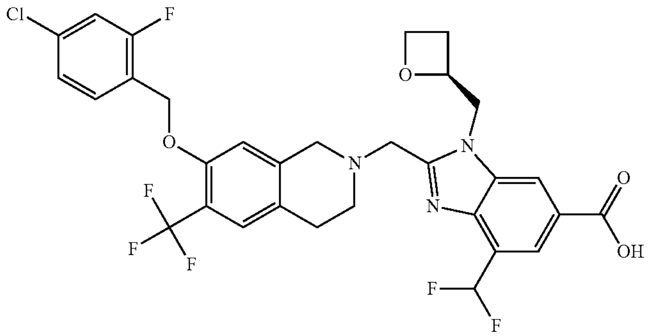 [SMILES: O=C(O)c1cc(C(F)F)c2nc(CN3CCc4cc(C(F)(F)F)c(OCc5ccc(Cl)cc5F)cc4C3)n(C[C@@H]3CCO3)c2c1] | 2.33 | 654.4 | 1 |
| I-147 | 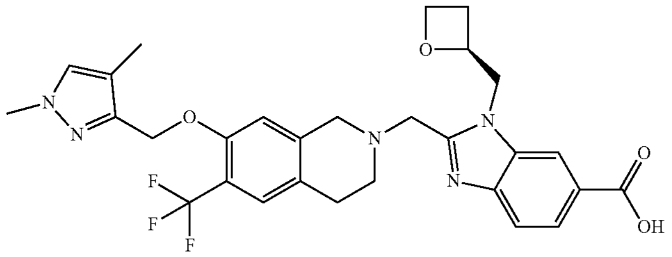 [SMILES: Cc1cn(C)nc1COc1cc2c(cc1C(F)(F)F)CCN(Cc1nc3ccc(C(=O)O)cc3n1C[C@@H]1CCO1)C2] | 1.64 | 570.5 | 1 |
| I-148 | 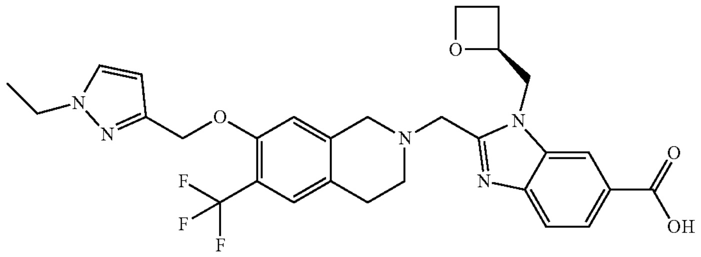 [SMILES: CCn1ccc(COc2cc3c(cc2C(F)(F)F)CCN(Cc2nc4ccc(C(=O)O)cc4n2C[C@@H]2CCO2)C3)n1] | 1.62 | 570.4 | 1 |

TABLE 26-continued
| | | | | |
|---|---|---|---|---|
| I-149 | 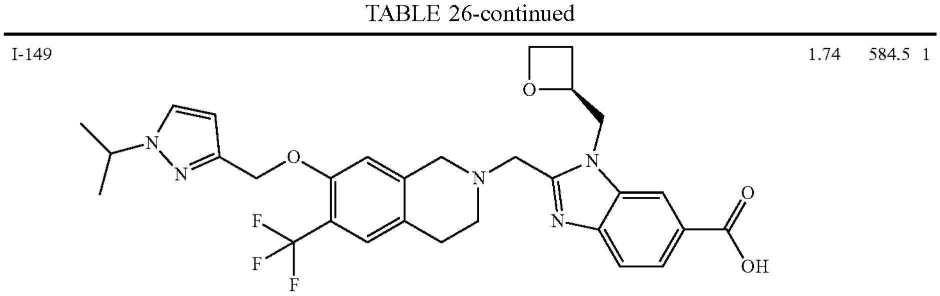 | 1.74 | 584.5 | 1 |
| I-150 | 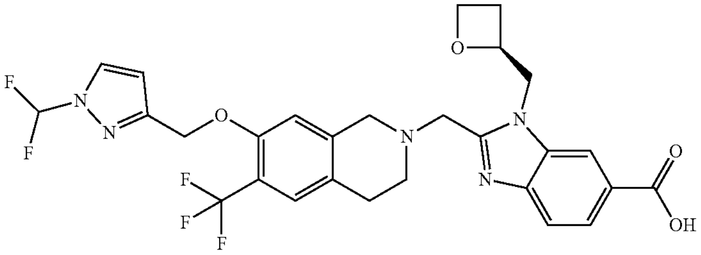 [SMILES: O=C(O)c1ccc2nc(CN3CCc4cc(C(F)(F)F)c(OCc5ccn(C(F)F)n5)cc4C3)n(C[C@@H]3CCO3)c2c1] | 1.7 | 592.4 | 1 |
| I-151 | 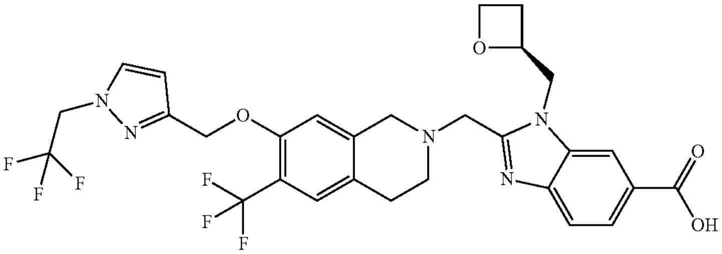 [SMILES: O=C(O)c1ccc2nc(CN3CCc4cc(C(F)(F)F)c(OCc5ccn(CC(F)(F)F)n5)cc4C3)n(C[C@@H]3CCO3)c2c1] | 1.73 | 624.4 | 1 |
TABLE 27
| | | | | |
|---|---|---|---|---|
| I-152 | 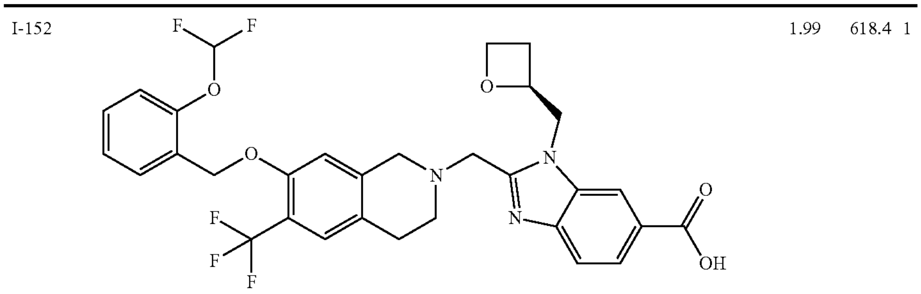 | 1.99 | 618.4 | 1 |
| I-153 | 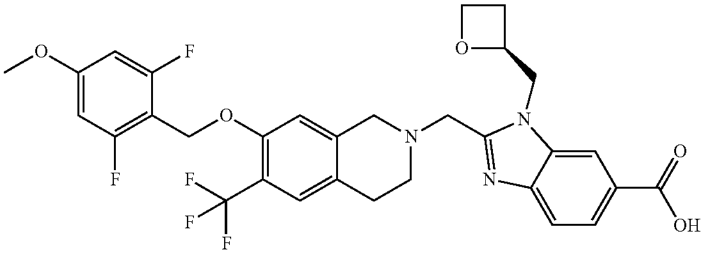 [SMILES: COc1cc(F)c(COc2cc3c(cc2C(F)(F)F)CCN(Cc2nc4ccc(C(=O)O)cc4n2C[C@@H]2CCO2)C3)c(F)c1] | 1.97 | 618.4 | 1 |

TABLE 27-continued
| | | | | |
|---|---|---|---|---|
| I-154 | 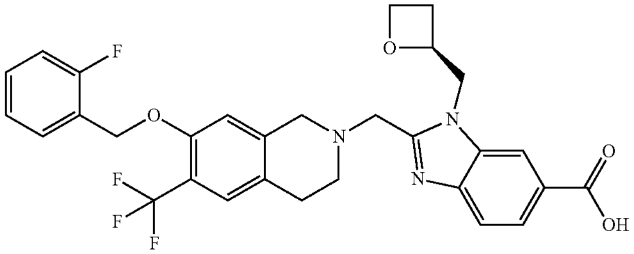 | 1.94 | 570.4 | 1 |
| I-155 | 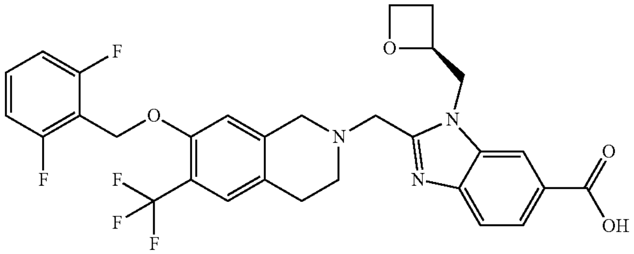 | 1.9 | 588.4 | 1 |
| I-156 | 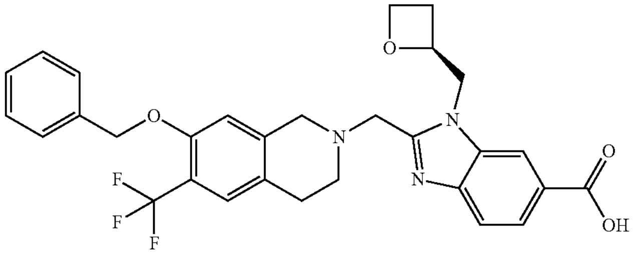 [SMILES: O=C(O)c1ccc2nc(CN3CCc4cc(C(F)(F)F)c(OCc5ccccc5)cc4C3)n(C[C@@H]3CCO3)c2c1] | 1.96 | 552.4 | 1 |
| I-157 | 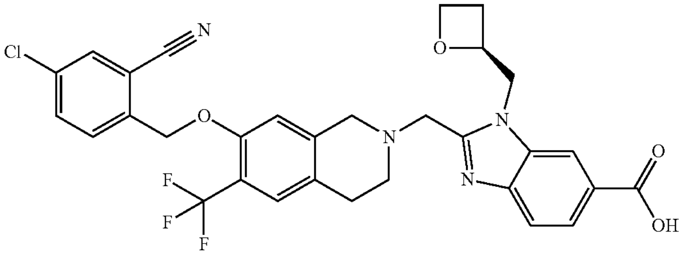 [SMILES: N#Cc1cc(Cl)ccc1COc1cc2c(cc1C(F)(F)F)CCN(Cc1nc3ccc(C(=O)O)cc3n1C[C@@H]1CCO1)C2] | 2.05 | 611.4 | 1 |
| I-158 | 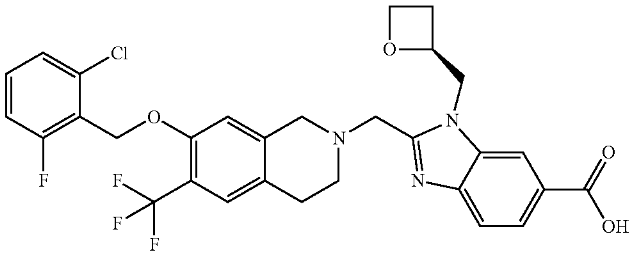 [SMILES: O=C(O)c1ccc2nc(CN3CCc4cc(C(F)(F)F)c(OCc5c(F)cccc5Cl)cc4C3)n(C[C@@H]3CCO3)c2c1] | 1.99 | 604.4 | 1 |

TABLE 28
| | | | | |
|---|---|---|---|---|
| I-159 | 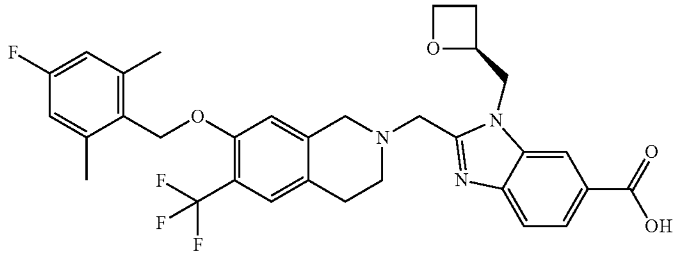 [SMILES: Cc1cc(F)cc(C)c1COc1cc2c(cc1C(F)(F)F)CCN(Cc1nc3ccc(C(=O)O)cc3n1C[C@@H]1CCO1)C2] | 2.14 | 598.4 | 1 |
| I-160 | 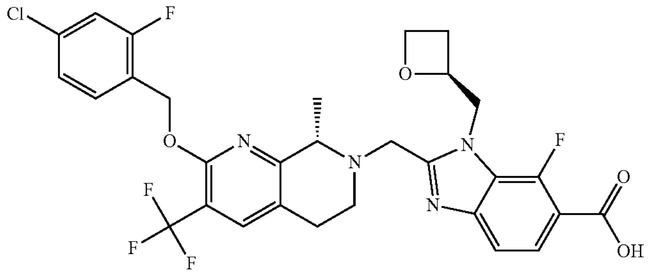 [SMILES: C[C@H]1c2nc(OCc3ccc(Cl)cc3F)c(C(F)(F)F)cc2CCN1Cc1nc2ccc(C(=O)O)c(F)c2n1C[C@@H]1CCO1] | 2.33 | 637.4 | 1 |
| I-161 | 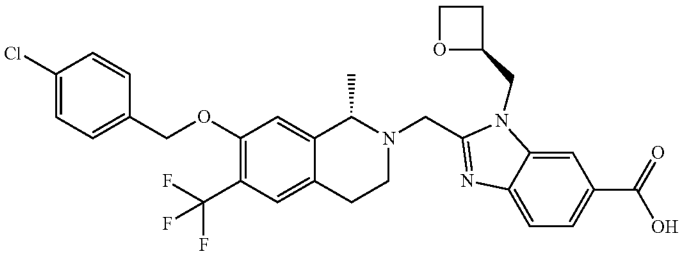 | 2.12 | 600.1 | 3 |
| I-162 | 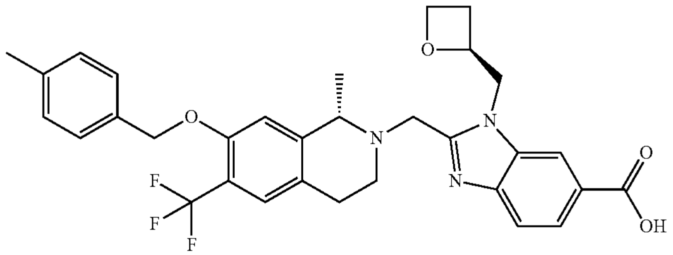 [SMILES: Cc1ccc(COc2cc3c(cc2C(F)(F)F)CCN(Cc2nc4ccc(C(=O)O)cc4n2C[C@@H]2CCO2)[C@H]3C)cc1] | 2.07 | 580.2 | 3 |
| I-163 | 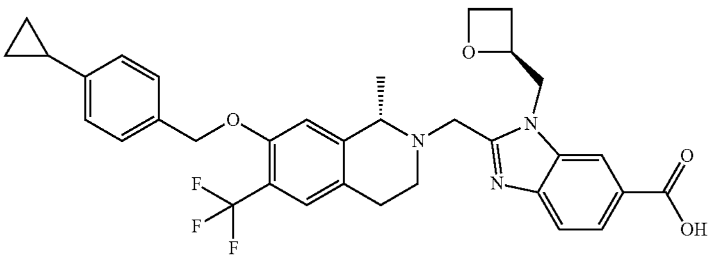 [SMILES: C[C@H]1c2cc(OCc3ccc(C4CC4)cc3)c(C(F)(F)F)cc2CCN1Cc1nc2ccc(C(=O)O)cc2n1C[C@@H]1CCO1] | 2.16 | 606.2 | 3 |
| I-164 | 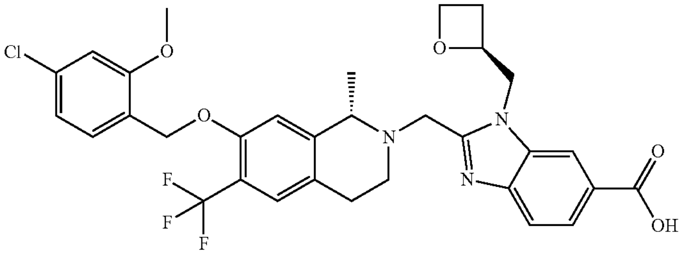 [SMILES: COc1cc(Cl)ccc1COc1cc2c(cc1C(F)(F)F)CCN(Cc1nc3ccc(C(=O)O)cc3n1C[C@@H]1CCO1)[C@H]2C] | 2.15 | 630.1 | 3 |

TABLE 28-continued
| | | | | |
|---|---|---|---|---|
| I-165 | 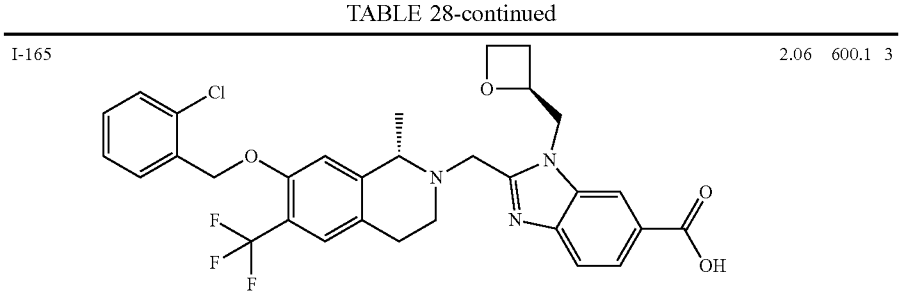 | 2.06 | 600.1 | 3 |
TABLE 29
| | | | | |
|---|---|---|---|---|
| I-166 | 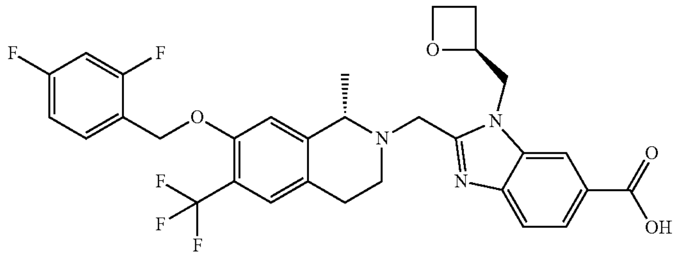 [SMILES: C[C@H]1c2cc(OCc3ccc(F)cc3F)c(C(F)(F)F)cc2CCN1Cc1nc2ccc(C(=O)O)cc2n1C[C@@H]1CCO1] | 2.00 | 602.1 | 3 |
| I-167 | 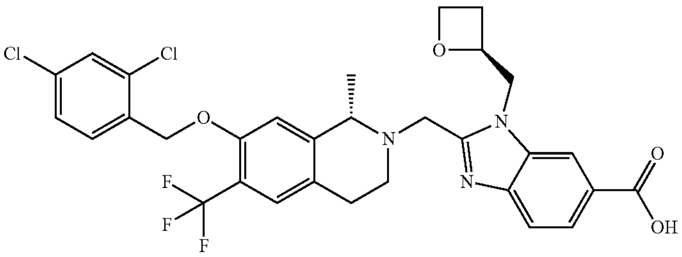 [SMILES: C[C@H]1c2cc(OCc3ccc(Cl)cc3Cl)c(C(F)(F)F)cc2CCN1Cc1nc2ccc(C(=O)O)cc2n1C[C@@H]1CCO1] | 2.24 | 634.1 | 3 |
| I-168 | 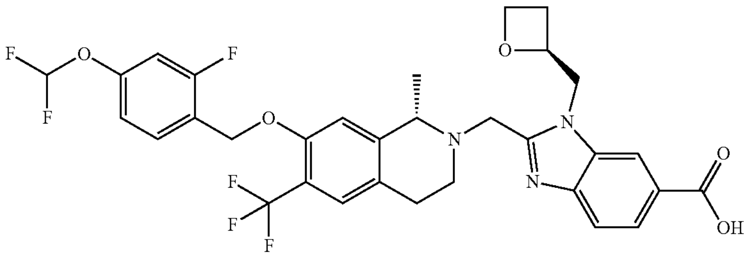 [SMILES: C[C@H]1c2cc(OCc3ccc(OC(F)F)cc3F)c(C(F)(F)F)cc2CCN1Cc1nc2ccc(C(=O)O)cc2n1C[C@@H]1CCO1] | 2.05 | 650.1 | 3 |
| I-169 | 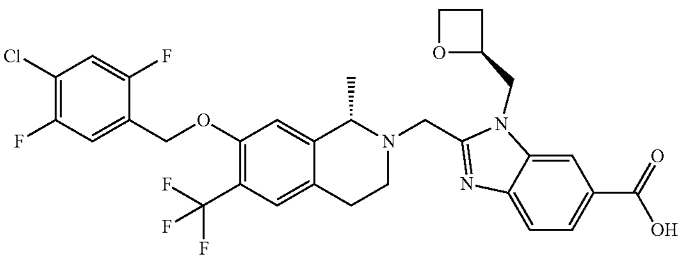 | 2.17 | 636.1 | 3 |

TABLE 29-continued
| | | | | |
|---|---|---|---|---|
| I-170 | 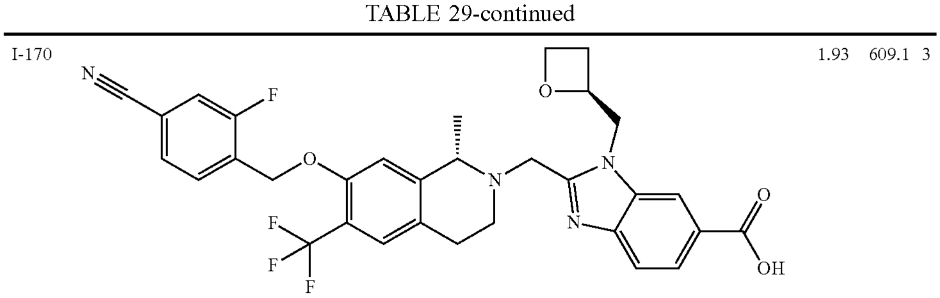 | 1.93 | 609.1 | 3 |
| I-171 | 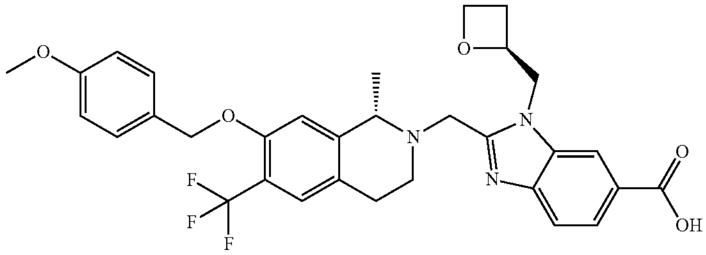 [SMILES: COc1ccc(COc2cc3c(cc2C(F)(F)F)CCN(Cc2nc4ccc(C(=O)O)cc4n2C[C@@H]2CCO2)[C@H]3C)cc1] | 1.95 | 596.1 | 3 |
| I-172 | 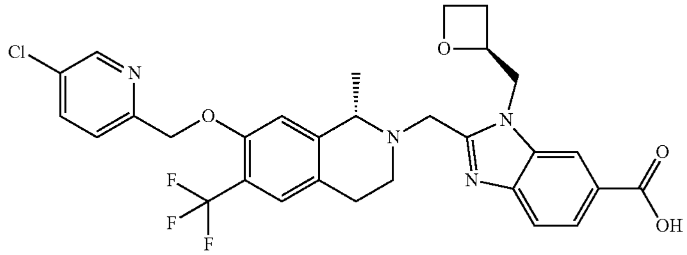 | 1.92 | 601.1 | 3 |
TABLE 30
| | | | | |
|---|---|---|---|---|
| I-173 | 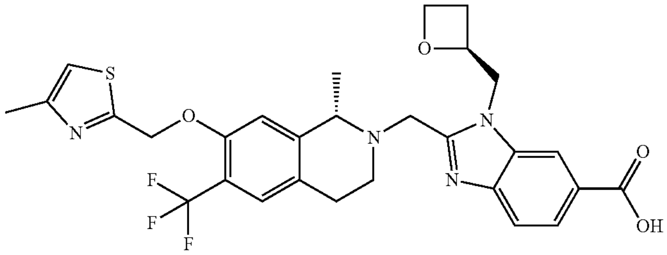 [SMILES: Cc1csc(COc2cc3c(cc2C(F)(F)F)CCN(Cc2nc4ccc(C(=O)O)cc4n2C[C@@H]2CCO2)[C@H]3C)n1] | 1.81 | 587.1 | 3 |
| I-174 | 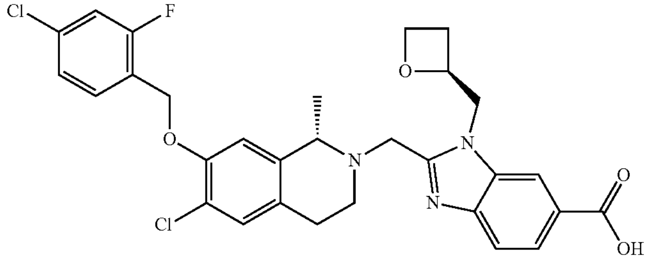 [SMILES: C[C@H]1c2cc(OCc3ccc(Cl)cc3F)c(Cl)cc2CCN1Cc1nc2ccc(C(=O)O)cc2n1C[C@@H]1CCO1] | 2.36 | 584.3 | 1 |

TABLE 30-continued
| | | | | |
|---|---|---|---|---|
| I-175 | 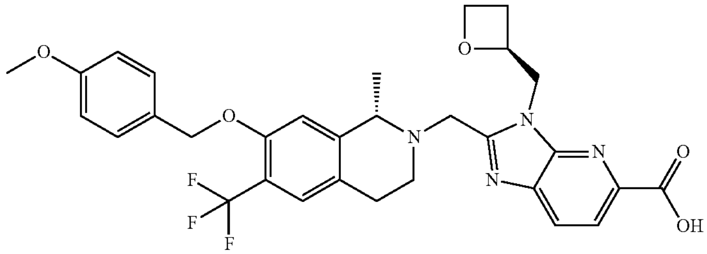 [SMILES: COc1ccc(COc2cc3c(cc2C(F)(F)F)CCN(Cc2nc4ccc(C(=O)O)nc4n2C[C@@H]2CCO2)[C@H]3C)cc1] | 1.89 | 597.1 | 3 |
| I-176 | 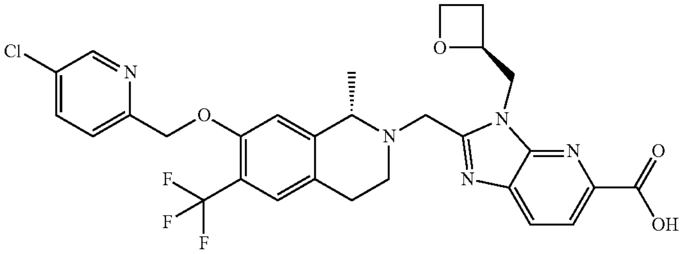 [SMILES: C[C@H]1c2cc(OCc3ccc(Cl)cn3)c(C(F)(F)F)cc2CCN1Cc1nc2ccc(C(=O)O)nc2n1C[C@@H]1CCO1] | 1.85 | 602.1 | 3 |
| I-177 | 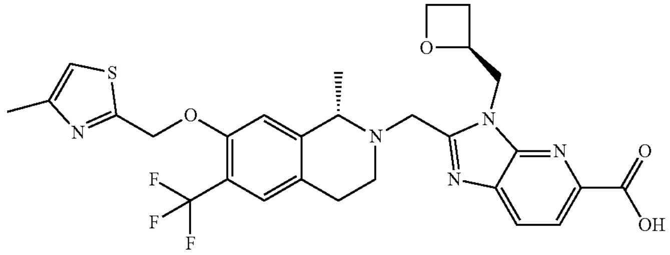 | 1.72 | 588.1 | 3 |
| I-178 | 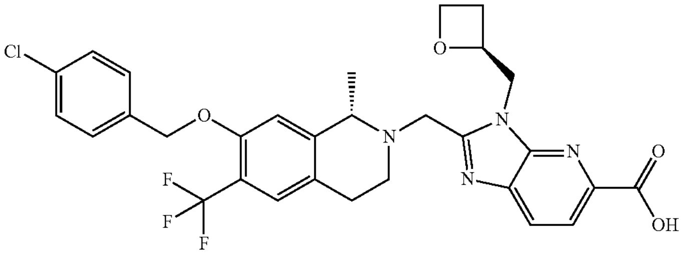 | 2.06 | 601.1 | 3 |
| I-179 | 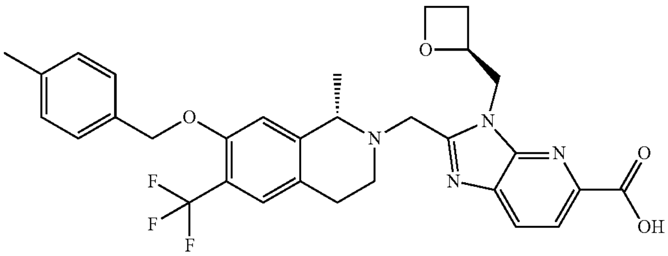 | 2.01 | 581.1 | 3 |

TABLE 31
| | | | | |
|---|---|---|---|---|
| I-180 | 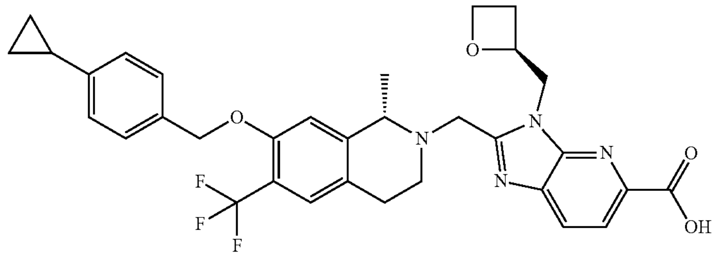 [SMILES: C[C@H]1c2cc(OCc3ccc(C4CC4)cc3)c(C(F)(F)F)cc2CCN1Cc1nc2ccc(C(=O)O)nc2n1C[C@@H]1CCO1] | 2.11 | 607.1 | 3 |
| I-181 | 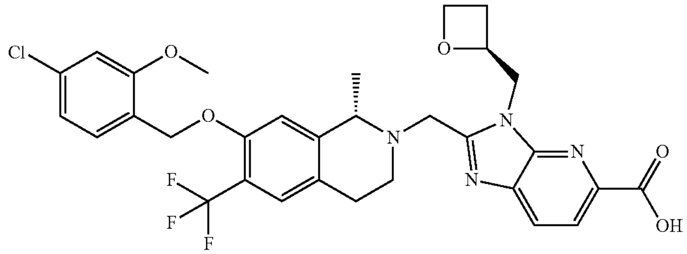 [SMILES: COc1cc(Cl)ccc1COc1cc2c(cc1C(F)(F)F)CCN(Cc1nc3ccc(C(=O)O)nc3n1C[C@@H]1CCO1)[C@H]2C] | 2.09 | 631.1 | 3 |
| I-182 | 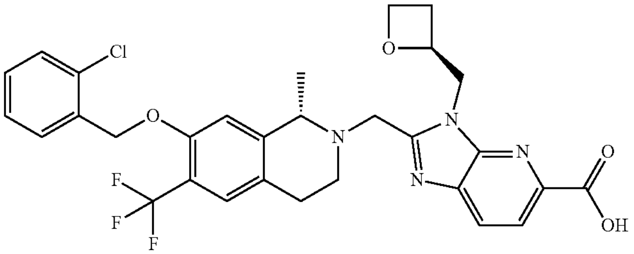 | 2.00 | 601.1 | 3 |
| I-183 | 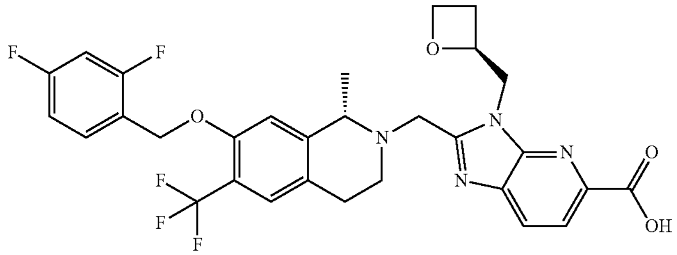 | 1.95 | 603.1 | 3 |
| I-184 | 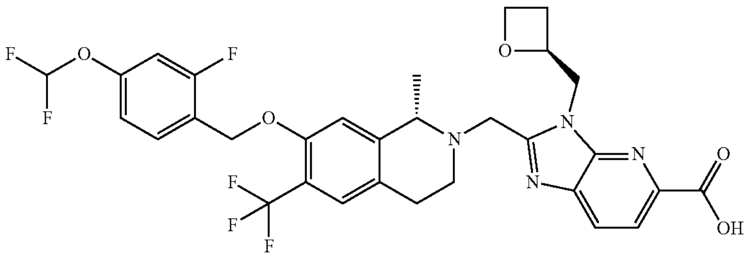 | 2.00 | 651.1 | 3 |
| I-185 | 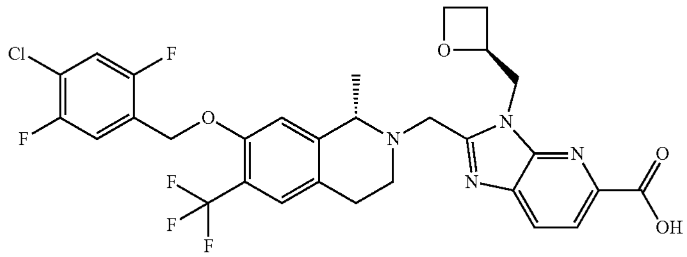 | 2.12 | 637.0 | 3 |

TABLE 31-continued
| | | | | |
|---|---|---|---|---|
| I-186 | 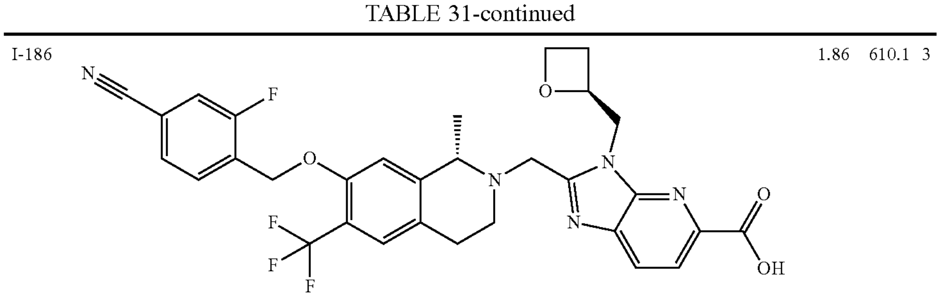 | 1.86 | 610.1 | 3 |
TABLE 32
| | | | | |
|---|---|---|---|---|
| I-187 | 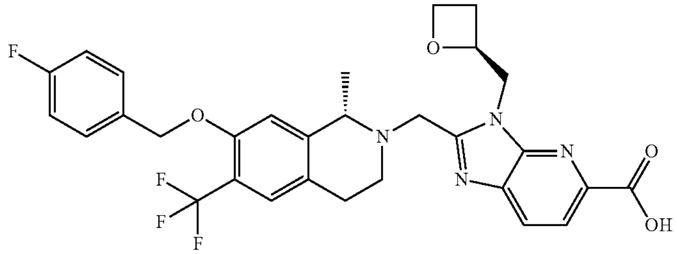 [SMILES: C[C@H]1c2cc(OCc3ccc(F)cc3)c(C(F)(F)F)cc2CCN1Cc1nc2ccc(C(=O)O)nc2n1C[C@@H]1CCO1] | 1.94 | 585.1 | 3 |
| I-188 | 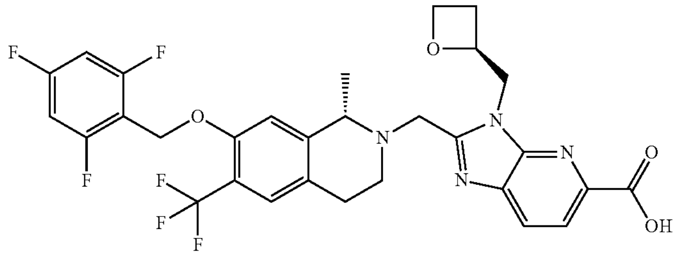 [SMILES: C[C@H]1c2cc(OCc3c(F)cc(F)cc3F)c(C(F)(F)F)cc2CCN1Cc1nc2ccc(C(=O)O)nc2n1C[C@@H]1CCO1] | 1.93 | 621.1 | 3 |
| I-189 | 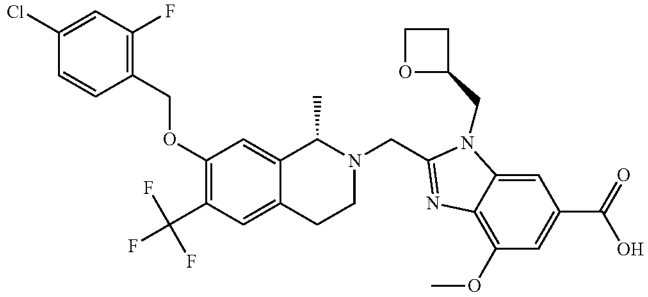 [SMILES: COc1cc(C(=O)O)cc2c1nc(CN1CCc3cc(C(F)(F)F)c(OCc4ccc(Cl)cc4F)cc3[C@@H]1C)n2C[C@@H]1CCO1] | 2.12 | 648.2 | 3 |
| I-190 | 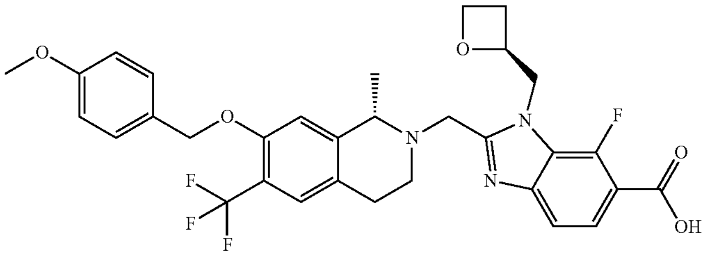 | 1.99 | 614.2 | 3 |

TABLE 32-continued
| | | | | |
|---|---|---|---|---|
| I-191 | 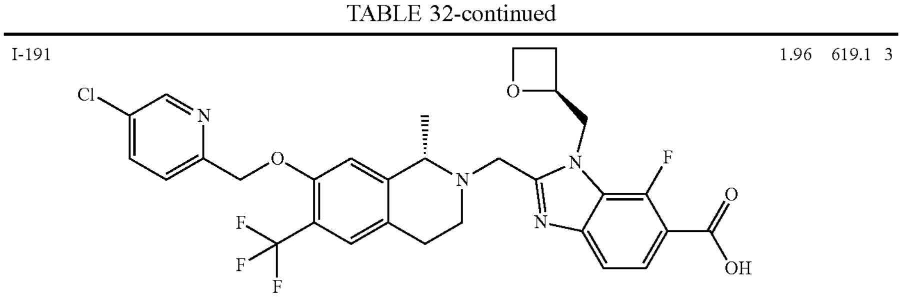 | 1.96 | 619.1 | 3 |
| I-192 | 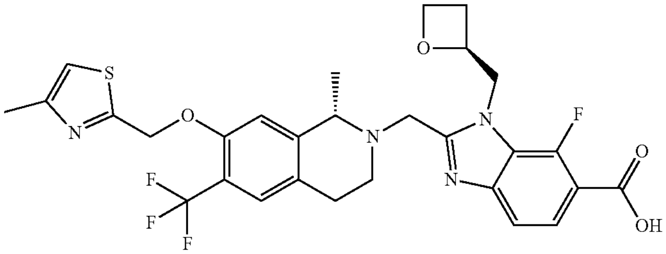 | 1.81 | 605.1 | 3 |
| I-193 | 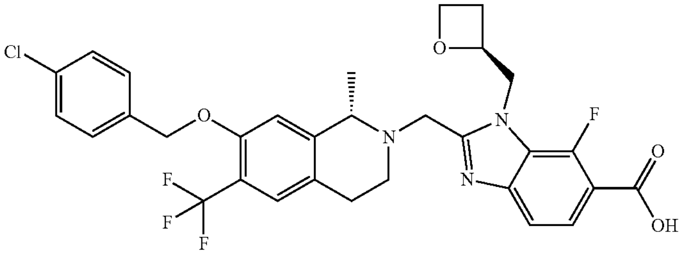 | 2.17 | 618.1 | 3 |
TABLE 33
| | | | | |
|---|---|---|---|---|
| I-194 | 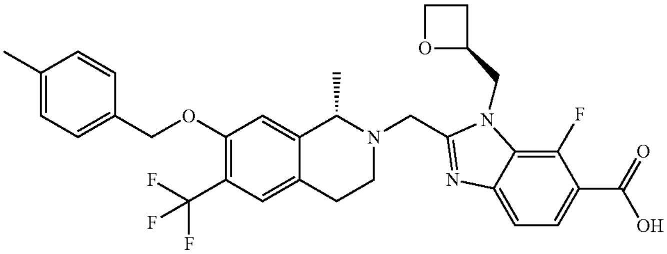 [SMILES: Cc1ccc(COc2cc3c(cc2C(F)(F)F)CCN(Cc2nc4ccc(C(=O)O)c(F)c4n2C[C@@H]2CCO2)[C@H]3C)cc1] | 2.10 | 598.2 | 3 |
| I-195 | 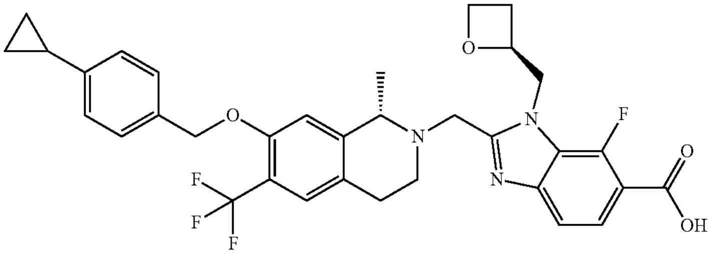 | 2.20 | 624.2 | 3 |

TABLE 33-continued
| | | | | |
|---|---|---|---|---|
| I-196 | 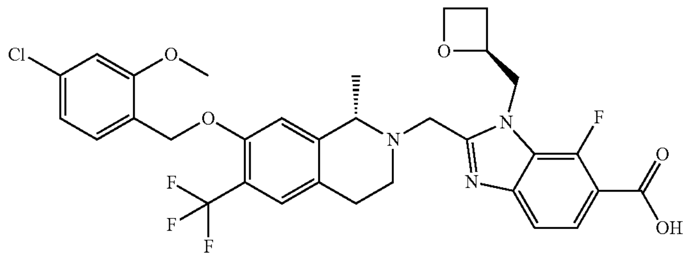 [SMILES: COc1cc(Cl)ccc1COc1cc2c(cc1C(F)(F)F)CCN(Cc1nc3ccc(C(=O)O)c(F)c3n1C[C@@H]1CCO1)[C@H]2C] | 2.19 | 648.1 | 3 |
| I-197 | 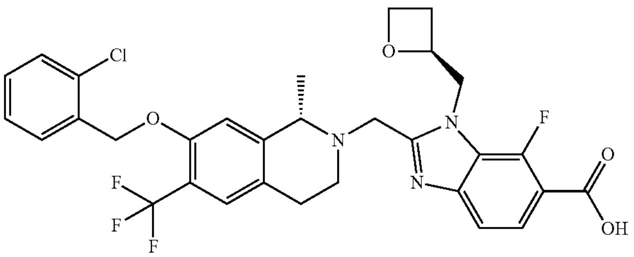 | 2.11 | 618.1 | 3 |
| I-198 | 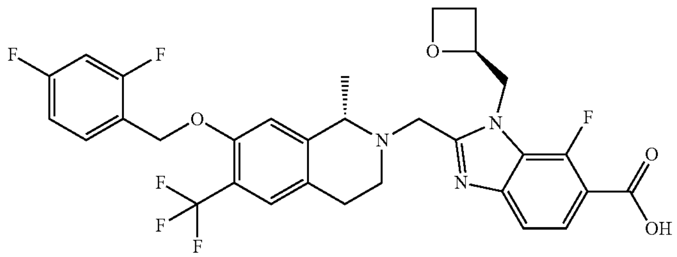 [SMILES: C[C@H]1c2cc(OCc3ccc(F)cc3F)c(C(F)(F)F)cc2CCN1Cc1nc2ccc(C(=O)O)c(F)c2n1C[C@@H]1CCO1] | 2.03 | 620.2 | 3 |
| I-199 | 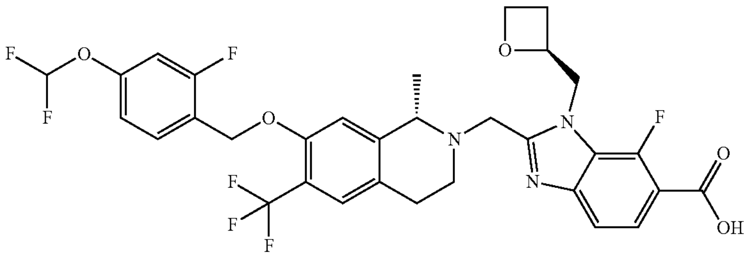 [SMILES: C[C@H]1c2cc(OCc3ccc(OC(F)F)cc3F)c(C(F)(F)F)cc2CCN1Cc1nc2ccc(C(=O)O)c(F)c2n1C[C@@H]1CCO1] | 2.08 | 668.2 | 3 |
| I-200 | 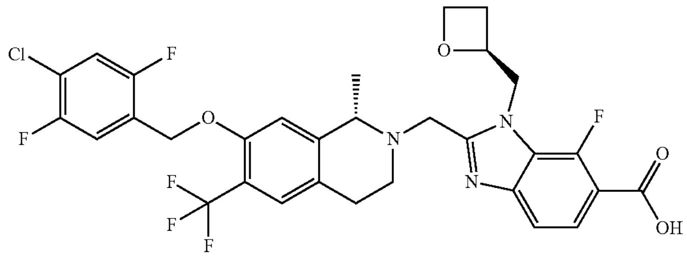 [SMILES: C[C@H]1c2cc(OCc3cc(F)c(Cl)cc3F)c(C(F)(F)F)cc2CCN1Cc1nc2ccc(C(=O)O)c(F)c2n1C[C@@H]1CCO1] | 2.22 | 654.1 | 3 |

TABLE 34
| | | | | |
|---|---|---|---|---|
| I-201 | 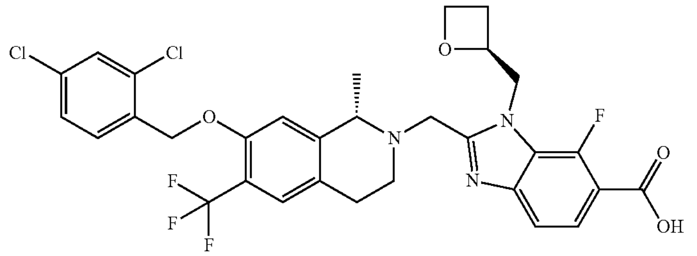 [SMILES: C[C@H]1c2cc(OCc3ccc(Cl)cc3Cl)c(C(F)(F)F)cc2CCN1Cc1nc2ccc(C(=O)O)c(F)c2n1C[C@@H]1CCO1] | 2.29 | 652.1 | 3 |
| I-202 | 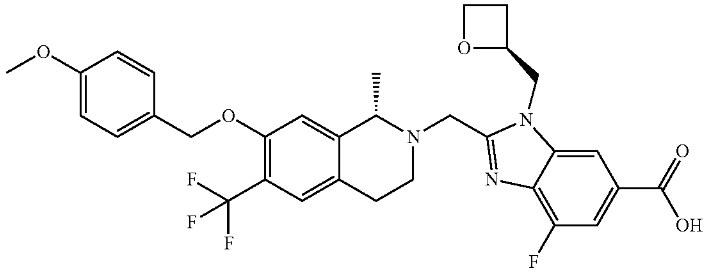 [SMILES: COc1ccc(COc2cc3c(cc2C(F)(F)F)CCN(Cc2nc4c(F)cc(C(=O)O)cc4n2C[C@@H]2CCO2)[C@H]3C)cc1] | 2.05 | 614.1 | 3 |
| I-203 | 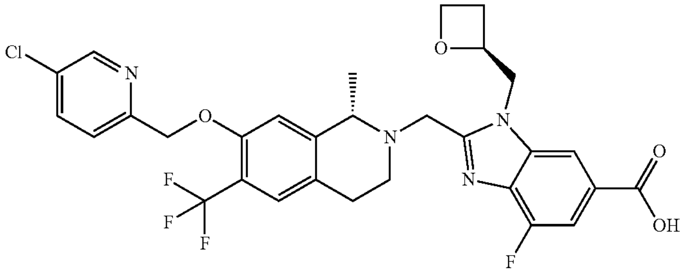 [SMILES: C[C@H]1c2cc(OCc3ccc(Cl)cn3)c(C(F)(F)F)cc2CCN1Cc1nc2c(F)cc(C(=O)O)cc2n1C[C@@H]1CCO1] | 2.02 | 619.1 | 3 |
| I-204 | 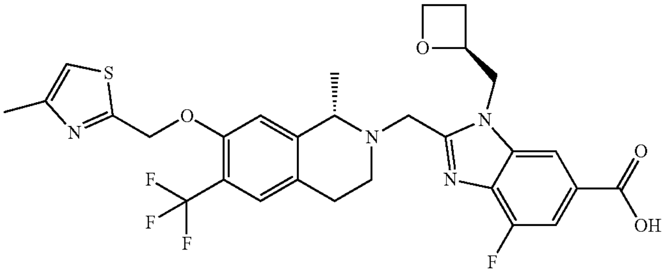 [SMILES: Cc1csc(COc2cc3c(cc2C(F)(F)F)CCN(Cc2nc4c(F)cc(C(=O)O)cc4n2C[C@@H]2CCO2)[C@H]3C)n1] | 1.87 | 605.1 | 3 |
| I-205 | 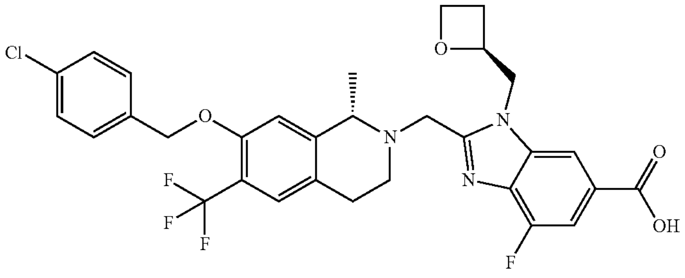 [SMILES: C[C@H]1c2cc(OCc3ccc(Cl)cc3)c(C(F)(F)F)cc2CCN1Cc1nc2c(F)cc(C(=O)O)cc2n1C[C@@H]1CCO1] | 2.24 | 618.0 | 3 |

TABLE 34-continued
| | | | | |
|---|---|---|---|---|
| I-206 | 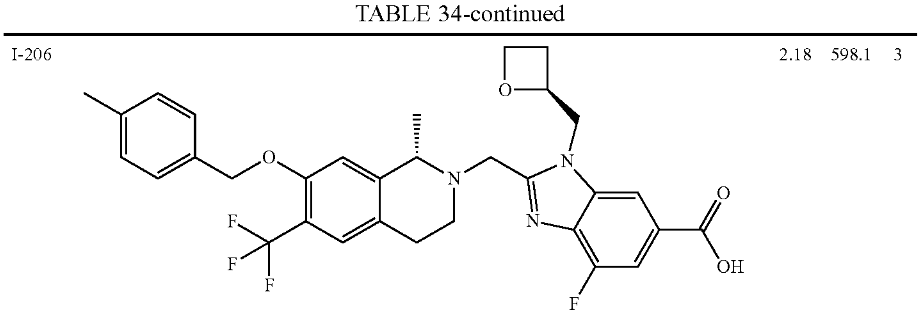 | 2.18 | 598.1 | 3 |
| I-207 | 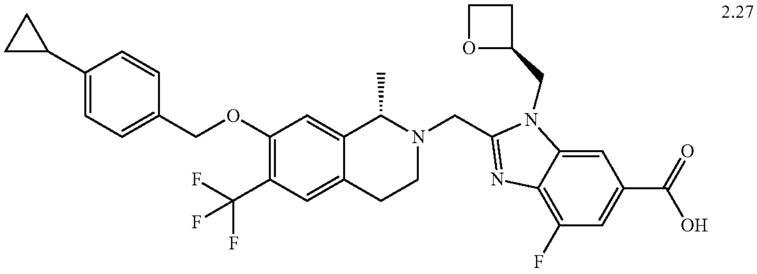 | 2.27 | 624.1 | 3 |
TABLE 35
| | | | | |
|---|---|---|---|---|
| I-208 | 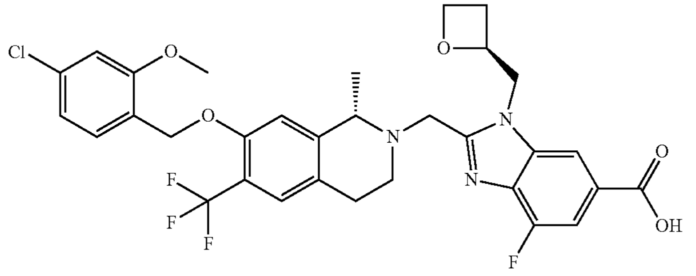 [SMILES: COc1cc(Cl)ccc1COc1cc2c(cc1C(F)(F)F)CCN(Cc1nc3c(F)cc(C(=O)O)cc3n1C[C@@H]1CCO1)[C@H]2C] | 2.26 | 648.0 | 3 |
| I-209 | 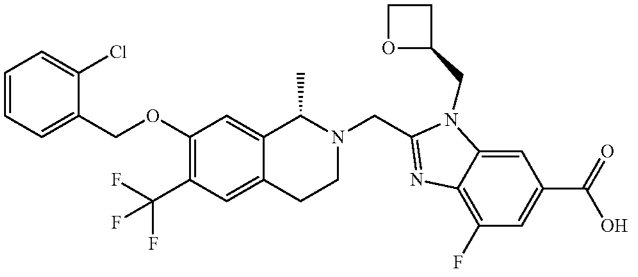 [SMILES: C[C@H]1c2cc(OCc3ccccc3Cl)c(C(F)(F)F)cc2CCN1Cc1nc2c(F)cc(C(=O)O)cc2n1C[C@@H]1CCO1] | 2.18 | 618.1 | 3 |
| I-210 | 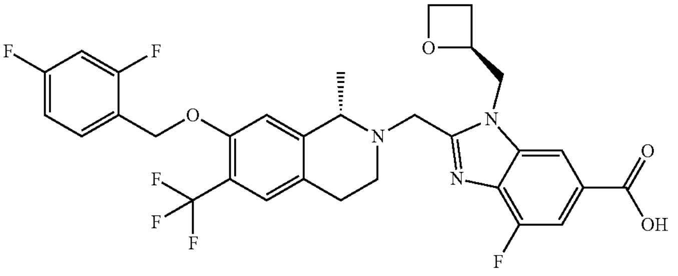 [SMILES: C[C@H]1c2cc(OCc3ccc(F)cc3F)c(C(F)(F)F)cc2CCN1Cc1nc2c(F)cc(C(=O)O)cc2n1C[C@@H]1CCO1] | 2.11 | 620.1 | 3 |

TABLE 35-continued
| | | | | |
|---|---|---|---|---|
| I-211 | 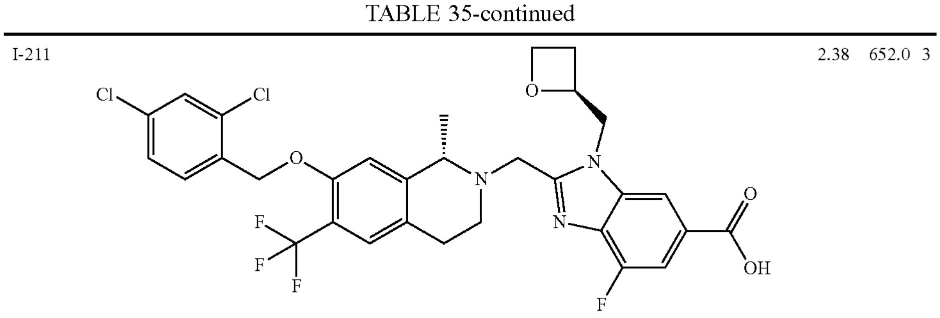 | 2.38 | 652.0 | 3 |
| I-212 | 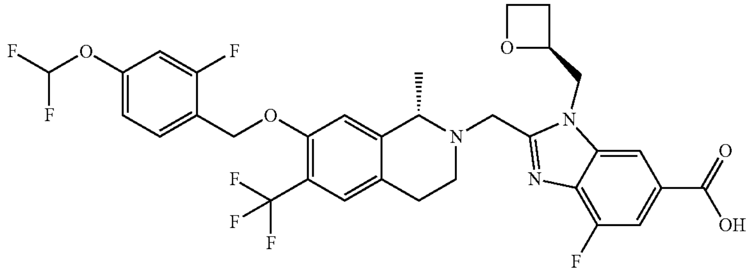 [SMILES: C[C@H]1c2cc(OCc3ccc(OC(F)F)cc3F)c(C(F)(F)F)cc2CCN1Cc1nc2c(F)cc(C(=O)O)cc2n1C[C@@H]1CCO1] | 2.15 | 668.1 | 3 |
| I-213 | 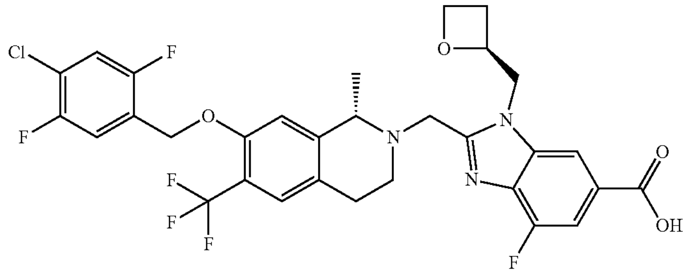 [SMILES: C[C@H]1c2cc(OCc3cc(F)c(Cl)cc3F)c(C(F)(F)F)cc2CCN1Cc1nc2c(F)cc(C(=O)O)cc2n1C[C@@H]1CCO1] | 2.29 | 654.0 | 3 |
| I-214 | 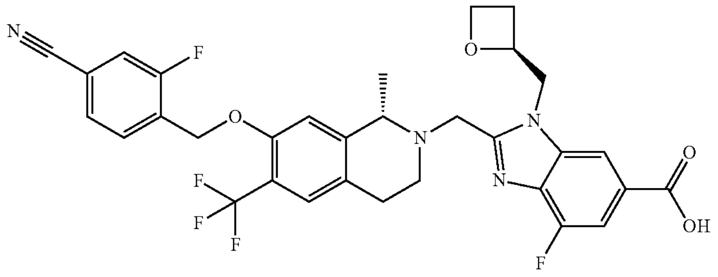 [SMILES: C[C@H]1c2cc(OCc3ccc(C#N)cc3F)c(C(F)(F)F)cc2CCN1Cc1nc2c(F)cc(C(=O)O)cc2n1C[C@@H]1CCO1] | 2.03 | 627.1 | 3 |
TABLE 36
| | | | | |
|---|---|---|---|---|
| I-215 | 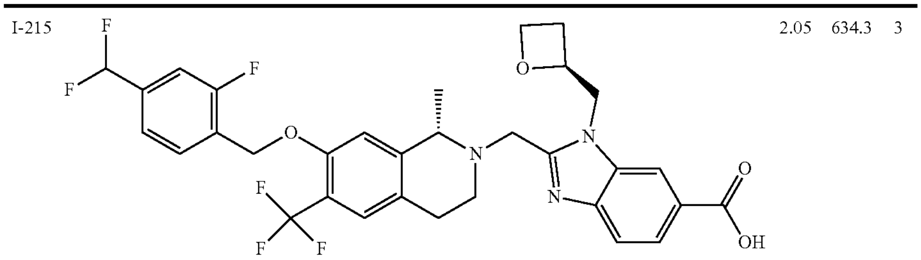 | 2.05 | 634.3 | 3 |

TABLE 36-continued
| | | | | |
|---|---|---|---|---|
| I-216 | 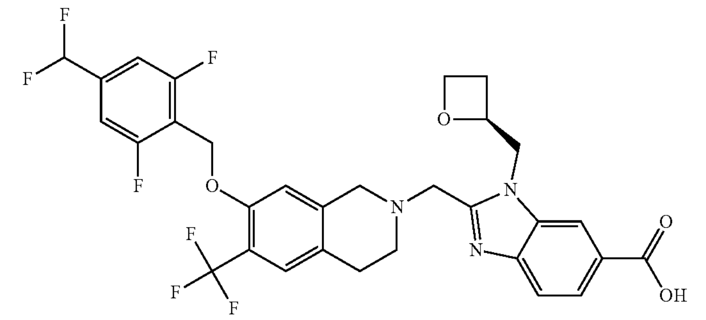 [SMILES: O=C(O)c1ccc2nc(CN3CCc4cc(C(F)(F)F)c(OCc5c(F)cc(C(F)F)cc5F)cc4C3)n(C[C@@H]3CCO3)c2c1] | 2.17 | 638.3 | 1 |
| I-217 | 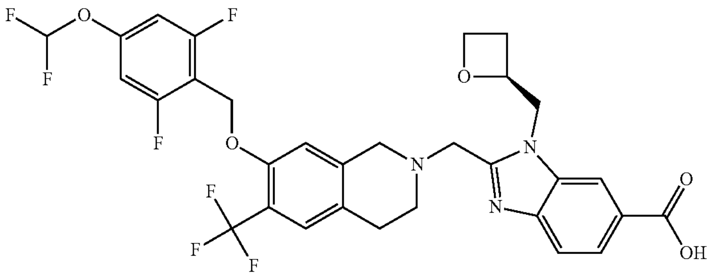 [SMILES: O=C(O)c1ccc2nc(CN3CCc4cc(C(F)(F)F)c(OCc5c(F)cc(OC(F)F)cc5F)cc4C3)n(C[C@@H]3CCO3)c2c1] | 2.28 | 654.3 | 1 |
| I-218 | 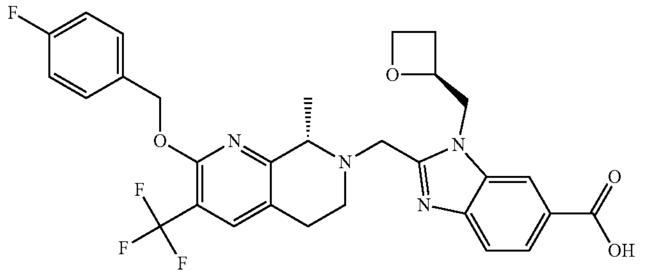 [SMILES: C[C@H]1c2nc(OCc3ccc(F)cc3)c(C(F)(F)F)cc2CCN1Cc1nc2ccc(C(=O)O)cc2n1C[C@@H]1CCO1] | 2.35 | 585.3 | 1 |
| I-219 | 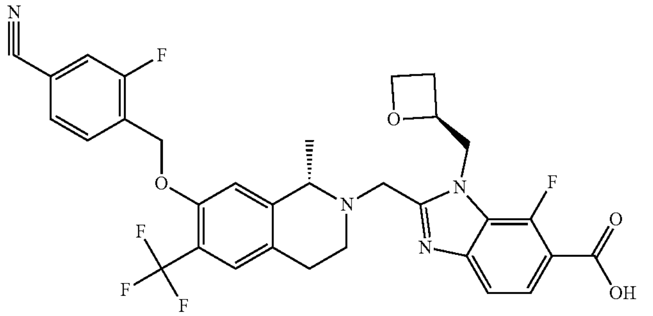 [SMILES: C[C@H]1c2cc(OCc3ccc(C#N)cc3F)c(C(F)(F)F)cc2CCN1Cc1nc2ccc(C(=O)O)c(F)c2n1C[C@@H]1CCO1] | 1.96 | 627.2 | 3 |
| I-220 | 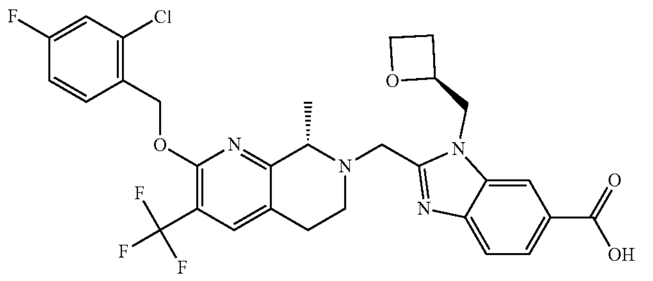 [SMILES: C[C@H]1c2nc(OCc3ccc(F)cc3Cl)c(C(F)(F)F)cc2CCN1Cc1nc2ccc(C(=O)O)cc2n1C[C@@H]1CCO1] | 2.14 | 619.3 | 3 |

TABLE 36-continued
| | | | | |
|---|---|---|---|---|
| I-221 | 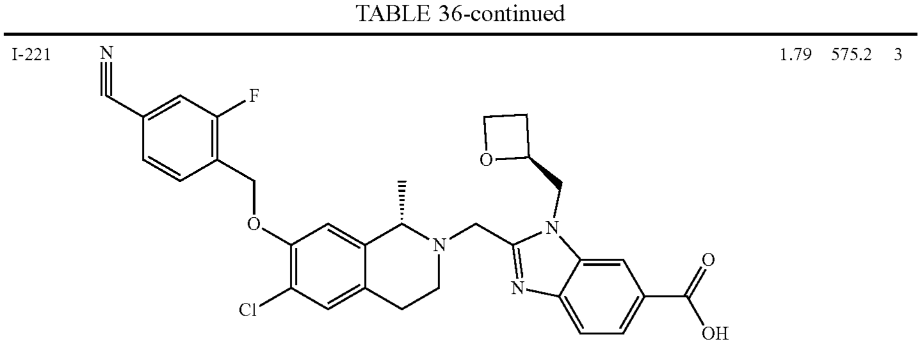 | 1.79 | 575.2 | 3 |
TABLE 37
| | | | | |
|---|---|---|---|---|
| I-222 | 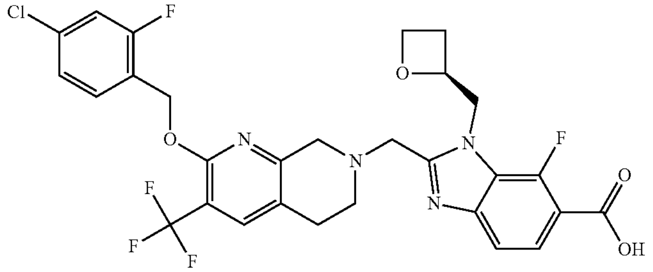 [SMILES: O=C(O)c1ccc2nc(CN3CCc4cc(C(F)(F)F)c(OCc5ccc(Cl)cc5F)nc4C3)n(C[C@@H]3CCO3)c2c1F] | 2.47 | 623.2 | 1 |
| I-223 | 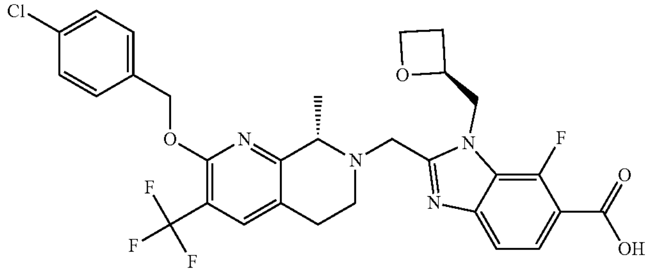 [SMILES: C[C@H]1c2nc(OCc3ccc(Cl)cc3)c(C(F)(F)F)cc2CCN1Cc1nc2ccc(C(=O)O)c(F)c2n1C[C@@H]1CCO1] | 2.18 | 619.2 | 3 |
| I-224 | 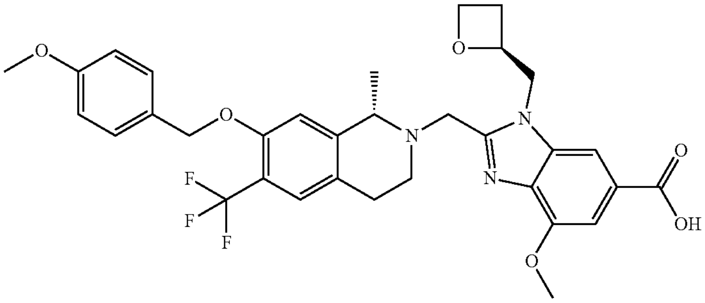 [SMILES: COc1ccc(COc2cc3c(cc2C(F)(F)F)CCN(Cc2nc4c(OC)cc(C(=O)O)cc4n2C[C@@H]2CCO2)[C@H]3C)cc1] | 1.96 | 626.1 | 3 |
| I-225 | 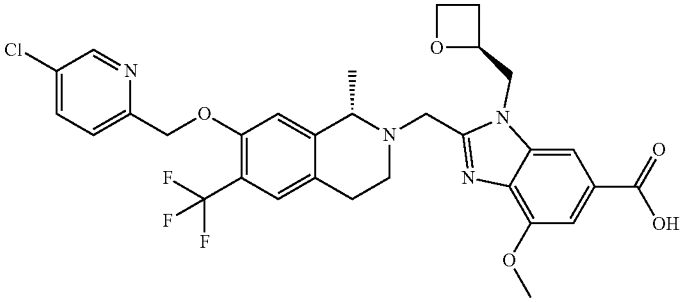 [SMILES: COc1cc(C(=O)O)cc2c1nc(CN1CCc3cc(C(F)(F)F)c(OCc4ccc(Cl)cn4)cc3[C@@H]1C)n2C[C@@H]1CCO1] | 1.93 | 631.1 | 3 |

TABLE 37-continued
| | | | | |
|---|---|---|---|---|
| I-226 | 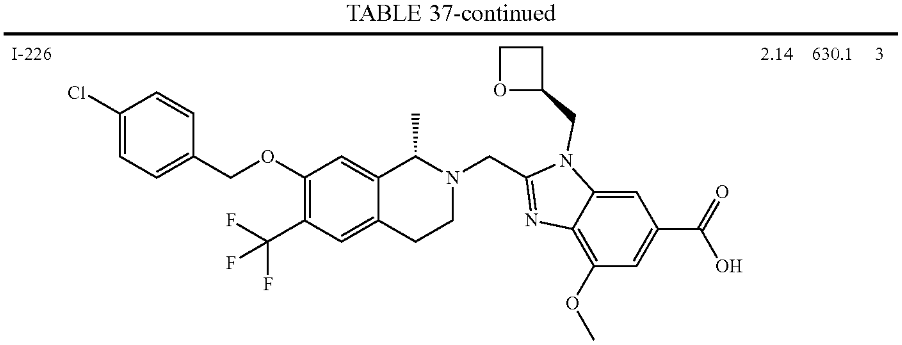 | 2.14 | 630.1 | 3 |
| I-227 | 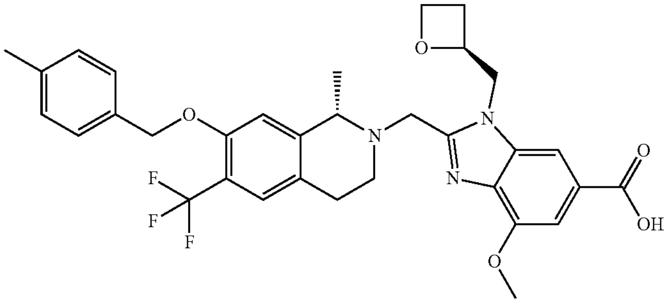 [SMILES: COc1cc(C(=O)O)cc2c1nc(CN1CCc3cc(C(F)(F)F)c(OCc4ccc(C)cc4)cc3[C@@H]1C)n2C[C@@H]1CCO1] | 2.09 | 610.2 | 3 |
TABLE 38
| | | | | |
|---|---|---|---|---|
| I-228 | 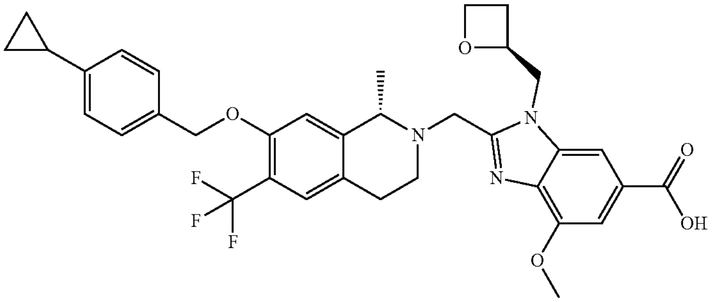 [SMILES: COc1cc(C(=O)O)cc2c1nc(CN1CCc3cc(C(F)(F)F)c(OCc4ccc(C5CC5)cc4)cc3[C@@H]1C)n2C[C@@H]1CCO1] | 2.18 | 636.3 | 3 |
| I-229 | 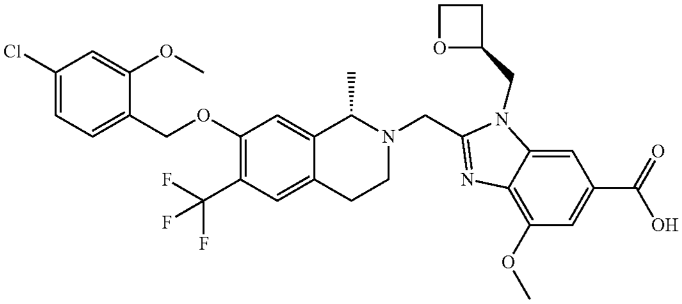 [SMILES: COc1cc(Cl)ccc1COc1cc2c(cc1C(F)(F)F)CCN(Cc1nc3c(OC)cc(C(=O)O)cc3n1C[C@@H]1CCO1)[C@H]2C] | 2.16 | 660.1 | 3 |

TABLE 38-continued
| | | | | |
|---|---|---|---|---|
| I-230 | 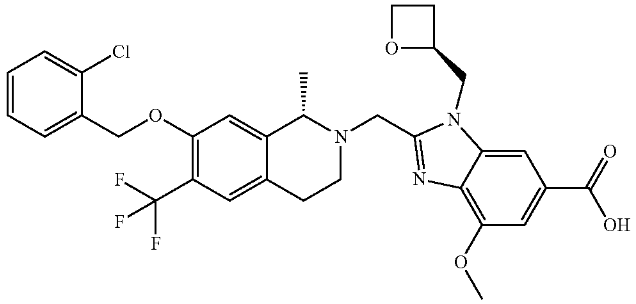 | 2.08 | 630.1 | 3 |
| I-231 | 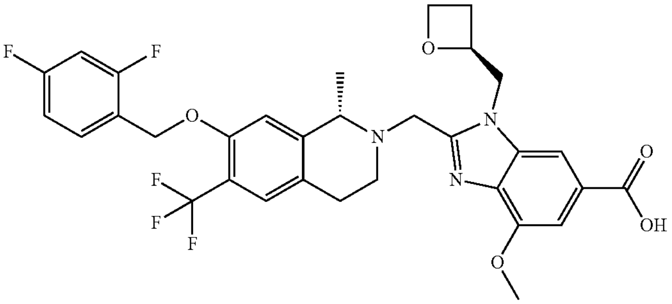 [SMILES: COc1cc(C(=O)O)cc2c1nc(CN1CCc3cc(C(F)(F)F)c(OCc4ccc(F)cc4F)cc3[C@@H]1C)n2C[C@@H]1CCO1] | 2.02 | 632.1 | 3 |
| I-232 | 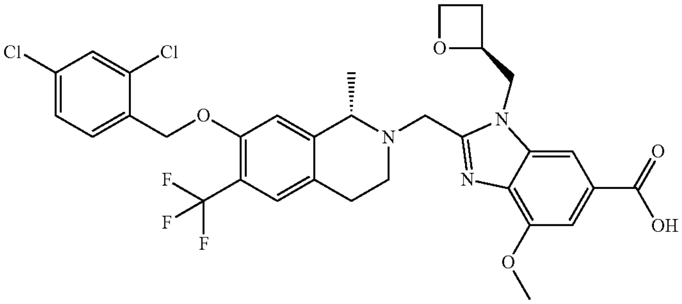 [SMILES: COc1cc(C(=O)O)cc2c1nc(CN1CCc3cc(C(F)(F)F)c(OCc4ccc(Cl)cc4Cl)cc3[C@@H]1C)n2C[C@@H]1CCO1] | 2.26 | 664.1 | 3 |
| I-233 | 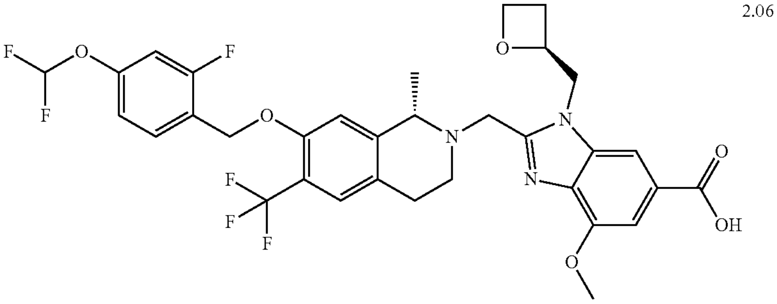 | 2.06 | 680.1 | 3 |

TABLE 39
| | | | | |
|---|---|---|---|---|
| I-234 | 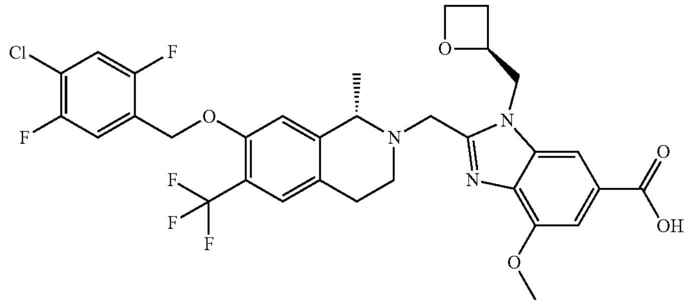 [SMILES: COc1cc(C(=O)O)cc2c1nc(CN1CCc3cc(C(F)(F)F)c(OCc4cc(F)c(Cl)cc4F)cc3[C@@H]1C)n2C[C@@H]1CCO1] | 2.18 | 666.1 | 3 |
| I-235 | 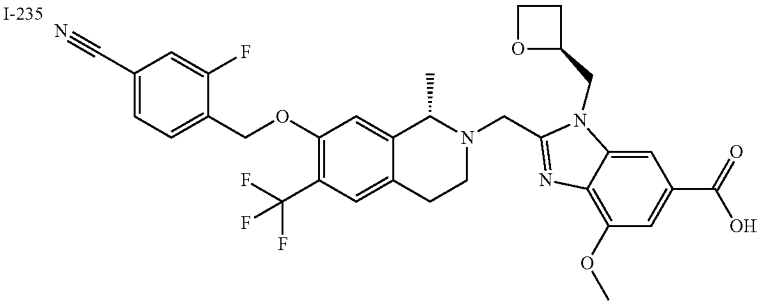 | 1.94 | 639.1 | 3 |
| I-236 | 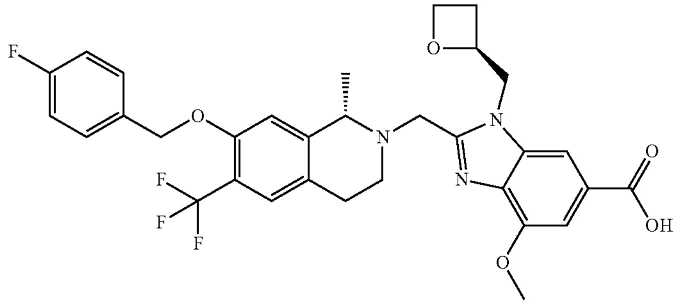 | 2.02 | 614.1 | 3 |
| I-237 | 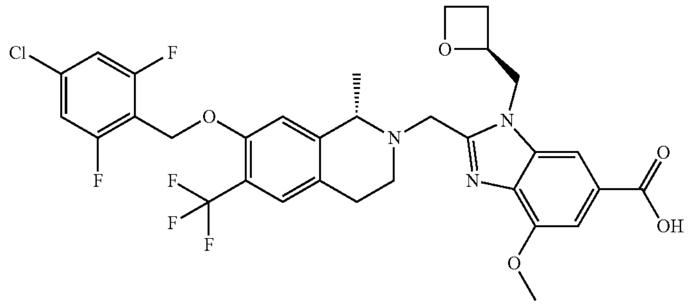 | 2.12 | 666.1 | 3 |
| I-238 | 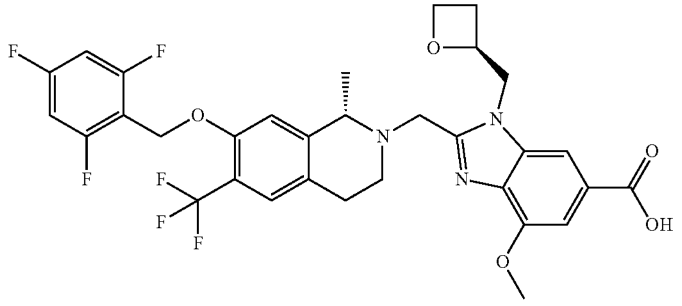 [SMILES: COc1cc(C(=O)O)cc2c1nc(CN1CCc3cc(C(F)(F)F)c(OCc4c(F)cc(F)cc4F)cc3[C@@H]1C)n2C[C@@H]1CCO1] | 2.00 | 650.1 | 3 |

TABLE 39-continued
| | | | | |
|---|---|---|---|---|
| I-239 | 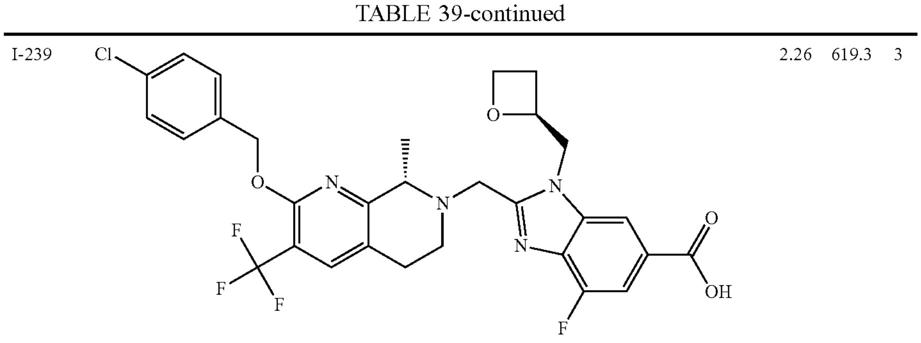 | 2.26 | 619.3 | 3 |
TABLE 40
| | | | | |
|---|---|---|---|---|
| I-240 | 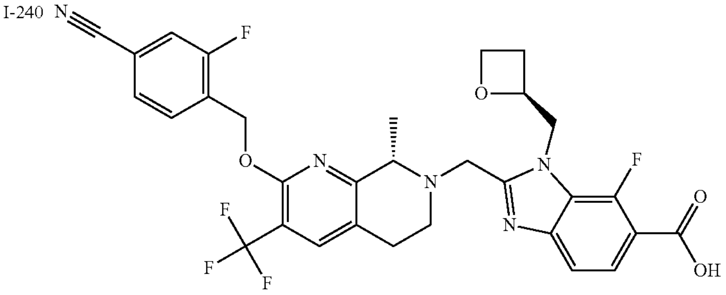 | 2.14 | 628.3 | 1 |
| I-241 | 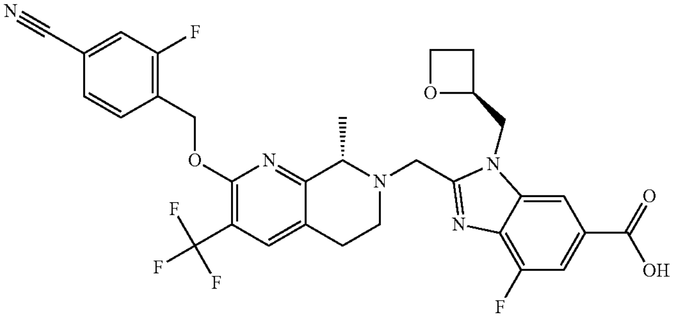 [SMILES: C[C@H]1c2nc(OCc3ccc(C#N)cc3F)c(C(F)(F)F)cc2CCN1Cc1nc2c(F)cc(C(=O)O)cc2n1C[C@@H]1CCO1] | 2.27 | 628.3 | 1 |
| I-242 | 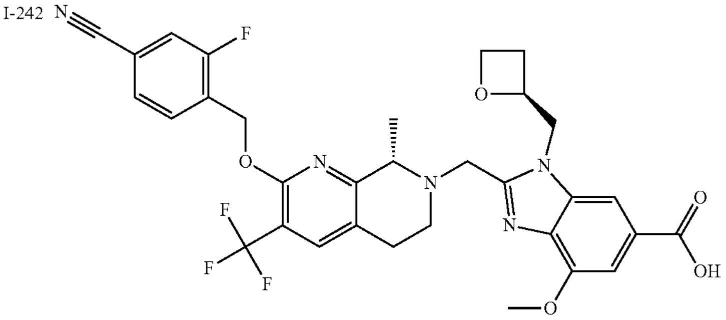 | 1.93 | 640.4 | 1 |

TABLE 40-continued
| | | | | |
|---|---|---|---|---|
| I-243 | 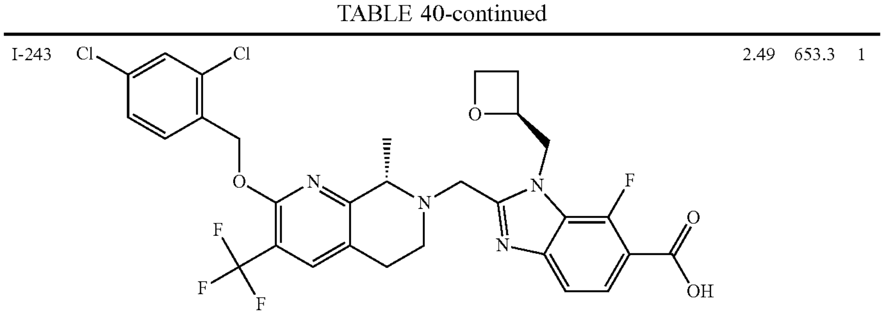 | 2.49 | 653.3 | 1 |
| I-244 | 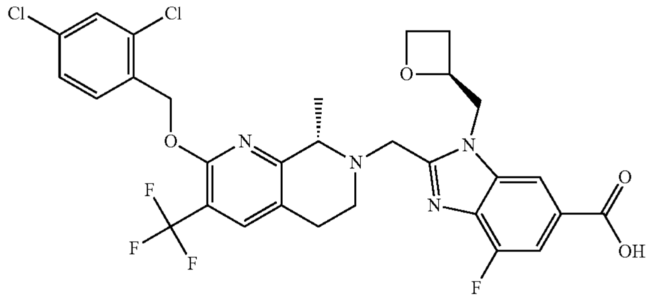 | 2.56 | 653.3 | 1 |
| I-245 | 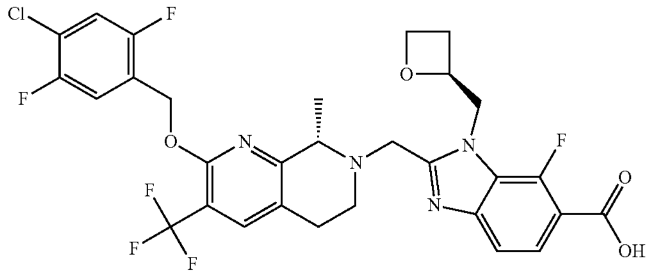 [SMILES: C[C@H]1c2nc(OCc3cc(F)c(Cl)cc3F)c(C(F)(F)F)cc2CCN1Cc1nc2ccc(C(=O)O)c(F)c2n1C[C@@H]1CCO1] | 2.33 | 655.4 | 1 |
| I-246 | 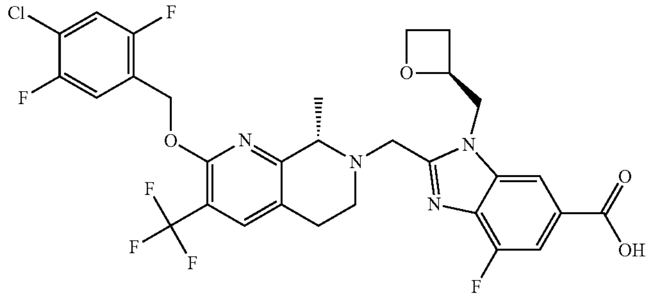 [SMILES: C[C@H]1c2nc(OCc3cc(F)c(Cl)cc3F)c(C(F)(F)F)cc2CCN1Cc1nc2c(F)cc(C(=O)O)cc2n1C[C@@H]1CCO1] | 2.42 | 655.4 | 1 |
TABLE 41
| | | | | |
|---|---|---|---|---|
| I-247 | 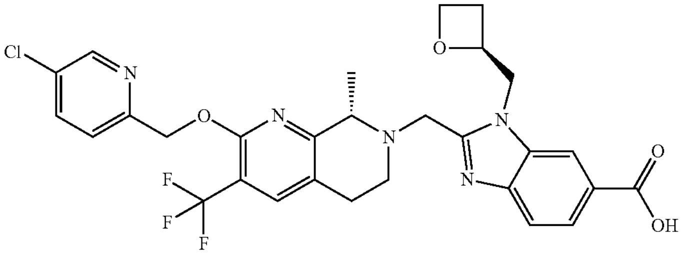 [SMILES: C[C@H]1c2nc(OCc3ccc(Cl)cn3)c(C(F)(F)F)cc2CCN1Cc1nc2ccc(C(=O)O)cc2n1C[C@@H]1CCO1] | 1.98 | 602.2 | 3 |

TABLE 41-continued
| | | | | |
|---|---|---|---|---|
| I-248 | 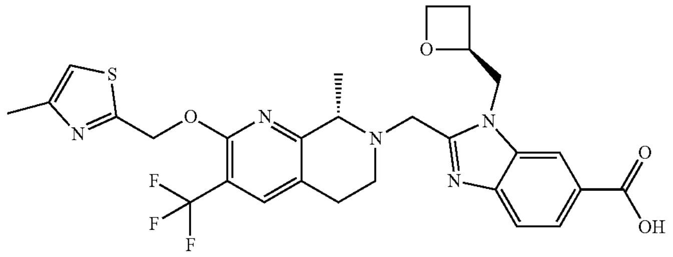 [SMILES: Cc1csc(COc2nc3c(cc2C(F)(F)F)CCN(Cc2nc4ccc(C(=O)O)cc4n2C[C@@H]2CCO2)[C@H]3C)n1] | 1.83 | 588.1 | 3 |
| I-249 | 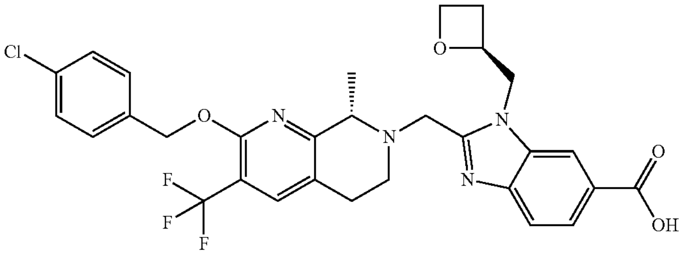 [SMILES: C[C@H]1c2nc(OCc3ccc(Cl)cc3)c(C(F)(F)F)cc2CCN1Cc1nc2ccc(C(=O)O)cc2n1C[C@@H]1CCO1] | 2.25 | 601.1 | 3 |
| I-250 | 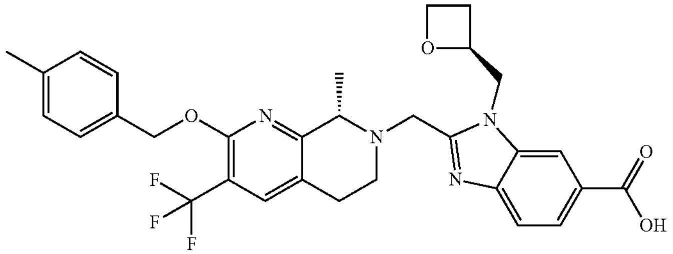 [SMILES: Cc1ccc(COc2nc3c(cc2C(F)(F)F)CCN(Cc2nc4ccc(C(=O)O)cc4n2C[C@@H]2CCO2)[C@H]3C)cc1] | 2.20 | 581.1 | 3 |
| I-251 | 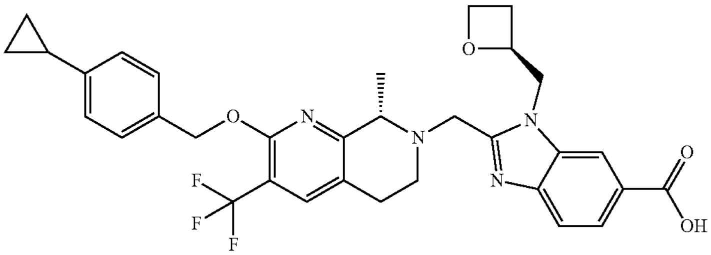 | 2.30 | 607.1 | 3 |
| I-252 | 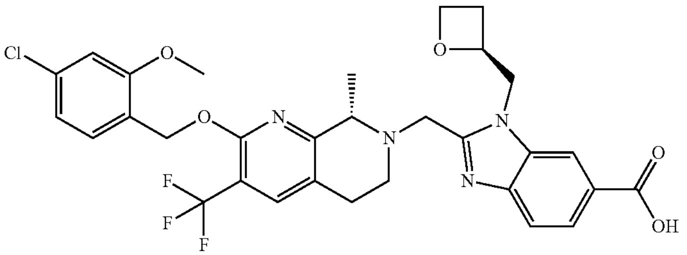 | 2.26 | 631.1 | 3 |
| I-253 | 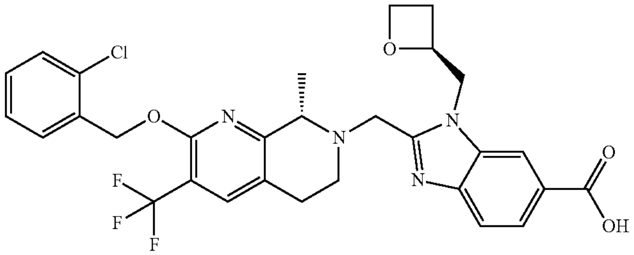 | 2.20 | 601.1 | 3 |

TABLE 42
| | | | | |
|---|---|---|---|---|
| I-254 | 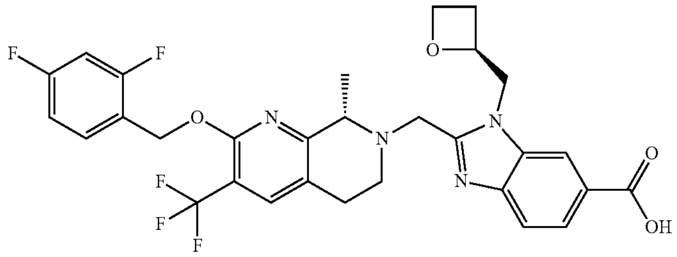 | 2.12 | 603.1 | 3 |
| I-255 | 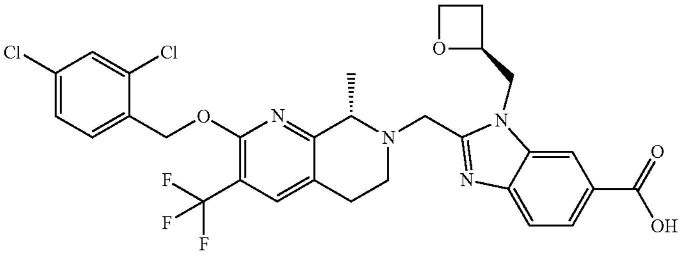 [SMILES: C[C@H]1c2nc(OCc3ccc(Cl)cc3Cl)c(C(F)(F)F)cc2CCN1Cc1nc2ccc(C(=O)O)cc2n1C[C@@H]1CCO1] | 2.41 | 635.1 | 3 |
| I-256 | 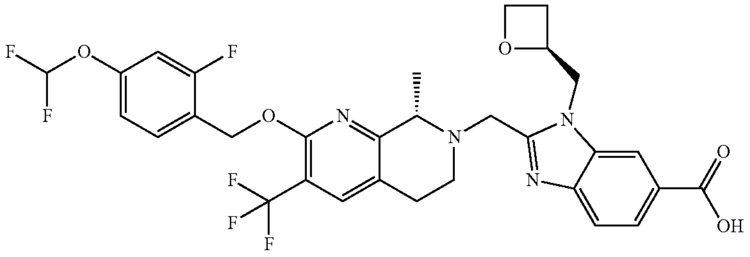 | 2.15 | 651.1 | 3 |
| I-257 | 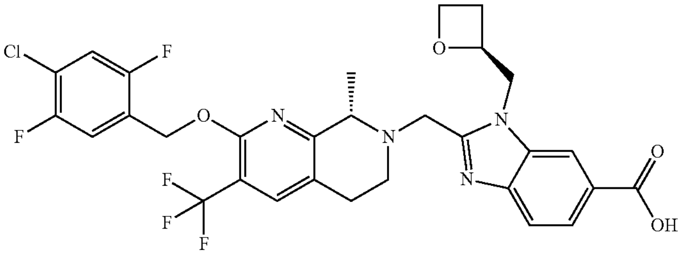 [SMILES: C[C@H]1c2nc(OCc3cc(F)c(Cl)cc3F)c(C(F)(F)F)cc2CCN1Cc1nc2ccc(C(=O)O)cc2n1C[C@@H]1CCO1] | 2.29 | 637.1 | 3 |
| I-258 | 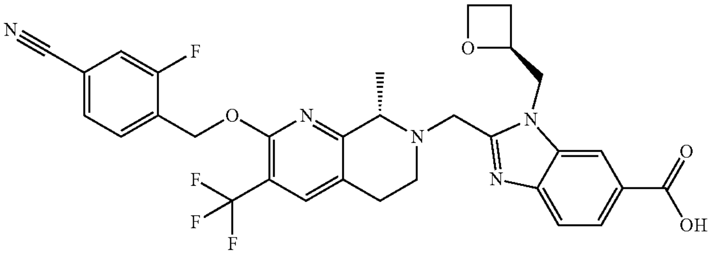 [SMILES: C[C@H]1c2nc(OCc3ccc(C#N)cc3F)c(C(F)(F)F)cc2CCN1Cc1nc2ccc(C(=O)O)cc2n1C[C@@H]1CCO1] | 2.02 | 610.2 | 3 |
| I-259 | 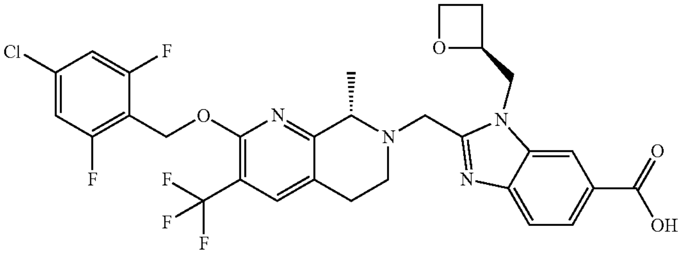 [SMILES: C[C@H]1c2nc(OCc3c(F)cc(Cl)cc3F)c(C(F)(F)F)cc2CCN1Cc1nc2ccc(C(=O)O)cc2n1C[C@@H]1CCO1] | 2.22 | 637.1 | 3 |

TABLE 42-continued
| | | | | |
|---|---|---|---|---|
| I-260 | 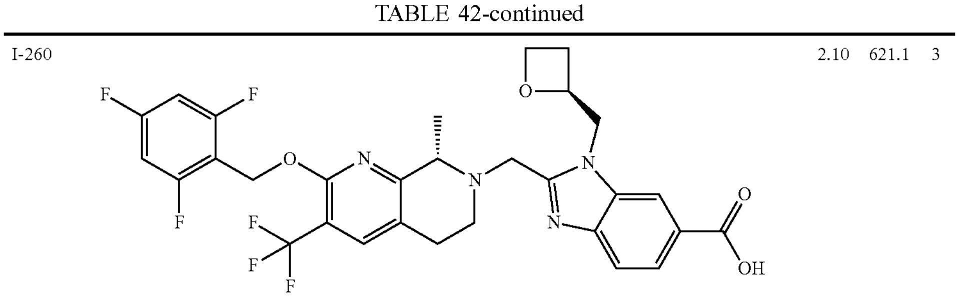 | 2.10 | 621.1 | 3 |
| I-261 | 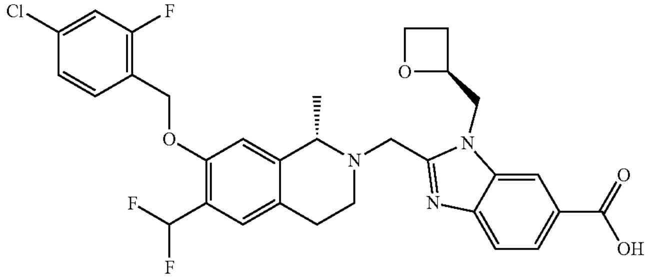 [SMILES: C[C@H]1c2cc(OCc3ccc(Cl)cc3F)c(C(F)F)cc2CCN1Cc1nc2ccc(C(=O)O)cc2n1C[C@@H]1CCO1] | 2 | 600.2 | 3 |
TABLE 43
| | | | | |
|---|---|---|---|---|
| I-262 | 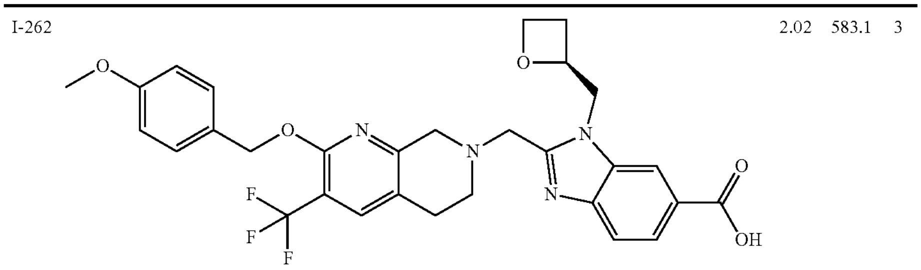 | 2.02 | 583.1 | 3 |
| I-263 | 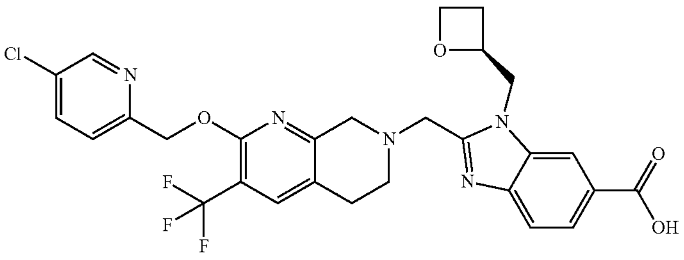 [SMILES: O=C(O)c1ccc2nc(CN3CCc4cc(C(F)(F)F)c(OCc5ccc(Cl)cn5)nc4C3)n(C[C@@H]3CCO3)c2c1] | 1.94 | 588.0 | 3 |
| I-264 | 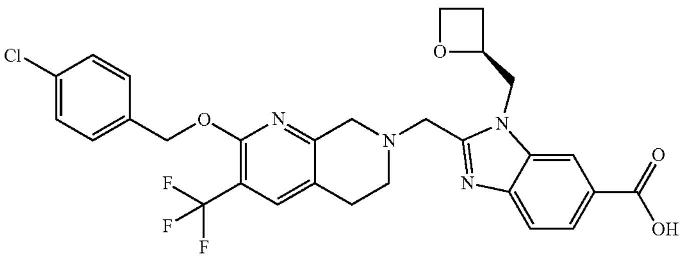 [SMILES: O=C(O)c1ccc2nc(CN3CCc4cc(C(F)(F)F)c(OCc5ccc(Cl)cc5)nc4C3)n(C[C@@H]3CCO3)c2c1] | 2.22 | 587.0 | 3 |

TABLE 43-continued
| | | | | |
|---|---|---|---|---|
| I-265 | 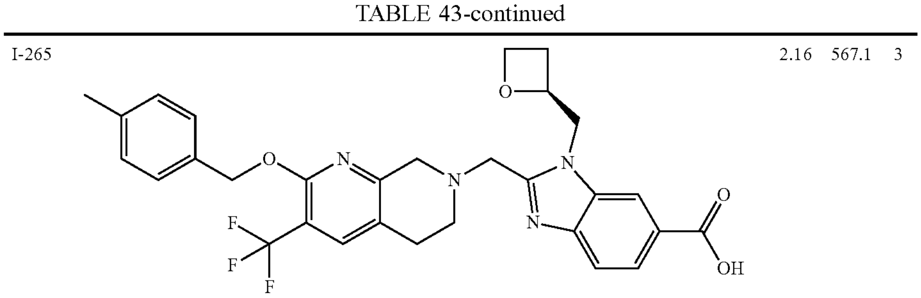 | 2.16 | 567.1 | 3 |
| I-266 | 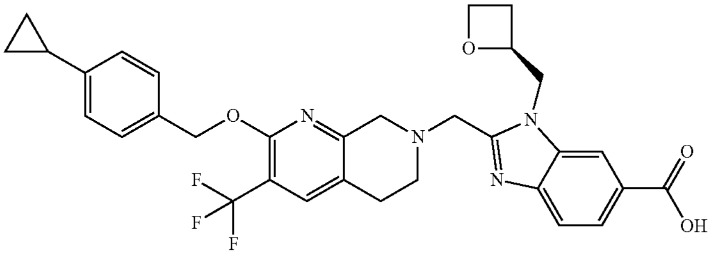 [SMILES: O=C(O)c1ccc2nc(CN3CCc4cc(C(F)(F)F)c(OCc5ccc(C6CC6)cc5)nc4C3)n(C[C@@H]3CCO3)c2c1] | 2.27 | 593.1 | 3 |
| I-267 | 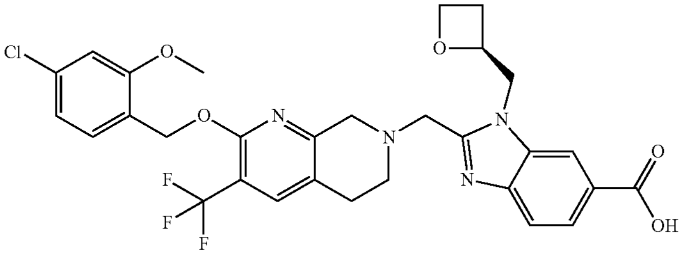 [SMILES: COc1cc(Cl)ccc1COc1nc2c(cc1C(F)(F)F)CCN(Cc1nc3ccc(C(=O)O)cc3n1C[C@@H]1CCO1)C2] | 2.25 | 617.0 | 3 |
| I-268 | 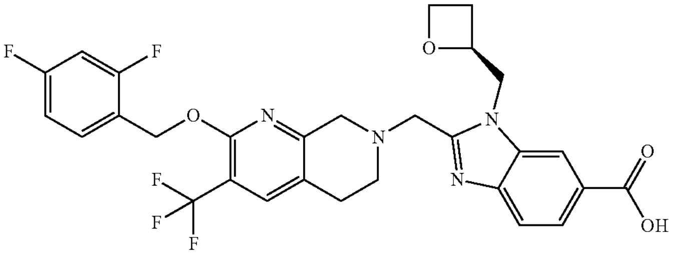 [SMILES: O=C(O)c1ccc2nc(CN3CCc4cc(C(F)(F)F)c(OCc5ccc(F)cc5F)nc4C3)n(C[C@@H]3CCO3)c2c1] | 2.09 | 589.1 | 3 |
TABLE 44
| | | | | |
|---|---|---|---|---|
| I-269 | 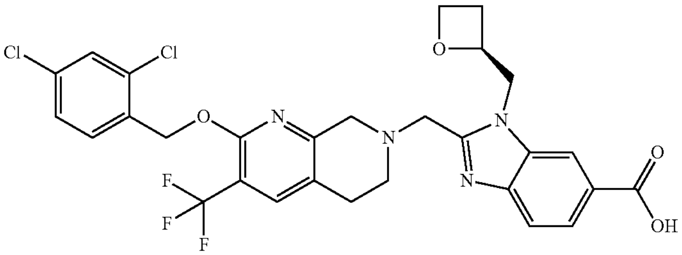 | 2.39 | 621.0 | 3 |

TABLE 44-continued
| | | | | |
|---|---|---|---|---|
| I-270 | 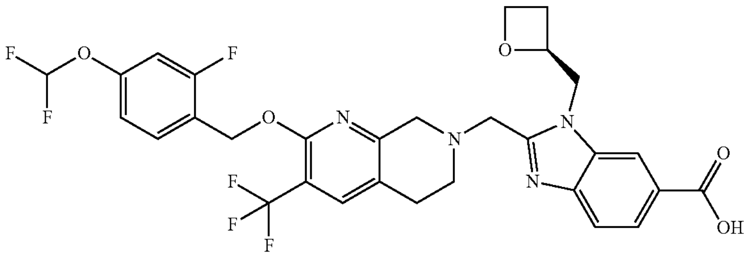 [SMILES: O=C(O)c1ccc2nc(CN3CCc4cc(C(F)(F)F)c(OCc5ccc(OC(F)F)cc5F)nc4C3)n(C[C@@H]3CCO3)c2c1] | 2.13 | 637.0 | 3 |
| I-271 | 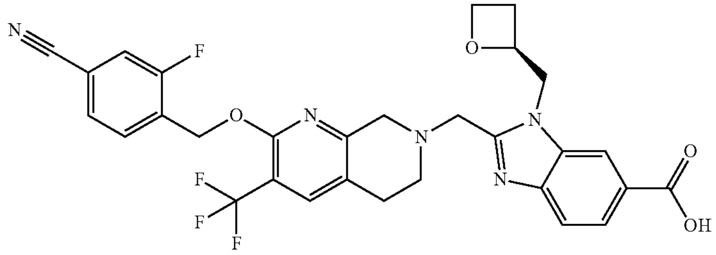 [SMILES: N#Cc1ccc(COc2nc3c(cc2C(F)(F)F)CCN(Cc2nc4ccc(C(=O)O)cc4n2C[C@@H]2CCO2)C3)c(F)c1] | 1.99 | 596.2 | 3 |
| I-272 | 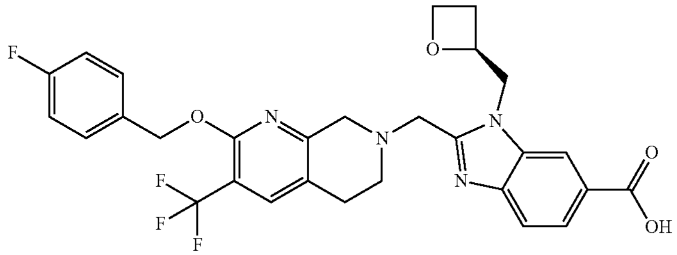 [SMILES: O=C(O)c1ccc2nc(CN3CCc4cc(C(F)(F)F)c(OCc5ccc(F)cc5)nc4C3)n(C[C@@H]3CCO3)c2c1] | 2.07 | 571.1 | 3 |
| I-273 | 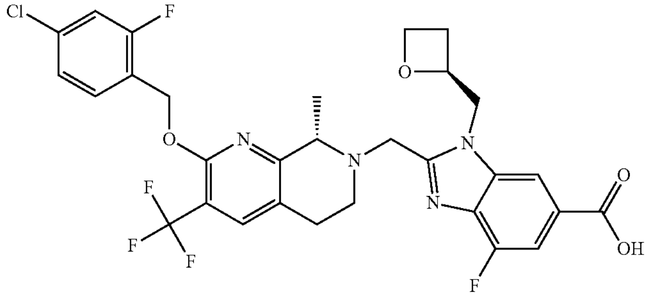 [SMILES: C[C@H]1c2nc(OCc3ccc(Cl)cc3F)c(C(F)(F)F)cc2CCN1Cc1nc2c(F)cc(C(=O)O)cc2n1C[C@@H]1CCO1] | 2.3 | 637.2 | 3 |
| I-274 | 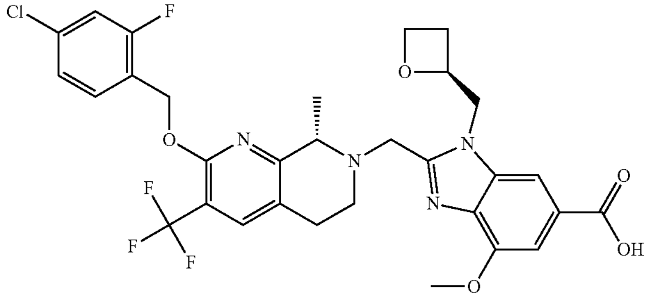 [SMILES: COc1cc(C(=O)O)cc2c1nc(CN1CCc3cc(C(F)(F)F)c(OCc4ccc(Cl)cc4F)nc3[C@@H]1C)n2C[C@@H]1CCO1] | 2.17 | 649.3 | 3 |

TABLE 44-continued
| | | | | |
|---|---|---|---|---|
| I-275 | 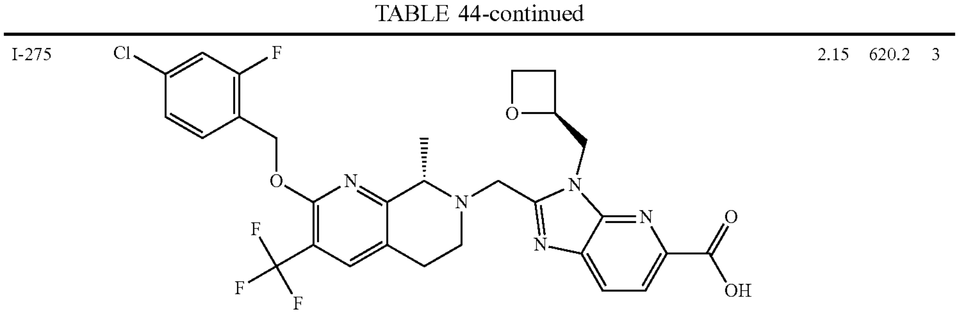 | 2.15 | 620.2 | 3 |
TABLE 45
| | | | | |
|---|---|---|---|---|
| I-276 | 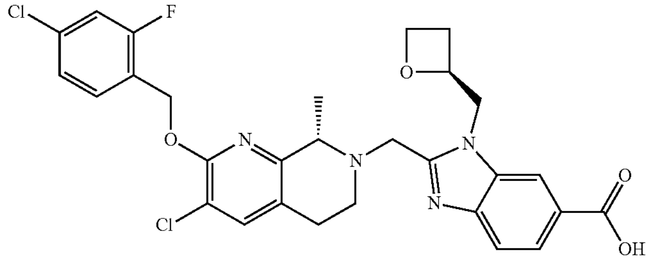 [SMILES: C[C@H]1c2nc(OCc3ccc(Cl)cc3F)c(Cl)cc2CCN1Cc1nc2ccc(C(=O)O)cc2n1C[C@@H]1CCO1] | 2.16 | 585.3 | 1 |
| I-277 | 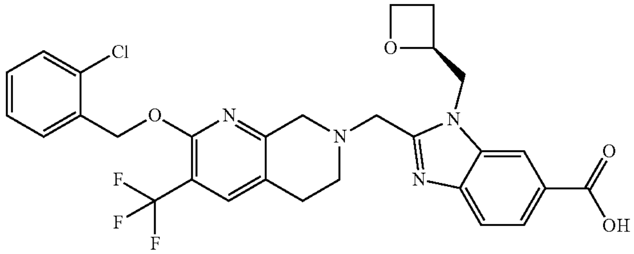 | 2.16 | 587.1 | 3 |
| I-278 | 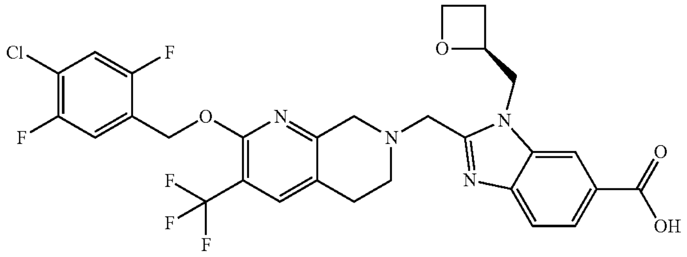 [SMILES: O=C(O)c1ccc2nc(CN3CCc4cc(C(F)(F)F)c(OCc5cc(F)c(Cl)cc5F)nc4C3)n(C[C@@H]3CCO3)c2c1] | 2.28 | 623.0 | 3 |
| I-279 | 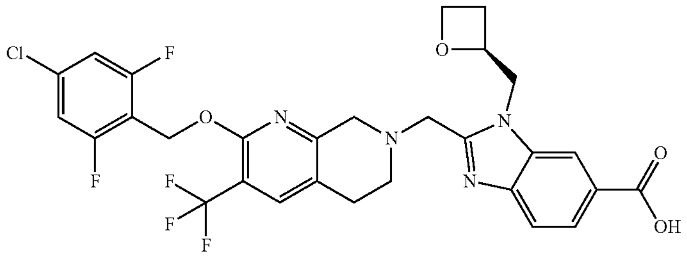 [SMILES: O=C(O)c1ccc2nc(CN3CCc4cc(C(F)(F)F)c(OCc5c(F)cc(Cl)cc5F)nc4C3)n(C[C@@H]3CCO3)c2c1] | 2.21 | 623.0 | 3 |

TABLE 45-continued
| | | | | |
|---|---|---|---|---|
| I-280 | 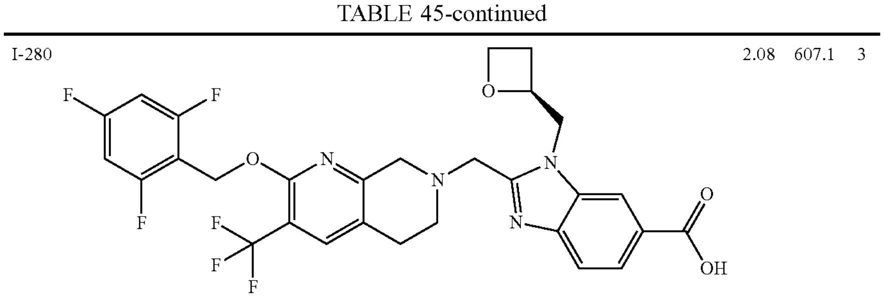 | 2.08 | 607.1 | 3 |
| I-281 | 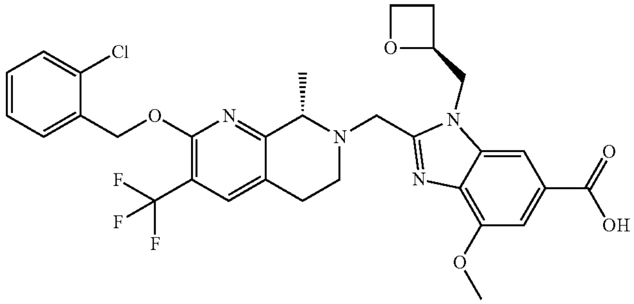 [SMILES: COc1cc(C(=O)O)cc2c1nc(CN1CCc3cc(C(F)(F)F)c(OCc4ccccc4Cl)nc3[C@@H]1C)n2C[C@@H]1CCO1] | 2.18 | 631.1 | 3 |
| I-282 | 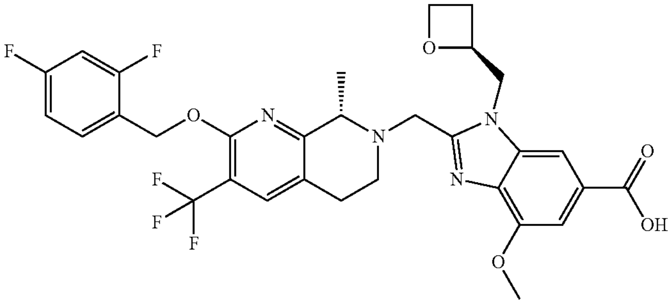 [SMILES: COc1cc(C(=O)O)cc2c1nc(CN1CCc3cc(C(F)(F)F)c(OCc4ccc(F)cc4F)nc3[C@@H]1C)n2C[C@@H]1CCO1] | 2.07 | 633.1 | 3 |
TABLE 46
| | | | | |
|---|---|---|---|---|
| I-283 | 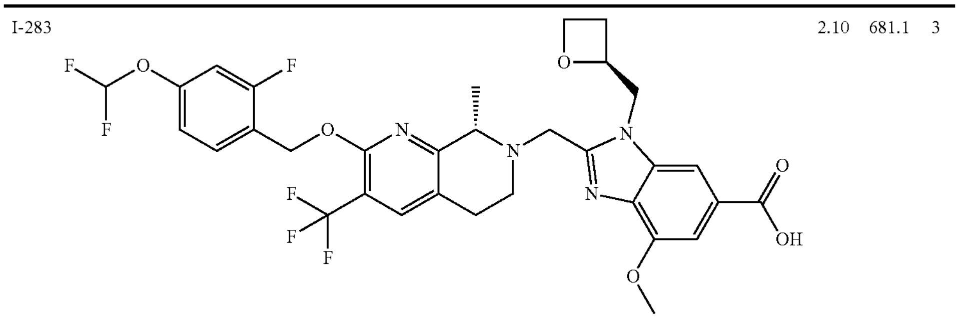 | 2.10 | 681.1 | 3 |
| I-284 | 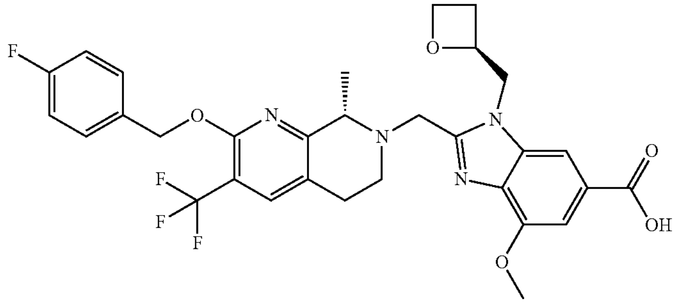 [SMILES: COc1cc(C(=O)O)cc2c1nc(CN1CCc3cc(C(F)(F)F)c(OCc4ccc(F)cc4)nc3[C@@H]1C)n2C[C@@H]1CCO1] | 2.05 | 615.1 | 3 |

TABLE 46-continued
| | | | | |
|---|---|---|---|---|
| I-285 | 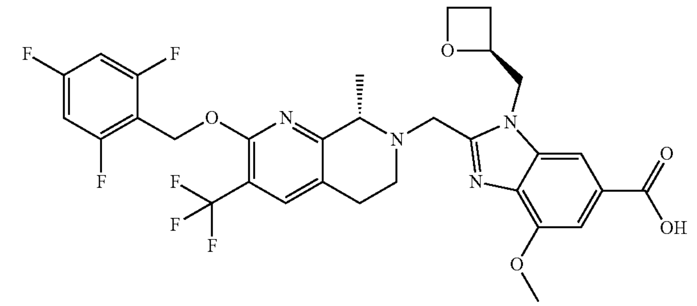 [SMILES: COc1cc(C(=O)O)cc2c1nc(CN1CCc3cc(C(F)(F)F)c(OCc4c(F)cc(F)cc4F)nc3[C@@H]1C)n2C[C@@H]1CCO1] | 2.04 | 651.1 | 3 |
| I-286 | 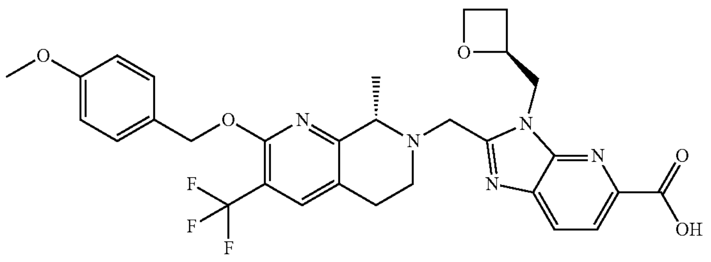 [SMILES: COc1ccc(COc2nc3c(cc2C(F)(F)F)CCN(Cc2nc4ccc(C(=O)O)nc4n2C[C@@H]2CCO2)[C@H]3C)cc1] | 2.00 | 598.1 | 3 |
| I-287 | 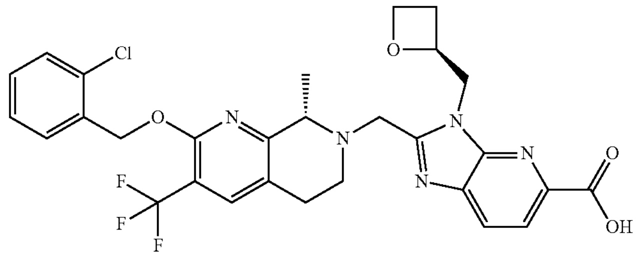 [SMILES: C[C@H]1c2nc(OCc3ccccc3Cl)c(C(F)(F)F)cc2CCN1Cc1nc2ccc(C(=O)O)nc2n1C[C@@H]1CCO1] | 2.22 | 602.1 | 3 |
| I-288 | 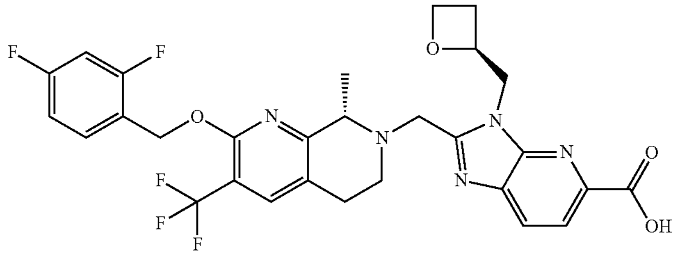 [SMILES: C[C@H]1c2nc(OCc3ccc(F)cc3F)c(C(F)(F)F)cc2CCN1Cc1nc2ccc(C(=O)O)nc2n1C[C@@H]1CCO1] | 2.08 | 604.1 | 3 |
| I-289 | 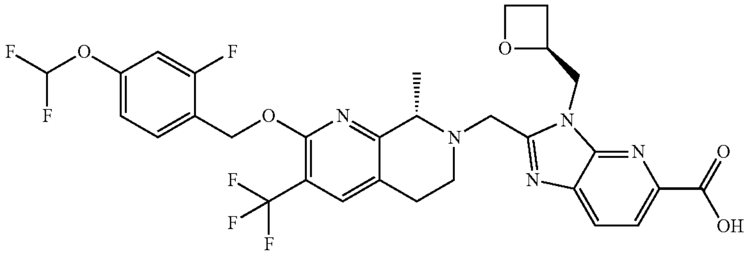 [SMILES: C[C@H]1c2nc(OCc3ccc(OC(F)F)cc3F)c(C(F)(F)F)cc2CCN1Cc1nc2ccc(C(=O)O)nc2n1C[C@@H]1CCO1] | 2.11 | 652.1 | 3 |

TABLE 47
| | | | | |
|---|---|---|---|---|
| I-290 | 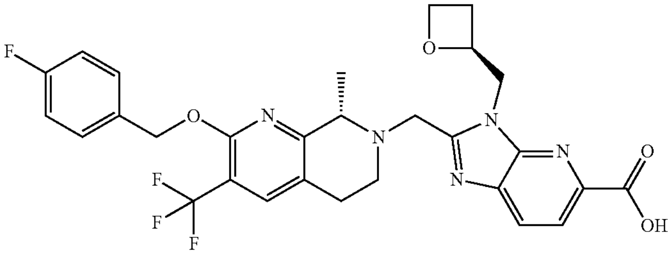 [SMILES: C[C@H]1c2nc(OCc3ccc(F)cc3)c(C(F)(F)F)cc2CCN1Cc1nc2ccc(C(=O)O)nc2n1C[C@@H]1CCO1] | 2.05 | 586.1 | 3 |
| I-291 | 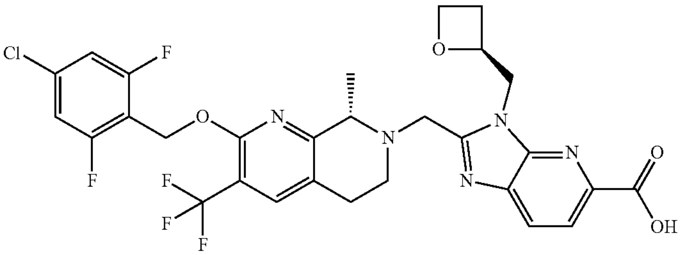 [SMILES: C[C@H]1c2nc(OCc3c(F)cc(Cl)cc3F)c(C(F)(F)F)cc2CCN1Cc1nc2ccc(C(=O)O)nc2n1C[C@@H]1CCO1] | 2.19 | 638.1 | 3 |
| I-292 | 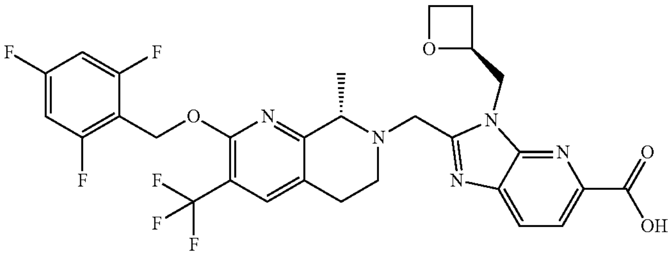 [SMILES: C[C@H]1c2nc(OCc3c(F)cc(F)cc3F)c(C(F)(F)F)cc2CCN1Cc1nc2ccc(C(=O)O)nc2n1C[C@@H]1CCO1] | 2.05 | 622.1 | 3 |
| I-293 | 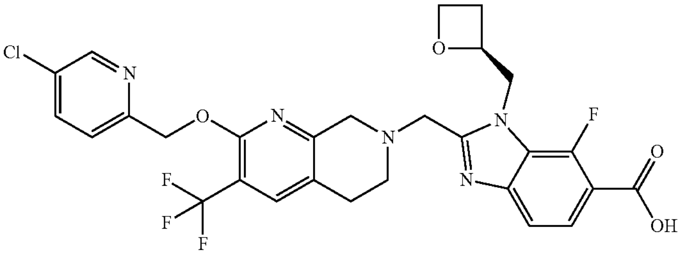 | 2.02 | 606.0 | 3 |
| I-294 | 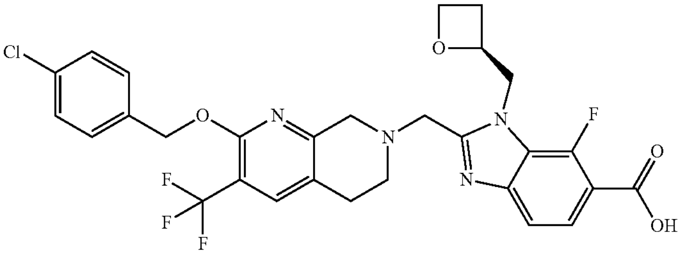 | 2.32 | 605.0 | 3 |
| I-295 | 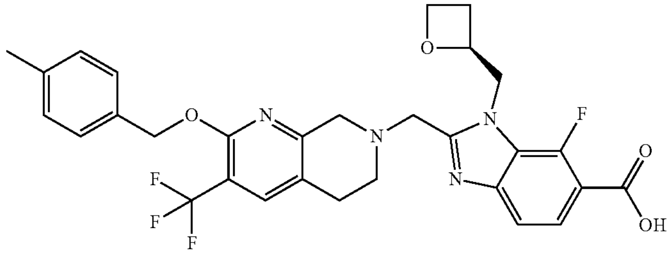 | 2.26 | 585.1 | 3 |

TABLE 47-continued
| | | | | |
|---|---|---|---|---|
| I-296 | 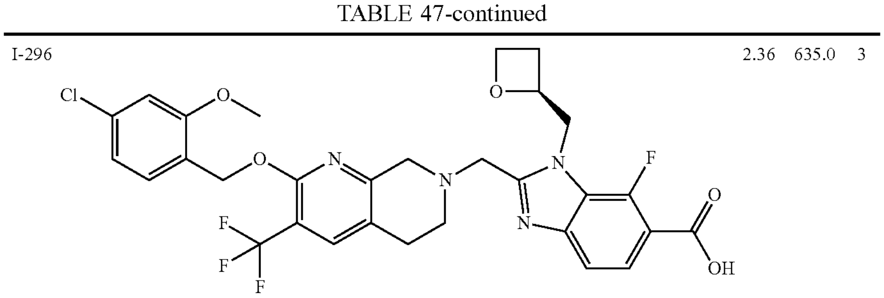 | 2.36 | 635.0 | 3 |
TABLE 48
| | | | | |
|---|---|---|---|---|
| I-297 | 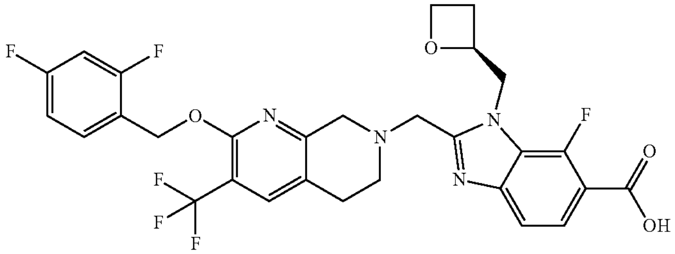 | 2.18 | 607.1 | 3 |
| I-298 | 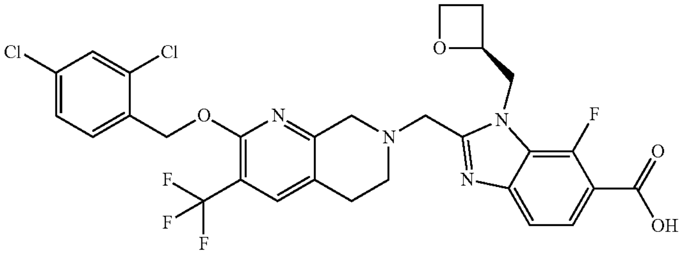 [SMILES: O=C(O)c1ccc2nc(CN3CCc4cc(C(F)(F)F)c(OCc5ccc(Cl)cc5Cl)nc4C3)n(C[C@@H]3CCO3)c2c1F] | 2.52 | 639.0 | 3 |
| I-299 | 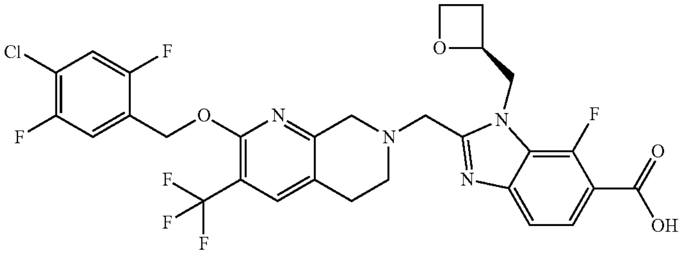 [SMILES: O=C(O)c1ccc2nc(CN3CCc4cc(C(F)(F)F)c(OCc5cc(F)c(Cl)cc5F)nc4C3)n(C[C@@H]3CCO3)c2c1F] | 2.39 | 641.0 | 3 |
| I-300 | 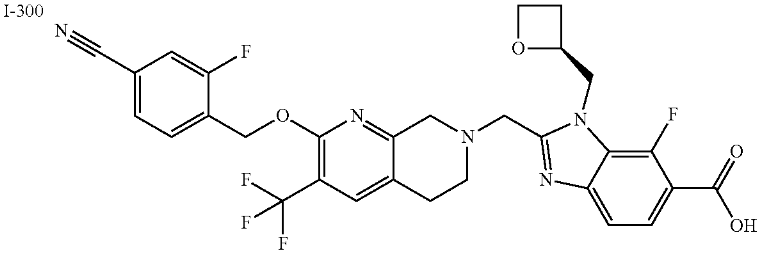 | 2.07 | 614.0 | 3 |

TABLE 48-continued
| | | | | |
|---|---|---|---|---|
| I-301 | 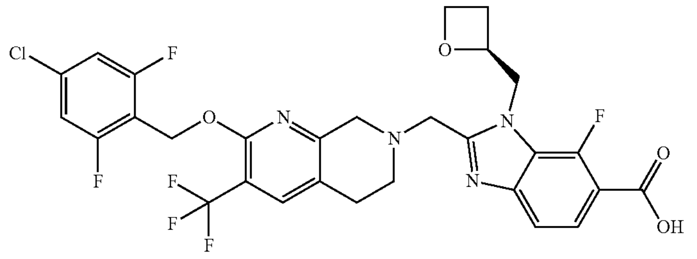 [SMILES: O=C(O)c1ccc2nc(CN3CCc4cc(C(F)(F)F)c(OCc5c(F)cc(Cl)cc5F)nc4C3)n(C[C@@H]3CCO3)c2c1F] | 2.31 | 641.1 | 3 |
| I-302 | 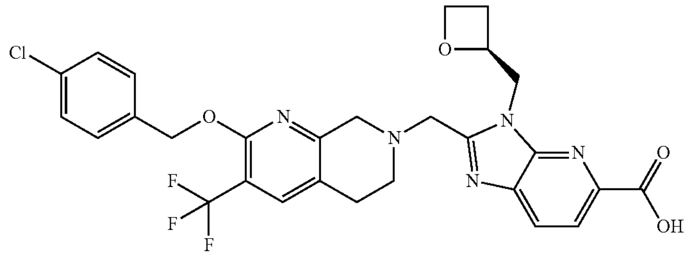 | 2.22 | 588.0 | 3 |
| I-303 | 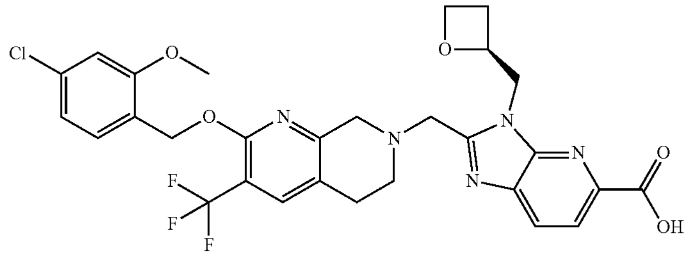 [SMILES: COc1cc(Cl)ccc1COc1nc2c(cc1C(F)(F)F)CCN(Cc1nc3ccc(C(=O)O)nc3n1C[C@@H]1CCO1)C2] | 2.27 | 618.0 | 3 |
TABLE 49
| | | | | |
|---|---|---|---|---|
| I-304 | 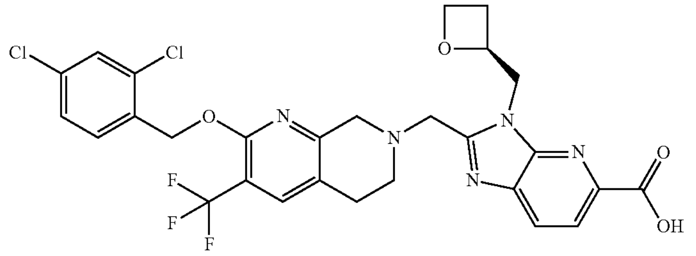 | 2.43 | 622.0 | 3 |
| I-305 | 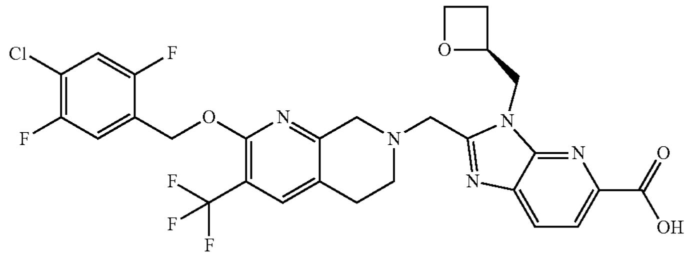 | 2.30 | 624.0 | 3 |

TABLE 49-continued
| | | | | |
|---|---|---|---|---|
| I-306 | 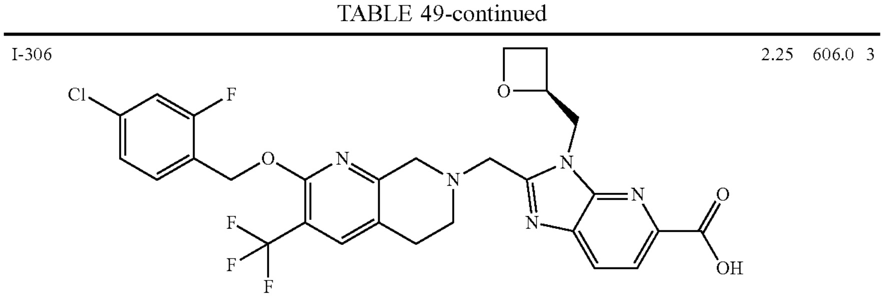 | 2.25 | 606.0 | 3 |
| I-307 | 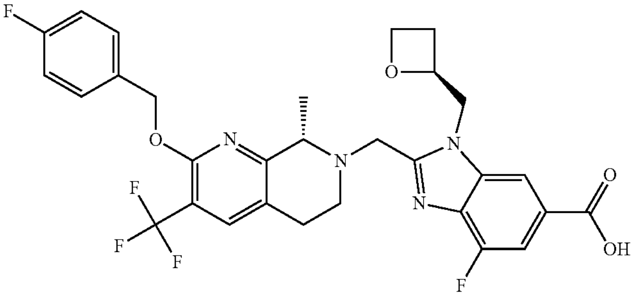 [SMILES: C[C@H]1c2nc(OCc3ccc(F)cc3)c(C(F)(F)F)cc2CCN1Cc1nc2c(F)cc(C(=O)O)cc2n1C[C@@H]1CCO1] | 2.24 | 603.4 | 1 |
| I-308 | 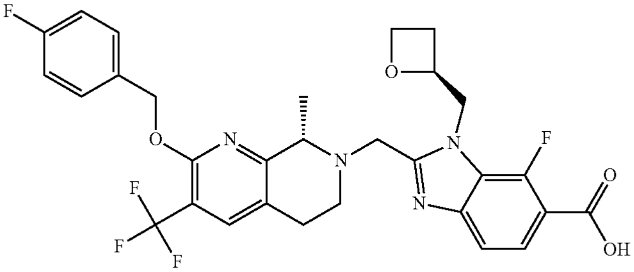 [SMILES: C[C@H]1c2nc(OCc3ccc(F)cc3)c(C(F)(F)F)cc2CCN1Cc1nc2ccc(C(=O)O)c(F)c2n1C[C@@H]1CCO1] | 2.14 | 603.4 | 1 |
TABLE 50
| | | | | |
|---|---|---|---|---|
| I-309 | 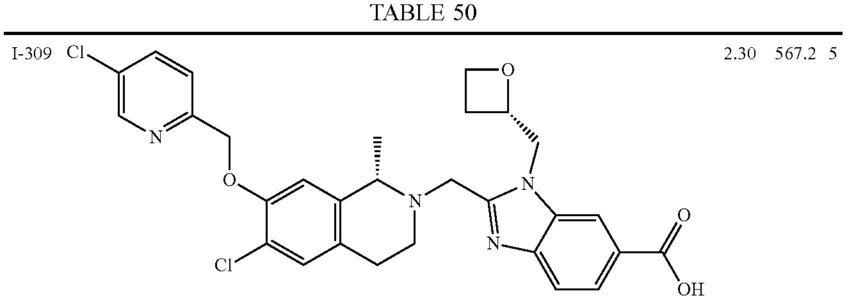 | 2.30 | 567.2 | 5 |
| I-310 | 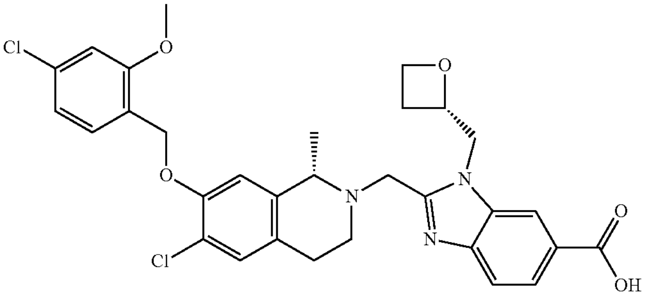 | 2.60 | 596.3 | 5 |

TABLE 50-continued
| | | | | |
|---|---|---|---|---|
| I-311 | 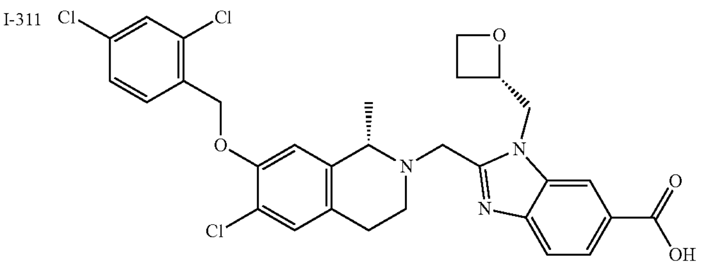 | 2.70 | 600.2 | 5 |
| I-312 | 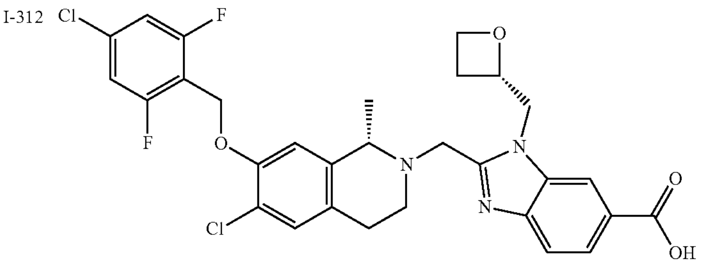 | 2.55 | 602.2 | 5 |
| I-313 | 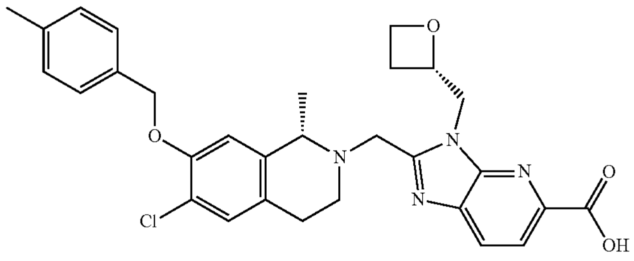 [SMILES: Cc1ccc(COc2cc3c(cc2Cl)CCN(Cc2nc4ccc(C(=O)O)nc4n2C[C@@H]2CCO2)[C@H]3C)cc1] | 2.43 | 547.3 | 5 |
| I-314 | 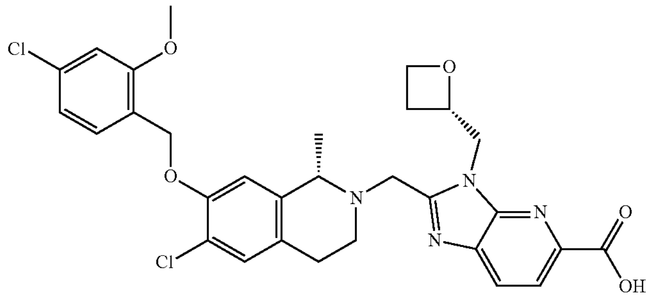 [SMILES: COc1cc(Cl)ccc1COc1cc2c(cc1Cl)CCN(Cc1nc3ccc(C(=O)O)nc3n1C[C@@H]1CCO1)[C@H]2C] | 2.51 | 597.3 | 5 |
| I-315 | 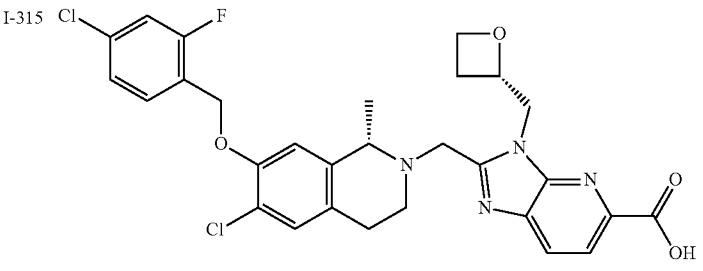 | 2.46 | 585.2 | 5 |

TABLE 51
| | | | | |
|---|---|---|---|---|
| I-316 | 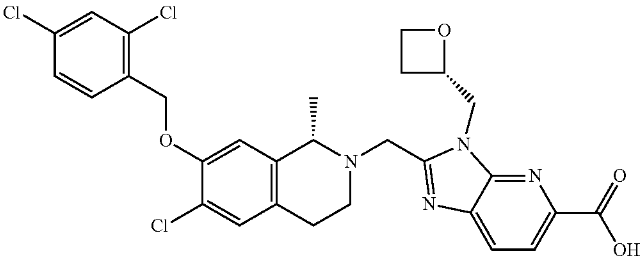 [SMILES: C[C@H]1c2cc(OCc3ccc(Cl)cc3Cl)c(Cl)cc2CCN1Cc1nc2ccc(C(=O)O)nc2n1C[C@@H]1CCO1] | 2.60 | 601.3 | 5 |
| I-317 | 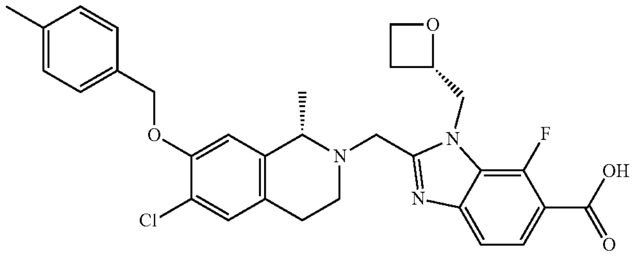 [SMILES: Cc1ccc(COc2cc3c(cc2Cl)CCN(Cc2nc4ccc(C(=O)O)c(F)c4n2C[C@@H]2CCO2)[C@H]3C)cc1] | 2.50 | 564.3 | 5 |
| I-318 | 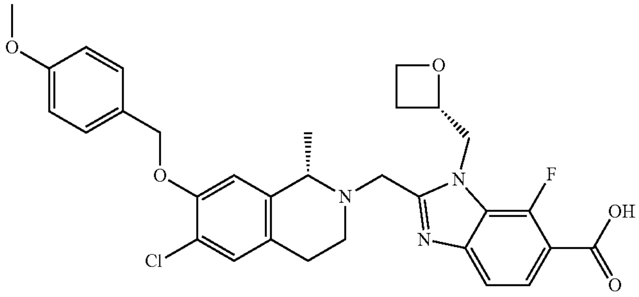 [SMILES: COc1ccc(COc2cc3c(cc2Cl)CCN(Cc2nc4ccc(C(=O)O)c(F)c4n2C[C@@H]2CCO2)[C@H]3C)cc1] | 2.38 | 580.3 | 5 |
| I-319 | 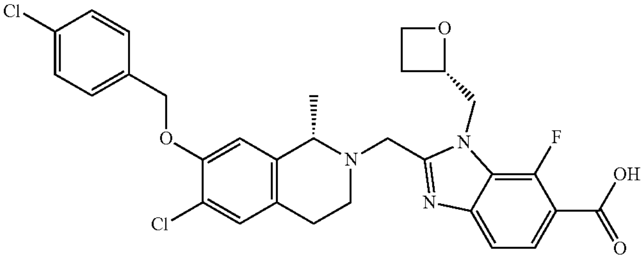 [SMILES: C[C@H]1c2cc(OCc3ccc(Cl)cc3)c(Cl)cc2CCN1Cc1nc2ccc(C(=O)O)c(F)c2n1C[C@@H]1CCO1] | 2.55 | 584.2 | 5 |
| I-320 | 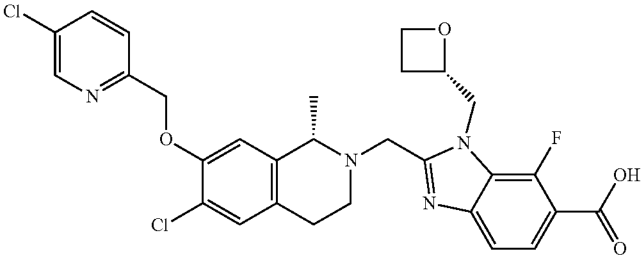 [SMILES: C[C@H]1c2cc(OCc3ccc(Cl)cn3)c(Cl)cc2CCN1Cc1nc2ccc(C(=O)O)c(F)c2n1C[C@@H]1CCO1] | 2.30 | 585.2 | 5 |

TABLE 51-continued
| | | | | |
|---|---|---|---|---|
| I-321 | 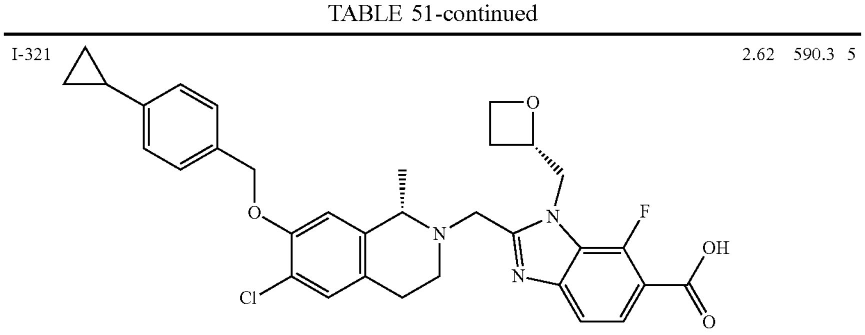 | 2.62 | 590.3 | 5 |
| I-322 | 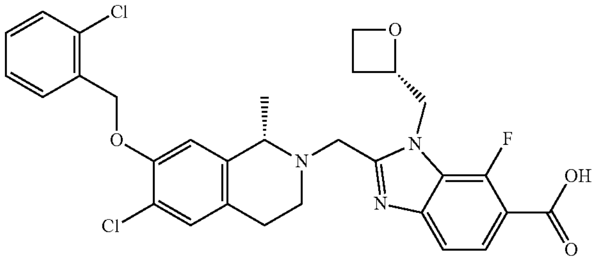 [SMILES: C[C@H]1c2cc(OCc3ccccc3Cl)c(Cl)cc2CCN1Cc1nc2ccc(C(=O)O)c(F)c2n1C[C@@H]1CCO1] | 2.50 | 584.2 | 5 |
TABLE 52
| | | | | |
|---|---|---|---|---|
| I-323 | 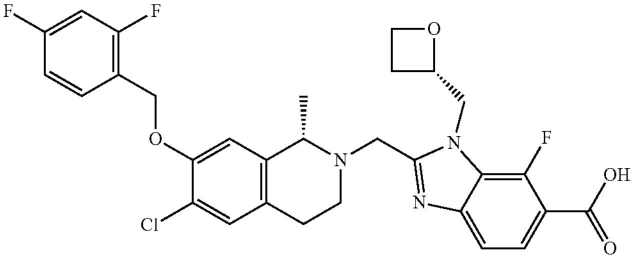 [SMILES: C[C@H]1c2cc(OCc3ccc(F)cc3F)c(Cl)cc2CCN1Cc1nc2ccc(C(=O)O)c(F)c2n1C[C@@H]1CCO1] | 2.45 | 586.3 | 5 |
| I-324 | 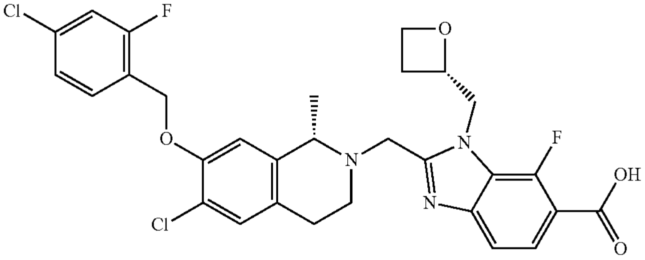 [SMILES: C[C@H]1c2cc(OCc3ccc(Cl)cc3F)c(Cl)cc2CCN1Cc1nc2ccc(C(=O)O)c(F)c2n1C[C@@H]1CCO1] | 2.58 | 602.2 | 5 |
| I-325 | 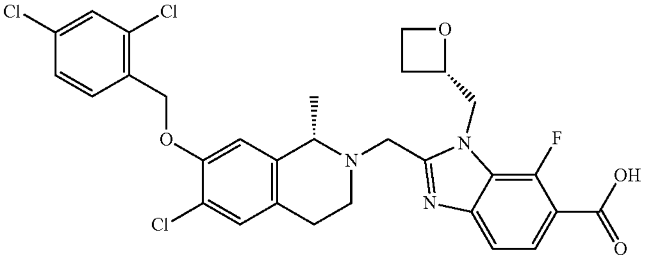 [SMILES: C[C@H]1c2cc(OCc3ccc(Cl)cc3Cl)c(Cl)cc2CCN1Cc1nc2ccc(C(=O)O)c(F)c2n1C[C@@H]1CCO1] | 2.69 | 618.2 | 5 |

TABLE 52-continued
| | | | | |
|---|---|---|---|---|
| I-326 | 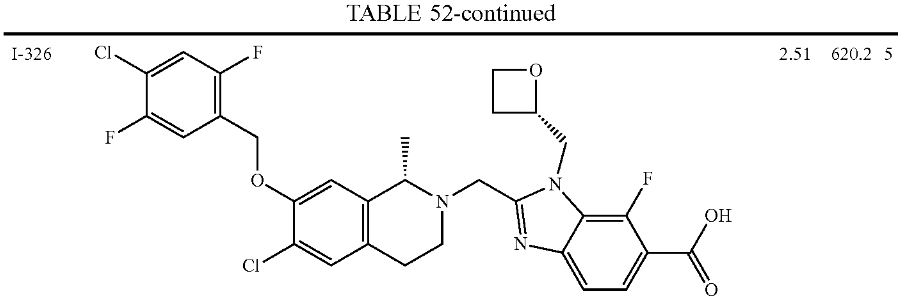 | 2.51 | 620.2 | 5 |
| I-327 | 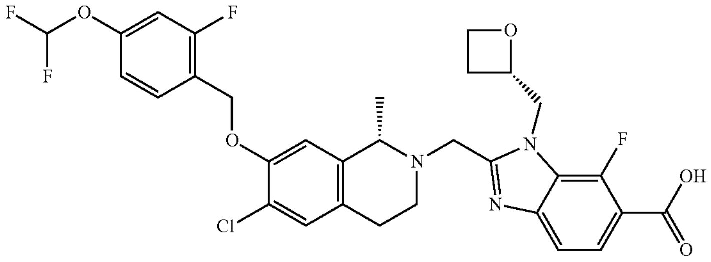 [SMILES: C[C@H]1c2cc(OCc3ccc(OC(F)F)cc3F)c(Cl)cc2CCN1Cc1nc2ccc(C(=O)O)c(F)c2n1C[C@@H]1CCO1] | 2.49 | 634.2 | 5 |
| I-328 | 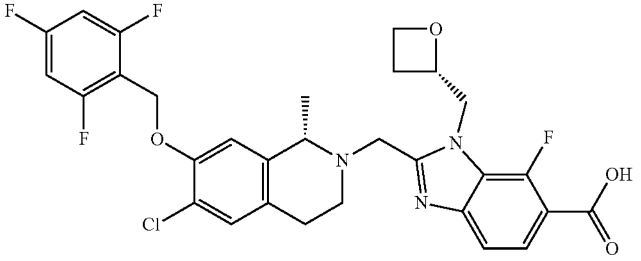 [SMILES: C[C@H]1c2cc(OCc3c(F)cc(F)cc3F)c(Cl)cc2CCN1Cc1nc2ccc(C(=O)O)c(F)c2n1C[C@@H]1CCO1] | 2.42 | 604.2 | 5 |
| I-329 | 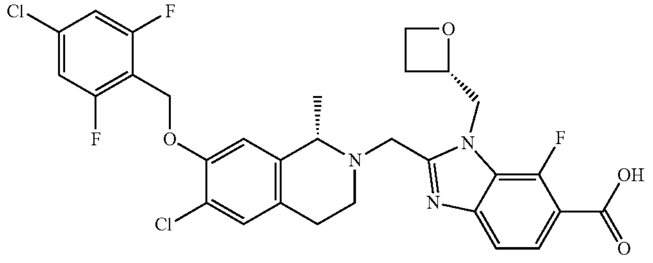 [SMILES: C[C@H]1c2cc(OCc3c(F)cc(Cl)cc3F)c(Cl)cc2CCN1Cc1nc2ccc(C(=O)O)c(F)c2n1C[C@@H]1CCO1] | 2.55 | 620.2 | 5 |
TABLE 53
| | | | | |
|---|---|---|---|---|
| I-330 | 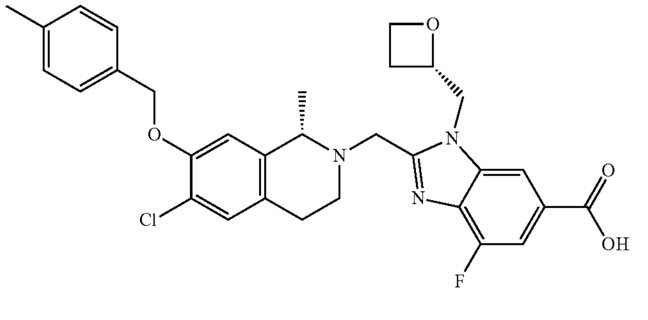 [SMILES: Cc1ccc(COc2cc3c(cc2Cl)CCN(Cc2nc4c(F)cc(C(=O)O)cc4n2C[C@@H]2CCO2)[C@H]3C)cc1] | 2.57 | 564.3 | 5 |

TABLE 53-continued
| | | | | |
|---|---|---|---|---|
| I-331 | 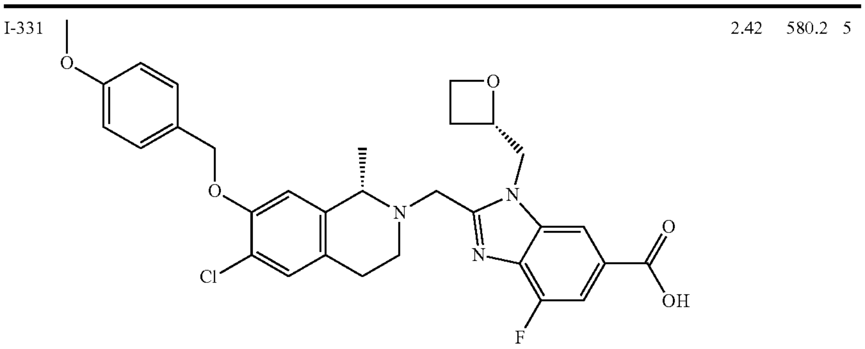 | 2.42 | 580.2 | 5 |
| I-332 | 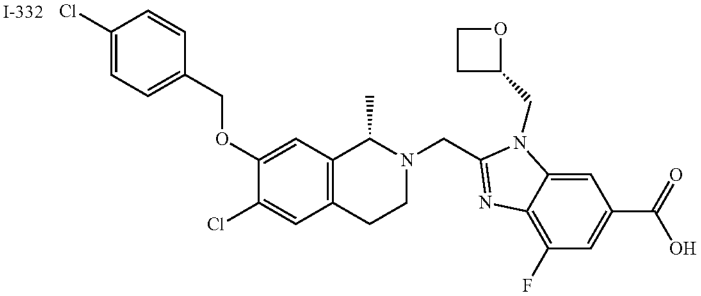 | 2.61 | 584.2 | 5 |
| I-333 | 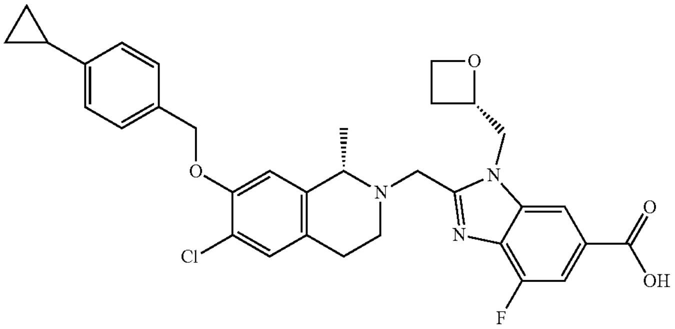 [SMILES: C[C@H]1c2cc(OCc3ccc(C4CC4)cc3)c(Cl)cc2CCN1Cc1nc2c(F)cc(C(=O)O)cc2n1C[C@@H]1CCO1] | 2.65 | 590.3 | 5 |
| I-334 | 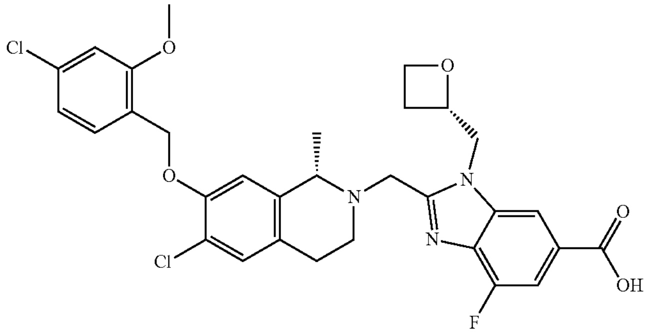 [SMILES: COc1cc(Cl)ccc1COc1cc2c(cc1Cl)CCN(Cc1nc3c(F)cc(C(=O)O)cc3n1C[C@@H]1CCO1)[C@H]2C] | 2.65 | 614.2 | 5 |
| I-335 | 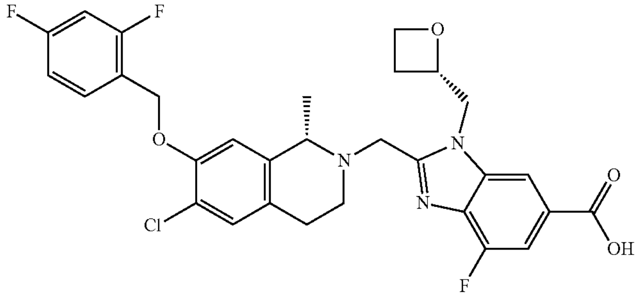 [SMILES: C[C@H]1c2cc(OCc3ccc(F)cc3F)c(Cl)cc2CCN1Cc1nc2c(F)cc(C(=O)O)cc2n1C[C@@H]1CCO1] | 2.50 | 586.3 | 5 |

TABLE 53-continued
| | | | | |
|---|---|---|---|---|
| I-336 | 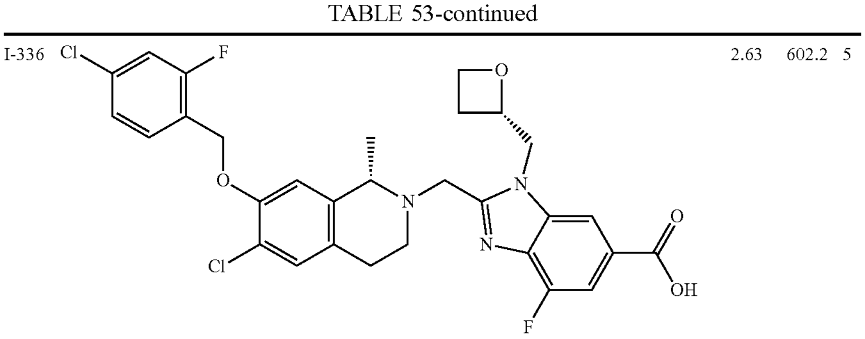 | 2.63 | 602.2 | 5 |
TABLE 54
| | | | | |
|---|---|---|---|---|
| I-337 | 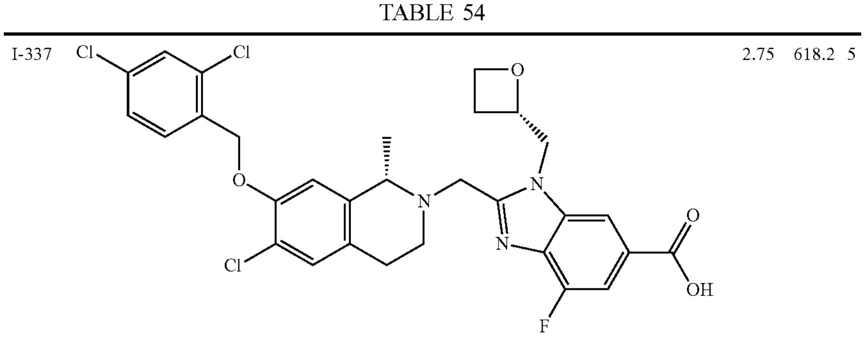 | 2.75 | 618.2 | 5 |
| I-338 | 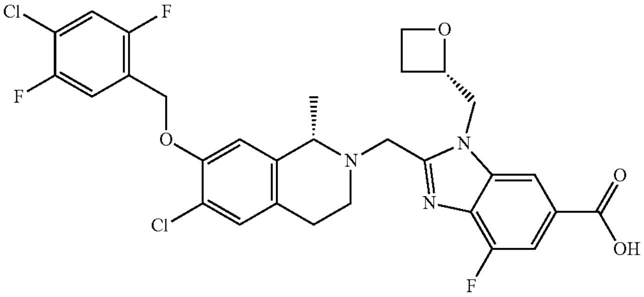 [SMILES: C[C@H]1c2cc(OCc3cc(F)c(Cl)cc3F)c(Cl)cc2CCN1Cc1nc2c(F)cc(C(=O)O)cc2n1C[C@@H]1CCO1] | 2.66 | 620.2 | 5 |
| I-339 | 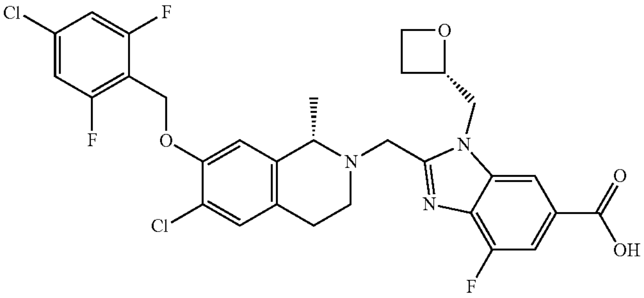 [SMILES: C[C@H]1c2cc(OCc3c(F)cc(Cl)cc3F)c(Cl)cc2CCN1Cc1nc2c(F)cc(C(=O)O)cc2n1C[C@@H]1CCO1] | 2.61 | 620.2 | 5 |
| I-340 | 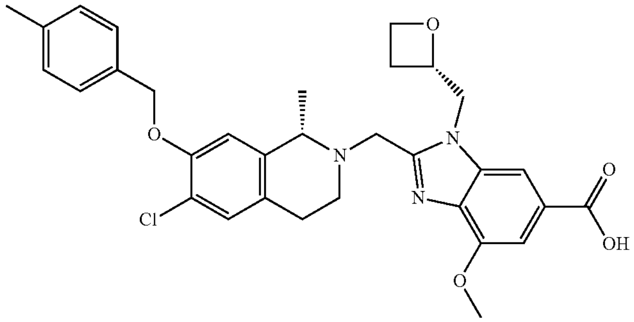 [SMILES: COc1cc(C(=O)O)cc2c1nc(CN1CCc3cc(Cl)c(OCc4ccc(C)cc4)cc3[C@@H]1C)n2C[C@@H]1CCO1] | 2.50 | 576.3 | 5 |

TABLE 54-continued
| | | | | |
|---|---|---|---|---|
| I-341 | 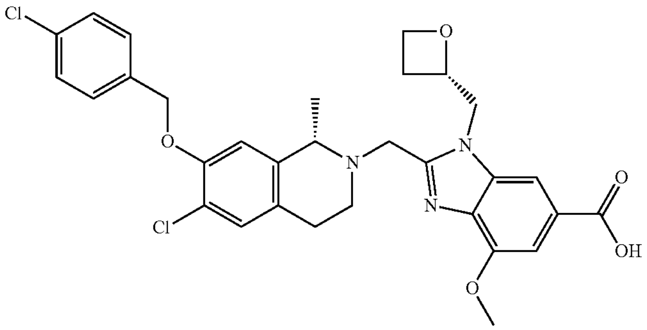 [SMILES: COc1cc(C(=O)O)cc2c1nc(CN1CCc3cc(Cl)c(OCc4ccc(Cl)cc4)cc3[C@@H]1C)n2C[C@@H]1CCO1] | 2.55 | 596.2 | 5 |
| I-342 | 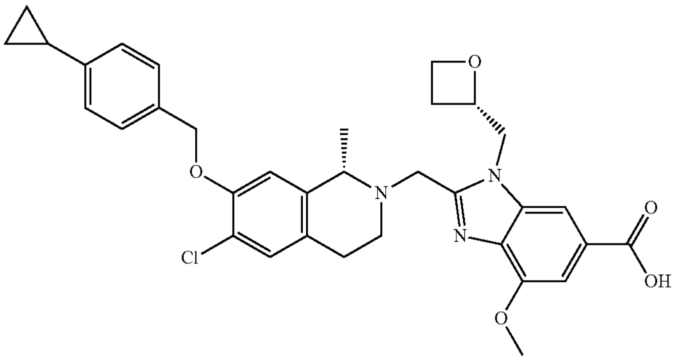 [SMILES: COc1cc(C(=O)O)cc2c1nc(CN1CCc3cc(Cl)c(OCc4ccc(C5CC5)cc4)cc3[C@@H]1C)n2C[C@@H]1CCO1] | 2.59 | 602.3 | 5 |
| I-343 | 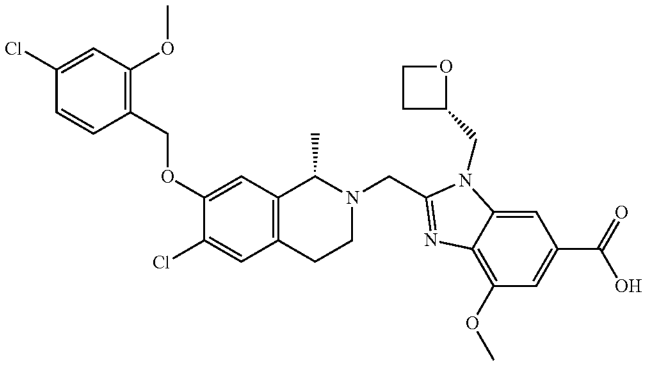 [SMILES: COc1cc(Cl)ccc1COc1cc2c(cc1Cl)CCN(Cc1nc3c(OC)cc(C(=O)O)cc3n1C[C@@H]1CCO1)[C@H]2C] | 2.60 | 626.3 | 5 |
TABLE 55
| | | | | |
|---|---|---|---|---|
| I-344 | 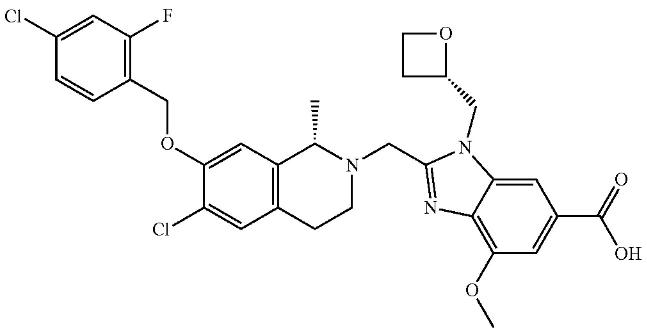 [SMILES: COc1cc(C(=O)O)cc2c1nc(CN1CCc3cc(Cl)c(OCc4ccc(Cl)cc4F)cc3[C@@H]1C)n2C[C@@H]1CCO1] | 2.57 | 614.2 | 5 |

TABLE 55-continued
| | | | | |
|---|---|---|---|---|
| I-345 | 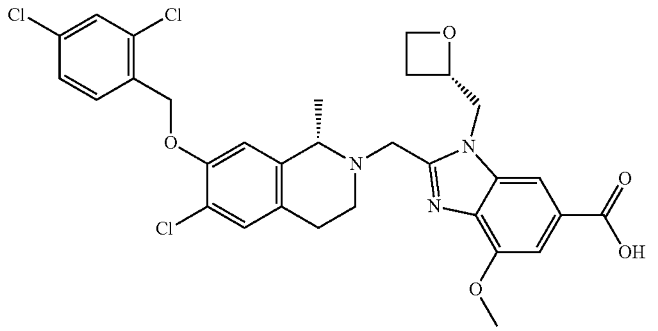 [SMILES: COc1cc(C(=O)O)cc2c1nc(CN1CCc3cc(Cl)c(OCc4ccc(Cl)cc4Cl)cc3[C@@H]1C)n2C[C@@H]1CCO1] | 2.68 | 630.2 | 5 |
| I-346 | 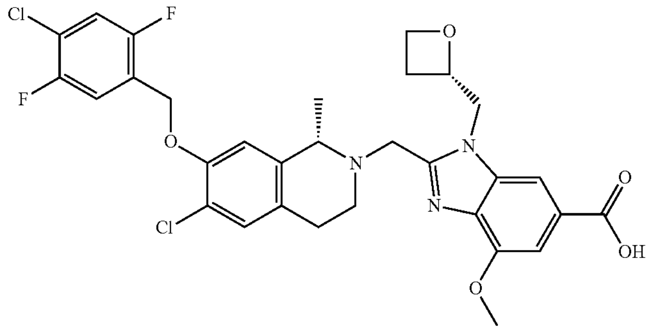 [SMILES: COc1cc(C(=O)O)cc2c1nc(CN1CCc3cc(Cl)c(OCc4cc(F)c(Cl)cc4F)cc3[C@@H]1C)n2C[C@@H]1CCO1] | 2.61 | 632.2 | 5 |
| I-347 | 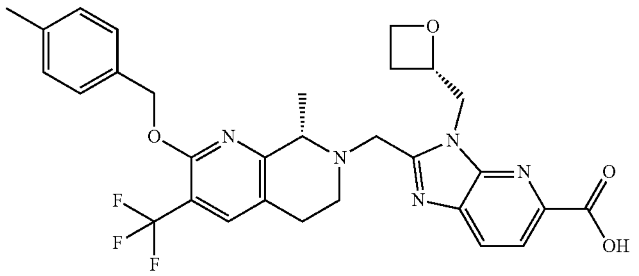 [SMILES: Cc1ccc(COc2nc3c(cc2C(F)(F)F)CCN(Cc2nc4ccc(C(=O)O)nc4n2C[C@@H]2CCO2)[C@H]3C)cc1] | 2.55 | 582.3 | 5 |
| I-348 | 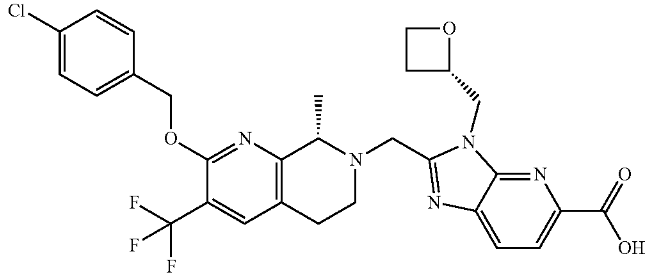 [SMILES: C[C@H]1c2nc(OCc3ccc(Cl)cc3)c(C(F)(F)F)cc2CCN1Cc1nc2ccc(C(=O)O)nc2n1C[C@@H]1CCO1] | 2.59 | 602.2 | 5 |
| I-349 | 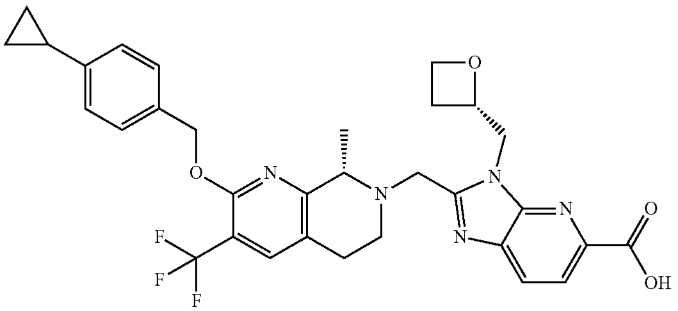 [SMILES: C[C@H]1c2nc(OCc3ccc(C4CC4)cc3)c(C(F)(F)F)cc2CCN1Cc1nc2ccc(C(=O)O)nc2n1C[C@@H]1CCO1] | 2.66 | 608.3 | 5 |

TABLE 55-continued
| | | | | |
|---|---|---|---|---|
| I-350 | 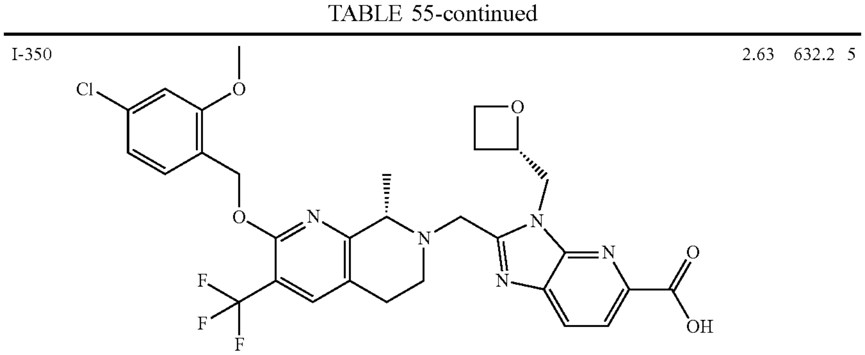 | 2.63 | 632.2 | 5 |
TABLE 56
| | | | | |
|---|---|---|---|---|
| I-351 | 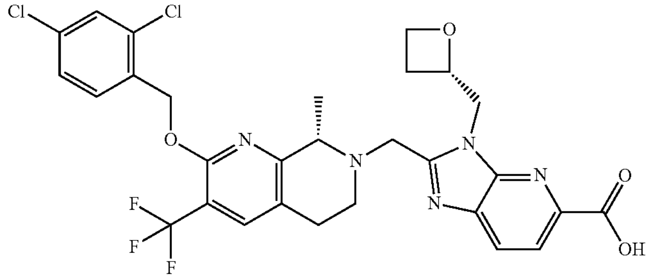 [SMILES: C[C@H]1c2nc(OCc3ccc(Cl)cc3Cl)c(C(F)(F)F)cc2CCN1Cc1nc2ccc(C(=O)O)nc2n1C[C@@H]1CCO1] | 2.73 | 636.2 | 5 |
| I-352 | 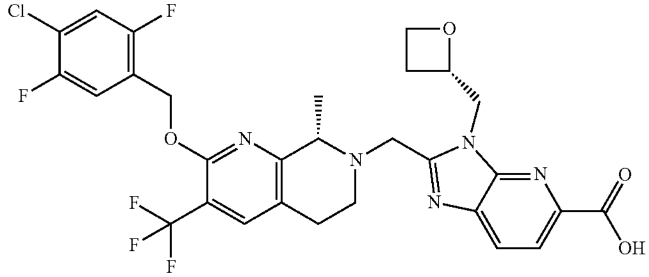 [SMILES: C[C@H]1c2nc(OCc3cc(F)c(Cl)cc3F)c(C(F)(F)F)cc2CCN1Cc1nc2ccc(C(=O)O)nc2n1C[C@@H]1CCO1] | 2.63 | 638.2 | 5 |
| I-353 | 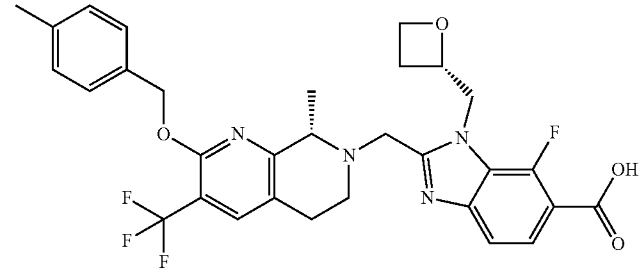 [SMILES: Cc1ccc(COc2nc3c(cc2C(F)(F)F)CCN(Cc2nc4ccc(C(=O)O)c(F)c4n2C[C@@H]2CCO2)[C@H]3C)cc1] | 2.64 | 599.3 | 5 |
| I-354 | 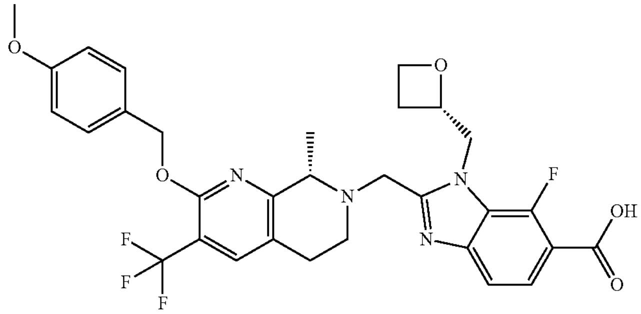 [SMILES: COc1ccc(COc2nc3c(cc2C(F)(F)F)CCN(Cc2nc4ccc(C(=O)O)c(F)c4n2C[C@@H]2CCO2)[C@H]3C)cc1] | 2.50 | 615.3 | 5 |

TABLE 56-continued
| | | | | |
|---|---|---|---|---|
| I-355 | 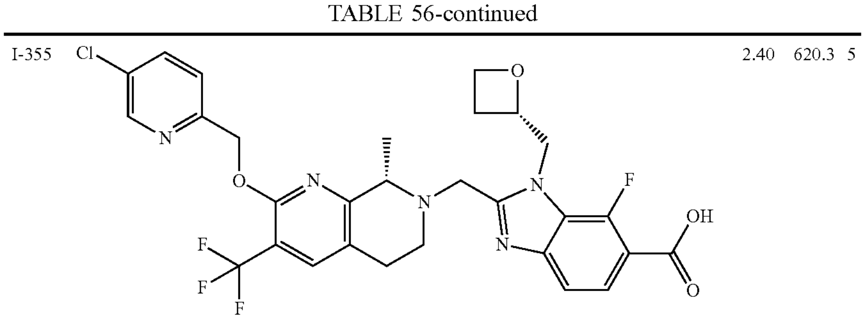 | 2.40 | 620.3 | 5 |
| I-356 | 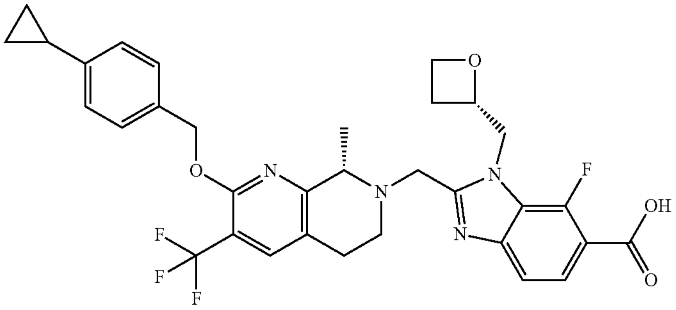 [SMILES: C[C@H]1c2nc(OCc3ccc(C4CC4)cc3)c(C(F)(F)F)cc2CCN1Cc1nc2ccc(C(=O)O)c(F)c2n1C[C@@H]1CCO1] | 2.73 | 625.3 | 5 |
| I-357 | 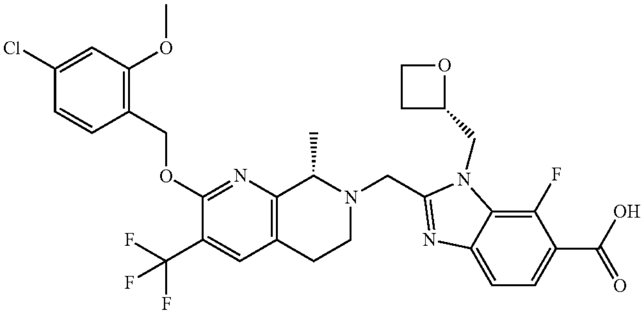 [SMILES: COc1cc(Cl)ccc1COc1nc2c(cc1C(F)(F)F)CCN(Cc1nc3ccc(C(=O)O)c(F)c3n1C[C@@H]1CCO1)[C@H]2C] | 2.70 | 649.3 | 5 |
TABLE 57
| | | | | |
|---|---|---|---|---|
| I-358 | 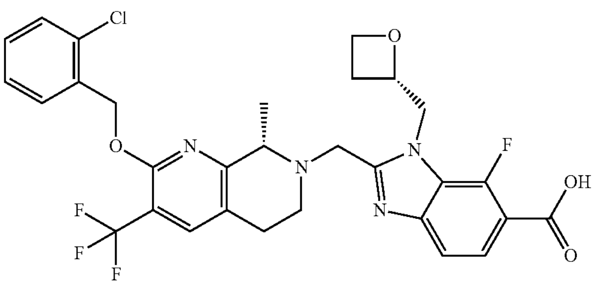 [SMILES: C[C@H]1c2nc(OCc3ccccc3Cl)c(C(F)(F)F)cc2CCN1Cc1nc2ccc(C(=O)O)c(F)c2n1C[C@@H]1CCO1] | 2.62 | 619.3 | 5 |
| I-359 | 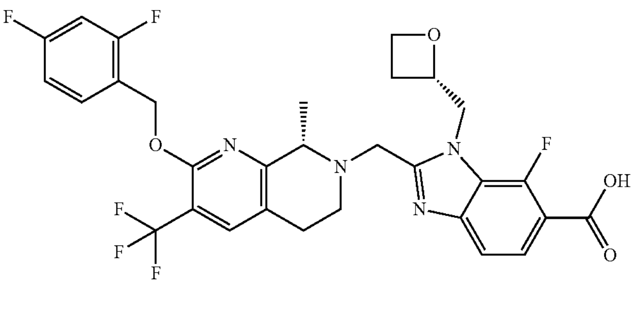 [SMILES: C[C@H]1c2nc(OCc3ccc(F)cc3F)c(C(F)(F)F)cc2CCN1Cc1nc2ccc(C(=O)O)c(F)c2n1C[C@@H]1CCO1] | 2.55 | 621.2 | 5 |

TABLE 57-continued
| | | | | |
|---|---|---|---|---|
| I-360 | 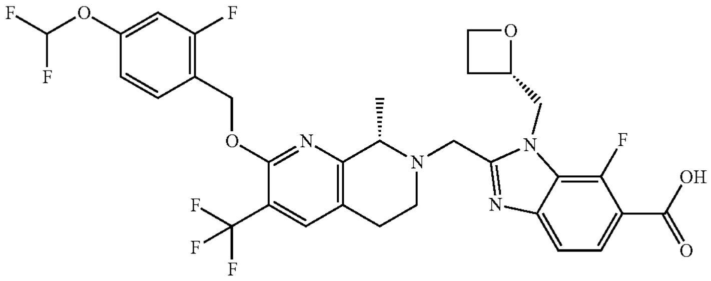 [SMILES: C[C@H]1c2nc(OCc3ccc(OC(F)F)cc3F)c(C(F)(F)F)cc2CCN1Cc1nc2ccc(C(=O)O)c(F)c2n1C[C@@H]1CCO1] | 2.59 | 669.2 | 5 |
| I-361 | 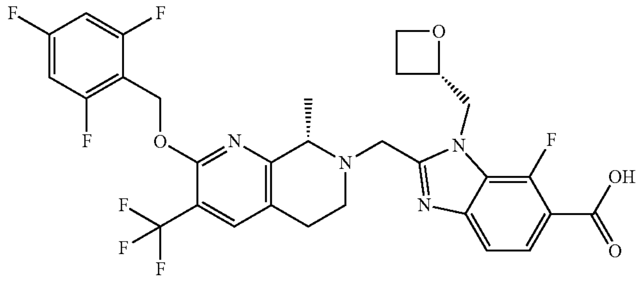 [SMILES: C[C@H]1c2nc(OCc3c(F)cc(F)cc3F)c(C(F)(F)F)cc2CCN1Cc1nc2ccc(C(=O)O)c(F)c2n1C[C@@H]1CCO1] | 2.54 | 639.2 | 5 |
| I-362 | 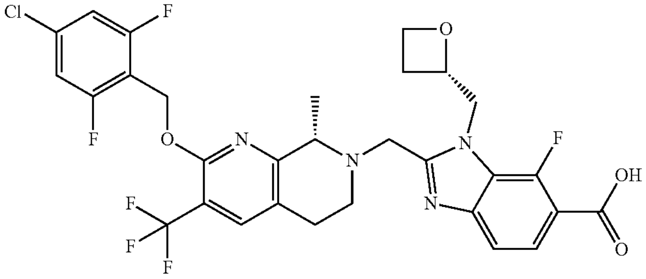 [SMILES: C[C@H]1c2nc(OCc3c(F)cc(Cl)cc3F)c(C(F)(F)F)cc2CCN1Cc1nc2ccc(C(=O)O)c(F)c2n1C[C@@H]1CCO1] | 2.65 | 655.2 | 5 |
| I-363 | 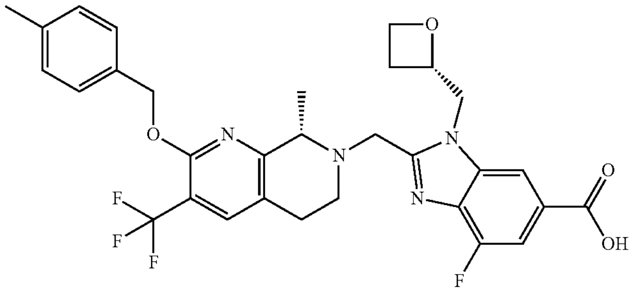 [SMILES: Cc1ccc(COc2nc3c(cc2C(F)(F)F)CCN(Cc2nc4c(F)cc(C(=O)O)cc4n2C[C@@H]2CCO2)[C@H]3C)cc1] | 2.69 | 599.3 | 5 |
| I-364 | 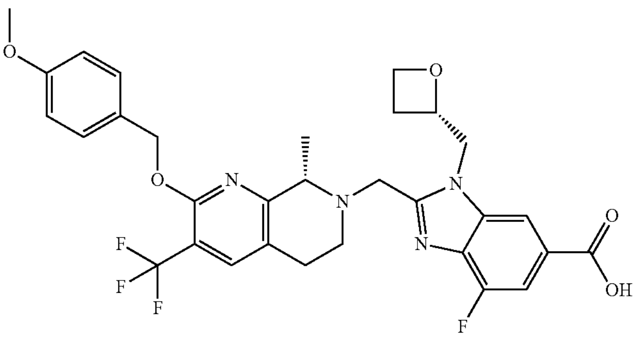 [SMILES: COc1ccc(COc2nc3c(cc2C(F)(F)F)CCN(Cc2nc4c(F)cc(C(=O)O)cc4n2C[C@@H]2CCO2)[C@H]3C)cc1] | 2.53 | 615.3 | 5 |

TABLE 58
| | | | | |
|---|---|---|---|---|
| I-365 | 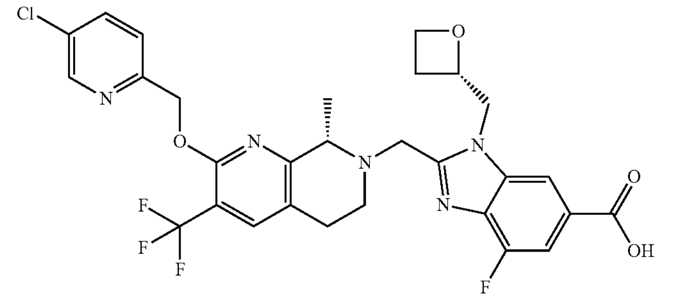 [SMILES: C[C@H]1c2nc(OCc3ccc(Cl)cn3)c(C(F)(F)F)cc2CCN1Cc1nc2c(F)cc(C(=O)O)cc2n1C[C@@H]1CCO1] | 2.47 | 620.3 | 5 |
| I-366 | 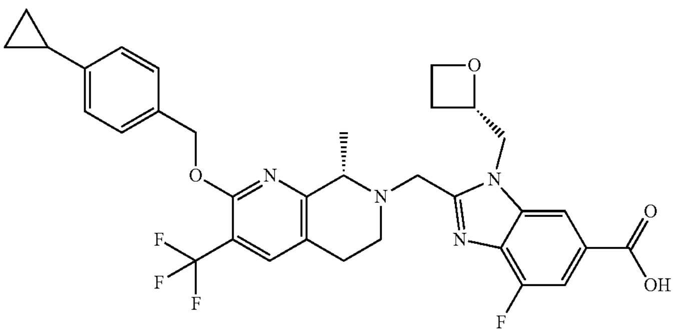 [SMILES: C[C@H]1c2nc(OCc3ccc(C4CC4)cc3)c(C(F)(F)F)cc2CCN1Cc1nc2c(F)cc(C(=O)O)cc2n1C[C@@H]1CCO1] | 2.78 | 625.3 | 5 |
| I-367 | 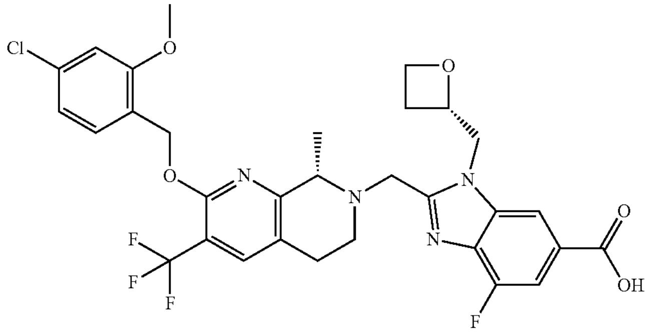 [SMILES: COc1cc(Cl)ccc1COc1nc2c(cc1C(F)(F)F)CCN(Cc1nc3c(F)cc(C(=O)O)cc3n1C[C@@H]1CCO1)[C@H]2C] | 2.75 | 649.3 | 5 |
| I-368 | 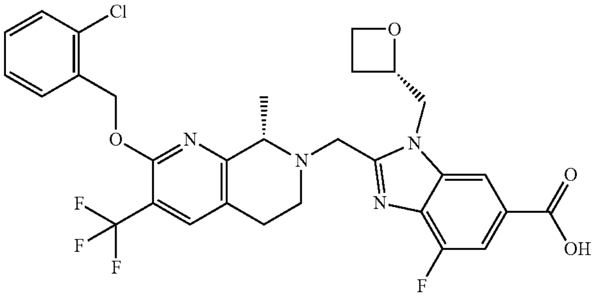 [SMILES: C[C@H]1c2nc(OCc3ccccc3Cl)c(C(F)(F)F)cc2CCN1Cc1nc2c(F)cc(C(=O)O)cc2n1C[C@@H]1CCO1] | 2.68 | 619.2 | 5 |
| I-369 | 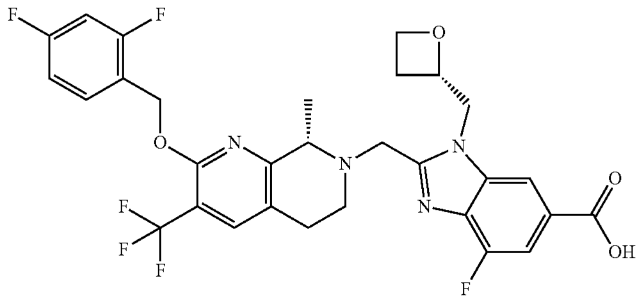 [SMILES: C[C@H]1c2nc(OCc3ccc(F)cc3F)c(C(F)(F)F)cc2CCN1Cc1nc2c(F)cc(C(=O)O)cc2n1C[C@@H]1CCO1] | 2.61 | 621.3 | 5 |

TABLE 58-continued
| | | | | |
|---|---|---|---|---|
| I-370 | 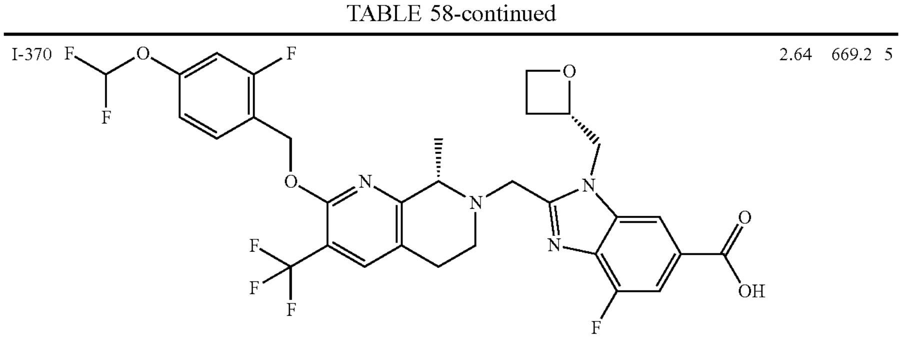 | 2.64 | 669.2 | 5 |
| I-371 | 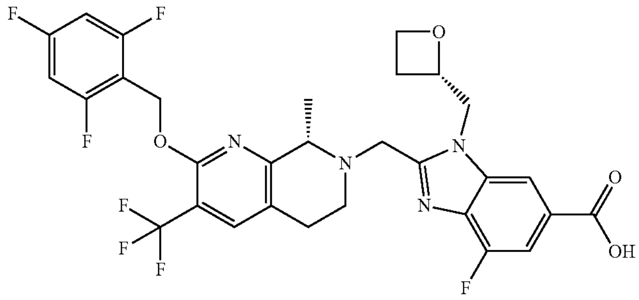 [SMILES: C[C@H]1c2nc(OCc3c(F)cc(F)cc3F)c(C(F)(F)F)cc2CCN1Cc1nc2c(F)cc(C(=O)O)cc2n1C[C@@H]1CCO1] | 2.60 | 639.2 | 5 |
TABLE 59
| | | | | |
|---|---|---|---|---|
| I-372 | 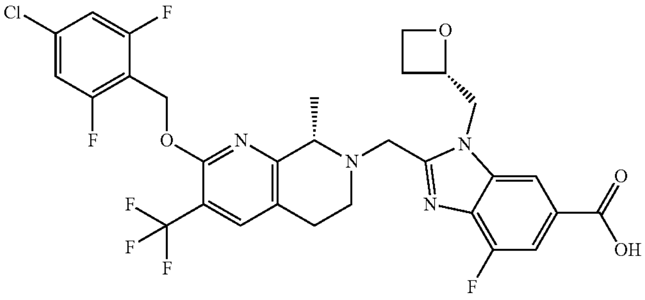 [SMILES: C[C@H]1c2nc(OCc3c(F)cc(Cl)cc3F)c(C(F)(F)F)cc2CCN1Cc1nc2c(F)cc(C(=O)O)cc2n1C[C@@H]1CCO1] | 2.71 | 655.2 | 5 |
| I-373 | 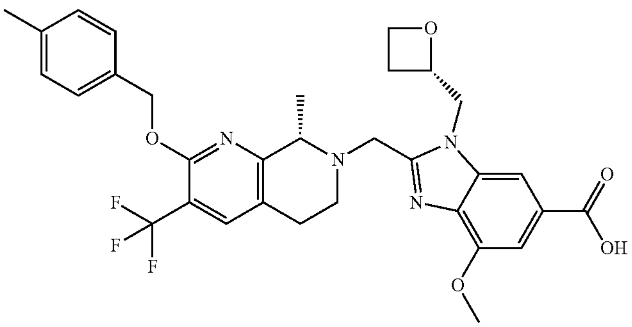 [SMILES: COc1cc(C(=O)O)cc2c1nc(CN1CCc3cc(C(F)(F)F)c(OCc4ccc(C)cc4)nc3[C@@H]1C)n2C[C@@H]1CCO1] | 2.63 | 611.3 | 5 |

TABLE 59-continued
| | | | | |
|---|---|---|---|---|
| I-374 | 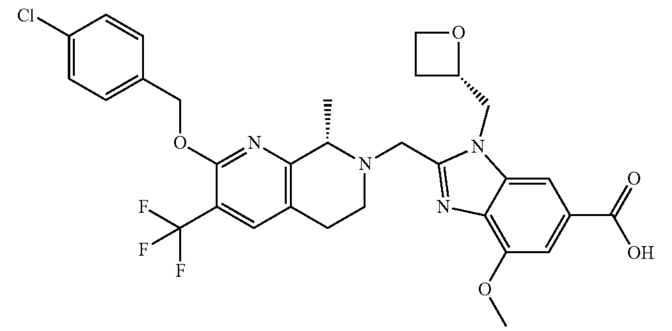 [SMILES: COc1cc(C(=O)O)cc2c1nc(CN1CCc3cc(C(F)(F)F)c(OCc4ccc(Cl)cc4)nc3[C@@H]1C)n2C[C@@H]1CCO1] | 2.66 | 631.2 | 5 |
| I-375 | 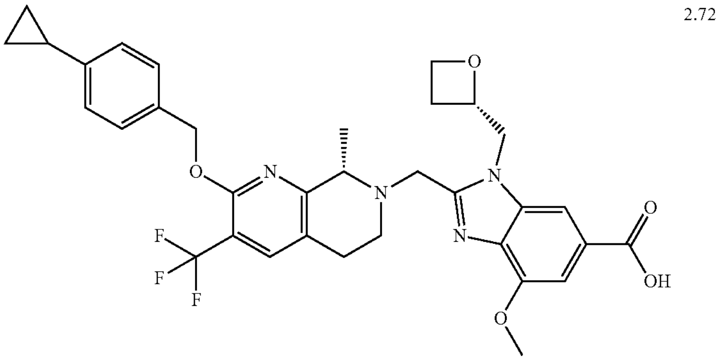 | 2.72 | 637.3 | 5 |
| I-376 | 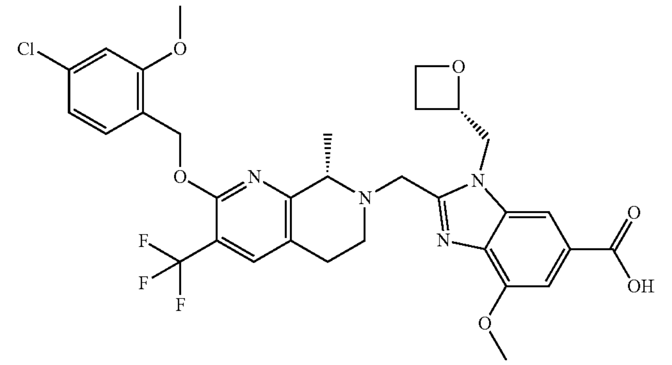 [SMILES: COc1cc(Cl)ccc1COc1nc2c(cc1C(F)(F)F)CCN(Cc1nc3c(OC)cc(C(=O)O)cc3n1C[C@@H]1CCO1)[C@H]2C] | 2.69 | 661.3 | 5 |
| I-377 | 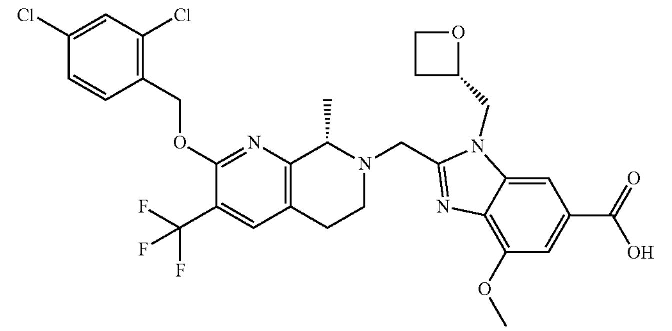 [SMILES: COc1cc(C(=O)O)cc2c1nc(CN1CCc3cc(C(F)(F)F)c(OCc4ccc(Cl)cc4Cl)nc3[C@@H]1C)n2C[C@@H]1CCO1] | 2.79 | 665.2 | 5 |

TABLE 60
| | | | | |
|---|---|---|---|---|
| I-378 | 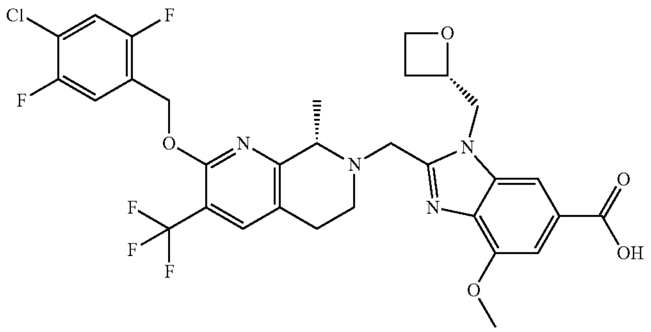 [SMILES: COc1cc(C(=O)O)cc2c1nc(CN1CCc3cc(C(F)(F)F)c(OCc4cc(F)c(Cl)cc4F)nc3[C@@H]1C)n2C[C@@H]1CCO1] | 2.69 | 667.2 | 5 |
| I-379 | 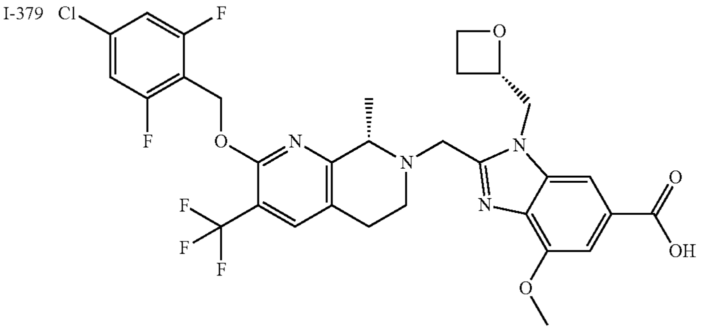 | 2.65 | 667.2 | 5 |
TABLE 61
| | | | | |
|---|---|---|---|---|
| I-380 | 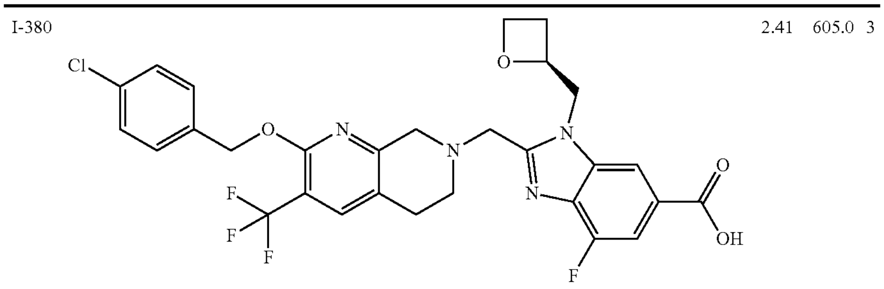 | 2.41 | 605.0 | 3 |
| I-381 | 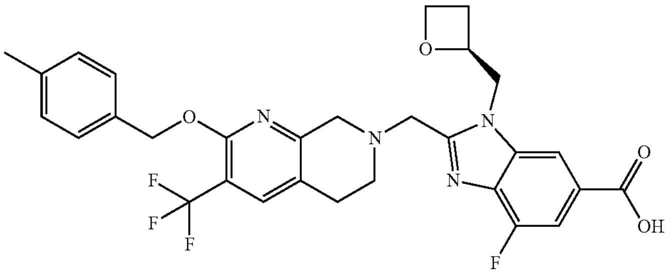 [SMILES: Cc1ccc(COc2nc3c(cc2C(F)(F)F)CCN(Cc2nc4c(F)cc(C(=O)O)cc4n2C[C@@H]2CCO2)C3)cc1] | 2.34 | 585.1 | 3 |
| I-382 | 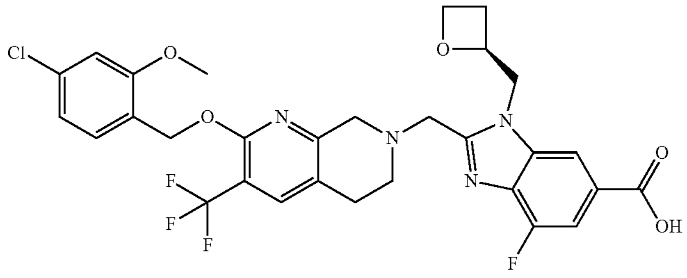 [SMILES: COc1cc(Cl)ccc1COc1nc2c(cc1C(F)(F)F)CCN(Cc1nc3c(F)cc(C(=O)O)cc3n1C[C@@H]1CCO1)C2] | 2.44 | 635.0 | 3 |

TABLE 61-continued
| | | | | |
|---|---|---|---|---|
| I-383 | 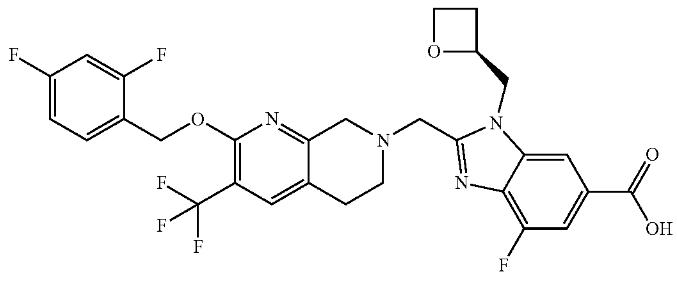 [SMILES: O=C(O)c1cc(F)c2nc(CN3CCc4cc(C(F)(F)F)c(OCc5ccc(F)cc5F)nc4C3)n(C[C@@H]3CCO3)c2c1] | 2.26 | 607.0 | 3 |
| I-384 | 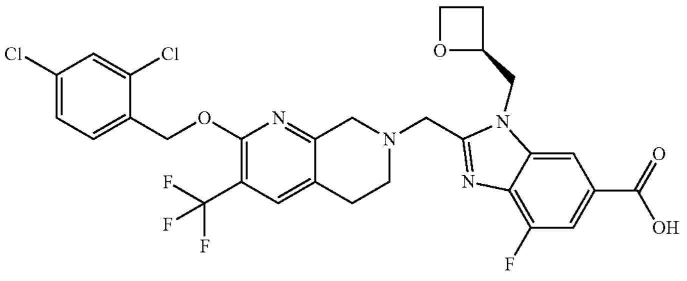 [SMILES: O=C(O)c1cc(F)c2nc(CN3CCc4cc(C(F)(F)F)c(OCc5ccc(Cl)cc5Cl)nc4C3)n(C[C@@H]3CCO3)c2c1] | 2.62 | 639.0 | 3 |
TABLE 62
| | | | | |
|---|---|---|---|---|
| I-385 | 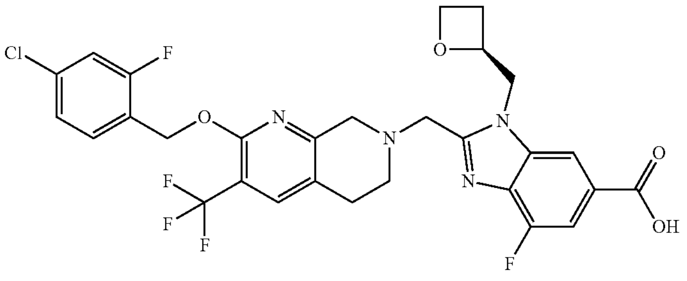 [SMILES: O=C(O)c1cc(F)c2nc(CN3CCc4cc(C(F)(F)F)c(OCc5ccc(Cl)cc5F)nc4C3)n(C[C@@H]3CCO3)c2c1] | 2.44 | 623.0 | 3 |
| I-386 | 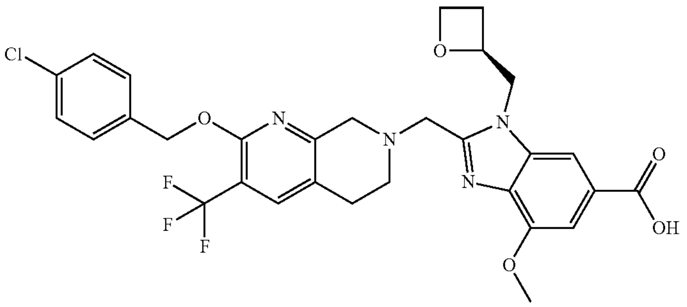 [SMILES: COc1cc(C(=O)O)cc2c1nc(CN1CCc3cc(C(F)(F)F)c(OCc4ccc(Cl)cc4)nc3C1)n2C[C@@H]1CCO1] | 2.18 | 617.0 | 3 |
| I-387 | 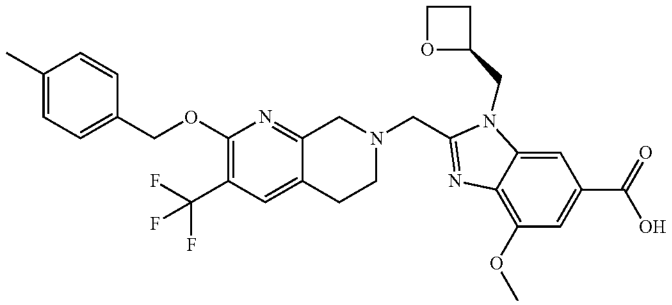 [SMILES: COc1cc(C(=O)O)cc2c1nc(CN1CCc3cc(C(F)(F)F)c(OCc4ccc(C)cc4)nc3C1)n2C[C@@H]1CCO1] | 2.12 | 597.1 | 3 |

TABLE 62-continued
| | | | | |
|---|---|---|---|---|
| I-388 | 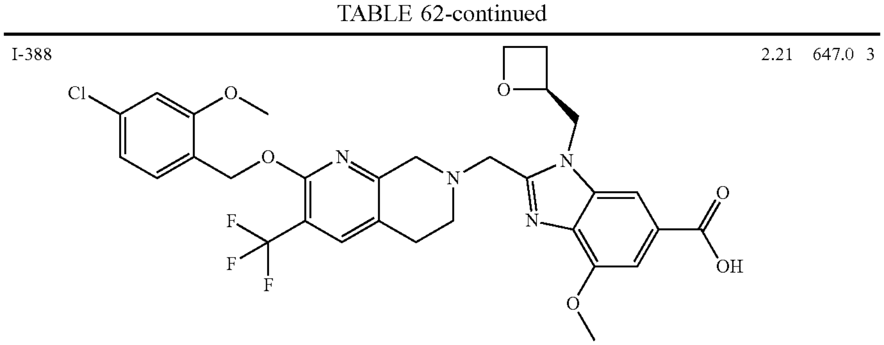 | 2.21 | 647.0 | 3 |
| I-389 | 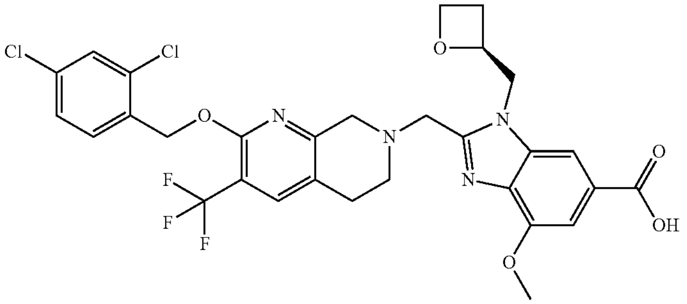 [SMILES: COc1cc(C(=O)O)cc2c1nc(CN1CCc3cc(C(F)(F)F)c(OCc4ccc(Cl)cc4Cl)nc3C1)n2C[C@@H]1CCO1] | 2.34 | 651.0 | 3 |
| I-390 | 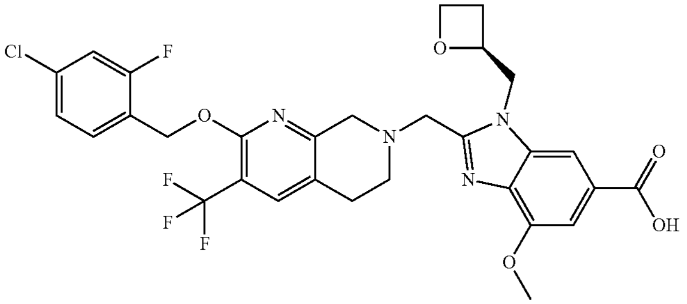 [SMILES: COc1cc(C(=O)O)cc2c1nc(CN1CCc3cc(C(F)(F)F)c(OCc4ccc(Cl)cc4F)nc3C1)n2C[C@@H]1CCO1] | 2.20 | 635.0 | 3 |
| I-391 | 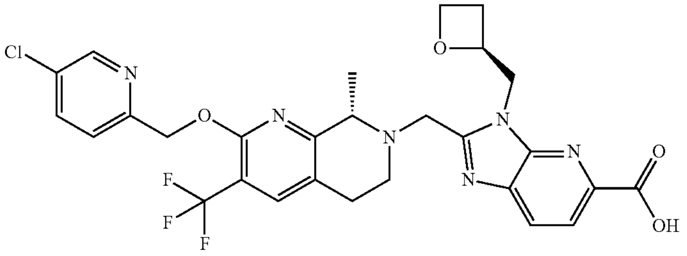 | 1.93 | 603.0 | 3 |
TABLE 63
| | | | | |
|---|---|---|---|---|
| I-392 | 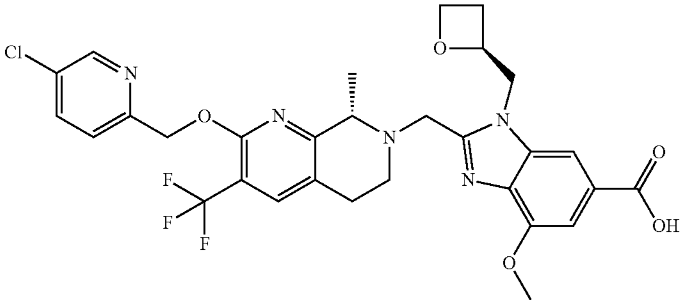 [SMILES: COc1cc(C(=O)O)cc2c1nc(CN1CCc3cc(C(F)(F)F)c(OCc4ccc(Cl)cn4)nc3[C@@H]1C)n2C[C@@H]1CCO1] | 1.95 | 632.1 | 3 |

TABLE 63-continued

| | | | | |
|---|---|---|---|---|
| I-393 | 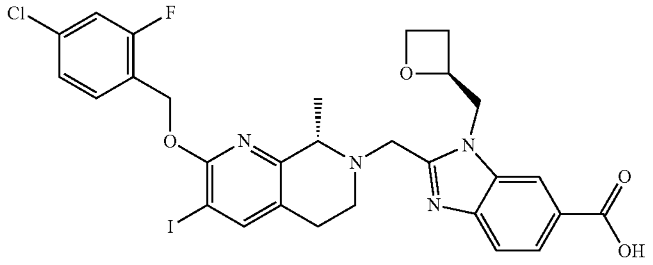 | 2.24 | 677.2 | 1 |
| I-394 | 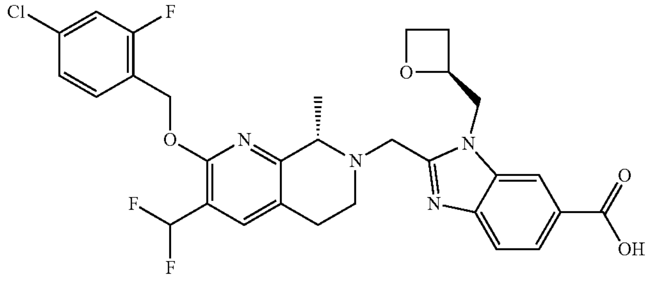 | 2.11 | 601.4 | 1 |
| I-395 | 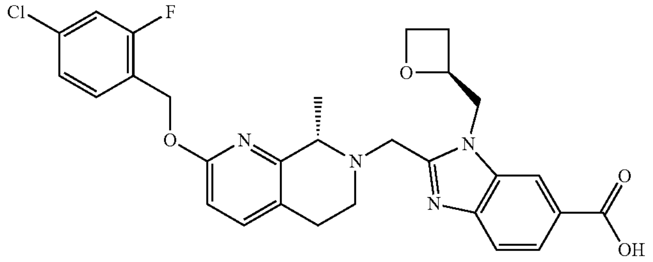 [SMILES: C[C@H]1c2nc(OCc3ccc(Cl)cc3F)ccc2CCN1Cc1nc2ccc(C(=O)O)cc2n1C[C@@H]1CCO1] | 1.92 | 551.3 | 1 |

TABLE 64

| Ex. No. | NMR |
|---|---|
| I-131 | 1H-NMR (DMSO-D6) δ: 0.97-1.01 (2H, m), 1.06-1.11 (2H, m), 2.32-2.40 (1H, m), 2.54-2.66 (1H, m), 2.78-2.87 (4H, m), 3.68 (2H, t, J = 16.9 Hz), 4.01 (1H, d, J = 13.4 Hz), 4.14 (1H, d, J = 13.6 Hz), 4.33 (1H, dt, J = 11.0, 4.5 Hz), 4.40-4.49 (1H, m), 4.61-4.66 (1H, m), 4.78 (1H, dd, J = 15.1, 7.1 Hz), 4.99-5.05 (1H, m), 5.18 (2H, s), 7.15 (1H, s), 7.32 (1H, s), 7.35 (1H, dd, J = 8.3, 1.8 Hz), 7.39 (1H, s), 7.48-7.51 (1H, m), 7.54 (1H, d, J = 8.3 Hz), 8.01 (1H, d, J = 1.0 Hz). |
| I-132 | 1H-NMR (DMSO-D6) δ: 2.36-2.45 (1H, m), 2.65 (3H, s), 2.67-2.75 (1H, m), 4.36-4.41 (1H, m), 4.49-4.55 (1H, m), 4.59-4.78 (4H, m), 5.05-5.12 (1H, m), 5.75 (2H, s), 7.36 (1H, dd, J = 8.0, 2.0 Hz), 7.53 (1H, d, J = 8.4 Hz), 7.53 (1H, dd, J = 10.0, 2.0 Hz), 7.61 (1H, d, J = 8.7 Hz), 7.66 (1H, t, J = 8.0 Hz), 7.76 (1H, dd, J = 8.8, 1.5 Hz), 7.97 (1H, d, J = 8.8 Hz), 8.25 (1H, s). |
| I-134 | 1H-NMR (DMSO-D6) δ: 2.35-2.43 (1H, m), 2.66-2.74 (1H, m), 2.80-2.88 (4H, m), 3.71 (2H, s), 4.04 (1H, d, J = 13.6 Hz), 4.16 (1H, d, J = 13.8 Hz), 4.36 (1H, dt, J = 11.0, 4.5 Hz), 4.48 (1H, dd, J = 14.6, 6.8 Hz), 4.70-4.74 (1H, m), 4.90 (1H, dd, J = 15.3, 7.3 Hz), 5.04-5.10 (1H, m), 5.19 (2H, s), 7.16 (1H, s), 7.36 (1H, dd, J = 8.3, 1.8 Hz), 7.40-7.44 (2H, m), 7.50 (1H, dd, J = 9.9, 1.9 Hz), 7.54 (1H, t, J = 8.2 Hz). |
| I-137 | 1H-NMR (DMSO-D6) δ: 2.33-241 (4H, m), 2.58-2.68 (1H, m), 2.78-2.87 (4H, m), 3.66 (2H, s), 3.99 (1H, d, J = 13.6 Hz), 4.13 (1H, d, J = 13.6 Hz), 4.30-4.37 (1H, m), 4.45 (1H, dd, J = 13.2, 8.0 Hz), 4.64 (1H, dd, J = 15.1, 2.2 Hz), 4.79 (1H, dd, J = 15.1, 7.0 Hz), 5.00-5.07 (1H, m), 5.41 (2H, s), 7.11 (1H, s), 7.28 (1H, d, J = 0.9 Hz), 7.41 (1H, s), 7.66 (1H, d, J = 8.7 Hz), 7.81 (1H, dd, J = 8.5, 1.4 Hz), 8.25 (1H, s). |
| I-138 | 1H-NMR (DMSO-D6) δ: 2.33-2.41 (1H, m), 2.58-2.67 (4H, m), 2.77-2.86 (4H, m), 3.67 (2H, s), 3.99 (1H, d, J = 13.6 Hz), 4.13 (1H, d, J = 13.4 Hz), 4.31-4.37 (1H, m), 4.45 (1H, dd, J = 13.7, 7.5 Hz), 4.65 (1H, dd, J = 15.2, 2.6 Hz), 4.79 (1H, dd, J = 15.2, 7.2 Hz), 5.04 (1H, ddd, J = 14.3, 7.1, 2.6 Hz), 5.16 (2H, s), 7.12 (1H, s), 7.39 (2H, d, J = 12.5 Hz), 7.66 (1H, d, J = 8.4 Hz), 7.82 (1H, dd, J = 8.5, 1.4 Hz), 8.25 (1H, s). |
| I-139 | 1H-NMR (DMSO-D6) δ: 2.33-2.42 (1H, m), 2.58-2.67 (1H, m), 2.76-2.86 (4H, m), 3.68 (2H, s), 3.81 (3H, s), 3.98 (1H, d, J = 13.4 Hz), 4.12 (1H, d, J = 13.4 Hz), 4.31-4.37 (1H, m), 4.45 (1H, dd, J = 13.2, 8.2 Hz), 4.64 (1H, dd, J = 15.1, 2.6 Hz), 4.78 (1H, dd, J = 15.2, 7.2 Hz), 5.00-5.07 (3H, m), 7.04-7.12 (3H, m), 7.36-7.39 (2H, m), 7.64 (1H, d, J = 8.5 Hz), 7.81 (1H, dd, J = 8.4, 1.5 Hz), 8.23 (1H, s). |

TABLE 64-continued

| Ex. No. | NMR |
|---|---|
| I-140 | 1H-NMR (DMSO-D6) δ: 2.28 (3H, s), 2.32-2.43 (1H, m), 2.60-2.68 (1H, m), 2.78-2.88 (4H, m), 3.67 (2H, s), 3.99 (1H, d, J = 13.6 Hz), 4.13 (1H, d, J = 13.4 Hz), 4.31-4.38 (1H, m), 4.45 (1H, dd, J = 13.6, 7.7 Hz), 4.64 (1H, dd, J = 15.2, 2.6 Hz), 4.79 (1H, dd, J = 15.1, 7.1 Hz), 5.04 (1H, ddd, J = 14.1, 7.0, 2.8 Hz), 5.10 (2H, s), 7.13 (1H, s), 7.26-7.31 (2H, m), 7.39-7.43 (2H, m), 7.63 (1H, d, J = 8.4 Hz), 7.81 (1H, dd, J = 8.4, 1.5 Hz), 8.23 (1H, s). |
| I-141 | 1H-NMR (DMSO-D6) δ: 2.28 (3H, s), 2.33-2.41 (1H, m), 2.59-2.67 (1H, m), 2.78-2.86 (4H, m), 3.68 (2H, s), 3.99 (1H, d, J = 13.6 Hz), 4.14 (1H, d, J = 13.4 Hz), 4.32-4.37 (1H, m), 4.45 (1H, dd, J = 13.7, 7.7 Hz), 4.65 (1H, dd, J = 15.1, 2.6 Hz), 4.80 (1H, dd, J = 15.2, 7.2 Hz), 5.04 (1H, ddd, J = 14.2, 7.0, 2.6 Hz), 5.13 (2H, s), 7.14 (1H, s), 7.38 (1H, s), 7.47 (2H, dd, J = 11.6, 8.8 Hz), 7.66 (1H, d, J = 8.4 Hz), 7.82 (1H, dd, J = 8.5, 1.4 Hz), 8.25 (1H, s). |

TABLE 65

| | |
|---|---|
| I-143 | 1H-NMR (DMSO-D6) δ: 2.33-2.39 (1H, m), 2.58-2.67 (1H, m), 2.77-2.86 (4H, m), 3.66 (2H, s), 3.99 (1H, d, J = 13.6 Hz), 4.13 (1H, d, J = 13.6 Hz), 4.31-4.36 (1H, m), 4.45 (1H, dd, J = 13.8, 7.5 Hz), 4.64 (1H, dd, J = 15.1, 2.5 Hz), 4.79 (1H, dd, J = 15.3, 7.3 Hz), 5.04 (1H, ddd, J = 14.2, 7.2, 2.6 Hz), 5.17 (2H, s), 7.06-7.43 (6H, m), 7.66 (1H, d, J = 8.4 Hz), 7.82 (1H, dd, J = 8.4, 1.4 Hz), 8.25 (1H, s). |
| I-144 | 1H-NMR (DMSO-D6) δ: 8.33 (1H, s), 7.82 (1H, dd, J = 8.5, 1.4 Hz), 7.70 (1H, d, J = 8.5 Hz), 7.55-7.47 (2H, m), 7.38-7.34 (2H, m), 7.14 (1H, s), 5.18 (2H, s), 4.77 (1H, d, J = 15.3 Hz), 4.53 (1H, d, J = 15.4 Hz), 4.28 (1H, dd, J = 14.7, 6.6 Hz), 4.11 (2H, dd, J = 33.7, 13.6 Hz), 3.94-3.87 (1H, m), 3.68 (2H, s), 2.82 (4H, s), 2.36 (2H, dd, J = 17.4, 8.8 Hz), 1.38 (3H, s). |
| I-147 | 1H-NMR (CDCl3) δ: 2.05 (3H, s), 2.36-2.45 (1H, m), 2.65-2.73 (1H, m), 2.85 (4H, s), 3.72 (2H, s), 3.79 (3H, s), 4.17 (2H, t, J = 13.9 Hz), 4.36 (1H, dt, J = 10.9, 4.5 Hz), 4.58-4.63 (1H, m), 4.66 (1H, dd, J = 15.5, 2.7 Hz), 4.74 (1H, dd, J = 15.5, 6.1 Hz), 5.05 (2H, s), 5.15-5.21 (1H, m), 6.86 (1H, s), 7.09 (1H, s), 7.29 (1H, s), 7.82 (1H, d, J = 8.5 Hz), 8.04 (1H, d, J = 9.4 Hz), 8.20 (1H, s). |
| I-148 | 1H-NMR (CDCl3) δ: 1.42 (3H, t, J = 7.3 Hz), 2.36-2.45 (1H, m), 2.64-2.73 (1H, m), 2.85 (4H, s), 3.69 (2H, s), 4.12 (2H, q, J = 7.3 Hz), 4.19 (2H, t, J = 14.7 Hz), 4.36 (1H, dt, J = 11.0, 4.5 Hz), 4.61 (1H, dd, J = 14.1, 7.9 Hz), 4.64-4.69 (1H, m), 4.73 (1H, dd, J = 15.5, 6.1 Hz), 5.11 (2H, s), 5.15-5.21 (1H, m), 6.31 (1H, d, J = 2.3 Hz), 6.76 (1H, s), 7.30 (1H, s), 7.33 (1H, d, J = 2.3 Hz), 7.82 (1H, d, J = 8.5 Hz), 8.05 (1H, dd, J = 8.5, 1.3 Hz), 8.20 (1H, s). |
| I-152 | 1H-NMR (CDCl3) δ: 2.37-2.46 (1H, m), 2.66-2.74 (1H, m), 2.87 (4H, s), 3.72 (2H, s), 4.16 (1H, d, J = 13.6 Hz), 4.21 (1H, d, J = 13.6 Hz), 4.37 (1H, dt, J = 11.0, 4.6 Hz), 4.61 (1H, dd, J = 13.8, 7.9 Hz), 4.68 (1H, dd, J = 15.4, 3.0 Hz), 4.74 (1H, dd, J = 15.4, 5.9 Hz), 5.12 (2H, s), 5.17-5.23 (1H, m), 6.53 (1H, t, J = 73.8 Hz), 6.70 (1H, s), 7.13 (1H, d, J = 7.5 Hz), 7.23-7.35 (3H, m), 7.60 (1H, d, J = 6.3 Hz), 7.84 (1H, d, J = 8.5 Hz), 8.06 (1H, dd, J = 8.5, 1.4 Hz), 8.22 (1H, d, J = 0.8 Hz). |
| I-153 | 1H-NMR (CDCl3) δ: 2.38-2.47 (1H, m), 2.66-2.74 (1H, m), 2.86 (4H, s), 3.73 (2H, s), 3.78 (3H, s), 4.18 (1H, d, J = 14.1 Hz), 4.22 (1H, d, J = 14.1 Hz), 4.38 (1H, dt, J = 10.9, 4.5 Hz), 4.62 (1H, dd, J = 13.9, 7.8 Hz), 4.68 (1H, dd, J = 15.3, 2.8 Hz), 4.76 (1H, dd, J = 15.3, 6.0 Hz), 5.02 (2H, s), 5.17-5.23 (1H, m), 6.43-6.48 (2H, m), 6.79 (1H, s), 7.29 (1H, s), 7.85 (1H, d, J = 8.5 Hz), 8.07 (1H, dd, J = 8.5, 1.3 Hz), 8.23 (1H, s). |
| I-154 | 1H-NMR (CDCl3) δ: 2.37-2.46 (1H, m), 2.65-2.74 (1H, m), 2.87 (4H, s), 3.71 (2H, s), 4.16 (1H, d, J = 13.7 Hz), 4.21 (1H, d, J = 13.7 Hz), 4.37 (1H, dt, J = 11.0, 4.6 Hz), 4.61 (1H, dd, J = 13.9, 7.8 Hz), 4.67 (1H, dd, J = 15.4, 2.9 Hz), 4.74 (1H, dd, J = 15.4, 6.0 Hz), 5.14 (2H, s), 5.17-5.22 (1H, m), 6.69 (1H, s), 7.05 (1H, t, J = 9.2 Hz), 7.16 (1H, t, J = 7.5 Hz), 7.30 (1H, t, J = 6.8 Hz), 7.34 (1H, s), 7.54 (1H, t, J = 7.7 Hz), 7.84 (1H, d, J = 8.5 Hz), 8.07 (1H, d, J = 8.7 Hz), 8.22 (1H, s). |
| I-155 | 1H-NMR (CDCl3) δ: 2.38-2.47 (1H, m), 2.66-2.75 (1H, m), 2.87 (4H, s), 3.74 (2H, s), 4.18 (1H, d, J = 13.8 Hz), 4.22 (1H, d, J = 13.8 Hz), 4.38 (1H, dt, J = 11.0, 4.5 Hz), 4.62 (1H, dd, J = 13.9, 7.8 Hz), 4.68 (1H, dd, J = 15.4, 2.8 Hz), 4.76 (1H, dd, J = 15.4, 6.1 Hz), 5.11 (2H, s), 5.17-5.23 (1H, m), 6.80 (1H, s), 6.88-6.94 (2H, m), 7.28-7.35 (2H, m), 7.85 (1H, d, J = 8.5 Hz), 8.07 (1H, dd, J = 8.5, 1.3 Hz), 8.23 (1H, s). |

TABLE 66

| | |
|---|---|
| I-156 | 1H-NMR (CDCl3) δ: 2.36-2.45 (1H, m), 2.65-2.73 (1H, m), 2.87 (4H, s), 3.68 (2H, s), 4.16 (1H, d, J = 13.6 Hz), 4.20 (1H, d, J = 13.6 Hz), 4.36 (1H, dt, J = 10.9, 4.5 Hz), 4.61 (1H, dd, J = 13.8, 7.9 Hz), 4.67 (1H, dd, J = 15.4, 2.9 Hz), 4.74 (1H, dd, J = 15.4, 6.0 Hz), 5.08 (2H, s), 5.16-5.22 (1H, m), 6.64 (1H, s), 7.29-7.41 (6H, m), 7.84 (1H, d, J = 8.5 Hz), 8.07 (1H, dd, J = 8.5, 1.3 Hz), 8.21 (1H, s). |
| I-157 | 1H-NMR (CDCl3) δ: 2.38-2.47 (1H, m), 2.67-2.75 (1H, m), 2.88 (4H, s), 3.75 (2H, s), 4.20 (2H, t, J = 14.0 Hz), 4.38 (1H, dt, J = 11.0, 4.5 Hz), 4.60-4.69 (2H, m), 4.75 (1H, dd, J = 15.2, 6.1 Hz), 5.22 (3H, s), 6.71 (1H, s), 7.36 (1H, s), 7.62-7.72 (3H, m), 7.84 (1H, d, J = 8.5 Hz), 8.06 (1H, dd, J = 8.5, 1.5 Hz), 8.22 (1H, d, J = 1.0 Hz). |

TABLE 66-continued

| | |
|---|---|
| I-158 | 1H-NMR (CDCl3) δ: 2.38-2.47 (1H, m), 2.67-2.75 (1H, m), 2.87 (4H, s), 3.74 (2H, s), 4.18 (1H, d, J = 13.6 Hz), 4.22 (1H, d, J = 13.6 Hz), 4.38 (1H, dt, J = 11.0, 4.6 Hz), 4.62 (1H, dd, J = 13.9, 8.0 Hz), 4.69 (1H, dd, J = 15.4, 2.9 Hz), 4.76 (1H, dd, J = 15.4, 6.0 Hz), 5.15-5.23 (3H, m), 6.81 (1H, s), 7.00-7.05 (1H, m), 7.22-7.31 (3H, m), 7.84 (1H, d, J = 8.5 Hz), 8.06 (1H, dd, J = 8.5, 1.5 Hz), 8.22 (1H, d, J = 0.9 Hz). |
| I-159 | 1H-NMR (CDCl3) δ: 2.33 (6H, s), 2.39-2.47 (1H, m), 2.67-2.76 (1H, m), 2.89 (4H, s), 3.74 (2H, s), 4.18 (1H, d, J = 13.4 Hz), 4.23 (1H, d, J = 13.4 Hz), 4.38 (1H, dt, J = 11.0, 4.6 Hz), 4.63 (1H, dd, J = 14.0, 7.8 Hz), 4.69 (1H, dd, J = 15.3, 3.1 Hz), 4.75 (1H, dd, J = 15.3, 6.0 Hz), 4.93 (2H, s), 5.18-5.24 (1H, m), 6.75 (1H, s), 6.77 (2H, s), 7.33 (1H, s), 7.84 (1H, d, J = 8.5 Hz), 8.06 (1H, dd, J = 8.5, 1.5 Hz), 8.22 (1H, d, J = 1.0 Hz). |
| I-160 | 1H-NMR (DMSO-D6) δ: 1.38 (3H, d, J = 6.8 Hz), 2.33-2.41 (1H, m), 2.64-2.86 (4H, m), 2.96-3.01 (1H, m), 3.87 (1H, dd, J = 13.0, 6.2 Hz), 4.10 (1H, d, J = 14.1 Hz), 4.21 (1H, d, J = 14.1 Hz), 4.31 (1H, dt, J = 11.0, 4.4 Hz), 4.47 (1H, dd, J = 13.7, 7.7 Hz), 4.74 (1H, dd, J = 15.4, 3.0 Hz), 4.84 (1H, dd, J = 15.4, 6.8 Hz), 5.07-5.13 (1H, m), 5.44 (1H, d, J = 12.8 Hz), 5.52 (1H, d, J = 12.8 Hz), 7.31 (1H, dd, J = 8.2, 1.8 Hz), 7.46-7.53 (3H, m), 7.68 (1H, dd, J = 8.4, 6.8 Hz), 7.90 (1H, s). |
| I-161 | 1H-NMR (CDCl3) δ: 1.37 (3H, d, J = 6.7 Hz), 2.35-2.44 (1H, m), 2.61-2.73 (2H, m), 2.78-2.84 (1H, m), 2.87-2.95 (1H, m), 3.09-3.16 (1H, m), 3.88 (1H, q, J = 6.6 Hz), 4.16-4.35 (3H, m), 4.59-4.77 (3H, m), 5.07 (2H, s), 5.20 (1H, ddd, J = 13.2, 7.1, 2.7 Hz), 6.66 (1H, s), 7.31-7.36 (5H, m), 7.82 (1H, d, J = 8.4 Hz), 8.05 (1H, dd, J = 8.5, 1.3 Hz), 8.19 (1H, s). |
| I-162 | 1H-NMR (CDCl3) δ: 1.37 (3H, d, J = 6.8 Hz), 2.34-2.44 (5H, m), 2.62-2.73 (2H, m), 2.77-2.80 (1H, m), 2.85-2.93 (1H, m), 3.07-3.13 (1H, m), 3.88 (1H, dd, J = 12.8, 6.1 Hz), 4.15-4.35 (3H, m), 4.58-4.77 (3H, m), 5.08 (2H, s), 5.20 (1H, ddd, J = 13.2, 7.0, 3.0 Hz), 6.69 (1H, s), 7.17 (2H, d, J = 7.9 Hz), 7.28-7.33 (3H, m), 7.82 (1H, d, J = 8.5 Hz), 8.05 (1H, dd, J = 8.5, 1.3 Hz), 8.20 (1H, s). |
| I-163 | 1H-NMR (CDCl3) δ: 0.66-0.70 (2H, m), 0.94-0.97 (2H, m), 1.25 (OH, s), 1.37 (3H, d, J = 7.0 Hz), 1.85-1.92 (1H, m), 2.34-2.43 (1H, m), 2.63-2.68 (2H, m), 2.77-2.92 (2H, m), 3.06-3.13 (1H, m), 3.87 (1H, dd, J = 12.5, 6.0 Hz), 4.16-4.34 (3H, m), 4.57-4.77 (3H, m), 5.06 (2H, s), 5.19 (1H, q, J = 6.7 Hz), 6.68 (1H, s), 7.06 (2H, d, J = 8.0 Hz), 7.30 (3H, d, J = 7.5 Hz), 7.81 (1H, d, J = 8.4 Hz), 8.04 (1H, d, J = 8.8 Hz), 8.20 (1H, s). |

TABLE 67

| | |
|---|---|
| I-164 | 1H-NMR (DMSO-D6) δ: 1.33 (3H, d, J = 6.8 Hz), 2.33-2.40 (1H, m), 2.59-2.66 (2H, m), 2.78-2.84 (2H, m), 2.97-3.04 (1H, m), 3.83 (3H, s), 3.96 (1H, q, J = 6.7 Hz), 4.09 (2H, dd, J = 19.4, 13.7 Hz), 4.30-4.33 (1H, m), 4.46 (1H, dd, J = 13.8, 7.7 Hz), 4.66 (1H, dd, J = 14.8, 2.5 Hz), 4.78 (1H, dd, J = 15.4, 7.0 Hz), 5.07-5.16 (3H, m), 7.06 (1H, dd, J = 8.1, 1.9 Hz), 7.10-7.15 (2H, m), 7.36 (1H, s), 7.40 (1H, d, J = 8.2 Hz), 7.63 (1H, d, J = 8.7 Hz), 7.80 (1H, dd, J = 8.5, 1.4 Hz), 8.23 (1H, s). |
| I-166 | 1H-NMR (CDCl3) δ: 1.40 (3H, d, J = 6.7 Hz), 2.38-2.43 (1H, m), 2.63-2.74 (2H, m), 2.77-2.83 (1H, m), 2.86-2.94 (1H, m), 3.08-3.15 (1H, m), 3.91 (1H, q, J = 6.4 Hz), 4.16-4.37 (3H, m), 4.58-4.79 (3H, m), 5.08-5.23 (3H, m), 6.73 (1H, s), 6.83 (1H, ddd, J = 10.6, 8.3, 2.0 Hz), 6.92 (1H, td, J = 8.3, 1.9 Hz), 7.32 (1H, s), 7.50-7.56 (1H, m), 7.81 (1H, d, J = 8.5 Hz), 8.04 (1H, dd, J = 8.4, 1.4 Hz), 8.19 (1H, d, J = 0.9 Hz). |
| I-167 | 1H-NMR (CDCl3) δ: 1.41 (3H, d, J = 6.8 Hz), 2.36-2.45 (1H, m), 2.65-2.72 (2H, m), 2.79-2.84 (1H, m), 2.88-2.96 (1H, m), 3.09-3.16 (1H, m), 3.92 (1H, q, J = 6.6 Hz), 4.17-4.37 (3H, m), 4.59-4.79 (3H, m), 5.10-5.23 (3H, m), 6.70 (1H, s), 7.31 (1H, dd, J = 8.3, 1.9 Hz), 7.34 (1H, s), 7.40 (1H, d, J = 2.0 Hz), 7.58 (1H, d, J = 8.3 Hz), 7.81 (1H, d, J = 8.5 Hz), 8.04 (1H, d, J = 8.5 Hz), 8.19 (1H, s). |
| I-169 | 1H-NMR (CDCl3) δ: 1.41 (3H, d, J = 6.7 Hz), 2.37-2.45 (1H, m), 2.64-2.74 (2H, m), 2.81-2.96 (2H, m), 3.10-3.17 (1H, m), 3.91 (1H, q, J = 6.4 Hz), 4.18-4.37 (3H, m), 4.58-4.80 (3H, m), 5.04-5.25 (3H, m), 6.70 (1H, s), 7.16 (1H, dd, J = 9.0, 5.8 Hz), 7.34-7.40 (2H, m), 7.82 (1H, d, J = 8.4 Hz), 8.05 (1H, d, J = 8.5 Hz), 8.20 (1H, s). |
| I-170 | 1H-NMR (CDCl3) δ: 1.41 (3H, d, J = 6.7 Hz), 2.35-2.44 (1H, m), 2.62-2.75 (2H, m), 2.79-2.86 (1H, m), 2.89-2.97 (1H, m), 3.10-3.17 (1H, m), 3.91 (1H, dd, J = 13.4, 7.0 Hz), 4.18 (1H, d, J = 13.3 Hz), 4.25-4.38 (2H, m), 4.59-4.79 (3H, m), 5.18-5.23 (3H, m), 6.72 (1H, s), 7.34-7.40 (2H, m), 7.53 (1H, d, J = 7.0 Hz), 7.74-7.81 (2H, m), 8.03 (1H, dd, J = 8.5, 1.4 Hz), 8.18 (1H, d, J = 1.0 Hz). |
| I-172 | 1H-NMR (CDCl3) δ: 1.38 (3H, d, J = 6.8 Hz), 2.36-2.44 (1H, m), 2.63-2.74 (2H, m), 2.77-2.84 (1H, m), 2.86-2.94 (1H, m), 3.08-3.14 (1H, m), 3.91 (1H, q, J = 6.7 Hz), 4.16-4.37 (3H, m), 4.60-4.77 (3H, m), 5.17-5.24 (3H, m), 6.72 (1H, s), 7.34 (1H, s), 7.57 (1H, d, J = 8.4 Hz), 7.73 (1H, dd, J = 8.4, 2.5 Hz), 7.81 (1H, d, J = 8.5 Hz), 8.04 (1H, dd, J = 8.5, 1.4 Hz), 8.20 (1H, s), 8.53 (1H, d, J = 2.1 Hz). |
| I-174 | 1H-NMR (DMSO-D6) δ: 1.31 (3H, d, J = 6.7 Hz), 2.31-2.39 (1H, m), 2.57-2.67 (1H, m), 2.74-2.82 (2H, m), 2.96-3.02 (1H, m), 3.88 (1H, dd, J = 12.7, 6.1 Hz), 4.08 (2H, dd, J = 16.3, 14.4 Hz), 4.29-4.34 (1H, m), 4.46 (1H, q, J = 7.0 Hz), 4.67 (1H, dd, J = 15.4, 2.2 Hz), 4.79 (1H, dd, J = 15.2, 7.2 Hz), 5.06-5.21 (3H, m), 7.06 (1H, s), 7.18 (1H, s), 7.36 (1H, dd, J = 8.0, 1.4 Hz), 7.50 (1H, dd, J = 9.9, 1.7 Hz), 7.58-7.67 (2H, m), 7.81 (1H, d, J = 8.4 Hz), 8.25 (1H, s). |
| I-176 | 1H-NMR (CDCl3) δ: 1.38 (3H, d, J = 6.7 Hz), 2.39-2.45 (1H, m), 2.62-2.90 (4H, m), 3.07-3.15 (1H, m), 3.90 (1H, q, J = 6.7 Hz), 4.22-4.34 (3H, m), 4.61 (1H, d, J = 7.0 Hz), 4.77 (1H, d, J = 14.1 Hz), 4.91 (1H, dd, J = 14.9, 6.3 Hz), 5.22 (3H, s), 6.72 (1H, s), 7.34 (1H, s), 7.57 (1H, d, J = 8.5 Hz), 7.73 (1H, dd, J = 8.4, 2.4 Hz), 8.16-8.25 (2H, m), 8.52 (1H, d, J = 2.1 Hz). |

TABLE 68

| | |
|---|---|
| I-177 | 1H-NMR (CDCl3) δ: 1.39 (3H, d, J = 6.8 Hz), 2.41-2.46 (4H, m), 2.60-2.69 (1H, m), 2.72-2.82 (2H, m), 2.86-2.94 (1H, m), 3.08-3.15 (1H, m), 3.92 (1H, q, J = 6.7 Hz), 4.24-4.35 (3H, m), 4.62 (1H, dd, J = 14.1, 7.6 Hz), 4.78 (1H, dd, J = 14.9, 3.0 Hz), 4.91 (1H, dd, J = 14.8, 6.1 Hz), 5.22 (1H, ddd, J = 13.7, 6.7, 2.9 Hz), 5.38 (2H, s), 6.78 (1H, s), 6.92 (1H, s), 7.34 (1H, s), 8.22 (2H, dd, J = 15.2, 8.2 Hz). |
| I-178 | 1H-NMR (CDCl3) δ: 1.38 (3H, d, J = 6.8 Hz), 2.37-2.44 (1H, m), 2.62-2.82 (3H, m), 2.85-2.93 (1H, m), 3.08-3.16 (1H, m), 3.88 (1H, dd, J = 13.2, 6.8 Hz), 4.20-4.31 (3H, m), 4.57-4.60 (1H, m), 4.75 (1H, d, J = 13.7 Hz), 4.91 (1H, dd, J = 14.6, 6.2 Hz), 5.09 (2H, s), 5.20 (1H, q, J = 6.9 Hz), 6.66 (1H, s), 7.32-7.38 (5H, m), 8.18 (2H, dd, J = 19.0, 7.7 Hz). |
| I-181 | 1H-NMR (CDCl3) δ: 1.40 (3H, d, J = 6.8 Hz), 2.37-2.44 (1H, m), 2.60-2.95 (4H, m), 3.08-3.15 (1H, m), 3.84-3.91 (4H, m), 4.23-4.33 (3H, m), 4.56-4.60 (1H, m), 4.77 (1H, d, J = 14.9 Hz), 4.91 (1H, dd, J = 14.8, 6.1 Hz), 5.09 (2H, dd, J = 15.1, 13.6 Hz), 5.19-5.23 (1H, m), 6.72 (1H, s), 6.87 (1H, d, J = 1.9 Hz), 6.98 (1H, dd, J = 8.2, 1.8 Hz), 7.32 (1H, s), 7.44 (1H, d, J = 8.2 Hz), 8.15-8.23 (2H, m). |
| I-184 | 1H-NMR (CDCl3) δ: 1.42 (3H, d, J = 6.8 Hz), 2.38-2.47 (1H, m), 2.62-2.84 (3H, m), 2.88-2.96 (1H, m), 3.11-3.17 (1H, m), 3.93 (1H, q, J = 6.6 Hz), 4.25-4.35 (3H, m), 4.62 (1H, dd, J = 14.0, 7.5 Hz), 4.79 (1H, dd, J = 14.8, 2.9 Hz), 4.92 (1H, dd, J = 14.9, 6.2 Hz), 5.12-5.24 (3H, m), 6.52 (1H, t, J = 73.2 Hz), 6.74 (1H, s), 6.89 (1H, dd, J = 10.6, 2.2 Hz), 6.97 (1H, d, J = 8.7 Hz), 7.34 (1H, s), 7.57 (1H, t, J = 8.3 Hz), 8.22 (2H, dd, J = 14.8, 8.3 Hz). |
| I-187 | 1H-NMR (CDCl3) δ: 1.38 (3H, d, J = 6.8 Hz), 2.38-2.44 (1H, m), 2.62-2.83 (3H, m), 2.86-2.93 (1H, m), 3.10-3.14 (1H, m), 3.89 (1H, dd, J = 13.6, 6.3 Hz), 4.21-4.32 (3H, m), 4.55-4.61 (1H, m), 4.76 (1H, d, J = 14.3 Hz), 4.91 (1H, dd, J = 15.1, 6.0 Hz), 5.09 (2H, s), 5.21 (1H, dd, J = 12.2, 7.5 Hz), 6.68 (1H, s), 7.07 (2H, t, J = 8.7 Hz), 7.33 (1H, s), 7.40 (2H, dd, J = 8.3, 5.5 Hz), 8.17-8.23 (2H, m). |
| I-188 | 1H-NMR (CDCl3) δ: 1.45 (3H, d, J = 6.8 Hz), 2.39-2.48 (1H, m), 2.61-2.68 (1H, m), 2.73-2.95 (3H, m), 3.10-3.17 (1H, m), 3.94 (1H, q, J = 6.7 Hz), 4.25-4.37 (3H, m), 4.63 (1H, dd, J = 13.9, 7.9 Hz), 4.80 (1H, dd, J = 14.8, 3.0 Hz), 4.93 (1H, dd, J = 15.0, 6.2 Hz), 5.08-5.15 (2H, m), 5.24 (1H, ddd, J = 13.7, 7.1, 3.1 Hz), 6.70 (2H, t, J = 8.0 Hz), 6.84 (1H, s), 7.30 (1H, s), 8.22 (2H, dd, J = 13.8, 8.2 Hz). |
| I-189 | 1H-NMR (DMSO-D6) δ: 1.34 (3H, d, J = 6.8 Hz), 2.30-2.38 (1H, m), 2.56-2.67 (2H, m), 2.76-2.88 (2H, m), 2.98-3.05 (1H, m), 3.91-3.98 (4H, m), 4.08 (2H, t, J = 14.4 Hz), 4.28-4.30 (1H, m), 4.45 (1H, dd, J = 13.5, 7.7 Hz), 4.64 (1H, dd, J = 15.0, 2.6 Hz), 4.75 (1H, dd, J = 15.2, 6.8 Hz), 5.07 (1H, ddd, J = 13.9, 6.8, 2.6 Hz), 5.24 (2H, dd, J = 16.2, 12.4 Hz), 7.20 (1H, s), 7.27 (1H, s), 7.34-7.38 (2H, m), 7.50 (1H, dd, J = 9.9, 1.9 Hz), 7.57 (1H, t, J = 8.2 Hz), 7.88 (1H, s). |
| I-190 | 1H-NMR (DMSO-D6) δ: 1.33 (3H, d, J = 6.7 Hz), 2.33-2.42 (1H, m), 2.60-2.86 (4H, m), 3.01-3.03 (1H, m), 3.75 (3H, s), 3.94 (1H, dd, J = 12.9, 6.3 Hz), 4.10 (2H, dd, J = 15.8, 14.2 Hz), 4.29-4.36 (1H, m), 4.48 (1H, dd, J = 14.2, 7.1 Hz), 4.72 (1H, dd, J = 15.3, 2.8 Hz), 4.87 (1H, dd, J = 15.6, 7.3 Hz), 5.08-5.16 (3H, m), 6.95 (2H, d, J = 8.7 Hz), 7.13 (1H, s), 7.36 (3H, d, J = 8.8 Hz), 7.46 (1H, d, J = 8.4 Hz), 7.64 (1H, t, J = 7.3 Hz). |

TABLE 69

| | |
|---|---|
| I-191 | 1H-NMR (DMSO-D6) δ: 1.33 (3H, d, J = 6.7 Hz), 2.33-2.41 (1H, m), 2.62-2.89 (4H, m), 2.98-3.06 (1H, m), 3.96 (1H, dd, J = 13.2, 6.5 Hz), 4.10 (2H, dd, J = 15.6, 14.1 Hz), 4.29-4.36 (1H, m), 4.47 (1H, dd, J = 14.2, 7.0 Hz), 4.72 (1H, dd, J = 15.6, 2.7 Hz), 4.86 (1H, dd, J = 15.2, 7.2 Hz), 5.09 (1H, dd, J = 14.9, 8.4 Hz), 5.30 (2H, t, J = 14.1 Hz), 7.14 (1H, s), 7.40 (1H, s), 7.46 (1H, d, J = 8.5 Hz), 7.52 (1H, d, J = 8.5 Hz), 7.65 (1H, t, J = 7.4 Hz), 8.04 (1H, dd, J = 8.4, 2.5 Hz), 8.64 (1H, d, J = 2.4 Hz). |
| I-193 | 1H-NMR (DMSO-D6) δ: 1.33 (3H, d, J = 6.7 Hz), 2.33-2.41 (1H, m), 2.61-2.87 (5H, m), 3.01-3.04 (1H, m), 3.94 (1H, q, J = 6.3 Hz), 4.10 (2H, dd, J = 16.8, 14.0 Hz), 4.31-4.34 (1H, m), 4.47 (1H, dd, J = 14.6, 7.0 Hz), 4.72 (1H, dd, J = 16.2, 3.1 Hz), 4.87 (1H, dd, J = 15.2, 7.3 Hz), 5.09 (1H, dd, J = 12.9, 8.4 Hz), 5.22 (2H, dd, J = 16.6, 12.6 Hz), 7.12 (1H, s), 7.37 (1H, s), 7.44-7.49 (6H, m), 7.66 (1H, dd, J = 8.2, 6.9 Hz). |
| I-194 | 1H-NMR (DMSO-D6) δ: 1.33 (3H, d, J = 6.7 Hz), 2.30 (3H, s), 2.33-2.42 (1H, m), 2.62-2.87 (4H, m), 3.00-3.03 (1H, m), 3.94 (1H, dd, J = 12.3, 5.9 Hz), 4.10 (2H, t. J = 15.1 Hz), 4.31-4.34 (1H, m), 4.48 (1H, dd, J = 14.1, 7.3 Hz), 4.72 (1H, dd, J = 15.4, 2.7 Hz), 4.86 (1H, dd, J = 15.1, 7.3 Hz), 5.08-5.19 (3H, m), 7.12 (1H, s), 7.19 (2H, d, J = 7.9 Hz), 7.30-7.36 (3H, m), 7.45 (1H, d, J = 8.5 Hz), 7.64 (1H, t, J = 7.3 Hz). |
| I-197 | 1H-NMR (DMSO-D6) δ: 1.36 (3H, d, J = 6.7 Hz), 2.35-2.41 (1H, m), 2.62-2.90 (4H, m), 3.02-3.05 (1H, m), 3.99 (1H, dd, J = 11.8, 5.3 Hz), 4.11 (2H, dd, J = 17.3, 14.1 Hz), 4.32-4.35 (1H, m), 4.48 (1H, dd, J = 13.6, 7.6 Hz), 4.73 (1H, dd, J = 15.4, 2.4 Hz), 4.87 (1H, dd, J = 15.3, 7.0 Hz), 5.09 (1H, dd, J = 13.9, 8.0 Hz), 5.25 (2H, dd, J = 16.9, 12.5 Hz), 7.18 (1H, s), 7.37-7.42 (3H, m), 7.46 (1H, d, J = 8.4 Hz), 7.50-7.53 (1H, m), 7.60-7.66 (2H, m). |
| I-198 | 1H-NMR (DMSO-D6) δ: 1.36 (3H, d, J = 6.7 Hz), 2.35-2.41 (1H, m), 2.65-2.86 (4H, m), 3.00-3.07 (1H, m), 3.97 (1H, q, J = 6.7 Hz), 4.10 (2H, dd, J = 15.9, 14.1 Hz), 4.31-4.35 (1H, m), 4.48 (1H, dd, J = 14.1, 7.0 Hz), 4.72 (1H, dd, J = 15.1, 3.3 Hz), 4.86 (1H, dd, J = 15.4, 7.2 Hz), 5.09 (1H, dd, J = 15.7, 8.3 Hz), 5.22 (2H, dd, J = 16.4, 11.9 Hz), 7.15 (1H, td, J = 8.4, 1.9 Hz), 7.21 (1H, s), 7.31 (1H, dt, J = 13.8, 5.2 Hz), 7.36 (1H, s), 7.43 (1H, d, J = 7.9 Hz), 7.60 (2H, dd, J = 15.2, 8.4 Hz). |
| I-200 | 1H-NMR (DMSO-D6) δ: 1.36 (3H, d, J = 6.8 Hz), 2.33-2.42 (1H, m), 2.62-2.90 (4H, m), 3.00-3.07 (1H, m), 3.98 (1H, dd, J = 12.7, 6.1 Hz), 4.08-4.15 (2H, m), 4.30-4.37 (1H, m), 4.48 (1H, dd, J = 13.9, 7.3 Hz), 4.72 (1H, dd, J = 15.2, 2.6 Hz), 4.87 (1H, dd, J = 15.2, 7.2 Hz), 5.09 (1H, dd, J = 14.5, 7.8 Hz), 5.25 (2H, dd, J = 16.9, 12.5 Hz), 7.22 (1H, s), 7.38 (1H, s), 7.45 (1H, d, J = 8.4 Hz), 7.56-7.66 (2H, m), 7.73 (1H, dd, J = 9.3, 6.1 Hz). |

TABLE 69-continued

| | |
|---|---|
| I-201 | 1H-NMR (DMSO-D6) δ: 1.36 (3H, d, J = 6.7 Hz), 2.34-2.41 (1H, m), 2.65-2.71 (2H, m), 2.79-2.90 (2H, m), 3.00-3.07 (1H, m), 3.99 (1H, q, J = 6.7 Hz), 4.07-4.15 (2H, m), 4.30-4.37 (1H, m), 4.48 (1H, dd, J = 13.7, 7.6 Hz), 4.73 (1H, dd, J = 15.1, 2.4 Hz), 4.87 (1H, dd, J = 15.2, 7.0 Hz), 5.09 (1H, q, J = 6.9 Hz), 5.24 (2H, dd, J = 17.9, 12.7 Hz), 7.19 (1H, s), 7.39 (1H, s), 7.46 (1H, d, J = 8.3 Hz), 7.52 (1H, dd, J = 8.3, 2.1 Hz), 7.60-7.67 (2H, m), 7.70 (1H, d, J = 2.0 Hz). |
| I-202 | 1H-NMR (DMSO-D6) δ: 1.33 (3H, d, J = 6.8 Hz), 2.32-2.36 (1H, m), 2.59-2.65 (2H, m), 2.77-2.85 (2H, m), 2.99-3.04 (1H, m), 3.75 (3H, s), 3.93 (1H, q, J = 6.7 Hz), 4.11 (2H, dd, J = 18.8, 13.9 Hz), 4.30-4.33 (1H, m), 4.46 (1H, dd, J = 13.4, 7.7 Hz), 4.69 (1H, dd, J = 15.0, 2.6 Hz), 4.82 (1H, dd, J = 15.2, 7.1 Hz), 5.07-5.14 (3H, m), 6.94 (2H, d, J = 8.7 Hz), 7.13 (1H, s), 7.35-7.37 (3H, m), 7.51 (1H, d, J = 11.4 Hz), 8.12 (1H, s). |

TABLE 70

| | |
|---|---|
| I-203 | 1H-NMR (DMSO-D6) δ: 1.32 (3H, d, J = 6.8 Hz), 2.31-2.37 (1H, m), 2.60-2.65 (2H, m), 2.76-2.88 (2H, m), 2.99-3.04 (1H, m), 3.94 (1H, q, J = 6.6 Hz), 4.11 (2H, dd, J = 17.7, 13.9 Hz), 4.27-4.34 (1H, m), 4.45 (1H, dd, J = 13.4, 7.9 Hz), 4.69 (1H, dd, J = 15.0, 2.6 Hz), 4.81 (1H, dd, J = 15.1, 7.0 Hz), 5.08 (1H, ddd, J = 14.0, 7.0, 2.6 Hz), 5.29 (2H, s), 7.14 (1H, s), 7.40 (1H, s), 7.49-7.54 (2H, m), 8.03 (1H, dd, J = 8.4, 2.5 Hz), 8.11 (1H, s), 8.64 (1H, d, J = 2.3 Hz). |
| I-205 | 1H-NMR (DMSO-D6) δ: 1.32 (3H, d, J = 6.8 Hz), 2.31-2.36 (1H, m), 2.58-2.66 (2H, m), 2.77-2.87 (2H, m), 3.01-3.03 (1H, m), 3.92 (1H, dd, J = 12.9, 6.0 Hz), 4.11 (2H, dd, J = 20.0, 13.9 Hz), 4.29-4.32 (1H, m), 4.45 (1H, dd, J = 13.5, 7.7 Hz), 4.69 (1H, dd, J = 15.0, 2.4 Hz), 4.82 (1H, dd, J = 15.2, 7.0 Hz), 5.08 (1H, ddd, J = 14.1, 6.8, 2.4 Hz), 5.22 (2H, dd, J = 15.6, 12.6 Hz), 7.12 (1H, s), 7.37 (1H, s), 7.43-7.53 (5H, m), 8.14 (1H, s). |
| I-206 | 1H-NMR (DMSO-D6) δ: 1.32 (3H, d, J = 6.7 Hz), 2.29-2.38 (4H, m), 2.59-2.65 (2H, m), 2.76-2.87 (2H, m), 2.97-3.05 (1H, m), 3.92 (1H, dd, J = 13.0, 6.1 Hz), 4.11 (2H, dd, J = 18.4, 13.9 Hz), 4.29-4.33 (1H, m), 4.45 (1H, dd, J = 13.5, 7.8 Hz), 4.69 (1H, dd, J = 15.2, 2.6 Hz), 4.81 (1H, dd, J = 15.3, 6.9 Hz), 5.06-5.18 (3H, m), 7.12-7.20 (3H, m), 7.30-7.36 (3H, m), 7.51 (1H, d, J = 12.3 Hz), 8.11 (1H, s). |
| I-209 | 1H-NMR (DMSO-D6) δ: 1.35 (3H, d, J = 6.7 Hz), 2.32-2.36 (1H, m), 2.59-2.68 (2H, m), 2.78-2.88 (2H, m), 3.00-3.06 (1H, m), 3.97 (1H, dd, J = 12.8, 6.0 Hz), 4.11 (2H, dd, J = 18.5, 13.9 Hz), 4.30-4.33 (1H, m), 4.46 (1H, dd, J = 13.5, 7.5 Hz), 4.69 (1H, dd, J = 15.0, 2.4 Hz), 4.81 (1H, dd, J = 15.3, 7.0 Hz), 5.09 (1H, ddd, J = 14.2, 7.0, 1.6 Hz), 5.25 (2H, dd, J = 16.3, 12.6 Hz), 7.19 (1H, s), 7.38-7.41 (3H, m), 7.48-7.53 (2H, m), 7.58-7.62 (1H, m), 8.11 (1H, s). |
| I-211 | 1H-NMR (DMSO-D6) δ: 1.35 (3H, d, J = 6.7 Hz), 2.34-2.38 (1H, m), 2.60-2.67 (2H, m), 2.79-2.88 (2H, m), 3.02-3.05 (1H, m), 3.97 (1H, q, J = 6.6 Hz), 4.11 (2H, dd, J = 18.9, 13.9 Hz), 4.30-4.33 (1H, m), 4.46 (1H, dd, J = 13.3, 7.9 Hz), 4.69 (1H, dd, J = 14.6, 2.2 Hz), 4.81 (1H, dd, J = 14.8, 7.0 Hz), 5.08 (1H, ddd, J = 13.9, 6.7, 2.8 Hz), 5.24 (2H, dd, J = 16.8, 12.9 Hz), 7.19 (1H, s), 7.39 (1H, s), 7.47-7.54 (2H, m), 7.61 (1H, d, J = 8.4 Hz), 7.70 (1H, d, J = 2.0 Hz), 8.09 (1H, s). |
| I-213 | 1H-NMR (DMSO-D6) δ: 1.35 (3H, d, J = 6.7 Hz), 2.30-2.39 (1H, m), 2.58-2.67 (2H, m), 2.78-2.87 (2H, m), 3.00-3.07 (1H, m), 3.96 (1H, q, J = 6.5 Hz), 4.12 (2H, dd, J = 20.5, 13.9 Hz), 4.30-4.33 (1H, m), 4.46 (1H, dd, J = 13.7, 7.8 Hz), 4.69 (1H, dd, J = 15.2, 2.5 Hz), 4.82 (1H, dd, J = 15.1, 7.0 Hz), 5.08 (1H, ddd, J = 13.9, 6.8, 2.8 Hz), 5.24 (2H, dd, J = 16.0, 12.7 Hz), 7.22 (1H, s), 7.38 (1H, s), 7.51 (1H, d, J = 11.4 Hz), 7.58 (1H, dd, J = 9.4, 6.3 Hz), 7.73 (1H, dd, J = 9.2, 6.1 Hz), 8.11 (1H, s). |
| I-214 | 1H-NMR (DMSO-D6) δ: 1.36 (3H, d, J = 6.7 Hz), 2.34-2.41 (1H, m), 2.65-2.71 (2H, m), 2.79-2.90 (2H, m), 3.00-3.07 (1H, m), 3.99 (1H, q, J = 6.7 Hz), 4.11 (2H, dd, J = 17.7, 14.1 Hz), 4.32-4.35 (1H, m), 4.48 (1H, dd, J = 13.7, 7.6 Hz), 4.73 (1H, dd, J = 15.1, 2.4 Hz), 4.87 (1H, dd, J = 15.2, 7.0 Hz), 5.09 (1H, q, J = 6.9 Hz), 5.24 (2H, dd, J = 17.9, 12.7 Hz), 7.19 (1H, s), 7.39 (1H, s), 7.46 (1H, d, J = 8.3 Hz), 7.52 (1H, dd, J = 8.3, 2.1 Hz), 7.60-7.67 (2H, m), 7.70 (1H, d, J = 2.0 Hz). |

TABLE 71

| | |
|---|---|
| I-215 | 1H-NMR (DMSO-D6) δ: 1.35 (3H, d, J = 6.7 Hz), 2.31-2.39 (1H, m), 2.57-2.67 (2H, m), 2.78-2.87 (2H, m), 2.99-3.06 (1H, m), 3.97 (1H, dd, J = 12.9, 6.1 Hz), 4.10 (2H, dd, J = 19.7, 13.7 Hz), 4.30-4.33 (1H, m), 4.46 (1H, dd, J = 13.6, 7.8 Hz), 4.67 (1H, dd, J = 15.2, 2.5 Hz), 4.79 (1H, dd, J = 15.0, 6.8 Hz), 5.08 (1H, ddd, J = 14.2, 7.2, 2.9 Hz), 5.31 (2H, dd, J = 15.8, 12.8 Hz), 7.06 (1H, t, J = 55.7 Hz), 7.21 (1H, s), 7.38 (1H, s), 7.49 (2H, t, J = 7.5 Hz), 7.64-7.71 (2H, m), 7.81 (1H, dd, J = 8.5, 1.3 Hz), 8.25 (1H, s). |
| I-216 | 1H-NMR (DMSO-D6) δ: 2.34-2.42 (1H, m), 2.59-2.67 (1H, m), 2.79-2.86 (4H, m), 3.70 (2H, s), 4.00 (1H, d, J = 13.6 Hz), 4.15 (1H, d, J = 13.6 Hz), 4.35 (1H, dt, J = 10.9, 4.5 Hz), 4.46 (1H, dd, J = 13.7, 7.7 Hz), 4.64-4.68 (1H, m) 4.81 (1H, dd, J = 15.4, 7.4 Hz), 5.02-5.08 (1H, m), 5.20 (2H, s), 7.06 (1H, t, J = 55.0 Hz), 7.20 (1H, s), 7.37 (1H, s), 7.44 (2H, d, J = 7.3 Hz), 7.67 (1H, d, J = 8.4 Hz), 7.82 (1H, dd, J = 8.4, 1.5 Hz), 8.27 (1H, s). |
| I-217 | 1H-NMR (DMSO-D6) δ: 2.34-2.42 (1H, m), 2.59-2.67 (1H, m), 2.79-2.86 (4H, m), 3.70 (2H, s), 4.00 (1H, d, J = 13.4 Hz), 4.15 (1H, d, J = 13.6 Hz), 4.35 (1H, dt, J = 10.9, 4.5 Hz), 4.46 (1H, dd, J = 13.3, 7.9 Hz), 4.64-4.68 (1H, m), 4.80 (1H, dd, J = 15.2, 7.2 Hz), 5.02-5.08 (1H, m), 5.12 (2H, s), 7.13 (2H, d, J = 8.4 Hz), 7.19 (1H, s), 7.37 (1H, s), 7.38 (1H, t, J = 73.0 Hz), 7.67 (1H, d, J = 8.5 Hz), 7.82 (1H, dd, J = 8.5, 1.5 Hz), 8.26 (1H, s). |

TABLE 71-continued

| | |
|---|---|
| I-218 | 1H-NMR (DMSO-D6) δ: 1.37 (3H, d, J = 6.8 Hz), 2.30-2.39 (1H, m), 2.57-2.69 (2H, m), 2.74-2.85 (2H, m), 2.96-3.01 (1H, m), 3.35 (1H, d, J = 6.5 Hz), 4.09 (1H, d, J = 13.8 Hz), 4.20 (1H, d, J = 13.8 Hz), 4.29 (1H, dt, J = 10.9, 4.5 Hz), 4.45 (1H, dd, J = 13.6, 7.7 Hz), 4.68 (1H, dd, J = 15.3 2.9 Hz), 4.77 (1H, dd, J = 15.3, 6.7 Hz), 5.06-5.12 (1H, m), 5.39 (1H, d, J = 12.7 Hz), 5.47 (1H, d, J = 12.7 Hz), 7.20 (2H, t, J = 8.8 Hz), 7.47 (2H, dd, J = 8.5, 5.6 Hz), 7.66 (1H, d, J = 8.4 Hz), 7.82 (1H, dd, J = 8.4, 1.4 Hz), 7.89 (1H, s), 8.26 (1H, s). |
| I-219 | 1H-NMR (DMSO-D6) δ: 1.36 (3H, d, J = 6.7 Hz), 2.33-2.42 (1H, m), 2.63-2.73 (2H, m), 2.78-2.90 (2H, m), 3.00-3.07 (1H, m), 3.88 (1H, d, J = 6.6 Hz), 4.11 (2H, dd, J = 18.4, 13.9 Hz), 4.32-4.35 (1H, m), 4.48 (1H, q, J = 7.1 Hz), 4.73 (1H, dd, J = 15.2, 2.7 Hz), 4.87 (1H, dd, J = 15.4 =, 7.0 Hz), 5.09 (1H, dd, J = 14.3, 7.2 Hz), 5.36 (2H, dd, J = 18.2, 13.3 Hz), 7.22 (1H, s), 7.39 (1H, s), 7.48 (1H, d, J = 8.5 Hz), 7.66 (1H, dd, J = 8.4, 6.8 Hz), 7.73 (1H, t, J = 7.5 Hz), 7.80 (1H, dd, J = 7.9, 1.1 Hz, 7.93 (1H, d, J = 9.9 Hz). |
| I-220 | 1H-NMR (DMSO-D6) δ: 1.37 (3H, d, J = 6.8 Hz), 2.33-2.37 (1H, m), 2.58-2.68 (2H, m), 2.73-2.84 (2H, m), 2.97-3.00 (1H, m), 3.88 (1H, dd, J = 13.4, 6.5 Hz), 4.08 (1H, d, J = 13.8 Hz), 4.20 (1H, d, J = 13.9 Hz), 4.28-4.30 (1H, m), 4.45 (1H, dd, J = 13.2, 8.1 Hz), 4.72 (2H, ddd, J = 31.8, 15.3, 4.8 Hz), 5.09 (1H, ddd, J = 14.0, 6.6, 2.9 Hz), 5.44 (1H, d, J = 12.9 Hz), 5.54 (1H, d, J = 12.9 Hz), 7.26 (1H, td, J = 8.5, 2.6 Hz), 7.50 (1H, dd, J = 8.8, 2.6 Hz), 7.58 (1H, dd, J = 8.7, 6.3 Hz), 7.66 (1H, d, J = 8.4 Hz), 7.81 (1H, dd, J = 8.5, 1.4 Hz), 7.90 (1H, s), 8.25 (1H, s). |
| I-221 | 1H-NMR (DMSO-D6) δ: 1.31 (3H, d, J = 6.7 Hz), 2.30-2.39 (1H, m), 2.58-2.65 (2H, m), 2.74-2.83 (2H, m), 2.98-3.02 (1H, m), 3.82-3.91 (1H, m), 4.02-4.12 (2H, m), 4.29-4.34 (1H, m), 4.45 (1H, dd, J = 13.6, 7.7 Hz), 4.67 (1H, dd, J = 15.0, 2.3 Hz), 4.79 (1H, dd, J = 15.1, 7.0 Hz), 5.08 (1H, ddd, J = 13.9, 6.9, 2.7 Hz), 5.25-5.32 (2H, m), 7.08 (1H, s), 7.20 (1H, s), 7.65 (1H, d, J = 8.4 Hz), 7.78-7.81 (3H, m), 7.92 (1H, d, J = 9.9 Hz), 3.25 (1H, s). |

TABLE 72

| | |
|---|---|
| I-222 | 1H-NMR (DMSO-D6) δ: 2.36-2.44 (1H, m), 2.65-2.74 (1H, m), 2.83-2.85 (4H, m), 3.68 (1H, d, J = 17.2 Hz), 3.74 (1H, d, J = 16.9 Hz), 4.04 (1H, d, J = 13.7 Hz), 4.17 (1H, d, J = 13.7 Hz), 4.36 (1H, dt, J = 11.1, 4.4 Hz), 4.47 (1H, dd, J = 14.6, 6.8 Hz), 4.66-4.70 (1H, m), 4.86 (1H, dd, J = 15.4, 7.5 Hz), 5.03-5.09 (1H, m), 5.42 (2H, s), 7.31 (1H, dd, J = 8.2, 1.8 Hz), 7.45-7.54 (3H, m), 7.67 (1H, t. J = 7.6 Hz), 7.93 (1H, s). |
| I-223 | 1H-NMR (DMSO-D6) δ: 1.37 (3H, d, J = 6.8 Hz), 2.33-2.41 (1H, m), 2.64-2.70 (2H, m), 2.76-2.85 (2H, m), 2.96-3.01 (1H, m), 3.86 (1H, dd, J = 13.2, 6.2 Hz), 4.09 (1H, d, J = 13.8 Hz), 4.21 (1H, d, J = 13.9 Hz), 4.28-4.31 (1H, m), 4.47 (1H, dd, J = 13.2, 7.9 Hz), 4.74 (1H, dd, J = 15.6, 3.1 Hz), 4.83 (1H, dd, J = 15.4, 6.8 Hz), 5.10 (1H, ddd, J = 13.5, 6.7, 2.9 Hz), 5.41 (1H, d, J = 13.1 Hz), 5.49 (1H, d, J = 12.9 Hz), 7.44 (4H, s), 7.48 (1H, d, J = 8.5 Hz), 7.66 (1H, t. J = 7.5 Hz), 7.90 (1H, s). |
| I-226 | 1H-NMR (DMSO-D6) δ: 1.31 (3H, d, J = 6.7 Hz), 2.31-2.36 (1H, m), 2.57-2.66 (2H, m), 2.75-2.86 (2H, m), 2.98-3.03 (1H, m), 3.89 (1H, q, J = 6.4 Hz), 3.94 (3H, s), 4.06 (2H, s), 4.27-4.29 (1H, m), 4.44 (1H, dd, J = 13.9, 7.6 Hz), 4.61 (1H, dd, J = 15.2, 2.6 Hz), 4.72 (1H, dd, J = 15.4, 6.4 Hz), 5.06 (1H, ddd, J = 14.0, 6.8, 2.7 Hz), 5.22 (2H, dd, J = 15.0, 12.5 Hz), 7.11 (1H, s), 7.28 (1H, s), 7.36 (1H, s), 7.46 (4H, dd, J = 11.7, 9.0 Hz), 7.81 (1H, s). |
| I-227 | 1H-NMR (DMSO-D6) δ: 1.31 (3H, d, J = 6.8 Hz), 2.29-2.37 (1H, m), 2.29 (3H, s), 2.59-2.67 (2H, m), 2.75-2.85 (2H, m), 2.97-3.02 (1H, m), 3.88-3.96 (4H, m), 4.06 (2H, s), 4.27-4.30 (1H, m), 4.44 (1H, dd, J = 13.6, 7.8 Hz), 4.62 (1H, dd, J = 15.5, 3.1 Hz), 4.71 (1H, dd, J = 15.4, 6.7 Hz), 5.06 (1H, ddd, J = 13.9, 7.0, 2.8 Hz), 5.16 (2H, dd, J = 15.1, 12.3 Hz), 7.12 (1H, s), 7.19 (2H, d, J = 7.9 Hz), 7.27-7.35 (4H, m), 7.80 (1H, s). |
| I-229 | 1H-NMR (DMSO-D6) δ: 1.33 (3H, d, J = 6.7 Hz), 2.32-2.36 (1H, m), 2.61-2.66 (2H, m), 2.77-2.84 (2H, m), 2.99-3.02 (1H, m), 3.84 (3H, s), 3.92-3.96 (4H, m), 4.06 (2H, s), 4.28-4.31 (1H, m), 4.45 (1H, dd, J = 13.4, 7.7 Hz), 4.62 (1H, dd, J = 15.1, 2.7 Hz), 4.73 (1H, dd, J = 15.4, 6.7 Hz), 5.06-5.14 (3H, m), 7.05 (1H, dd, J = 8.0, 1.9 Hz), 7.10-7.15 (2H, m), 7.28 (1H, s), 7.35 (1H, s), 7.40 (1H, d, J = 8.2 Hz), 7.83 (1H, s). |
| I-231 | 1H-NMR (DMSO-D6) δ: 1.35 (3H, d, J = 6.7 Hz), 2.29-2.38 (1H, m), 2.59-2.65 (2H, m), 2.76-2.86 (2H, m), 3.00-3.03 (1H, m), 3.92-3.95 (4H, m), 4.04-4.09 (2H, m), 4.28-4.31 (1H, m), 4.45 (1H, dd, J = 13.6, 7.8 Hz), 4.64 (1H, dd, J = 15.0, 2.4 Hz), 4.74 (1H, dd, J = 15.2, 6.7 Hz), 5.07 (1H, ddd, J = 14.1, 7.0, 2.9 Hz), 5.22 (2H, dd, J = 15.7, 12.1 Hz), 7.15 (1H, td, J = 8.5, 2.1 Hz), 7.20 (1H, s), 7.28-7.33 (2H, m), 7.36 (1H, s), 7.60 (1H, dd, J = 15.2, 8.5 Hz), 7.85 (1H, s). |
| I-232 | 1H-NMR (DMSO-D6) δ: 1.35 (3H, d, J = 6.8 Hz), 2.29-2.38 (1H, m), 2.59-2.67 (2H, m), 2.76-2.87 (2H, m), 3.00-3.02 (1H, m), 3.93-3.95 (4H, m), 4.07 (2H, s), 4.28-4.30 (1H, m), 4.45 (1H, dd, J = 13.6, 7.7 Hz), 4.63 (1H, dd, J = 15.0, 2.3 Hz), 4.72 (1H, dd, J = 15.0, 6.7 Hz), 5.07 (1H, ddd, J = 13.1, 6.7, 2.3 Hz), 5.24 (2H, dd, J = 16.1, 12.7 Hz), 7.18 (1H, s), 7.28 (1H, s), 7.38 (1H, s), 7.52 (1H, dd, J = 8.3, 2.1 Hz), 7.61 (1H, d, J = 8.4 Hz), 7.70 (1H, d, J = 2.1 Hz), 7.81 (1H, s). |
| I-233 | 1H-NMR (DMSO-D6) δ: 1.35 (3H, d, J = 6.8 Hz), 2.33-2.36 (1H, m), 2.60-2.66 (2H, m), 2.77-2.84 (2H, m), 3.00-3.03 (1H, m), 3.92-3.94 (4H, m), 4.07 (2H, s), 4.27-4.32 (1H, m), 4.45 (1H, dd, J = 14.5, 6.7 Hz), 4.63 (1H, dd, J = 14.9, 2.6 Hz), 4.73 (1H, dd, J = 15.2, 6.8 Hz), 5.05-5.08 (1H, m), 5.22 (2H, dd, J = 15.2, 12.5 Hz), 7.08-7.50 (6H, m), 7.60 (1H, t. J = 8.6 Hz), 7.82 (1H, s). |

TABLE 73

| | |
|---|---|
| I-234 | 1H-NMR (DMSO-D6) δ: 1.35 (3H, d, J = 6.7 Hz), 2.33-2.35 (1H, m), 2.59-2.67 (2H, m), 2.79-2.86 (2H, m), 3.00-3.04 (1H, m), 3.90-3.95 (4H, m), 4.06 (2H, s), 4.28-4.30 (1H, m), 4.45 (1H, dd, J = 13.9, 7.2 Hz), 4.61 (1H, dd, J = 15.4, 3.1 Hz), 4.71 (1H, dd, J = 15.2, 6.5 Hz), 5.07 (1H, ddd, J = 14.0, 6.5, 2.7 Hz), 5.24 (2H, dd, J = 14.9, 12.4 Hz), 7.22 (1H, s), 7.28 (1H, d, J = 1.0 Hz), 7.38 (1H, s), 7.58 (1H, dd, J = 9.3, 6.3 Hz), 7.73 (1H, dd, J = 9.2, 6.0 Hz), 7.78 (1H, s). |
| I-235 | 1H-NMR (DMSO-D6) δ: 1.34 (3H, d, J = 6.7 Hz), 2.33-2.33 (1H, m), 2.58-2.66 (2H, m), 2.78-2.86 (2H, m), 3.00-3.04 (1H, m), 3.90-3.93 (4H, m), 4.05 (2H, s), 4.26-4.31 (1H, m), 4.45 (1H, dd, J = 13.6, 7.8 Hz), 4.59 (1H, dd, J = 15.6, 2.8 Hz), 4.68 (1H, dd, J = 15.2, 6.1 Hz), 5.07 (1H, ddd, J = 14.5, 7.6, 2.5 Hz), 5.35 (2H, dd, J = 15.7, 13.9 Hz), 7.21 (1H, s), 7.30 (1H, s), 7.38 (1H, s), 7.70-7.75 (2H, m), 7.79 (1H, dd, J = 8.1, 1.2 Hz), 7.92 (1H, dd, J = 9.9, 1.2 Hz). |
| I-236 | 1H-NMR (DMSO-D6) δ: 1.31 (3H, d, J = 6.7 Hz), 2.30-2.34 (1H, m), 2.60-2.67 (2H, m), 2.75-2.86 (2H, m), 2.97-3.02 (1H, m), 3.87-3.94 (4H, m), 4.06 (2H, s), 4.27-4.30 (1H, m), 4.44 (1H, dd, J = 13.4, 8.0 Hz), 4.62 (1H, dd, J = 14.9, 2.8 Hz), 4.71 (1H, dd, J = 15.2, 6.8 Hz), 5.06 (1H, ddd, J = 14.0, 6.3, 2.6 Hz), 5.20 (2H, dd, J = 14.7, 12.0 Hz), 7.12 (1H, s), 7.23 (2H, t. J = 8.9 Hz), 7.28 (1H, d, J = 1.0 Hz), 7.36 (1H, s), 7.47 (2H, dd, J = 8.6, 5.7 Hz), 7.80 (1H, s). |
| I-237 | 1H-NMR (DMSO-D6) δ: 1.37 (3H, d, J = 6.7 Hz), 2.31-2.34 (1H, m), 2.59-2.66 (2H, m), 2.76-2.84 (2H, m), 2.99-3.03 (1H, m), 3.94 (4H, s), 4.07 (2H, s), 4.27-4.32 (1H, m), 4.45 (1H, dd, J = 13.7, 7.5 Hz), 4.63 (1H, dd, J = 15.4, 2.8 Hz), 4.72 (1H, dd, J = 15.1, 7.0 Hz), 5.07 (1H, ddd, J = 14.3, 7.5, 3.3 Hz), 5.21 (2H, dd, J = 18.3, 11.5 Hz), 7.26 (2H, d, J = 15.2 Hz), 7.34 (1H, s), 7.46 (2H, d, J = 7.5 Hz), 7.81 (1H, s). |
| I-238 | 1H-NMR (DMSO-D6) δ: 1.37 (3H, d, J = 6.8 Hz), 2.32-2.37 (1H, m), 2.60-2.65 (2H, m), 2.75-2.87 (2H, m), 2.99-3.03 (1H, m), 3.93-3.95 (4H, m), 4.08 (2H, s), 4.28-4.31 (1H, m), 4.45 (1H, dd, J = 13.8, 7.8 Hz), 4.65 (1H, dd, J = 15.0, 2.9 Hz), 4.74 (1H, dd, J = 15.2, 6.6 Hz), 5.08 (1H, ddd, J = 14.0, 6.7, 2.5 Hz), 5.19 (2H, dd, J = 18.7, 11.3 Hz), 7.23-7.31 (4H, m), 7.34 (1H, s), 7.86 (1H, s). |
| I-239 | 1H-NMR (DMSO-D6) δ: 1.36 (3H, d, J = 6.8 Hz), 2.32-2.38 (1H, m), 2.60-2.66 (2H, m), 2.76-2.82 (2H, m), 2.97-3.01 (1H, m), 3.85 (1H, dd, J = 13.6, 6.4 Hz), 4.10 (1H, d, J = 13.6 Hz), 4.21 (1H, d, J = 14.2 Hz), 4.25-4.32 (1H, m), 4.45 (1H, dd, J = 13.4, 7.6 Hz), 4.74 (2H, ddd, J = 33.7, 15.0, 4.5 Hz), 5.09 (1H, ddd, J = 13.8, 7.1, 2.7 Hz), 5.41 (1H, d, J = 13.1 Hz), 5.49 (1H, d, J = 12.9 Hz), 7.44 (4H, s), 7.51 (1H, d, J = 11.4 Hz), 7.90 (1H, s), 8.12 (1H, s). |
| I-240 | 1H-NMR (DMSO-D6) δ: 1.34 (3H, d, J = 6.7 Hz), 2.33-2.41 (1H, m), 2.64-2.86 (4H, m), 2.95-3.00 (1H, m), 3.86 (1H, dd, J = 13.1, 6.3 Hz), 4.08 (1H, d, J = 14.1 Hz), 4.20 (1H, d, J = 14.1 Hz), 4.30 (1H, dt, J = 11.0, 4.5 Hz), 4.47 (1H, dd, J = 13.8, 7.4 Hz), 4.73 (1H, dd, J = 15.4, 2.9 Hz), 4.83 (1H, dd, J = 15.4, 6.9 Hz), 5.07-5.13 (1H, m), 5.54 (1H, d, J = 13.7 Hz), 5.63 (1H, d, J = 13.7 Hz), 7.49 (1H, d, J = 8.5 Hz), 7.64 (1H, d, J = 8.0 Hz), 7.68 (1H, d, J = 8.4 Hz), 7.73-7.75 (1H, m), 7.90-7.92 (2H, m). |
| I-241 | 1H-NMR (DMSO-D6) δ: 1.33 (3H, d, J = 6.8 Hz), 2.29-2.37 (1H, m), 2.57-2.85 (4H, m), 2.95-3.00 (1H, m), 3.86 (1H, q, J = 6.5 Hz), 4.10 (1H, d, J = 14.1 Hz), 4.20 (1H, d, J = 14.1 Hz), 4.29 (1H, dt, J = 10.9, 4.5 Hz), 4.45 (1H, dd, J = 13.7, 7.5 Hz), 4.70 (1H, dd, J = 15.3, 2.7 Hz), 4.79 (1H, dd, J = 15.3, 6.8 Hz), 5.05-5.11 (1H, m), 5.54 (1H, d, J = 13.7 Hz), 5.62 (1H, d, J = 13.7 Hz), 7.52 (1H, d, J = 11.3 Hz), 7.65 (1H, t, J = 7.6 Hz), 7.74 (1H, dd, J = 8.0, 1.3 Hz), 7.90-7.92 (2H, m), 8.15 (1H, s). |

TABLE 74

| | |
|---|---|
| I-242 | 1H-NMR (DMSO-D6) δ: 1.32 (3H, d, J = 6.8 Hz), 2.27-2.36 (1H, m), 2.56-2.85 (4H, m), 2.94-3.00 (1H, m), 3.83 (1H, q, J = 6.7 Hz), 3.96 (3H, s), 4.04 (1H, d, J = 13.8 Hz), 4.16 (1H, d, J = 13.8 Hz), 4.26 (1H, dt, J = 10.8, 4.5 Hz), 4.44 (1H, dd, J = 13.6, 7.9 Hz), 4.64 (1H, dd, J = 15.4, 2.9 Hz), 4.72 (1H, dd, J = 15.4, 6.5 Hz), 5.04-5.10 (1H, m), 5.54 (1H, d, J = 13.6 Hz), 5.62 (1H, d, J = 13.6 Hz), 7.27 (1H, d, J = 0.9 Hz), 7.65 (1H, t, J = 7.6 Hz), 7.74 (1H, dd, J = 7.9, 1.4 Hz), 7.89-7.92 (3H, m). |
| I-243 | 1H-NMR (DMSO-D6) δ: 1.37 (3H, d, J = 6.8 Hz), 2.33-2.41 (1H, m), 2.64-2.86 (4H, m), 2.96-3.01 (1H, m), 3.88 (1H, q, J = 6.5 Hz), 4.09 (1H, d, J = 14.1 Hz), 4.21 (1H, d, J = 14.1 Hz), 4.30 (1H, dt, J = 11.0, 4.5 Hz), 4.47 (1H, dd, J = 13.8, 7.5 Hz), 4.74 (1H, dd, J = 15.4, 3.1 Hz), 4.83 (1H, dd, J = 15.4, 6.8 Hz), 5.07-5.13 (1H, m), 5.46 (1H, d, J = 13.3 Hz), 5.55 (1H, d, J = 13.3 Hz), 7.46-7.54 (3H, m), 7.65-7.69 (2H, m), 7.92 (1H, s). |
| I-244 | 1H-NMR (DMSO-D6) δ: 1.36 (3H, d, J = 6.8 Hz), 2.29-2.37 (1H, m), 2.56-2.85 (4H, m), 2.95-3.00 (1H, m), 3.88 (1H, q, J = 6.4 Hz), 4.10 (1H, d, J = 13.9 Hz), 4.21 (1H, d, J = 13.9 Hz), 4.29 (1H, dt, J = 10.9, 4.5 Hz), 4.45 (1H, dd, J = 13.5, 7.8 Hz), 4.71 (1H, dd, J = 15.3, 2.6 Hz), 4.79 (1H, dd, J = 15.3, 6.6 Hz), 5.06-5.12 (1H, m), 5.46 (1H, d, J = 13.3 Hz), 5.55 (1H, d, J = 13.3 Hz), 7.46-7.55 (3H, m), 7.67 (1H, d, J = 2.0 Hz), 7.92 (1H, s), 8.14 (1H, s). |
| I-245 | 1H-NMR (DMSO-D6) δ: 1.38 (3H, d, J = 6.7 Hz), 2.33-2.41 (1H, m), 2.64-2.85 (4H, m), 2.97-3.02 (1H, m), 3.88 (1H, q, J = 6.4 Hz), 4.10 (1H, d, J = 14.1 Hz), 4.21 (1H, d, J = 14.1 Hz), 4.30 (1H, dt, J = 11.0, 4.5 Hz), 4.47 (1H, dd, J = 14.1, 7.3 Hz), 4.74 (1H, dd, J = 15.5, 3.1 Hz), 4.83 (1H, dd, J = 15.5, 6.9 Hz), 5.07-5.13 (1H, m), 5.43 (1H, d, J = 13.1 Hz), 5.51 (1H, d, J = 13.1 Hz), 7.47-7.54 (2H, m), 7.65-7.72 (2H, m), 7.92 (1H, s). |
| I-246 | 1H-NMR (DMSO-D6) δ: 1.37 (3H, d, J = 6.7 Hz), 2.29-2.38 (1H, m), 2.57-2.85 (4H, m), 2.96-3.01 (1H, m), 3.88 (1H, q, J = 6.6 Hz), 4.11 (1H, d, J = 14.1 Hz), 4.21 (1H, d, J = 14.1 Hz), 4.29 (1H, dt, J = 10.9, 4.5 Hz), 4.45 (1H, dd, J = 13.6, 7.8 Hz), 4.71 (1H, dd, J = 15.4, 2.7 Hz), 4.80 (1H, dd, J = 15.4, 7.0 Hz), 5.06-5.12 (1H, m), 5.43 (1H, d, J = 12.9 Hz), 5.51 (1H, d, J = 12.9 Hz), 7.50-7.54 (2H, m), 7.70 (1H, dd, J = 9.3, 6.1 Hz), 7.92 (1H, s), 8.15 (1H, d, J = 0.9 Hz). |
| I-249 | 1H-NMR (DMSO-D6) δ: 1.36 (3H, d, J = 6.7 Hz), 2.33-2.37 (1H, m), 2.59-2.69 (2H, m), 2.76-2.82 (2H, m), 2.96-2.99 (1H, m), 3.81-3.85 (1H, m), 4.07 (1H, d, J = 13.7 Hz), 4.19 (1H, d, J = 13.6 Hz), 4.25-4.32 (1H, m), 4.45 (1H, dd, J = 14.1, 7.3 Hz), 4.70 (2H, ddd, J = 30.2, 15.3, 4.8 Hz), 5.07-5.10 (1H, m), 5.40 (1H, d, J = 12.9 Hz), 5.48 (1H, d, J = 13.1 Hz), 7.44 (4H, s), 7.61 (1H, d, J = 8.5 Hz), 7.80 (1H, dd, J = 8.3, 1.2 Hz), 7.89 (1H, s), 8.21 (1H, s). |

TABLE 74-continued

| | |
|---|---|
| I-250 | 1H-NMR (DMSO-D6) δ: 1.38 (3H, d, J = 6.7 Hz), 2.28 (3H, s), 2.31-2.39 (1H, m), 2.57-2.65 (2H, m), 2.74-2.83 (2H, m), 2.96-3.01 (1H, m), 3.85 (1H, dd, J = 13.3, 6.8 Hz), 4.07 (1H, d, J = 13.7 Hz), 4.20 (1H, d, J = 13.8 Hz), 4.25-4.31 (1H, m), 4.45 (1H, dd, J = 13.4, 7.5 Hz), 4.71 (2H, ddd, J = 29.9, 15.2, 5.0 Hz), 5.07-5.10 (1H, m), 5.35 (1H, d, J = 12.4 Hz), 5.43 (1H, d, J = 12.7 Hz), 7.16 (2H, d, J = 7.8 Hz), 7.31 (2H, d, J = 7.9 Hz), 7.61 (1H, d, J = 8.2 Hz), 7.80 (1H, dd, J = 8.4, 1.5 Hz), 7.87 (1H, s), 8.21 (1H, s). |

TABLE 75

| | |
|---|---|
| I-254 | 1H-NMR (DMSO-D6) δ: 1.38 (3H, d, J = 6.7 Hz), 2.34-2.38 (1H, m), 2.58-2.66 (2H, m), 2.74-2.83 (2H, m), 2.96-3.00 (1H, m), 3.86 (1H, dd, J = 13.2, 5.8 Hz), 4.07 (1H, d, J = 13.9 Hz), 4.19 (1H, d, J = 13.8 Hz), 4.27-4.30 (1H, m), 4.45 (1H, dd, J = 13.2, 7.7 Hz), 4.70 (2H, ddd, J = 29.5, 15.6, 4.8 Hz), 5.06-5.11 (1H, m), 5.41 (1H, d, J = 12.4 Hz), 5.51 (1H, d, J = 12.4 Hz), 7.11 (1H, td, J = 8.4, 2.1 Hz), 7.28 (1H, dt, J = 13.7, 5.1 Hz), 7.52-7.60 (2H, m), 7.80 (1H, dd, J = 8.5, 1.4 Hz), 7.88 (1H, s), 8.19 (1H, s). |
| I-255 | 1H-NMR (DMSO-D6) δ: 1.36 (3H, d, J = 6.8 Hz), 2.32-2.38 (1H, m), 2.60-2.66 (2H, m), 2.73-2.83 (2H, m), 2.95-2.98 (1H, m), 3.86 (1H, dd, J = 13.0, 6.2 Hz), 4.07 (1H, d, J = 13.8 Hz), 4.19 (1H, d, J = 13.8 Hz), 4.27-4.30 (1H, m), 4.45 (1H, dd, J = 13.6, 8.0 Hz), 4.70 (2H, ddd, J = 29.2, 15.3, 4.7 Hz), 5.05-5.11 (1H, m), 5.46 (1H, d, J = 13.3 Hz), 5.54 (1H, d, J = 13.4 Hz), 7.47 (1H, dd, J = 8.3, 2.1 Hz), 7.53 (1H, d, J = 8.3 Hz), 7.60 (1H, d, J = 8.3 Hz), 7.67 (1H, d, J = 2.1 Hz), 7.80 (1H, dd, J = 8.4, 1.4 Hz), 7.91 (1H, s), 8.20 (1H, s). |
| I-257 | 1H-NMR (DMSO-D6) δ: 1.37 (3H, d, J = 6.7 Hz), 2.33-2.38 (1H, m), 2.59-2.69 (2H, m), 2.74-2.84 (2H, m), 2.94-3.01 (1H, m), 3.87 (1H, q, J = 6.4 Hz), 4.08 (1H, d, J = 13.7 Hz), 4.19 (1H, d, J = 13.9 Hz), 4.26-4.31 (1H, m), 4.45 (1H, dd, J = 13.2, 8.2 Hz), 4.71 (2H, ddd, J = 32.1, 15.2, 4.7 Hz), 5.07-5.10 (1H, m), 5.43 (1H, d, J = 12.7 Hz), 5.51 (1H, d, J = 12.9 Hz), 7.52 (1H, dd, J = 9.4, 6.3 Hz), 7.61 (1H, d, J = 8.4 Hz), 7.70 (1H, dd, J = 9.2, 6.2 Hz), 7.80 (1H, dd, J = 8.4, 1.4 Hz), 7.91 (1H, s), 8.21 (1H, s). |
| I-258 | 1H-NMR (CDCl3) δ: 1.43 (3H, d, J = 6.7 Hz), 2.36-2.43 (1H, m), 2.68-2.81 (4H, m), 3.02-3.06 (1H, m), 3.80-3.85 (1H, m), 4.11 (1H, d, J = 13.7 Hz), 4.30-4.42 (2H, m), 4.61-4.76 (3H, m), 5.18-5.24 (1H, m), 5.56 (2H, dd, J = 35.5, 14.2 Hz), 7.37 (1H, dd, J = 9.5, 1.2 Hz), 7.47 (1H, dd, J = 8.0, 1.2 Hz), 7.64 (2H, t, J = 7.3 Hz), 7.80 (1H, d, J = 8.8 Hz), 8.03 (1H, dd, J = 8.5, 1.5 Hz), 8.18 (1H, s). |
| I-259 | 1H-NMR (DMSO-D6) δ: 1.39 (3H, d, J = 6.8 Hz), 2.31-2.38 (1H, m), 2.57-2.67 (2H, m), 2.74-2.83 (2H, m), 2.97-3.01 (1H, m), 3.85 (1H, q, J = 6.9 Hz), 4.08 (1H, d, J = 13.8 Hz), 4.19 (1H, d, J = 13.8 Hz), 4.27-4.32 (1H, m), 4.46 (1H, dd, J = 13.7, 7.7 Hz), 4.64-4.77 (2H, m), 5.09 (1H, ddd, J = 13.8, 6.8, 2.9 Hz), 5.42 (1H, d, J = 12.3 Hz), 5.51 (1H, d, J = 12.3 Hz), 7.40 (2H, d, J = 7.5 Hz), 7.63 (1H, d, J = 8.4 Hz), 7.81 (1H, dd, J = 8.4, 1.4 Hz), 7.88 (1H, s), 8.23 (1H, s). |
| I-261 | 1H-NMR (DMSO-D6) δ: 1.33 (3H, d, J = 6.7 Hz), 2.34-2.38 (1H, m), 2.58-2.65 (2H, m), 2.76-2.86 (2H, m), 3.00-3.04 (1H, m), 3.93 (1H, dd, J = 13.6, 6.7 Hz), 4.09 (2H, dd, J = 16.9, 13.9 Hz), 4.30-4.33 (1H, m), 4.46 (1H, dd, J = 13.5, 7.6 Hz), 4.67 (1H, d, J = 13.2 Hz), 4.79 (1H, dd, J = 15.4, 6.9 Hz), 5.08 (1H, ddd, J = 14.0, 6.8, 2.5 Hz), 5.20 (2H, dd, J = 15.5, 12.5 Hz), 7.01 (2H, t, J = 55.0 Hz), 7.07 (1H, s), 7.24 (1H, s), 7.34 (1H, dd, J = 8.4, 1.8 Hz), 7.50 (1H, dd, J = 9.9, 1.9 Hz), 7.58-7.66 (2H, m), 7.81 (1H, dd, J = 8.5, 1.3 Hz), 8.24 (1H, s). |
| I-263 | 1H-NMR (CDCl3) δ: 2.38-2.42 (1H, m), 2.69-2.72 (1H, m), 2.80-2.87 (4H, m), 3.72 (2H, s), 4.18 (2H, s), 4.35-4.37 (1H, m), 4.59-4.72 (3H, m), 5.17-5.22 (1H, m), 5.52 (2H, s), 7.26 (37H, s), 7.44 (1H, d, J = 8.4 Hz), 7.64-7.68 (2H, m), 7.81 (1H, d, J = 8.4 Hz), 8.03 (1H, d, J = 8.5 Hz), 8.18 (1H, s), 8.52 (1H, d, J = 2.3 Hz). |
| I-264 | 1H-NMR (CDCl3) δ: 2.37-2.45 (1H, m), 2.66-2.75 (1H, m), 2.80-2.90 (4H, m), 3.72 (2H, s), 4.18-4.23 (2H, m), 4.33-4.40 (1H, m), 4.59-4.76 (3H, m), 5.19 (1H, ddd, J = 13.4, 7.2, 2.6 Hz), 5.38 (2H, s), 7.30 (2H, d, J = 8.5 Hz), 7.35 (2H, d, J = 8.5 Hz), 7.61 (1H, s), 7.83 (1H, d, J = 8.5 Hz), 8.05 (1H, dd, J = 8.5, 1.1 Hz), 8.20 (1H, s). |

TABLE 76

| | |
|---|---|
| I-266 | 1H-NMR (DMSO-D6) δ: 0.62-0.66 (2H, m), 0.90-0.95 (2H, m), 1.85-1.92 (1H, m), 2.34-2.40 (1H, m), 2.61-2.66 (1H, m), 2.80-2.85 (4H, m), 3.66 (2H, dd, J = 23.3, 17.3 Hz), 4.02 (1H, d, J = 13.6 Hz), 4.15 (1H, d, J = 13.7 Hz), 4.32-4.35 (1H, m), 4.45 (1H, dd, J = 13.8, 7.5 Hz), 4.63 (1H, dd, J = 15.2, 2.7 Hz), 4.76 (1H, dd, J = 15.5, 7.1 Hz), 5.04 (1H, ddd, J = 14.1, 6.9, 3.0 Hz), 5.32 (2H, s), 7.05 (2H, d, J = 8.2 Hz), 7.27 (2H, d, J = 8.2 Hz), 7.63 (1H, d, J = 8.3 Hz), 7.81 (1H, dd, J = 8.4, 1.5 Hz), 7.90 (1H, s), 8.22 (1H, s). |
| I-267 | 1H-NMR (DMSO-D6) δ: 2.32-2.41 (1H, m), 2.59-2.67 (1H, m), 2.80-2.85 (4H, m), 3.68 (2H, dd, J = 24.6, 17.3 Hz), 3.81 (3H, s), 4.02 (1H, d, J = 13.6 Hz), 4.15 (1H, d, J = 13.7 Hz), 4.32-4.35 (1H, m), 4.45 (1H, dd, J = 13.7, 7.8 Hz), 4.63 (1H, dd, J = 15.0, 2.7 Hz), 4.76 (1H, dd, J = 15.2, 7.0 Hz), 5.04 (1H, ddd, J = 14.1, 6.8, 2.7 Hz), 5.32 (2H, s), 7.02 (1H, dd, J = 8.0, 1.9 Hz), 7.10 (1H, d, J = 1.9 Hz), 7.34 (1H, d, J = 8.2 Hz), 7.63 (1H, d, J = 8.7 Hz), 7.81 (1H, dd, J = 8.4, 1.4 Hz), 7.91 (1H, s), 8.22 (1H, s). |
| I-268 | 1H-NMR (DMSO-D6) δ: 2.33-2.42 (1H, m), 2.61-2.65 (1H, m), 2.78-2.85 (4H, m), 3.69 (2H, dd, J = 23.4, 17.3 Hz), 4.03 (1H, d, J = 13.6 Hz), 4.16 (1H, d, J = 13.6 Hz), 4.31-4.36 (1H, m), 4.45 (1H, dd, J = 13.7, 7.4 Hz), 4.63 (1H, dd, J = 15.2, 2.6 Hz), 4.77 (1H, dd, J = 15.2, 7.0 Hz), 5.04 (1H, ddd, J = 13.9, 6.7, 2.9 Hz), 5.40 (2H, s), 7.10 (1H, td, J = 8.5, 2.2 Hz), 7.27 (1H, td, J = 8.5, 2.3 Hz), 7.55 (1H, dd, J = 15.3, 8.5 Hz), 7.64 (1H, d, J = 8.3 Hz), 7.81 (1H, dd, J = 8.5, 1.3 Hz), 7.91 (1H, s), 8.23 (1H, s). |

TABLE 76-continued

| | |
|---|---|
| I-269 | 1H-NMR (DMSO-D6) δ: 2.33-2.40 (1H, m), 2.59-2.67 (1H, m), 2.82 (4H, d, J = 4.1 Hz), 3.69 (2H, dd, J = 23.5, 17.1 Hz), 4.02 (1H, d, J = 13.7 Hz), 4.15 (1H, d, J = 13.6 Hz), 4.32-4.35 (1H, m), 4.45 (1H, dd, J = 13.6, 7.6 Hz), 4.62 (1H, dd, J = 15.1, 2.6 Hz), 4.76 (1H, dd, J = 15.1, 7.1 Hz), 5.04 (1H, ddd, J = 14.0, 6.8, 2.8 Hz), 5.43 (2H, s), 7.47 (1H, dd, J = 8.3, 2.1 Hz), 7.55 (1H, d, J = 8.3 Hz), 7.62 (1H, d, J = 8.5 Hz), 7.66 (1H, d, J = 2.0 Hz), 7.81 (1H, dd, J = 8.5, 1.4 Hz), 7.94 (1H, s), 8.21 (1H, s). |
| I-270 | 1H-NMR (DMSO-D6) δ: 2.33-2.42 (1H, m), 2.59-2.68 (1H, m), 2.78-2.86 (4H, m), 3.70 (2H, dd, J = 23.5, 17.0 Hz), 4.03 (1H, d, J = 13.6 Hz), 4.16 (1H, d, J = 13.6 Hz), 4.33-4.35 (1H, m), 4.45 (1H, dd, J = 13.6, 7.7 Hz), 4.63 (1H, dd, J = 15.2, 2.5 Hz), 4.77 (1H, dd, J = 15.1, 7.1 Hz), 5.04 (1H, ddd, J = 14.2, 7.0, 2.8 Hz), 5.40 (2H, s), 7.04 (1H, dd, J = 8.4, 2.1 Hz), 7.16 (1H, dd, J = 10.9, 2.4 Hz), 7.30 (1H, t, J = 73.4 Hz), 7.55 (1H, t, J = 8.5 Hz), 7.64 (1H, d, J = 8.4 Hz), 7.81 (1H, dd, J = 8.4, 1.4 Hz), 7.91 (1H, s), 8.23 (1H, s). |
| I-271 | 1H-NMR (CDCl3) δ: 2.39-2.44 (1H, m), 2.68-2.76 (1H, m), 2.83-2.88 (4H, m), 3.73 (2H, s), 4.21 (2H, dd, J = 16.8, 13.7 Hz), 4.34-4.39 (1H, m), 4.61-4.73 (3H, m), 5.17-5.23 (1H, m), 5.52 (2H, s), 7.35 (1H, d, J = 9.2 Hz), 7.46 (1H, d, J = 8.0 Hz), 7.61-7.67 (2H, m), 7.83 (1H, d, J = 8.4 Hz), 8.05 (1H, d, J = 8.2 Hz), 8.20 (1H, s). |
| I-273 | 1H-NMR (DMSO-D6) δ: 1.37 (3H, d, J = 6.5 Hz), 2.31-2.38 (1H, m), 2.57-2.66 (2H, m), 2.73-2.83 (2H, m), 2.94-3.00 (1H, m), 3.87 (1H, dd, J = 13.7, 7.0 Hz), 4.10 (1H, d, J = 13.7 Hz), 4.21 (1H, d, J = 13.9 Hz), 4.27-4.31 (1H, m), 4.45 (1H, dd, J = 13.7, 7.5 Hz), 4.68-4.80 (2H, m), 5.09 (1H, dd, J = 13.9, 7.3 Hz), 5.44 (1H, d, J = 12.7 Hz), 5.52 (1H, d, J = 12.9 Hz), 7.32 (1H, dd, J = 8.0, 1.4 Hz), 7.46-7.53 (3H, m), 7.90 (1H, s), 8.13 (1H, s). |

TABLE 77

| | |
|---|---|
| I-274 | 1H-NMR (DMSO-D6) δ: 1.36 (3H, d, J = 6.8 Hz), 2.30-2.36 (1H, m), 2.56-2.66 (2H, m), 2.72-2.85 (2H, m), 2.95-3.00 (1H, m), 3.84 (1H, q, J = 6.6 Hz), 3.96 (3H, s), 4.05 (1H, d, J = 13.7 Hz), 4.17 (1H, d, J = 13.8 Hz), 4.25-4.29 (1H, m), 4.44 (1H, dd, J = 13.4, 7.2 Hz), 4.62-4.75 (2H, m), 5.07 (1H, dd, J = 13.2, 9.1 Hz), 5.44 (1H, d, J = 12.8 Hz), 5.52 (1H, d, J = 12.8 Hz), 7.28 (1H, s), 7.32 (1H, dd, J = 8.2, 1.2 Hz), 7.46-7.54 (2H, m), 7.88 (2H, d, J = 7.7 Hz). |
| I-275 | 1H-NMR (DMSO-D6) δ: 1.40 (3H, d, J = 6.7 Hz), 2.45-2.78 (5H, m, overlap with DMSO), 2.97-3.02 (1H, m), 3.88 (1H, dd, J = 12.9, 6.8 Hz), 4.14 (1H, d, J = 14.3 Hz), 4.24-4.33 (2H, m), 4.45 (1H, dd, J = 13.7, 7.5 Hz), 4.71 (1H, dd, J = 14.5, 4.1 Hz), 4.79 (1H, dd, J = 15.1, 5.7 Hz), 5.12-5.19 (1H, m), 5.44 (1H, d, J = 12.8 Hz), 5.53 (1H, d, J = 12.9 Hz), 7.32 (1H, dd, J = 8.3, 1.8 Hz), 7.46-7.53 (2H, m), 7.90 (1H, s), 7.99 (1H, d, J = 8.3 Hz), 8.14 (1H, d, J = 8.0 Hz). |
| I-276 | 1H-NMR (DMSO-D6) δ: 1.34 (3H, d, J = 6.8 Hz), 2.30-2.38 (1H, m), 2.56-2.78 (4H, m), 2.92-2.99 (1H, m), 3.79 (1H, q, J = 6.6 Hz), 4.06 (1H, d, J = 13.8 Hz), 4.18 (1H, d, J = 13.8 Hz), 4.29 (1H, dt, J = 10.8, 4.5 Hz), 4.45 (1H, dd, J = 13.6, 7.8 Hz), 4.68 (1H, dd, J = 15.2, 2.7 Hz), 4.76 (1H, dd, J = 15.2, 6.5 Hz), 5.06-5.12 (1H, m), 5.37 (1H, d, J = 12.8 Hz), 5.45 (1H, d, J = 12.8 Hz), 7.31 (1H, dd, J = 8.3, 1.8 Hz), 7.47 (1H, dd, J = 9.9, 2.0 Hz), 7.54 (1H, t, J = 8.3 Hz), 7.67 (1H, d, J = 8.5 Hz), 7.69 (1H, s), 7.82 (1H, dd, J = 8.5, 1.3 Hz), 8.26 (1H, s). |
| I-278 | 1H-NMR (CDCl3) δ: 2.37-2.46 (1H, m), 2.67-2.75 (1H, m), 2.81-2.89 (4H, m), 3.74 (2H, s), 4.22 (2H, s), 4.34-4.41 (1H, m), 4.61-4.75 (3H, m), 5.20 (1H, ddd, J = 13.2, 6.9, 2.5 Hz), 5.42 (2H, s), 7.12 (1H, dd, J = 8.8, 6.0 Hz), 7.28-7.31 (1H, m), 7.63 (1H, s), 7.84 (1H, d, J = 8.5 Hz), 8.06 (1H, d, J = 8.4 Hz), 8.21 (1H, s). |
| I-279 | 1H-NMR (CDCl3) δ: 2.41-2.45 (1H, m), 2.70-2.73 (1H, m), 2.79-2.90 (4H, m), 3.70-3.79 (2H, m), 4.23 (2H, s), 4.36-4.42 (1H, m), 4.61-4.78 (3H, m), 5.21 (1H, ddd, J = 13.5, 7.0, 2.8 Hz), 5.38-5.41 (2H, m), 6.91-6.94 (2H, m), 7.59 (1H, s), 7.85 (1H, d, J = 8.5 Hz), 8.07 (1H, dd, J = 8.5, 1.4 Hz), 8.23 (1H, d, J = 0.9 Hz). |
| I-280 | 1H-NMR (DMSO-D6) δ: 2.34-2.40 (1H, m), 2.59-2.68 (1H, m), 2.78-2.86 (4H, m), 3.69 (2H, dd, J = 23.4, 17.1 Hz), 4.03 (1H, d, J = 13.6 Hz), 4.16 (1H, d, J = 13.6 Hz), 4.32-4.35 (1H, m), 4.45 (1H, dd, J = 13.7, 7.7 Hz), 4.63 (1H, dd, J = 15.2, 2.9 Hz), 4.77 (1H, dd, J = 15.2, 7.2 Hz), 5.04 (1H, ddd, J = 13.9, 6.8, 2.6 Hz), 5.38 (2H, s), 7.21 (2H, t, J = 8.7 Hz), 7.65 (1H, d, J = 8.3 Hz), 7.82 (1H, dd, J = 8.4, 1.4 Hz), 7.90 (1H, s), 8.24 (1H, s). |
| I-282 | 1H-NMR (DMSO-D6) δ: 1.38 (3H, d, J = 6.7 Hz), 2.30-2.36 (1H, m), 2.58-2.67 (2H, m), 2.75-2.81 (2H, m), 2.96-2.98 (1H, m), 3.85 (1H, q, J = 6.8 Hz), 3.96 (3H, s), 4.05 (1H, d, J = 13.8 Hz), 4.17 (1H, d, J = 13.7 Hz), 4.26-4.28 (1H, m), 4.45 (1H, dd, J = 13.4, 7.5 Hz), 4.62-4.74 (2H, m), 5.08 (1H, ddd, J = 13.4, 6.8, 2.5 Hz), 5.42 (1H, d, J = 12.5 Hz), 5.51 (1H, d, J = 12.4 Hz), 7.11 (1H, td, J = 8.3, 2.4 Hz), 7.26-7.31 (2H, m), 7.56 (1H, dd, J = 15.4, 8.5 Hz), 7.87 (2H, d, J = 10.5 Hz). |
| I-284 | 1H-NMR (DMSO-D6) δ: 1.36 (3H, d, J = 6.8 Hz), 2.30-2.35 (1H, m), 2.56-2.68 (2H, m), 2.75-2.83 (2H, m), 2.96-3.00 (1H, m), 3.83 (1H, dd, J = 13.3, 6.3 Hz), 3.96 (3H, s), 4.05 (1H, d, J = 13.9 Hz), 4.17 (1H, d, J = 13.8 Hz), 4.25-4.28 (1H, m), 4.44 (1H, dd, J = 13.5, 8.1 Hz), 4.63-4.73 (2H, m), 5.08 (1H, ddd, J = 13.6, 6.9, 3.4 Hz), 5.39 (1H, d, J = 12.7 Hz), 5.47 (1H, d, J = 12.7 Hz), 7.21 (2H, t, J = 8.9 Hz), 7.28 (1H, d, J = 0.9 Hz), 7.47 (2H, dd, J = 8.7, 5.6 Hz), 7.87 (2H, d, J = 9.5 Hz). |

TABLE 78

| | |
|---|---|
| I-285 | 1H-NMR (DMSO-D6) δ: 1.39 (3H, d, J = 6.8 Hz), 2.29-2.37 (1H, m), 2.60-2.65 (2H, m), 2.74-2.82 (2H, m), 2.96-2.99 (1H, m), 3.85 (1H, dd, J = 13.0, 6.3 Hz), 3.96 (3H, s), 4.05 (1H, d, J = 13.7 Hz), 4.17 (1H, d, J = 13.8 Hz), 4.26-4.29 (1H, m), 4.45 (1H, dd, J = 13.4, 7.7 Hz), 4.65-4.72 (2H, m), 5.08 (1H, ddd, J = 13.6, 6.7, 3.0 Hz), 5.40 (1H, d, J = 12.5 Hz), 5.51 (1H, d, J = 12.3 Hz), 7.23 (2H, t, J = 8.7 Hz), 7.28 (1H, d, J = 0.9 Hz), 7.87 (2H, d, J = 6.1 Hz). |

TABLE 78-continued

| | |
|---|---|
| I-287 | 1H-NMR (DMSO-D6) δ: 1.38 (3H, d, J = 6.8 Hz), 2.41-2.46 (1H, m), 2.59-2.84 (4H, m), 2.95-3.01 (1H, m), 3.86 (1H, dd, J = 13.1, 6.7 Hz), 4.12 (1H, d, J = 13.9 Hz), 4.23-4.32 (2H, m), 4.45 (1H, dd, J = 13.7, 7.7 Hz), 4.74 (2H, ddd, J = 31.5, 14.8, 4.9 Hz), 5.12-5.18 (1H, m), 5.41 (1H, d, J = 13.1 Hz), 5.49 (1H, d, J = 12.9 Hz), 7.44 (4H, s), 7.90 (1H, s), 7.95 (1H, d, J = 8.2 Hz), 8.08 (1H, d, J = 8.2 Hz). |
| I-288 | 1H-NMR (DMSO-D6) δ: 1.41 (3H, d, J = 6.8 Hz), 2.42-2.46 (1H, m), 2.59-2.84 (5H, m), 2.97-3.02 (1H, m), 3.88 (1H, q, J = 6.7 Hz), 4.12 (1H, d, J = 13.9 Hz), 4.25-4.32 (2H, m), 4.45 (1H, dd, J = 13.9, 7.7 Hz), 4.74 (2H, ddd, J = 31.2, 14.7, 5.0 Hz), 5.12-5.18 (1H, m), 5.42 (1H, d, J = 12.5 Hz), 5.51 (1H, d, J = 12.5 Hz), 7.11 (1H, td, J = 8.3, 1.8 Hz), 7.29 (1H, td, J = 10.1, 2.0 Hz), 7.55 (1H, dd, J = 15.1, 8.5 Hz), 7.89 (1H, s), 7.93 (1H, d, J = 8.2 Hz), 8.04 (1H, d, J = 7.5 Hz). |
| I-290 | 1H-NMR (DMSO-D6) δ: 1.40 (3H, d, J = 6.7 Hz), 2.45-2.84 (5H, m, overlap with DMSO), 2.98-3.02 (1H, m), 3.86 (1H, q, J = 6.5 Hz), 4.12 (1H, d, J = 14.2 Hz), 4.25-4.32 (2H, m), 4.45 (1H, dd, J = 13.9, 7.3 Hz), 4.74 (2H, ddd, J = 30.7, 14.8, 5.1 Hz), 5.12-5.18 (1H, m), 5.39 (1H, d, J = 12.9 Hz), 5.47 (1H, d, J = 12.5 Hz), 7.21 (2H, t, J = 8.9 Hz), 7.47 (2H, dd, J = 8.7, 5.6 Hz), 7.89 (1H, s), 7.93 (1H, d, J = 8.2 Hz), 8.05 (1H, d, J = 8.7 Hz). |
| I-291 | 1H-NMR (DMSO-D6) δ: 1.41 (3H, d, J = 6.7 Hz), 2.42-2.50 (1H, m, overlap with DMSO), 2.62-2.83 (4H, m), 2.98-3.01 (1H, m), 3.86 (1H, dd, J = 13.1, 6.8 Hz), 4.13 (1H, d, J = 13.9 Hz), 4.26-4.32 (2H, m), 4.46 (1H, dd, J = 14.1, 7.8 Hz), 4.74 (2H, ddd, J = 34.1, 14.7, 5.1 Hz), 5.12-5.18 (1H, m), 5.43 (1H, d, J = 12.2 Hz), 5.51 (1H, d, J = 12.3 Hz), 7.41 (2H, d, J = 7.5 Hz), 7.88 (1H, s), 7.94 (1H, d, J = 8.4 Hz), 8.06 (1H, d, J = 8.0 Hz). |
| I-294 | 1H-NMR (CDCl3) δ: 2.39-2.47 (1H, m), 2.75-2.88 (5H, m), 3.73 (2H, s), 4.21 (2H, dd, J = 20.2, 13.7 Hz), 4.37 (1H, dd, J = 13.7, 6.0 Hz), 4.62 (1H, q, J = 6.9 Hz), 4.76 (1H, d, J = 15.1 Hz), 4.93 (1H, dd, J = 14.7, 6.4 Hz), 5.18-5.23 (1H, m), 5.38 (2H, s), 7.30 (2H, d, J = 8.4 Hz), 7.35 (2H, d, J = 8.5 Hz), 7.54-7.62 (2H, m), 7.88 (1H, t, J = 7.5 Hz). |
| I-295 | 1H-NMR (CDCl3) δ: 2.34 (3H, s), 2.42-2.47 (1H, m), 2.72-2.87 (5H, m), 3.70-3.79 (2H, m), 4.21 (2H, dd, J = 23.1, 13.6 Hz), 4.39 (1H, dd, J = 15.1, 6.1 Hz), 4.64 (1H, q, J = 7.2 Hz), 4.77 (1H, d, J = 13.6 Hz), 4.95 (1H, dd, J = 15.1, 7.2 Hz), 5.22 (1H, dd, J = 13.4, 7.0 Hz), 5.38 (2H, s), 7.15 (2H, d, J = 7.9 Hz), 7.32 (2H, d, J = 7.9 Hz), 7.57-7.60 (2H, m), 7.88 (1H, t, J = 7.7 Hz). |
| I-298 | 1H-NMR (CDCl3) δ: 2.42-2.44 (1H, m), 2.75-2.88 (5H, m), 3.70-3.81 (2H, m), 4.22 (2H, dd, J = 19.0, 13.7 Hz), 4.37 (1H, dd, J = 13.9, 5.3 Hz), 4.62 (1H, q, J = 7.0 Hz), 4.76 (1H, d, J = 14.8 Hz), 4.93 (1H, dd, J = 14.9, 6.3 Hz), 5.18-5.24 (1H, m), 5.45 (2H, s), 7.24 (1H, dd, J = 8.7, 2.4 Hz, overlap with CHCl3), 7.37 (1H, d, J = 2.0 Hz), 7.49 (1H, d, J = 8.3 Hz), 7.59 (1H, d, J = 8.4 Hz), 7.63 (1H, s), 7.88 (1H, t, J = 7.5 Hz). |

TABLE 79

| | |
|---|---|
| I-300 | 1H-NMR (CDCl3) δ: 2.40-2.46 (1H, m), 2.75-2.89 (5H, m), 3.74 (2H, s), 4.22 (2H, dd, J = 16.1, 14.4 Hz), 4.37 (1H, dd, J = 14.5, 5.7 Hz), 4.63 (1H, dd, J = 13.7, 7.1 Hz), 4.76 (1H, d, J = 14.6 Hz), 4.91 (1H, dd, J = 15.1, 6.3 Hz), 5.18-5.24 (1H, m), 5.53 (2H, s), 7.35 (1H, d, J = 8.4 Hz), 7.46 (1H, d, J = 7.9 Hz), 7.58 (1H, d, J = 8.5 Hz), 7.63-7.66 (2H, m), 7.89 (1H, t, J = 7.5 Hz). |
| I-302 | 1H-NMR (CDCl3) δ: 2.40-2.42 (1H, m), 2.77-2.86 (5H, m), 3.73 (2H, s), 4.21-4.33 (3H, m), 4.60-4.63 (1H, m), 4.75 (1H, d, J = 14.3 Hz), 4.87 (1H, dd, J = 13.9, 5.6 Hz), 5.20-5.22 (1H, m), 5.38 (2H, s), 7.30 (2H, d, J = 8.5 Hz), 7.35 (2H, d, J = 8.5 Hz), 7.61 (1H, s), 8.22 (2H, s). |
| I-304 | 1H-NMR (CDCl3) δ: 2.41-2.43 (1H, m), 2.76-2.87 (5H, m), 3.76 (2H, s), 4.27-4.35 (3H, m), 4.60-4.63 (1H, m), 4.72-4.79 (1H, m), 4.85-4.89 (1H, m), 5.20-5.23 (1H, m), 5.45 (2H, s), 7.23-7.29 (1H, m, overlap with CHCl3), 7.38 (1H, d, J = 1.6 Hz), 7.49 (1H, d, J = 8.3 Hz), 7.64 (1H, s), 8.22 (2H, s). |
| I-306 | 1H-NMR (CDCl3) δ: 2.38-2.45 (1H, m), 2.75-2.89 (5H, m), 3.75 (2H, s), 4.27-4.35 (3H, m), 4.61-4.64 (1H, m), 4.73-4.79 (1H, m), 4.88 (1H, dd, J = 13.6, 5.6 Hz), 5.21-5.23 (1H, m), 5.43 (2H, s), 7.08 (1H, dd, J = 9.8, 2.0 Hz), 7.12 (1H, dd, J = 8.0, 1.4 Hz), 7.43 (1H, t, J = 8.0 Hz), 7.62 (1H, s), 8.23 (2H, s). |
| I-307 | 1H-NMR (DMSO-D6) δ: 1.37 (3H, d, J = 6.7 Hz), 2.30-2.38 (1H, m), 2.57-2.85 (4H, m), 2.97-3.03 (1H, m), 3.84-3.89 (1H, m), 4.11 (1H, d, J = 14.1 Hz), 4.21 (1H, d, J = 14.1 Hz), 4.29 (1H, dt, J = 11.0, 4.5 Hz), 4.45 (1H, dd, J = 13.7, 7.7 Hz), 4.69-4.74 (1H, m), 4.80 (1H, dd, J = 15.3, 6.7 Hz), 5.06-5.12 (1H, m), 5.40 (1H, d, J = 12.8 Hz), 5.47 (1H, d, J = 12.8 Hz), 7.21 (2H, t. J = 8.8 Hz), 7.45-7.54 (3H, m), 7.89 (1H, s), 8.16 (1H, s). |
| I-308 | 1H-NMR (DMSO-D6) δ: 1.38 (3H, d, J = 6.7 Hz), 2.33-2.42 (1H, m), 2.64-2.85 (4H, m), 2.97-3.04 (1H, m), 3.87 (1H, dd, J = 13.4, 6.7 Hz), 4.10 (1H, d, J = 14.1 Hz), 4.22 (1H, d, J = 14.1 Hz), 4.30 (1H, dt, J = 11.0, 4.3 Hz), 4.47 (1H, dd, J = 13.9, 7.3 Hz), 4.72-4.77 (1H, m), 4.84 (1H, dd, J = 15.4, 6.8 Hz), 5.07-5.13 (1H, m), 5.39 (1H, d, J = 12.7 Hz), 5.48 (1H, d, J = 12.7 Hz), 7.21 (2H, t, J = 8.8 Hz), 7.45-7.51 (3H, m), 7.66-7.70 (1H, m), 7.89 (1H, s). |
| I-309 | 1H-NMR (DMSO-D6) δ: 1.28 (3H, d, J = 6.7 Hz), 2.30-2.38 (1H, m), 2.57-2.64 (1H, m), 2.71-2.77 (2H, m), 2.94-3.00 (1H, m), 3.86 (1H, dd, J = 12.9, 6.1 Hz), 4.07 (2H, t. J = 14.7 Hz), 4.27-4.34 (1H, m), 4.45 (1H, dd, J = 13.7, 7.3 Hz), 4.66 (1H, dd, J = 15.4, 2.7 Hz), 4.78 (1H, dd, J = 15.2, 7.0 Hz), 5.07 (1H, ddd, J = 13.9, 6.6, 2.7 Hz), 5.24 (2H, s), 7.01 (1H, s), 7.20 (1H, s), 7.59 (1H, d, J = 8.4 Hz), 7.64 (1H, d, J = 8.5 Hz), 7.80 (1H, dd, J = 8.5, 1.4 Hz), 8.01 (1H, dd, J = 8.4, 2.5 Hz), 8.24 (1H, s), 8.64 (1H, d, J = 2.3 Hz). |
| I-310 | 1H-NMR (DMSO-D6) δ: 1.30 (3H, d, J = 6.7 Hz), 2.33-2.38 (1H, m), 2.60-2.77 (4H, m), 2.96-3.02 (1H, m), 3.83-3.89 (4H, m), 4.06 (2H, dd, J = 13.7, 11.3 Hz), 4.30-4.33 (1H, m), 4.46 (1H, dd, J = 13.9, 7.7 Hz), 4.66 (1H, dd, J = 15.4, 3.2 Hz), 4.78 (1H, dd, J = 15.1, 7.3 Hz), 5.04-5.11 (3H, m), 6.98 (1H, s), 7.05 (1H, dd, J = 8.1, 1.9 Hz), 7.13-7.17 (2H, m), 7.45 (1H, d, J = 8.2 Hz), 7.63 (1H, d, J = 8.3 Hz), 7.80 (1H, dd, J = 8.4, 1.4 Hz), 8.22 (1H, s). |

TABLE 79-continued

| | |
|---|---|
| I-311 | 1H-NMR (DMSO-D6) δ: 1.31 (3H, d, J = 6.7 Hz), 2.34-2.38 (1H, m), 2.57-2.67 (2H, m), 2.74-2.82 (2H, m), 2.95-3.01 (1H, m), 3.89 (1H, q, J = 6.7 Hz), 4.08 (2H, dd, J = 16.7, 14.1 Hz), 4.30-4.33 (1H, m), 4.46 (1H, dd, J = 13.6, 7.7 Hz), 4.67 (1H, dd, J = 15.2, 2.8 Hz), 4.79 (1H, dd, J = 15.3, 7.0 Hz), 5.08 (1H, ddd, J = 14.0, 7.1, 3.2 Hz), 5.18 (2H, dd, J = 14.7, 12.7 Hz), 7.05 (1H, s), 7.19 (1H, s), 7.51 (1H, dd, J = 8.3, 2.1 Hz), 7.65 (2H, dd, J = 8.3, 6.0 Hz), 7.70 (1H, d, J = 2.1 Hz), 7.80 (1H, dd, J = 8.5, 1.4 Hz), 8.24 (1H, s). |

TABLE 80

| | |
|---|---|
| I-312 | 1H-NMR (DMSO-D6) δ: 1.33 (3H, d, J = 6.7 Hz), 2.32-2.40 (1H, m), 2.58-2.68 (2H, m), 2.74-2.80 (2H, m), 2.97-3.02 (1H, m), 3.89 (1H, q, J = 6.6 Hz), 4.07-4.10 (2H, m), 4.31-4.33 (1H, m), 4.44-4.48 (1H, m), 4.68 (1H, dd, J = 15.2, 2.6 Hz), 4.80 (1H, dd, J = 15.3, 7.0 Hz), 5.05-5.17 (3H, m), 7.08 (1H, s), 7.16 (1H, s), 7.45-7.48 (2H, m), 7.66 (1H, d, J = 8.5 Hz), 7.81 (1H, dd, J = 8.5, 1.6 Hz), 8.26 (1H, d, J = 1.0 Hz). |
| I-313 | 1H-NMR (DMSO-D6) δ: 1.31 (3H, d, J = 6.7 Hz), 2.30 (3H, s), 2.43-2.50 (1H, m), 2.59-2.65 (2H, m), 2.72-2.82 (2H, m), 2.95-3.02 (1H, m), 3.86 (1H, q, J = 6.7 Hz), 4.09-4.16 (2H, m), 4.27-4.30 (1H, m), 4.45 (1H, dd, J = 13.6, 7.5 Hz), 4.68 (1H, dd, J = 14.6, 3.8 Hz), 4.79 (1H, dd, J = 14.7, 6.3 Hz), 5.08-5.14 (3H, m), 7.01 (1H, s), 7.15-7.21 (3H, m), 7.34 (2H, d, J = 8.0 Hz), 7.91 (1H, d, J = 8.2 Hz), 8.01 (1H, d, J = 8.2 Hz). |
| I-315 | 1H-NMR (DMSO-D6) δ: 1.33 (3H, d, J = 6.7 Hz), 2.40-2.63 (3H, m, overlap with DMSO), 2.75-2.81 (2H, m), 2.99-3.01 (1H, m), 3.89 (1H, q, J = 6.5 Hz), 4.16 (2H, s), 4.28-4.33 (1H, m), 4.46 (1H, dd, J = 13.9, 7.8 Hz), 4.70 (1H, dd, J = 14.7, 4.2 Hz), 4.81 (1H, dd, J = 14.7, 6.2 Hz), 5.10-5.21 (3H, m), 7.07 (1H, s), 7.18 (1H, s), 7.36 (1H, dd, J = 8.2, 1.8 Hz), 7.50 (1H, dd, J = 10.0, 2.0 Hz), 7.61 (1H, t, J = 8.1 Hz), 7.95 (1H, d, J = 8.3 Hz), 8.08 (1H, d, J = 7.9 Hz). |
| I-316 | 1H-NMR (DMSO-D6) δ: 1.33 (3H, d, J = 6.7 Hz), 2.45-2.50 (1H, m, overlap with DMSO), 2.61-2.67 (2H, m), 2.74-2.84 (2H, m), 2.99-3.02 (1H, m), 3.90 (1H, q, J = 6.6 Hz), 4.16 (2H, s), 4.29-4.31 (1H, m), 4.46 (1H, dd, J = 13.7, 7.7 Hz), 4.70 (1H, dd, J = 14.7, 4.0 Hz), 4.81 (1H, dd, J = 14.7, 6.4 Hz), 5.11-5.21 (3H, m), 7.06 (1H, s), 7.19 (1H, s), 7.51 (1H, dd, J = 8.3, 2.1 Hz), 7.66 (1H, d, J = 8.4 Hz), 7.70 (1H, d, J = 2.0 Hz), 7.95 (1H, d, J = 8.2 Hz), 8.08 (1H, d, J = 8.2 Hz). |
| I-318 | 1H-NMR (DMSO-D6) δ: 1.31 (3H, d, J = 6.7 Hz), 2.37-2.41 (1H, m), 2.55-2.60 (1H, m), 2.65-2.82 (3H, m), 2.96-2.99 (1H, m), 3.75 (3H, s), 3.87 (1H, q, J = 6.6 Hz), 4.08 (2H, s), 4.29-4.36 (1H, m), 4.48 (1H, dd, J = 13.8, 7.7 Hz), 4.72 (1H, dd, J = 15.0, 2.7 Hz), 4.87 (1H, dd, J = 15.4, 7.2 Hz), 5.04-5.09 (3H, m), 6.95 (2H, d, J = 8.8 Hz), 7.02 (1H, s), 7.16 (1H, s), 7.38 (2H, d, J = 8.8 Hz), 7.47 (1H, d, J = 8.5 Hz), 7.65 (1H, dd, J = 8.3, 6.7 Hz). |
| I-319 | 1H-NMR (DMSO-D6) δ: 1.30 (3H, d, J = 6.7 Hz), 2.36-2.42 (1H, m), 2.66-2.83 (4H, m), 2.96-3.03 (1H, m), 3.86 (1H, dd, J = 13.1, 6.3 Hz), 4.07 (2H, s), 4.28-4.35 (1H, m), 4.47 (1H, dd, J = 14.8, 6.7 Hz), 4.71 (1H, dd, J = 15.2, 2.7 Hz), 4.85 (1H, dd, J = 15.6, 7.2 Hz), 5.06-5.19 (3H, m), 7.00 (1H, s), 7.18 (1H, s), 7.42-7.50 (5H, m), 7.61 (1H, t, J = 7.5 Hz). |
| I-320 | 1H-NMR (DMSO-D6) δ: 1.29 (3H, d, J = 6.7 Hz), 2.35-2.40 (1H, m), 2.64-2.83 (4H, m), 2.97-3.00 (1H, m), 3.88 (1H, q, J = 6.4 Hz), 4.08 (2H, s), 4.31-4.33 (1H, m), 4.47 (1H, dd, J = 13.8, 7.8 Hz), 4.71 (1H, dd, J = 15.4, 3.5 Hz), 4.86 (1H, dd, J = 15.4, 7.1 Hz), 5.05-5.12 (1H, m), 5.24 (2H, s), 7.02 (1H, s), 7.20 (1H, s), 7.45 (1H, d, J = 8.4 Hz), 7.59-7.66 (2H, m), 8.01 (1H, dd, J = 8.4, 2.5 Hz), 8.64 (1H, d, J = 2.4 Hz). |
| I-323 | 1H-NMR (DMSO-D6) δ: 1.33 (3H, d, J = 6.7 Hz), 2.36-2.42 (1H, m), 2.69-2.79 (4H, m), 2.98-3.01 (1H, m), 3.90 (1H, q, J = 6.7 Hz), 4.08 (2H, s), 4.30-4.36 (1H, m), 4.48 (1H, dd, J = 13.7, 7.5 Hz), 4.72 (1H, dd, J = 15.4, 2.9 Hz), 4.87 (1H, dd, J = 15.2, 7.0 Hz), 5.08-5.19 (3H, m), 7.08 (1H, s), 7.12-7.18 (2H, m), 7.31 (1H, td, J = 10.1, 3.0 Hz), 7.46 (1H, d, J = 8.5 Hz), 7.60-7.67 (2H, m). |

TABLE 81

| | |
|---|---|
| I-324 | 1H-NMR (DMSO-D6) δ: 1.32 (3H, d, J = 6.5 Hz), 2.38-2.40 (1H, m), 2.67-2.82 (4H, m), 2.98-3.01 (1H, m), 3.90 (1H, q, J = 6.8 Hz), 4.07-4.11 (2H, m), 4.33 (1H, dd, J = 14.5, 6.0 Hz), 4.48 (1H, q, J = 6.9 Hz), 4.72 (1H, dd, J = 15.9, 2.7 Hz), 4.87 (1H, dd, J = 15.2, 6.9 Hz), 5.08-5.21 (3H, m), 7.07 (1H, s), 7.18 (1H, s), 7.36 (1H, d, J = 8.3 Hz), 7.45-7.52 (2H, m), 7.59-7.67 (2H, m). |
| I-325 | 1H-NMR (DMSO-D6) δ: 1.33 (3H, d, J = 6.7 Hz), 2.35-2.41 (1H, m), 2.57-2.84 (4H, m), 2.96-3.03 (1H, m), 3.91 (1H, q, J = 6.6 Hz), 4.05-4.12 (2H, m), 4.29-4.36 (1H, m), 4.48 (1H, dd, J = 14.2, 7.2 Hz), 4.72 (1H, dd, J = 15.4, 2.9 Hz), 4.87 (1H, dd, J = 15.4, 7.3 Hz), 5.08-5.21 (3H, m), 7.06 (1H, s), 7.20 (1H, s), 7.46 (1H, d, J = 8.4 Hz), 7.51 (1H, dd, J = 8.3, 2.1 Hz), 7.61-7.68 (2H, m), 7.70 (1H, d, J = 2.1 Hz). |
| I-326 | 1H-NMR (DMSO-D6) δ: 1.33 (3H, d, J = 6.7 Hz), 2.36-2.41 (1H, m), 2.55-2.84 (4H, m), 2.96-3.02 (1H, m), 3.90 (1H, q, J = 6.7 Hz), 4.09 (2H, dd, J = 15.6, 14.6 Hz), 4.30-4.36 (1H, m), 4.48 (1H, dd, J = 14.4, 7.0 Hz), 4.72 (1H, dd, J = 15.4, 2.9 Hz), 4.87 (1H, dd, J = 15.2, 7.3 Hz), 5.07-5.20 (3H, m), 7.09 (1H, s), 7.19 (1H, s), 7.46 (1H, d, J = 8.5 Hz), 7.64 (2H, dd, J = 9.2, 6.5 Hz), 7.73 (1H, dd, J = 9.2, 6.1 Hz). |
| I-327 | 1H-NMR (DMSO-D6) δ: 1.33 (3H, d, J = 6.7 Hz), 2.39-2.41 (1H, m), 2.61-2.83 (4H, m), 2.96-3.03 (1H, m), 3.90 (1H, dd, J = 12.7, 6.1 Hz), 4.07-4.11 (2H, m), 4.30-4.37 (1H, m), 4.48 (1H, dd, J = 13.7, 7.7 Hz), 4.73 (1H, dd, J = 15.5, 2.8 Hz), 4.87 (1H, dd, J = 15.4, 7.0 Hz), 5.06-5.20 (3H, m), 7.07-7.11 (2H, m), 7.14-7.50 (4H, m), 7.62-7.67 (2H, m). |

TABLE 81-continued

| | |
|---|---|
| I-329 | 1H-NMR (DMSO-D6) δ: 1.34 (3H, d, J = 6.7 Hz), 2.37-2.42 (1H, m), 2.58-2.82 (4H, m), 2.97-3.02 (1H, m), 3.90 (1H, dd, J = 12.7, 6.2 Hz), 4.07-4.10 (2H, m), 4.32-4.35 (1H, m), 4.48 (1H, dd, J = 13.8, 7.5 Hz), 4.73 (1H, dd, J = 15.0, 2.4 Hz), 4.87 (1H, dd, J = 15.2, 6.9 Hz), 5.08-5.17 (3H, m), 7.09 (1H, s), 7.17 (1H, s), 7.43-7.49 (3H, m), 7.64 (1H, t, J = 7.5 Hz). |
| I-330 | 1H-NMR (DMSO-D6) δ: 1.29 (3H, d, J = 6.7 Hz), 2.30-2.36 (4H, m), 2.56-2.80 (4H, m), 2.94-3.02 (1H, m), 3.85 (1H, q, J = 6.5 Hz), 4.09 (2H, dd, J = 15.5, 14.2 Hz), 4.27-4.34 (1H, m), 4.45 (1H, dd, J = 13.3, 7.9 Hz), 4.68 (1H, dd, J = 15.1, 2.5 Hz), 4.81 (1H, dd, J = 15.2, 7.2 Hz), 5.04-5.11 (3H, m), 7.01 (1H, s), 7.15-7.21 (3H, m), 7.34 (2H, d, J = 8.0 Hz), 7.51 (1H, dd, J = 11.4, 1.0 Hz), 8.12 (1H, s). |
| I-332 | 1H-NMR (DMSO-D6) δ: 1.29 (3H, d, J = 6.7 Hz), 2.29-2.37 (1H, m), 2.62-2.76 (4H, m), 2.94-3.01 (1H, m), 3.85 (1H, dd, J = 12.9, 6.1 Hz), 4.09 (2H, dd, J = 16.3, 14.1 Hz), 4.29-4.32 (1H, m), 4.45 (1H, dd, J = 13.6, 7.7 Hz), 4.69 (1H, dd, J = 15.2, 2.5 Hz), 4.81 (1H, dd, J = 15.1, 7.1 Hz), 5.06-5.19 (3H, m), 7.01 (1H, s), 7.18 (1H, s), 7.45-7.52 (5H, m), 8.12 (1H, s). |
| I-333 | 1H-NMR (DMSO-D6) δ: 0.63-0.69 (2H, m), 0.92-0.96 (2H, m), 1.29 (3H, d, J = 6.7 Hz), 1.87-1.94 (1H, m), 2.34-2.36 (1H, m), 2.56-2.80 (4H, m), 2.95-3.02 (1H, m), 3.85 (1H, q, J = 6.7 Hz), 4.09 (2H, dd, J = 16.0, 14.5 Hz), 4.28-4.34 (1H, m), 4.45 (1H, dd, J = 13.8, 7.3 Hz), 4.68 (1H, dd, J = 15.6, 2.8 Hz), 4.81 (1H, dd, J = 15.3, 6.9 Hz), 5.05-5.12 (3H, m), 7.00-7.17 (4H, m), 7.32 (2H, d, J = 8.0 Hz), 7.51 (1H, d, J = 11.7 Hz), 8.12 (1H, s). |
| I-334 | 1H-NMR (DMSO-D6) δ: 1.30 (3H, d, J = 6.5 Hz), 2.33-2.38 (1H, m), 2.58-2.78 (4H, m), 2.96-3.01 (1H, m), 3.84-3.89 (4H, m), 4.09 (2H, dd, J = 16.4, 14.0 Hz), 4.28-4.35 (1H, m), 4.45 (1H, dd, J = 13.4, 7.9 Hz), 4.69 (1H, dd, J = 15.0, 2.3 Hz), 4.81 (1H, dd, J = 15.2, 7.5 Hz), 5.06-5.09 (3H, m), 7.00 (1H, s), 7.05 (1H, dd, J = 8.1, 1.9 Hz), 7.12-7.18 (2H, m), 7.45 (1H, d, J = 8.2 Hz), 7.51 (1H, d, J = 12.2 Hz), 8.11 (1H, s). |

TABLE 82

| | |
|---|---|
| I-336 | 1H-NMR (DMSO-D6) δ: 1.32 (3H, d, J = 6.7 Hz), 2.34-2.37 (1H, m), 2.57-2.61 (2H, m), 2.73-2.82 (2H, m), 2.96-3.00 (1H, m), 3.88 (1H, dd, J = 13.3, 6.4 Hz), 4.10 (2H, dd, J = 17.0, 14.0 Hz), 4.28-4.35 (1H, m), 4.46 (1H, dd, J = 13.7, 7.8 Hz), 4.70 (1H, dd, J = 15.4, 2.7 Hz), 4.82 (1H, dd, J = 15.4, 7.1 Hz), 5.08 (1H, ddd, J = 14.2, 7.3, 2.4 Hz), 5.18 (2H, dd, J = 13.2, 12.5 Hz), 7.07 (1H, s), 7.18 (1H, s), 7.36 (1H, dd, J = 8.3, 1.8 Hz), 7.48-7.53 (2H, m), 7.61 (1H, t, J = 8.2 Hz), 8.13 (1H, s). |
| I-337 | 1H-NMR (DMSO-D6) δ: 1.32 (3H, d, J = 6.7 Hz), 2.32-2.35 (1H, m), 2.56-2.63 (2H, m), 2.74-2.83 (2H, m), 2.98-3.01 (1H, m), 3.89 (1H, q, J = 6.4 Hz), 4.09 (2H, dd, J = 16.9, 14.0 Hz), 4.30-4.33 (1H, m), 4.45 (1H, dd, J = 13.4, 8.0 Hz), 4.69 (1H, dd, J = 15.1, 2.4 Hz), 4.82 (1H, dd, J = 15.4, 7.1 Hz), 5.08 (1H, ddd, J = 14.1, 6.8, 2.7 Hz), 5.19 (2H, dd, J = 14.7, 12.8 Hz), 7.06 (1H, s), 7.19 (1H, s), 7.49-7.53 (2H, m), 7.64-7.70 (2H, m), 8.12 (1H, s). |
| I-339 | 1H-NMR (DMSO-D6) δ: 1.33 (3H, d, J = 6.7 Hz), 2.34-2.39 (1H, m), 2.59-2.64 (2H, m), 2.74-2.79 (2H, m), 2.97-3.00 (1H, m), 3.88 (1H, q, J = 6.7 Hz), 4.09 (2H, s), 4.28-4.35 (1H, m), 4.46 (1H, dd, J = 13.4, 7.9 Hz), 4.68 (1H, dd, J = 15.2, 2.6 Hz), 4.79 (1H, dd, J = 15.2, 6.8 Hz), 5.06-5.17 (3H, m), 7.10 (1H, s), 7.16 (1H, s), 7.45-7.52 (3H, m), 8.06 (1H, s). |
| I-341 | 1H-NMR (DMSO-D6) δ: 1.28 (3H, d, J = 6.5 Hz), 2.31-2.34 (1H, m), 2.55-2.61 (2H, m), 2.70-2.78 (2H, m), 2.95-3.01 (1H, m), 3.82 (1H, dd, J = 13.0, 6.8 Hz), 3.94 (3H, s), 4.04 (2H, s), 4.25-4.30 (1H, m), 4.44 (1H, dd, J = 14.4, 8.0 Hz), 4.62 (1H, dd, J = 15.4, 2.8 Hz), 4.72 (1H, dd, J = 15.5, 5.6 Hz), 5.03-5.09 (1H, m), 5.16 (2H, s), 7.00 (1H, s), 7.17 (1H, s), 7.27 (1H, s), 7.44-7.49 (4H, m), 7.82 (1H, s). |
| I-344 | 1H-NMR (DMSO-D6) δ: 1.31 (3H, d, J = 6.7 Hz), 2.29-2.37 (1H, m), 2.56-2.63 (2H, m), 2.71-2.80 (2H, m), 2.94-2.99 (1H, m), 3.85 (1H, dd, J = 13.1, 6.3 Hz), 3.95 (3H, s), 4.05 (2H, s), 4.27-4.30 (1H, m), 4.45 (1H, dd, J = 13.3, 8.0 Hz), 4.63 (1H, d, J = 12.3 Hz), 4.73 (1H, dd, J = 15.3, 6.7 Hz), 5.06 (1H, ddd, J = 13.9, 6.8, 2.9 Hz), 5.15-5.20 (2H, m), 7.06 (1H, s), 7.18 (1H, s), 7.27 (1H, d, J = 0.9 Hz), 7.36 (1H, dd, J = 8.2, 1.7 Hz), 7.50 (1H, dd, J = 9.9, 2.0 Hz), 7.61 (1H, t, J = 8.2 Hz), 7.84 (1H, s). |
| I-346 | 1H-NMR (DMSO-D6) δ: 1.31 (3H, d, J = 6.7 Hz), 2.29-2.37 (1H, m), 2.57-2.62 (2H, m), 2.70-2.80 (2H, m), 2.97-2.99 (1H, m), 3.86 (1H, q, J = 6.6 Hz), 3.95 (3H, s), 4.03-4.07 (2H, m), 4.27-4.30 (1H, m), 4.44 (1H, dd, J = 13.5, 7.7 Hz), 4.63 (1H, dd, J = 15.1, 2.6 Hz), 4.74 (1H, dd, J = 15.3, 6.7 Hz), 5.07 (1H, ddd, J = 14.1, 6.9, 2.9 Hz), 5.18 (2H, t, J = 12.9 Hz), 7.08 (1H, s), 7.19 (1H, s), 7.27 (1H, d, J = 0.9 Hz), 7.64 (1H, dd, J = 9.3, 6.3 Hz), 7.73 (1H, dd, J = 9.2, 6.1 Hz), 7.86 (1H, s). |
| I-347 | 1H-NMR (DMSO-D6) δ: 1.41 (3H, d, J = 6.8 Hz), 2.29 (3H, s), 2.39-2.46 (1H, m), 2.60-2.85 (4H, m), 2.94-3.01 (1H, m), 3.84-3.88 (1H, m), 4.11 (1H, d, J = 13.9 Hz), 4.23-4.31 (2H, m), 4.45 (1H, dd, J = 13.5, 7.6 Hz), 4.69 (1H, dd, J = 14.7, 3.9 Hz), 4.77 (1H, dd, J = 14.7, 5.9 Hz), 5.12-5.18 (1H, m), 5.36 (1H, d, J = 12.5 Hz), 5.44 (1H, d, J = 12.5 Hz), 7.17 (2H, d, J = 7.9 Hz), 7.31 (2H, d, J = 7.9 Hz), 7.87 (1H, s), 7.90 (1H, d, J = 8.3 Hz), 8.00 (1H, d, J = 8.3 Hz). |
| I-348 | 1H-NMR (DMSO-D6) δ: 1.38 (3H, d, J = 6.7 Hz), 2.39-2.46 (1H, m), 2.60-2.86 (4H, m), 2.96-3.02 (1H, m), 3.83-3.88 (1H, m), 4.12 (1H, d, J = 13.8 Hz), 4.23-4.32 (2H, m), 4.45 (1H, dd, J = 13.5, 7.8 Hz), 4.69 (1H, dd, J = 14.8, 4.3 Hz), 4.77 (1H, dd, J = 14.8, 6.0 Hz), 5.12-5.18 (1H, m), 5.41 (1H, d, J = 13.1 Hz), 5.49 (1H, d, J = 13.1 Hz), 7.44 (4H, s), 7.90 (1H, s), 7.92 (1H, d, J = 8.3 Hz), 8.04 (1H, d, J = 8.3 Hz). |

TABLE 83

| | |
|---|---|
| I-349 | 1H-NMR (DMSO-D6) δ: 0.63-0.67 (2H, m), 0.93 (2H, dt, J = 11.8, 3.1 Hz), 1.41 (3H, d, J = 6.7 Hz), 1.86-1.93 (1H, m), 2.37-2.46 (1H, m), 2.58-2.83 (4H, m), 2.96-3.02 (1H, m), 3.84-3.88 (2H, m), 4.12 (1H, d, J = 13.8 Hz), 4.23-4.31 (2H, m), 4.45 (1H, dd, J = 13.8, 7.7 Hz), 4.69 (1H, dd, J = 14.7, 3.8 Hz), 4.77 (1H, dd, J = 14.7, 5.9 Hz), 5.12-5.18 (1H, m), 5.35 (1H, d, J = 12.5 Hz), 5.42 (1H, d, J = 12.5 Hz), 7.06 (2H, d, J = 8.0 Hz), 7.29 (2H, d, J = 8.0 Hz), 7.87 (1H, s), 7.92 (1H, d, J = 8.3 Hz), 8.02 (1H, d, J = 8.3 Hz). |
| I-350 | 1H-NMR (DMSO-D6) δ: 1.39 (3H, d, J = 6.8 Hz), 2.39-2.46 (1H, m), 2.59-2.85 (4H, m), 2.94-3.01 (1H, m), 3.83 (3H, s), 3.89-3.84 (1H, m), 4.11 (1H, d, J = 13.8 Hz), 4.23-4.31 (2H, m), 4.45 (1H, dd, J = 13.9, 7.6 Hz), 4.69 (1H, dd, J = 14.8, 4.0 Hz), 4.77 (1H, dd, J = 14.8, 6.1 Hz), 5.12-5.18 (1H, m), 5.34 (1H, d, J = 13.3 Hz), 5.43 (1H, d, J = 13.3 Hz), 7.02 (1H, dd, J = 8.1, 1.8 Hz), 7.12 (1H, d, J = 1.8 Hz), 7.34 (1H, d, J = 8.1 Hz), 7.89 (1H, s), 7.92 (1H, d, J = 8.2 Hz), 8.02 (1H, d, J = 8.2 Hz). |
| I-351 | 1H-NMR (DMSO-D6) δ: 1.38 (3H, d, J = 6.7 Hz), 2.37-2.46 (1H, m), 2.61-2.89 (4H, m), 2.94-3.02 (1H, m), 3.85-3.89 (1H, m), 4.11 (1H, d, J = 13.9 Hz), 4.23-4.31 (2H, m), 4.45 (1H, dd, J = 14.2, 7.1 Hz), 4.69 (1H, dd, J = 14.7, 3.4 Hz), 4.76 (1H, dd, J = 14.7, 5.8 Hz), 5.11-5.17 (1H, m), 5.46 (1H, d, J = 13.3 Hz), 5.55 (1H, d, J = 13.3 Hz), 7.48 (1H, d, J = 8.3 Hz), 7.53 (1H, d, J = 8.3 Hz), 7.68 (1H, s), 7.90-7.92 (2H, m), 8.01 (1H, d, J = 8.2 Hz). |
| I-352 | 1H-NMR (DMSO-D6) δ: 1.40 (3H, d, J = 6.8 Hz), 2.39-2.47 (1H, m), 2.61-2.89 (4H, m), 2.95-3.02 (1H, m), 3.88 (1H, q, J = 6.8 Hz), 4.14 (1H, d, J = 13.8 Hz), 4.24-4.33 (2H, m), 4.45 (1H, q, J = 7.1 Hz), 4.71 (1H, dd, J = 14.6, 3.3 Hz), 4.79 (1H, dd, J = 14.6, 5.6 Hz), 5.12-5.18 (1H, m), 5.43 (1H, d, J = 13.2 Hz), 5.51 (1H, d, J = 13.2 Hz), 7.50-7.54 (1H, m), 7.69-7.73 (1H, m), 7.92 (1H, s), 7.97 (1H, d, J = 8.3 Hz), 8.11 (1H, d, J = 8.3 Hz). |
| I-354 | 1H-NMR (DMSO-D6) δ: 1.41 (3H, d, J = 6.7 Hz), 2.35-2.42 (1H, m), 2.67-2.85 (4H, m), 2.97-3.02 (1H, m), 3.74 (3H, s), 3.88 (1H, q, J = 6.7 Hz), 4.09 (1H, d, J = 14.3 Hz), 4.22 (1H, d, J = 13.7 Hz), 4.31 (1H, dd, J = 14.2, 6.7 Hz), 4.47 (1H, dd, J = 14.5, 6.8 Hz), 4.75 (1H, d, J = 14.6 Hz), 4.83 (1H, dd, J = 15.5, 6.6 Hz), 5.08-5.13 (1H, m), 5.09-5.12 (1H, m), 5.33 (1H, d, J = 12.3 Hz), 5.41 (1H, d, J = 12.7 Hz), 6.92 (2H, d, J = 7.8 Hz), 7.36 (2H, d, J = 7.8 Hz), 7.48 (1H, d, J = 8.8 Hz), 7.64-7.68 (1H, m), 7.87 (1H, s). |
| I-355 | 1H-NMR (DMSO-D6) δ: 1.27 (3H, d, J = 6.8 Hz), 2.34-2.41 (1H, m), 2.69-2.87 (4H, m), 2.93-2.99 (1H, m), 3.79-3.84 (1H, m), 4.05 (1H, d, J = 14.8 Hz), 4.19 (1H, d, J = 13.4 Hz), 4.28 (1H, dd, J = 15.0, 6.3 Hz), 4.46 (1H, dd, J = 13.9, 7.4 Hz), 4.72 (1H, d, J = 13.3 Hz), 4.80 (1H, dd, J = 14.6, 6.1 Hz), 5.08-5.10 (1H, br m), 5.49 (1H, d, J = 13.9 Hz), 5.56 (1H, d, J = 14.2 Hz), 7.39-7.45 (2H, m), 7.61 (1H, br s), 7.92 (1H, s), 7.96 (1H, dd, J = 8.5, 2.5 Hz), 8.61 (1H, d, J = 2.3 Hz). |
| I-356 | 1H-NMR (DMSO-D6) δ: 0.63-0.67 (2H, m), 0.91-0.95 (2H, m), 1.39 (3H, d, J = 6.7 Hz), 1.86-1.93 (1H, m), 2.35-2.41 (1H, m), 2.66-2.84 (4H, m), 2.96-3.01 (1H, m), 3.87 (1H, q, J = 6.7 Hz), 4.09 (1H, d, J = 14.1 Hz), 4.22 (1H, d, J = 14.1 Hz), 4.28-4.33 (1H, m), 4.47 (1H, dd, J = 14.1, 7.2 Hz), 4.74 (1H, dd, J = 15.2, 2.9 Hz), 4.83 (1H, dd, J = 15.6, 6.5 Hz), 5.07-5.13 (1H, m), 5.35 (1H, d, J = 12.5 Hz), 5.42 (1H, d, J = 12.5 Hz), 7.06 (2H, d, J = 8.0 Hz), 7.29 (2H, d, J = 8.0 Hz), 7.49 (1H, d, J = 8.5 Hz), 7.67 (1H, t, J = 7.5 Hz), 7.87 (1H, s). |

TABLE 84

| | |
|---|---|
| I-357 | 1H-NMR (DMSO-D6) δ: 1.38 (3H, d, J = 6.5 Hz), 2.35-2.42 (1H, m), 2.63-2.85 (4H, m), 2.96-3.01 (1H, m), 3.83 (3H, s), 3.85-3.90 (1H, m), 4.09 (1H, d, J = 14.1 Hz), 4.21 (1H, d, J = 14.1 Hz), 4.28-4.33 (1H, m), 4.47 (1H, dd, J = 14.2, 7.7 Hz), 4.74 (1H, d, J = 15.1 Hz), 4.83 (1H, dd, J = 15.4, 6.7 Hz), 5.07-5.13 (1H, br m), 5.34 (1H, d, J = 13.7 Hz), 5.43 (1H, d, J = 13.7 Hz), 7.02 (1H, d, J = 8.3 Hz), 7.12 (1H, s), 7.34 (1H, d, J = 8.0 Hz), 7.48 (1H, d, J = 8.5 Hz), 7.66 (1H, t, J = 7.6 Hz), 7.89 (1H, s). |
| I-358 | 1H-NMR (DMSO-D6) δ: 1.37 (3H, d, J = 6.8 Hz), 2.34-2.41 (1H, m), 2.64-2.86 (4H, m), 2.96-3.01 (1H, m), 3.89 (1H, q, J = 6.8 Hz), 4.09 (1H, d, J = 14.1 Hz), 4.22 (1H, d, J = 14.1 Hz), 4.28-4.33 (1H, m), 4.47 (1H, dd, J = 14.0, 7.2 Hz), 4.74 (1H, dd, J = 15.4, 2.9 Hz), 4.83 (1H, dd, J = 15.4, 6.8 Hz), 5.07-5.13 (1H, br m), 5.47 (1H, d, J = 13.3 Hz), 5.58 (1H, d, J = 13.3 Hz), 7.35-7.39 (2H, m), 7.48-7.54 (3H, m), 7.67 (1H, t, J = 7.5 Hz), 7.91 (1H, s). |
| I-359 | 1H-NMR (DMSO-D6) δ: 1.39 (3H, d, J = 6.7 Hz), 2.35-2.42 (1H, m), 2.66-2.86 (4H, m), 2.96-3.01 (1H, m), 3.86-3.91 (1H, m), 4.10 (1H, d, J = 14.1 Hz), 4.22 (1H, d, J = 14.1 Hz), 4.28-4.33 (1H, m), 4.47 (1H, q, J = 7.1 Hz), 4.75 (1H, d, J = 14.2 Hz), 4.84 (1H, dd, J = 15.4, 6.6 Hz), 5.07-5.13 (1H, br m), 5.42 (1H, d, J = 12.5 Hz), 5.51 (1H, d, J = 12.8 Hz), 7.11 (1H, t, J = 8.7 Hz), 7.28 (1H, t, J = 10.0 Hz), 7.49 (1H, d, J = 8.5 Hz), 7.55 (1H, dd, J = 15.6, 8.3 Hz), 7.67 (1H, t, J = 7.5 Hz), 7.89 (1H, s). |
| I-360 | 1H-NMR (DMSO-D6) δ: 1.40 (3H, d, J = 6.7 Hz), 2.35-2.40 (1H, m), 2.67-2.85 (4H, m), 2.96-3.01 (1H, m), 3.87-3.92 (1H, m), 4.10 (1H, d, J = 13.8 Hz), 4.22 (1H, d, J = 13.8 Hz), 4.28-4.34 (1H, m), 4.47 (1H, q, J = 6.8 Hz), 4.75 (1H, d, J = 12.9 Hz), 4.84 (1H, dd, J = 15.3, 6.9 Hz), 5.07-5.13 (1H, br m), 5.42 (1H, d, J = 12.7 Hz), 5.51 (1H, d, J = 12.2 Hz), 7.05 (1H, d, J = 8.4 Hz), 7.18 (1H, d, J = 10.9 Hz), 7.30 (1H, t, J = 73.6 Hz), 7.49 (1H, d, J = 8.2 Hz), 7.56 (1H, t, J = 8.5 Hz), 7.67 (1H, t, J = 7.6 Hz), 7.89 (1H, s). |
| I-361 | 1H-NMR (DMSO-D6) δ: 1.41 (3H, d, J = 6.7 Hz), 2.36-2.42 (1H, m), 2.65-2.86 (4H, m), 2.97-3.02 (1H, m), 3.88 (1H, q, J = 6.7 Hz), 4.10 (1H, d, J = 14.1 Hz), 4.21 (1H, d, J = 13.8 Hz), 4.28-4.34 (1H, m), 4.48 (1H, dd, J = 14.1, 7.5 Hz), 4.74 (1H, dd, J = 15.4, 3.2 Hz), 4.83 (1H, dd, J = 15.4, 7.0 Hz), 5.08-5.13 (1H, br m), 5.40 (1H, d, J = 12.5 Hz), 5.51 (1H, d, J = 12.0 Hz), 7.23 (2H, t, J = 8.7 Hz), 7.47 (1H, d, J = 8.5 Hz), 7.65 (1H, t, J = 7.7 Hz), 7.88 (1H, s). |
| I-362 | 1H-NMR (DMSO-D6) δ: 1.40 (3H, d, J = 6.8 Hz), 2.35-2.42 (1H, m), 2.65-2.86 (4H, m), 2.96-3.01 (1H, m), 3.84-3.89 (1H, m), 4.10 (1H, d, J = 13.9 Hz), 4.21 (1H, d, J = 13.3 Hz), 4.28-4.33 (1H, m), 4.48 (1H, q, J = 7.0 Hz), 4.71-4.76 (1H, m), 4.83 (1H, dd, J = 15.1, 6.7 Hz), 5.08-5.13 (1H, br m), 5.42 (1H, d, J = 11.9 Hz), 5.51 (1H, d, J = 12.5 Hz), 7.40 (2H, d, J = 7.7 Hz), 7.49 (1H, d, J = 8.2 Hz), 7.66 (1H, t, J = 7.3 Hz), 7.88 (1H, s). |

TABLE 84-continued

| | |
|---|---|
| I-363 | 1H-NMR (DMSO-D6) δ: 1.38 (3H, d, J = 6.7 Hz), 2.28 (3H, s), 2.31-2.38 (1H, m), 2.59-2.83 (4H, m), 2.96-3.03 (1H, m), 3.86 (1H, q, J = 6.7 Hz), 4.10 (1H, d, J = 14.1 Hz), 4.21 (1H, d, J = 14.1 Hz), 4.29 (1H, dt, J = 11.1, 4.5 Hz), 4.45 (1H, dd, J = 13.7, 7.7 Hz), 4.71 (1H, dd, J = 15.6, 2.9 Hz), 4.79 (1H, dd, J = 15.2, 6.5 Hz), 5.06-5.12 (1H, m), 5.36 (1H, d, J = 12.4 Hz), 5.44 (1H, d, J = 12.4 Hz), 7.17 (2H, d, J = 7.9 Hz), 7.31 (2H, d, J = 7.9 Hz), 7.52 (1H, d, J = 11.3 Hz), 7.87 (1H, s), 8.14 (1H, s). |

TABLE 85

| | |
|---|---|
| I-365 | 1H-NMR (DMSO-D6) δ: 1.26 (3H, d, J = 6.7 Hz), 2.28-2.36 (1H, m), 2.56-2.84 (4H, m), 2.93-2.99 (1H, m), 3.81 (1H, q, J = 6.7 Hz), 4.06 (1H, d, J = 14.1 Hz), 4.19 (1H, d, J = 14.1 Hz), 4.27 (1H, dt, J = 10.9, 4.5 Hz), 4.44 (1H, dd, J = 13.6, 8.0 Hz), 4.68 (1H, dd, J = 15.1, 2.8 Hz), 4.76 (1H, dd, J = 15.3, 6.5 Hz), 5.05-5.11 (1H, m), 5.49 (1H, d, J = 14.2 Hz), 5.56 (1H, d, J = 13.9 Hz), 7.41 (1H, d, J = 8.4 Hz), 7.51 (1H, d, J = 11.4 Hz), 7.93 (1H, s), 7.96 (1H, dd, J = 8.4, 2.5 Hz), 8.10 (1H, s), 8.61 (1H, d, J = 2.5 Hz). |
| I-366 | 1H-NMR (DMSO-D6) δ: 0.65 (2H, dt, J = 8.4, 3.1 Hz), 0.93 (2H, dt, J = 11.8, 3.1 Hz), 1.38 (3H, d, J = 6.8 Hz), 1.86-1.92 (1H, m), 2.30-2.38 (1H, m), 2.59-2.83 (4H, m), 2.94-3.03 (1H, m), 3.86 (1H, q, J = 6.8 Hz), 4.10 (1H, d, J = 14.1 Hz), 4.21 (1H, d, J = 14.1 Hz), 4.29 (1H, dt, J = 11.0, 4.5 Hz), 4.45 (1H, dd, J = 13.6, 7.9 Hz), 4.70 (1H, dd, J = 15.5, 2.6 Hz), 4.78 (1H, dd, J = 15.5, 6.5 Hz), 5.06-5.12 (1H, m), 5.35 (1H, d, J = 12.5 Hz), 5.42 (1H, d, J = 12.5 Hz), 7.06 (2H, d, J = 8.2 Hz), 7.29 (2H, d, J = 8.2 Hz), 7.51 (1H, d, J = 11.5 Hz), 7.87 (1H, s), 8.11 (1H, s). |
| I-367 | 1H-NMR (DMSO-D6) δ: 1.37 (3H, d, J = 6.8 Hz), 2.31-2.38 (1H, m), 2.58-2.85 (4H, m), 2.96-3.01 (1H, m), 3.83 (3H, s), 3.85-3.90 (1H, m), 4.10 (1H, d, J = 13.9 Hz), 4.21 (1H, d, J = 13.9 Hz), 4.29 (1H, dt, J = 10.9, 4.5 Hz), 4.45 (1H, dd, J = 13.9, 7.5 Hz), 4.71 (1H, dd, J = 15.2, 2.7 Hz), 4.80 (1H, dd, J = 15.5, 6.8 Hz), 5.06-5.12 (1H, m), 5.35 (1H, d, J = 13.1 Hz), 5.43 (1H, d, J = 13.3 Hz), 7.02 (1H, dd, J = 8.2, 1.8 Hz), 7.11 (1H, d, J = 1.8 Hz), 7.34 (1H, d, J = 8.2 Hz), 7.52 (1H, d, J = 11.3 Hz), 7.89 (1H, s), 8.15 (1H, s). |
| I-368 | 1H-NMR (DMSO-D6) δ: 1.36 (3H, d, J = 6.7 Hz), 2.30-2.38 (1H, m), 2.57-2.85 (4H, m), 2.95-3.00 (1H, m), 3.88 (1H, q, J = 6.7 Hz), 4.08 (1H, d, J = 13.9 Hz), 4.21 (1H, d, J = 13.9 Hz), 4.29 (1H, dt, J = 10.7, 4.5 Hz), 4.45 (1H, dd, J = 13.8, 7.7 Hz), 4.69 (1H, dd, J = 15.4, 2.4 Hz), 4.77 (1H, dd, J = 15.4, 6.5 Hz), 5.06-5.11 (1H, m), 5.48 (1H, d, J = 13.2 Hz), 5.58 (1H, d, J = 13.2 Hz), 7.34-7.39 (2H, m), 7.48-7.54 (3H, m), 7.91 (1H, s), 8.09 (1H, s). |
| I-369 | 1H-NMR (DMSO-D6) δ: 1.38 (2H, d, J = 6.7 Hz), 2.30-2.38 (1H, m), 2.57-2.84 (4H, m), 2.96-3.01 (1H, m), 3.88 (1H, q, J = 6.7 Hz), 4.11 (1H, d, J = 13.9 Hz), 4.21 (1H, d, J = 13.9 Hz), 4.30 (1H, dt, J = 11.0, 4.4 Hz), 4.45 (1H, dd, J = 13.9, 7.5 Hz), 4.71 (1H, dd, J = 15.3, 2.5 Hz), 4.80 (1H, dd, J = 15.3, 6.7 Hz), 5.06-5.12 (1H, m), 5.42 (1H, d, J = 12.7 Hz), 5.51 (1H, d, J = 12.7 Hz), 7.08-7.13 (1H, m), 7.25-7.31 (1H, m), 7.51-7.59 (2H, m), 7.89 (1H, s), 8.15 (1H, s). |
| I-370 | 1H-NMR (DMSO-D6) δ: 1.39 (3H, d, J = 6.7 Hz), 2.30-2.38 (1H, m), 2.57-2.85 (4H, m), 2.96-3.01 (1H, m), 3.89 (1H, q, J = 6.7 Hz), 4.11 (1H, d, J = 14.1 Hz), 4.21 (1H, d, J = 14.1 Hz), 4.30 (1H, dt, J = 11.0, 4.4 Hz), 4.46 (1H, dd, J = 13.7, 7.6 Hz), 4.72 (1H, dd, J = 15.4, 2.4 Hz), 4.80 (1H, dd, J = 15.4, 6.8 Hz), 5.06-5.12 (1H, m), 5.43 (1H, d, J = 12.5 Hz), 5.52 (1H, d, J = 12.5 Hz), 7.06 (1H, d, J = 8.3 Hz), 7.18 (1H, dd, J = 10.9, 2.1 Hz), 7.30 (1H, t. J = 73.5 Hz), 7.51-7.58 (2H, m), 7.89 (1H, s), 8.16 (1H, s). |
| I-371 | 1H-NMR (DMSO-D6) δ: 1.40 (3H, d, J = 6.7 Hz), 2.31-2.39 (1H, m), 2.58-2.85 (4H, m), 2.96-3.02 (1H, m), 3.87 (1H, q, J = 6.7 Hz), 4.09 (1H, d, J = 13.8 Hz), 4.20 (1H, d, J = 13.8 Hz), 4.30 (1H, dt, J = 10.9, 4.5 Hz), 4.46 (1H, dd, J = 13.8, 7.8 Hz), 4.69 (1H, dd, J = 15.2, 2.8 Hz), 4.77 (1H, dd, J = 15.2, 6.5 Hz), 5.06-5.12 (1H, m), 5.41 (1H, d, J = 12.4 Hz), 5.51 (1H, d, J = 12.4 Hz), 7.23 (2H, t, J = 8.7 Hz), 7.51 (1H, d, J = 11.7 Hz), 7.88 (1H, s), 8.07 (1H, s). |

TABLE 86

| | |
|---|---|
| I-372 | 1H-NMR (DMSO-D6) δ: 1.39 (3H, d, J = 6.8 Hz), 2.30-2.38 (1H, m), 2.57-2.85 (4H, m), 2.96-3.01 (1H, m), 3.87 (1H, q, J = 6.4 Hz), 4.11 (1H, d, J = 13.9 Hz), 4.21 (1H, d, J = 14.2 Hz), 4.30 (1H, dt, J = 10.7, 4.5 Hz), 4.46 (1H, dd, J = 14.1, 7.2 Hz), 4.69-4.74 (1H, m), 4.81 (1H, dd, J = 15.4, 6.4 Hz), 5.06-5.12 (1H, m), 5.43 (1H, d, J = 12.3 Hz), 5.52 (1H, d, J = 12.3 Hz), 7.40 (2H, d, J = 7.4 Hz), 7.53 (1H, d, J = 11.2 Hz), 7.88 (1H, s), 8.16 (1H, s). |
| I-374 | 1H-NMR (DMSO-D6) δ: 1.35 (3H, d, J = 6.7 Hz), 2.28-2.36 (1H, m), 2.57-2.85 (4H, m), 2.95-3.01 (1H, m), 3.82 (1H, q, J = 6.7 Hz), 3.96 (3H, s), 4.05 (1H, d, J = 13.7 Hz), 4.17 (1H, d, J = 13.7 Hz), 4.24-4.29 (1H, m), 4.44 (1H, q, J = 6.8 Hz), 4.63-4.67 (1H, m), 4.72 (1H, dd, J = 15.7, 6.1 Hz), 5.04-5.10 (1H, m), 5.41 (1H, d, J = 12.9 Hz), 5.48 (1H, d, J = 12.9 Hz), 7.27 (1H, s), 7.44 (4H, s), 7.89 (2H, s). |
| I-376 | 1H-NMR (DMSO-D6) δ: 1.36 (3H, d, J = 6.7 Hz), 2.28-2.37 (1H, m), 2.58-2.83 (4H, m), 2.94-3.00 (1H, m), 3.82-3.87 (4H, m), 3.96 (3H, s), 4.04 (1H, d, J = 13.8 Hz), 4.17 (1H, d, J = 13.8 Hz), 4.26 (1H, dt, J = 10.7, 4.5 Hz), 4.44 (1H, dd, J = 13.7, 7.5 Hz), 4.64 (1H, dd, J = 15.4, 2.9 Hz), 4.71 (1H, dd, J = 15.4, 6.3 Hz), 5.05-5.10 (1H, m), 5.34 (1H, d, J = 13.2 Hz), 5.43 (1H, d, J = 13.2 Hz), 7.02 (1H, dd, J = 8.2, 1.8 Hz), 7.11 (1H, d, J = 1.8 Hz), 7.28 (1H, s), 7.34 (1H, d, J = 8.2 Hz), 7.87 (2H, d, J = 5.3 Hz). |
| I-377 | 1H-NMR (DMSO-D6) δ: 1.36 (3H, d, J = 6.7 Hz), 2.30-2.36 (1H, m), 2.57-2.85 (4H, m), 2.95-3.00 (1H, m), 3.85 (1H, q, J = 6.4 Hz), 3.96 (3H, s), 4.05 (1H, d, J = 13.8 Hz), 4.17 (1H, d, J = 13.8 Hz), 4.26 (1H, dt, J = 10.8, 4.4 Hz), 4.44 (1H, dd, J = 13.9, 7.7 Hz), 4.64 (1H, dd, J = 15.5, 2.8 Hz), 4.71 (1H, dd, J = 15.5, 6.2 Hz), 5.04-5.10 (1H, m), 5.46 (1H, d, J = 13.4 Hz), 5.55 (1H, d, J = 13.4 Hz), 7.28 (1H, s), 7.48 (1H, d, J = 8.3 Hz), 7.54 (1H, d, J = 8.3 Hz), 7.68 (1H, s), 7.87 (1H, s), 7.91 (1H, s). |

TABLE 86-continued

| | |
|---|---|
| I-378 | 1H-NMR (DMSO-D6) δ: 1.36 (3H, d, J = 6.7 Hz), 2.30-2.36 (1H, m), 2.57-2.85 (4H, m), 2.95-3.00 (1H, m), 3.85 (1H, q, J = 6.3 Hz), 3.96 (3H, s), 4.06 (1H, d, J = 13.8 Hz), 4.17 (1H, d, J = 13.8 Hz), 4.26 (1H, dt, J = 11.0, 4.5 Hz), 4.44 (1H, dd, J = 13.8, 7.5 Hz), 4.65 (1H, dd, J = 15.7, 2.5 Hz), 4.72 (1H, dd, J = 15.7, 6.0 Hz), 5.04-5.10 (1H, m), 5.43 (1H, d, J = 13.1 Hz), 5.51 (1H, d, J = 13.1 Hz), 7.27 (1H, s), 7.52 (1H, dd, J = 9.5, 6.3 Hz), 7.70 (1H, dd, J = 9.2, 6.1 Hz), 7.89 (1H, s), 7.91 (1H, s). |
| I-379 | 1H-NMR (DMSO-D6) δ: 1.38 (3H, d, J = 6.7 Hz), 2.28-2.37 (1H, m), 2.58-2.83 (4H, m), 2.95-3.01 (1H, m), 3.84 (1H, q, J = 6.1 Hz), 3.97 (3H, s), 4.06 (1H, d, J = 13.7 Hz), 4.17 (1H, d, J = 13.7 Hz), 4.27 (1H, dt, J = 10.9, 4.4 Hz), 4.45 (1H, dd, J = 13.6, 7.7 Hz), 4.65 (1H, dd, J = 15.4, 2.9 Hz), 4.72 (1H, dd, J = 15.4, 6.1 Hz), 5.05-5.11 (1H, m), 5.42 (1H, d, J = 12.3 Hz), 5.52 (1H, d, J = 12.3 Hz), 7.28 (1H, s), 7.40 (2H, d, J = 7.4 Hz), 7.88 (1H, s), 7.90 (1H, s). |
| I-380 | 1H-NMR (DMSO-D6) δ: 2.33-2.41 (1H, m), 2.59-2.67 (1H, m), 2.80-2.88 (4H, m), 3.67 (2H, dd, J = 22.8, 17.1 Hz), 4.04 (1H, d, J = 13.7 Hz), 4.16 (1H, d, J = 13.7 Hz), 4.32-4.35 (1H, m), 4.45 (1H, dd, J = 13.4, 7.5 Hz), 4.65 (1H, dd, J = 15.1, 2.3 Hz), 4.79 (1H, dd, J = 15.4, 7.2 Hz), 5.01-5.07 (1H, m), 5.39 (2H, s), 7.43 (4H, s), 7.51 (1H, d, J = 11.5 Hz), 7.93 (1H, s), 8.09 (1H, s). |

TABLE 87

| | |
|---|---|
| I-381 | 1H-NMR (DMSO-D6) δ: 2.28 (3H, s), 2.33-2.41 (1H, m), 2.59-2.67 (1H, m), 2.78-2.88 (4H, m), 3.68 (2H, dd, J = 23.5, 16.8 Hz), 4.04 (1H, d, J = 13.7 Hz), 4.16 (1H, d, J = 13.7 Hz), 4.32-4.35 (1H, m), 4.45 (1H, dd, J = 13.8, 7.4 Hz), 4.65 (1H, dd, J = 15.2, 2.5 Hz), 4.79 (1H, dd, J = 15.1, 7.2 Hz), 5.04 (1H, ddd, J = 14.1, 7.0, 2.7 Hz), 5.34 (2H, s), 7.16 (2H, d, J = 7.9 Hz), 7.29 (2H, d, J = 8.0 Hz), 7.52 (1H, d, J = 11.5 Hz), 7.90 (1H, s), 8.10 (1H, s). |
| I-384 | 1H-NMR (DMSO-D6) δ: 2.36-2.41 (1H, m), 2.61-2.68 (1H, m), 2.79-2.86 (4H, m), 3.70 (2H, dd, J = 23.5, 16.8 Hz), 4.03 (1H, d, J = 13.8 Hz), 4.14 (1H, d, J = 13.7 Hz), 4.32-4.35 (1H, m), 4.45 (1H, dd, J = 13.7, 7.5 Hz), 4.62 (1H, dd, J = 15.4, 2.6 Hz), 4.75 (1H, dd, J = 15.2, 7.0 Hz), 5.03-5.05 (1H, m), 5.44 (2H, s), 7.46-7.50 (2H, m), 7.55 (1H, d, J = 8.4 Hz), 7.66 (1H, d, J = 2.0 Hz), 7.94 (1H, s), 8.00 (1H, s). |
| I-385 | 1H-NMR (DMSO-D6) δ: 2.34-2.39 (1H, m), 2.58-2.65 (1H, m), 2.80-2.85 (4H, m), 3.70 (2H, dd, J = 23.6, 17.1 Hz), 4.04 (1H, d, J = 13.7 Hz), 4.16 (1H, d, J = 13.7 Hz), 4.31-4.36 (1H, m), 4.45 (1H, q, J = 7.1 Hz), 4.64 (1H, dd, J = 15.1, 2.4 Hz), 4.78 (1H, dd, J = 15.3, 7.0 Hz), 5.04 (1H, ddd, J = 14.6, 7.2, 2.4 Hz), 5.42 (2H, s), 7.31 (1H, dd, J = 8.3, 1.9 Hz), 7.44-7.55 (3H, m), 7.92 (1H, s), 8.06 (1H, s). |
| I-388 | 1H-NMR (DMSO-D6) δ: 2.31-2.39 (1H, m), 2.59-2.65 (1H, m), 2.78-2.85 (4H, m), 3.66 (2H, dd, J = 24.5, 17.3 Hz), 3.81 (3H, s), 3.96 (3H, s), 3.99 (1H, d, J = 13.4 Hz), 4.11 (1H, d, J = 13.4 Hz), 4.30-4.33 (1H, m), 4.44 (1H, dd, J = 12.9, 8.2 Hz), 4.57-4.61 (1H, m), 4.72 (1H, dd, J = 15.4, 7.1 Hz), 5.03 (1H, ddd, J = 14.4, 7.3, 2.7 Hz), 5.32 (2H, s), 7.02 (1H, dd, J = 8.0, 1.9 Hz), 7.10 (1H, d, J = 1.9 Hz), 7.28 (1H, d, J = 0.8 Hz), 7.34 (1H, d, J = 8.0 Hz), 7.85 (1H, s), 7.91 (1H, s). |
| I-389 | 1H-NMR (CDCl3) δ: 2.35-2.43 (1H, m), 2.66-2.72 (1H, m), 2.79-2.86 (4H, m), 3.73 (2H, s), 4.10 (3H, s), 4.17 (1H, d, J = 13.3 Hz), 4.25 (1H, d, J = 13.3 Hz), 4.33-4.35 (1H, m), 4.61 (1H, dd, J = 13.9, 7.8 Hz), 4.68 (2H, d, J = 4.3 Hz), 5.16-5.22 (1H, m), 5.45 (2H, s), 7.23-7.27 (1H, m, overlap with CHCl3), 7.38 (1H, d, J = 2.0 Hz), 7.45-7.52 (2H, m), 7.62 (1H, s), 7.87 (1H, d, J = 1.0 Hz). |
| I-390 | 1H-NMR (DMSO-D6) δ: 2.31-2.39 (1H, m), 2.59-2.63 (1H, m), 2.78-2.85 (4H, m), 3.67 (2H, dd, J = 22.5, 17.1 Hz), 3.96 (3H, s), 4.00 (1H, d, J = 13.6 Hz), 4.12 (1H, d, J = 13.6 Hz), 4.30-4.33 (1H, m), 4.44 (1H, dd, J = 13.6, 7.7 Hz), 4.60 (1H, dd, J = 15.1, 2.7 Hz), 4.72 (1H, dd, J = 15.3, 7.0 Hz), 5.03 (1H, ddd, J = 14.1, 7.0, 2.6 Hz), 5.42 (2H, s), 7.27-7.34 (2H, m), 7.45-7.54 (2H, m), 7.86 (1H, s), 7.92 (1H, s). |
| I-392 | 1H-NMR (DMSO-D6) δ: 1.25 (3H, d, J = 6.8 Hz), 2.28-2.33 (1H, m), 2.54-2.84 (4H, m), 2.93-2.96 (1H, m), 3.79 (1H, dd, J = 13.6, 6.7 Hz), 3.96 (3H, s), 4.02 (1H, d, J = 13.8 Hz), 4.16 (1H, d, J = 13.9 Hz), 4.21-4.28 (1H, m), 4.43 (1H, dd, J = 13.5, 7.8 Hz), 4.60-4.73 (2H, m), 5.06 (1H, ddd, J = 14.0, 6.7, 2.5 Hz), 5.49 (1H, d, J = 14.1 Hz), 5.55 (1H, d, J = 14.1 Hz), 7.27 (1H, d, J = 0.9 Hz), 7.41 (1H, d, J = 8.4 Hz), 7.87 (1H, s), 7.92 (1H, s), 7.97 (1H, dd, J = 8.4, 2.5 Hz), 8.61 (1H, d, J = 2.3 Hz). |

TABLE 88

| | |
|---|---|
| I-393 | 1H-NMR (DMSO-D6) δ: 1.33 (3H, d, J = 6.7 Hz), 2.29-2.38 (1H, m), 2.55-2.75 (4H, m), 2.91-2.97 (1H, m), 3.76 (1H, q, J = 6.6 Hz), 4.05 (1H, d, J = 13.9 Hz), 4.17 (1H, d, J = 13.9 Hz), 4.29 (1H, ct, J = 10.9, 4.4 Hz), 4.45 (1H, dc, J = 13.6, 7.7 Hz), 4.65-4.70 (1H, m), 4.76 (1H, dd, J = 15.2, 6.7 Hz), 5.05-5.11 (1H, m), 5.32 (1H, d, J = 12.9 Hz), 5.40 (1H, d, J = 12.9 Hz), 7.32 (1H, dd, J = 8.2, 1.7 Hz), 7.47 (1H, dd, J = 10.0, 2.0 Hz), 7.54 (1H, t, J = 8.1 Hz), 7.66 (1H, d, J = 8.5 Hz), 7.81 (1H, dd, J = 8.5, 1.3 Hz), 8.25 (1H, s). |
| I-394 | 1H-NMR (DMSO-D6) δ: 1.35 (3H, d, J = 6.7 Hz), 2.30-2.38 (1H, m), 2.56-2.83 (4H, m), 2.95-3.00 (1H, m), 3.83 (1H, q, J = 6.5 Hz), 4.07 (1H, d, J = 13.9 Hz), 4.19 (1H, d, J = 13.9 Hz), 4.29 (1H, dt, J = 10.9, 4.5 Hz), 4.45 (1H, dd, J = 13.6, 7.7 Hz), 4.68 (1H, dd, J = 15.4, 2.8 Hz), 4.77 (1H dd, J = 15.4, 6.7 Hz), 5.06-5.12 (1H, m), 5.39 (1H, d, J = 12.9 Hz), 5.48 (1H, d, J = 12.9 Hz), 7.05 (1H, t, J = 54.8 Hz), 7.30 (1H, dd, J = 8.2, 1.9 Hz), 7.46 (1H, dd, J = 10.0, 1.9 Hz), 7.55 (1H, t, J = 8.2 Hz), 7.67 (1H, d, J = 8.4 Hz), 7.72 (1H, s), 7.82 (1H, dd, J = 8.4, 1.5 Hz), 8.26 (1H, s). |

TABLE 88-continued

| | |
|---|---|
| I-395 | 1H-NMR (DMSO-D6) δ: 1.36 (3H, d, J = 6.8 Hz), 2.32-2.37 (1H, m), 2.55-2.75 (4H, m), 2.92-2.99 (1H, m), 3.76 (1H, dd, J = 13.0, 6.3 Hz), 4.05 (1H, d, J = 13.7 Hz), 4.20 (1H, d, J = 13.8 Hz), 4.28-4.31 (1H, m), 4.45 (1H, dd, J = 13.7, 7.7 Hz), 4.70 (1H, dd, J = 15.4, 2.9 Hz), 4.77 (1H, dd, J = 15.2, 6.5 Hz), 5.10 (1H, ddd, J = 13.9, 7.0, 2.9 Hz), 5.28 (1H, d, J = 12.7 Hz), 5.36 (1H, d, J = 12.7 Hz), 6.67 (1H, d, J = 8.3 Hz), 7.28 (1H, dd, J = 8.3, 1.8 Hz), 7.44-7.47 (2H, m), 7.54 (1H, t, J = 8.2 Hz), 7.67 (1H, d, J = 8.4 Hz), 7.81 (1H, dd, J = 8.4, 1.5 Hz), 8.26 (1H, s). |
| I-247 | 1H-NMR (CDCl3) δ: 1.43 (3H, d, J = 6.7 Hz), 2.36-2.44 (1H, m), 2.62-2.79 (4H, m), 3.00-3.05 (1H, m), 3.83 (1H, dd, J = 13.1, 6.5 Hz), 4.09 (1H, d, J = 13.6 Hz), 4.30-4.41 (2H, m), 4.59-4.74 (3H, m), 5.18-5.21 (1H, m), 5.55 (2H, dd, J = 19.6, 14.5 Hz), 7.46 (1H, d, J = 8.7 Hz), 7.62 (1H, s), 7.68 (1H, dd, J = 8.4, 2.4 Hz), 7.80 (1H, d, J = 8.4 Hz), 8.03 (1H, dd, J = 8.5, 1.4 Hz), 8.19 (1H, d, J = 1.0 Hz), 8.53 (1H, d, J = 2.4 Hz). |

Biological Test Examples for the compounds of the present invention will be described below. The compounds of the present invention can be tested essentially as described in test examples below.

The compound represented by formula (I), formula (II) or formula (III) according to the present invention has a GLP-1 receptor agonist activity effect.

Specifically, in the evaluation method described below, the EC50 value is preferably 5000 nM or less, more preferably 1000 nM or less, even more preferably 100 nM or less.

Test Example 1: (Measurement of GLP-1 Receptor Agonist Activity)

Cell Culture

Human GLP-1 receptor stably expressing cells (hGLP-1R/CHO-K1 cells) are cultured in an α-MEM medium (Sigma) containing 10% FBS (Hyclone), 2% GlutaMAX (Gibco), 1% G418 (Nacalai Tesque), and 1% Penicillin-Streptomycin Mixed Solution (Sigma) at 37° C. under 5% $CO_2$ conditions, and recovered by treating a 10 fold diluted 5.0 g/l-trypsin/5.3 mmol/l-EDTA solution (Nacalai Tesque) and cryopreserved.

cAMP Assay

A DMSO solution containing the compound of the present invention or human GLP-1 (7-36) (Phoenix Pharmaceuticals) is dispensed into a 384-well microplate (Greiner) at 62.5 nL/well, and in addition, 400 μM Forskolin (Nacalai Tesque) is dispensed therein at 7.5 nL/well. Subsequently, the frozen GLP-1 R/CHO-K1 cells are thawed in a thermostatic bath at 37° C., suspended in HBSS buffer (GIBCO) containing 0.1% BSA (Sigma), 20 mM HEPES (GIBCO), 0.1 mM IBMX (Sigma), and 0.2 mM RO20-1724 (Calbiochem) at $2\times10^4$ cells/mL, and the cell suspension is added at 6 μL/well. The solution was incubated at 37° C. for 1 hour and intracellular cAMP concentration is measured using cAMP Gs dynamic kit (Cisbio) according to the protocol attached to the product. Specifically, cAMP-d2 and Anti-cAMP-Cryptate are each added in an amount of 3 μL/well, the mixture is incubated at room temperature for 1 hour, and time-resolved fluorescence is measured using PHERAstar (BMG Labtech).

Assuming that the cAMP concentration when human GLP-1 (7-36) is dispensed to a final concentration of 2 nM is 100% and the cAMP concentration when only DMSO is dispensed is 0%, the 50% effective concentration ($EC_{50}$) and the maximum effect (Emax) of the compound of the present invention are calculated using an increase in the cAMP concentration as an index, using TIBCO Spotfire (TIBCO Software). The dilution concentration or the dilution solvent are changed as necessary.

The compounds of the present invention were tested essentially as described above. $EC_{50}$ and Emax of each compound of the present invention are shown in the following table.

TABLE 89

| Ex. No. | EC50(nM) | Emax(%) |
|---|---|---|
| I-001 | 47.5 | 75 |
| I-002 | 43.3 | 92.2 |
| I-004 | 43.9 | 75.3 |
| I-006 | 54.5 | 86 |
| I-007 | 19.8 | 75.7 |
| I-008 | 48.7 | 84.3 |
| I-009 | 27.3 | 81.3 |
| I-011 | 70.8 | 92.7 |
| I-015 | 74.3 | 81.3 |
| I-016 | 50.3 | 79 |
| I-020 | 75.8 | 89 |
| I-022 | 15 | 92.3 |
| I-023 | 4.56 | 86 |
| I-024 | 26.4 | 92.7 |
| I-026 | 6.35 | 85 |
| I-027 | 9.48 | 80 |
| I-028 | 78.6 | 84 |
| I-029 | 94.6 | 81.3 |
| I-030 | 3.56 | 92.3 |
| I-031 | 8.92 | 91 |

TABLE 90

| Ex. No. | EC50(nM) | Emax(%) |
|---|---|---|
| I-032 | 92.7 | 146 |
| I-033 | 1.49 | 109 |
| I-034 | 8.71 | 103 |
| I-035 | 0.298 | 129 |
| I-036 | 99.5 | 66 |
| I-037 | 0.663 | 126 |
| I-039 | 43.8 | 83.3 |
| I-040 | 37.7 | 147 |
| I-041 | 45.2 | 102 |
| I-042 | 73.8 | 95 |
| I-043 | 13.2 | 109 |
| I-044 | 9.98 | 103 |
| I-045 | 81.5 | 93.7 |
| I-046 | 4.33 | 118 |
| I-047 | 4.3 | 105 |
| I-048 | 75.4 | 130 |
| I-049 | 5.03 | 95 |
| I-050 | 238 | 67.7 |
| I-051 | 24.2 | 87.3 |
| I-052 | 24.5 | 92 |
| I-053 | 14.6 | 115 |
| I-054 | 0.948 | 104 |
| I-055 | 78.8 | 87.3 |
| I-056 | 6.04 | 110 |
| I-059 | 29.9 | 112 |
| I-061 | 1.56 | 113 |
| I-062 | 11.6 | 98.3 |
| I-063 | 98.1 | 128 |

TABLE 90-continued

| Ex. No. | EC50(nM) | Emax(%) |
|---|---|---|
| I-064 | 5.74 | 102 |
| I-065 | 9.82 | 116 |
| I-066 | 8.72 | 124 |
| I-067 | 3.33 | 130 |
| I-068 | 3.54 | 114 |
| I-069 | 7.28 | 116 |
| I-070 | 23.4 | 119 |
| I-071 | 63.9 | 114 |
| I-072 | 12.6 | 127 |
| I-074 | 40 | 100 |
| I-076 | 1.59 | 108 |
| I-078 | 28.6 | 112 |
| I-079 | 6.8 | 103 |
| I-080 | 3.89 | 103 |
| I-081 | 7.66 | 101 |
| I-082 | 2.32 | 103 |
| I-083 | 21.4 | 93 |
| I-084 | 91.9 | 106 |
| I-085 | 4.47 | 111 |
| I-086 | 17.9 | 106 |
| I-088 | 7.81 | 147 |
| I-090 | 6.6 | 106 |
| I-093 | 16.6 | 111 |
| I-094 | 28.5 | 102 |
| I-095 | 10.5 | 112 |
| I-097 | 2.42 | 105 |
| I-098 | 10.9 | 120 |
| I-099 | 1.43 | 114 |
| I-100 | 95.2 | 90.7 |
| I-101 | 2.23 | 113 |
| I-102 | 5.09 | 106 |
| I-103 | 5.6 | 113 |
| I-104 | 4.78 | 102 |
| I-106 | 6.88 | 101 |

TABLE 91

| Ex. No. | EC50(nM) | Emax(%) |
|---|---|---|
| I-107 | 3.5 | 101 |
| I-108 | 8.33 | 108 |
| I-109 | 0.472 | 114 |
| I-110 | 0.685 | 114 |
| I-111 | 2.51 | 126 |
| I-112 | 1.1 | 114 |
| I-113 | 1.46 | 124 |
| I-114 | 0.604 | 132 |
| I-115 | 0.538 | 124 |
| I-116 | 0.158 | 119 |
| I-117 | 0.327 | 117 |
| I-118 | 0.658 | 113 |
| I-119 | 0.569 | 119 |
| I-120 | 2.43 | 103 |
| I-121 | 1.21 | 119 |
| I-122 | 1.22 | 97 |
| I-123 | 3.76 | 97.7 |
| I-124 | 1.71 | 102 |
| I-126 | 0.427 | 99.7 |
| I-126 | 1.52 | 98.7 |
| I-127 | 1.15 | 111 |
| I-128 | 40.3 | 81.3 |
| I-129 | 0.329 | 122 |
| I-130 | 0.307 | 139 |

TABLE 92

| Ex. No. | EC50(nM) | Emax(%) |
|---|---|---|
| I-131 | 89 | 119 |
| I-132 | 0.881 | 105 |
| I-133 | 4.5 | 112 |
| I-134 | 1.18 | 119 |
| I-135 | 27.6 | 91 |

TABLE 92-continued

| Ex. No. | EC50(nM) | Emax(%) |
|---|---|---|
| I-136 | 5.73 | 107 |
| I-137 | 5.56 | 114 |
| I-138 | 68.8 | 94.3 |
| I-139 | 1.23 | 117 |
| I-140 | 18 | 96 |
| I-143 | 25.3 | 101 |
| I-145 | 0.0938 | 108 |
| I-146 | 40.3 | 102 |
| I-147 | 99.3 | 88 |
| I-148 | 32.5 | 95 |
| I-149 | 101 | 93.7 |
| I-150 | 18.3 | 92 |
| I-151 | 124 | 93.7 |
| I-152 | 5.88 | 111 |
| I-153 | 5.34 | 104 |
| I-154 | 38.4 | 97.7 |
| I-155 | 25.9 | 93.7 |
| I-156 | 36.8 | 89 |
| I-157 | 4.29 | 109 |
| I-158 | 16.3 | 94 |
| I-159 | 13.3 | 92.3 |
| I-160 | 0.0524 | 118 |
| I-161 | 1.28 | 110 |
| I-162 | 1.37 | 106 |
| I-163 | 10.6 | 131 |

TABLE 93

| Ex. No. | EC50(nM) | Emax(%) |
|---|---|---|
| I-164 | 0.302 | 104 |
| I-165 | 2.74 | 103 |
| I-166 | 1.23 | 111 |
| I-167 | 0.707 | 102 |
| I-168 | 2.24 | 104 |
| I-169 | 1.21 | 101 |
| I-170 | 1.24 | 120 |
| I-171 | 2.37 | 98.7 |
| I-172 | 0.946 | 113 |
| I-173 | 2.3 | 102 |
| I-174 | 1.58 | 109 |
| I-175 | 3.58 | 101 |
| I-176 | 2.12 | 98.3 |
| I-177 | 3.09 | 107 |
| I-178 | 1.97 | 111 |
| I-179 | 1.88 | 99 |
| I-180 | 8.94 | 97.3 |
| I-181 | 0.374 | 116 |
| I-182 | 3.31 | 126 |
| I-183 | 2.54 | 98 |
| I-184 | 4.75 | 98 |
| I-185 | 2.2 | 106 |
| I-186 | 3.28 | 111 |
| I-187 | 4.2 | 105 |
| I-188 | 1.79 | 90.3 |
| I-189 | 0.0651 | 122 |
| I-190 | 1.08 | 109 |
| I-191 | 0.644 | 130 |
| I-192 | 1.2 | 123 |
| I-193 | 0.73 | 115 |
| I-194 | 0.741 | 111 |
| I-195 | 3.29 | 96.3 |
| I-196 | 0.136 | 106 |
| I-197 | 1.33 | 119 |
| I-198 | 1.17 | 128 |
| I-199 | 0.86 | 128 |
| I-200 | 0.577 | 102 |
| I-201 | 0.274 | 123 |
| I-202 | 1.66 | 105 |
| I-203 | 0.31 | 104 |
| I-204 | 0.509 | 117 |
| I-205 | 0.447 | 109 |
| I-206 | 0.511 | 110 |
| I-207 | 1.72 | 90.3 |
| I-208 | 0.0824 | 109 |

TABLE 93-continued

| Ex. No. | EC50(nM) | Emax(%) |
|---|---|---|
| I-209 | 0.984 | 112 |
| I-210 | 0.434 | 113 |
| I-211 | 0.181 | 103 |
| I-212 | 1 | 104 |
| I-213 | 0.366 | 122 |
| I-214 | 0.392 | 104 |
| I-215 | 1.82 | 106 |
| I-216 | 8.62 | 103 |
| I-217 | 2.34 | 103 |
| I-218 | 0.179 | 109 |
| I-219 | 1.2 | 114 |
| I-220 | 0.251 | 110 |
| I-221 | 6.07 | 125 |
| I-222 | 0.734 | 108 |
| I-223 | 0.12 | 103 |

TABLE 94

| Ex. No. | EC50(nM) | Emax(%) |
|---|---|---|
| I-224 | 1.41 | 110 |
| I-225 | 0.348 | 104 |
| I-226 | 0.628 | 112 |
| I-227 | 0.3 | 103 |
| I-228 | 2.41 | 106 |
| I-229 | 0.0656 | 105 |
| I-230 | 0.693 | 109 |
| I-231 | 0.282 | 106 |
| I-232 | 0.223 | 117 |
| I-233 | 1.29 | 97.7 |
| I-234 | 0.354 | 109 |
| I-235 | 0.378 | 102 |
| I-236 | 0.429 | 106 |
| I-237 | 0.103 | 102 |
| I-238 | 0.36 | 106 |
| I-239 | 0.0882 | 95.3 |
| I-240 | 0.0648 | 122 |
| I-241 | 0.0302 | 125 |
| I-242 | 0.0124 | 116 |
| I-243 | 0.0556 | 111 |
| I-244 | 0.0394 | 123 |
| I-245 | 0.0605 | 109 |
| I-246 | 0.0264 | 120 |
| I-247 | 0.351 | 121 |
| I-248 | 0.902 | 124 |
| I-249 | 0.13 | 145 |
| I-250 | 0.164 | 121 |
| I-251 | 0.807 | 120 |
| I-262 | 0.0798 | 125 |
| I-253 | 0.366 | 119 |
| I-254 | 0.177 | 126 |
| I-255 | 0.102 | 122 |
| I-256 | 0.389 | 119 |
| I-257 | 0.0747 | 115 |
| I-258 | 0.0911 | 107 |
| I-259 | 0.104 | 134 |
| I-260 | 0.128 | 115 |
| I-261 | 1.27 | 105 |
| I-262 | 4.47 | 109 |
| I-263 | 8.8 | 105 |
| I-264 | 2.36 | 121 |
| I-265 | 3.18 | 100 |
| I-266 | 4.04 | 111 |
| I-267 | 0.861 | 112 |
| I-268 | 1.97 | 108 |
| I-269 | 1.16 | 109 |
| I-270 | 0.69 | 116 |
| I-271 | 1.66 | 118 |
| I-272 | 3.94 | 107 |
| I-273 | 0.0301 | 121 |
| I-274 | 0.0134 | 120 |
| I-275 | 0.246 | 107 |
| I-276 | 0.0521 | 114 |
| I-277 | 3.2 | 96.3 |

TABLE 95

| Ex. No. | EC50(nM) | Emax(%) | Ex. No. | EC50(nM) | Emax(%) |
|---|---|---|---|---|---|
| I-278 | 0.806 | 109 | I-302 | 1.76 | 110 |
| I-279 | 0.362 | 110 | I-303 | 0.681 | 119 |
| I-280 | 0.79 | 105 | I-304 | 0.869 | 115 |
| I-281 | 0.00739 | 120 | I-305 | 0.949 | 107 |
| I-282 | 0.00918 | 114 | I-306 | 0.876 | 98.7 |
| I-283 | 0.0283 | 118 | I-307 | 0.0609 | 115 |
| I-284 | 0.016 | 119 | I-308 | 0.0871 | 115 |
| I-285 | 0.00862 | 130 | I-380 | 0.382 | 108 |
| I-286 | 0.444 | 115 | I-381 | 0.702 | 116 |
| I-287 | 0.103 | 116 | I-382 | 0.159 | 125 |
| I-288 | 0.171 | 115 | I-383 | 0.516 | 109 |
| I-289 | 0.311 | 117 | I-384 | 0.126 | 114 |
| I-290 | 0.266 | 118 | I-385 | 0.198 | 112 |
| I-291 | 0.0864 | 120 | I-386 | 0.0877 | 112 |
| I-292 | 0.146 | 121 | I-387 | 0.178 | 122 |
| I-293 | 2.99 | 114 | I-388 | 0.0523 | 115 |
| I-294 | 0.676 | 97.7 | I-389 | 0.05 | 115 |
| I-295 | 1.29 | 108 | I-390 | 0.046 | 107 |
| I-296 | 0.167 | 117 | I-391 | 0.396 | 107 |
| I-297 | 0.818 | 102 | I-392 | 0.0156 | 135 |
| I-298 | 0.317 | 109 | I-393 | 0.099 | 121 |
| I-299 | 0.42 | 115 | I-394 | 0.0497 | 108 |
| I-300 | 0.296 | 112 | I-395 | 0.618 | 89.7 |
| I-301 | 0.281 | 117 | I-025 | 109 | 78.7 |

TABLE 96

| Ex. No. | EC50(nM) | Emax(%) |
|---|---|---|
| I-309 | 2.28 | 84.3 |
| I-310 | 0.415 | 91 |
| I-311 | 0.972 | 124 |
| I-312 | 2.03 | 102 |
| I-313 | 7.87 | 94 |
| I-314 | 0.537 | 98.3 |
| I-315 | 2.1 | 94.3 |
| I-316 | 1.66 | 117 |
| I-317 | 2.56 | 97.7 |
| I-318 | 4.55 | 91.3 |
| I-319 | 2.43 | 95.3 |
| I-320 | 1.63 | 90.3 |
| I-321 | 9.85 | 84 |
| I-322 | 3.51 | 89 |
| I-323 | 1.7 | 101 |
| I-324 | 0.466 | 100 |
| I-325 | 0.655 | 105 |
| I-326 | 1.31 | 109 |
| I-327 | 1.06 | 100 |
| I-328 | 1.73 | 87.3 |
| I-329 | 1.16 | 96.7 |
| I-330 | 1.22 | 93 |
| I-331 | 2.7 | 102 |
| I-332 | 1.38 | 105 |
| I-333 | 8.05 | 116 |
| I-334 | 0.223 | 114 |
| I-335 | 1.23 | 98 |
| I-336 | 0.696 | 100 |
| I-337 | 0.325 | 104 |
| I-338 | 1.27 | 100 |
| I-339 | 0.377 | 105 |
| I-340 | 0.31 | 105 |
| I-341 | 0.236 | 125 |
| I-342 | 1.95 | 97.3 |
| I-343 | 0.063 | 111 |
| I-344 | 0.0824 | 110 |
| I-345 | 0.096 | 129 |
| I-346 | 0.354 | 117 |
| I-347 | 0.241 | 110 |
| I-348 | 0.206 | 129 |
| I-349 | 1.27 | 117 |
| I-350 | 0.0964 | 113 |
| I-351 | 0.156 | 121 |
| I-352 | 0.122 | 113 |
| I-353 | 0.0558 | 115 |
| I-354 | 0.139 | 122 |

TABLE 96-continued

| Ex. No. | EC50(nM) | Emax(%) |
|---|---|---|
| I-355 | 0.102 | 119 |
| I-356 | 0.25 | 118 |
| I-357 | 0.0425 | 123 |
| I-358 | 0.136 | 120 |

TABLE 97

| Ex. No. | EC50(nM) | Emax(%) |
|---|---|---|
| I-359 | 0.0474 | 123 |
| I-360 | 0.104 | 115 |
| I-361 | 0.0778 | 108 |
| I-362 | 0.0408 | 133 |
| I-363 | 0.0911 | 115 |
| I-364 | 0.148 | 118 |
| I-365 | 0.0736 | 115 |
| I-366 | 0.421 | 114 |
| I-367 | 0.0214 | 107 |
| I-368 | 0.2 | 102 |
| I-369 | 0.0526 | 112 |
| I-370 | 0.143 | 109 |
| I-371 | 0.0495 | 122 |
| I-372 | 0.023 | 117 |
| I-373 | 0.0194 | 122 |
| I-374 | 0.0208 | 100 |
| I-375 | 0.0814 | 103 |
| I-376 | 0.0152 | 106 |
| I-377 | 0.0176 | 126 |
| I-378 | 0.0146 | 95.3 |
| I-379 | 0.0121 | 96 |

From the above results, since the compound of the present invention exhibited GLP-1 receptor agonist activity, the compound is expected to have an effect as a therapeutic or prophylactic agent for a disease involving the GLP-1 receptor.

Test Example 2: (Metabolism Stability Test)

Using commercially available pooled human liver microsomes, a compound of the present invention is reacted for a constant time, and a remaining rate is calculated by comparing a reacted sample and an unreacted sample, thereby, a degree of metabolism in liver is assessed.

A reaction is performed (oxidative reaction) at 37° C. for 0 minute or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human liver microsomes. After the reaction, 50 μL of the reaction solution is added to 100 μL of a methanol/acetonitrile=1/1 (v/v), mixed and centrifuged at 3000 rpm for 15 minutes. The compound of the present invention in the supernatant is quantified by LC/MS/MS, and a remaining amount of the compound of the present invention after the reaction is calculated, letting a compound amount at 0 minute reaction time to be 100%.

The compounds of the present invention can be tested essentially as described above.

Test Example 2-2: Metabolism Stability Test

Using commercially available pooled human liver microsomes, a compound of the present invention is reacted for a constant time, and a remaining rate is calculated by comparing a reacted sample and an unreacted sample, thereby, a degree of metabolism in liver is assessed.

A reaction is performed (oxidative reaction) at 37° C. for 0 minute or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human liver microsomes. After the reaction, 70 μL of the reaction solution is added to 140 μL of a methanol/acetonitrile=1/1 (v/v), mixed and centrifuged at 3000 rpm for 15 minutes. The compound of the present invention in the centrifuged supernatant is quantified by LC/MS/MS or solid-phase extraction (SPE)/MS. The ratio of the amount of the compound after the reaction, with respect to the amount of the compound at 0 minutes of the reaction defined as 100%, is shown as the residual rate. Hydrolysis reaction is performed in the absence of NADPH, and glucuronidation reaction is performed in the presence of 5 mmol/L UDP-glucuronic acid instead of NADPH. Then, the same operation is carried out. The dilution concentration or the dilution solvent are changed as necessary.

The compounds of the present invention were tested essentially as described above. Results are shown below.

(Result) The residual rate of the compound at a concentration of 0.5 μmol/L is shown.

Compound I-033: 87.1%
Compound I-035: 87.1%
Compound I-109: 99.6%
Compound I-117: 96.9%
Compound I-123: >99.9%
Compound I-145: 94.0%
Compound I-160: 92.4%

Test Example 3: (Solubility Test)

The solubility of the compound of the present invention is determined under 1% DMSO addition conditions. 10 mmol/L solution of the compound is prepared with DMSO, and 6 μL of the solution of the compound of the present invention is added to 594 μL of pH 6.8 artificial intestinal juice (118 mL of 0.2 mol/L NaOH test solution and water are added to 250 mL of 0.2 mol/L potassium dihydrogen phosphate test solution to reach 1000 mL). The mixture is left standing for 16 hours at 25° C., and the mixture is vacuum-filtered. The filtrate is two-fold diluted with methanol/water=1/1 (V/V), and the compound concentration in the filtrate is measured with HPLC or LC/MS/MS by the absolute calibration method.

The compounds of the present invention can be tested essentially as described above.

Test Example 3-2: (Solubility Test)

The solubility of the compound of the present invention is determined under 1% DMSO addition conditions. 10 mmol/L solution of the compound is prepared with DMSO, and 2 μL of the solution of the compound of the present invention is added to 594 μL of pH 6.8 artificial intestinal juice (118 mL of 0.2 mol/L NaOH test solution and water are added to 250 mL of 0.2 mol/L potassium dihydrogen phosphate test solution to reach 1000 mL). The mixture is shaken for 1 hour or more (3 hours depending on operability) at a room temperature, and then, the mixture is vacuum-filtered. The filtrate is 100-fold diluted (filtrate 2 μL+MeCN/MeOH/purified water=1/1/2 (V/V/V) 198 μL), and the compound concentration in the filtrate is measured with HPLC or LC/MS/MS by the absolute calibration method.

The compounds of the present invention can be tested essentially as described above.

Test Example 3-3: (Solubility Test)

The solubility of the compound of the present invention is determined under 1% DMSO addition conditions. A 10 mmol/L solution of the compound is prepared with DMSO, and 2 μL of the solution of the compound of the present invention is added, respectively, to 198 μL of the second fluid for the dissolution test in the Japanese Pharmacopeia (JP 17). The mixture is left standing and shaken for 3 hours at 25° C., and then, the mixture is vacuum-filtered. The filtrate is 100-fold diluted with methanol/acetonitrile=1/1 (V/V), and the compound concentration in the filtrate is measured with LC/MS/MS by the absolute calibration method.

The compounds of the present invention can be tested essentially as described above.

Test Example 3-4: (Solubility Test)

The solubility of the compound of the present invention is determined under 1% DMSO addition conditions. A 10 mmol/L solution of the compound is prepared with DMSO, and 2 μL of the solution of the compound of the present invention is added, respectively, to 198 μL of the second fluid for the dissolution test in the Japanese Pharmacopeia (JP 17). The mixture is shaken for 3 hour at a room temperature, and the mixture is vacuum-filtered. The filtrate is 100-fold diluted with methanol/acetonitrile=1/1 (V/V), and the compound concentration in the filtrate is measured with LC/MS/MS by the absolute calibration method.

The compounds of the present invention can be tested essentially as described above.

Test Example 4: (CYP Inhibition Test)

Using commercially available pooled human liver microsome, and employing, as markers, 7-ethoxyresorufin O-deethylation (CYP1A2), tolbutamide methyl-hydroxylation (CYP2C9), mephenytoin 4'-hydroxylation (CYP2C19), dextromethorphan O-demethylation (CYP2D6), and terfenadine hydroxylation (CYP3A4) as typical substrate metabolism reactions of human main five CYP enzyme forms (CYP1A2, 2C9, 2C19, 2D6, 3A4), an inhibitory degree of each metabolite production amount by the compound of the present invention was assessed.

The reaction conditions are as follows: substrate, 0.5 μmol/L ethoxyresorufin (CYP1A2), 100 μmol/L tolbutamide (CYP2C9), 30 μmol/L or 50 μmol/L S-mephenytoin (CYP2C19), 5 μmol/L dextromethorphan (CYP2D6), 1 μmol/L terfenadine (CYP3A4); reaction time, 15 minutes; reaction temperature, 37° C.; enzyme, 0.2 mg protein/mL of pooled human liver microsome; concentrations of the compound of the present invention, 1, 5, 10, 20 μmol/L (four points).

Each five kinds of substrates, human liver microsomes, or compound of the present invention in 50 mmol/L Hepes buffer are added to a 96-well plate at the composition as described above, and NADPH, as a cofactor is added to initiate metabolism reactions. After reaction at 37° C. for 15 minutes, the reaction is terminated by the addition of a solution of methanol/acetonitrile=1/1 (V/V). After the centrifugation at 3000 rpm for 15 minutes, resorufin ($CYP1A_2$ metabolite) in the supernatant is quantified by a fluorescent multilabel counter or LC/MS/MS and hydroxytolbutamide (CYP2C9 metabolite), 4' hydroxymephenyto in (CYP2C19 metabolite), dextromethorphan (CYP2D6 metabolite), and terfenadine alcohol metabolite (CYP3A4 metabolite) are quantified by LC/MS/MS.

The sample adding only DMSO as a solvent to a reaction system instead of a solution dissolving a compound of the present invention is adopted as a control (100%). Remaining activity (%) is calculated and ICH is calculated by reverse presumption by a logistic model using a concentration and an inhibition rate.

The compounds of the present invention can be tested essentially as described above.

Test Example 5: (BA Test)

Materials and methods for experiments to evaluate oral absorption (1) Experimental animals: Mice or SD rats are used.

(2) Rearing condition: Mice or SD rats are allowed free access to solid feed and sterilized tap water.

(3) Setting of dosage and grouping: Oral administration and Intravenous administration were performed with the predetermined dosages. Grouping is set as below. (Dosage can be changed per compound)

Oral administration 2 to 60 μmol/kg or 1 to 30 mg/kg (n=2 to 3)

Intravenous administration 1 to 20 μmol/kg or 0.5 to 10 mg/kg (n=2 to 3)

(4) Preparation of administration solutions: Oral administration is performed as solution or suspension. Intravenous administration is performed after solubilization.

(5) Routes of administration: Oral administration is performed mandatory into the stomach by oral sonde. Intravenous administration is performed from caudal vein or femoral vein by a needled syringe.

(6) Evaluation items: Blood was collected over time, and the plasma concentration of the compound of the present invention is measured using LC/MS/MS.

(7) Statistical analysis: An area under plasma concentration-time curve (AUC) is calculated as to change in the concentration of the compound of the present invention in plasma by the moment analysis method, and bioavailability (BA) of the compound of the present invention is calculated from a dose ratio and an AUC ratio between the oral administration group and the intravenous administration group.

The compounds of the present invention can be tested essentially as described above.

Test Example 6: Clearance Evaluation Test

Materials and Methods for Experiments (1) Experimental animals: SD rats are used.

(2) Rearing condition: SD rats are allowed free access to solid feed and sterilized tap water.

(3) Setting of dosage and grouping: Intravenous administration was performed with the predetermined dosage. Grouping is set as below.

Intravenous administration 1 μmol/kg (n=2)

(4) Preparation of administration solutions: Administration is performed after solubilization by using dimethyl sulfoxide/propylene glycol=1/1 as the solvent.

(5) Routes of administration: Intravenous administration is performed from caudal vein by a needled syringe.

(6) Evaluation items: Blood is collected serially and concentration of a compound according to the present invention in plasma is measured by LC/MS/MS.

(7) Statistical analysis: About transition of concentration of a compound according to the present invention in plasma, total clearance (CLtot) of a compound according to the present invention is calculated by the moment analysis method. The dilution concentration or the dilution solvent are changed as necessary.

The compounds of the present invention can be tested essentially as described above.

Test Example 6-2: Clearance Evaluation Test

Materials and Methods for Experiments (1) Experimental animals: Dogs (Marshall Beagles) are used.

(2) Rearing condition: The dogs are allowed to freely take solid food and sterilized tap water.

(3) Setting of dosage and grouping: Intravenous administration was performed with the predetermined dosage. Grouping is set as below.

Intravenous administration: 0.1 to 1 mg/kg (n=2)

(4) Preparation of administration solutions: For administration, the mixture is solubilized using any solvent of dimethylacetamide/ethanol/carbonate buffer=2/3/5, ethanol/carbonate buffer=1/1, and dimethylacetamide/polyethylene glycol 400/20% hydroxypropyl-ß-cyclodextrin=1/1/2.

(5) Routes of administration: Intravenous administration is performed from caudal vein by a needled syringe.

(6) Evaluation items: Blood is collected serially and concentration of a compound according to the present invention in plasma is measured by LC/MS/MS.

(7) Statistical analysis: About transition of concentration of a compound according to the present invention in plasma, total clearance (CLtot) of a compound according to the present invention is calculated by the moment analysis method. The dilution concentration or the dilution solvent are changed as necessary.

The compounds of the present invention can be tested essentially as described above.

Test Example 7: (CYP3A4 (MDZ) MBI Test)

CYP3A4 (MDZ) MBI test is a test of investigating mechanism based inhibition potential on CYP3A4 by the enhancement of inhibitory degree of a metabolic reaction caused by the compound of the present invention. The inhibition of CYP3A4 is evaluated in pooled human liver microsomes by using the 1-hydroxylation reaction of midazolam (MDZ) as an index.

The reaction conditions are as follows: substrate, 10 μmol/L MDZ; pre-reaction time, 0 or 30 minutes; substrate reaction time, 2 minutes; reaction temperature, 37° C.; protein content of pooled human liver microsomes, at pre-reaction time 0.5 mg/mL, at reaction time 0.05 mg/mL (at 10-fold dilution); concentrations of the compound of the present invention, 1, 5, 10, 20 μmol/L (four points).

Pooled human liver microsomes and a solution of the compound of the present invention in K-Pi buffer (pH 7.4) as a pre-reaction solution are added to a 96-well plate at the composition of the pre-reaction. A part of pre-reaction solution is transferred to another 96-well plate, and 1/10 diluted by K-Pi buffer containing a substrate. NADPH as a co-factor is added to initiate a reaction as a marker reaction (without preincubation). After a predetermined time of a reaction, methanol/acetonitrile=1/1 (V/V) solution is added to stop the reaction. In addition, NADPH is added to a remaining pre-reaction solution to initiate a pre-reaction (with preincubation). After a predetermined time of a pre-reaction, a part is transferred to another 96-well plate, and 1/10 diluted by K-Pi buffer containing a substrate to initiate a reaction as a marker reaction. After reaction for a given time, the reaction is terminated by the addition of a solution of methanol/acetonitrile=1/1 (V/V). Each plate where the index reaction has been performed is centrifuged at 3000 rpm for 15 minutes. Then, midazolam 1-hydroxide in the centrifugation supernatants is quantified by LC/MS/MS.

The sample adding DMSO to a reaction system instead of a solution dissolving the compound of the present invention is adopted as a control (100%). Remaining activity (%) is calculated at each concentration of the compound of the present invention compared to control, and IC value is calculated by reverse-presumption by a logistic model using a concentration and an inhibition rate. Shifted IC value is calculated as "IC of preincubation at 0 min/IC of preincubation at 30 min". When a shifted IC is 1.5 or more, this is defined as positive. When a shifted IC is 1.0 or less, this is defined as negative.

The compounds of the present invention can be tested essentially as described above.

Test Example 7-2: (CYP3A4 (MDZ) MBI Test)

CYP3A4 (MDZ) MBI test is a test of investigating mechanism based inhibition potential on CYP3A4 by the enhancement of inhibitory degree of a metabolic reaction caused by the compound of the present invention. The inhibition of CYP3A4 is evaluated in pooled human liver microsomes by using the 1-hydroxylation reaction of midazolam (MDZ) as an index.

The reaction conditions are as follows: substrate, 10 μmol/L MDZ; pre-reaction time, 0 or 30 minutes; substrate reaction time, 2 minutes; reaction temperature, 37° C.; protein content of pooled human liver microsomes, at pre-reaction time 0.5 mg/mL, at reaction time 0.05 mg/mL (at 10-fold dilution); concentrations of the compound of the present invention, 0.83, 5, 10, 20 μmol/L (four points).

Pooled human liver microsomes and a solution of the compound of the present invention in K-Pi buffer (pH 7.4) as a pre-reaction solution are added to a 96-well plate at the composition of the pre-reaction. A part of pre-reaction solution is transferred to another 96-well plate, and 1/10 diluted by K-Pi buffer containing a substrate. NADPH as a co-factor is added to initiate a reaction as a marker reaction (without preincubation). After a predetermined time of a reaction, methanol/acetonitrile=1/1 (V/V) solution is added to stop the reaction. In addition, NADPH is added to a remaining pre-reaction solution to initiate a pre-reaction (with preincubation). After a predetermined time of a pre-reaction, a part is transferred to another 96-well plate, and 1/10 diluted by K-Pi buffer containing a substrate to initiate a reaction as a marker reaction. After reaction for a given time, the reaction is terminated by the addition of a solution of methanol/acetonitrile=1/1 (V/V). Each plate where the index reaction has been performed is centrifuged at 3000 rpm for 15 minutes. Then, midazolam 1-hydroxide in the centrifugation supernatants is quantified by LC/MS/MS.

The sample adding DMSO to a reaction system instead of a solution dissolving the compound of the present invention is adopted as a control (100%). Remaining activity (%) is calculated at each concentration of the compound of the present invention compared to control, and IC value is calculated by reverse-presumption by a logistic model using a concentration and an inhibition rate. Shifted IC value was calculated as "IC of preincubation at 0 min/IC of preincubation at 30 min". When a shifted IC is 1.5 or more, this is defined as positive. When a shifted IC is less than 1.1, this is defined as negative.

The compounds of the present invention can be tested essentially as described above.

Test Example 8: (Powder Solubility Test)

Appropriate quantity of the compound of the present invention is put in suitable containers. 200 μL of JP-1 solution (water is added to 2.0 g of sodium chloride and 7.0 mL of hydrochloric acid to reach 1000 mL), 200 μL of JP-2 solution (500 mL of water is added to 500 mL of phosphate buffer (pH 6.8)) or 20 mmol/L sodium taurocholate (TCA)/JP-2 solution (JP-2 solution is added to 1.08 g of TCA to reach 100 mL) is independently added to each container. When total amount is dissolved after adding the test reagent, the compound of the present invention is added appropriately. The containers are hermetically sealed, shaken at 37° C. for 1 hour, and then filtered. Each filtrate is diluted 2-fold by addition of 100 μL of methanol to 100 μL of the filtrate. The dilution rate is changed as necessary. After checking that there is no bubble and precipitate, the container is sealed and shaken. The compound of the present invention is measured using HPLC by absolute calibration curve method.

The compounds of the present invention can be tested essentially as described above.

Test Example 8-2: (Powder Solubility Test)

Appropriate quantity of the compound of the present invention is put in suitable containers. 200 μL of JP-1 fluid (water is added to 2.0 g of sodium chloride and 7.0 mL of hydrochloric acid to reach 1000 mL), 200 μL of JP-2 fluid (1.70 g of sodium dihydrogen phosphate and 1.775 g of anhydrous disodium hydrogen phosphate are dissolved in 1000 mL of water to obtain a buffer solution of pH 6.8 to 6.9), or 20 mmol/L sodium taurocholate (TCA)/JP-2 fluid (JP-2 fluid is added to 1.08 g of TCA to reach 100 mL) is independently added to each container. When total amount is dissolved after adding the test reagent, the compound of the present invention is added appropriately. The containers are hermetically sealed, shaken at 37° C. for 1 hour, and then filtered. Each filtrate is diluted 2-fold by addition of 100 μL of methanol to 100 μL of the filtrate. The dilution rate is changed as necessary. After checking that there is no bubble and precipitate, the container is sealed and shaken. The compound of the present invention is measured using HPLC by absolute calibration curve method.

The compounds of the present invention can be tested essentially as described above.

Test Example 9: (Fluctuation Ames Test)

The compound of the present invention is evaluated for its mutagenicity.

Cryopreserved *Salmonella typhimurium* (TA98 strain and TA100 strain), 20 μL, was inoculated to 10 mL of a liquid nutrient medium (2.5% Oxoid nutrient broth No. 2) and shake-precultured at 37° C. for 10 hours. The bacterial solution of the TA98 strain, 8.0 to 11.0 mL, is centrifuged (2000×g, 10 min) to remove the culture solution. The bacteria was suspended in 8.0 to 11.0 mL of a Micro F buffer ($K_2HPO_4$: 3.5 g/L, $KH_2PO_4$: 1 g/L, $(NH_4)_2SO_4$: 1 g/L, trisodium citrate dihydrate: 0.25 g/L, $MgSO_4 \cdot 7H_2O$: 0.1 g/L), the suspension was added to 120 mL of an Exposure medium (Micro F buffer containing Biotin: 8 μg/mL, histidine: 0.2 μg/mL, glucose: 8 mg/mL). The TA100 strain was added to 120 mL of the Exposure medium relative to 3.1 mL of the bacterial solution to prepare a test bacterial solution. 12 μL each of a DMSO solution of the compound of the present invention (several serial dilutions from maximum dose 50 mg/mL at 2- to 3-fold common ratio), DMSO as a negative control, and 50 μg/mL of a 4-nitroquinoline-1-oxide DMSO solution for the TA98 strain and 0.25 μg/mL of a 2-(2-furyl)-3-(5-nitro-2-furyl)acrylamide DMSO solution for the TA100 strain under non-metabolic activation conditions or 40 μg/mL of a 2-aminoanthracene DMSO solution for the TA98 strain and 20 μg/mL of a 2-aminoanthracene DMSO solution for the TA100 strain under metabolic activation conditions as a positive control, and 588 μL of the test bacterial solution (a mixed solution of 498 μL of the test bacterial solution and 90 μL of S9 mix under metabolic activation conditions) are mixed, and the mixture is shake-cultured at 37° C. for 90 minutes. The bacterial solution, 230 μL exposed to the compound of the present invention is mixed with 1150 μL of an indicator medium (Micro F buffer containing biotin: 8 μg/mL, histidine: 0.2 μg/mL, glucose: 8 mg/mL, and bromocresol purple: 37.5 μg/mL), and the mixture is dispensed into 48 wells/dose of a microplate at 50 μL/well and statically cultured at 37° C. for 3 days. The color of the solution in a well containing a bacterium that has acquired growth ability due to a mutation in amino acid (histidine) synthase gene is changed from purple to yellow depending on pH change. Therefore, yellow-colored wells with bacterial growth among the 48 wells per dose are counted and evaluated by comparison with the negative control group. Negativity to mutagenicity is indicated by (−), and positivity thereto is indicated by (+)

The compounds of the present invention can be tested essentially as described above.

Test Example 9-2: (Fluctuation Ames Test)

The compound of the present invention is evaluated for its mutagenicity.

Cryopreserved *Salmonella typhimurium* (TA98 strain and TA100 strain), 20 μL, was inoculated to 10 mL of a liquid nutrient medium (2.5% Oxoid nutrient broth No. 2) and shake-precultured at 37° C. for 10 hours. The bacterial solution of the TA98 strain, 8.0 to 11.0 mL, is centrifuged (2000×g, 10 min) to remove the culture solution. The bacteria was suspended in 8.0 to 11.0 mL of a Micro F buffer ($K_2HPO_4$: 3.5 g/L, $KH_2PO_4$: 1 g/L, $(NH_4)_2SO_4$: 1 g/L, trisodium citrate dihydrate: 0.25 g/L, $MgSO_4 \cdot 7H_2O$: 0.1 g/L), the suspension was added to 120 mL of an Exposure medium (Micro F buffer containing Biotin: 8 μg/mL, histidine: 0.2 μg/mL, glucose: 8 mg/mL). A bacterial solution of the TA100 strain, 3.0 mL, was added to 120 mL of an exposure medium to prepare a test bacterial solution. 12 μL each of a DMSO solution of the compound of the present invention (several serial dilutions from maximum dose 50 mg/mL at 2- to 3-fold common ratio), DMSO as a negative control, and 50 μg/mL of a 4-nitroquinoline-1-oxide DMSO solution for the TA98 strain and 0.25 μg/mL of a 2-(2-furyl)-3-(5-nitro-2-furyl)acrylamide DMSO solution for the TA100 strain under non-metabolic activation conditions or 40 μg/mL of a 2-aminoanthracene DMSO solution for the TA98 strain and 20 μg/mL of a 2-aminoanthracene DMSO solution for the TA100 strain under metabolic activation conditions as a positive control, and 588 μL of the test bacterial solution (a mixed solution of 498 μL of the test bacterial solution and 90 μL of S9 mix under metabolic activation conditions) are mixed, and the mixture is shake-cultured at 37° C. for 90 minutes. A microbial cell solution exposed to the compound of the present invention and an Indicator medium (Micro F buffer containing 8 μg/mL biotin, 0.2 μg/mL histidine, 8 mg/mL glucose, and 37.5 μg/mL Bromo Cresol Purple) are mixed at a ratio of 23:115, and 50 μL of the microbial cell solution containing Indicator (2760 μL in total) is dispensed to microplate 48 wells/dose, and this is incubated at 37° C. for 3 days. The color of the solution in a well containing a bacterium that has acquired growth ability due to a mutation in amino acid (histidine) synthase gene is changed from purple to yellow depending on pH change. Therefore, yellow-colored wells with bacterial growth among the 48 wells per dose are counted and evaluated by comparison with the negative control group. Negativity to mutagenicity is indicated by (−), and positivity thereto is indicated by (+).

The compounds of the present invention can be tested essentially as described above.

Test Example 10: (hERG Test)

For the purpose of evaluating the compound of the present invention for the risk of electrocardiogram QT interval prolongation, the effect of the compound of the present invention on delayed rectifier $K^+$ current ($I_{Kr}$) which plays an important role in a ventricular repolarization process is studied using CHO cells caused to express a human ether-a-go-go related gene (hERG) channel.

The cells are kept at a membrane potential of −80 mV by the whole cell patch clamp method using a fully automated patch clamp system (QPatch; Sophion Bioscience A/S), given a leak potential of −50 mV, and then given depolarization stimulation of +20 mV for 2 seconds and further repolarization stimulation of −50 mV for 2 seconds. $I_{Kr}$ induced by this procedure is recorded. After the generated current was stabilized, extracellular solution (NaCl: 145 mmol/L, KCl: 4 mmol/L, $CaCl_2$: 2 mmol/L, $MgCl_2$: 1 mmol/L, glucose: 10 mmol/L, HEPES (4-(2-hydroxyethyl)-1-piperazineethanesulfonic acid): 10 mmol/L, pH=7.4), in which the compound of the present invention had been dissolved at an objective concentration, was applied to the cell at room temperature for 10 minutes. From the recording $I_{Kr}$, an absolute value of the tail peak current was measured based on the current value at the resting membrane potential using analysis software (Falster Patch; Sophion Bioscience A/S). Further, the % inhibition of tail peak current for the compound of the present invention relative to the tail peak current after application of the vehicle is calculated to assess influence of the compound of the present invention on $I_{Kr}$.

The compounds of the present invention can be tested essentially as described above.

Test Example 10-2: (hERG Test)

For the purpose of evaluating the compound of the present invention for the risk of electrocardiogram QT interval prolongation, the effect of the compound of the present invention on delayed rectifier $K^+$ current ($I_{Kr}$) which plays an important role in a ventricular repolarization process is studied using CHO cells caused to express a human ether-a-go-go related gene (hERG) channel.

The cells are kept at a membrane potential of −80 mV by the whole cell patch clamp method using a fully automated patch clamp system (QPatch; Sophion Bioscience A/S), given a leak potential of −50 mV, and then given depolarization stimulation of +20 mV for 2 seconds and further repolarization stimulation of −50 mV for 2 seconds. $I_{Kr}$ induced by this procedure is recorded. An extracellular fluid (NaCl: 145 mmol/L, KCl: 4 mmol/L, $CaCl_2$): 2 mmol/L, $MgCl_2$: 1 mmol/L, glucose: 10 mmol/L, HEPES (4-(2-hydroxyethyl)-1-piperazineethanesulfonic acid): 10 mmol/L, pH=7.4) with dimethyl sulfoxide adjusted to 0.1% is used as a vehicle to apply the vehicle and an extracellular fluid containing the compound of the present invention dissolved at a concentration of interest to the cells under conditions of room temperature for 7 minutes or more. From the obtained $I_{Kr}$, the absolute value of the maximum tail current based on the current value at the membrane potential where the cells have been kept is measured using analytical software (QPatch Assay software; Sophion Bioscience A/S). The maximum tail current after the application of the compound of the present invention with respect to the maximum tail current after the application of the vehicle is further calculated as the rate of inhibition to evaluate the influence of the compound of the present invention on $I_{Kr}$. The dilution concentration or the dilution solvent are changed as necessary.

The compounds of the present invention can be tested essentially as described above.

Formulation Example

The compound of the present invention can be administered as a pharmaceutical composition by any conventional route, in particular enterally, for example, orally, for example, in the form of tablets or capsules, or parenterally, for example, in the form of injectable solutions or suspensions, topically, for example, in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, the oral composition can be a tablet, a granular preparation, or a capsule, each containing an excipient, a disintegrating agent, a binder, a lubricating agent, and the like, as well as an active ingredient and the like. Furthermore, the composition for injection can be prepared as a solution or a suspension, may be sterilized, and may contain a preservative, a stabilizer, a buffering agent, and the like.

The compound of the present invention can be administered as a pharmaceutical composition by any conventional route, particularly enterally, for example, orally, for example, in the form of a tablet or a capsule; parenterally, for example, in the form of an injectable preparation or a suspension; and topically, for example, in the form of a lotion, a gel, an ointment or a cream, or as a pharmaceutical composition in a transnasal form or a suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, the oral composition can be a tablet, a granular preparation, or a capsule, each containing an excipient, a disintegrating agent, a binder, a lubricating agent, and the like, as well as an active ingredient and the like. Furthermore, the composition for injection can be prepared as a solution or a suspension, may be sterilized, and may contain a preservative, a stabilizer, a buffering agent, and the like.

INDUSTRIAL APPLICABILITY

The compounds according to the present invention have GLP-1 receptor agonist activity and are considered to be useful as a therapeutic and/or preventive agent for diseases or conditions associated with the GLP-1 receptor.

The invention claimed is:

1. A compound represented by formula (I):

(I)

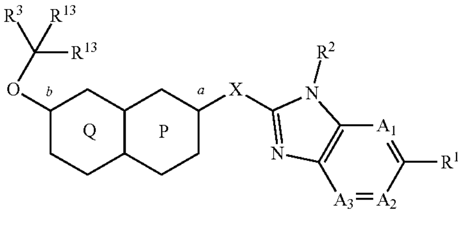

wherein $A_1$ is $C(R^5)$ or N, $A_2$ is $C(R^6)$ or N, $A_3$ is $C(R^7)$ or N, $R^5$, $R^6$, and $R^7$ are each independently a hydrogen atom, halogen, cyano, substituted or unsubstituted alkyl, substituted or unsubstituted alkyloxy, or substituted or unsubstituted non-aromatic carbocyclyl, $R^1$ is carboxy or $CH_2COOH$, $R^2$ is substituted or unsubstituted alkyl, or substituted or unsubstituted non-aromatic heterocyclyl, —X— is —C(RX)$R^9$)—, $R^8$ and $R^9$ are each independently a hydrogen atom, halogen, or substituted or unsubstituted alkyl, $R^{11}$ is a hydrogen atom, or substituted or unsubstituted alkyl, the ring represented by:

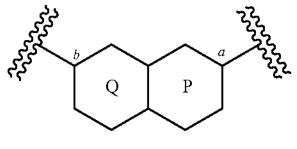

is a ring represented by:

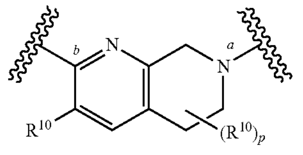

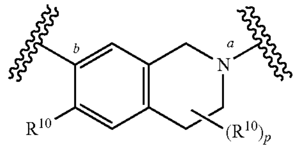

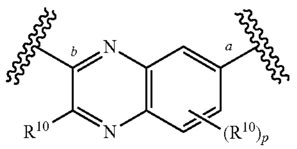

or

-continued

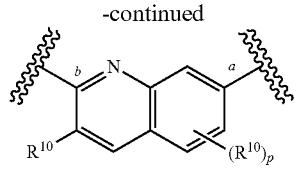

wherein $R^{10}$ is each independently halogen, cyano, hydroxy, substituted or unsubstituted alkyl, oxo, substituted or unsubstituted non-aromatic carbocyclyl, or substituted or unsubstituted alkyloxy, and p is an integer of 0 to 6, $R^{13}$ is each independently a hydrogen atom, halogen, or substituted or unsubstituted alkyl, and $R^3$ is substituted or unsubstituted aromatic carbocyclyl, substituted or unsubstituted non-aromatic carbocyclyl, substituted or unsubstituted aromatic heterocyclyl, or substituted or unsubstituted non-aromatic heterocyclyl, or a pharmaceutically acceptable salt thereof.

2. The compound according to claim 1 or a pharmaceutically acceptable salt thereof, wherein p is an integer of 1 to 6.

3. The compound according to claim 1 or a pharmaceutically acceptable salt thereof, wherein $R^{10}$ is each independently halogen, cyano, or substituted or unsubstituted alkyl.

4. The compound according to claim 1 or a pharmaceutically acceptable salt thereof, wherein $R^3$ is a group represented by:

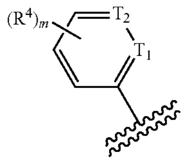

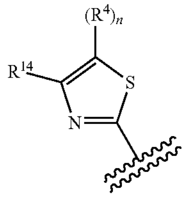

or

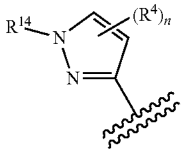

wherein $T_1$ is a carbon atom or a nitrogen atom, $T_2$ is a carbon atom or a nitrogen atom, $R^4$ is each independently halogen, cyano, substituted or unsubstituted alkyl, substituted or unsubstituted alkyloxy, substituted or unsubstituted aromatic carbocyclyl, substituted or unsubstituted non-aromatic carbocyclyl, or substituted or unsubstituted alkylsulfonyl, $R^{14}$ is a hydrogen atom, or substituted or unsubstituted alkyl, m is an integer of 0 to 5, and n is an integer of 0 to 2.

5. The compound according to claim 4 or a pharmaceutically acceptable salt thereof, wherein $R^3$ is a group represented by:

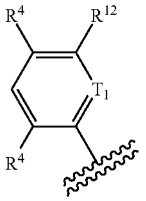
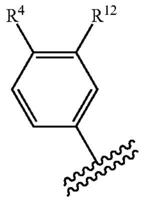
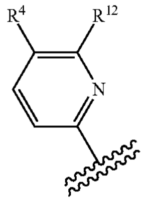
or
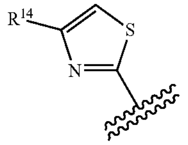

wherein $T_1$ is $C(R^{12})$ or N, $R^{12}$ is each independently a hydrogen atom, halogen, cyano, substituted or unsubstituted alkyl, substituted or unsubstituted alkyloxy, substituted or unsubstituted aromatic carbocyclyl, substituted or unsubstituted non-aromatic carbocyclyl, or substituted or unsubstituted alkylsulfonyl, and $R^4$ and $R^{14}$ are the same as those in claim 4.

6. The compound according to claim 5 or a pharmaceutically acceptable salt thereof, wherein $R^3$ is a group represented by:

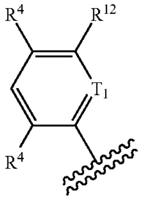
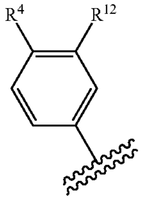
or
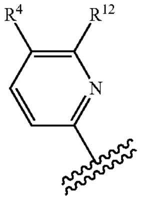

wherein $T_1$ is $C(R^{12})$ or N, $R^{12}$ is each independently a hydrogen atom or halogen, $R^4$ is each independently halogen, cyano, substituted or unsubstituted alkyl, substituted or unsubstituted alkyloxy, or substituted or unsubstituted non-aromatic carbocyclyl.

7. The compound according to claim 4 or a pharmaceutically acceptable salt thereof, wherein $R^4$ is each independently halogen, and $R^{12}$ is each independently a hydrogen atom or halogen.

8. The compound according to claim 1 or a pharmaceutically acceptable salt thereof, wherein $R^{13}$ is each independently a hydrogen atom or substituted or unsubstituted alkyl.

9. The compound according to claim 1 or a pharmaceutically acceptable salt thereof, wherein (i) $A_1$ is $C(R^5)$, $A_2$ is $C(R^6)$, and $A_3$ is $C(R^7)$, (ii) $A_1$ is N, $A_2$ is $C(R^6)$, and $A_3$ is $C(R^7)$, (iii) $A_1$ is $C(R^5)$, $A_2$ is $C(R^6)$, and $A_3$ is N, or (iv) $A_1$ is N, $A_2$ is $C(R^6)$, and $A_3$ is N.

10. The compound according to claim 9 or a pharmaceutically acceptable salt thereof, wherein (i) $A_1$ is $C(R^5)$, $A_2$ is $C(R^6)$, and $A_3$ is $C(R^7)$, or (ii) $A_1$ is N, $A_2$ is $C(R^6)$, and $A_3$ is $C(R^7)$.

11. The compound according to claim 9 or a pharmaceutically acceptable salt thereof, wherein $R^5$ is a hydrogen atom or halogen, $R^6$ is a hydrogen atom, and $R^7$ is a hydrogen atom, halogen, or substituted or unsubstituted alkyloxy.

12. The compound according to claim 1 or a pharmaceutically acceptable salt thereof, wherein $R^1$ is carboxy.

13. The compound according to claim 1 or a pharmaceutically acceptable salt thereof, wherein $R^2$ is alkyl, alkyl substituted with substituted or unsubstituted non-aromatic heterocycle, or alkyl substituted with substituted or unsubstituted aromatic heterocycle.

14. The compound according to claim 13 or a pharmaceutically acceptable salt thereof, wherein $R^2$ is alkyl substituted with substituted or unsubstituted non-aromatic heterocycle, or alkyl substituted with substituted or unsubstituted aromatic heterocycle.

15. The compound according to claim 1 or a pharmaceutically acceptable salt thereof, wherein $R^8$ and $R^9$ are hydrogen atoms.

16. The compound according to claim 1 or a pharmaceutically acceptable salt thereof, wherein the compound is selected from the group consisting of

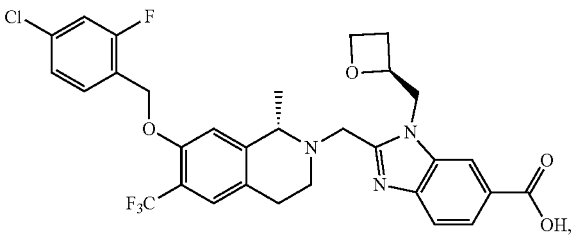
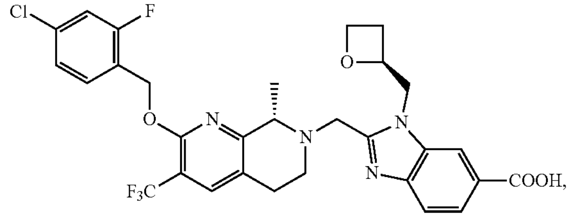
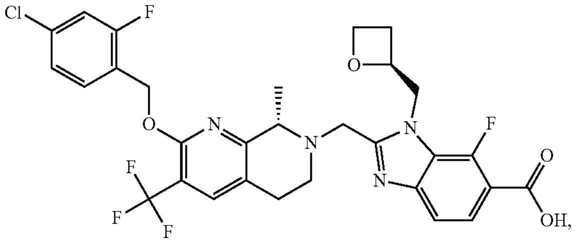
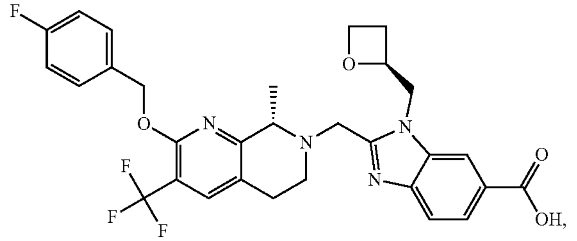
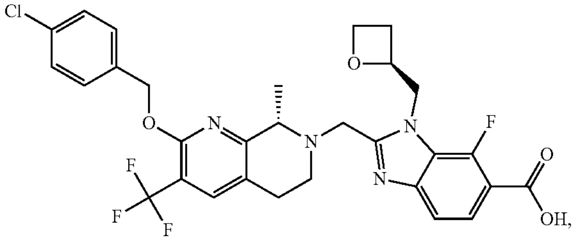

-continued
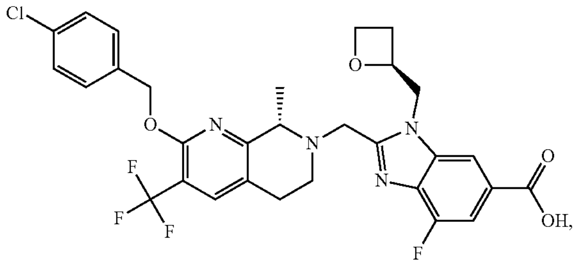
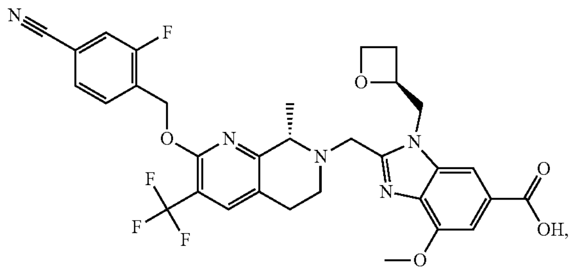
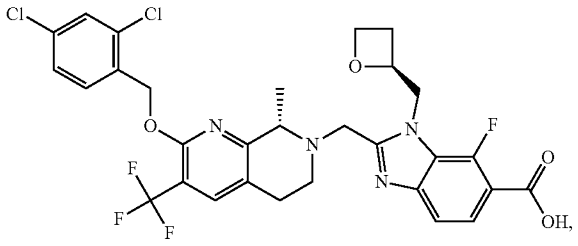
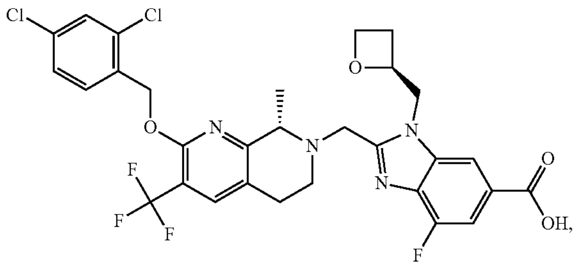
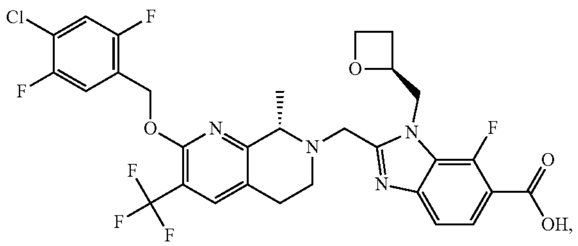
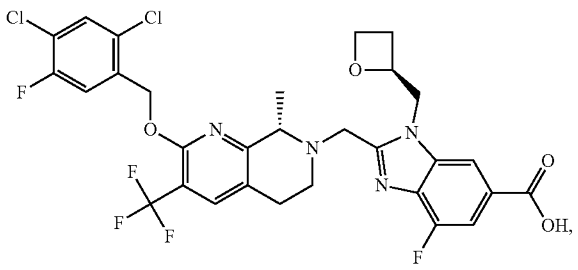
-continued
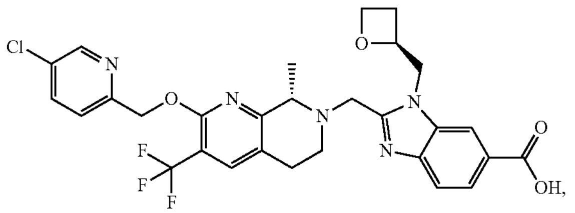
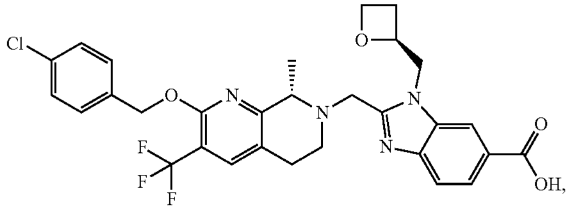
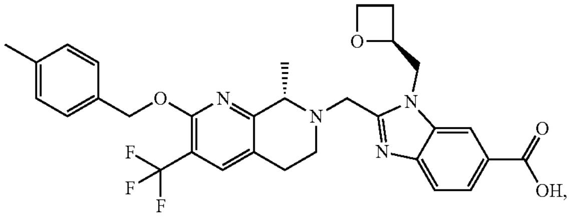
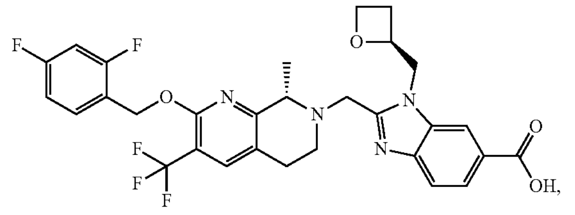
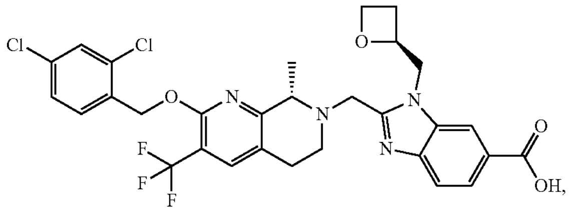
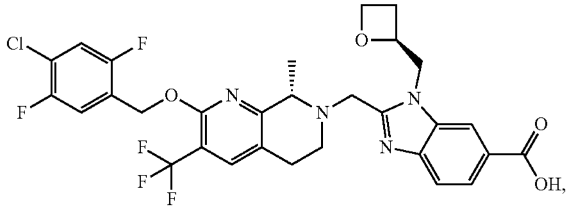
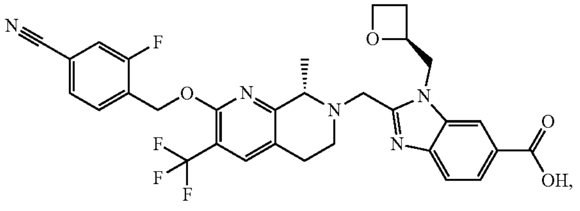
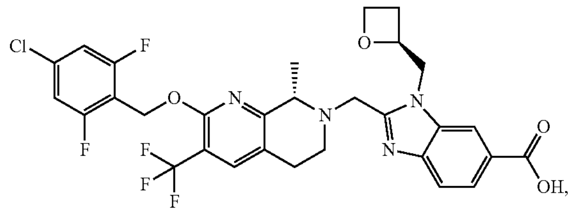

-continued

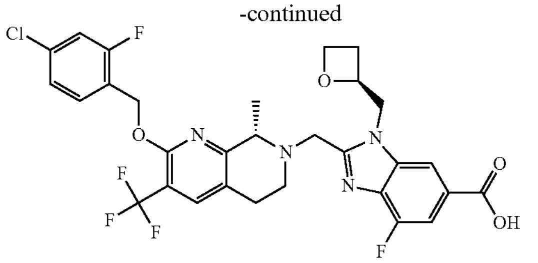

and

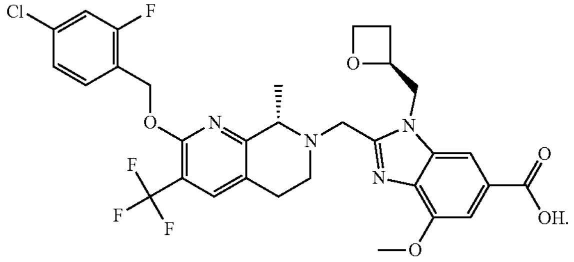

17. A pharmaceutical composition comprising the compound according to claim 1 or a pharmaceutically acceptable salt of thereof, and at least one pharmaceutically acceptable carrier or diluent.

18. A method of activating the GLP-1 receptor, comprising administering a therapeutically effective amount of the compound according to claim 1 or a pharmaceutically acceptable salt thereof to a patient in need thereof.

19. The method of claim 18, wherein activating the GLP-1 receptor treats at least one disease selected from the group consisting of obesity, non-insulin-dependent diabetes mellitus (type 2 diabetes mellitus), hyperglycemia, impaired glucose tolerance, insulin-dependent diabetes mellitus (type 1 diabetes mellitus), diabetic complication, hypertension, dyslipidemia, arteriosclerosis, myocardial infarction, coronary heart disease, cerebral infarction, non-alcoholic steatohepatitis, Parkinson's disease, and dementia.

* * * * *